United States Patent
Biddle et al.

(10) Patent No.: US 10,766,888 B1
(45) Date of Patent: Sep. 8, 2020

(54) HMOX1 INDUCERS

(71) Applicant: Mitobridge Inc., Cambridge, MA (US)

(72) Inventors: Margaret Biddle, Cambridge, MA (US); Arthur Kluge, Lincoln, MA (US); Sanjita Sasmal, Bangalore (IN); Bharat Lagu, Acton, MA (US); Xinyuan Wu, Chestnut Hill, MA (US); Takashi Ogiyama, Ibaraki (JP); Eric Bell, Somerville, MA (US)

(73) Assignee: Mitobridge Inc., Cambridge, MA (US)

( * ) Notice: Subject to any disclaimer, the term of this patent is extended or adjusted under 35 U.S.C. 154(b) by 0 days.

(21) Appl. No.: 16/843,426

(22) Filed: Apr. 8, 2020

Related U.S. Application Data

(60) Provisional application No. 62/932,629, filed on Nov. 8, 2019, provisional application No. 62/833,031, filed on Apr. 12, 2019.

(51) Int. Cl.
| | |
|---|---|
| *C07D 413/12* | (2006.01) |
| *C07D 413/14* | (2006.01) |
| *C07D 417/14* | (2006.01) |
| *A61P 9/08* | (2006.01) |
| *C07D 513/04* | (2006.01) |
| *C07D 403/12* | (2006.01) |
| *C07D 417/12* | (2006.01) |

(52) U.S. Cl.
CPC ............ *C07D 413/14* (2013.01); *A61P 9/08* (2018.01); *C07D 403/12* (2013.01); *C07D 413/12* (2013.01); *C07D 417/12* (2013.01); *C07D 417/14* (2013.01); *C07D 513/04* (2013.01)

(58) Field of Classification Search
CPC .................................................. C07D 413/12
See application file for complete search history.

(56) References Cited

U.S. PATENT DOCUMENTS

2011/0201604 A1   8/2011   Mjalli et al.

FOREIGN PATENT DOCUMENTS

| EP | 2992880 A1 | 3/2016 | |
|---|---|---|---|
| WO | 2007/095124 A2 | 8/2007 | |
| WO | WO-2008/153701 A1 | 12/2008 | |
| WO | 2011/103018 A1 | 8/2011 | |
| WO | 2012/094580 A2 | 7/2012 | |
| WO | 2016/089648 A1 | 6/2016 | |
| WO | WO-2018/037223 A1 * | 3/2018 | ........... C07D 413/12 |

OTHER PUBLICATIONS

Attucks et al., Induction of Heme Oxygenase I (HMOX1) by HPP-4382: A Novel Modulator of Bach1 Activity. PLoS One. 2014;9(7):e101044, 12 pages.
Invitation to Pay Additional Fees for Application No. PCT/US2020/027240, dated May 26, 2020, 12 pages.
Kolavi et al., Heterocycles derived from dimethyldithioimidocarbonates of thiadiazole and thiazole. Journal of Sulfur Chemistry. 2006;27(3):225-231.

* cited by examiner

*Primary Examiner* — Laura L Stockton
(74) *Attorney, Agent, or Firm* — McCarter & English, LLP; Steven G. Davis; Wei Song

(57) ABSTRACT

The present invention is related to compounds of structure (I) as heme oxygenase 1 (HMOX 1) inducers.

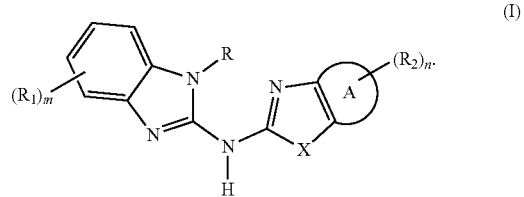

The present invention is also related a method of controlling the activity or the amount, or both the activity and the amount, of heme-oxygenase 1 in a mammalian subject. The definitions of the variables are provided herein.

11 Claims, 6 Drawing Sheets

HMOX1 INDUCERS

CROSS-REFERENCE TO RELATED APPLICATIONS

This application claims the benefit of U.S. Provisional Application No. 62/833,031, filed on Apr. 12, 2019 and U.S. Provisional Application No. 62/932,629, filed on Nov. 8, 2019. The entire teachings of the aforementioned applications are incorporated herein by reference.

FIELD OF THE INVENTION

This application is directed to HMOX1 (heme oxygenase 1) inducers, and methods for their use, such as to control the activity or the amount, or both the activity and the amount, of heme-oxygenase in a mammalian subject.

BACKGROUND OF THE INVENTION

Oxidative stress represents an imbalance between cellular reactive oxygen species (ROS) production and cellular responses to ROS such as degrading ROS species and producing endogenous anti-oxidant molecules.

ROS serve critical cellular signaling needs, but can have deleterious effects if overproduced or left unchecked. Increased ROS levels in a cell can result in damage to components such as lipids, proteins, polysaccharides, and DNA. Prolonged oxidative stress is also linked to chronic diseases that affect nearly every major organ system. For example, prolonged oxidative stress is implicated in the onset or progression of disease states such as neurodegenerative diseases, lung diseases, cardiovascular diseases, renal diseases, diabetes, inflammatory pain, and cancer. Accordingly, strategies to mitigate oxidative stress are desirable for a number of therapeutic settings.

Under normal physiological conditions, production of ROS is counterbalanced by a well-defined and conserved set of cellular pathways that respond to, limit, and repair the damage due to ROS. This adaptive set of genes are called the phase II system. They encode enzymes that degrade ROS directly as well as increase levels of cells' endogenous antioxidant molecules, including glutathione and bilirubin.

Of the phase II enzyme system, HMOX1, a human gene that encodes for the enzyme heme oxygenase 1, has been found to be a key component. The role of HMOX1 is to metabolize heme into bilirubin, carbon monoxide, and free iron by a two-step process. The first and rate-limiting step is the production of biliverdin and carbon monoxide from heme by HMOX1. The second step is the production of bilirubin from biliverdin by biliverdin reductase. Both bilirubin and carbon monoxide have been shown to scavenge ROS and to have potent anti-oxidant and anti-inflammatory activities.

Agents that induce production of HMOX1 have been shown to have beneficial activity in models of diabetes, cardiovascular disease, hypertension, and pulmonary function. Heme, heavy metal ions (e.g., arsenite, cadmium, iron, lead, chromium and mercury), and electrophiles (e.g., natural products such as sulforaphane and curcumin) can all induce production of HMOX1. Induction of HMOX1 and other phase II genes are controlled by a number of transcription factors that are responsive to heavy metals, heme, and electrophiles. The transcription factors Nrf2, Bach1, and small Maf proteins are particularly important in this process. For example, a common sequence called antioxidant responsive element (ARE) is present in a promoter of each gene of the phase II enzymes, and its expression is induced by the transcription factor Nrf2 (NF-E2 related factor 2).

HMOX1 is also induced as part of a generalized stress response to stimuli such as thermal shock, oxidative stress and cytokines such as interleukin-1 (IL-1), tumor necrosis factor and interleukin-6 (IL-6). This stress response is seen as beneficial in that it results in protection of vulnerable cells from multiple insults.

It has been reported that HMOX1 can be induced by small molecules that bind to the transcription factor Bach1. Heme binding to Bach1 has been shown to reduce DNA binding activity of Bach1 and induce gene transcription. See Ogawa K et al. EMBO J (2001) 20:2835-284. Additionally, a small molecule has been reported to induce HMOX1 through binding to Bach1. See Attucks O C et al. PLOS ONE (2014) 9(7): e101044, WO2011/103018 and WO2012/094580.

As such, there is a need for new HMOX1 inducers and/or Bach 1 binders/inhibitors for the above referenced therapeutic indications.

SUMMARY OF THE INVENTION

The applicant has discovered novel compounds which are effective HMOX1 inducers (see Examples 1-142). In particular, it has been demonstrated that certain compounds of the present invention effectively induced production of HMOX1 (see Example 143). Also, certain compounds of the invention have a combination of desirable properties, including potent HMOX1 induction activity (Example 143), significantly reduced hERG inhibition compared to certain comparator compounds (see Example 145), good solubility (Example 144) and a strong impact on HMOX1 protein expression in vivo (Example 151). Moreover, the applicant has also discovered that the compounds disclosed herein bind to Bach 1 (see Example 146).

In one embodiment, provided herein is a compound represented by the following structural Formula (I):

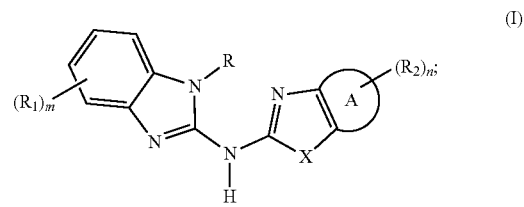

or a pharmaceutically acceptable salt thereof, the definition of each variable is provided below.

Pharmaceutical compositions of the compounds of the invention are also disclosed herein. Particular embodiments comprise a pharmaceutically acceptable carrier or diluent and one or more of the compounds of the invention, or a pharmaceutically acceptable salt thereof.

The compounds of Formula (I) and pharmaceutically acceptable salts thereof are useful as agents that induce the production of and/or increase the activity of HMOX1, and thus may be useful to treat various chronic diseases that are associated, at least in part, with oxidative stress including, but not limited to: fibrotic diseases, neurodegenerative disease, cardiovascular disease, renal disease, inflammatory disease, liver disease, eye disease, thyroid disease, viral infection, osteoporosis, pregnancy disorders, endometriosis, diabetes, cancers, skin diseases, mitochondrial diseases, hematological disorders, and muscle diseases.

Another embodiment of the present invention comprises treating the above-referenced diseases or conditions in a subject by administering to the subject an effective amount of one or more compounds of the invention, or a pharmaceutically acceptable salt thereof, or a pharmaceutical composition comprising the disclosed compound(s).

Also provided herein is the use of one or more compounds of the invention, or a pharmaceutically acceptable salt thereof, or a pharmaceutical composition comprising one or more compounds of the invention, for the preparation of a medicament for the treatment of the above-referenced diseases or conditions.

In another embodiment, provided herein is the compounds of the invention, or a pharmaceutically acceptable salt thereof, or a pharmaceutical composition comprising one or more of the disclosed compounds for use in treating the above-referenced diseases or conditions.

BRIEF DESCRIPTION OF THE DRAWINGS

FIG. 1A depicts that the compound of Example 17 induces HMOX1 expression much more strongly than DMF. FIG. 1B depicts that the compound of Example 17 and DMF induce FTH1 expression with comparable fold increases.

DETAILED DESCRIPTION

Figure 1A:
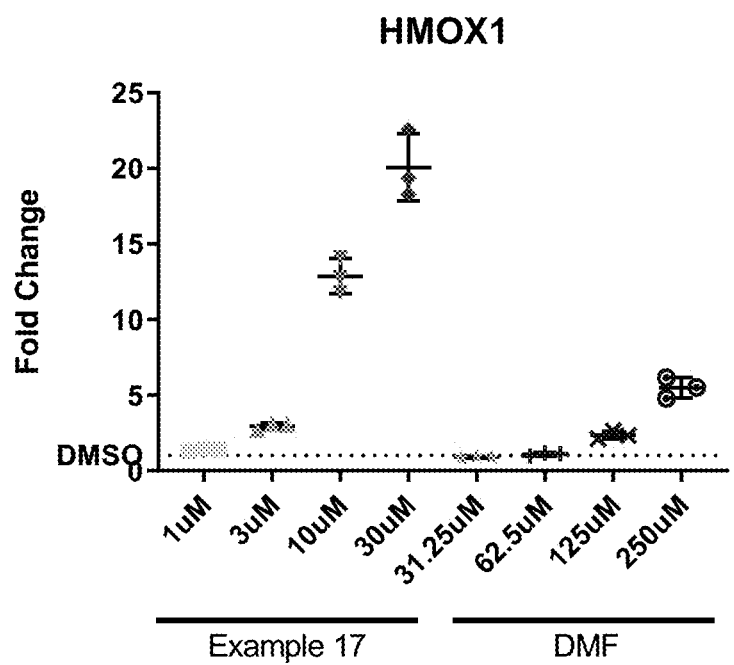
FIGS. 1A and 1B depict graphs showing significant fold change of Gene-Specific mRNA in HepG2 cells treated with the compound of Example 17 or Nrf2 activator DMF.

In response to elevated reactive oxygen species (ROS) levels, cells induce expression of oxidative stress-responsive genes, such as genes encoding proteins that degrade ROS or increase levels of the cell's endogenous antioxidant molecules. One such gene is HMOX1. Induction of expression of HMOX1 and other oxidative stress-responsive genes is regulated in part by the transcription factor Nrf2. Under basal conditions, the adaptor protein Keap1 forms a heterodimer with Nrf2, targeting Nrf2 for proteolysis and suppressing Nrf2-mediated transcription. Upon exposure of cells to chemical electrophiles or agents that elevate ROS, the interaction of Keap1 with Nrf2 is weakened and Nrf2 levels in the cell increase, which in turn increases Nrf2 levels in the nucleus and leads to induction of oxidative stress-responsive genes. Nrf2 activity is also regulated by the transcriptional repressor Bach1, which occludes binding of Nrf2 to the promoter region of oxidative stress-responsive genes.

In order to mitigate the effects of oxidative stress in a cell, e.g., in disease settings, it is therefore desirable to identify compounds that promote the induction of expression of oxidative stress-responsive genes, for example, compounds that modulate the interaction of Nrf2 with Keap1 or the interaction of Bach1 with the Maf recognition element (MARE) to increase cytoprotective gene transcription. However, it is also desirable that such compounds not act as electrophiles or otherwise incite a stress response in the cell.

Compounds of the Invention

Disclosed herein are embodiments of compounds having a general structure of Formula (I).

In a first embodiment, the invention provides a compound represented by the following structural formula (I):

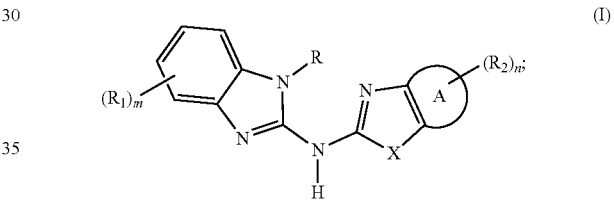

or a pharmaceutically acceptable salt thereof, wherein:

Ring A is 5-7 membered monocyclic cycloalkyl, 5-7 membered monocyclic heterocyclyl, 5-6 membered heteroaryl, or phenyl;

X is —S—, —O—, or —NR$^b$—;

when X is —S— and ring A is phenyl, then R is 3-7 membered monocyclic heterocyclyl optionally substituted with one or more groups selected from the group consisting of halo, —CN, —OH, —(C$_1$-C$_4$)alkyl, —(C$_1$-C$_4$)haloalkyl, —(C$_1$-C$_4$)hydroxyalkyl, —(C$_1$-C$_4$)alkoxy, —C$_1$-C$_4$)haloalkoxy, and —NR$^a$R$^a$;

when X is —S— and ring A is 5-7 membered monocyclic cycloalkyl, 5-7 membered monocyclic heterocyclyl, or 5-6 membered heteroaryl; or when X is —O— or —NR$^b$—; then R is —H, —(C$_1$-C$_4$)alkyl, or —(CH$_2$)$_t$3-7 membered monocyclic heterocyclyl, wherein the —(C$_1$-C$_4$)alkyl or 3-7 membered monocyclic heterocyclyl represented by R is optionally substituted with one or more groups selected from the group consisting of halo, —CN, —OH, —(C$_1$-C$_4$)alkyl, —(C$_1$-C$_4$)haloalkyl, —(C$_1$-C$_4$)hydroxyalkyl, —(C$_1$-C$_4$)alkoxy, —(C$_1$-C$_4$)haloalkoxy, —SO$_2$R$^a$, and —NR$^a$R$^a$;

each R$_1$ is independently —H, halogen, —(CH$_2$)$_k$COOH, —(CH$_2$)$_k$CO(C$_1$-C$_4$)alkyl, —(CH$_2$)$_k$COO(C$_1$-C$_4$)alkyl, —(CH$_2$)$_p$C(=O)NR$^a$R$_3$, —CH(CF$_3$)NR$^a$R$_3$, —C(=NOH)CF$_3$, or —CH(CF$_3$)OR$_3$, wherein the (C$_1$-C$_4$)alkyl in the group represented by R$_1$ is optionally substituted with one or more groups selected from the group consisting of halo, —CN, —OH, —(C$_1$-C$_4$)hydroxyalkyl, —(C$_1$-C$_4$)alkoxy, —(C$_1$-C$_4$)haloalkoxy, and —NR$^a$R$^a$;

each $R_2$ is independently —H, halo, CN, —$(C_1$-$C_4)$alkyl, —OH, —$(C_1$-$C_4)$alkoxy, —COOH, —C(=O)$(C_1$-$C_4)$alkyl, —C(=O)O$(C_1$-$C_4)$alkyl, —C(=O)NR$^a$$(C_1$-$C_4)$alkyl, —NR$^a$R$^a$, 3-6 membered monocyclic cycloalkyl, —O(CH$_2$)$_i$3-7 membered monocyclic heterocyclyl, 3-7 membered monocyclic heterocyclyl, or 5-6 membered heteroaryl, wherein the —$(C_1$-$C_4)$alkyl, —$(C_1$-$C_4)$alkoxy, heterocyclyl, or heteroaryl represented by $R_2$ or in the group represented by $R_2$ is optionally substituted with one or more groups selected from the group consisting of halo, —CN, —OH, —$(C_1$-$C_4)$alkoxy, —$(C_1$-$C_4)$haloalkyl, —$(C_1$-$C_4)$hydroxyalkyl, —$(C_1$-$C_4)$haloalkoxy, and —NR$^a$R$^a$;

each $R_3$ is independently H, $(C_1$-$C_4)$alkyl, $(C_1$-$C_4)$alkoxy, —(CH$_2$)$_{p1}$3-7 membered monocyclic heterocyclyl, —(CH$_2$)$_{p1}$NH3-7 membered monocyclic heterocyclyl, 5-6 membered heteroaryl, —O(CH$_2$)$_{p2}$NR$^a$C(=O)$(C_1$-$C_4)$alkyl, —(CH$_2$)$_{p2}$O(CH$_2$)$_{p2}$O(C=O)$(C_1$-$C_4)$alkyl, or (CH$_2$)$_{p2}$NR$^a$C(=O)$(C_1$-$C_4)$alkyl, wherein the alkyl, alkoxy, heteroaryl, or heterocyclyl represented by $R_3$ or in the group represented by $R_3$ is optionally substituted with one or more groups selected from the group consisting of halo, —CN, —OH, —$(C_1$-$C_4)$alkyl, —$(C_1$-$C_4)$haloalkyl, —$(C_1$-$C_4)$hydroxyalkyl, —$(C_1$-$C_4)$alkoxy, —$(C_1$-$C_4)$haloalkoxy, —$(C_1$-$C_4)$carboxyalkoxy, —S(O)$_2$$(C_1$-$C_4)$alkyl, —$(C_1$-$C_4)$hydroxyalkoxy, and —NR$^a$R$^a$;

each $R^a$ is independently —H or —$(C_1$-$C_4)$alkyl;

each $R^b$ is independently —H or —$(C_1$-$C_4)$alkyl; wherein the —$(C_1$-$C_4)$alkyl represented by $R^b$ is optionally substituted with one or more groups selected from halo, —CN, —OH, —$(C_3$-$C_6)$cycloalkyl, phenyl, 3-7 membered monocyclic heterocyclyl, and 5-6 membered heteroaryl;

i is 0 or 1;

k is 0, 1, 2, 3, or 4;

m is 0, 1, 2, 3, or 4;

n is 0, 1, 2, 3, or 4;

p is 0, 1, 2, 3, or 4;

$p_1$ is 0, 1, 2, 3, or 4; and $p_2$ is 2, 3, or 4.

In a second embodiment, the invention provides a compound according to the previous embodiment, wherein the compound is represented by the following structural formula (II):

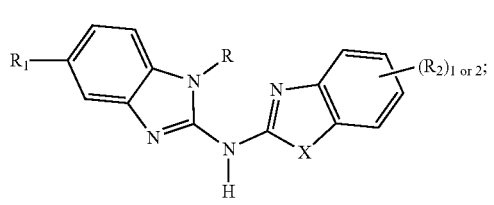

or a pharmaceutically acceptable salt thereof, wherein the remainder of the variables are as defined in the first embodiment.

In a third embodiment, the invention provides a compound according to the first embodiment, wherein the compound is represented by structural formula (II'):

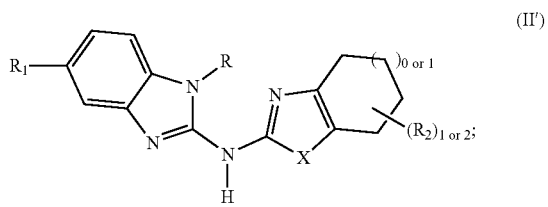

or a pharmaceutically acceptable salt thereof, wherein the remainder of the variables are as defined in the first embodiment.

In a fourth embodiment, the invention provides a compound according to the first or second embodiment, wherein the compound is represented by structural formula (II-A):

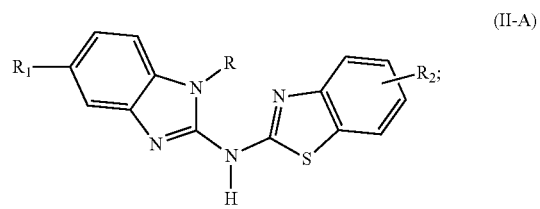

or a pharmaceutically acceptable salt thereof, wherein the remainder of the variables are as defined in the first embodiment.

In a fifth embodiment, the invention provides a compound according to the first or second embodiment, wherein the compound is represented by structural formula (II-B):

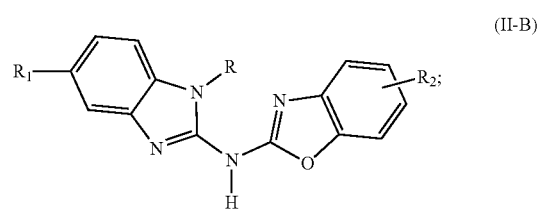

or a pharmaceutically acceptable salt thereof, wherein the remainder of the variables are as defined in the first embodiment.

In a sixth embodiment, the invention provides a compound according to the first or second embodiment, wherein the compound is represented by structural formula (II-C):

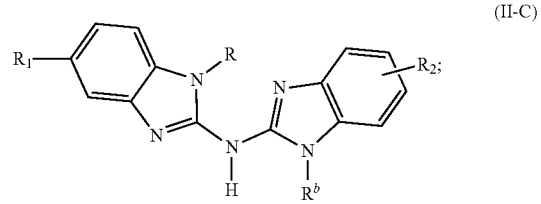

or a pharmaceutically acceptable salt thereof, wherein the remainder of the variables are as defined in the first embodiment.

In a seventh embodiment, the invention provides a compound according to the first or third embodiment, wherein the compound is represented by structural formula (II'-A):

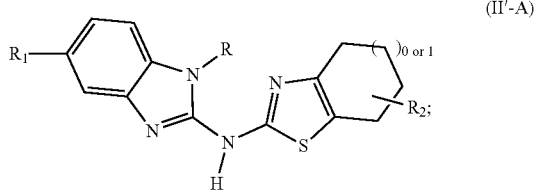

(II'-A)

or a pharmaceutically acceptable salt thereof, wherein the remainder of the variables are as defined in the first embodiment.

In an eighth embodiment, the invention provides a compound according to the sixth embodiment, or a pharmaceutically acceptable salt thereof, wherein $R^b$ is —H or —($C_1$-$C_4$)alkyl, wherein the —($C_1$-$C_4$)alkyl represented by $R^b$ is optionally substituted with one or more groups selected from halo, —CN, and —OH. wherein the remainder of the variables are as defined in the first embodiment. In a preferred embodiment, $R^b$ is —H.

In a ninth embodiment, the invention provides a compound according to the first, second, third, fifth, sixth, seventh, and eighth embodiment, or a pharmaceutically acceptable salt thereof, wherein R is —($C_1$-$C_4$)alkyl optionally substituted with —($C_1$-$C_4$)alkoxy; or —$(CH_2)_i$3-6 membered monocyclic heterocyclyl optionally substituted with one or more groups selected from the group consisting of halo, —CN, —OH, —($C_1$-$C_4$)alkyl, —($C_1$-$C_4$)haloalkyl, —($C_1$-$C_4$)hydroxyalkyl, —($C_1$-$C_4$)alkoxy, —($C_1$-$C_4$)haloalkoxy, and —$NR^aR^a$, wherein the remainder of the variables are as defined in the first or eighth embodiment.

In a tenth embodiment, the invention provides a compound according to the first, second, third, fourth, fifth, sixth, seventh, or eighth embodiment, or a pharmaceutically acceptable salt thereof, wherein R is azetidinyl, azepanyl, morpholinyl, pyrrolidinyl, piperidinyl, piperazinyl, oxetanyl, tetrahydrofuranyl, or tetrahydropyranyl, each of which is optionally substituted with one or more groups selected from the group consisting of halo, —OH, —($C_1$-$C_4$)alkyl, and —$NH_2$, wherein the remainder of the variables are as defined in the first or eighth embodiment.

In an eleventh embodiment, the invention provides a compound according to the first, second, third, fourth, fifth, sixth, seventh, eighth, ninth, or tenth embodiment, or a pharmaceutically acceptable salt thereof, wherein $R_1$ is —$(CH_2)_k$COOH, —$(CH_2)_k$CO($C_1$-$C_4$)alkyl optionally substituted with halo, —$(CH_2)_p$C(=O)$NR^aR_3$, —C(=NOH)$CF_3$, or —CH($CF_3$)$NR^aR_3$, wherein the remainder of the variables are as defined in the first, eighth, ninth or tenth embodiment.

In a twelfth embodiment, the invention provides a compound according to the first, second, third, fourth, fifth, sixth, seventh, eighth, ninth, tenth, or eleventh embodiment, or a pharmaceutically acceptable salt thereof, wherein $R_2$ is H; halogen; CN; —($C_1$-$C_4$)alkyl optionally substituted with halo; —($C_1$-$C_4$)alkoxy optionally substituted with halo, hydroxy, methoxy, or ethoxy; —C(=O)($C_1$-$C_4$)alkyl; 3-4 membered monocyclic cycloalkyl; —$O(CH_2)_i$3-7 membered monocyclic heterocyclyl, 3-7 membered monocyclic heterocyclyl, or 5-6 membered heteroaryl, wherein the heterocyclyl, or heteroaryl represented by $R_2$ or in the group represented by $R_2$ is optionally substituted with halo, hydroxy, or —($C_1$-$C_4$)alkoxy, wherein the remainder of the variables are as defined in the first, eighth, ninth, tenth, or eleventh embodiment. In a preferred embodiment, $R_2$ is H or —$OCF_3$.

In a thirteenth embodiment, the invention provides a compound according to the first, second, third, fifth, sixth, seventh, eighth, ninth, eleventh, or twelfth embodiment, or a pharmaceutically acceptable salt thereof, wherein R is —($C_1$-$C_4$)alkyl optionally substituted with methoxy or —$SO_2CH_3$; —($CH_2$)tetrahydrofuranyl; —($CH_2$)oxetanyl optionally substituted with hydroxy; pyrrolidinyl; piperidinyl; or tetrahydropyranyl; wherein the pyrrolidinyl or piperidinyl is optionally substituted with —($C_1$-$C_4$)alkyl, wherein the remainder of the variables are as defined in the first, eighth, ninth, tenth, eleventh, or twelfth embodiment. In a preferred embodiment, the pyrrolidinyl or piperidinyl is optionally substituted with —$CH_3$.

In a fourteenth embodiment, the invention provides a compound according to the first, second, third, fourth, fifth, sixth, seventh, eighth, ninth, tenth, eleventh, twelfth, or thirteenth embodiment, or a pharmaceutically acceptable salt thereof, wherein $R_1$ is —COOH, —C(=O)$CF_3$, —CH($CF_3$)($NH_2$), —C(=NOH)$CF_3$, or —C(=O)$NHR_3$, wherein the remainder of the variables are as defined in the first, eighth, ninth, tenth, eleventh, twelfth, or thirteenth embodiment.

In a fifteenth embodiment, the invention provides a compound according to the first, second, third, fourth, fifth, sixth, seventh, eighth, ninth, tenth, eleventh, twelfth, thirteenth, or fourteenth embodiment, or a pharmaceutically acceptable salt thereof, wherein $R_3$ is ($C_1$-$C_4$) alkyl, ($C_1$-$C_4$)alkoxy, $(CH_2)_{p1}$3-6 membered monocyclic heterocyclyl, or $(CH_2)_{p2}$NHC(=O)($C_1$-$C_4$)alkyl, wherein the alkyl, alkoxy, or heterocyclyl represented by $R_3$ or in the group represented by $R_3$ is optionally substituted with one or more groups selected from the group consisting of halo, —OH, —($C_1$-$C_4$)alkyl, —($C_1$-$C_4$)haloalkyl, —($C_1$-$C_4$)hydroxyalkyl, —($C_1$-$C_4$)alkoxy, —($C_1$-$C_4$)haloalkoxy, —$S(O)_2$($C_1$-$C_4$)alkyl, —($C_1$-$C_4$)hydroxyalkoxy, and —$NR^aR^a$, wherein the remainder of the variables are as defined in the first, eighth, ninth, tenth, eleventh, twelfth, thirteenth, or fourteenth embodiment.

In a sixteenth embodiment, the invention provides a compound according to the first, second, third, fourth, fifth, sixth, seventh, eighth, ninth, tenth, eleventh, twelfth, thirteenth, fourteenth, or fifteenth embodiment, or a pharmaceutically acceptable salt thereof, wherein $R_2$ is H; halogen; CN; —($C_1$-$C_4$)alkyl optionally substituted with halo; —($C_1$-$C_4$)alkoxy optionally substituted with halo, hydroxy, methoxy, or ethoxy; —C(=O)($C_1$-$C_4$)alkyl; cyclopropyl; O-tetrahydropyranyl; N-pyrrolidinyl; or thiazolyl, wherein the remainder of the variables are as defined in the first, eighth, ninth, tenth, eleventh, twelfth, thirteenth, fourteenth, or fifteenth embodiment.

In a seventeenth embodiment, the invention provides a compound according to the fifth embodiment, wherein the compound is represented by structural formula (III-B):

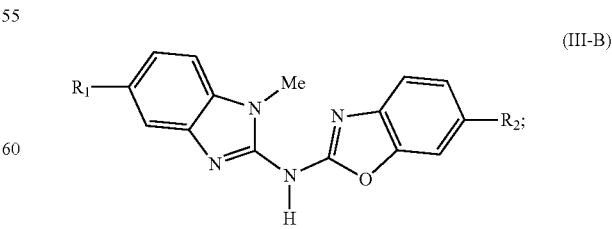

(III-B)

or a pharmaceutically acceptable salt thereof, wherein the remainder of the variables are as defined in the first embodiment.

In an eighteenth embodiment, the invention provides a compound according to the first, second, third, fourth, fifth, sixth, seventh, eighth, ninth, tenth, eleventh, twelfth, thirteenth, fourteenth, fifteenth, sixteenth, or seventeenth embodiment, or a pharmaceutically acceptable salt thereof, wherein $R_1$ is —COOH or —C(=O)NHR$_3$; $R_3$ is —(C$_1$-C$_4$)alkyl, -hydroxy(C$_1$-C$_4$)alkyl, -methoxy(C$_1$-C$_4$)alkyl, -amino(C$_1$-C$_4$)alkyl, —(C$_1$-C$_4$)hydroxyalkoxy(C$_1$-C$_4$)alkyl, or —(CH$_2$)$_{p2}$NHC(=O)(dimethylamino(C$_1$-C$_4$)alkyl), wherein the remainder of the variables are as defined in the first, eighth, ninth, tenth, eleventh, twelfth, thirteenth, fourteenth, fifteenth, sixteenth, or seventeenth embodiment.

In a nineteenth embodiment, the invention provides a compound according to the first, second, third, fourth, fifth, sixth, seventh, eighth, ninth, tenth, eleventh, twelfth, thirteenth, fourteenth, fifteenth, sixteenth, seventeenth, or eighteenth embodiment, or a pharmaceutically acceptable salt thereof, wherein $R_2$ is H, halo, —(C$_1$-C$_4$)haloalkyl, —(C$_1$-C$_4$)haloalkoxy, —(C$_1$-C$_4$)alkoxy optionally substituted with methoxy, or —N-pyrrolidinyl, wherein the remainder of the variables are as defined in the first, eighth, ninth, tenth, eleventh, twelfth, thirteenth, fourteenth, fifteenth, sixteenth, seventeenth, or eighteenth embodiment. In a preferred embodiment, $R_2$ is H, F, CF$_3$, OCHF$_2$, OCF$_3$, OCH$_2$CH$_2$OCH$_3$, or —N-pyrrolidinyl.

In a twentieth embodiment, the invention provides a compound according to the first, second, third, fourth, fifth, sixth, seventh, eighth, ninth, tenth, eleventh, twelfth, thirteenth, fourteenth, fifteenth, sixteenth, seventeenth, eighteenth, or nineteenth embodiment, or a pharmaceutically acceptable salt thereof, wherein $R_2$ is H, $R_1$ is —C(=O)NH(C$_1$-C$_4$)alkyl optionally substituted with —OH, NH$_2$, oxetanyl, or —(C$_1$-C$_4$)hydroxyalkoxy; or —C(=O)NH(CH$_2$)$_{p2}$NHC(=O)(dimethylamino (C$_1$-C$_4$)alkyl); or $R_2$ is F, $R_1$ is —C(=O)NH(methoxy(C$_1$-C$_4$)alkyl); or $R_2$ is —N-pyrrolidinyl, $R_1$ is —C(=O)NH((C$_1$-C$_4$)hydroxyalkoxy(C$_1$-C$_4$)alkyl), $R_2$ is CF$_3$, OCHF$_2$, or OCF$_3$, $R_1$ is —COOH; or $R_2$ is OCH$_2$CH$_2$OCH$_3$, $R_1$ is —C(=O)NH((C$_1$-C$_4$)hydroxyalkoxy(C$_1$-C$_4$)alkyl), —C(=O)NH(hydroxy(C$_1$-C$_4$)alkyl), —C(=O)NH(methoxy(C$_1$-C$_4$)alkyl), or —C(=O)NH(hydroxy(C$_1$-C$_4$)alkoxy);

wherein the remainder of the variables are as defined in the first, eighth, ninth, tenth, eleventh, twelfth, thirteenth, fourteenth, fifteenth, sixteenth, seventeenth, eighteenth, or nineteenth embodiment.

In a twentyfirst embodiment, the invention provides a compound according to the seventeenth embodiment, or a pharmaceutically acceptable salt thereof, wherein $R_1$ is —C(=O)NH(C$_1$-C$_4$)alkyl optionally substituted with —OH, NH$_2$, —(C$_1$-C$_4$)alkoxy, or —(C$_1$-C$_4$)hydroxyalkoxy, and $R_2$ is H, or OCH$_2$CH$_2$OCH$_3$.

In a twentysecond embodiment, the invention provides a compound according to the twentyfirst embodiment, or a pharmaceutically acceptable salt thereof, wherein $R_2$ is H, wherein the remainder of the variables are as defined in the twentyfirst embodiment.

In a twentythird embodiment, the invention provides a compound according to the twentysecond embodiment, or a pharmaceutically acceptable salt thereof, wherein $R_1$ is —C(=O)NH(C$_1$-C$_4$)alkyl substituted with —(C$_1$-C$_4$)hydroxyalkoxy, wherein the remainder of the variables are as defined in the twentysecond embodiment.

In a twentyfourth embodiment, the invention provides a compound according to the twentyfirst embodiment, or a pharmaceutically acceptable salt thereof, wherein $R_1$ is —C(=O)NH(C$_1$-C$_4$)alkyl substituted with —(C$_1$-C$_4$)alkoxy, and $R_2$ is OCH$_2$CH$_2$OCH$_3$.

In one embodiment, the compound or a pharmaceutically acceptable salt thereof is selected from the compounds disclosed in examples and Table 1.

Definitions

The term "pharmaceutically-acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically-acceptable salts are well known in the art. For example, S. M. Berge et al. describes pharmacologically acceptable salts in J. Pharm. Sci., 1977, 66, 1-19.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric, hydrobromic, phosphoric, metaphosphoric, nitric, and sulfuric acids) and of organic acids (such as acetic, benzenesulfonic, benzoic, ethanesulfonic, methanesulfonic, and succinic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

The term "halo" as used herein means halogen and includes chloro, fluoro, bromo and iodo.

The term "alkyl" used alone or as part of a larger moiety, such as "alkoxy" or "haloalkyl" and the like, means saturated aliphatic straight-chain or branched monovalent hydrocarbon radical. Unless otherwise specified, an alkyl group typically has 1-5 carbon atoms, i.e. (C$_1$-C$_5$)alkyl. As used herein, a "(C$_1$-C$_4$)alkyl" group means a radical having from 1 to 4 carbon atoms in a linear or branched arrangement. Examples include methyl, ethyl, n-propyl, iso-propyl, and the like.

The term "alkoxy" means an alkyl radical attached through an oxygen linking atom, represented by —O-alkyl. For example, "(C$_1$-C$_4$)alkoxy" includes methoxy, ethoxy, propoxy, and butoxy.

The terms "haloalkyl" and "haloalkoxy" means alkyl or alkoxy, as the case may be, substituted with one or more halogen atoms.

The term "cycloalkyl" refers to a monocyclic saturated hydrocarbon ring system. Unless otherwise specified, cycloalkyl has from 3-7 carbon atoms. For example, a C$_3$-C$_6$ cycloalkyl includes cyclopropyl, cyclobutyl, cyclopentyl and cyclohexyl. Unless otherwise described, a "cycloalkyl" has from three to six carbon atoms.

The term "heteroaryl", "heteroaromatic", "heteroaryl ring", "heteroaryl group", "heteroaromatic ring", or "heteroaromatic group", used alone or as part of a larger moiety as in "heteroaralkyl" or "heteroarylalkoxy", refers to monocyclic aromatic ring groups having five or six ring atoms (i.e., "5-6 membered") selected from carbon and at least one (typically 1 to 4, more typically 1 or 2) heteroatoms (e.g., oxygen, nitrogen, or sulfur).

Examples of monocyclic heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl), thienyl (e.g., 2-thienyl, 3-thienyl), pyrimidinyl, pyridinyl and pyridazinyl.

The term "heterocyclyl" refers to a monocyclic non-aromatic ring radical containing from 3-7 ring atoms (i.e., "3-7 membered") selected from carbon atom and 1 or 2 heteroatoms. Each heteroatom is independently selected from nitrogen, quaternary nitrogen, oxidized nitrogen (e.g., NO); oxygen; and sulfur, including sulfoxide and sulfone. Representative heterocyclyl groups include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A "substituted heterocylyl group" is substituted at any one or more substitutable ring atom, which is a ring carbon or ring nitrogen atom bonded to a hydrogen.

As used herein, many moieties (e.g., alkyl, alkylene, cycloalkyl, cycloalkylene, aryl, arylene, heteroaryl, heteroarylene, heterocyclyl or heterocyclylene) are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents. Where if more than one substituent is present, then each substituent may be independently selected. Such means for substitution are well-known in the art and/or taught by the instant disclosure. The optional substituents can be any substituents that are suitable to attach to the moiety.

Suitable substituents are those which do not have a significant adverse effect on the ability of the compound to induce HMOX1. Where suitable substituents are not specifically enumerated, exemplary substituents include, but are not limited to: $(C_1-C_5)$alkyl, $(C_1-C_5)$hydroxyalkyl, $(C_1-C_5)$haloalkyl, $(C_1-C_5)$ alkoxy, $(C_1-C_5)$ haloalkoxy, halogen, hydroxyl, —CN, —NH$_2$, —NO$_2$, —OR$^{c1}$, —NR$^{a1}$R$^{b1}$, —S(O)$_{ii}$R$^{a1}$, —NR$^{a1}$S(O)$_{ii}$R$^{b1}$, —S(O)$_{ii}$NR$^{a1}$R$^{b1}$, —C(=O)OR$^{a1}$, —OC(=O)OR$^{a1}$, —C(=S)OR$^{a1}$, —O(C=S)R$^{a1}$, —C(=O)NR$^{a1}$R$^{b1}$, —NR$^{a1}$C(=O)R$^{b1}$, —C(=S)NR$^{a1}$R$^{b1}$, NR$^{a1}$C(=S)R$^{b1}$, —NR$^{a1}$(C=O)OR$^{b1}$, —O(C=O) NR$^{a1}$R$^{b1}$, —NR$^{a1}$(C=S)OR$^{b1}$, —O(C=S)NR$^{a1}$R$^{b1}$, —NR$^{a1}$(C=O)NR$^{a1}$R$^{b1}$, —NR$^{a1}$(C=S)NR$^{a1}$R$^{b1}$, —C(=S)R$^{a1}$, —C(=O)R$^{a1}$, phenyl, or 5-6 membered heteroaryl. Each R$^{a1}$ and each R$^{b1}$ are independently selected from —H and $(C_1-C_5)$alkyl, optionally substituted with hydroxyl or $(C_1-C_3)$alkoxy; R$^{c1}$ is —H, $(C_1-C_5)$haloalkyl or $(C_1-C_5)$alkyl, wherein the $(C_1-C_5)$alkyl is optionally substituted with hydroxyl or $(C_1-C_3)$alkoxy; and ii is 1 or 2.

Pharmaceutical Compositions

The compounds disclosed herein are HMOX1 inducers. The pharmaceutical composition of the present invention comprises one or more HMOX1 inducers, or a pharmaceutically acceptable salt thereof, and a pharmaceutically acceptable carrier or diluent.

"Pharmaceutically acceptable carrier" and "pharmaceutically acceptable diluent" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, hydroxymethycellulose, fatty acid esters, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The pharmaceutical compositions of the present invention optionally include one or more pharmaceutically acceptable carriers and/or diluents therefor, such as lactose, starch, cellulose and dextrose. Other excipients, such as flavoring agents, sweeteners, and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Methods of Treatment

In certain embodiments, the invention provides methods of increasing the activity of or the amount of HMOX1 in a human subject comprising: administering to a human subject an effective amount of the compounds of the invention, or a pharmaceutically acceptable salt thereof, or an effective amount of the pharmaceutical composition thereof.

In certain embodiments, the invention provides methods of activating transcription factor Nrf2 in a human subject comprising: administering to a human subject an effective amount of the compounds of the invention, or a pharmaceutically acceptable salt thereof, or an effective amount of the pharmaceutical composition thereof.

In certain embodiments, the invention provides methods of reducing the amount of ROS in a human subject comprising: administering to a human subject an effective amount of the compounds of the invention, or a pharmaceutically acceptable salt thereof, or an effective amount of the pharmaceutical composition thereof.

In certain embodiments, the invention provides methods for using an effective amount of the compounds of the invention, or a pharmaceutically acceptable salt thereof, or an effective amount of the pharmaceutical composition thereof. The compounds of the invention and pharmaceutical compositions thereof may be useful for a variety of therapeutic applications including, for example, treating and/or reducing a wide variety of diseases and disorders including, for example, fibrotic diseases, neurodegenerative disease, cardiovascular disease, renal disease, inflammatory disease, liver disease, eye disease, thyroid disease, viral infection, osteoporosis, pregnancy disorders, endometriosis, diabetes, cancers, skin diseases, mitochondrial diseases, hematological disorders, and muscle diseases. The methods comprise administering to a subject in need thereof a pharmaceutically effective amount of one or more compounds of the invention, a pharmaceutically acceptable salt thereof, and/or pharmaceutical compositions thereof.

Compounds that increase levels or activity of HMOX1 are potentially useful in treating diseases or conditions that may be associated at least in part with oxidative stress such as, but not limited to, fibrotic diseases, neurodegenerative disease, cardiovascular disease, renal disease, inflammatory disease, liver disease, eye disease, thyroid disease, viral infection, osteoporosis, pregnancy disorders, endometriosis, diabetes, cancers, skin diseases, mitochondrial diseases, hematological disorders, and muscle diseases. As used herein, the diseases or conditions associated with oxidative stress also include chronic effects (e.g., tissue damage, chronic inflammation) associated with persistent or long-term increases in oxidative stress due to the diseases or conditions described herein.

Fibrotic diseases associated with oxidative stress include, but are not limited to, fibrotic diseases of the lung such as chronic obstructive pulmonary disease (COPD), idiopathic pulmonary fibrosis, and sarcoidosis; fibrotic diseases of the liver including those caused by alcoholic cirrhosis, steatosis, cholestasis, drug side effect, and viral infection; and fibrotic diseases of the skin including autoimmune diseases such as scleroderma and psoriasis.

Neurodegenerative diseases associated with oxidative stress include, but are not limited to, Friedreich's ataxia, Alzheimer's disease, Parkinson's disease, amyotrophic lateral sclerosis, multiple sclerosis, cerebral nerve degenerative disease, and Charcot-Marie-Tooth syndrome.

Cardiovascular diseases associated with oxidative stress include, but are not limited to, hypertension, heart failure, hypercholesterolaemia, atherosclerosis, arteriosclerosis, thrombosis, acute coronary thrombosis, deep vein thrombosis, peripheral vascular disease, congestive heart failure, acute coronary syndrome, failure of arterial fistula for dialysis, ischemia reperfusion injury, primary pulmonary hypertension, primary pulmonary arterial hypertension, and secondary pulmonary arterial hypertension.

Renal diseases associated with oxidative stress include, but are not limited to, acute kidney injury, polycystic kidney disease, Alport syndrome, diabetic nephropathy, glomerular nephritis, lupus nephritis, sickle cell nephropathy, and acute tubular necrosis.

Inflammatory diseases associated with oxidative stress include, but are not limited to, asthma, chronic obstructive pulmonary disease, idiopathic pulmonary fibrosis, inflammatory bowel syndrome, Crohn's disease, celiac disease, ulcerative colitis, chronic inflammatory bowel disease, scleroderma, dermatitis, systemic lupus erythematosus, esophagitis, vasculitis, pancreatitis, tendonitis, osteoarthritis, rheumatoid arthritis, ankylosing spondylitis, and chronic inflammation of the brain.

Liver diseases associated with oxidative stress include, but are not limited to, drug induced liver toxicity, nonalcoholic steatohepatitis, and hepatitis, e.g., hepatitis B infection and hepatitis C infection.

Eye diseases and conditions associated with oxidative stress include, but are not limited to, conjunctivitis, glaucoma, uveitis, wound healing (e.g., after surgery such as LASIK), eye trauma, corneal grafts, Fuchs' endothelial corneal dystrophy, macular degeneration, cataracts, light retinopathy, retinitis pigmentosa, diabetic retinopathy, and retinopathy of prematurity, as well as inflammation and tissue damage associated with these diseases.

Thyroid diseases associated with oxidative stress include, but are not limited to, Graves' disease, follicular adenoma, and papillary and follicular carcinomas.

Lung diseases associated with oxidative stress include, but are not limited to, bronchitis, asthma, chronic obstructive pulmonary disease, idiopathic pulmonary fibrosis, pulmonary bronchitis, bronchiectasis, pulmonary edema, and emphysema.

Skin diseases associated with oxidative stress include, but are not limited to, dermatitis, scleroderma, and psoriasis.

Viral infections associated with oxidative stress include both viral replication of viruses, as well as tissue damage (e.g., fibrosis) due to oxidative stress resulting from chronic viral infection, for viruses including but are not limited to human immunodeficiency virus, hepatitis B, hepatitis C, and herpesvirus.

Diabetic conditions include, but are not limited to, type 1 diabetes mellitus, type 2 diabetes mellitus, gestational diabetes, pre-diabetes, hyperglycemia, and metabolic syndrome as well as secondary conditions resulting from diabetic conditions (e.g., congestive heart failure and nephropathy).

Mitochondrial disease associated with oxidative stress include, but are not limited to, mitochondrial myopathies, Leber's hereditary optic neuropathy (LHON), myoclonic epilepsy with ragged red fibers (MERFF), mitochondrial encephalomyopathy, lactic acidosis and stroke-like episodes (MELAS) or Leigh's Syndrome.

Hematological disorders associated with oxidative stress include, but are not limited to, Diamond Blackfan anemia, myelodysplastic syndrome, sickle cell disease and beta-thales semia.

Muscle diseases associated with oxidative stress include, but are not limited to, Duchenne muscular dystrophy, limb girdle muscular dystrophy, Becker muscular dystrophy, myotonic dystrophy and rhabdomyolysis.

Cancers associated with oxidative stress include, but are not limited to, breast cancer, colorectal cancer, lung cancer, ovarian cancer, uterine cancer, prostate cancer, leukemias, lymphomas, brain cancer (including glioblastoma multiforme and neuroblastoma), head and neck cancer, pancreatic cancer, melanoma, hepatocellular carcinoma, renal cancer, and soft tissue sarcomas. In one embodiment, the cancer is breast cancer, colon cancer, and ovarian cancer. In one embodiment, the cancer is selected from leukemia, acute myeloid leukemia, chronic myelogenous leukemia, breast cancer, brain cancer, colon cancer, colorectal cancer, head and neck cancer, hepatocellular carcinoma, lung adenocarcinoma, metastatic melanoma, pancreatic cancer, prostate cancer, ovarian cancer and renal cancer. In one embodiment, the cancer is lung cancer, colon cancer, brain cancer, neuroblastoma, prostate cancer, melanoma, glioblastoma multiforme or ovarian cancer. In another embodiment, the cancer is lung cancer, breast cancer, colon cancer, brain cancer, neuroblastoma, prostate cancer, melanoma, glioblastoma multiforme or ovarian cancer. In yet another embodiment, the cancer is breast cancer, colon cancer and lung cancer. In another embodiment, the cancer is a breast cancer. In yet another embodiment, the cancer is a basal sub-type breast cancer or a luminal B sub-type breast cancer. In yet another embodiment, the cancer is a basal sub-type breast cancer. In yet another embodiment, the basal sub-type breast cancer is ER (estrogen receptor), HER2 and PR (progesterone receptor) negative breast cancer. In yet another embodiment, the cancer is a soft tissue cancer. A "soft tissue cancer" is an art-recognized term that encompasses tumors derived from any soft tissue of the body. Such soft tissue connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. Thus, soft tissue cancers can be of fat tissue, muscle tissue, nerve tissue, joint tissue, blood vessels, lymph vessels, and fibrous tissues. Soft tissue cancers can be benign or malignant. Generally, malignant soft tissue cancers are referred to as sarcomas, or soft tissue sarcomas. There are many types of soft tissue tumors, including lipoma, lipoblastoma, hibernoma, liposarcoma, leiomyoma, leiomyosarcoma, rhabdomyoma, rhabdomyosarcoma, neurofibroma, schwannoma (neurilemoma), neuroma, malignant schwannoma, neurofibrosarcoma, neurogenic sarcoma, nodular tenosynovitis, synovial sarcoma, hemangioma, glomus tumor, hemangiopericytoma, hemangioendothelioma, angiosarcoma, Kaposi sarcoma, lymphangioma, fibroma, elastofibroma, superficial fibromatosis, fibrous histiocytoma, fibrosarcoma, fibromatosis, dermatofibrosarcoma protuberans (DFSP), malignant fibrous histiocytoma (MFH), myxoma, granular cell tumor, malignant mesenchymomas, alveolar soft-part sarcoma, epithelioid sarcoma, clear cell sarcoma, and desmoplastic small cell tumor. In a particular embodiment, the soft tissue cancer is a sarcoma selected from the group consisting of a fibrosarcoma, a gastrointestinal sarcoma, a leiomyosarcoma, a dedifferentiated liposarcoma, a pleomorphic liposarcoma, a malignant fibrous histiocytoma, a round cell sarcoma, and a synovial sarcoma.

Thus the present invention provides a method of treatment comprising administering to a subject a compound of Formula (I) or a pharmaceutically acceptable salt thereof so as to treat at least one of the diseases or conditions listed above.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

Methods of Administration and Dosage Forms

The precise amount of compound administered to provide an "effective amount" to the subject will depend on the mode of administration, the type, and severity of the disease or condition, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the invention being used by following, for example, dosages reported in the literature and recommended in the Physician's Desk Reference (57th Ed., 2003).

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, The Pharmacological Basis of Therapeutics, current ed.; Pergamon; and Remington's, Pharmaceutical Sciences (current edition), Mack Publishing Co., Easton, Pa.

In addition, the disclosed HMOX1 inducers can be co-administered with other therapeutic agents. As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The particular mode of administration and the dosage regimen will be selected by the attending clinician, taking into account the particulars of the case (e.g. the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a disease using the disclosed HMOX1 inducers for guidance.

The compounds or the corresponding pharmaceutical compositions taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The pharmaceutical composition of the invention is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

Exemplification

The abbreviations used in the entire specification may be summarized herein below with their particular meaning:
ACN—Acetonitrile;
AcOH—Acetic acid;
$Ac_2O$—Acetic anhydride;
$AlCl_3$—Aluminum chloride;
anh.—Anhydrous;
Aq.—Aqueous;
BOC—tert-Butyloxycarbonyl;
bs—Broad singlet;
Conc.—Concentrated;
° C.—degree Celsius;
CDI—Carbonyldiimidazole;
$CH_3MgBr$—Methylmagnesium bromide;
$CS_2$—Carbon disulfide;
d—Doublet;
δ—Delta;
DCM—Dichloromethane;
DIPEA—N,N-Diisopropylethylamine
DMFA—N, N-Dimethylformamide;
DMSO—Dimethylsulfoxide;
DMSO—$d_6$—Deuterated dimethylsulfoxide;
$D_2O$—Deuterated water;
DPPA—Diphenylphosphoryl azide;
EDC.HCl—1-(3-Dimethylaminopropyl)-3-ethylcarbodiimide hydrochloride;
EtOH—ethanol;
EtOAc—Ethyl acetate;
g—Gram;
h—Hour;
$^1$H—Proton;
$H_2$—Hydrogen;
HATU—N-[(Dimethylamino)-1H-1,2,3-triazolo-[4,5-b]pyridin-1-ylmethylene]-N-methylmethanaminium hexafluorophosphate N-oxide;
HBTU—N,N,N',N'-Tetramethyl-O-(1H-benzotriazol-1-yl)uronium hexafluorophosphate;
$^1$HNMR—Proton nuclear magnetic resonance;
$HNO_3$—Nitric acid;
$H_2O$—Water;
HCl—Hydrochloric acid;
Hz—Hertz;
$H_2SO_4$—Sulfuric acid;
J—Coupling constant;
$K_2CO_3$—Potassium carbonate;
KOH—Potassium hydroxide;
$K_3PO_4$—Potassium phosphate;
LC—Liquid chromatography;
LiOH. $H_2O$—Lithium hydroxide monohydrate;
$M^+$—Molecular ion;
m—Multiplet;
M—Molar;
m-CPBA—meta-Chloroperbenzoic acid;
MeI—Methyl iodide;
MeOH—Methanol;
mg—Milligrams;
min—Minutes;
MHz—Mega Hertz (frequency);
mL—Milliters;
mM—Millimolar;
mmol—Millimoles;
MS—Mass spectroscopy;
m/z—Mass to charge ratio;
N—Normality;
$NaBH_4$—Sodium borohydride;
NaH—Sodium hydride;
$NaHCO_3$—sodium hydrogencarbonate;
$NaNO_2$—Sodium nitrite;
$NaNO_3$—Sodium nitrate;
NaOEt—Sodium ethoxide;
NaOH—Sodium hydroxide;
NaOMe—Sodium methoxide;
NBS—N-Bromosuccinimide
Pd/C—Palladium on Carbon;
$Pd(OAc)_2$—Palladium (II) acetate;
$POCl_3$—Phosphorus Oxychloride;
$P_2S_5$—Phosphorus pentasulfide;
$PtO_2$—Platinum dioxide:
%—Percentage;
pH—potential of Hydrogen;
psi—Pounds per square inch;
q—Quartet;
RT—Room temperature;
s—Singlet;
$SOCl_2$—Thionyl chloride;
t—Triplet;
TBAF—Tetra-n-butylammonium fluoride;
TBDMSC1—tert-Butyldimethylchlorosilane;
TEA—Triethyl amine;
TFA—Trifluoroacetic acid;
THF—Tetrahydrofuran;
TLC—Thin layer chromatography.

Examples 1h and 1i. Synthesis of 2-(benzo[d]ox-azol-2-ylamino)-1-methyl-1H-benzo[d]imidazole-5-carboxylic acid and Synthesis of 2-(benzo[d]ox-azol-2-ylamino)-N-(2-methoxyethyl)-1-methyl-1H-benzo[d]imidazole-5-carboxamide

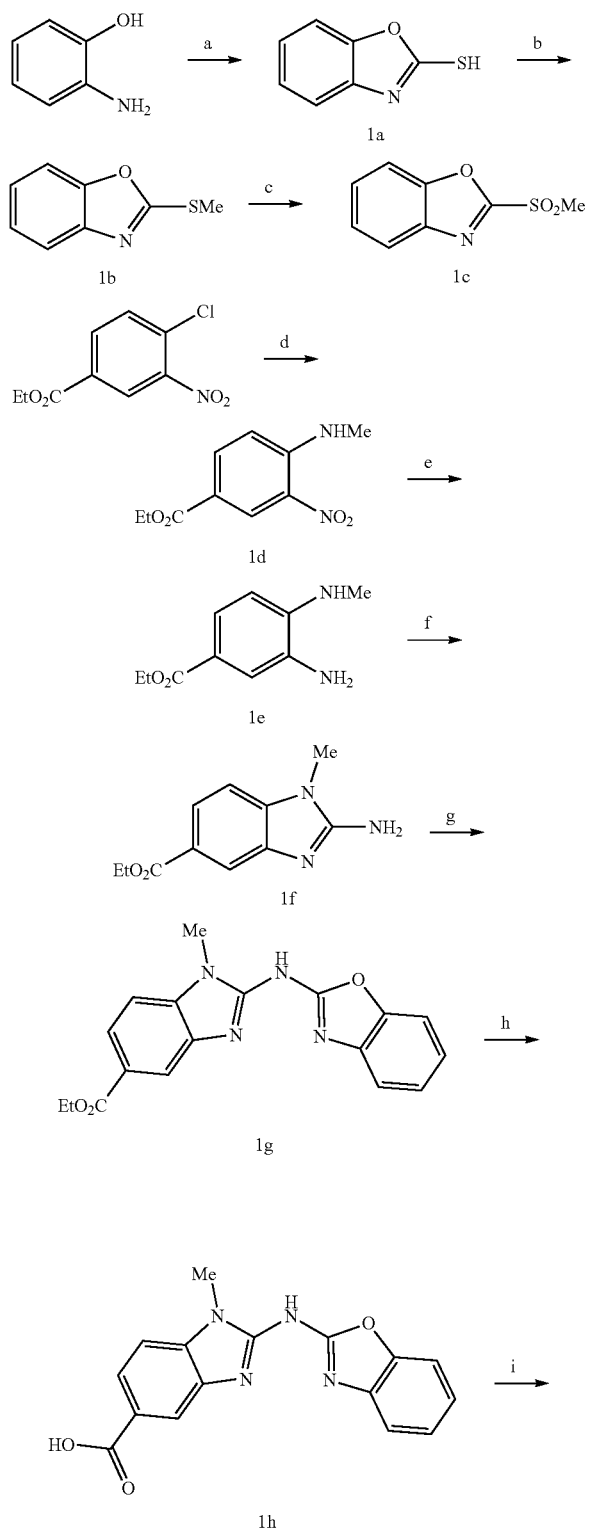

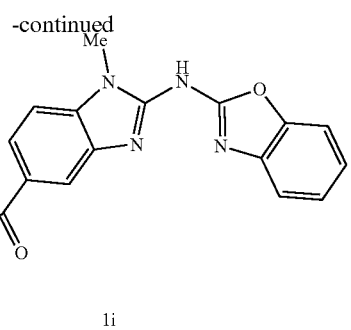

Conditions: a) Carbon disulfide, KOH, Ethanol, Reflux, 16 h; b) K₂CO₃, Methyl iodide, Acetonitrile, 0° C. - RT, 5 h; c) m-CPBA, DCM, 0° C. - RT, 4 h; d) Methyl amine, DMF, 60° C., 16 h; e) 10% Pd/C, MeOH, H₂, RT, 5 H; f) Cyanogen bromide, THF, H₂O, 50° C., 16 h; g) NaH, 2-(methylsulfonyl)benzo[d]oxazole 1,4-Dioxane, RT, 16 h; h) LiOH•H₂O, THF, Ethanol, Water, 60° C., 16 h; i) 2-methoxyethylamine, DPPA, DIPEA, DMF, 0° C.-RT, 16 h Step-a: Synthesis of benzo[d]oxazole-2-thiol (1a)

To a solution of 2-aminophenol (4.0 g, 36.7 mmol) in ethanol (80 mL) at RT was added powdered potassium hydroxide (3.59 g, 64.2 mmol) and carbon disulfide (20 mL, 330.3 mmol) and the reaction mixture was refluxed for 16 h. The reaction mixture was concentrated, diluted with water (100 mL) and acidified with 1 N HCl. The solid obtained was filtered and dried under vacuum to afford the title compound (4.0 g, 72%); $^1$H NMR (400 MHz, DMSO-$d_6$): δ 13.85 (bs, 1H), 7.51-7.49 (m, 1H), 7.32-7.23 (m, 3H); LC-MS: m/z 152.0 (M+1)$^+$.

Step-b: Synthesis of 2-(methylthio)benzo[d]oxazole (1b)

To a solution of benzo[d]oxazole-2-thiol (3.0 g, 19.9 mmol) in acetonitrile (50 mL) at 0° C. was added potassium carbonate (3.01 g, 21.9 mmol) and methyl iodide (1.36 mL, 21.9 mmol) and the reaction mixture was stirred at RT for 5 h. The reaction mixture was diluted with water (60 mL), extracted with EtOAc (2×100 mL). The combined organic layer was washed with water (50 mL), brine (50 mL), dried over anhydrous sodium sulfate and concentrated under vacuum to afford the product which was used in the next step without any further purification (2.5 g, 76%); $^1$H NMR (400 MHz, DMSO-$d_6$): δ 7.65-7.62 (m, 2H), 7.34-7.30 (m, 2H), 2.76 (s, 3H); LC-MS: m/z 166.0 (M+1)$^+$.

Step-c: Synthesis of 2-(methylsulfonyl)benzo[d]oxazole (1c)

To a solution of 2-(methylthio)benzo[d]oxazole (500 mg, 3.0 mmol) in DCM (20 mL) at 0° C. was added meta-chloroperbenzoic acid (938 mg, 9.1 mmol) and the reaction mixture was stirred at RT for 4 h. The reaction mixture was diluted with water (40 mL) and aqueous layer was extracted with DCM (2×100 mL). The combined organic layer was washed with saturated sodium bicarbonate solution (6×150 mL), water (50 mL), brine (50 mL), dried over anhydrous sodium sulfate and concentrated under vacuum to afford the product which was immediately used in the next step without any further purification (300 mg); LC-MS: m/z 198.0 (M+1)$^+$.

Step-d: Synthesis of ethyl 4-(methylamino)-3-nitrobenzoate (1d)

To a solution of ethyl 4-chloro-3-nitrobenzoate (30.0 g, 131 mmol) in DMFA (100 mL) at RT was added methyl amine (26.8 mL (40% aqueous solution), 262 mmol) and the reaction mixture was stirred at 60° C. for 16 h. The reaction mixture was cooled to RT, diluted with cold water (1000 mL) and stirred at RT for 1 h. The solid obtained was filtered and dried under vacuum to afford the product as a yellow solid (26.0 g, 89%); $^1$H NMR (400 MHz, DMSO-$d_6$): δ 8.62 (d, J=2.0 Hz, 1H), 8.59 (bs, 1H), 7.99 (dd, J=2.0 Hz, J=8.8 Hz, 1H), 7.07 (d, J=8.8 Hz, 1H), 4.29 (q, J=6.8 Hz, 2H), 3.01 (d, J=5.2 Hz, 3H), 1.31 (t, J=6.8 Hz, 3H); LC-MS: m/z 225.0 (M+1)$^+$.

Step-e: Synthesis of ethyl 3-amino-4-(methylamino)benzoate (1e)

To a solution of ethyl 4-(methylamino)-3-nitrobenzoate (13.0 g, 58 mmol) in methanol (180 mL) was added slurry of 10% Pd/C (1.3 g in 10 mL of ethanol) under nitrogen atmosphere. The flask was kept in a Parr shaker at RT under hydrogen pressure (60 psi) for 5 h. The reaction mixture was filtered through celite bed and concentrated under vacuum to afford the title compound (10.0 g, 88%); $^1$H NMR (400 MHz, DMSO-$d_6$): δ 7.23 (dd, J=1.6 Hz, J=8.4 Hz 1H), 7.16 (d, J=1.6 Hz, 1H), 6.39 (d, J=8.4 Hz, 1H), 5.38-5.37 (m, 1H), 4.66 (s, 2H), 4.18 (q, J=7.2 Hz, 2H), 2.77 (d, J=5.2 Hz, 3H), 1.26 (t, J=7.2 Hz, 3H); LC-MS: m/z 195.1 (M−1)$^+$.

Step-f: Synthesis of ethyl 2-amino-1-methyl-1H-benzo[d]imidazole-5-carboxylate (1f)

To a solution of ethyl 3-amino-4-(methylamino) benzoate (5.6 g, 28.8 mmol) in THF (23 mL) and water (56 mL) at RT was added cyanogen bromide (3.7 g, 34.6 mmol) and the reaction mixture was stirred at 50° C. for 16 h. The reaction mixture was cooled to RT, diluted with water (50 mL) and ethyl acetate (50 mL). The aqueous layer was basified with saturated sodium bicarbonate solution and extracted with EtOAc (2×250 mL). Combined organic layer was washed with water (100 mL), brine (100 mL), dried over anhydrous sodium sulfate and concentrated under vacuum to give the product which was used in the next step without further purification (5.2 g, 82%); $^1$H NMR (400 MHz, DMSO-$d_6$): δ 7.70 (d, J=1.2 Hz, 1H), 7.59 (dd, J=1.2 Hz, J=8.4 Hz, 1H), 7.20 (d, J=8.4 Hz, 1H), 6.64 (s, 2H), 4.27 (q, J=6.8 Hz, 2H), 3.53 (s, 3H), 1.32 (t, J=6.8 Hz, 3H).

Step-g: Synthesis of ethyl 2-(benzo[d]oxazol-2-ylamino)-1-methyl-1H-benzo[d]imidazole-5-carboxylate (1g)

To a solution of ethyl 2-amino-1-methyl-1H-benzo[d] imidazole-5-carboxylate (150 mg, 0.68 mmol) in 1,4-dioxane (4 mL) at RT was added sodium hydride (96 mg, 2.4 mmol) and the reaction mixture was stirred for 15 min followed by the addition of 2-(methylsulfonyl)benzo[d]oxazole (202 mg, 1.0 mmol). The reaction mixture was stirred at RT for 16 h and concentrated, diluted with water (20 mL) and acidified (pH~6) with 1 N HCl. The solid obtained was filtered, dried under vacuum and purified by combiflash column chromatography using 100% DCM as an eluent to afford the title compound (50 mg, 22%); $^1$H NMR (400 MHz, DMSO-$d_6$): δ 12.30 (bs, 1H), 8.24 (s, 1H), 7.88 (d, J=8.4 Hz, 1H), 7.53-7.43 (m, 3H), 7.22 (t, J=7.2 Hz, 1H), 7.13 (t, J=7.6 Hz, 1H), 4.33 (q, J=7.2 Hz, 2H), 3.64 (s, 3H), 1.35 (t, J=7.2 Hz, 3H); LC-MS: m/z 337.0 (M+1)$^+$.

Step-h: Synthesis of 2-(benzo[d]oxazol-2-ylamino)-1-methyl-1H-benzo[d]imidazole-5-carboxylic acid (1h)

To a stirred solution of ethyl 2-(benzo[d]oxazol-2-ylamino)-1-methyl-1H-benzo[d]imidazole-5-carboxylate (50 mg, 0.15 mmol) in a mixture of solvent of THF (1 mL), ethanol (1 mL) and water (0.5 mL), was added lithium hydroxide monohydrate (19 mg, 0.45 mmol). The reaction mixture was heated at 60° C. for 16 h. The reaction mixture was cooled to RT and concentrated under reduced pressure. The residue was dissolved in water, acidified with 1 N HCl to obtain the solid which was filtered and dried under vacuum to afford the title compound (35 mg, 76%); $^1$H NMR (400 MHz, DMSO-$d_6$): δ 12.60 (bs, 2H), 8.20 (d, J=1.6 Hz, 1H), 7.87 (dd, J=1.6 Hz, J=8.0 Hz, 1H), 7.51-7.48 (m, 2H), 7.44 (d, J=7.2 Hz, 1H), 7.23-7.20 (m, 1H), 7.15-7.11 (m, 1H), 3.64 (s, 3H); LC-MS: m/z 308.6 (M+1)$^+$.

Step-i: Synthesis of 2-(benzo[d]oxazol-2-ylamino)-N-(2-methoxyethyl)-1-methyl-1H-benzo[d]imidazole-5-carboxamide (1i)

To a stirred solution of 2-(benzo[d]oxazol-2-ylamino)-1-methyl-1H-benzo[d]imidazole-5-carboxylic acid (30 mg, 0.1 mmol) in DMFA (1.0 mL) at 0° C. was added N-ethyl-diisopropyl amine (0.02 mL, 0.1 mmol) and diphenylphosphoryl azide (0.02 mL, 0.1 mmol). The reaction mixture was stirred for 30 min, followed by the addition of 2-methoxyethylamine (8 mg, 0.1 mmol). The reaction mixture was then stirred at RT for 16 h. Once the reaction was completed (monitored by TLC), the reaction mixture was diluted with cold water (15 mL) and stirred for 15 min. The solid obtained was filtered, washed with diethyl ether and dried under vacuum to afford the title compound (22 mg, 53%) as white solid; $^1$H NMR (400 MHz, DMSO-$d_6$): δ 12.2 (bs, 1H), 8.45 (t, J=4.9 Hz, 1H), 8.08 (s, 1H), 7.76 (dd, J=1.5 Hz, J=8.3 Hz, 1H), 7.47 (d, J=8.3 Hz, 1H), 7.44-7.39 (m, 2H), 7.25-7.19 (m, 1H), 7.13-7.10 (m, 1H), 3.63 (s, 3H), 3.48-3.44 (m, 4H), 3.29 (s, 3H); LC-MS: m/z 364.0 (M−1).

Examples 2d and 2e. Synthesis of 1-(tetrahydro-2H-pyran-4-yl)-2-((6-(trifluoromethoxy)benzo[d]thiazol-2-yl)amino)-1H-benzo[d]imidazole-5-carboxylic acid and Synthesis of N-(2-methoxyethyl)-1-(tetrahydro-2H-pyran-4-yl)-2-((6-(trifluoromethoxy)benzo[d]thiazol-2-yl)amino)-1H-benzo[d]imidazole-5-carboxamide

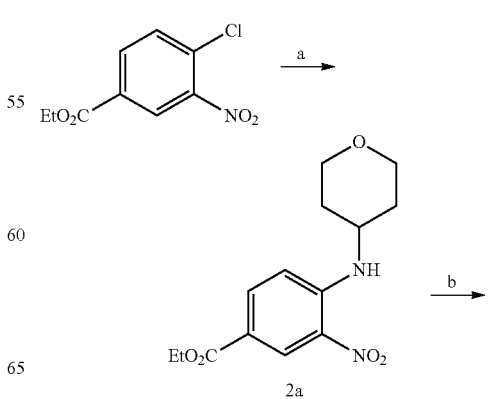

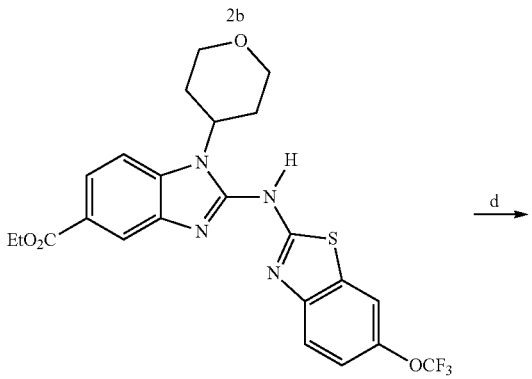

2b

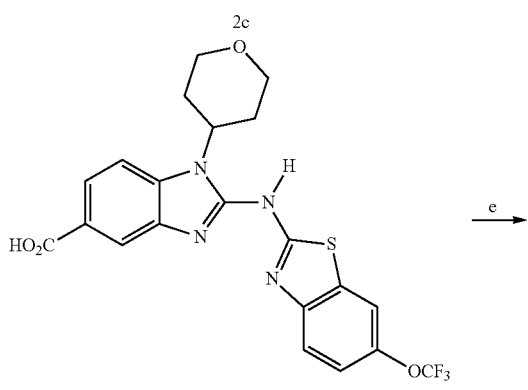

2c

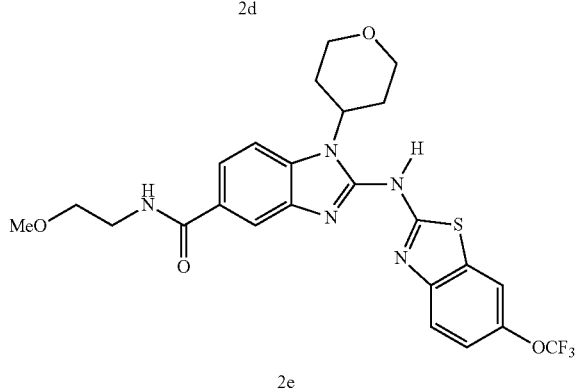

2d

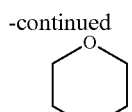

2e

Conditions: a) tetrahydro-2H-pyran-4-amine, K₂CO₃, DMSO, 70° C., 16 h; b) 10% Pd/C, MeOH, H₂, RT, 5 h; c) 2-Amino-(trifluoromethoxy)benzothiazole, 1,1′-Thiocarbonyldiimidazole, EDC·HCl, DMF, 100° C., 16 h; d) LiOH·H₂O, THF, MeOH, Water, 60° C., 16 h; e) 2-methoxyethylamine, DPPA, DIPEA, DMF, 0° C.-RT, 16 h Step-a: Synthesis of ethyl 3-nitro-4-((tetrahydro-2H-pyran-4-yl)amino)benzoate (2a)

To a stirred solution of ethyl 4-chloro-3-nitrobenzoate (1.0 g, 4.4 mmol) in DMSO (10 mL) was added potassium carbonate (1.2 g, 8.7 mmol) and tetrahydro-2H-pyran-4-amine (0.53 g, 5.2 mmol) at RT. Then the reaction mixture was heated to 70° C. and stirred for 16 h and then cooled to RT. The reaction mixture was diluted with cold water and the solid obtained was filtered and dried under vacuum to afford the title compound (1.1 g, 86%); $^1$H NMR (400 MHz, DMSO-d$_6$): δ 8.62 (d, J=2.0 Hz, 1H), 8.23 (d, J=7.8 Hz, 1H), 7.97 (dd, J=1.9 Hz, J=8.8 Hz, 1H), 7.29 (d, J=9.3 Hz, 1H), 4.29 (q, J=7.3 Hz, 2H), 3.96-3.94 (m, 1H), 3.90-3.83 (m, 2H), 3.51-3.45 (m, 2H), 1.96-1.93 (m, 2H), 1.66-1.61 (m, 2H), 1.31 (t, J=7.3 Hz, 3H); LC-MS: m/z 294.8 (M+1)$^+$.

Step-b: Synthesis of ethyl 3-amino-4-((tetrahydro-2H-pyran-4-yl)amino)benzoate (2b)

The title compound was synthesized using the same procedure which was followed for intermediate 1e using ethyl 3-nitro-4-((tetrahydro-2H-pyran-4-yl)amino)benzoate as starting material (Yield:100%); $^1$H NMR (400 MHz, DMSO-d$_6$): δ 7.19 (d, J=8.0 Hz, 1H), 7.17 (s, 1H), 6.52 (d, J=8.3 Hz, 1H), 4.99 (d, J=7.3 Hz, 1H), 4.97 (s, 2H), 4.18 (q, J=7.3 Hz, 2H), 3.89-3.87 (m, 2H), 3.57-3.53 (m, 1H), 3.45-3.40 (m, 2H), 1.92-1.89 (m, 2H), 1.48-1.38 (m, 2H), 1.25 (t, J=7.4 Hz, 3H); LC-MS: m/z 264.8 (M+1)$^+$.

Step-c: Synthesis of ethyl 1-(tetrahydro-2H-pyran-4-yl)-2-((6-(trifluoromethoxy)benzo[d]thiazol-2-yl)amino)-1H-benzo[d]imidazole-5-carboxylate (2c)

To a stirred solution of 2-amino-6-(trifluoromethoxy)benzothiazole (177 mg, 0.76 mmol) in DMFA (55 mL) was added 1,1′-thiocarbonyldiimidazole (270 mg, 1.5 mmol) and the solution was heated at 100° C. for 4 h. The reaction mixture was cooled to RT. EDC.HCl (291 mg, 1.5 mmol) was added and the reaction mixture was heated at 60° C. for 10 min, followed by the addition of ethyl 3-amino-4-((tetrahydro-2H-pyran-4-yl)amino)benzoate (200 mg, 0.76 mmol). Then the reaction mixture was heated at 100° C. for 16 h. It was cooled to RT, diluted with water (50 mL) and extracted with EtOAc (2×50 mL). The combined organic layers were washed with water (30 mL), brine (30 mL), dried over anhydrous sodium sulfate and concentrated under vacuum. The residue was purified by combiflash column chromatography using 100% DCM as an eluent to afford the title compound (120 mg, 31%); LC-MS: m/z 505.0 (M−1).

Step-d: Synthesis of 1-(tetrahydro-2H-pyran-4-yl)-2-((6-(trifluoromethoxy)benzo[d]thiazol-2-yl)amino)-1H-benzo[d]imidazole-5-carboxylic acid (2d)

The title compound was synthesized using the same procedure which was followed for intermediate 1h, using ethyl 1-(tetrahydro-2H-pyran-4-yl)-2-((6-(trifluoromethoxy)benzo[d]thiazol-2-yl)amino)-1H-benzo[d]imidazole-5-carboxylate as starting material (Yield:53%); $^1$H NMR (400 MHz, DMSO-d$_6$): δ 12.91 (bs, 1H), 12.57 (bs, 1H), 8.24 (s, 1H), 8.02-7.64 (m, 4H), 7.37 (s, 1H), 4.96-4.94 (m, 1H), 4.20-4.05 (m, 2H), 3.59-3.52 (m, 2H), 2.60-2.44 (m, 2H), 1.79-1.76 (m, 2H); LC-MS: m/z 477.0 (M−1).

Step-e: Synthesis of N-(2-methoxyethyl)-1-(tetrahydro-2H-pyran-4-yl)-2-((6-(trifluoromethoxy)benzo[d]thiazol-2-yl)amino)-1H-benzo[d]imidazole-5-carboxamide (2e)

The title compound was synthesized using the procedure which was followed for intermediate 1i using 1-(tetrahydro-2H-pyran-4-yl)-2-((6-(trifluoromethoxy) benzo[d]thiazol-2-yl)amino)-1H-benzo[d]imidazole-5-carboxylic acid as starting material (Yield:18%); $^1$H NMR (400 MHz, DMSO-d$_6$): δ 8.25 (t, J=5.4 Hz, 1H), 7.90 (d, J=1.5 Hz, 1H), 7.71-7.64 (m, 2H), 7.33 (d, J=0.9 Hz, 1H), 7.16-7.13 (m, 1H), 6.87 (d, J=8.8 Hz, 1H), 5.23-5.17 (m, 1H), 4.11-4.10 (m, 2H), 3.65 (t, J=11.2 Hz, 2H), 3.35-3.32 (m, 4H), 3.28 (s, 3H), 2.66-2.60 (m, 2H), 1.92-1.90 (m, 2H); LC-MS: m/z 536.0 (M+1)$^+$.

Example 3d and 3e. Synthesis of 1-(1-methylpiperidin-4-yl)-2-((6-(trifluoromethoxy)benzo[d]thiazol-2-yl)amino)-1H-benzo[d]imidazole-5-carboxylic acid and Synthesis of N-(2-methoxyethyl)-1-(1-methylpiperidin-4-yl)-2-((6-(trifluoromethoxy)benzo[d]thiazol-2-yl)amino)-1H-benzo[d]imidazole-5-carboxamide

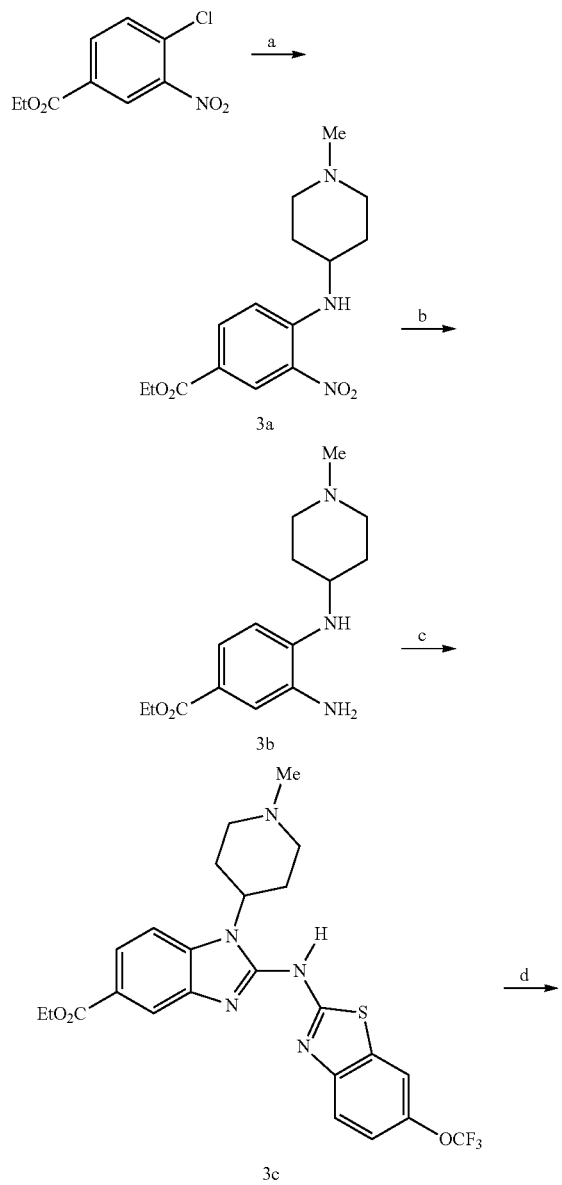

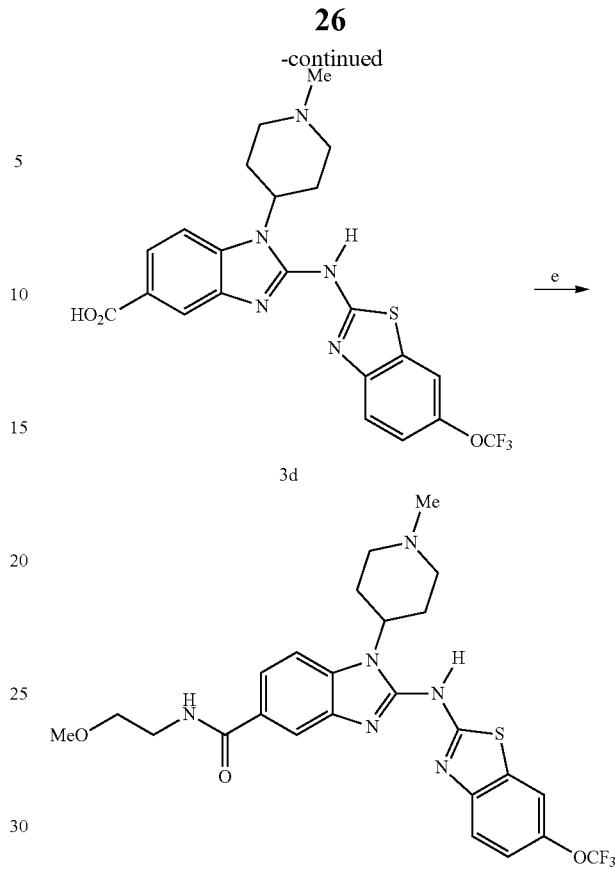

Conditions: a) 1-methylpiperidin-4-amine, DIPEA, DMF, 70° C., 16 h; b) 10% Pd/C, MeOH, H$_2$, RT, 2 h; c) 2-Amino-6-(trifluoromethoxy)benzothiazole, 1,1'-Thiocarbonyldiimidazole, EDC•HCl, DMF, 100° C., 16 h; d) LiOH•H$_2$O, THF, EtOH, Water, 60° C., 16 h; e) 2-methoxyethylamine, DPPA, DIPEA, DMF, 0° C.-RT, 16 h Step-a: Synthesis of ethyl 4-((1-methylpiperidin-4-yl)amino)-3-nitrobenzoate (3a)

To a stirred solution of ethyl 4-chloro-3-nitrobenzoate (500 mg, 2.2 mmol) in DMFA (5 mL) was added 1-methylpiperidin-4-amine (0.30 mL, 2.6 mmol) and N-ethyldiisopropyl amine (0.8 mL, 5.0 mmol). The reaction mixture was heated to 70° C. and continued stirring for 16 h at the same temperature. Reaction mixture was cooled to RT, diluted with water (50 mL) and extracted with EtOAc (2×100 mL). The combined organic layer was washed with water (50 mL), brine (30 mL), dried over anhydrous sodium sulfate and concentrated under vacuum to afford the title compound (620 mg, 92%); $^1$H NMR (400 MHz, DMSO-d$_6$): δ 8.62 (s, 1H), 8.25 (d, J=8.0 Hz, 1H), 7.97 (d, J=9.2 Hz, 1H), 7.23 (d, J=9.2 Hz, 1H), 4.30 (q, J=7.6 Hz, 2H), 3.71 (bs, 1H), 2.69-2.66 (m, 2H), 2.18 (s, 3H), 2.16-2.13 (m, 2H), 1.96-1.93 (m, 2H), 1.67-1.58 (m, 2H), 1.33 (t, J=7.6 Hz, 3H); LC-MS: m/z 307.7 (M+1)$^+$.

Step-b: Synthesis of ethyl 3-amino-4-((1-methylpiperidin-4-yl)amino)benzoate (3b)

The title compound was synthesized using the same procedure which was followed for intermediate 1e using ethyl 4-((1-methylpiperidin-4-yl)amino)-3-nitrobenzoate as the starting material and stirring for 2 h (Yield:100%); $^1$H NMR (400 MHz, DMSO-d$_6$): δ 7.19-7.16 (m, 2H), 6.47 (d, J=8.4 Hz, 1H), 4.96 (d, J=7.2 Hz, 1H), 4.78 (bs, 2H), 4.18 (q, J=7.2 Hz, 2H), 3.37-3.31 (m, 1H), 2.86-2.83 (m, 2H), 2.25 (s, 3H), 2.19-2.13 (m, 2H), 1.94-1.91 (m, 2H), 1.54-1.45 (m, 2H), 1.26 (t, J=6.8 Hz, 3H);
LC-MS: m/z 278.2 (M+1)$^+$.

Step-c: Synthesis of ethyl 1-(1-methylpiperidin-4-yl)-2-((6-(trifluoromethoxy)benzo[d]thiazol-2-yl)amino)-1H-benzo[d]imidazole-5-carboxylate (3c)

The title compound was synthesized using the same procedure which was followed for intermediate 2c using ethyl 3-amino-4-((1-methylpiperidin-4-yl)amino)benzoate as starting material (Yield:15%); $^1$H NMR (400 MHz, DMSO-d$_6$): δ 12.6 (bs, 1H), 8.14 (s, 1H), 7.91 (s, 1H), 7.79 (d, J=8.3 Hz, 1H), 7.62 (d, J=8.3 Hz, 1H), 7.55 (s, 1H), 7.35 (d, J=8.8 Hz, 1H), 4.74-4.68 (m 1H), 4.34 (q, J=6.8 Hz, 2H), 3.01-2.98 (m, 2H), 2.67-2.56 (m, 2H), 2.30 (s, 3H), 2.20-2.15 (m, 2H), 1.79-1.76 (m, 2H), 1.35 (t, J=6.9 Hz, 3H); LC-MS: m/z 520.1 (M+1)$^+$.

Step-d: Synthesis of 1-(1-methylpiperidin-4-yl)-2-((6-(trifluoromethoxy)benzo[d]thiazol-2-yl)amino)-1H-benzo[d]imidazole-5-carboxylic acid (3d)

The title compound was synthesized using the same procedure which was followed for intermediate 1h using ethyl 1-(1-methylpiperidin-4-yl)-2-((6-(trifluoromethoxy)benzo[d]thiazol-2-yl)amino)-1H-benzo[d]imidazole-5-carboxylate as starting material (Yield:56%); $^1$H NMR (400 MHz, DMSO-d$_6$): δ 12.40 (bs, 1H), 8.12 (s, 1H), 7.91 (s, 1H), 7.78 (d, J=8.3 Hz, 1H), 7.60 (d, J=8.3 Hz, 1H), 7.58 (bs, 1H), 7.34 (d, J=8.9 Hz, 1H), 4.79-4.68 (m 1H), 3.02-2.99 (m, 2H), 2.57-2.54 (m, 2H), 2.30 (s, 3H), 2.21-2.15 (m, 2H), 1.79-1.77 (m, 2H); LC-MS: m/z 491.6 (M+1)$^+$.

Step-e: Synthesis of N-(2-methoxyethyl)-1-(1-methylpiperidin-4-yl)-2-((6-(trifluoromethoxy)benzo[d]thiazol-2-yl)amino)-1H-benzo[d]imidazole-5-carboxamide (3e)

The title compound was synthesized using the same procedure which was followed for intermediate 1i using 1-(1-methylpiperidin-4-yl)-2-((6-(trifluoromethoxy)benzo[d]thiazol-2-yl)amino)-1H-benzo[d]imidazole-5-carboxylic acid as starting material (Yield:40%); $^1$H NMR (400 MHz, DMSO-d$_6$): δ 12.40 (bs, 1H), 8.44 (s, 1H), 8.09 (s, 1H), 7.91 (s, 1H), 7.70-7.58 (m, 3H), 7.35 (d, J=6.8 Hz, 1H), 4.75-4.65 (m, 1H), 3.50-3.43 (m, 4H), 3.28 (s, 3H), 3.02-2.99 (m, 2H), 2.60-2.54 (m, 2H), 2.31 (s, 3H), 2.20-2.15 (m, 2H), 1.79-1.76 (m, 2H); LC-MS: m/z 549.2 (M+1)$^+$.

Example 4d and 4e. Synthesis of 1-(1-methylpyrrolidin-3-yl)-2-((6-(trifluoromethoxy)benzo[d]thiazol-2-yl)amino)-1H-benzo[d]imidazole-5-carboxylic acid and Synthesis of N-(2-methoxyethyl)-1-(1-methylpyrrolidin-3-yl)-2-((6-(trifluoromethoxy)benzo[d]thiazol-2-yl)amino)-1H-benzo[d]imidazole-5-carboxamide

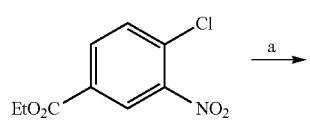

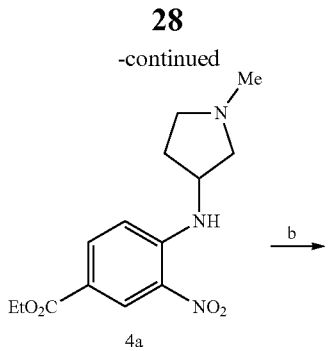

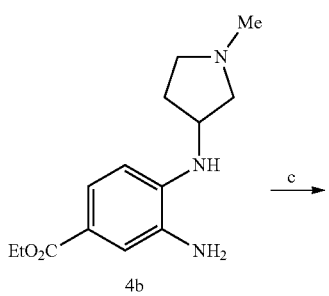

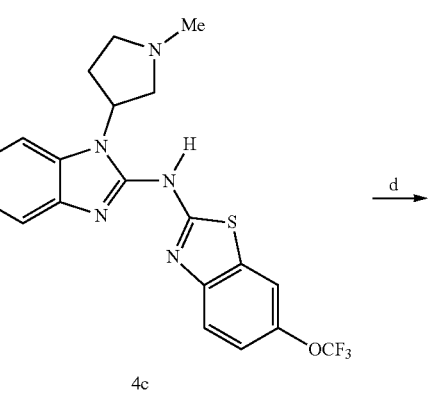

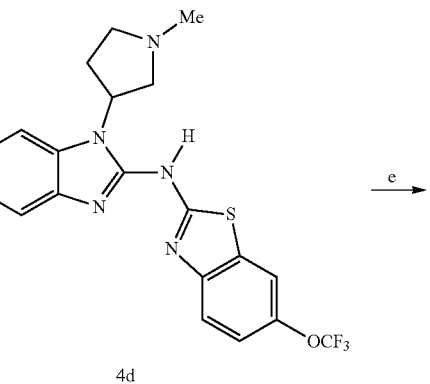

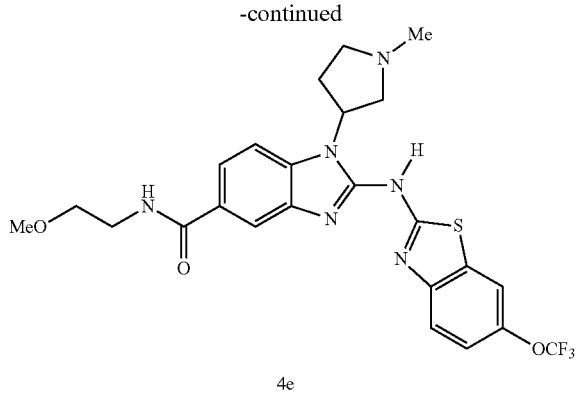

4e

Conditions: a) 1-methylpyrrolidin-3-amine, DIPEA, DMF, 70° C., 16 h; b) 10% Pd/C, MeOH, H$_2$, 2 h; c) 2-Amino-6-(trifluoromethoxy)benzothiazole, 1,1'-Thiocarbonyldiimidazole, EDC•HCl, DMF, 100° C., 16 h; d) LiOH•H$_2$O, THF, MeOH, Water, 60° C., 16 h; e) 2-methoxyethylamine, DPPA, DIPEA, DMF, 0° C.-RT, 16

Step-a: Synthesis of ethyl 4-((1-methylpyrrolidin-3-yl)amino)-3-nitrobenzoate (4a)

The title compound was synthesized using the same procedure which was followed for intermediate 3a using ethyl 4-chloro-3-nitrobenzoate and 1-methylpyrrolidin-3-amine as starting materials (Yield:79%); $^1$H NMR (400 MHz, DMSO-d$_6$): δ 8.62 (d, J=1.9 Hz, 1H), 8.39 (d, J=6.8 Hz, 1H), 7.98 (dd, J=2.0 Hz, J=8.8 Hz, 1H), 7.15 (d, J=9.3 Hz, 1H), 4.32-4.36 (m, 3H), 2.80-2.75 (m, 1H), 2.70-2.59 (m, 2H), 2.42-2.30 (m, 2H), 2.29 (s, 3H), 1.73-1.65 (m, 1H), 1.31 (t, J=7.4 Hz, 3H); LC-MS: m/z 294.1 (M+1)$^+$.

Step-b: Synthesis of ethyl 3-amino-4-((1-methylpyrrolidin-3-yl)amino)benzoate (4b)

The title compound was synthesized using the same procedure which was followed for intermediate 1e using ethyl 4-((1-methylpyrrolidin-3-yl)amino)-3-nitrobenzoate as starting material and stirring for 2h (Yield: 78%); $^1$H NMR (400 MHz, DMSO-d$_6$): δ 7.19-7.15 (m, 2H), 6.38 (d, J=8.3 Hz, 1H), 5.16 (d, J=6.9 Hz, 1H), 4.81 (s, 2H), 4.18 (q, J=7.3 Hz, 2H), 3.95 (bs, 1H), 2.74-2.70 (m, 1H), 2.44-2.34 (m, 2H), 2.28-2.22 (m, 1H), 2.25 (s, 3H), 1.67-1.63 (m, 1H), 1.25 (t, J=7.3 Hz, 3H); LC-MS: m/z 264.1 (M+1)$^+$.

Step-c: Synthesis of ethyl 1-(1-methylpyrrolidin-3-yl)-2-((6-(trifluoromethoxy)benzo[d]thiazol-2-yl)amino)-1H-benzo[d]imidazole-5-carboxylate (4c)

The title compound was synthesized using the same procedure which was followed for intermediate 2c using ethyl 3-amino-4-((1-methylpyrrolidin-3-yl)amino)benzoate as starting material. Product obtained was used in the next step without further purification; LC-MS: m/z 506.1 (M+1)$^+$.

Step-d: Synthesis of 1-(1-methylpyrrolidin-3-yl)-2-((6-(trifluoromethoxy)benzo[d]thiazol-2-yl)amino)-1H-benzo[d]imidazole-5-carboxylic acid (4d)

The title compound was synthesized using the same procedure which was followed for intermediate 1h using ethyl 1-(1-methylpyrrolidin-3-yl)-2-((6-(trifluoromethoxy)benzo[d]thiazol-2-yl)amino)-1H-benzo[d]imidazole-5-carboxylate as starting material, using THF, MeOH and water (2:2:1) as solvent (Yield:13%); $^1$H NMR (400 MHz, DMSO-d$_6$+D$_2$O): δ 8.03 (s, 1H), 7.83 (s, 1H), 7.78 (d, J=8.3 Hz, 1H), 7.59-7.54 (m, 2H), 7.32 (d, J=8.8 Hz, 1H), 5.50 (bs, 1H), 3.86-3.75 (m, 2H), 3.35 (bs, 1H), 3.07-3.05 (m, 1H), 2.91 (s, 3H), 2.28-2.0 (m, 2H); LC-MS: m/z 478.1 (M+1)$^+$.

Step-e: Synthesis of N-(2-methoxyethyl)-1-(1-methylpyrrolidin-3-yl)-2-((6-(trifluoromethoxy)benzo[d]thiazol-2-yl)amino)-1H-benzo[d]imidazole-5-carboxamide (4e)

The title compound was synthesized using the same procedure which was followed for intermediate 1i using 1-(1-methylpyrrolidin-3-yl)-2-((6-(trifluoromethoxy)benzo[d]thiazol-2-yl)amino)-1H-benzo[d]imidazole-5-carboxylic acid as starting material (Yield: 30%); $^1$H NMR (400 MHz, DMSO-d$_6$): δ 8.10 (bs, 1H), 8.04 (s, 1H), 7.85 (s, 1H), 7.76 (bs, 1H), 7.68 (d, J=8.3 Hz, 1H), 7.62 (bs, 1H), 7.30 (d, J=8.8 Hz, 1H), 5.50 (bs, 1H), 3.52-3.44 (m, 4H), 3.30 (s, 3H), 2.76-2.65 (m, 2H), 2.50 (s, 3H, merged with DMSO peak), 2.31-2.30 (m, 2H), 2.15-2.13 (m, 2H); LC-MS: m/z 535.0 (M+1)$^+$.

Example 5. Synthesis of N-(2-methoxyethyl)-1-methyl-2-((4,5,6,7-tetrahydrobenzo[d]thiazol-2-yl)amino)-1H-benzo[d]imidazole-5-carboxamide

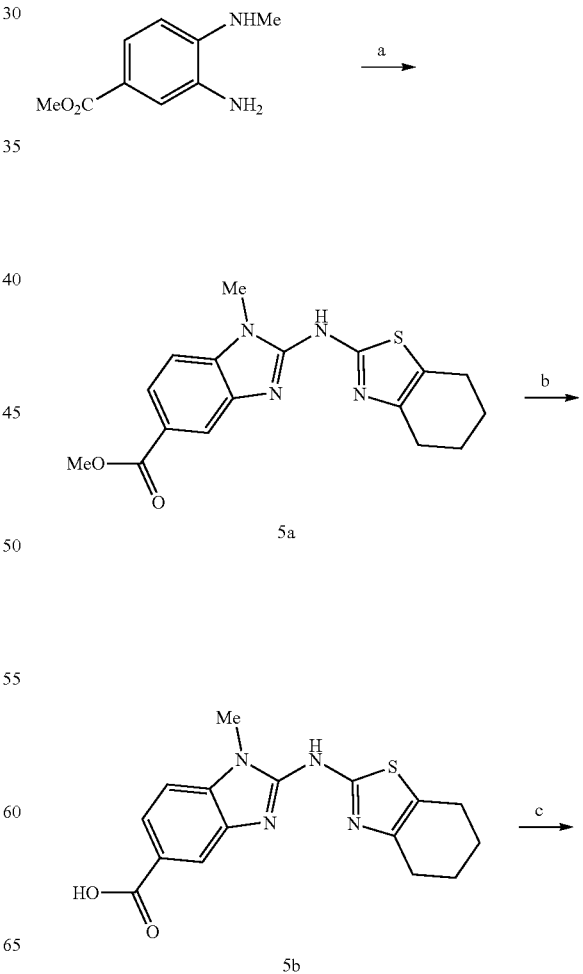

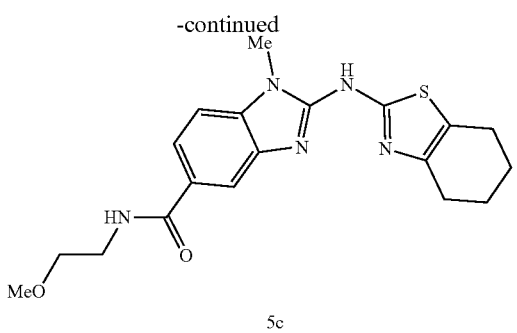

5c

Conditions: a) 4,5,6,7-tetrahydrobenzo[d]thiazol-2-amine, 1,1'-Thiocarbonyldiimidazole, EDC·HCl, DMF, 100° C., 16 h; b) LiOH·H₂O, THF, MeOH, Water, 60° C., 16 h; c) 2-methoxyethylamine, DPPA, DIPEA, DMF, 0° C.-RT, 16 h

Step-a: Synthesis of methyl 1-methyl-2-((4,5,6,7-tetrahydrobenzo[d]thiazol-2-yl)amino)-1H-benzo[d]imidazole-5-carboxylate (5a)

To a stirred solution of 4,5,6,7-tetrahydrobenzo[d]thiazol-2-amine (216 mg, 1.4 mmol) in DMFA (5 mL) was added 1,1'-thiocarbonyldiimidazole (494 mg, 2.8 mmol) and the solution was heated at 100° C. for 2 h. The reaction mixture was cooled to RT. EDC.HCl (533 mg, 2.8 mmol) was added and the reaction mixture was heated at 60° C. for 10 min, followed by the addition of methyl 3-amino-4-(methylamino)benzoate (250 mg, 1.4 mmol). The reaction mixture was heated at 100° C. for 16 h. It was cooled to RT, diluted with water (50 mL) and extracted with EtOAc (2×50 mL). The combined organic layers were washed with water (30 mL), brine (30 mL), dried over anhydrous sodium sulfate and concentrated under vacuum. The residue was purified by combi flash column chromatography using 100% DCM as an eluent to afford the title compound (110 mg, 23%); ¹H NMR (400 MHz, DMSO-d₆): δ 12.01 (bs, 1H), 7.97 (s, 1H), 7.73 (dd, J=1.6 Hz, J=8.4 Hz, 1H), 7.37 (d, J=8.4 Hz, 1H), 3.84 (s, 3H), 3.61 (s, 3H), 2.50 (bs, 4H, merged with DMSO peak), 1.78 (bs, 4H); LC-MS: m/z 341.0 (M−1).

Step-b: Synthesis of 1-methyl-2-((4,5,6,7-tetrahydrobenzo[d]thiazol-2-yl)amino)-1H-benzo[d]imidazole-5-carboxylic acid (5b)

The title compound was synthesized using the same procedure which was followed for intermediate 1h using methyl 1-methyl-2-((4,5,6,7-tetrahydrobenzo[d]thiazol-2-yl)amino)-1H-benzo[d]imidazole-5-carboxylate as starting material, using THF, MeOH and water (2:2:1) as solvent (Yield: 83%); ¹H NMR (400 MHz, DMSO-d₆): δ 12.20 (bs, 2H), 7.95 (s, 1H), 7.73 (dd, J=0.8 Hz, J=8.4 Hz, 1H), 7.34 (d, J=8.4 Hz, 1H), 3.61 (s, 3H), 2.50 (bs, 4H, merged with DMSO peak), 1.78 (bs, 4H); LC-MS: m/z 327.0 (M−1).

Step-c: Synthesis of N-(2-methoxyethyl)-1-methyl-2-((4,5,6,7-tetrahydrobenzo[d]thiazol-2-yl)amino)-1H-benzo[d]imidazole-5-carboxamide (5c)

The title compound was synthesized using the same procedure which was followed for compound 1i using 1-methyl-2-((4,5,6,7-tetrahydrobenzo[d]thiazol-2-yl)amino)-1H-benzo[d]imidazole-5-carboxylic acid as starting material (Yield: 30%); ¹H NMR (400 MHz, DMSO-d₆): δ 12.0 (bs, 1H), 8.34 (bs, 1H), 7.95 (s, 1H), 7.64 (d, J=8.4 Hz, 1H), 7.32 (d, J=8.4 Hz, 1H), 3.60 (s, 3H), 3.48-3.42 (m, 4H), 3.28 (s, 3H), 2.50 (bs, 4H, merged with DMSO peak), 1.78 (bs, 4H); LC-MS: m/z 384.0 (M−1).

Example 6. Synthesis of 2-((6,6-dimethyl-4,5,6,7-tetrahydrobenzo[d]thiazol-2-yl)amino)-N-(2-(2-hydroxyethoxy)ethyl)-1-methyl-1H-benzo[d]imidazole-5-carboxamide

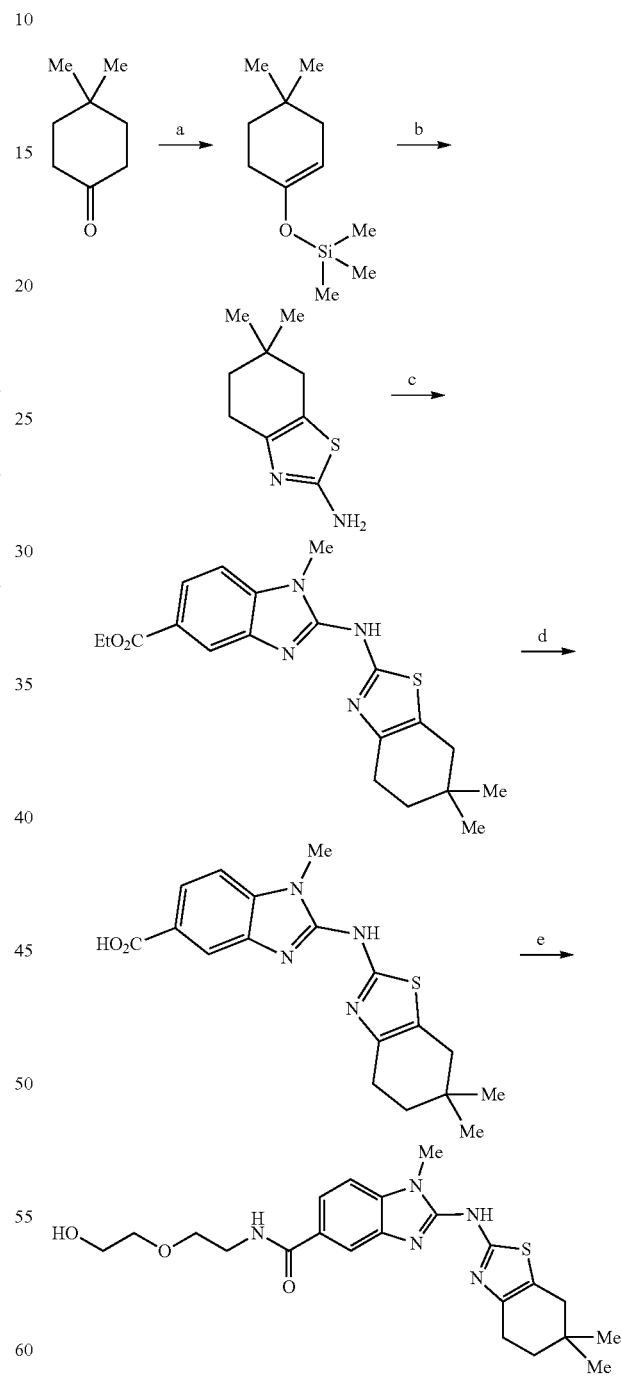

Conditions: a) Trimethylsilyl trifluoromethanesulfonate, TEA, DCM, 0° C., 1.5 h; b) NBS, Sodium acetate, THF, water, RT, 2 h; Thiourea, 80° C., 6 h; RT, 16 h; c) ethyl 3-amino-4-(methylamino)benzoate, 1,1'-Thiocarbonyldiimidazole, EDC·HCl, DMF, 100° C., 18 h; d) LiOH·H₂O, THF, EtOH, water, 80° C., 16 h; e) 2-(2-Aminoethoxy)ethan-1-ol, HBTU, DIPEA, DMF, 0° C.-RT, 16 h

Step-a: Synthesis of ((4,4-dimethylcyclohex-1-en-1-yl)oxy)trimethylsilane

To a solution of 4,4-dimethylcyclohexan-1-one (3.0 g, 23.8 mmol) in DCM (180 mL) at 0° C. was added triethylamine (9.95 mL, 71.42 mmol). The reaction mixture was stirred for 5 min followed by the addition of trimethylsilyl trifluoromethanesulfonate (6.5 g, 29.28 mmol in 54 mL of DCM). The reaction mixture was stirred at 0° C. for 1.5 h and then quenched with saturated sodium bicarbonate solution (30 mL) and water (100 mL). The organic layer was separated and washed with water (2×50 mL), brine solution (50 mL), dried over anhydrous sodium sulfate and concentrated under vacuum to afford the titled compound (3.8 g, 81%) which was used in the next step without further purification; $^1$H NMR (400 MHz, CDCl$_3$): δ 4.74 (t, J=4.0 Hz, 1H), 1.99-1.97 (m, 2H), 1.80 (d, J=2.0 Hz, 2H), 1.39 (t, J=6.8 Hz, 2H), 1.16 (s, 6H), 0.15 (s, 9H).

Step-b: Synthesis of 6,6-dimethyl-4,5,6,7-tetrahydrobenzo[d]thiazol-2-amine

To a solution of ((4,4-dimethylcyclohex-1-en-1-yl)oxy)trimethylsilane (3.8 g, 19.16 mmol) in THF (40 mL) and water (40 mL) at RT was added N-bromosuccinimide (4.09 g, 23.0 mmol) and sodium acetate (0.22 g, 2.7 mmol). The reaction mixture was then stirred for 2 h. Thiourea (1.43 g, 18.8 mmol) was added and the reaction mixture was heated at 80° C. for 6 h with stirring. Then it was cooled to RT and continued stirring for 16 h. The reaction mixture was quenched with water (30 mL) and extracted with DCM (2×50 mL). The aqueous layer was basified (pH_9) with 2 M sodium hydroxide and stirred for 2 h at RT. The solid precipitated was filtered and dried under vacuum to afford the titled compound (1.3 g, 37%) which was used in the next step without further purification; $^1$H NMR (400 MHz, DMSO-d$_6$): δ 6.55 (bs, 2H), 2.35 (t, J=6.4 Hz, 2H), 2.26 (s, 2H), 1.46 (t, J=6.0 Hz, 2H), 0.95 (s, 6H); LC-MS: m/z 183.1 (M+1)$^+$.

Step-c: Synthesis of ethyl 2-((6,6-dimethyl-4,5,6,7-tetrahydrobenzo[d]thiazol-2-yl)amino)-1-methyl-1H-benzo[d]imidazole-5-carboxylate To a stirred solution of 6,6-dimethyl-4,5,6,7-tetrahydrobenzo[d]thiazol-2-amine (809 mg, 4.44 mmol) in DMFA (10 mL) was added 1,1'-thiocarbonyldiimidazole (1.58 g, 8.88 mmol) and the solution was heated at 100° C. for 2 h. The reaction mixture was cooled to RT and EDC.HCl (1.70 g, 8.88 mmol) was added. The reaction mixture was heated at 50° C. for 10 min, followed by the addition of ethyl 3-amino-4-(methylamino) benzoate (800 mg, 4.44 mmol). It was then heated at 100° C. for 16 h and cooled to RT. The reaction mixture was diluted with water (50 mL) and extracted with EtOAc (2×100 mL). The combined organic layers were washed with water (30 mL), brine (30 mL), dried over anhydrous sodium sulfate and concentrated under vacuum. The residue was purified by combi flash column chromatography using 100% DCM as an eluent to afford the titled compound (500 mg, 32%); $^1$H NMR (400 MHz, DMSO-d$_6$): δ 12.10 (bs, 1H), 7.98 (s, 1H), 7.74 (d, J=8.4 Hz, 1H), 7.37 (d, J=8.4 Hz, 1H), 4.30 (q, J=7.2 Hz, 2H), 3.61 (s, 3H), 2.50 (2H merged with DMSO peak), 2.33 (s, 2H), 1.56 (t, J=6.0 Hz, 2H), 1.33 (t, J=7.2 Hz, 3H), 1.00 (s, 6H); LC-MS: m/z 385.1 (M+1)$^+$.

Step-d: Synthesis of 2-((6,6-dimethyl-4,5,6,7-tetrahydrobenzo[d]thiazol-2-yl)amino)-1-methyl-1H-benzo[d]imidazole-5-carboxylic acid To a stirred solution of ethyl 2-((6,6-dimethyl-4,5,6,7-tetrahydrobenzo[d]thiazol-2-yl)amino)-1-methyl-1H-benzo[d]imidazole-5-carboxylate (500 mg, 1.30 mmol) in a mixture of THF (4 mL), ethanol (4 mL) and water (2 mL) was added lithium hydroxide monohydrate (136 mg, 3.25 mmol). The reaction mixture was heated at 80° C. for 16 h and then cooled to RT and concentrated under reduced pressure. The residue was dissolved in water, acidified with 1 N HCl to obtain the solid which was filtered and dried under vacuum to afford the titled compound (300 mg, 65%); $^1$H NMR (400 MHz, DMSO-d$_6$): δ 8.00 (s, 1H), 7.86 (d, J=8.4 Hz, 1H), 7.54 (d, J=8.4 Hz, 1H), 3.64 (s, 3H), 2.50 (2H merged with DMSO peak), 2.38 (s, 2H), 1.58 (t, J=6.0 Hz, 2H), 1.01 (s, 6H); LC-MS: m/z 357.1 (M+1)$^+$.

Step-e: Synthesis of 2-((6,6-dimethyl-4,5,6,7-tetrahydrobenzo[d]thiazol-2-yl)amino)-N-(2-(2-hydroxyethoxy)ethyl)-1-methyl-1H-benzo[d]imidazole-5-carboxamide To a stirred solution of 2-((6,6-dimethyl-4,5,6,7-tetrahydrobenzo[d]thiazol-2-yl)amino)-1-methyl-1H-benzo[d]imidazole-5-carboxylic acid (100 mg, 0.28 mmol) in DMFA (2 mL) at 0° C. was added N-ethyldiisopropyl amine (0.04 mL, 0.28 mmol) and HBTU (106 mg, 0.28 mmol). The reaction mixture was stirred for 30 min, followed by the addition of 2-(2-aminoethoxy)ethan-1-ol (0.02 mL, 0.28 mmol) and stirring was continued at RT for 16 h. Once the reaction was completed (monitored by TLC), the reaction mixture was diluted with cold water (20 mL) and stirred for 15 min. The solid obtained was filtered and dried under vacuum. The residue was purified by combi flash column chromatography using 2% MeOH in DCM as an eluent to afford the titled compound (50 mg, 40%); $^1$H NMR (400 MHz, DMSO-d$_6$): δ 12.0 (bs, 1H), 8.34 (s, 1H), 7.95 (s, 1H), 7.64 (d, J=8.4 Hz, 1H), 7.32 (d, J=8.4 Hz, 1H), 4.60 (bs, 1H), 3.60 (s, 3H), 3.56-3.42 (m, 8H), 2.50 (2H merged with DMSO peak), 2.32 (m, 2H), 1.55 (t, J=6.0 Hz, 2H), 1.00 (s, 6H); LC-MS: m/z 444.1 (M+1)$^+$.

Example 7. Synthesis of N-(2-(2-hydroxyethoxy)ethyl)-1-methyl-2-((6-methyl-4,5,6,7-tetrahydrobenzo[d]thiazol-2-yl)amino)-1H-benzo[d]imidazole-5-carboxamide

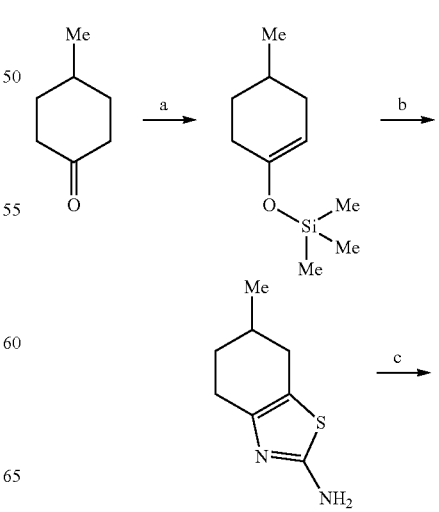

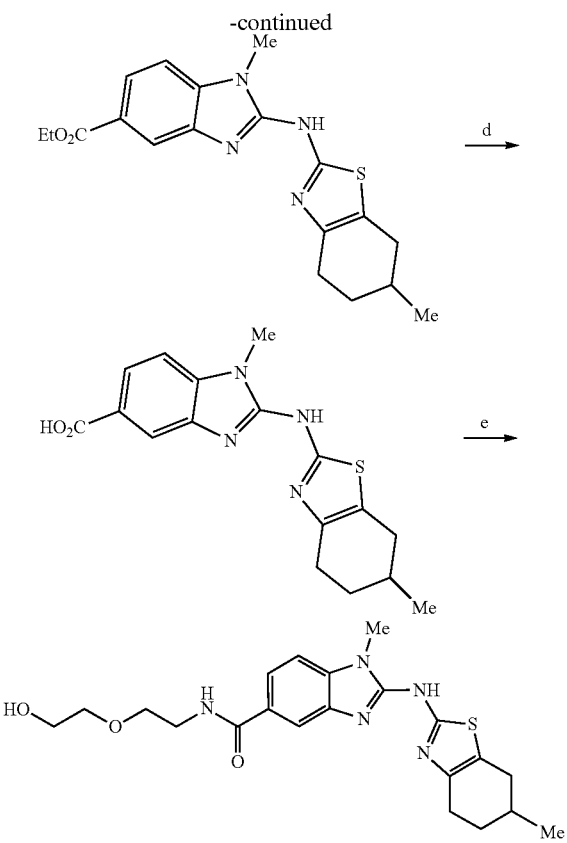

Conditions: a) Trimethylsilyl trifluoromethanesulfonate, TEA, DCM, 0° C., 1.5 h; b) NBS, Sodium acetate, EtOH, water, RT, 2 h; Thiourea, 80° C., 6 h; RT, 16 h; c) ethyl 3-amino-4-(methylamino)benzoate, 1,1'-Thiocarbonyldiimidazole, EDC·HCl, DMF, 100° C., 16 h; d) LiOH·H$_2$O, THF, EtOH, water, 60° C., 16 h; e) 2-(2-Aminoethoxy)ethan-1-ol, HBTU, DIPEA, DMF, 0° C.-RT, 16 h

Step-a: Synthesis of trimethyl((4-methylcyclohex-1-en-1-yl)oxy)silane

To a solution of 4-methylcyclohexan-1-one (2.0 g, 17.8 mmol) in DCM (50 mL) at 0° C. was added triethylamine (7.5 mL, 53.4 mmol) and stirred for 5 min followed by the addition of trimethylsilyl trifluoromethanesulfonate (4.95 g, 22.3 mmol in 30 mL of DCM). The reaction mixture was stirred at 0° C. for 1.5 h and then quenched with saturated sodium hydrogen carbonate solution (20 mL) and water (100 mL). The organic layer was separated and washed with water (2×100 mL), brine solution (50 mL), dried over anhydrous sodium sulfate and concentrated under vacuum to afford the titled compound (3.4 g, 100%); $^1$H NMR (400 MHz, DMSO-d$_6$): δ 4.74-4.71 (m, 1H), 2.66-2.49 (m, 1H), 2.16-1.99 (m, 2H), 1.89-1.88 (m, 1H), 1.62-1.57 (m, 2H), 1.25-1.22 (m, 1H), 0.89 (d, J=2.4 Hz, 3H), 0.27 (s, 9H).

Step-b: Synthesis of 6-methyl-4,5,6,7-tetrahydrobenzo[d]thiazol-2-amine

To a solution of trimethyl((4-methylcyclohex-1-en-1-yl)oxy)silane (3.3 g, 17.9 mmol) in THF (25 mL) and water (25 mL) at RT was added N-bromosuccinimide (3.83 g, 21.5 mmol) and sodium acetate (0.20 g, 2.5 mmol) and then stirred for 2 h. Thiourea (1.43 g, 18.8 mmol) was added and the reaction mixture was heated at 80° C. for 6 h with stirring. The reaction mixture was then cooled to RT and continued stirring for 16 h. The reaction mixture was quenched with water (30 mL) and extracted with DCM (2×100 mL). The aqueous layer was basified (pH_9) with 2 M sodium hydroxide and extracted with DCM (3×100 mL). The combined organic layers were washed with brine solution (50 mL), dried over anhydrous sodium sulfate and concentrated under vacuum to afford the titled compound (1.9 g, 63%); $^1$H NMR (400 MHz, DMSO-d$_6$): δ 6.55 (bs, 2H), 2.57-2.51 (m, 1H), 2.40-2.36 (m, 2H), 2.12-2.05 (m, 1H), 1.79-1.74 (m, 2H), 1.35-1.34 (m, 1H), 1.00 (d, J=6.4 Hz, 3H); LC-MS: m/z 169.2 (M+1)$^+$.

Step-c: Synthesis of ethyl 1-methyl-2-((6-methyl-4,5,6,7-tetrahydrobenzo[d]thiazol-2-yl)amino)-1H-benzo[d]imidazole-5-carboxylate To a stirred solution of 6-methyl-4,5,6,7-tetrahydrobenzo[d]thiazol-2-amine (400 mg, 2.38 mmol) in DMFA (10 mL) was added 1,1'-thiocarbonyldiimidazole (848 mg, 4.76 mmol) and the solution was heated at 100° C. for 2 h. The reaction mixture was cooled to RT and EDC.HCl (914 mg, 4.76 mmol) was added. The reaction mixture was heated at 50° C. for 10 min, followed by the addition of ethyl 3-amino-4-(methylamino)benzoate (462 mg, 2.38 mmol). The reaction mixture was heated at 100° C. for 16 h. It was cooled to RT, diluted with water (50 mL) and extracted with EtOAc (2×50 mL). The combined organic layers were washed with water (30 mL), brine (30 mL), dried over anhydrous sodium sulfate and concentrated under vacuum. The residue was purified by combi flash column chromatography using 100% DCM as an eluent to afford the title compound (400 mg, 45%); $^1$H NMR (400 MHz, DMSO-d$_6$): δ 12.03 (bs, 1H), 7.98 (s, 1H), 7.73 (dd, J=1.0 Hz, J=8.3 Hz, 1H), 7.37 (d, J=8.3 Hz, 1H), 4.30 (q, J=7.2 Hz, 2H), 3.62 (s, 3H), 2.67-2.60 (m, 1H), 2.50 (2H merged with DMSO peak), 2.18-2.11 (m, 1H), 1.87-1.84 (m, 2H), 1.46-1.42 (m, 1H), 1.34 (t, J=7.1 Hz, 3H), 1.05 (d, J=6.3 Hz, 3H); LC-MS: m/z 371.05 (M+1)$^+$.

Step-d: Synthesis of 1-methyl-2-((6-methyl-4,5,6,7-tetrahydrobenzo[d]thiazol-2-yl)amino)-1H-benzo[d]imidazole-5-carboxylic acid The title compound was synthesized using the same procedure which was followed for compound 1h, using ethyl 1-methyl-2-((6-methyl-4,5,6,7-tetrahydrobenzo[d]thiazol-2-yl)amino)-1H-benzo[d]imidazole-5-carboxylate as starting material (Yield: 100%); $^1$H NMR (400 MHz, DMSO-d$_6$): δ 13.01 (bs, 1H), 12.83 (bs, 1H), 8.01 (s, 1H), 7.87 (d, J=8.4 Hz, 1H), 7.56 (d, J=8.4 Hz, 1H), 3.67 (s, 3H), 2.67-2.66 (m, 1H), 2.52 (2H merged with DMSO peak), 2.33-2.21 (m, 1H), 1.91-1.86 (m, 2H), 1.48-1.43 (m, 1H), 1.06 (d, J=6.4 Hz, 3H); LC-MS: m/z 343.05 (M+1)$^+$.

Step-e: Synthesis of N-(2-(2-hydroxyethoxy)ethyl)-1-methyl-2-((6-methyl-4,5,6,7-tetrahydrobenzo[d]thiazol-2-yl)amino)-1H-benzo[d]imidazole-5-carboxamide The title compound was synthesized using the same procedure which was followed for Example 6 Step-e using 1-methyl-2-((6-methyl-4,5,6,7-tetrahydrobenzo[d]thiazol-2-yl)amino)-1H-benzo[d]imidazole-5-carboxylic acid and 2-(2-aminoethoxy)ethan-1-ol as starting materials (Yield: 48%); $^1$H NMR (400 MHz, DMSO-d$_6$): δ 11.99 (bs, 1H), 8.35 (t, J=5.6 Hz, 1H), 7.95 (s, 1H), 7.64 (d, J=8.0 Hz, 1H), 7.32 (d, J=8.4 Hz, 1H), 4.62 (t, J=5.0 Hz, 1H), 3.61 (s, 3H), 3.55-3.50 (m, 4H), 3.47-3.42 (m, 4H), 2.67-2.66 (m, 1H), 2.52 (2H merged with DMSO peak), 2.17-2.16 (m, 1H), 1.90-1.88 (m, 2H), 1.45-1.40 (m, 1H), 1.05 (d, J=6.4 Hz, 3H); LC-MS: m/z 430.10 (M+1)⁺.

Example 8. Synthesis of 2-((5,6-dihydro-4H-cyclopenta[d]thiazol-2-yl)amino)-N-(2-methoxyethyl)-1-methyl-1H-benzo[d]imidazole-5-carboxamide

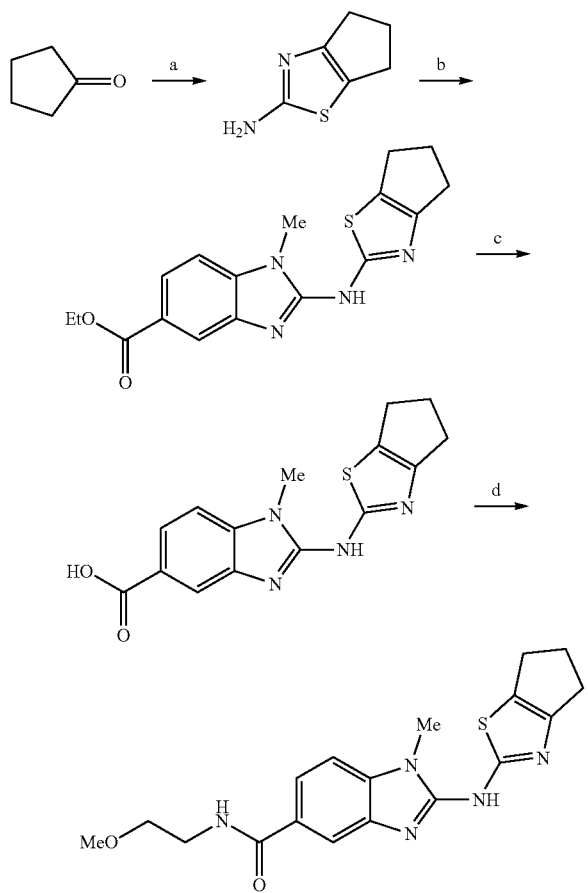

Conditions: a) Iodine, Thiourea, 110° C., 12 h; b) ethyl 3-amino-4-(methylamino)benzoate, 1,1'-Thiocarbonyl diimidazole, EDC•HCl, DMF, 100° C., 16 h; c) LiOH•H₂O, THF, Ethanol, Water, 60° C., 16 h; h) 2-methoxyethyl amine, DPPA, DIPEA, DMF, 0° C.-RT, 16h Step-a: Synthesis of 5,6-dihydro-4H-cyclopenta[d]thiazol-2-amine A mixture of cyclopentanone (1.0 g, 11.9 mmol), thiourea (1.8 g, 23.8 mmol) and iodine (3.0 g, 11.9 mmol) was stirred in a sealed tube at 110° C. for 12 h. The reaction mixture was cooled to RT and hot water (30 mL) was added and stirred for 30 min. The reaction mixture was extracted with diethyl ether (2×20 mL), aqueous layer was basified (pH~8) with solid sodium bicarbonate and extracted with DCM (3×30 mL). The combined organic layer was washed with brine (20 mL), dried over anhydrous sodium sulfate and concentrated under vacuum. The resulted residue was purified by combiflash chromatography using 10% methanol in DCM and 0.1% of aqueous ammonia as eluent to afford the title compound (160 mg, 10%); ¹H NMR (400 MHz, CDCl₃): δ 4.77 (bs, 2H), 2.79-2.74 (m, 2H), 2.68-2.64 (m, 2H), 2.41-2.34 (m, 2H); LC-MS: m/z 141.1 (M+1)⁺.

Step-b: Synthesis of ethyl 2-((5,6-dihydro-4H-cyclopenta[d]thiazol-2-yl)amino)-1-methyl-1H-benzo[d]imidazole-5-carboxylate The title compound was synthesized using the same procedure which was followed for compound 5a using ethyl 3-amino-4-(methylamino)benzoate and 5,6-dihydro-4H-cyclopenta[d]thiazol-2-amine as starting materials (Yield: 23%); ¹H NMR (400 MHz, DMSO-d₆): δ 12.0 (bs, 1H), 8.05 (s, 1H), 7.77 (d, J=8.0 Hz, 1H), 7.38 (d, J=8.4 Hz, 1H), 4.30 (q, J=6.8 Hz, 2H), 3.56 (s, 3H), 2.80-2.72 (m, 4H), 2.36-2.33 (m, 2H), 1.33 (t, J=6.8 Hz, 3H); LC-MS: m/z 343.0 (M+1)⁺.

Step-c: Synthesis of 2-((5,6-dihydro-4H-cyclopenta[d]thiazol-2-yl)amino)-1-methyl-1H-benzo[d]imidazole-5-carboxylic acid The title compound was synthesized using the same procedure which was followed for compound 1h, using ethyl 2-((5,6-dihydro-4H-cyclopenta[d]thiazol-2-yl)amino)-1-methyl-1H-benzo[d]imidazole-5-carboxylate as starting material (Yield: 55%); LC-MS: m/z 315.1 (M+1)⁺.

Step-d: Synthesis of 2-((5,6-dihydro-4H-cyclopenta[d]thiazol-2-yl)amino)-N-(2-methoxyethyl)-1-methyl-1H-benzo[d]imidazole-5-carboxamide The title compound was synthesized using the same procedure which was followed for compound 1i using 2-((5,6-dihydro-4H-cyclopenta[d]thiazol-2-yl)amino)-1-methyl-1H-benzo[d]imidazole-5-carboxylic acid as starting material (Yield: 13%); ¹H NMR (400 MHz, DMSO-d₆): δ 12.0 (bs, 1H), 8.36 (bs, 1H), 7.95 (s, 1H), 7.67 (d, J=7.6 Hz, 1H), 7.33 (d, J=8.4 Hz, 1H), 3.56 (s, 3H), 3.47-3.42 (m, 4H), 3.28 (s, 3H), 2.77-2.67 (m, 4H), 2.36-2.33 (m, 2H); LC-MS: m/z 372.0 (M+1)⁺.

Example 9. Synthesis of N-(2-(2-hydroxyethoxy)ethyl)-1-methyl-2-((4,5,6,7-tetrahydrothiazolo[5,4-c]pyridin-2-yl)amino)-1H-benzo[d]imidazole-5-carboxamide hydrochloride

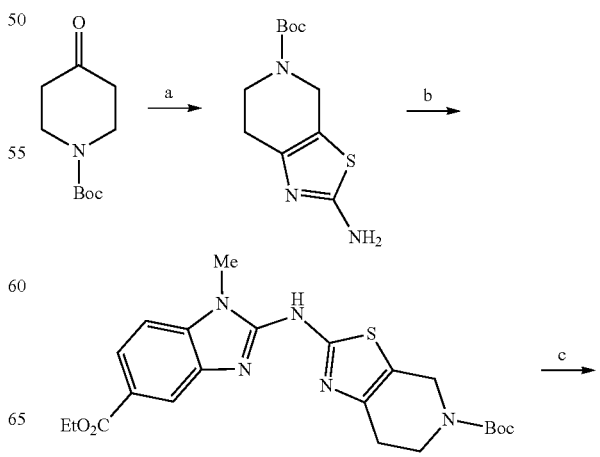

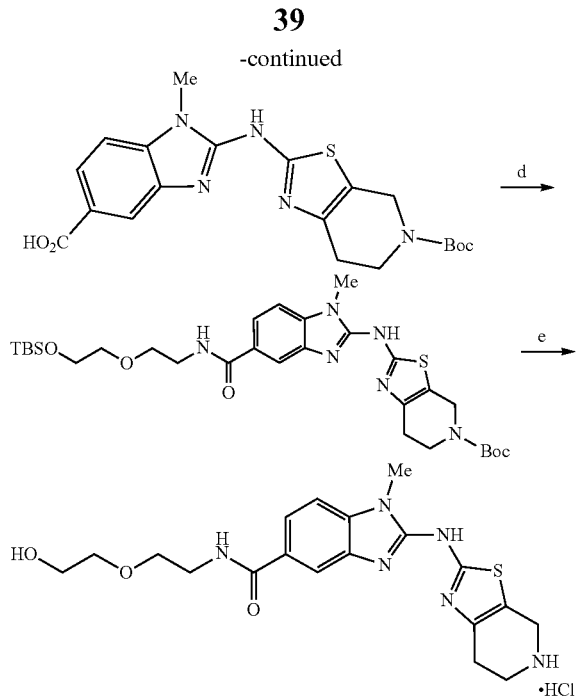

Conditions: a) i) Pyrrolidone hydrobromide, THF, reflux, 10 min ii) Thiourea, EtOH, reflux, 3 h; b) ethyl 3-amino-4-(methylamino)benzoate, 1,1'-thiocarbonyldiimidazole, EDC, DMF, 100° C., 18 h; c) LiOH•H$_2$O, THF, MeOH, H$_2$O, 50° C., 16 h; d) 2-(2-((tert-butyldimethylsilyl)oxy)ethoxy)ethan-1-amine, HBTU, DIPEA, DMF, 0° C.-RT, 16 h; e) 4 M HCl in 1,4-Dioxane, 1,4-Dioxane, 0° C.-RT, 16 h Step-a: Synthesis of tert-butyl 2-amino-6,7-dihydrothiazolo[5,4-c]pyridine-5(4H)-carboxylate To a stirred solution of tert-butyl 4-oxopiperidine-1-carboxylate (3.0 g, 15.07 mmol) in THF (70 mL) at RT was added pyrrolidone hydrobromide (7.47 g, 15.07 mmol) and the reaction mixture was refluxed for 10 min. The reaction mixture was cooled to RT, the precipitated solid was removed by filtration and the filtrate was concentrated. The residue obtained was dissolved in ethanol (80 mL) followed by the addition of thiourea (1.53 g, 20.14 mmol) and the reaction mixture was refluxed for 3 h. The reaction mixture was cooled to RT, concentrated under vacuum. The residue was purified by combiflash chromatography using 5% methanol in DCM as an eluent to afford the title compound (450 mg, 12%); $^1$H NMR (400 MHz, DMSO-d$_6$): δ 6.80 (s, 2H), 4.29 (s, 2H), 3.56 (t, J=5.6 Hz, 2H), 2.43 (bs, 2H), 1.41 (s, 9H); LC-MS: m/z 256.2 (M+1)$^+$.

Step-b: Synthesis of tert-butyl 2-((5-(ethoxycarbonyl)-1-methyl-1H-benzo[d]imidazol-2-yl)amino)-6,7-dihydrothiazolo[5,4-e]pyridine-5(4H)-carboxylate To a stirred solution of tert-butyl 2-amino-6,7-dihydrothiazolo[5,4-c]pyridine-5(4H)-carboxylate (424 mg, 1.66 mmol) in DMFA (6 mL) was added 1,1'-thiocarbonyldiimidazole (593 mg, 3.33 mmol) and the solution was heated at 100° C. for 2 h. The reaction mixture was cooled to RT and EDC HCl (639 mg, 3.33 mmol) was added. The reaction mixture was heated at 50° C. for 10 min, followed by the addition of ethyl 3-amino-4-(methylamino)benzoate (300 mg, 1.66 mmol). The reaction mixture was heated at 100° C. for 16 h. It was cooled to RT, diluted with water (50 mL) and extracted with EtOAc (2×50 mL). The combined organic layers were washed with water (30 mL), brine (30 mL), dried over anhydrous sodium sulfate and concentrated under vacuum. The residue was purified by combiflash chromatography using 0.4% methanol in DCM as an eluent to afford the titled compound (130 mg, 18%); $^1$H NMR (400 MHz, DMSO-d$_6$): δ 12.10 (bs, 1H), 8.03 (bs, 1H), 7.77 (d, J=8.4 Hz, 1H), 7.39 (d, J=8.4 Hz, 1H), 4.39 (bs, 2H), 4.30 (q, J=6.8 Hz, 2H), 3.67-3.59 (m, 5H), 2.50 (2H merged with DMSO peak), 1.43 (s, 9H), 1.34 (t, J=6.8 Hz, 3H); LC-MS: m/z 458.2 (M+1)$^+$.

Step-c: Synthesis of 2-((5-(tert-butoxycarbonyl)-4,5,6,7-tetrahydrothiazolo[5,4-c]pyridin-2-yl)amino)-1-methyl-1H-benzo[d]imidazole-5-carboxylic acid The title compound was synthesized using the same procedure which was followed for compound 1h using tert-butyl 2-((5-(ethoxycarbonyl)-1-methyl-1H-benzo[d]imidazol-2-yl)amino)-6,7-dihydrothiazolo[5,4-c]pyridine-5(4H)-carboxylate as starting material and THF, methnol, water (2:2:1) as solvent. (Yield: 70%); $^1$H NMR (400 MHz, DMSO-d$_6$): δ 12.50 (bs, 1H), 8.00 (s, 1H), 7.78 (d, J=8.4 Hz, 1H), 7.40 (d, J=8.4 Hz, 1H), 4.40 (s, 2H), 3.66 (t, J=4.8 Hz, 2H), 3.60 (s, 3H), 2.66-2.63 (m, 2H), 1.43 (s, 9H); LC-MS: m/z 430.1 (M+1)$^+$.

Step-d: Synthesis of tert-butyl 2-((5-((2-(2-((tert-butyldimethylsilyl)oxy)ethoxy)ethyl)carbamoyl)-1-methyl-1H-benzo[d]imidazol-2-yl)amino)-6,7-dihydrothiazolo[5,4-c]pyridine-5(4H)-carboxylate The title compound was synthesized using the same procedure which was followed for Example 6 Step-e using 2-((5-(tert-butoxycarbonyl)-4,5,6,7-tetrahydrothiazolo[5,4-c]pyridin-2-yl)amino)-1-methyl-1H-benzo[d]imidazole-5-carboxylic acid and 2-(2-((tert-butyldimethylsilyl)oxy)ethoxy)ethan-1-amine as starting materials (Yield: 40%); LC-MS: m/z 631.2 (M+1)$^+$.

Step-e: Synthesis of N-(2-(2-hydroxyethoxy)ethyl)-1-methyl-2-((4,5,6,7-tetrahydrothiazolo-[5,4-c]pyridin-2-yl)amino)-1H-benzo[d]imidazole-5-carboxamide hydrochloride To a stirred solution of tert-butyl 2-((5-((2-(2-((tert-butyldimethylsilyl)oxy)ethoxy)ethyl)carbamoyl)-1-methyl-1H-benzo[d]imidazol-2-yl)amino)-6,7-dihydrothiazolo[5,4-c]pyridine-5(4H)-carboxylate (50 mg, 0.08 mmol) in 1,4-dioxane (0.8 mL) at 0° C. was added 4 M HCl in 1,4-dioxane (0.3 mL) and stirred at RT for 16 h. The reaction mixture was concentrated under reduced pressure. The residue was triturated with diethyl ether and solvent was decanted. The solid obtained was dried under vacuum to afford the title compound (12 mg, 33%); $^1$H NMR (400 MHz, CD$_3$OD): δ 8.01 (s, 1H), 7.87 (d, J=8.0 Hz, 1H), 7.55 (d, J=8.4 Hz, 1H), 4.35 (s, 2H), 3.74 (s, 3H), 3.71-3.53 (m, 10H), 3.05 (t, J=6.0 Hz, 2H); LC-MS: m/z 417.1 (M+1)$^+$.

Example 10. Synthesis of 2-((5-acetyl-4,5,6,7-tetrahydrothiazolo[5,4-c]pyridin-2-yl)amino)-N-(2-(2-hydroxyethoxy)ethyl)-1-methyl-1H-benzo[d]imidazole-5-carboxamide

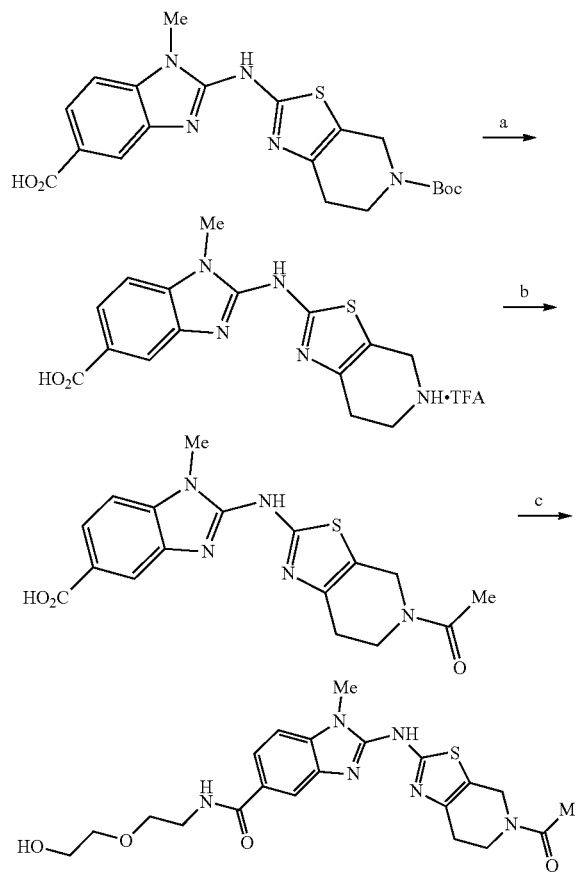

Conditions: a) TFA, DCM, 0° C.-RT, 16 h; b) Ac₂O, Pyridine, 0° C.-RT, 16 h; c) 2-(2-aminoethoxy)ethan-1-ol, HBTU, DIPEA, DMF, 0° C.-RT, 16 h Step-a: Synthesis of 1-methyl-2-((4,5,6,7-tetrahydrothiazolo[5,4-c]pyridin-2-yl)amino)-1H-benzo[d]imidazole-5-carboxylic acid trifluoroacetic acid salt To a stirred solution of 2-((5-(tert-butoxycarbonyl)-4,5,6,7-tetrahydrothiazolo[5,4-c]pyridin-2-yl)amino)-1-methyl-1H-benzo[d]imidazole-5-carboxylic acid (170 mg, 0.39 mmol) in DCM (5 mL) at 0° C. was added TFA (0.1 mL, 1.19 mmol) and stirred at RT for 16 h. The reaction mixture was concentrated under reduced pressure and the residue obtained was triturated with diethyl ether and solvent was decanted. The residue was dried under vacuum to afford the title compound (180 mg, 100%); ¹H NMR (400 MHz, DMSO-d₆): δ 9.22 (s, 2H), 8.04 (s, 1H), 7.81 (dd, J=1.6 Hz, J=8.4 Hz, 1H), 7.42 (d, J=8.4 Hz, 1H), 4.23 (s, 2H), 3.60 (s, 3H), 3.48-3.46 (m, 2H), 2.89 (bs, 2H); LC-MS: m/z 330.1 (M+1)⁺.

Step-b: Synthesis of 2-((5-acetyl-4,5,6,7-tetrahydrothiazolo[5,4-c]pyridin-2-yl)amino)-1-methyl-1H-benzo[d]imidazole-5-carboxylic acid To a stirred solution of 1-methyl-2-((4,5,6,7-tetrahydrothiazolo[5,4-c]pyridin-2-yl)amino)-1H-benzo[d]imidazole-5-carboxylic acid trifluoroacetic acid salt (180 mg, 0.55 mmol) in pyridine (2 mL) at 0° C. was added acetic anhydride (0.06 mL, 0.6 mmol) and stirred at RT for 16 h. The reaction mixture was diluted with water (15 mL), and extracted with EtOAc (2×50 mL). The combined organic layers were washed with 1 N HCl (30 mL), water (20 mL), brine (20 mL), dried over anhydrous sodium sulfate and concentrated under vacuum and the residue obtained was triturated with diethyl ether and solvent was decanted. The obtained solid was dried under vacuum to afford the title compound (70 mg, 46%); LC-MS: m/z 372.1 (M+1)⁺.

Step-c: Synthesis of 2-((5-acetyl-4,5,6,7-tetrahydrothiazolo[5,4-c]pyridin-2-yl)amino)-N-(2-(2-hydroxyethoxy)ethyl)-1-methyl-1H-benzo[d]imidazole-5-carboxamide The title compound was synthesized using the same procedure which was followed for Example 6 Step-e using 2-((5-acetyl-4,5,6,7-tetrahydrothiazolo[5,4-c]pyridin-2-yl)amino)-1-methyl-1H-benzo[d]imidazole-5-carboxylic acid and 2-(2-aminoethoxy)ethan-1-ol as starting materials (Yield: 29%); ¹H NMR (400 MHz, DMSO-d₆): δ 12.0 (bs, 1H), 8.38 (s, 1H), 7.96 (d, J=3.6 Hz, 1H), 7.67 (d, J=7.6 Hz, 1H), 7.35 (d, J=8.4 Hz, 1H), 4.62-4.49 (m, 3H), 3.78-3.73 (m, 2H), 3.60-3.41 (m, 10H), 3.30 (2H merged with DMSO moisture peak), 2.09 (s, 3H); LC-MS: m/z 459.1 (M+1)⁺.

Example 11. Synthesis of 2-((6,7-dihydro-4H-pyrano[4,3-d]thiazol-2-yl)amino)-N-(2-methoxyethyl)-1-methyl-1H-benzo[d]imidazole-5-carboxamide

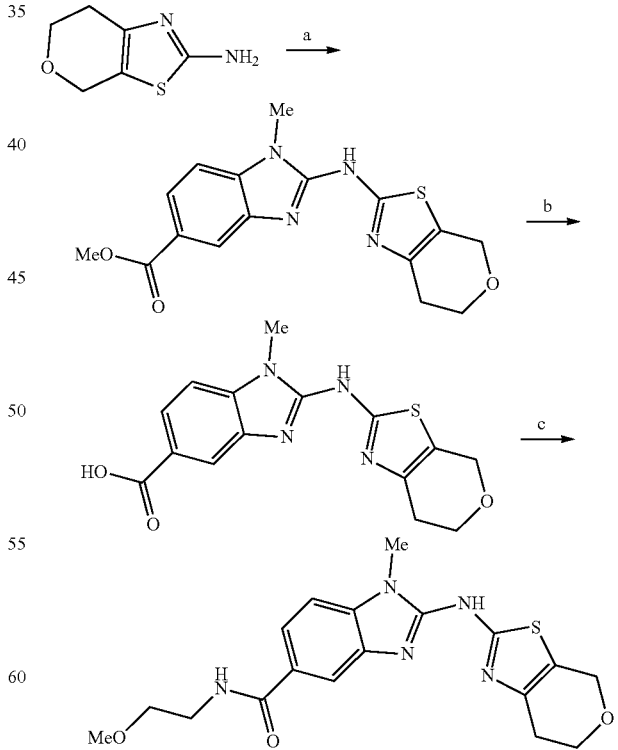

Conditions: a) Methyl 3-amino-4-(methylamino)benzoate, 1,1'-thiocarbonyldiimidazole, EDC, DMF, 100° C., 16 h; b) LiOH·H₂O, THF, MeOH, H₂O, 60° C., 16 h; c) 2-methoxyethan-1-amine, DPPA, DIPEA, DMF, 0° C.-RT, 16 h Step-a: Synthesis of methyl 2-((6,7-dihydro-4H-pyrano[4,3-d]thiazol-2-yl)amino)-1-methyl-1H-benzo[d]imidazole-5-carboxylate The title compound was synthesized using the same procedure which was followed for compound 5a using methyl 3-amino-4-(methylamino)benzoate and 6,7-dihydro-4H-pyrano[4,3-d]thiazol-2-amine as starting materials and stirring 16 h (Yield: 20%); $^1$H NMR (400 MHz, DMSO-$d_6$): δ 12.20 (bs, 1H), 8.02 (s, 1H), 7.77 (d, J=8.0 Hz, 1H), 7.40 (d, J=8.4 Hz, 1H), 4.58 (s, 2H), 3.93 (t, J=5.6 Hz, 2H), 3.84 (s, 3H), 3.60 (s, 3H), 2.50 (2H, merged with DMSO peak); LC-MS: m/z 343.0 (M−1).

Step-b: Synthesis of 2-((6,7-dihydro-4H-pyrano[4,3-d]thiazol-2-yl)amino)-1-methyl-1H-benzo[d]imidazole-5-carboxylic acid The title compound was synthesized using the same procedure which was followed for compound 1h using methyl 2-((6,7-dihydro-4H-pyrano[4,3-d]thiazol-2-yl)amino)-1-methyl-1H-benzo[d]imidazole-5-carboxylate as starting material and using THF, methanol and water (2:2:1) as solvent (Yield: 52%); δ 12.40 (bs, 2H), 7.98 (s, 1H), 7.75 (d, J=8.0 Hz, 1H), 7.36 (d, J=8.0 Hz, 1H), 4.58 (s, 2H), 3.92 (t, J=4.8 Hz, 2H), 3.59 (s, 3H), 2.50 (2H, merged with DMSO peak); LC-MS: m/z 330.7 (M+1)$^+$.

Step-c: Synthesis of 2-((6,7-dihydro-4H-pyrano[4,3-d]thiazol-2-yl)amino)-N-(2-methoxyethyl)-1-methyl-1H-benzo[d]imidazole-5-carboxamide The title compound was synthesized using the same procedure which was followed for compound 1i using 2-((6,7-dihydro-4H-pyrano[4,3-d]thiazol-2-yl)amino)-1-methyl-1H-benzo[d]imidazole-5-carboxylic acid and 2-methoxyethylamine as starting materials. The crude product was purified by combiflash chromatography using 1.2% methanol in DCM as an eluent (Yield: 34%); $^1$H NMR (400 MHz, DMSO-$d_6$): δ 12.20 (bs, 1H), 8.40 (bs, 1H), 7.96 (s, 1H), 7.66 (bs, 1H), 7.35 (d, J=8.4 Hz, 1H), 4.58 (bs, 2H), 3.93 (s, 2H), 3.58 (s, 3H), 3.48-3.42 (m, 4H), 3.27 (s, 3H), 2.50 (2H, merged with DMSO peak); LC-MS: m/z 387.6 (M+1)$^+$.

Example 12. Synthesis of 2-((1H-benzo[d]imidazol-2-yl)amino)-N-(2-methoxyethyl)-1-methyl-1H-benzo[d]imidazole-5-carboxamide

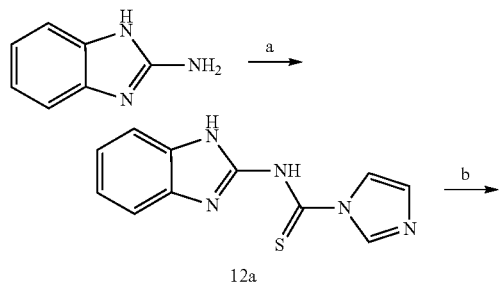

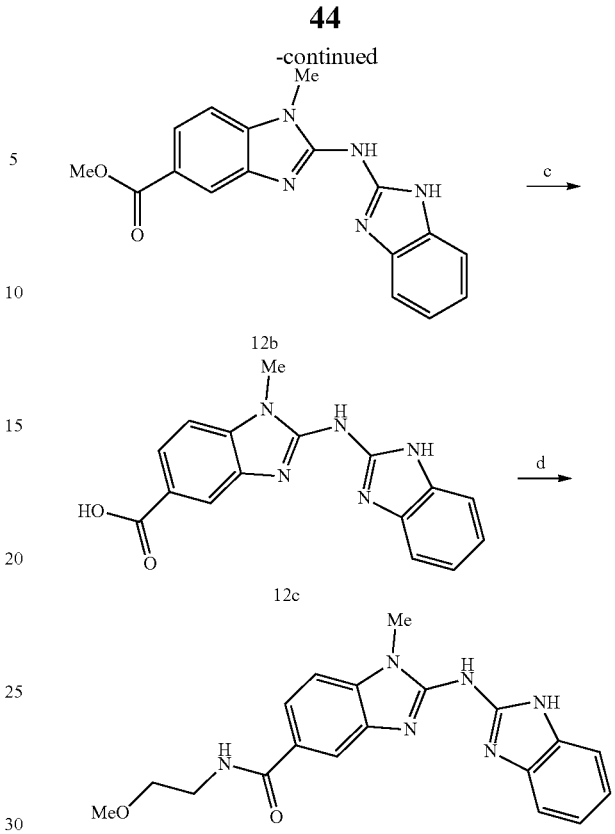

Example 12

Conditions: a) 1,1'-Thiocarbonyldiimidazole, Acetonitrile, RT, 16 h; b) methyl 3-amino-4-(methylamino)benzoate, EDC•HCl, DMF, 100° C., 16 h; d) LiOH•H$_2$O, THF, MeOH, Water, 60° C., 16 h; e) 2-methoxyethan-1-amine, DPPA, DIPEA, DMF, 0° C.-RT, 16 h Step-a: Synthesis of N-(1H-benzo[d]imidazol-2-yl)-1H-imidazole-1-carbothioamide To a solution of 1H-benzo[d]imidazol-2-amine (1.0 g, 7.5 mmol) in acetonitrile (10 mL) at RT was added 1,1'-thiocarbonyldiimidazole (1.34 g, 7.5 mmol) and it was stirred at RT for 16 h. The reaction mixture was filtered and the solid obtained was dried under vacuum to afford the title compound (1.1 g, 60%); $^1$H NMR (400 MHz, DMSO-$d_6$): δ 13.18 (bs, 2H), 8.55 (s, 1H), 7.93 (d, J=1.2 Hz, 1H), 7.63-7.59 (m, 2H), 7.36-7.32 (m, 2H), 6.99 (d, J=1.2 Hz, 1H).

Step-b: Synthesis of methyl 2-((1H-benzo[d]imidazol-2-yl)amino)-1-methyl-1H-benzo[d]imidazole-5-carboxylate To a stirred solution of N-(1H-benzo[d]imidazol-2-yl)-1H-imidazole-1-carbothioamide (188 mg, 0.77 mmol) in DMFA (5 mL) was added EDC.HCl (297 mg, 1.5 mmol) and heated to 60° C. for 10 min. The reaction mixture was cooled to RT, followed by the addition of methyl 3-amino-4-(methylamino)benzoate (150 mg, 0.77 mmol) and it was heated at 100° C. for 16 h. The reaction mixture was cooled to RT, diluted with water (30 mL) and extracted with EtOAc (2×50 mL). The combined organic layer was washed with water (30 mL), brine (30 mL), dried over anhydrous sodium sulfate and concentrated under vacuum. The residue was purified by combi flash column chromatography using 2% methanol in DCM as eluent to afford the title compound (40 mg, 16%); $^1$H NMR (400 MHz, DMSO-$d_6$): δ 12.12 (bs, 2H), 8.05 (d, J=1.6 Hz, 1H), 7.73 (dd, J=1.6 Hz, J=8.4 Hz, 1H), 7.37-7.34 (m, 3H), 7.12-7.08 (m, 2H), 3.85 (s, 3H), 3.65 (s, 3H); LC-MS: m/z 322.0 (M+1)$^+$.

Step-c: Synthesis of 2-((1H-benzo[d]imidazol-2-yl)amino)-1-methyl-1H-benzo[d]imidazole-5-carboxylic acid The title compound was synthesized using the same procedure which was followed for intermediate 1h, using methyl 2-((1H-benzo[d]imidazol-2-yl)amino)-1-methyl-1H-benzo[d]imidazole-5-carboxylate as starting material and methanol, THF and water as solvent (Yield: 92%); $^1$H NMR (400 MHz, DMSO-d$_6$): δ 13.0 (bs, 3H), 7.92 (s, 1H), 7.89 (d, J=1.6 Hz, 1H), 7.60 (d, J=8.4 Hz, 1H), 7.45-7.41 (m, 2H), 7.29-7.26 (m, 2H), 3.68 (s, 3H); LC-MS: m/z 308.1 (M+1)$^+$.

Step-d: Synthesis of 2-01H-benzo[d]imidazol-2-yl)amino)-N-(2-methoxyethyl)-1-methyl-1H-benzo[d]imidazole-5-carboxamide The title compound was synthesized using the same procedure which was followed for compound 1i using 2-((1H-benzo[d]imidazol-2-yl)amino)-1-methyl-1H-benzo[d]imidazole-5-carboxylic acid as starting material (Yield: 14%); $^1$H NMR (400 MHz, DMSO-d$_6$): δ 12.10 (bs, 2H), 8.33 (t, J=4.8 Hz, 1H), 7.98 (d, J=0.8 Hz, 1H), 7.62 (dd, J=1.2 Hz, J=8.0 Hz, 1H), 7.35-7.30 (m, 3H), 7.11-7.07 (m, 2H), 3.64 (s, 3H), 3.50-3.42 (m, 4H), 3.29 (s, 3H); LC-MS: m/z 365.0 (M+1)$^+$.

Example 13 and 14. Synthesis of 1-methyl-2-((5-(trifluoromethoxy)-1H-benzo[d]imidazol-2-yl)amino)-1H-benzo[d]imidazole-5-carboxylic acid and Synthesis of N-(2-methoxyethyl)-1-methyl-2-((5-(trifluoromethoxy)-1H-benzo[d]imidazol-2-yl)amino)-1H-benzo[d]imidazole-5-carboxamide

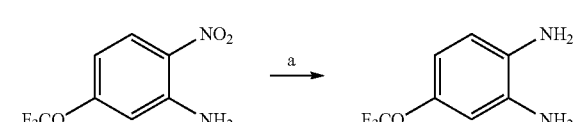

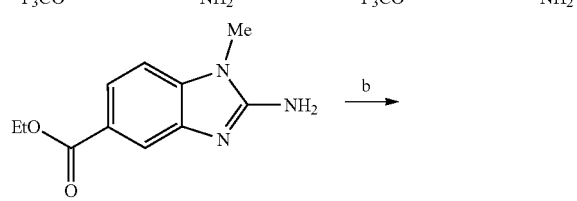

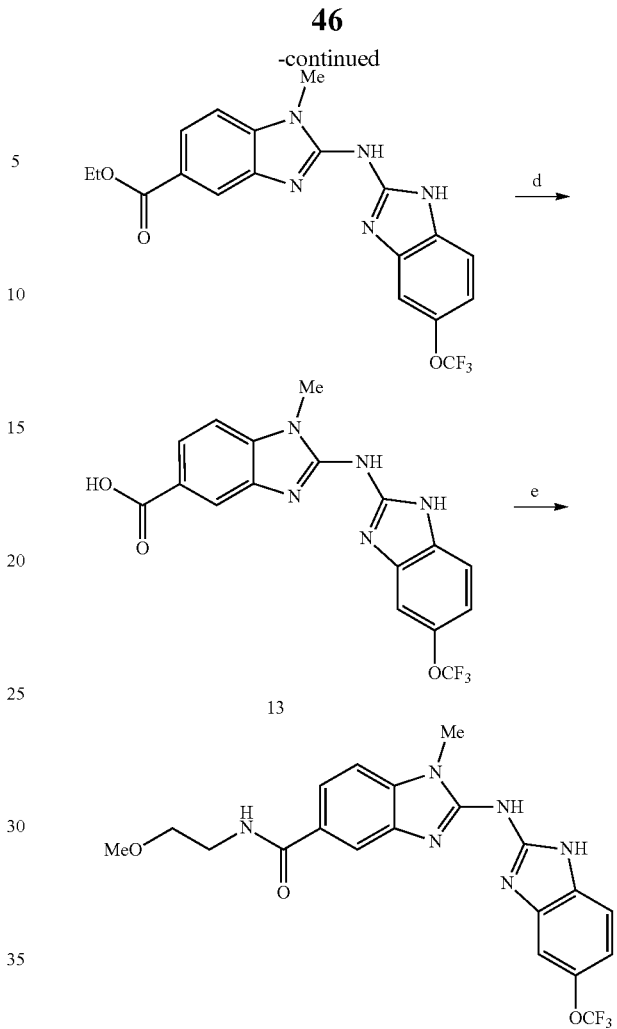

Conditions: a) 10% Pd/C, MeOH, H$_2$, RT, 16 h; b) 1,1′-Thiocarbonyldiimidazole, Acetonitrile, 60° C., 16 h; c) 4-(trifluoromethoxy)benzene-1,2-diamine, EDC•HCl, DMF, 100° C., 16 h; d) LiOH•H$_2$O, THF, EtOH, Water, 60° C., 16 h; e) 2-methoxyethan-1-amine, DPPA, DIPEA, DMF, 0° C.-RT, 16 h Step-a: Synthesis of 4-(trifluoromethoxy)benzene-1,2-diamine To a solution of methyl 2-nitro-5-(trifluoromethoxy)aniline (2.0 g, 9.0 mmol) in methanol (40 mL) was added 10% Pd/C (1.0 g) under nitrogen atmosphere. Then the reaction mixture was stirred under hydrogen gas for 16 h. The reaction mixture was filtered through a bed of celite and concentrated under vacuum to afford the title compound (1.6 g, 93%); $^1$H NMR (400 MHz, DMSO-d$_6$): δ 6.48 (d, J=8.0 Hz, 1H), 6.45 (d, J=1.6 Hz, 1H), 6.29 (dd, J=2.0 Hz, J=8.0 Hz, 1H), 4.80 (s, 2H), 4.58 (s, 2H); LC-MS: m/z 193.0 (M+1)$^+$.

Step-b: Synthesis of ethyl 2-(1H-imidazole-1-carbothioamido)-1-methyl-1H-benzo[d]imidazole-5-carboxylate To a solution of ethyl 2-amino-1-methyl-1H-benzo[d]imidazole-5-carboxylate (500 mg, 2.28 mmol) in acetonitrile (10 mL) at RT was added 1,1′-thiocarbonyldiimidazole (529 mg, 2.97 mmol) and reaction mixture was stirred at 60°

C. for 16 h. It was cooled to RT and stirred for 30 min. The solid obtained was filtered and dried under vacuum to afford the title compound (500 mg, 66%); $^1$H NMR (400 MHz, DMSO-d$_6$): δ 13.40 (bs, 1H), 8.68 (s, 1H), 8.40 (d, J=1.2 Hz, 1H), 8.03 (s, 1H), 7.99 (dd, J=1.2 Hz, J=8.4 Hz, 1H), 7.75 (d, J=8.4 Hz, 1H), 7.01 (s, 1H), 4.35 (q, J=7.2 Hz, 2H), 3.79 (s, 3H), 1.36 (t, J=7.2 Hz, 3H); LC-MS: m/z 328.2 (M−1).

Step-c: Synthesis of ethyl 1-methyl-2-((5-(trifluoromethoxy)-1H-benzo[d]imidazol-2-yl)amino)-1H-benzo[d]imidazole-5-carboxylate The title compound was synthesized using the same procedure which was followed for Example 12 Step-b, using ethyl 2-(1H-imidazole-1-carbothioamido)-1-methyl-1H-benzo[d]imidazole-5-carboxylate and 4-(trifluoromethoxy)benzene-1,2-diamine as starting materials (Yield: 27%); $^1$H NMR-VT at 90° C. (400 MHz, DMSO-d$_6$): δ 12.0 (bs, 2H), 8.09 (s, 1H), 7.77 (d, J=8.4 Hz, 1H), 7.35 (d, J=8.4 Hz, 2H), 7.28 (s, 1H), 7.0 (d, J=8.4 Hz, 1H), 4.35 (q, J=6.8 Hz, 2H), 3.63 (s, 3H), 1.35 (t, J=6.8 Hz, 3H); LC-MS: m/z 420.0 (M+1)$^+$.

Step-d: Synthesis of 1-methyl-2-((5-(trifluoromethoxy)-1H-benzo[d]imidazol-2-yl)amino)-1H-benzo[d]imidazole-5-carboxylic acid The title compound was synthesized using the same procedure which was followed for intermediate 1h, using ethyl 1-methyl-2-((5-(trifluoromethoxy)-1H-benzo[d]imidazol-2-yl)amino)-1H-benzo[d]imidazole-5-carboxylate (Yield: 77%); $^1$H NMR (400 MHz, DMSO-d$_6$): δ 12.60 (bs, 3H), 8.05 (d, J=1.6 Hz, 1H), 7.82 (dd, J=1.6 Hz, J=8.4 Hz, 1H), 7.45 (d, J=8.4 Hz, 1H), 7.40 (d, J=8.8 Hz, 1H), 7.34 (s, 1H), 7.09 (dd, J=1.2 Hz, J=8.8 Hz, 1H), 3.65 (s, 3H); LC-MS: m/z 392.0 (M+1)$^+$.

Step-e: Synthesis of N-(2-methoxyethyl)-1-methyl-2-((5-(trifluoromethoxy)-1H-benzo[d]imidazol-2-yl)amino)-1H-benzo[d]imidazole-5-carboxamide The title compound was synthesized using the same procedure which was followed for compound 1i using 1-methyl-2-((5-(trifluoromethoxy)-1H-benzo[d]imidazol-2-yl)amino)-1H-benzo[d]imidazole-5-carboxylic acid as starting material (Yield: 43%); $^1$H NMR (400 MHz, DMSO-d$_6$): δ 12.20 (bs, 2H), 8.37 (bs, 1H), 8.0 (d, J=1.2 Hz, 1H), 7.68 (dd, J=1.2 Hz, J=8.4 Hz, 1H), 7.36 (d, J=8.4 Hz, 2H), 7.30 (s, 1H), 7.01 (d, J=8.4 Hz, 1H), 3.63 (s, 3H), 3.59-3.43 (m, 4H), 3.29 (s, 3H); LC-MS: m/z 449.0 (M+1)$^+$.

Example 15. Synthesis of 1-methyl-2-((1-methyl-5-(trifluoromethoxy)-1H-benzo[d]imidazol-2-yl)amino)-1H-benzo[d]imidazole-5-carboxylic acid

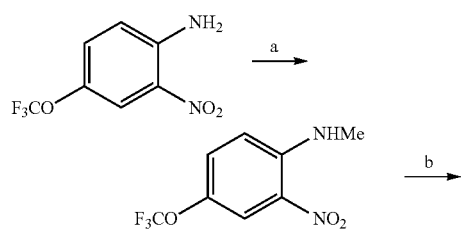

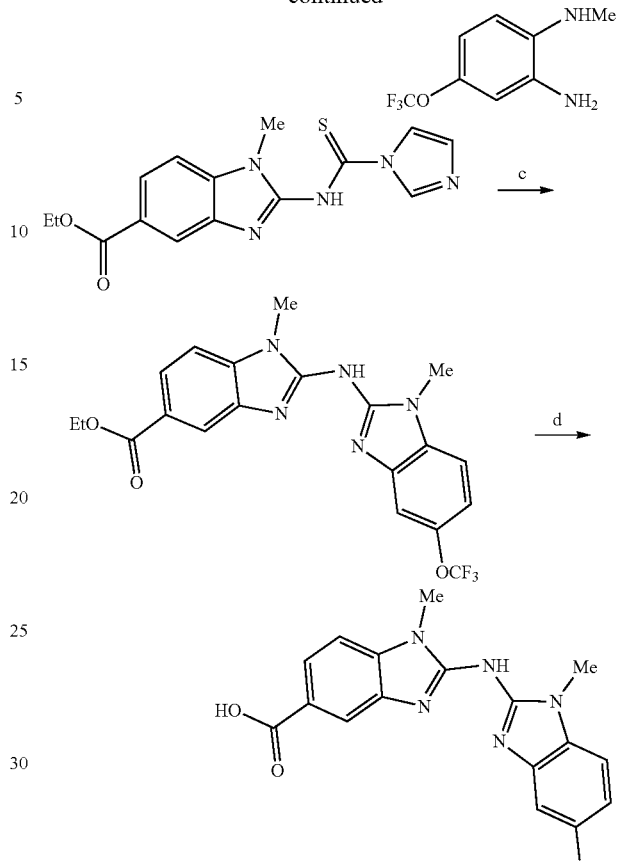

Conditions: a) NaH, Methyl iodide, DMF, 0° C. - RT, 1 h; b) 10% Pd/C, MeOH, H$_2$, RT, 6 h; c) N1-methyl-4-(trifluoromethoxy)benzene-1,2-diamine, EDC•HCl, DMF, 100° C., 16 h; d) LiOH•H$_2$O, THF, EtOH, H$_2$O, 60° C., 16 h Step-a: Synthesis of N-methyl-2-nitro-4-(trifluoromethoxy)aniline To a stirred solution of 2-nitro-4-(trifluoromethoxy)aniline (2.0 mg, 9.0 mmol) in DMFA (20 mL) at 0° C. was added sodium hydride (60% dispersion in mineral oil) (0.4 g, 10.0 mmol) and the reaction mixture was stirred for 10 min. Methyl iodide (0.56 mL, 9.0 mmol) was added to the reaction mixture and stirred at RT for 1 h. The reaction mixture was quenched with saturated ammonium chloride solution and extracted with ethyl acetate (2×100 mL). The combined organic layer was washed with water (50 mL), brine (50 mL), dried over anhydrous sodium sulfate and concentrated under vacuum. The residue was purified by combiflash chromatography using 5% ethyl acetate in hexane as an eluent to afford the title compound (1.8 g, 85%); $^1$H NMR (400 MHz, DMSO-d$_6$): δ 8.28 (d, J=4.0 Hz, 1H), 8.00 (d, J=2.4 Hz, 1H), 7.61 (dd, J=2.4 Hz, J=9.2 Hz, 1H), 7.10 (d, J=9.2 Hz, 1H), 2.98 (d, J=5.2 Hz, 3H); LC-MS: m/z 237.0 (M+1)$^+$.

Step-b: Synthesis of N$^1$-methyl-4-(trifluoromethoxy)benzene-1,2-diamine

The title compound was synthesized using the same procedure which was followed for compound 1e using N-methyl-2-nitro-4-(trifluoromethoxy)aniline as starting material and stirring for 6 h (Yield: 92%); $^1$H NMR (400 MHz, DMSO-d$_6$): δ 6.44 (s, 1H), 6.42 (d, J=10.4 Hz, 1H), 6.33 (d, J=8.4 Hz, 1H), 4.84 (bs, 2H), 2.70 (s, 3H); LC-MS: m/z 207.0 (M+1)$^+$.

Step-c: Synthesis of ethyl 1-methyl-2-((1-methyl-5-(trifluoromethoxy)-1H-benzo[d]imidazol-2-yl) amino)-1H-benzo[d]imidazole-5-carboxylate The title compound was synthesized using the same procedure which was followed for Example 12 Step-b using ethyl 2-(1H-imidazole-1-carbothioamido)-1-methyl-1H-benzo[d]imidazole-5-carboxylate and N1-methyl-4-(trifluoromethoxy)benzene-1,2-diamine as starting materials (Yield: 37%); LC-MS: m/z 434.2 (M+1)$^+$.

Step-d: Synthesis of 1-methyl-2-((1-methyl-5-(trifluoromethoxy)-1H-benzo[d]imidazol-2-yl)amino)-1H-benzo[d]imidazole-5-carboxylic acid The title compound was synthesized using the same procedure which was followed for compound 1h using ethyl 1-methyl-2-((1-methyl-5-(trifluoromethoxy)-1H-benzo[d]imidazol-2-yl)amino)-1H-benzo[d]imidazole-5-carboxylate as starting material (Yield: 53%); $^1$H NMR (400 MHz, DMSO-d$_6$): δ 12.5 (bs, 2H), 8.10 (d, J=1.2 Hz, 1H), 7.79 (dd, J=1.6 Hz, J=8.4 Hz, 1H), 7.44 (s, 1H), 7.41-7.37 (m, 2H), 7.08 (d, J=8.8 Hz, 1H), 3.70 (s, 3H), 3.68 (s, 3H); LC-MS: m/z 406.1 (M+1)$^+$.

Example 16. Synthesis of 2-(benzo[d]oxazol-2-ylamino)-N-(2-hydroxyethyl)-1-methyl-1H-benzo[d]imidazole-5-carboxamide

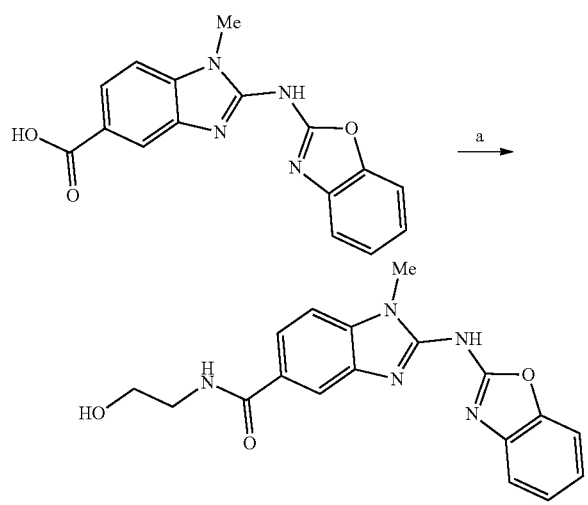

Conditions: a) 2-aminoethan-1-ol, HBTU, DIPEA, DMF, 0° C. - RT, 16 h

To a stirred solution of 2-(benzo[d]oxazol-2-ylamino)-1-methyl-1H-benzo[d]imidazole-5-carboxylic acid (50 mg, 0.16 mmol) in DMFA (1.0 mL) at 0° C. was added N-ethyldiisopropyl amine (0.03 mL, 0.16 mmol) and HBTU (62 mg, 0.16 mmol). The reaction mixture was stirred for 30 min, followed by the addition of 2-aminoethan-1-ol (10 mg, 0.16 mmol) and stirring was continued at RT for 16 h. Once the reaction was completed (monitored by TLC), the reaction mixture was diluted with cold water (20 mL) and stirred for 15 min. The solid obtained was filtered, washed with diethyl ether and dried under vacuum to afford the title compound (25 mg, 44%) as white solid; $^1$H NMR (400 MHz, DMSO-d$_6$): δ 12.30 (bs, 1H), 8.36 (t, J=5.4 Hz, 1H), 8.08 (d, J=0.9 Hz, 1H), 7.78-7.76 (m, 1H), 7.48 (d, J=8.3 Hz, 2H), 7.43 (d, J=7.8 Hz, 1H), 7.21 (t, J=7.3 Hz, 1H), 7.12 (t, J=7.3 Hz, 1H), 4.72 (bs, 1H), 3.63 (s, 3H), 3.54 (t, J=6.4 Hz, 2H), 3.37-3.34 (m, 2H); LC-MS: m/z 352.2 (M+1)$^+$.

Example 17. Synthesis of 2-(benzo[d]oxazol-2-ylamino)-N-(2-(2-hydroxyethoxy)ethyl)-1-methyl-1H-benzo[d]imidazole-5-carboxamide

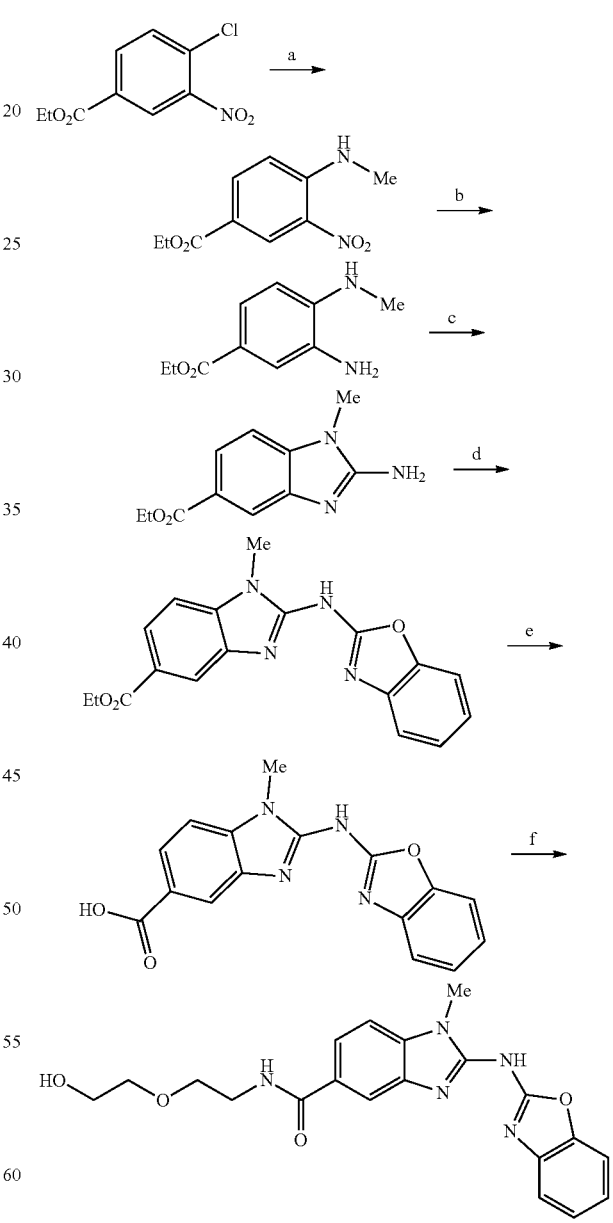

Conditions: a) Methyl amine, DMF, 60° C., 16 h; b) 10% Pd/C, MeOH, H$_2$, RT, 3 h; c) Cyanogen bromide, THF, H$_2$O, 60° C., 16 h; d) NaH, 2-chlorobenzo[d]oxazole, 1,4-Dioxane, RT, 16 h; e) LiOH•H$_2$O, THF, Ethanol, Water, 60° C., 16 h; f) 2-(2-aminoethoxy)ethan-1-ol, HBTU, DIPEA, DMF, 0° C. - RT, 16 h

Step-a: Synthesis of ethyl 4-(methylamino)-3-nitrobenzoate

To a solution of ethyl 4-chloro-3-nitrobenzoate (30.0 g, 131 mmol) in DMFA (100 mL) at RT was added methyl amine (26.8 mL (40% aqueous solution), 262 mmol) and the reaction mixture was stirred at 60° C. for 16 h. The reaction mixture was cooled to RT, diluted with cold water (1000 mL) and stirred for 1 h. The solid obtained was filtered and dried under vacuum to afford the product as a yellow solid (28.0 g, 96%); ¹H NMR (400 MHz, DMSO-d₆): δ 8.62 (d, J=2.0 Hz, 1H), 8.59 (bs, 1H), 7.99 (dd, J=2.0 Hz, J=8.8 Hz, 1H), 7.07 (d, J=8.8 Hz, 1H), 4.29 (q, J=6.8 Hz, 2H), 3.01 (d, J=5.2 Hz, 3H), 1.31 (t, J=6.8 Hz, 3H); LC-MS: m/z 225.0 (M+1)⁺.

Step-b: Synthesis of ethyl 3-amino-4-(methylamino)benzoate

To a solution of ethyl 4-(methylamino)-3-nitrobenzoate (27.0 g, 120 mmol) in methanol (300 mL) was added slurry of 10% Pd/C (2.8 g in 15 mL of ethanol) under nitrogen atmosphere. The flask was kept in a Parr shaker at RT under hydrogen (60 psi) for 3 h. The reaction mixture was filtered through celite bed and concentrated under vacuum to afford the title compound (19.0 g, 82%); ¹H NMR (400 MHz, DMSO-d₆): δ 7.23 (dd, J=1.6 Hz, J=8.4 Hz 1H), 7.16 (d, J=1.6 Hz, 1H), 6.39 (d, J=8.4 Hz, 1H), 5.38-5.37 (m, 1H), 4.66 (s, 2H), 4.18 (q, J=7.2 Hz, 2H), 2.77 (d, J=5.2 Hz, 3H), 1.26 (t, J=7.2 Hz, 3H); LC-MS: m/z 195.1 (M+1)⁺.

Step-c: Synthesis of ethyl 2-amino-1-methyl-1H-benzo[d]imidazole-5-carboxylate To a solution of ethyl 3-amino-4-(methylamino)benzoate (17.0 g, 87.6 mmol) in THF (68 mL) and water (170 mL) at RT was added cyanogen bromide (11.13 g, 105.2 mmol) and the reaction mixture was stirred at 60° C. for 16 h. The reaction mixture was cooled to RT and basified with saturated sodium bicarbonate solution. The solid obtained was filtered and dried under vacuum to afford the title compound which was used in the next step without further purification (18.0 g, 94%); ¹H NMR (400 MHz, DMSO-d₆): δ 7.70 (d, J=1.2 Hz, 1H), 7.59 (dd, J=1.2 Hz, J=8.4 Hz, 1H), 7.20 (d, J=8.4 Hz, 1H), 6.64 (s, 2H), 4.27 (q, J=6.8 Hz, 2H), 3.53 (s, 3H), 1.32 (t, J=6.8 Hz, 3H); LC-MS: m/z 220.1 (M+1)⁺.

Step-d: Synthesis of ethyl 2-(benzo[d]oxazol-2-ylamino)-1-methyl-1H-benzo[d]imidazole-5-carboxylate To a solution of ethyl 2-amino-1-methyl-1H-benzo[d]imidazole-5-carboxylate (4.0 g, 18.3 mmol) in 1,4-dioxane (40 mL) at 0° C. was added sodium hydride (60% dispersion in mineral oil) (1.09 g, 27.4 mmol) portion wise and stirred for 10 min. 2-chlorobenzo[d]oxazole (2.79 g, 18.3 mmol) was added to the reaction mixture and stirred at RT for 16 h. The reaction mixture was poured over cold water (100 mL) and stirred at RT for 5 to 10 min. The obtained solid was filtered, dried under vacuum and purified by combiflash column chromatography using 100% DCM as an eluent to afford the title compound (4.0 g, 60%); ¹H NMR (400 MHz, DMSO-d₆): δ 12.30 (bs, 1H), 8.24 (s, 1H), 7.88 (d, J=8.4 Hz, 1H), 7.53-7.43 (m, 3H), 7.22 (t, J=7.2 Hz, 1H), 7.13 (t, J=7.6 Hz, 1H), 4.33 (q, J=7.2 Hz, 2H), 3.64 (s, 3H), 1.35 (t, J=7.2 Hz, 3H); LC-MS: m/z 337.0 (M+1)⁺.

Step-e: Synthesis of 2-(benzo[d]oxazol-2-ylamino)-1-methyl-1H-benzo[d]imidazole-5-carboxylic acid To a stirred solution of ethyl 2-(benzo[d]oxazol-2-ylamino)-1-methyl-1H-benzo[d]imidazole-5-carboxylate (4.0 g, 11.90 mmol) in a mixture of solvent of THF (20 mL), ethanol (20 mL) and water (10 mL) was added lithium hydroxide monohydrate (1.25 g, 29.76 mmol). The reaction mixture was heated at 60° C. with stirring for 16 h. The reaction mixture was cooled to RT and concentrated under reduced pressure. The residue was dissolved in water (60 mL), acidified with 1 N HCl to obtain the solid which was filtered and dried under vacuum to afford the title compound (3.4 g, 93%); ¹H NMR (400 MHz, DMSO-d₆): δ 12.60 (bs, 2H), 8.20 (d, J=1.6 Hz, 1H), 7.87 (dd, J=1.6 Hz, J=8.0 Hz, 1H), 7.51-7.48 (m, 2H), 7.44 (d, J=7.2 Hz, 1H), 7.23-7.20 (m, 1H), 7.15-7.11 (m, 1H), 3.64 (s, 3H); LC-MS: m/z 309.1 (M+1)⁺.

Step-f: Synthesis of 2-(benzo[d]oxazol-2-ylamino)-N-(2-(2-hydroxyethoxy)ethyl)-1-methyl-1H-benzo[d]imidazole-5-carboxamide To a stirred solution of 2-(benzo[d]oxazol-2-ylamino)-1-methyl-1H-benzo[d]imidazole-5-carboxylic acid (3.0 g, 9.74 mmol) in DMFA (30 mL) at 0° C. was added N-ethyldiisopropyl amine (4.36 mL, 24.25 mmol) and HBTU (4.06 g, 10.71 mmol). The reaction mixture was stirred for 30 min, followed by the addition of 2-(2-aminoethoxy)ethan-1-ol (1.02 g, 9.74 mmol) and stirring was continued at RT for 16 h. Once the reaction was completed (monitored by TLC), the reaction mixture was diluted with cold water (300 mL) and stirred for 30 min. The solid obtained was filtered, dried under vacuum and purified by combiflash column chromatography using 5% methanol in DCM as an eluent to afford the title compound (2.9 g, 75%) as white solid; ¹H NMR (400 MHz, DMSO-d₆): δ 12.20 (bs, 1H), 8.43 (t, J=5.3 Hz, 1H), 8.07 (s, 1H), 7.76 (d, J=8.4 Hz, 1H), 7.48 (d, J=7.9 Hz, 2H), 7.43 (d, J=7.8 Hz, 1H), 7.21 (t, J=7.3 Hz, 1H), 7.11 (t, J=7.3 Hz, 1H), 4.60 (bs, 1H), 3.63 (s, 3H), 3.57-3.42 (m, 8H); LC-MS: m/z 396.2 (M+1)⁺.

Example 18. Synthesis of N-(2-aminoethyl)-2-(benzo[d]oxazol-2-ylamino)-1-methyl-1H-benzo[d]imidazole-5-carboxamide hydrochloride

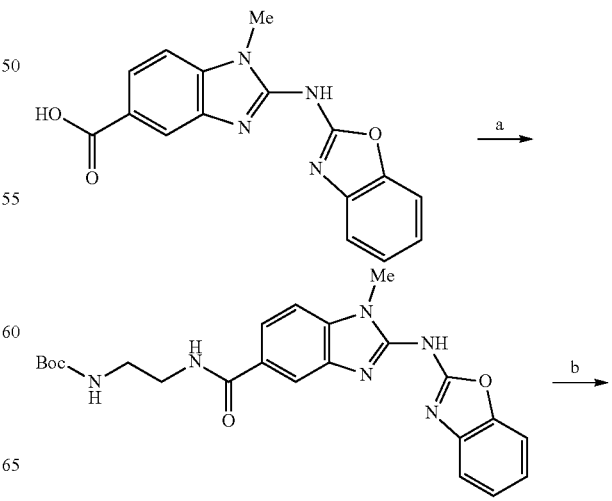

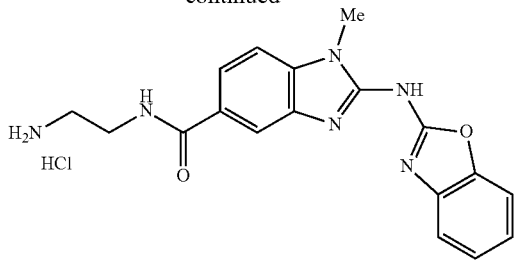

Conditions: a) tert-butyl (2-aminoethyl)carbamate, HBTU, DIPEA, DMF, 0° C - RT, 16 h; b) 4N HCl in 1,4-Dioxane, THF, 0° C. - RT 3 h

Step-a: Synthesis of tert-butyl (2-(2-(benzo[d]oxazol-2-ylamino)-1-methyl-1H-benzo[d]imidazole-5-carboxamido)ethyl)carbamate The title compound was synthesized using the same procedure which was followed for Example 6 Step-e using 2-(benzo[d]oxazol-2-ylamino)-1-methyl-1H-benzo[d]imidazole-5-carboxylic acid and tert-butyl (2-aminoethyl)carbamate as starting materials (Yield: 51%); $^1$H NMR (400 MHz, DMSO-$d_6$): δ 12.20 (bs, 1H), 8.41 (t, J=5.1 Hz, 1H), 8.08 (s, 1H), 7.75 (d, J=8.3 Hz, 1H), 7.48 (d, J=8.4 Hz, 2H), 7.43 (d, J=7.8 Hz, 1H), 7.23-7.19 (m, 1H), 7.14-7.09 (m, 1H), 6.92 (d, J=5.4 Hz, 1H), 3.64 (s, 3H), 3.34-3.33 (m, 2H merged with DMSO moisture peak), 3.15-3.10 (m, 2H), 1.38 (s, 9H); LC-MS: m/z 451.55 (M+1)$^+$.

Step-b: Synthesis of N-(2-aminoethyl)-2-(benzo[d]oxazol-2-ylamino)-1-methyl-1H-benzo[d]imidazole-5-carboxamide hydrochloride To a solution of tert-butyl (2-(2-(benzo[d]oxazol-2-ylamino)-1-methyl-1H-benzo[d]imidazole-5-carboxamido)ethyl)carbamate (50 mg, 0.11 mmol) in THF (2 mL) at 0° C. was added 4 N HCl in 1,4-dioxane (0.5 mL) and reaction mixture was stirred at RT for 3 h. The reaction mixture was concentrated on rotary evaporator and stirred in diethyl ether (10 mL). The solid obtained was filtered and dried under vacuum to afford the titled compound (35 mg, 81%); $^1$H NMR (400 MHz, DMSO-$d_6$): δ 12.40 (bs, 1H), 8.70 (s, 1H), 8.13 (s, 1H), 7.96 (bs, 3H), 7.86 (d, J=8.3 Hz, 1H), 7.56 (d, J=8.3 Hz, 1H), 7.48 (d, J=7.9 Hz, 2H), 7.25 (t, J=7.6 Hz, 1H), 7.17 (t, J=7.8 Hz, 1H), 3.67 (s, 3H), 3.55 (q, J=5.7 Hz, 2H), 3.03-2.99 (m, 2H); LC-MS: m/z 351.10 (M+1)$^+$.

Example 19. Synthesis of 2-(benzo[d]oxazol-2-ylamino)-N-(2-(2-(dimethylamino)acetamido)ethyl)-1-methyl-1H-benzo[d]imidazole-5-carboxamide

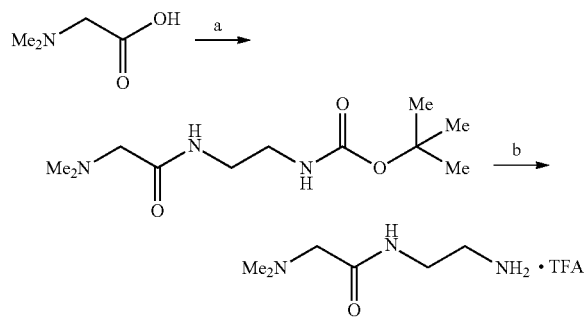

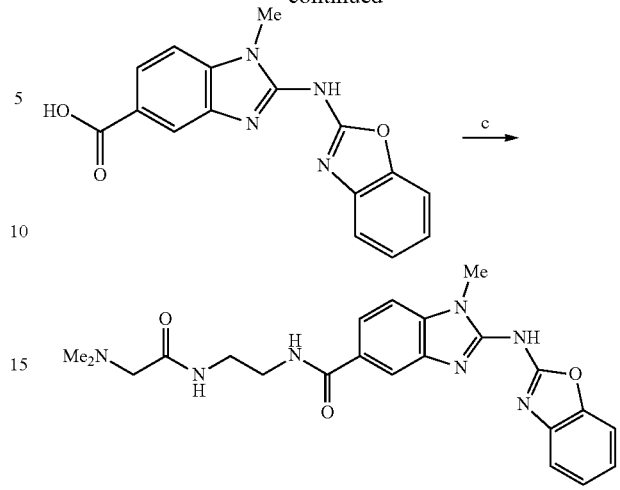

Conditions: a) tert-butyl (2-aminoethyl)carbamate, HBTU, DIPEA, DMF, 0° C. - RT, 16 h; b) TFA, DCM, 0° C. - RT, 16 h; c) N-(2-aminoethyl)-2-(dimethylamino)acetamide trifluoroacetate, HBTU, DIPEA, DMF, 0° C. - RT, 16 h

Step-a: Synthesis of tert-butyl (2-(2-(dimethylamino)acetamido)ethyl)carbamate To a stirred solution of dimethylglycine (1.0 g, 9.71 mmol) in DMFA (10 mL) at 0° C. was added N-ethyldiisopropyl amine (1.69 mL, 9.71 mmol) and HBTU (3.68 g, 9.71 mmol). The reaction mixture was stirred for 30 min, followed by the addition of tert-butyl (2-aminoethyl)carbamate (1.55 g, 9.71 mmol). The reaction mixture was stirred at RT for 16 h. Once the reaction was completed (monitored by TLC), the reaction mixture was diluted with cold water (50 mL) and extracted with EtOAc (2×100 mL). The combined organic layers were washed with water (3×30 mL), brine solution (50 mL), dried over anhydrous sodium sulfate and concentrated under vacuum. The solid obtained was stirred in diethyl ether (20 mL) for 5 min, filtered and dried under vacuum to afford the title compound (600 mg, 25%); $^1$H NMR (400 MHz, DMSO-$d_6$): δ 7.77 (t, J=5.6 Hz, 1H), 6.83 (t, J=5.2 Hz, 1H), 3.11 (q, J=6.2 Hz, 2H), 2.99 (q, J=6.1 Hz, 2H), 2.82 (s, 2H), 2.18 (s, 6H), 1.37 (s, 9H); LC-MS: m/z 246.15 (M+1)$^+$.

Step-b: Synthesis of N-(2-aminoethyl)-2-(dimethylamino)acetamide trifluoroacetate To a solution of tert-butyl (2-(2-(dimethylamino)acetamido)ethyl)carbamate (600 mg, 2.45 mmol) in DCM (15 mL) at 0° C. was added TFA (0.56 mL, 7.34 mmol) and reaction mixture was stirred at RT for 16 h. The reaction mixture was concentrated on rotary evaporator and dried under vacuum to afford the titled compound (600 mg, 100%); $^1$H NMR (400 MHz, DMSO-$d_6$): δ 9.75 (bs, 1H), 8.75 (t, J=5.6 Hz, 1H), 7.90 (bs, 2H), 3.88 (s, 2H), 3.38 (q, J=6.2 Hz, 2H), 2.91 (q, J=5.9 Hz, 2H), 2.82 (s, 6H); LC-MS: m/z 146.20 (M+1)$^+$.

Step-c: Synthesis of 2-(benzo[d]oxazol-2-ylamino)-N-(2-(2-(dimethylamino)acetamido)ethyl)-1-methyl-1H-benzo[d]imidazole-5-carboxamide To a stirred solution of 2-(benzo[d]oxazol-2-ylamino)-1-methyl-1H-benzo[d]imidazole-5-carboxylic acid (100 mg, 0.32 mmol) in DMFA (4 mL) at 0° C. was added N-ethyl-diisopropyl amine (0.17 mL, 0.97 mmol) and HBTU (123 mg, 0.32 mmol). The reaction mixture was stirred for 30 min, followed by the addition of N-(2-aminoethyl)-2-(dimethylamino)acetamide trifluoroacetate (145 mg, 0.39 mmol). The reaction mixture was then stirred at RT for 16 h. Once the reaction was completed (monitored by TLC), the reaction mixture was diluted with cold water (15 mL). The solid obtained was filtered, washed with diethyl ether and dried under vacuum to afford the title compound (40 mg, 28%) as a white solid; $^1$H NMR (400 MHz, DMSO-$d_6$): δ 12.20 (bs, 1H), 8.44 (t, J=4.9 Hz, 1H), 8.07 (s, 1H), 7.92 (bs, 1H), 7.74 (d, J=7.8 Hz, 1H), 7.49-7.47 (m, 2H), 7.43 (d, J=7.8 Hz, 1H), 7.21 (t, J=7.6 Hz, 1H), 7.12 (t, J=7.6 Hz, 1H), 3.63 (s, 3H), 3.37 (t, J=5.2 Hz, 2H), 3.35 (2H merged with DMSO moisture peak), 2.86 (s, 2H), 2.19 (s, 6H); LC-MS: m/z 436.0 (M+1)$^+$.

Example 20. Synthesis of 2-(benzo[d]oxazol-2-ylamino)-1-methyl-N-(2-morpholinoethyl)-1H-benzo[d]imidazole-5-carboxamide The title compound was synthesized using the same procedure which was followed for compound 1i using 2-morpholinoethan-1-amine and 2-(benzo[d]oxazol-2-ylamino)-1-methyl-1H-benzo[d]imidazole-5-carboxylic acid as starting materials. $^1$H NMR (400 MHz, DMSO-$d_6$): δ 12.21 (bs, 1H), 8.33 (s, 1H), 8.06 (s, 1H), 7.73 (d, J=8.4 Hz, 1H), 7.48 (d, J=8.4 Hz, 1H), 7.43 (d, J=8.0 Hz, 2H), 7.21 (t, J=7.2 Hz, 1H), 7.11 (t, J=8.0 Hz, 1H), 3.63 (s, 3H), 3.58 (t, J=3.6 Hz, 4H), 3.41 (q, J=6.4 Hz, 2H), 3.30 (2H merged with DMSO moisture peak), 2.43 (bs, 4H); LC-MS: m/z 421.2 (M+1)$^+$.

Example 21. Synthesis of 2-(benzo[d]oxazol-2-ylamino)-N-(2-(dimethylamino)ethyl)-1-methyl-1H-benzo[d]imidazole-5-carboxamide The title compound was synthesized using the same procedure which was followed for compound 1i using N,N-dimethylethane-1,2-diamine and 2-(benzo[d]oxazol-2-ylamino)-1-methyl-1H-benzo[d]imidazole-5-carboxylic acid as starting materials. $^1$H NMR (400 MHz, DMSO-$d_6$): δ 12.21 (bs, 1H), 8.29 (t, J=5.2 Hz, 1H), 8.07 (s, 1H), 7.74 (d, J=8.4 Hz, 1H), 7.48-7.42 (m, 3H), 7.21 (t, J=7.6 Hz, 1H), 7.11 (t, J=8.0 Hz, 1H), 3.63 (s, 3H), 3.39-3.35 (m, 2H), 2.50-2.42 (m, 2H), 2.19 (s, 6H); LC-MS: m/z 379.2 (M+1)$^+$.

Example 22. Synthesis of 2-(benzo[d]oxazol-2-ylamino)-N-(2-((4,5-dihydro-1H-imidazol-2-yl)amino)ethyl)-1-methyl-1H-benzo[d]imidazole-5-carboxamide The title compound was synthesized using the same procedure which was followed for compound 1i using N$^1$-(4,5-dihydro-1H-imidazol-2-yl)ethane-1,2-diamine and 2-(benzo[d]oxazol-2-ylamino)-1-methyl-1H-benzo[d]imidazole-5-carboxylic acid as starting materials. $^1$H NMR (400 MHz, DMSO-$d_6$): δ 12.30 (bs, 2H), 8.52 (bs, 1H), 8.20 (bs, 1H), 8.09 (s, 1H), 7.75 (d, J=8.4 Hz, 1H), 7.52-7.43 (m, 3H), 7.21 (t, J=7.2 Hz, 1H), 7.12 (t, J=8.0 Hz, 1H), 3.64 (s, 3H), 3.59 (s, 2H), 3.45-3.43 (m, 2H), 3.36-3.34 (m, 4H); LC-MS: m/z 417.05 (M−1)$^−$.

Example 23. Synthesis of 2-(benzo[d]oxazol-2-ylamino)-N-(2-hydroxypropyl)-1-methyl-1H-benzo[d]imidazole-5-carboxamide The title compound was synthesized using the same procedure which was followed for compound 1i using 1-aminopropan-2-ol and 2-(benzo[d]oxazol-2-ylamino)-1-methyl-1H-benzo[d]imidazole-5-carboxylic acid as starting materials. $^1$H NMR (400 MHz, DMSO-$d_6$): δ12.30 (bs, 1H), 8.36 (t, J=5.6 Hz, 1H), 8.19 (d, J=1.2 Hz, 1H), 7.78 (dd, J=1.2 Hz, J=8.4 Hz, 1H), 7.52-7.36 (m, 3H), 7.21-7.19 (m, 1H), 7.14-7.09 (m, 1H), 4.87-4.78 (m, 1H), 3.81 (q, J=6.0 Hz, 1H), 3.64 (s, 3H), 3.24-3.20 (m, 2H), 1.14 (d, J=6.8 Hz, 3H); LC-MS: m/z 366.2 (M+1)$^+$.

Example 24. Synthesis of 2-(benzo[d]oxazol-2-ylamino)-N-(2,3-dihydroxypropyl)-1-methyl-1H-benzo[d]imidazole-5-carboxamide The title compound was synthesized using the same procedure which was followed for compound 1i using 3-aminopropane-1,2-diol and 2-(benzo[d]oxazol-2-ylamino)-1-methyl-1H-benzo[d]imidazole-5-carboxylic acid as starting materials. $^1$H NMR (400 MHz, DMSO-$d_6$): δ 12.30 (bs, 1H), 8.31 (t, J=5.2 Hz, 1H), 8.08 (s, 1H), 7.77 (dd, J=1.6 Hz, J=8.4 Hz, 1H), 7.49-7.42 (m, 3H), 7.21 (t, J=8.0 Hz, 1H), 7.11 (t, J=7.2 Hz, 1H), 4.82 (d, J=4.4 Hz, 1H), 4.58 (bs, 1H), 3.64 (s, 3H), 3.45-3.37 (m, 3H), 3.26-3.19 (m, 2H); LC-MS: m/z 382.1 (M+1)$^+$.

Example 25. Synthesis of 2-(benzo[d]oxazol-2-ylamino)-N-(2-(2-hydroxypropoxy)ethyl)-1,6-dimethyl-1H-benzo[d]imidazole-5-carboxamide The title compound was synthesized using the same procedure which was followed for compound 1i using 1-(2-aminoethoxy)propan-2-ol and 2-(benzo[d]oxazol-2-ylamino)-1-methyl-1H-benzo[d]imidazole-5-carboxylic acid as starting materials. $^1$H NMR (400 MHz, DMSO-$d_6$): δ 12.30 (bs, 1H), 8.42 (t, J=5.2 Hz, 1H), 8.07 (s, 1H), 7.75 (dd, J=1.2 Hz, J=8.4 Hz, 1H), 7.49-7.42 (m, 3H), 7.21 (t, J=7.6 Hz, 1H), 7.11 (t, J=8.0 Hz, 1H), 4.57 (bs, 1H), 3.75 (q, J=5.6 Hz, 1H), 3.63 (s, 3H), 3.57-3.54 (m, 2H), 3.46-3.43 (m, 2H), 3.29-3.23 (m, 2H), 1.03 (d, J=6.4 Hz, 3H); LC-MS: m/z 410.2 (M+1)$^+$.

Example 26. Synthesis of 2-(benzo[d]oxazol-2-ylamino)-N-((3-hydroxyoxetan-3-yl)methyl)-1-methyl-1H-benzo[d]imidazole-5-carboxamide The title compound was synthesized using the same procedure which was followed for compound 1i using 3-(aminomethyl)oxetan-3-ol and 2-(benzo[d]oxazol-2-ylamino)-1-methyl-1H-benzo[d]imidazole-5-carboxylic acid as starting materials. $^1$H NMR (400 MHz, DMSO-$d_6$): δ 12.30 (bs, 1H), 8.55 (t, J=5.2 Hz, 1H), 8.10 (d, J=1.2 Hz, 1H), 7.79 (dd, J=1.6 Hz, J=8.4 Hz, 1H), 7.51-7.42 (m, 3H), 7.21 (t, J=7.6 Hz, 1H), 7.14 (t, J=7.6 Hz, 1H), 5.90 (s, 1H), 4.52 (d, J=6.8 Hz, 2H), 4.41 (d, J=6.4 Hz, 2H), 3.64 (s, 3H), 3.59 (d, J=6.0 Hz, 2H); LC-MS: m/z 394.2 (M+1)$^+$.

Example 27. Synthesis of 2-(benzo[d]oxazol-2-ylamino)-N-(2-(2-hydroxy-2-methylpropoxy)ethyl)-1-methyl-1H-benzo[d]imidazole-5-carboxamide The title compound was synthesized using the same procedure which was followed for compound 1i using 1-(2-aminoethoxy)-2-methylpropan-2-ol and 2-(benzo[d]oxazol-2-ylamino)-1-methyl-1H-benzo[d]imidazole-5-carboxylic acid as starting materials. $^1$H NMR (400 MHz, DMSO-$d_6$): δ 12.30 (bs, 1H), 8.43 (t, J=5.2 Hz, 1H), 8.07 (d, J=1.2 Hz, 1H), 7.75 (dd, J=2.4 Hz, J=8.4 Hz, 1H), 7.49-7.42 (m, 3H), 7.21 (dd, J=1.2 Hz, J=7.6 Hz, 1H), 7.12 (dd, J=1.2

Hz, J=7.6 Hz, 1H), 4.34 (bs, 1H), 3.63 (s, 3H), 3.57 (t, J=6.4 Hz, 2H), 3.47-3.43 (m, 2H), 3.20 (s, 2H), 1.09 (s, 6H); LC-MS: m/z 424.2 (M+1)+.

Example 28. Synthesis of 2-(benzo[d]oxazol-2-ylamino)-1-methyl-N-(2-(pyrrolidin-1-yl)ethyl)-1H-benzo[d]imidazole-5-carboxamide The title compound was synthesized using the same procedure which was followed for compound 1i using 2-(pyrrolidin-1-yl)ethan-1-amine and 2-(benzo[d]oxazol-2-ylamino)-1-methyl-1H-benzo[d]imidazole-5-carboxylic acid as starting materials. $^1$H NMR (400 MHz, DMSO-$d_6$): δ 12.24 (bs, 1H), 8.38 (t, J=5.6 Hz, 1H), 8.07 (s, 1H), 7.74 (d, J=8.4 Hz, 1H), 7.49-7.42 (m, 3H), 7.21 (t, J=6.8 Hz, 1H), 7.11 (t, J=7.2 Hz, 1H) 3.69 (s, 3H), 3.48-3.37 (m, 2H), 2.64-2.57 (m, 2H), 2.50 (4H merged in DMSO peak), 1.66 (bs, 4H); LC-MS: m/z 405.2 (M+1)+.

Example 29. Synthesis of 2-(2-(2-(benzo[d]oxazol-2-ylamino)-1-methyl-1H-benzo[d]imidazole-5-carboxamido)ethoxy)acetic acid

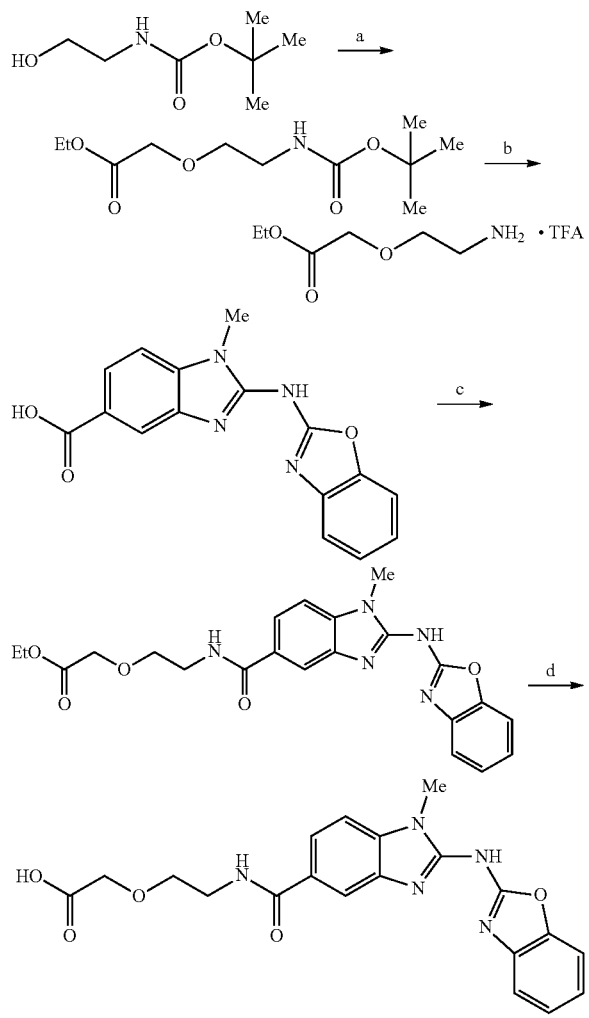

Conditions: a) ethyl 2-bromoacetate, NaH, KI, THF, 0° C. - RT, 2 h; b) TFA, DCM, RT, 5 h; c) ethyl 2-(2-aminoethoxy)acetate trifluoro acetate, HBTU, DIPEA, DMF, 0° C. - RT, 16h; d) LiOH•H₂O, Ethanol, THF, Water, RT, 3 h Step-a: Synthesis of ethyl 2-(2-((tert-butoxycarbonyl)amino)ethoxy)acetate To a solution of tert-butyl (2-hydroxyethyl)carbamate (1.0 g, 6.21 mmol) in THF (10 mL) at 0° C. was added sodium hydride (60% dispersion in mineral oil) (397 mg, 9.93 mmol) by portions followed by the addition of potassium iodide (164 mg, 0.99 mmol) and ethylbromo acetate (2.07 g, 12.42 mmol). The reaction mixture was stirred at RT for 2 h. The reaction mixture was diluted with cold water (60 mL) and extracted with ethyl acetate (3×60 mL). The combined organic layers were washed with water (30 mL), brine solution (30 mL), dried over anhydrous sodium sulfate and concentrated under vacuum. The residue was purified by combiflash column chromatography using 1% methanol in dichloromethane as an eluent to afford the titled compound (1.0 g, 65%); $^1$H NMR (400 MHz, DMSO-$d_6$): δ 6.74 (bs, 1H), 4.14-4.08 (m, 4H), 3.45 (t, J=5.6 Hz, 2H), 3.08 (q, J=6.2 Hz, 2H), 1.37 (s, 9H), 1.19 (t, J=6.8 Hz, 3H); LC-MS: m/z 148.1 (M-Boc)+.

Step-b: Synthesis of ethyl 2-(2-aminoethoxy)acetate trifluoroacetic acid salt

To a stirred solution of ethyl 2-(2-((tert-butoxycarbonyl)amino)ethoxy)acetate (1.0 g, 4.05 mmol) in DCM (5 mL) at RT was added trifluoroacetic acid (1 mL) and stirred at RT for 5 h. The reaction mixture was concentrated under reduced pressure to afford the titled compound (1.1 g, 100%) which was used in the next step without any further purification; $^1$H NMR (400 MHz, DMSO-$d_6$): δ 7.88 (bs, 3H), 4.17 (s, 2H), 4.14 (q, J=6.8 Hz, 2H), 3.68 (t, J=5.0 Hz, 2H), 3.01 (q, J=5.2 Hz, 2H), 1.21 (t, J=7.0 Hz, 3H); LC-MS: m/z 148.2 (M+1)+.

Step-c: Synthesis of ethyl 2-(2-(2-(benzo[d]oxazol-2-ylamino)-1-methyl-1H-benzo[d]imidazole-5-carboxamido)ethoxy)acetate To a stirred solution of 2-(benzo[d]oxazol-2-ylamino)-1-methyl-1H-benzo[d]imidazole-5-carboxylic acid (150 mg, 0.48 mmol) in DMFA (2 mL) at 0° C. was added N-ethyldiisopropyl amine (0.26 mL, 1.46 mmol) and HBTU (184 mg, 0.48 mmol). The reaction mixture was stirred for 30 min, followed by the addition of ethyl 2-(2-aminoethoxy) acetate trifluoroacetate (129 mg, 0.53 mmol). The reaction mixture was then stirred at RT for 16 h. Once the reaction was completed (monitored by TLC), the reaction mixture was diluted with cold water (6 mL) and stirred for 5 min. The solid precipitated was filtered and dried under vacuum to afford the titled compound (125 mg, 59%); $^1$H NMR (400 MHz, DMSO-$d_6$): δ 12.3 (bs, 1H), 8.46 (bs, 1H), 8.08 (s, 1H), 7.76 (d, J=8.4 Hz, 1H), 7.49-7.47 (m, 2H), 7.43 (d, J=7.6 Hz, 1H), 7.21 (t, J=8.0 Hz, 1H), 7.14 (t, J=7.6 Hz, 1H), 4.15 (s, 2H), 4.12 (q, J=7.0 Hz, 2H), 3.65-3.62 (m, 5H), 3.47 (q, J=5.8 Hz, 2H), 1.19 (t, J=7.0 Hz, 3H); LC-MS: m/z 438.1 (M+1)+.

Step-d: Synthesis of 2-(2-(2-(benzo[d]oxazol-2-ylamino)-1-methyl-1H-benzo[d]imidazole-5-carboxamido)ethoxy)acetic acid To a solution of ethyl 2-(2-(2-(benzo[d]oxazol-2-ylamino)-1-methyl-1H-benzo[d]imidazole-5-carboxamido) ethoxy)acetate (110 mg, 0.25 mmol) in a mixture of solvents of THF (1 mL), ethanol (1 mL) and water (0.5 mL) was added lithium hydroxide monohydrate (26 mg, 0.63 mmol).

The reaction mixture was stirred at RT for 3 h. The reaction mixture was concentrated under reduced pressure, the residue was dissolved in water (5 mL) and acidified with 1 N HCl to obtain the solid which was filtered and dried under vacuum to afford the titled compound (80 mg, 78%); $^1$H NMR (400 MHz, DMSO-$d_6$): δ 12.60 (bs, 1H), 8.47 (s, 1H), 8.08 (s, 1H), 7.77 (d, J=8.4 Hz, 1H), 7.50-7.43 (m, 3H), 7.22 (t, J=7.6 Hz, 1H), 7.13 (t, J=7.2 Hz, 1H), 4.06 (s, 2H), 3.64 (bs, 5H), 3.45 (q, J=5.2 Hz, 2H); LC-MS: m/z 410.4 (M+1)$^+$.

Example 30. 2-(2-(2-(benzo[d]oxazol-2-ylamino)-1-methyl-1H-benzo[d]imidazole-5-carboxamido)ethoxy)ethyl DL-valinate hydrochloride Step-b: Synthesis of 2-(2-(2-(benzo[d]oxazol-2-ylamino)-1-methyl-1H-benzo[d]imidazole-5-carboxamido)ethoxy)ethyl (tert-butoxycarbonyl)-DL-valinate To a stirred solution of 2-(benzo[d]oxazol-2-ylamino)-N-(2-(2-hydroxyethoxy)ethyl)-1-methyl-1H-benzo[d]imidazole-5-carboxamide (70 mg, 0.18 mmol) and (tert-butoxycarbonyl)-DL-valine (42 mg, 0.19 mmol) in DMFA (5 mL) at 0° C. was added N-ethyldiisopropyl amine (0.04 mL, 0.21 mmol) and HATU (80 mg, 0.21 mmol). The reaction mixture was stirred at RT for 16 h. Once the reaction was completed (monitored by TLC), the reaction mixture was diluted with

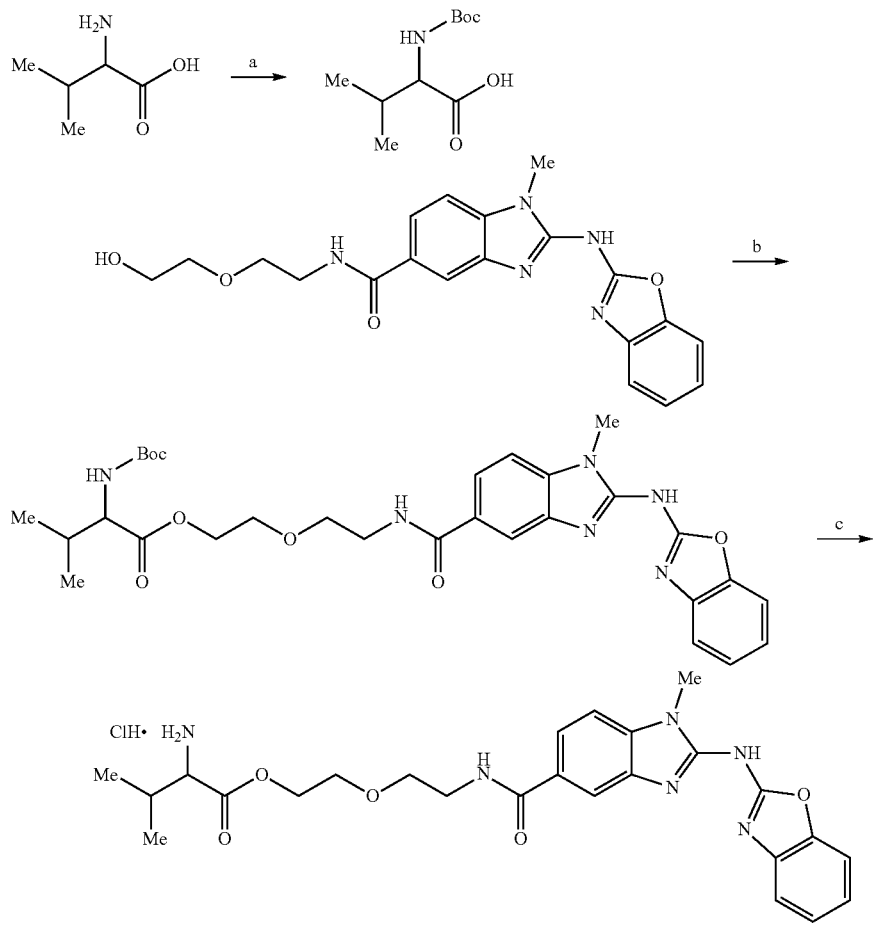

Conditions: a) Di-tert-butyl dicarbonate, Sodium hydroxide, THF, Water, RT, 16 h; b) (tert-butoxycarbonyl)valine, HATU, DIPEA, DMF, 0° C. - RT, 16 h; c) 4N HCl in 1,4-dioxane, 1,4-dioxane, 10° C. - RT, 16 h Step-a: Synthesis of (tert-butoxycarbonyl)-DL-valine To a stirred solution of DL-valine (2.0 g, 17.07 mmol) in THF (25 mL) and water (20 mL) at RT was added sodium hydroxide (0.82 g, 20.5 mmol) and di-tert-butyl dicarbonate (4.09 g, 18.77 mmol) and the reaction mixture was stirred for 16 h. The mixture was cooled to 0° C., acidified with 1 N HCl and extracted with EtOAc (2×50 mL). The combined organic layers were washed with brine solution (30 mL), dried over anhydrous sodium sulfate and concentrated under vacuum. Crude product (1.8 g) was used in the next step without any further purification.

cold water (20 mL) and extracted with ethyl acetate (2×30 mL). The combined organic layers were washed with water (20 mL), brine solution (20 mL), dried over anhydrous sodium sulfate and concentrated under vacuum. The residue was purified by combiflash column chromatography using 4.1% methanol in dichloromethane as an eluent to afford the titled compound (40 mg, 38%); LC-MS: m/z 595.7 (M+1)$^+$.

Step-c: Synthesis of 2-(2-(2-(benzo[d]oxazol-2-ylamino)-1-methyl-1H-benzo[d]imidazole-5-carboxamido)ethoxy)ethyl DL-valinate hydrochloride To a stirred solution of 2-(2-(2-(benzo[d]oxazol-2-ylamino)-1-methyl-1H-benzo[d]imidazole-5-carboxamido)

ethoxy)ethyl (tert-butoxycarbonyl)-DL-valinate (40 mg, 0.07 mmol) in 1,4-dioxane (5 mL) at 10° C. was added 4 N HCl in 1,4-dioxane (0.03 mL, 0.13 mmol) and the reaction mixture was stirred at RT for 16 h. Once the reaction was completed (monitored by TLC), the reaction mixture was concentrated under reduced pressure and lyophilized for 18 h to afford the titled compound (19 mg, 53%) as hydrochloride salt; $^1$H NMR (400 MHz, DMSO-$d_6$): δ 12.50 (s, 1H), 8.52 (bs, 1H), 8.40 (bs, 3H), 8.09 (s, 1H), 7.80 (d, J=8.4 Hz, 1H), 7.54 (d, J=7.6 Hz, 1H), 7.48 (d, J=7.6 Hz, 2H), 7.25 (t, J=7.2 Hz, 1H), 7.17 (t, J=8.0 Hz, 1H), 4.43-4.40 (m, 2H), 4.28-4.25 (m, 2H), 3.95 (bs, 1H), 3.70-3.67 (s, 3H), 3.61-3.57 (m, 2H), 3.45-3.44 (m, 2H), 2.15-2.11 (m, 1H), 0.97 (d, J=6.8 Hz, 3H), 0.92 (d, J=6.8 Hz, 3H); LC-MS: m/z 495.1 (M+1)$^+$.

Examples 31 and 32. Synthesis of 1-methyl-2-((6-(trifluoromethyl)benzo[d]oxazol-2-yl)amino)-1H-benzo[d]imidazole-5-carboxylic acid and Synthesis of N-(2-methoxyethyl)-1-methyl-2-((6-(trifluoromethyl)benzo[d]oxazol-2-yl)amino)-1H-benzo[d]imidazole-5-carboxamide

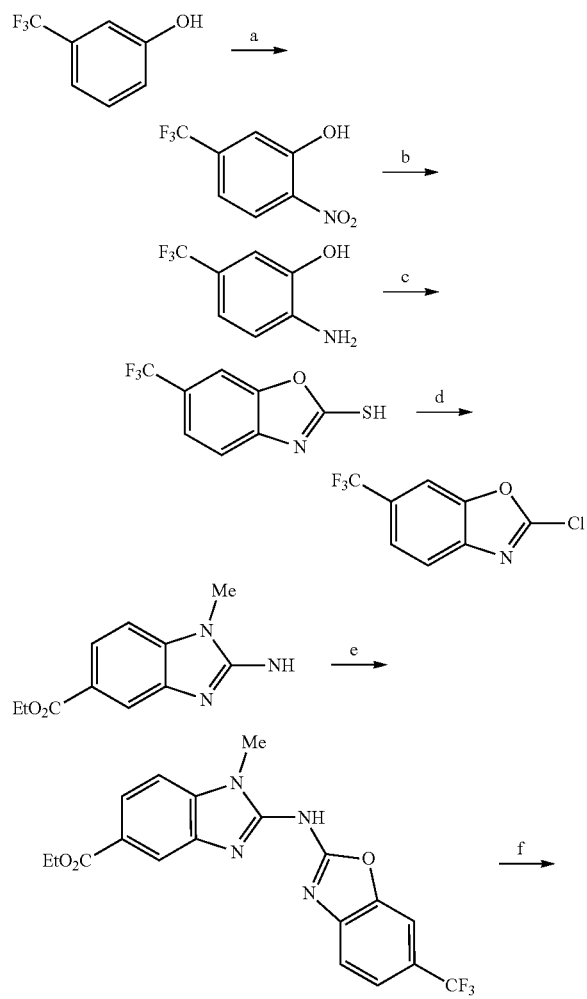

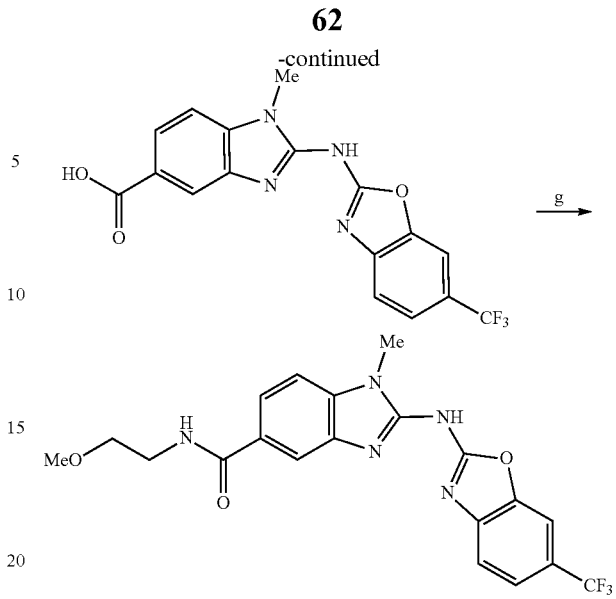

Conditions: a) HNO$_3$, Acetic acid, 0° C- RT, 16 h; b) 10% Pd/C, MeOH, H$_2$, RT, 16 h; c) Potassium ethyl xanthate, Ethanol, Reflux, 16 h; d) SOCl$_2$, Cat•DMF, reflux, 3 h; e) NaH, 2-chloro-6-(trifluoromethyl)benzo[d]oxazole, 1,4-Dioxane, RT, 16 h; f) LiOH•H$_2$O, THF, Ethanol, Water, 60° C., 16 h; g) 2-methoxyethylamine, DPPA, DIPEA, DMF, 0°C. - RT, 16 h Step-a: Synthesis of 2-nitro-5-(trifluoromethyl)phenol To a solution of 3-(trifluoromethyl)phenol (5.0 g, 30.86 mmol) in acetic acid (50 mL) was added 60% aqueous nitric acid (3.5 mL) dropwise at 0° C. Then the mixture was stirred at this temperature for 1.5 h and stirring was continued at RT for 16 h. The mixture was poured into ice water (80 mL) and extracted with EtOAc (2×100 mL). The combined organic layers were washed with brine solution (50 mL), dried over anhydrous sodium sulfate and concentrated in vacuum. The residue was purified by combiflash column chromatography using 5% ethyl acetate in hexane as eluent to afford the titled compound (1.0 g, 16%); $^1$H NMR (400 MHz, DMSO-$d_6$): δ 11.75 (bs, 1H), 8.06 (d, J=8.3 Hz, 1H), 7.41 (d, J=1.4 Hz, 1H), 7.32 (dd, J=1.4 Hz, J=8.3 Hz, 1H); LC-MS: m/z 206.0 (M−1)$^-$.

Step-b: Synthesis of 2-amino-5-(trifluoromethyl)phenol

To a solution of 2-nitro-5-(trifluoromethyl)phenol (1.0 g, 4.83 mmol) in methanol (15 mL) was added 10% Pd/C (100 mg) under nitrogen atmosphere. The reaction mixture was stirred under hydrogen balloon for 16 h. The reaction mixture was filtered through a celite bed and the filtrate was concentrated under vacuum to afford the title compound (850 mg, 99%); $^1$H NMR (400 MHz, DMSO-$d_6$): δ 9.58 (bs, 1H), 6.88 (s, 1H), 6.86 (s, 1H), 6.66 (d, J=7.8 Hz, 1H), 5.18 (s, 2H); LC-MS: m/z 178.0 (M+1)$^+$.

Step-c: Synthesis of 6-(trifluoromethyl)benzo[d]oxazole-2-thiol

To a solution of 2-amino-5-(trifluoromethyl)phenol (850 mg, 4.8 mmol) in ethanol (10 mL) at RT was added potassium ethyl-xanthate (1.69 g, 10.56 mmol) and the reaction mixture was refluxed for 16 h. The reaction mixture was concentrated under vacuum and diluted with cold water (50 mL), acidified with 1 N HCl. The solid obtained was filtered and dried under vacuum to afford the title compound (1.0 g, 95%); $^1$H NMR (400 MHz, DMSO-d$_6$): δ 14.2 (bs, 1H), 7.98 (s, 1H), 7.66 (d, J=8.4 Hz, 1H), 7.41 (d, J=7.8 Hz, 1H); LC-MS: m/z 217.9 (M–1)$^-$.

Step-d: Synthesis of 2-chloro-6-(trifluoromethyl) benzo[d]oxazole

To a solution of 6-(trifluoromethyl)benzo[d]oxazole-2-thiol (500 mg, 2.28 mmol) in thionyl chloride (4 mL) at RT was added dimethyl formamide (catalytic amount) and the reaction mixture was refluxed for 3 h. The reaction mixture concentrated, diluted with cold water (30 mL) and extracted with EtOAc (2×30 mL). The combined organic layers were washed with brine solution (20 mL), dried over anhydrous sodium sulfate and concentrated under vacuum to afford the title compound (290 mg, 57%); $^1$H NMR (400 MHz, DMSO-d$_6$): δ 8.31 (s, 1H), 7.97 (d, J=8.3 Hz, 1H), 7.80 (d, J=8.3 Hz, 1H).

Step-e: Synthesis of ethyl 1-methyl-2-((6-(trifluoromethyl)benzo[d]oxazol-2-yl)amino)-1H-benzo[d]imidazole-5-carboxylate To a solution of ethyl 2-amino-1-methyl-1H-benzo[d]imidazole-5-carboxylate (240 mg, 1.09 mmol) in 1,4-dioxane (8 mL) at 0° C. was added sodium hydride (60% dispersion in mineral oil) (109 mg, 2.74 mmol) followed by the addition of 2-chloro-6-(trifluoromethyl)benzo[d]oxazole (290 mg, 1.31 mmol). The reaction mixture was stirred at RT for 16 h. The reaction mixture was concentrated, diluted with cold water (15 mL) and stirred at RT for 30 min. The solid obtained was filtered, dried under vacuum and purified by combiflash column chromatography using 100% DCM as an eluent to afford the title compound (150 mg, 34%); $^1$H NMR (400 MHz, DMSO-d$_6$): δ 12.40 (bs, 1H), 8.25 (d, J=1.5 Hz, 1H), 7.89 (dd, J=1.5 Hz, J=8.3 Hz, 1H), 7.83 (s, 1H), 7.61-7.51 (m, 3H), 4.33 (q, J=6.9 Hz, 2H), 3.66 (s, 3H), 1.36 (t, J=6.9 Hz, 3H); LC-MS: m/z 405.30 (M+1)$^+$.

Step-f: Synthesis of 1-methyl-2-((6-(trifluoromethyl)benzo[d]oxazol-2-yl)amino)-1H-benzo[d]imidazole-5-carboxylic acid (Example 31)

To a stirred solution of ethyl 1-methyl-2-((6-(trifluoromethyl)benzo[d]oxazol-2-yl)amino)-1H-benzo[d]imidazole-5-carboxylate (80 mg, 0.20 mmol) in a mixture of solvent of THF (0.5 mL), ethanol (0.5 mL) and water (0.25 mL) was added lithium hydroxide monohydrate (20 mg, 0.50 mmol). The reaction mixture was heated at 60° C. for 16 h. The reaction mixture was cooled to RT and concentrated under reduced pressure. The residue was dissolved in water, acidified with 1 N HCl to obtain the solid which was filtered and dried under vacuum to afford the title compound (55 mg, 81%); $^1$H NMR (400 MHz, DMSO-d$_6$): δ 12.80 (bs, 1H), 12.40 (bs, 1H), 8.22 (s, 1H), 7.89 (d, J=8.3 Hz, 1H), 7.84 (s, 1H), 7.63-7.53 (m, 3H), 3.67 (s, 3H); LC-MS: m/z 377.05 (M+1)$^+$.

Step-g: Synthesis of N-(2-methoxyethyl)-1-methyl-2-((6-(trifluoromethyl)benzo[d]oxazol-2-yl)amino)-1H-benzo[d]imidazole-5-carboxamide (Example 32)

To a stirred solution of 1-methyl-2-((6-(trifluoromethyl)benzo[d]oxazol-2-yl)amino)-1H-benzo[d]imidazole-5-carboxylic acid (50 mg, 0.13 mmol) in DMFA (1.5 mL) at 0° C. was added N-ethyldiisopropyl amine (0.02 mL, 0.13 mmol) and diphenylphosphoryl azide (0.02 mL, 0.13 mmol). The reaction mixture was stirred for 30 min, followed by the addition of 2-methoxyethylamine (0.01 mL, 0.13 mmol) and the reaction mixture was then stirred at RT for 16 h. Once the reaction was completed (monitored by TLC), the reaction mixture was diluted with cold water (15 mL) and stirred for 15 min. The solid obtained was filtered, washed with diethyl ether and dried under vacuum to afford the title compound (28 mg, 49%); $^1$H NMR (400 MHz, DMSO-d$_6$): δ 12.40 (bs, 1H), 8.48 (s, 1H), 8.10 (s, 1H), 7.83 (s, 1H), 7.79 (d, J=8.4 Hz, 1H), 7.61-7.51 (m, 3H), 3.67 (s, 3H), 3.48-3.44 (m, 4H), 3.30 (s, 3H); LC-MS: m/z 434.1 (M+1)$^+$.

Example 33. Synthesis of N-(2-hydroxyethyl)-1-methyl-2-((6-(trifluoromethyl)benzo[d]oxazol-2-yl)amino)-1H-benzo[d]imidazole-5-carboxamide

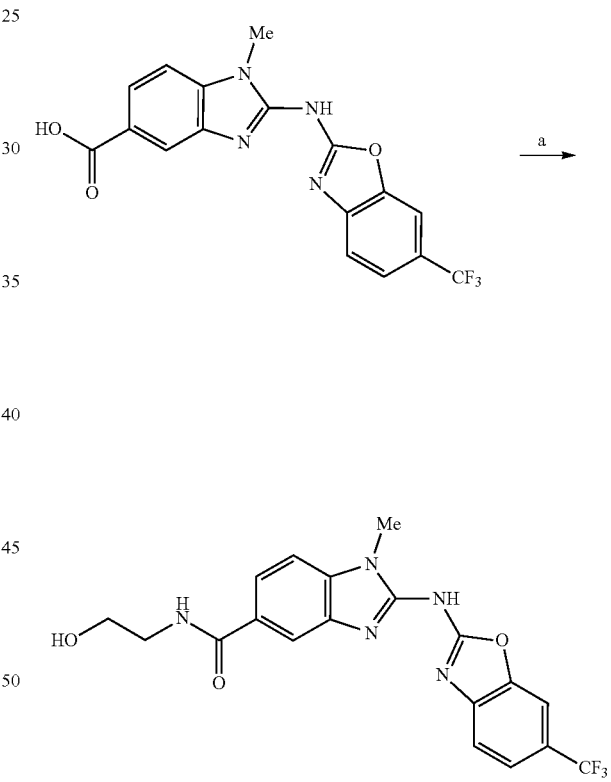

Conditions: a) 2-aminoethan-1-ol, HBTU, DIPEA, DMF, 0° C. - RT, 16 h

The title compound was synthesized using the same procedure which was followed for Example 6 Step-e using 1-methyl-2-((6-(trifluoromethyl)benzo[d]oxazol-2-yl)amino)-1H-benzo[d]imidazole-5-carboxylic acid as starting materials (Yield: 34%); $^1$H NMR (400 MHz, DMSO-d$_6$): δ 12.40 (bs, 1H), 8.39 (t, J=5.3 Hz, 1H), 8.10 (s, 1H), 7.82 (s, 1H), 7.80 (d, J=8.3 Hz, 1H), 7.61-7.51 (m, 3H), 4.72 (t, J=5.2 Hz, 1H), 3.67 (s, 3H), 3.54-3.51 (m, 2H), 3.37-3.34 (m, 2H); LC-MS: m/z 420.0 (M+1)$^+$.

Example 34. Synthesis of N-(2-(2-hydroxyethoxy)ethyl)-1-methyl-2-(((6-(trifluoromethyl)benzo[d]oxazol-2-yl)amino)-1H-benzo[d]imidazole-5-carboxamide

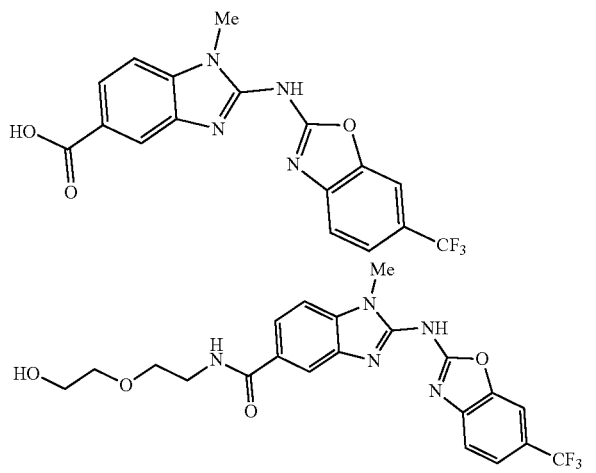

Conditions: a) 2-(2-aminoethoxy)ethan-1-ol, HBTU, DIPEA, DMF, 0° C. - RT 16 h

The title compound was synthesized using the same procedure which was followed for Example 6 Step-e using 1-methyl-2-((6-(trifluoromethyl)benzo[d]oxazol-2-yl)amino)-1H-benzo[d]imidazole-5-carboxylic acid and 2-(2-aminoethoxy)ethan-1-ol as starting materials (Yield: 50%); $^1$H NMR (400 MHz, DMSO-$d_6$): δ 12.40 (bs, 1H), 8.46 (bs, 1H), 8.10 (s, 1H), 7.83 (s, 1H), 7.79 (d, J=8.3 Hz, 1H), 7.62-7.52 (m, 3H), 4.60 (bs, 1H), 3.67 (s, 3H), 3.58-3.44 (m, 8H); LC-MS: m/z 464.20 (M+1)$^+$.

Example 35. Synthesis of N-(2-hydroxypropyl)-1-methyl-2-((6-(trifluoromethyl)benzo[d]oxazol-2-yl)amino)-1H-benzo[d]imidazole-5-carboxamide The title compound was synthesized using the same procedure which was followed for compound 1i using 1-aminopropan-2-ol and 1-methyl-2-((6-(trifluoromethyl)benzo[d]oxazol-2-yl)amino)-1H-benzo[d]imidazole-5-carboxylic acid as starting materials. $^1$H NMR (400 MHz, DMSO-$d_6$): δ 12.30 (bs, 1H), 8.35 (t, J=1.2 Hz, 1H), 8.10 (d, J=1.2 Hz, 1H), 7.82-7.79 (m, 2H), 7.61-7.51 (m, 3H), 4.76 (d, J=4.0 Hz, 1H), 3.84-3.80 (m, 1H), 3.67 (s, 3H), 3.26-3.21 (m, 2H), 1.09 (d, J=6.4 Hz, 3H); LC-MS: m/z 434.2 (M+1)$^+$.

Example 36. Synthesis of 1-methyl-N-(2-(pyrrolidin-1-yl)ethyl)-2-((6-(trifluoromethyl)benzo[d]oxazol-2-yl)amino)-1H-benzo[d]imidazole-5-carboxamide The title compound was synthesized using the same procedure which was followed for compound 1i using 2-(pyrrolidin-1-yl)ethan-1-amine and 1-methyl-2-((6-(trifluoromethyl)benzo[d]oxazol-2-yl)amino)-1H-benzo[d]imidazole-5-carboxylic acid as starting materials. $^1$H NMR (400 MHz, DMSO-$d_6$): δ 12.30 (bs, 1H), 8.39 (t, J=5.2 Hz, 1H), 8.09 (s, 1H), 7.82 (s, 1H), 7.77 (d, J=8.4 Hz, 1H), 7.61-7.51 (m, 3H), 3.66 (s, 3H), 3.43-3.38 (m, 2H), 2.61 (t, J=7.2 Hz, 2H), 2.5 (m, 4H Merged in DMSO peak), 1.69 (bs, 4H); LC-MS: m/z 473.1 (M+1)$^+$.

Example 37. Synthesis of 1-methyl-N-(2-(piperidin-1-yl)ethyl)-2-((6-(trifluoromethyl)benzo[d]oxazol-2-yl)amino)-1H-benzo[d]imidazole-5-carboxamide The title compound was synthesized using the same procedure which was followed for compound 1i using 2-(piperidin-1-yl)ethan-1-amine and 1-methyl-2-(((6-(trifluoromethyl)benzo[d]oxazol-2-yl)amino)-1H-benzo[d]imidazole-5-carboxylic acid as starting materials. $^1$H NMR (400 MHz, DMSO-$d_6$): δ 12.30 (bs, 1H), 8.32 (t, J=5.6 Hz, 1H), 8.07 (s, 1H), 7.82 (s, 1H), 7.75 (d, J=8.0 Hz, 1H), 7.61-7.51 (m, 3H), 3.66 (s, 3H), 3.41-3.36 (m, 2H), 2.43-2.32 (m, 6H), 1.53-1.38 (m, 6H); LC-MS: m/z 487.15 (M+1)$^+$.

Example 38. Synthesis of N-(2-(2-hydroxypropoxy)ethyl)-1-methyl-2-((6-(trifluoromethyl)benzo[d]oxazol-2-yl)amino)-1H-benzo[d]imidazole-5-carboxamide The title compound was synthesized using the same procedure which was followed for compound 1i using 1-(2-aminoethoxy)propan-2-ol and 1-methyl-2-((6-(trifluoromethyl)benzo[d]oxazol-2-yl)amino)-1H-benzo[d]imidazole-5-carboxylic acid as starting materials. $^1$H NMR (400 MHz, DMSO-$d_6$): δ 12.30 (bs, 1H), 8.46 (t, J=5.6 Hz, 1H), 8.09 (s, 1H), 7.83 (s, 1H), 7.78 (d, J=8.8 Hz, 1H), 7.62-7.52 (m, 3H), 4.58 (d, J=4.4 Hz, 1H), 3.77-3.73 (m, 1H), 3.66 (s, 3H), 3.56 (t, J=6.0 Hz, 2H), 3.45 (t, J=5.2 Hz, 2H), 2.29-2.23 (m, 2H), 1.04 (d, J=6.4 Hz, 3H); LC-MS: m/z 478.2 (M+1)$^+$.

Example 39. Synthesis of N-(2,3-dihydroxypropyl)-1-methyl-2-((6-(trifluoromethyl)benzo[d]oxazol-2-yl)amino)-1H-benzo[d]imidazole-5-carboxamide The title compound was synthesized using the same procedure which was followed for compound 1i using 3-aminopropane-1,2-diol and 1-methyl-2-((6-(trifluoromethyl)benzo[d]oxazol-2-yl)amino)-1H-benzo[d]imidazole-5-carboxylic acid as starting materials. $^1$H NMR (400 MHz, DMSO-$d_6$): δ 12.40 (bs, 1H), 8.39 (t, J=5.2 Hz, 1H), 8.10 (s, 1H), 7.84 (s, 1H), 7.80 (d, J=8.4 Hz, 1H), 7.62-7.53 (m, 3H), 4.87 (d, J=4.4 Hz, 1H), 4.62 (bs, 1H), 3.67 (s, 4H), 3.45-3.40 (m, 1H), 3.30 (2H merged with DMSO moisture peak), 3.25-3.19 (m, 1H); LC-MS: m/z 450.15 (M+1)$^+$.

Example 40. Synthesis of N-(2-(2-(dimethylamino)acetamido)ethyl)-1-methyl-2-((6-(trifluoromethyl)benzo[d]oxazol-2-yl)amino)-1H-benzo[d]imidazole-5-carboxamide The title compound was synthesized using the same procedure which was followed for Example 19 Step-c using N-(2-aminoethyl)-2-(dimethylamino)acetamide trifluoroacetate and 1-methyl-2-((6-(trifluoromethyl)benzo[d]oxazol-2-yl)amino)-1H-benzo[d]imidazole-5-carboxylic acid as starting materials. $^1$H NMR (400 MHz, DMSO-$d_6$): δ 12.30 (bs, 1H), 8.47 (bs, 1H), 8.09 (s, 1H), 7.92 (bs, 1H), 7.83 (s, 1H), 7.76 (d, J=8.4 Hz, 1H), 7.61-7.52 (m, 3H), 3.66 (s, 3H), 3.38-3.35 (m, 4H), 2.86 (s, 2H), 2.19 (s, 6H); LC-MS: m/z 504.2 (M+1)$^+$.

Example 41. Synthesis of 2-(2-(1-methyl-2-((6-(trifluoromethyl)benzo[d]oxazol-2-yl)amino)-1H-benzo[d]imidazole-5-carboxamido)ethoxy)acetic acid

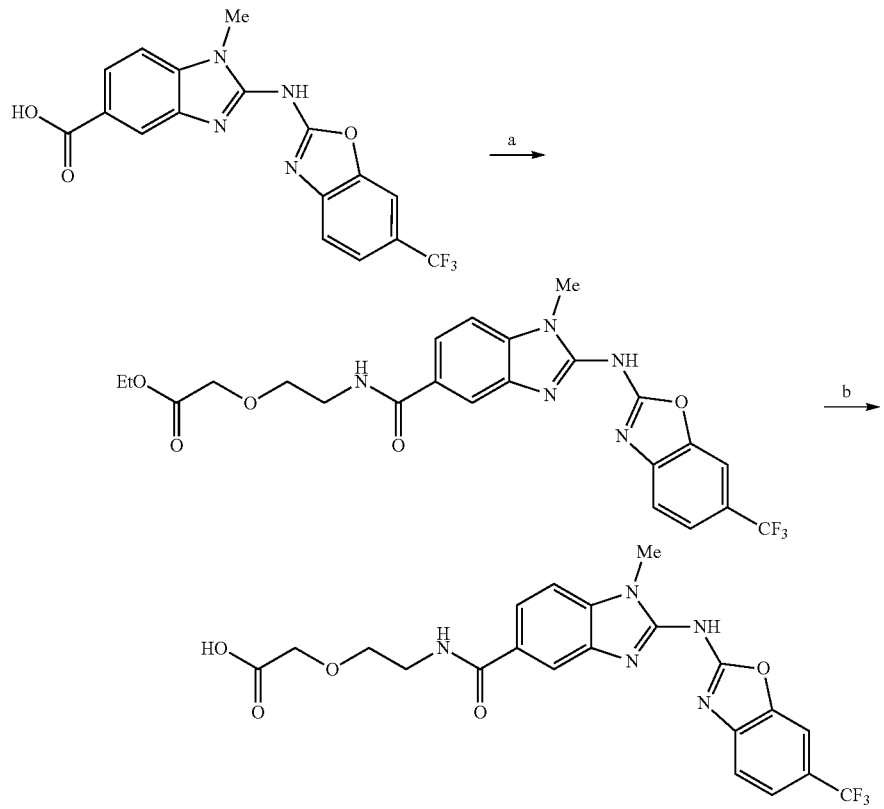

Conditions: a) ethyl 2-(2-aminoethoxy)acetate trifluoraro acetate, HBTU, DIPEA, DMF, 0° C. - RT, 16 h; b) LiOH•H$_2$O, Ethanol, THF, Water, RT, 3 h Step-a: Synthesis of ethyl 2-(2-(1-methyl-2-((6-(trifluoromethyl)benzo[d]oxazol-2-yl)amino)-1H-benzo[d]imidazole-5-carboxamido)ethoxy)acetate The title compound was synthesized using the same procedure which was followed for Example 29 Step-c using 1-methyl-2-((6-(trifluoromethyl)benzo[d]oxazol-2-yl) amino)-1H-benzo[d]imidazole-5-carboxylic acid and ethyl 2-(2-aminoethoxy)acetate trifluoraro aetate as starting materials (Yield: 65%); $^1$H NMR (400 MHz, DMSO-d$_6$): δ 12.38 (bs, 1H), 8.49 (bs, 1H), 8.10 (s, 1H), 7.82 (s, 1H), 7.79 (d, J=8.8 Hz, 1H), 7.61-7.52 (m, 3H), 4.15-4.09 (m, 4H), 3.66-3.62 (m, 5H), 3.48-3.46 (m, 2H), 1.19 (t, J=7.0 Hz, 3H); LC-MS: m/z 506.1 (M+1)$^+$.

Step-b: Synthesis of 2-(2-(1-methyl-2-((6-(trifluoromethyl)benzo[d]oxazol-2-yl)amino)-1H-benzo[d] imidazole-5-carboxamido)ethoxy)acetic acid The title compound was synthesized using the same procedure which was followed for Example 29 Step-d using ethyl 2-(2-(1-methyl-2-((6-(trifluoromethyl)benzo[d]oxazol-2-yl)amino)-1H-benzo[d]imidazole-5-carboxamido) ethoxy)acetate as starting material (Yield:75%); $^1$H NMR (400 MHz, DMSO-d$_6$): δ 12.70 (bs, 1H), 12.30 (bs, 1H), 8.49 (bs, 1H), 8.10 (s, 1H), 7.82-7.78 (m, 2H), 7.61-7.51 (m, 3H), 4.06 (s, 2H), 3.66-3.62 (m, 5H), 3.48-3.41 (m, 2H); LC-MS: m/z 478.2 (M+1)$^+$.

Example 42. Synthesis of N-(2-(2-hydroxy-2-methylpropoxy)ethyl)-1-methyl-2-((6-(trifluoromethyl) benzo[d]oxazol-2-yl)amino)-1H-benzo[d]imidazole-5-carboxamide The title compound was synthesized using the same procedure which was followed for compound 1i using 1-(2-aminoethoxy)-2-methylpropan-2-ol and 1-methyl-2-((6-(trifluoromethyl)benzo[d]oxazol-2-yl)amino)-1H-benzo [d]imidazole-5-carboxylic acid as starting materials. $^1$H NMR (400 MHz, DMSO-d$_6$): δ 12.40 (bs, 1H), 8.83 (s, 1H), 8.08 (s, 1H), 7.81 (s, 1H), 7.77 (d, J=8.4 Hz, 1H), 7.58-7.52 (m, 3H), 4.32 (bs, 1H), 3.66 (s, 3H), 3.58-3.56 (m, 2H), 3.46-3.44 (m, 2H), 3.21 (s, 2H), 1.08 (s, 6H); LC-MS: m/z 492.1 (M+1)$^+$.

Example 43. Synthesis of N-(2-(2-hydroxyethoxy) ethyl)-1-methyl-2-((5-(trifluoromethyl)benzo[d]oxazol-2-yl)amino)-1H-benzo[d]imidazole-5-carboxamide

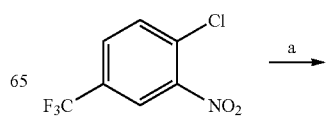

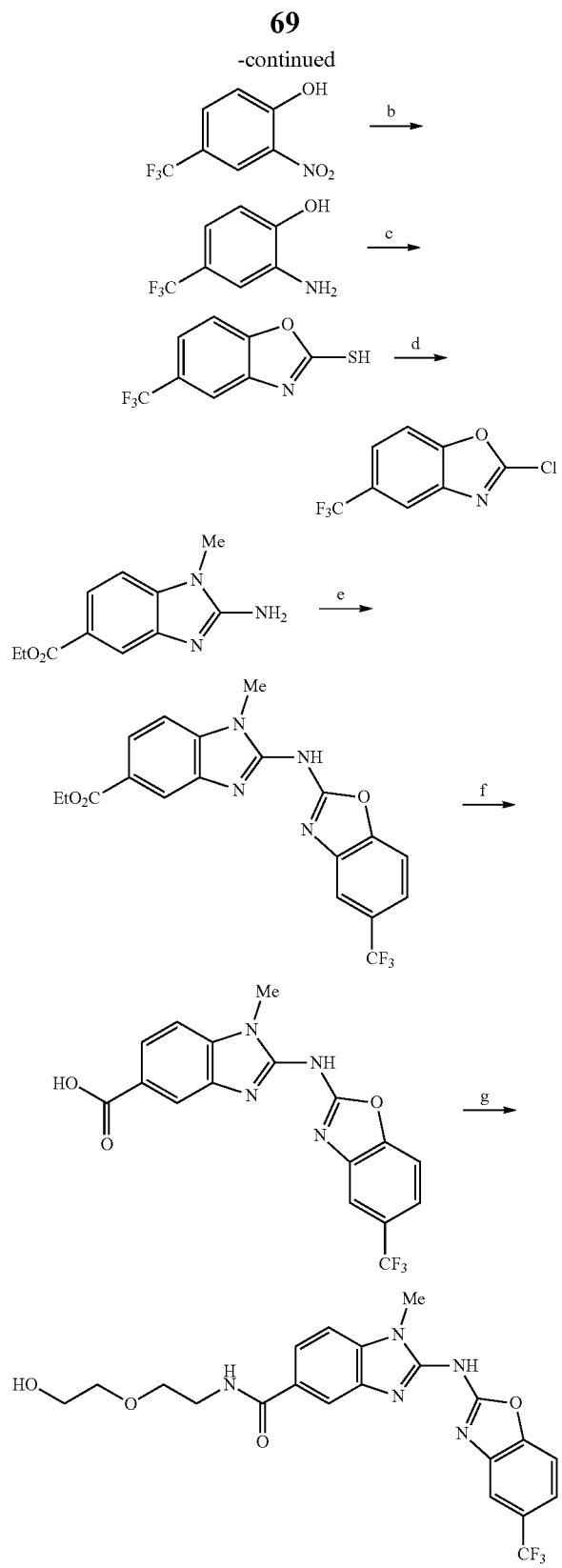

Conditions: a) NaOH, DMSO, 60° C., 16 h; b) 10% Pd/C, MeOH, H₂, RT, 16 h; c) Potassium ethyl xanthate, Ethanol, Reflux, 16 h; d) SOCl₂, Cat•DMF, reflux, 1 h; e) NaH, 2-chloro-5-(trifluoromethyl)benzo[d]oxazole, 1,4-Dioxane, RT, 16 h; f) LiOH•H₂O, THF, Methanol, Water, 50° C., 16 h; g) 2-(2-aminoethoxy)ethan-1-ol, HBTU, DIPEA, DMF, 0° C. - RT, 16 h Step-a: Synthesis of 2-nitro-4-(trifluoromethyl)phenol To a solution of 1-chloro-2-nitro-4-(trifluoromethyl)benzene (10.0 g, 44.3 mmol) in DMSO (100 mL) at RT was added sodium hydroxide (4.44 g, 110.7 mmol) and the mixture was stirred at 60° C. for 16 h. The reaction mixture was cooled to RT, diluted with water (250 mL) and extracted with EtOAc (200 mL). The aqueous layer was acidified to pH~1 with 3 N HCl and extracted with EtOAc (2×250 mL), organic layer was washed with brine solution (50 mL), dried over anhydrous sodium sulfate and concentrated under vacuum to afford the titled compound (7.0 g, 81%); $^1$H NMR (400 MHz, DMSO-$d_6$): δ 11.99 (bs, 1H), 8.22 (d, J=1.6 Hz, 1H), 7.88 (dd, J=2.0 Hz, J=8.8 Hz, 1H), 7.30 (d, J=8.8 Hz, 1H).

Step-b: Synthesis of 2-amino-4-(trifluoromethyl)phenol

To a solution of 2-nitro-4-(trifluoromethyl)phenol (5.0 g, 24.15 mmol) in methanol (50 mL) was added 10% Pd/C (2.5 g) under nitrogen atmosphere. The reaction mixture was stirred under hydrogen balloon for 16 h. The reaction mixture was filtered through a celite bed and the filtrate was concentrated under vacuum to afford the title compound (3.0 g, 70%); $^1$H NMR (400 MHz, DMSO-$d_6$): δ 9.85 (bs, 1H), 6.87 (d, J=2.0 Hz, 1H), 6.77-6.70 (m, 2H), 5.0 (bs, 2H); LC-MS: m/z 178.1 (M+1)$^+$.

Step-c: Synthesis of 5-(trifluoromethyl)benzo[d]oxazole-2-thiol

To a solution of 2-amino-4-(trifluoromethyl)phenol (3.0 g, 16.9 mmol) in ethanol (45 mL) at RT was added potassium ethyl-xanthate (6.78 g, 42.4 mmol) and the reaction mixture was refluxed for 16 h. The reaction mixture was concentrated under vacuum and diluted with cold water (100 mL), acidified with 3 N HCl. The precipitated solid was filtered and dried under vacuum to afford the title compound (3.0 g, 81%); $^1$H NMR (400 MHz, DMSO-$d_6$): δ 14.2 (bs, 1H), 7.72 (d, J=8.4 Hz, 1H), 7.64 (d, J=8.4 Hz, 1H), 7.51 (s, 1H); LC-MS: m/z 220.0 (M+1)$^+$.

Step-d: Synthesis of 2-chloro-5-(trifluoromethyl)benzo[d]oxazole

To a solution of 5-(trifluoromethyl)benzo[d]oxazole-2-thiol (2.0 g, 9.1 mmol) in thionyl chloride (10 mL) at RT was added N,N-dimethyl formamide (catalytic amount) and the reaction mixture was refluxed for 1 h. The reaction mixture concentrated, diluted with cold water (60 mL) and extracted with EtOAc (2×100 mL). The combined organic layers were washed with brine solution (50 mL), dried over anhydrous sodium sulfate and concentrated under vacuum to afford the title compound (1.3 g, 65%); $^1$H NMR (400 MHz, DMSO-$d_6$): δ 8.23 (s, 1H), 8.02 (d, J=8.8 Hz, 1H), 7.85 (d, J=8.8 Hz, 1H).

Step-e: Synthesis of ethyl 1-methyl-2-((5-(trifluoromethyl)benzo[d]oxazol-2-yl)amino)-1H-benzo[d]imidazole-5-carboxylate To a solution of ethyl 2-amino-1-methyl-1H-benzo[d]imidazole-5-carboxylate (200 mg, 0.91 mmol) in 1,4-dioxane (10 mL) at 0° C. was added sodium hydride (60% dispersion in mineral oil) (91 mg, 2.27 mmol) and stirred for 15 min followed by the addition of 2-chloro-5-(trifluoromethyl)benzo[d]oxazole (222 mg, 1.0 mmol) and stirring was continued at RT for 16 h. The reaction mixture was concentrated, diluted with cold water (50 mL) and acidified with 3 N HCl and extracted with ethyl acetate (2×50 mL). The combined organic layers were washed with water (30 mL), brine solution (30 mL), dried over anhydrous sodium sulfate and concentrated under vacuum. The residue was purified by combiflash column chromatography using 100% dichloromethane as an eluent to afford the titled compound (150 mg, 40%); $^1$H NMR (400 MHz, DMSO-d$_6$): δ 12.41 (bs, 1H), 8.25 (s, 1H), 7.90 (dd, J=1.2 Hz, J=8.4 Hz, 1H), 7.67-7.64 (m, 2H), 7.57 (d, J=8.4 Hz, 1H), 7.49 (d, J=8.4 Hz, 1H), 4.33 (q, J=7.2 Hz, 2H), 3.66 (s, 3H), 1.35 (t, J=7.2 Hz, 3H); LC-MS: m/z 405.00 (M+1)$^+$.

Step-f: Synthesis of 1-methyl-2-((5-(trifluoromethyl)benzo[d]oxazol-2-yl)amino)-1H-benzo[d]imidazole-5-carboxylic acid To a stirred solution ethyl 1-methyl-2-((5-(trifluoromethyl)benzo[d]oxazol-2-yl)amino)-1H-benzo[d]imidazole-5-carboxylate (150 mg, 0.37 mmol) in a mixture of solvents of THF (2 mL), methanol (2 mL) and water (2 mL) was added lithium hydroxide monohydrate (78 mg, 1.85 mmol). The reaction mixture was heated at 50° C. for 16 h. The reaction mixture was cooled to RT and concentrated under reduced pressure. The residue was dissolved in water (30 mL), acidified to pH~2 with 3 N HCl and stirred for 1 h. The solid precipitated was filtered and dried under vacuum to afford the title compound (140 mg, 100%); $^1$H NMR (400 MHz, DMSO-d$_6$): δ 12.85 (bs, 1H), 12.40 (bs, 1H), 8.18 (s, 1H), 7.87 (d, J=8.4 Hz, 1H), 7.67 (s, 1H), 7.63 (d, J=8.4 Hz, 1H), 7.52 (d, J=8.4 Hz, 1H), 7.46 (d, J=8.0 Hz, 1H), 3.64 (s, 3H); LC-MS: m/z 377.1 (M+1)$^+$.

Step-g: Synthesis of N-(2-(2-hydroxyethoxy)ethyl)-1-methyl-2-((5-(trifluoromethyl)benzo[d]oxazol-2-yl)amino)-1H-benzo[d]imidazole-5-carboxamide To a stirred solution of 1-methyl-2-((5-(trifluoromethyl)benzo[d]oxazol-2-yl)amino)-1H-benzo[d]imidazole-5-carboxylic acid (80 mg, 0.21 mmol) in DMFA (5 mL) at 0° C. was added N-ethyldiisopropyl amine (0.04 mL, 0.21 mmol) and HBTU (81 mg, 0.21 mmol). The reaction mixture was stirred for 15 min, followed by the addition of 2-(2-aminoethoxy)ethan-1-ol (22 mg, 0.21 mmol). The reaction mixture was then stirred at RT for 16 h. Once the reaction was completed (monitored by TLC), the reaction mixture was diluted with cold water (30 mL) and stirred for 1 h. The solid precipitated was filtered and dried under vacuum. The solid was stirred in diethyl ether (15 mL), filtered and dried under vacuum to afford the titled compound (80 mg, 85%); $^1$H NMR (400 MHz, DMSO-d$_6$): δ 12.33 (bs, 1H), 8.46 (t, J=5.4 Hz, 1H), 8.09 (d, J=1.2 Hz, 1H), 7.78 (dd, J=1.6 Hz, J=8.4 Hz, 1H), 7.68 (s, 1H), 7.64 (d, J=8.4 Hz, 1H), 7.52 (d, J=8.0 Hz, 1H), 7.48 (d, J=8.4 Hz, 1H), 4.60 (t, J=5.2 Hz, 1H), 3.66 (s, 3H), 3.58-3.43 (m, 8H); LC-MS: m/z 464.2 (M+1)$^+$.

Examples 44 and 45. Synthesis of 1-methyl-2-((6-(trifluoromethoxy)benzo[d]oxazol-2-yl)amino)-1H-benzo[d]imidazole-5-carboxylic acid and Synthesis of N-(2-methoxyethyl)-1-methyl-2-((6-(trifluoromethoxy)benzo[d]oxazol-2-yl)amino)-1H-benzo[d]imidazole-5-carboxamide

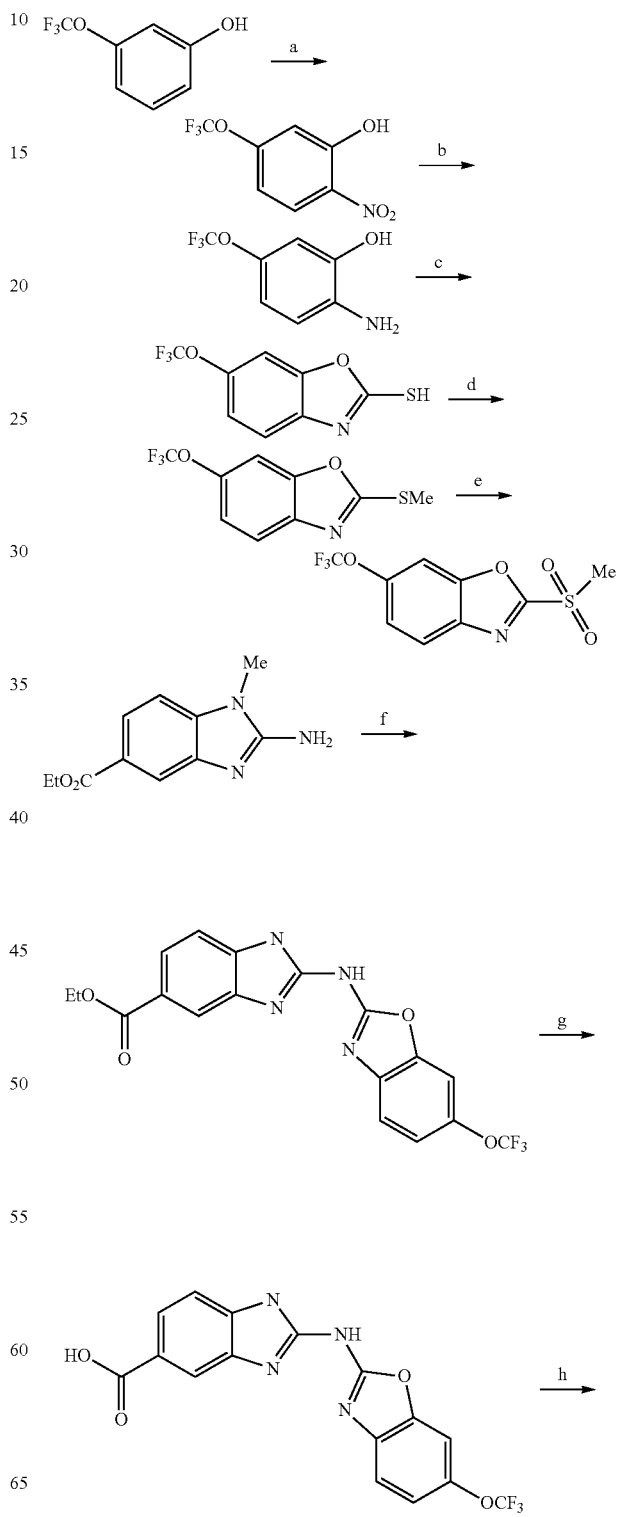

-continued

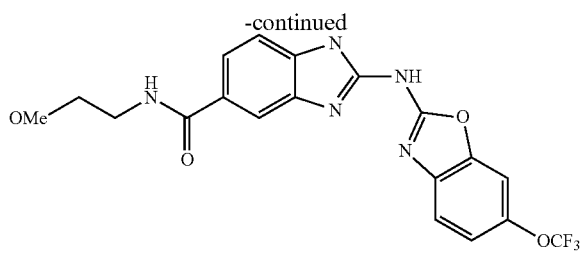

Conditions: a) HNO₃, Acetic acid, 16° C. - RT, 16 h; b) 10% Pd/C, MeOH, H₂, RT, 5 h; c) Carbon disulfide, KOH, Ethanol, Reflux, 6 h; d) K₂CO₃, Methyl iodide, Acetonitrile, RT, 16 h; e) m-CPBA, DCM, 0° C. - RT, 6 h; f) NaH, 2-(methylsulfonyl)-6-(trifluoromethoxy) benzo[d]oxazole, 1,4-Dioxane, RT, 16 h; g) LiOH·H₂O, THF, Ethanol, Water, 60° C., 16 h; h) 2-methoxyethyl amine, DPPA, DIPEA, DMF, 0° C. - RT, 16 h

Step-a: Synthesis of 2-nitro-5-(trifluoromethoxy)phenol

To a solution of 3-(trifluoromethoxy)phenol (1 g, 5.6 mmol) in acetic acid (10 mL) was added 60% aqueous nitric acid (1 mL) dropwise at 10-15° C. The mixture was stirred at this temperature for 1.5 h and continued to stir at RT for 16 h. The mixture was poured into ice water (20 mL) and extracted with EtOAc (2×25 mL). The combined organic layers were washed with brine solution (25 mL), dried over anhydrous sodium sulfate and concentrated in vacuum. The residue was purified by combiflash chromatography using 5% EtOAc in hexanes as eluent to afford the title compound (300 mg, 24%); $^1$H NMR (400 MHz, CDCl₃): δ 10.73 (s, 1H), 8.18 (d, J=9.6 Hz, 1H), 6.99 (s, 1H), 6.83 (d, J=9.2 Hz, 1H); LC-MS: m/z 222.0 (M−1).

Step-b: Synthesis of 2-amino-5-(trifluoromethoxy)phenol

To a solution of 2-nitro-5-(trifluoromethoxy)phenol (300 mg, 1.35 mmol) in methanol (6 mL) was added 10% Pd/C (60 mg) under nitrogen atmosphere. The reaction mixture was stirred under hydrogen gas for 5 h. The reaction mixture was filtered through a bed of celite and concentrated under vacuum to afford the title compound (250 mg, 96%); $^1$H NMR (400 MHz, DMSO-d₆): δ 9.60 (s, 1H), 6.59-6.57 (m, 2H), 6.53-6.50 (m, 1H), 4.68 (bs, 2H); LC-MS: m/z 194.0 (M+1)⁺.

Step-c: Synthesis of 6-(trifluoromethoxy)benzo[d]oxazole-2-thiol

To a solution of 2-amino-5-(trifluoromethoxy)phenol (250 mg, 1.3 mmol) in ethanol (5 mL) at RT was added powdered potassium hydroxide (127 mg, 2.3 mmol) and carbon disulfide (1 mL, 17.0 mmol). The reaction mixture was refluxed for 6 h. After cooling to RT, the mixture was concentrated in vacuo. The residue was diluted with cold water (100 mL), acidified with 1 N HCl. The solid obtained was filtered and dried under vacuum to afford the title compound (200 mg, 66%); $^1$H NMR (400 MHz, DMSO-d₆): δ 14.10 (bs, 1H), 7.73 (s, 1H), 7.32 (s, 2H); LC-MS: m/z 235.9 (M+1)⁺.

Step-d: Synthesis of 2-(methylthio)-6-(trifluoromethoxy)benzo[d]oxazole

The title compound was synthesized using the same procedure which was followed for compound 1b using 6-(trifluoromethoxy)benzo[d]oxazole-2-thiol as starting material and stirring at RT for 16 h (Yield: 94%); $^1$H NMR (400 MHz, DMSO-d₆): δ 7.85 (d, J=1.6 Hz, 1H), 7.73 (d, J=8.0 Hz, 1H), 7.37-7.34 (m, 1H), 2.77 (s, 3H); LC-MS: m/z 250.1 (M+1)⁺.

Step-e: Synthesis of 2-(methylsulfonyl)-6-(trifluoromethoxy)benzo[d]oxazole

The title compound was synthesized using the same procedure which was followed for compound 1c using 2-(methylthio)-6-(trifluoromethoxy)benzo[d]oxazole as starting material and stirring at RT for 6 h (Yield: 94%); $^1$H NMR (400 MHz, DMSO-d₆): δ 8.22 (s, 1H), 8.15 (d, J=8.8 Hz, 1H), 7.62 (d, J=8.8 Hz, 1H), 3.67 (s, 3H).

Step-f: Synthesis of ethyl 1-methyl-2-((6-(trifluoromethoxy)benzo[d]oxazol-2-yl)amino)-1H-benzo[d]imidazole-5-carboxylate To a solution of ethyl 2-amino-1-methyl-1H-benzo[d]imidazole-5-carboxylate (100 mg, 0.46 mmol) in 1,4-dioxane (2 mL) at RT was added sodium hydride (60% dispersion in mineral oil) (64 mg, 1.6 mmol) followed by the addition of 2-(methylsulfonyl)-6-(trifluoromethoxy)benzo[d]oxazole (167 mg, 0.6 mmol). The reaction mixture was stirred at RT for 16 h. It was then concentrated, diluted with cold water (15 mL) and acidified with 1 N HCl. The solid obtained was filtered, dried under vacuum and purified by combiflash column chromatography using 100% DCM as an eluent to afford the title compound (30 mg, 16%); $^1$H NMR (400 MHz, DMSO-d₆): δ 12.40 (bs, 1H), 8.24 (s, 1H), 7.89 (dd, J=1.6 Hz, J=8.4 Hz, 1H), 7.58-7.50 (m, 3H), 7.22 (d, J=8.0 Hz, 1H), 4.33 (q, J=7.6 Hz, 2H), 3.65 (s, 3H), 1.35 (t, J=7.2 Hz, 3H); LC-MS: m/z 421.0 (M+1)⁺.

Step-g: Synthesis of 1-methyl-2-((6-(trifluoromethoxy)benzo[d]oxazol-2-yl)amino)-1H-benzo[d]imidazole-5-carboxylic acid The title compound was synthesized using the same procedure which was followed for compound 1h, using ethyl 1-methyl-2-((6-(trifluoromethoxy)benzo[d]oxazol-2-yl)amino)-1H-benzo[d]imidazole-5-carboxylate as starting material (Yield: 72%); $^1$H NMR (400 MHz, DMSO-d₆): δ 12.80 (bs, 1H), 12.30 (bs, 1H), 8.20 (s, 1H), 7.88 (d, J=8.4 Hz, 1H), 7.58 (s, 1H), 7.52 (d, J=8.8 Hz, 2H), 7.22 (d, J=8.0 Hz, 1H), 3.65 (s, 3H); LC-MS: m/z 393.0 (M+1)⁺.

Step-h: Synthesis of N-(2-methoxyethyl)-1-methyl-2-((6-(trifluoromethoxy) benzo[d]oxazol-2-yl)amino)-1H-benzo[d]imidazole-5-carboxamide The title compound was synthesized using the same procedure which was followed for compound 1i using 1-methyl-2-((6-(trifluoromethoxy)benzo[d]oxazol-2-yl)amino)-1H-benzo[d]imidazole-5-carboxylic acid as starting material (Yield: 23%); $^1$H NMR (400 MHz, DMSO-d₆): δ 12.30 (bs, 1H), 8.47 (t, J=5.2 Hz, 1H), 8.08 (s, 1H), 7.78 (d, J=8.4 Hz, 1H), 7.57 (s, 1H), 7.52-7.49 (m, 2H), 7.21 (d, J=8.4 Hz, 1H), 3.64 (s, 3H), 3.48-3.44 (m, 4H), 3.28 (s, 3H); LC-MS: m/z 450.0 (M+1)⁺.

Example 46. Synthesis of 1-methyl-N-(1H-pyrazol-4-yl)-2-((6-(trifluoromethoxy)benzo[d]oxazol-2-yl)amino)-1H-benzo[d]imidazole-5-carboxamide The title compound was synthesized using the same procedure which was followed for compound 1i using 1H-pyrazol-4-amine and 1-methyl-2-((6-(trifluoromethoxy)benzo[d]oxazol-2-yl)amino)-1H-benzo[d]imidazole-5-carboxylic acid as starting materials. ¹H NMR (400 MHz, DMSO-d₆): δ 12.65 (bs, 1H), 12.30 (bs, 1H), 10.40 (s, 1H), 8.17 (d, J=1.2 Hz, 1H), 8.02 (bs, 1H), 7.89 (dd, J=1.2 Hz, J=8.4 Hz, 1H), 7.69 (bs, 1H), 7.58-7.49 (m, 3H), 7.21 (d, J=8.4 Hz, 1H), 3.67 (s, 3H); LC-MS: m/z 458.0 (M+1)⁺.

Example 47. Synthesis of N-(1,3-dihydroxy-2-(hydroxymethyl)propan-2-yl)-1-methyl-2-((6-(trifluoromethoxy)benzo[d]oxazol-2-yl)amino)-1H-benzo[d]imidazole-5-carboxamide The title compound was synthesized using the same procedure which was followed for compound 1i using 2-amino-2-(hydroxymethyl)propane-1,3-diol and 1-methyl-2-((6-(trifluoromethoxy)benzo[d]oxazol-2-yl)amino)-1H-benzo[d]imidazole-5-carboxylic acid as starting materials. ¹H NMR (400 MHz, DMSO-d₆): δ 12.30 (bs, 1H), 8.05 (s, 1H), 7.43 (d, J=8.4 Hz, 1H), 7.57 (s, 1H), 7.50 (d, J=5.8 Hz, 2H), 7.26 (s, 1H), 7.21 (d, J=8.4 Hz, 1H), 4.83 (bs, 3H), 3.71 (bs, 6H), 3.65 (s, 3H); LC-MS: m/z 496.3 (M+1)⁺.

Example 48. Synthesis of N-(1,3-dihydroxypropan-2-yl)-1-methyl-2-((6-(trifluoromethoxy)benzo[d]oxazol-2-yl)amino)-1H-benzo[d]imidazole-5-carboxamide The title compound was synthesized using the same procedure which was followed for compound 1i using 2-amino-propane-1,3-diol and 1-methyl-2-((6-(trifluoromethoxy)benzo[d]oxazol-2-yl)amino)-1H-benzo[d]imidazole-5-carboxylic acid as starting materials. ¹H NMR (400 MHz, DMSO-d₆): δ 12.30 (bs, 1H), 8.09 (s, 1H), 7.88 (d, J=7.6 Hz, 1H), 7.81 (d, J=8.4 Hz, 1H), 7.57 (d, J=1.2 Hz, 1H), 7.51 (d, J=8.0 Hz, 2H), 7.21 (dd, J=1.6 Hz, J=8.4 Hz, 1H), 4.66 (t, J=6.0 Hz, 2H), 4.00-3.95 (m, 1H), 3.65 (s, 3H), 3.54 (t, J=6.0 Hz, 4H); LC-MS: m/z 466.0 (M+1)⁺.

Example 49. Synthesis of N-(2-(2-(dimethylamino)acetamido)ethyl)-1-methyl-2-((6-(trifluoromethoxy)benzo[d]oxazol-2-yl)amino)-1H-benzo[d]imidazole-5-carboxamide The title compound was synthesized using the same procedure which was followed for Example 19 Step-c using N-(2-aminoethyl)-2-(dimethylamino)acetamide trifluoroacetate and 1-methyl-2-((6-(trifluoromethoxy)benzo[d]oxazol-2-yl)amino)-1H-benzo[d]imidazole-5-carboxylic acid as starting materials. ¹H NMR (400 MHz, DMSO-d₆): δ 12.0 (bs, 1H), 8.45 (t, J=4.4 Hz, 1H), 8.07 (s, 1H), 7.91 (t, J=5.6 Hz, 1H), 7.75 (d, J=8.4 Hz, 1H), 7.56 (s, 1H), 7.50 (d, J=8.4 Hz, 2H), 7.21 (d, J=8.0 Hz, 1H), 3.64 (s, 3H), 3.36 (t, J=5.6 Hz, 2H), 3.30 (2H merged with DMSO moisture peak), 2.85 (s, 2H), 2.18 (s, 6H); LC-MS: m/z 520.5 (M+1)⁺.

Example 50. Synthesis of 1-methyl-N-(1-methyl-1H-pyrazol-4-yl)-2-((6-(trifluoromethoxy)benzo[d]oxazol-2-yl)amino)-1H-benzo[d]imidazole-5-carboxamide The title compound was synthesized using the same procedure which was followed for compound 1i using 1-methyl-1H-pyrazol-4-amine and 1-methyl-2-((6-(trifluoromethoxy)benzo[d]oxazol-2-yl)amino)-1H-benzo[d]imidazole-5-carboxylic acid as starting materials. ¹H NMR (400 MHz, DMSO-d₆): δ 12.30 (bs, 1H), 10.40 (s, 1H), 8.17 (s, 1H), 8.03 (s, 1H), 7.88 (d, J=8.0 Hz, 1H), 7.58-7.51 (m, 4H), 7.22 (d, J=7.6 Hz, 1H), 3.83 (s, 3H), 3.66 (s, 3H); LC-MS: m/z 472.0 (M+1)⁺.

Example 51. Synthesis of 1-methyl-N-(oxetan-3-yl)-2-((6-(trifluoromethoxy)benzo[d]oxazol-2-yl)amino)-1H-benzo[d]imidazole-5-carboxamide The title compound was synthesized using the same procedure which was followed for compound 1i using oxetan-3-amine and 1-methyl-2-((6-(trifluoromethoxy)benzo[d]oxazol-2-yl)amino)-1H-benzo[d]imidazole-5-carboxylic acid as starting materials. ¹H NMR (400 MHz, DMSO-d₆): δ 12.30 (bs, 1H), 9.07 (d, J=6.0 Hz, 1H), 8.10 (s, 1H), 7.85 (d, J=8.4 Hz, 1H), 7.57 (s, 1H), 7.52 (t, J=8.8 Hz, 2H), 7.21 (d, J=8.4 Hz, 1H), 5.05-5.00 (m, 1H), 4.78 (t, J=6.4 Hz, 2H), 4.62 (t, J=6.4 Hz, 2H), 3.65 (s, 3H); LC-MS: m/z 448.0 (M+1)⁺.

Example 52. Synthesis of N-((3-hydroxyoxetan-3-yl)methyl)-1-methyl-2-((6-(trifluoromethoxy)benzo[d]oxazol-2-yl)amino)-1H-benzo[d]imidazole-5-carboxamide The title compound was synthesized using the same procedure which was followed for compound 1i using 3-(aminomethyl)oxetan-3-ol and 1-methyl-2-((6-(trifluoromethoxy)benzo[d]oxazol-2-yl)amino)-1H-benzo[d]imidazole-5-carboxylic acid as starting materials. ¹H NMR (400 MHz, DMSO-d₆): δ 12.30 (bs, 1H), 8.54 (t, J=6.0 Hz, 1H), 8.10 (d, J=1.2 Hz, 1H), 7.80 (dd, J=1.2 Hz, J=8.8 Hz, 1H), 7.57 (d, J=1.6 Hz, 1H), 7.53-7.49 (m, 2H), 7.21 (dd, J=1.6 Hz, J=8.8 Hz, 1H), 5.88 (s, 1H), 4.52 (d, J=6.4 Hz, 2H), 4.41 (d, J=6.4 Hz, 2H), 3.65 (s, 3H), 3.59 (d, J=6.0 Hz, 2H); LC-MS: m/z 478.2 (M+1)⁺.

Example 53. Synthesis of N-(2-hydroxyethyl)-1-methyl-2-((6-(trifluoromethoxy)benzo[d]oxazol-2-yl)amino)-1H-benzo[d]imidazole-5-carboxamide The title compound was synthesized using the same procedure which was followed for compound 1i using 2-aminoethan-1-ol and 1-methyl-2-((6-(trifluoromethoxy)benzo[d]oxazol-2-yl)amino)-1H-benzo[d]imidazole-5-carboxylic acid as starting materials. ¹H NMR (400 MHz, DMSO-d₆): δ 12.30 (bs, 1H), 8.38 (t, J=5.2 Hz, 1H), 8.09 (d, J=1.2 Hz, 1H), 7.78 (dd, J=1.6 Hz, J=8.8 Hz, 1H), 7.57 (s, 1H), 7.52-7.49 (m, 2H), 7.22 (d, J=8.0 Hz, 1H), 4.72 (t, J=5.2 Hz, 1H), 3.64 (s, 3H), 3.54 (q, J=6.0 Hz, 2H), 3.37-3.30 (m, 2H); LC-MS: m/z 436.0 (M+1)⁺.

Example 54. Synthesis of 1-methyl-N-(2-(methylsulfonyl)ethyl)-2-((6-(trifluoromethoxy)benzo[d]oxazol-2-yl)amino)-1H-benzo[d]imidazole-5-carboxamide The title compound was synthesized using the same procedure which was followed for compound 1i using 2-(methylsulfonyl)ethan-1-amine hydrochloride and 1-methyl-2-((6-(trifluoromethoxy)benzo[d]oxazol-2-yl)amino)-1H-benzo[d]imidazole-5-carboxylic acid as starting materials. ¹H NMR (400 MHz, DMSO-d₆): δ 12.30 (bs, 1H), 8.68 (t, J=5.2 Hz, 1H), 8.09 (d, J=1.6 Hz, 1H), 7.76 (dd, J=1.6 Hz, J=8.4 Hz, 1H), 7.57 (s, 1H), 7.53-7.50 (m, 2H), 7.27-7.20 (m, 1H), 3.70 (q, J=6.0 Hz, 2H), 3.65 (s, 3H), 3.40 (t, J=6.8 Hz, 2H), 3.05 (s, 3H); LC-MS: m/z 497.9 (M+1)⁺.

Examples 55 and 56. Synthesis of 2-((6-(2-methoxyethoxy)benzo[d]oxazol-2-yl)amino)-1-methyl-1H-benzo[d]imidazole-5-carboxylic acid and Synthesis of 2-((6-(2-methoxyethoxy)benzo[d]oxazol-2-yl)amino)-N-(2-methoxyethyl)-1-methyl-1H-benzo[d]imidazole-5-carboxamide

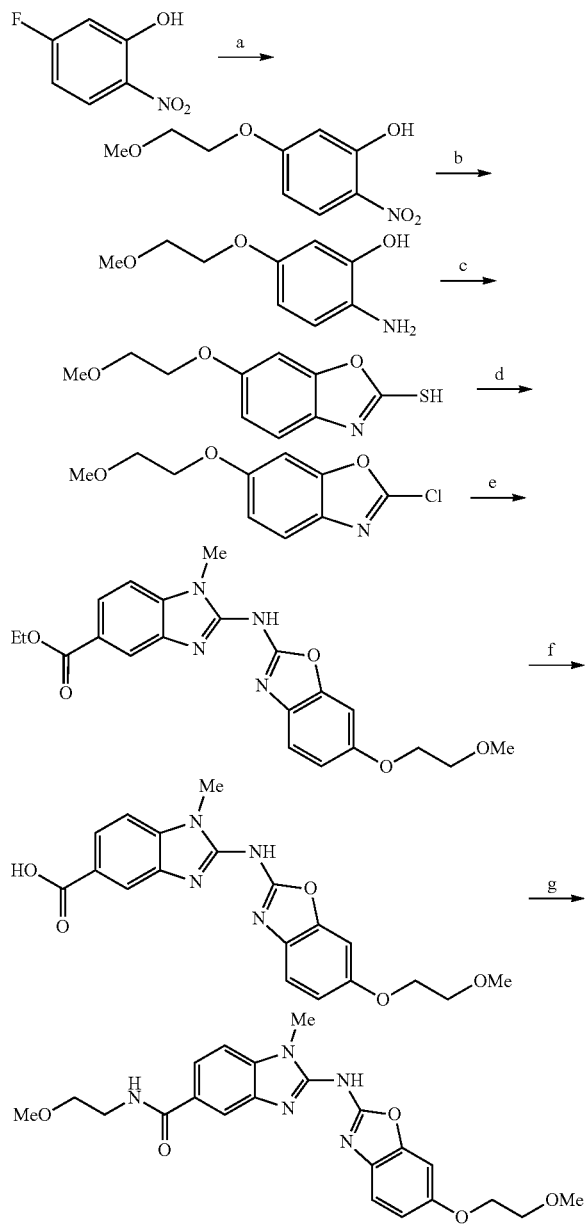

Conditions: a) 2-methoxyethan-1-ol, Sodium, 100° C., 16 h; b) 10% Pd/C, MeOH, H$_2$, RT, 16 h; c) Potassium ethyl xanthate, Ethanol, Reflux, 16 h; d) SOCl$_2$, Cat•DMF, reflux, 2 h; e) NaH, ethyl 2-amino-1-methyl-1H-benzo[d]imidazole-5-carboxylate, 1,4-Dioxane, RT, 16 h; f) LiOH•H$_2$O, THF, Ethanol, Water, 60° C., 8 h; g) 2-methoxyethylamine, DPPA, DIPEA, DMF, 0° C. - RT, 16 h Step-a: Synthesis of 5-(2-methoxyethoxy)-2-nitrophenol To a stirred 2-methoxyethan-1-ol (50 mL) at 0° C. was added sodium metal (2.29 g, 95.46 mmol) and the reaction mixture was allowed to stir at RT for 30 min, followed by the addition of 5-fluoro-2-nitrophenol (5.0 g, 31.82 mmol). The reaction mixture was heat to 100° C. for 16 h. Once the reaction was completed (monitored by TLC), the reaction mixture was cooled to 0° C., diluted with cold water (200 mL) and acidified with 1 N HCl. The solid obtained was filtered and dried under vacuum to afford the title compound (4.0 g, 59%) as a yellow solid; $^1$H NMR (400 MHz, DMSO-d$_6$): δ 10.93 (s, 1H), 7.96 (d, J=9.3 Hz, 1H), 6.64-6.58 (m, 2H), 4.19-4.17 (m, 2H), 3.67-3.65 (m, 2H), 3.30 (s, 3H).

Step-b: Synthesis of 2-amino-5-(2-methoxyethoxy)phenol

The title compound was synthesized using the same procedure which was followed for compound 1e using 5-(2-methoxyethoxy)-2-nitrophenol as starting material (Yield: 96%); LC-MS: m/z 184.1 (M+1)$^+$.

Step-c: Synthesis of 6-(2-methoxyethoxy)benzo[d]oxazole-2-thiol

The title compound was synthesized using the same procedure which was followed for Example 32 Step-c using 2-amino-5-(2-methoxyethoxy)phenol as starting material (Yield: 76%); $^1$H NMR (400 MHz, DMSO-d$_6$): δ 13.78 (s, 1H), 7.29 (d, J=2.4 Hz, 1H), 7.19 (d, J=8.8 Hz, 1H), 6.96 (dd, J=2.4 Hz, J=8.8 Hz, 1H), 4.18-4.16 (m, 2H), 3.73-3.71 (m, 2H), 3.36 (s, 3H); LC-MS: m/z 226.0 (M+1)$^+$.

Step-d: Synthesis of 2-chloro-6-(2-methoxyethoxy)benzo[d]oxazole

The title compound was synthesized using the same procedure which was followed for Example 32 Step-d using 6-(2-methoxyethoxy)benzo[d]oxazole-2-thiol as starting material and stirred for 2 h (Yield: 69%); LC-MS: m/z 228.05 (M+1)$^+$.

Step-e: Synthesis of ethyl 2-((6-(2-methoxyethoxy)benzo[d]oxazol-2-yl)amino)-1-methyl-1H-benzo[d]imidazole-5-carboxylate The title compound was synthesized using the same procedure which was followed for compound Example 32 Step-e using ethyl 2-amino-1-methyl-1H-benzo[d]imidazole-5-carboxylate and 2-chloro-6-(2-methoxyethoxy)benzo[d]oxazole as starting materials (Yield: 24%); $^1$H NMR (400 MHz, DMSO-d$_6$): δ 12.20 (bs, 1H), 8.21 (d, J=1.5 Hz, 1H), 7.86 (dd, J=1.5 Hz, J=8.3 Hz, 1H), 7.49 (d, J=8.3 Hz, 1H), 7.35 (d, J=8.8 Hz, 1H), 7.14 (d, J=2.4 Hz, 1H), 6.83 (dd, J=2.4 Hz, J=8.8 Hz, 1H), 4.33 (q, J=7.2 Hz, 2H), 4.12 (t, J=4.6 Hz, 2H), 3.67 (t, J=4.6 Hz, 2H), 3.62 (s, 3H), 3.32 (s, 3H), 1.35 (t, J=7.1 Hz, 3H); LC-MS: m/z 411.0 (M+1)$^+$.

Step-f: Synthesis of 2-((6-(2-methoxyethoxy)benzo[d]oxazol-2-yl)amino)-1-methyl-1H-benzo[d]imidazole-5-carboxylic acid The title compound was synthesized using the same procedure which was followed for compound 1h, using ethyl 2-((6-(2-methoxyethoxy)benzo[d]oxazol-2-yl)amino)-1-methyl-1H-benzo[d]imidazole-5-carboxylate as starting material (Yield: 77%); $^1$H NMR (400 MHz, DMSO-d$_6$): δ 12.15 (bs, 2H), 8.17 (d, J=1.5 Hz, 1H), 7.85 (dd, J=2.0 Hz, J=8.8 Hz, 1H), 7.47 (d, J=8.3 Hz, 1H), 7.36 (d, J=8.3 Hz, 1H), 7.13 (d, J=2.4 Hz, 1H), 6.82 (dd, J=2.4 Hz, J=8.3 Hz, 1H), 4.12 (t, J=4.6 Hz, 2H), 3.67 (t, J=4.6 Hz, 2H), 3.62 (s, 3H), 3.32 (s, 3H); LC-MS: m/z 383.0 (M+1)$^+$.

Step-g: Synthesis of 2-((6-(2-methoxyethoxy)benzo[d]oxazol-2-yl)amino)-N-(2-methoxyethyl)-1-methyl-1H-benzo[d]imidazole-5-carboxamide The title compound was synthesized using the same procedure which was followed for compound 1i using 2-((6-(2-methoxyethoxy)benzo[d]oxazol-2-yl)amino)-1-methyl-1H-benzo[d]imidazole-5-carboxylic acid as starting material (Yield: 29%); $^1$H NMR (400 MHz, DMSO-d$_6$): δ 12.15 (bs, 1H), 8.44 (t, J=5.4 Hz, 1H), 8.05 (d, J=1.5 Hz, 1H), 7.75 (dd, J=1.4 Hz, J=8.3 Hz, 1H), 7.45 (d, J=8.3 Hz, 1H), 7.35 (d, J=8.3 Hz, 1H), 7.13 (d, J=2.4 Hz, 1H), 6.82 (dd, J=2.4 Hz, J=8.3 Hz, 1H), 4.12-4.10 (m, 2H), 3.68-3.66 (m, 2H), 3.62 (s, 3H), 3.49-3.43 (m, 4H), 3.32 (s, 3H), 3.28 (s, 3H); LC-MS: m/z 440.60 (M+1)$^+$.

Example 57. Synthesis of N-(2-hydroxyethyl)-2-((6-(2-methoxyethoxy)benzo[d]oxazol-2-yl)amino)-1-methyl-1H-benzo[d]imidazole-5-carboxamide

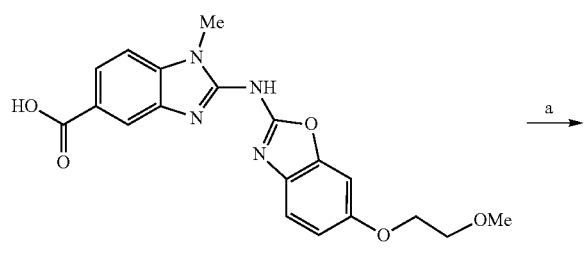

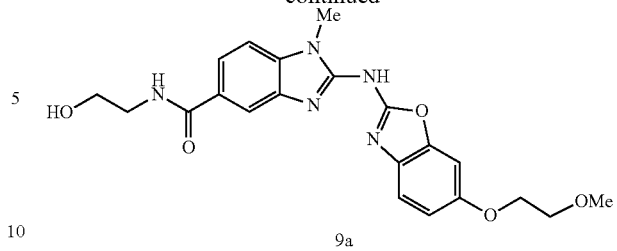

9a

Conditions: a) 2-aminoethan-1-ol, HBTU, DIPEA, DMF, 0° C. - RT, 16 h

The title compound was synthesized using the same procedure which was followed for Example 6 Step-e using 2-((6-(2-methoxyethoxy)benzo[d]oxazol-2-yl)amino)-1-methyl-1H-benzo[d]imidazole-5-carboxylic acid as starting material (Yield: 27%); $^1$H NMR (400 MHz, DMSO-d$_6$): δ 12.16 (bs, 1H), 8.35 (t, J=5.4 Hz, 1H), 8.05 (d, J=1.0 Hz, 1H), 7.75 (dd, J=1.5 Hz, J=8.3 Hz, 1H), 7.45 (d, J=8.3 Hz, 1H), 7.35 (d, J=8.8 Hz, 1H), 7.12 (d, J=2.4 Hz, 1H), 6.81 (dd, J=2.5 Hz, J=8.4 Hz, 1H), 4.72 (bs, 1H), 4.11 (t, J=4.6 Hz, 2H), 3.67 (t, J=4.6 Hz, 2H), 3.61 (s, 3H), 3.53 (t, J=5.3 Hz, 2H), 3.35 (t, J=6.0 Hz, 2H), 3.32 (s, 3H); LC-MS: m/z 426.45 (M+1)$^+$.

Example 58. Synthesis of N-(2-(2-hydroxyethoxy)ethyl)-2-((6-(2-methoxyethoxy)benzo[d]oxazol-2-yl)amino)-1-methyl-1H-benzo[d]imidazole-5-carboxamide

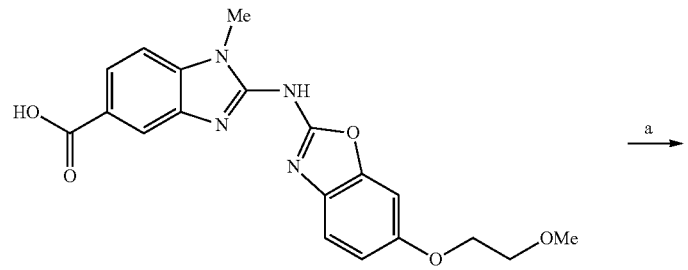

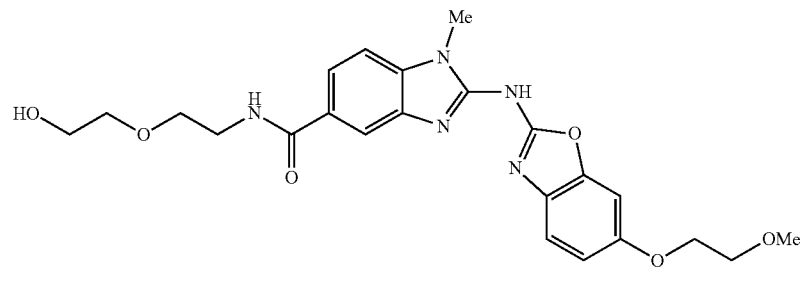

10a

Conditions: a) 2-(2-aminoethoxy)ethan-1-ol, HBTU, DIPEA, DMF, 0° C. - RT, 16 h

The title compound was synthesized using the same procedure which was followed for Example 6 Step-e using 2-((6-(2-methoxyethoxy)benzo[d]oxazol-2-yl)amino)-1-methyl-1H-benzo[d]imidazole-5-carboxylic acid and 2-(2-aminoethoxy)ethan-1-ol as starting materials (Yield: 61%); $^1$H NMR (400 MHz, DMSO-d$_6$): δ 12.15 (bs, 1H), 8.41 (t, J=5.4 Hz, 1H), 8.05 (d, J=0.9 Hz, 1H), 7.74 (dd, J=1.5 Hz, J=8.3 Hz, 1H), 7.45 (d, J=8.3 Hz, 1H), 7.35 (d, J=8.8 Hz, 1H), 7.12 (d, J=1.9 Hz, 1H), 6.82 (dd, J=2.4 Hz, J=8.8 Hz, 1H), 4.60 (bs, 1H), 4.13 (t, J=4.6 Hz, 2H), 3.67 (t, J=4.6 Hz, 2H), 3.62 (s, 3H), 3.57-3.42 (m, 8H), 3.32 (s, 3H); LC-MS: m/z 470.25 (M+1)$^+$.

Examples 59 and 60. Synthesis of 2-((6-isopropyl-benzo[d]oxazol-2-yl)amino)-1-methyl-1H-benzo[d]imidazole-5-carboxylic acid and Synthesis of 2-((6-isopropylbenzo[d]oxazol-2-yl)amino)-N-(2-methoxyethyl)-1-methyl-1H-benzo[d]imidazole-5-carboxamide

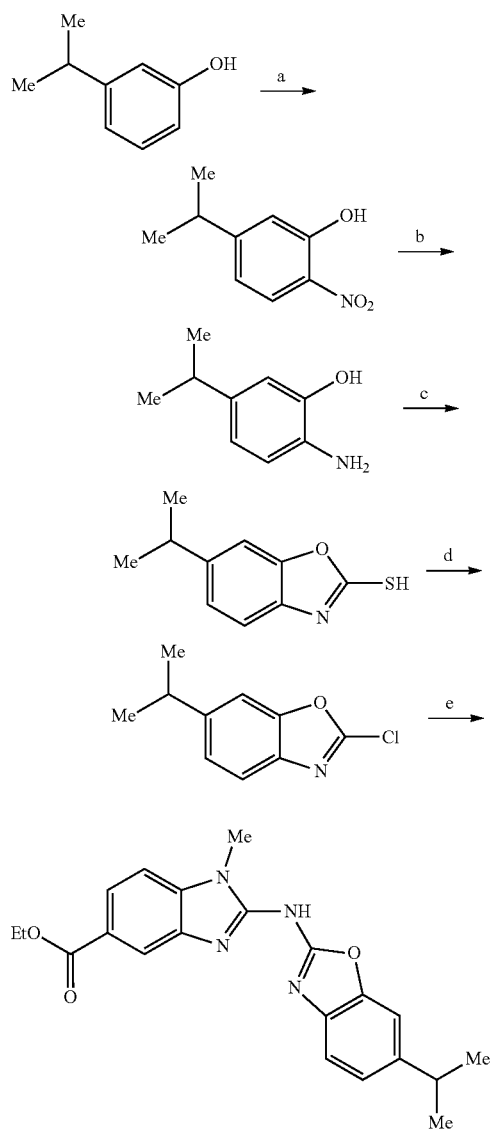

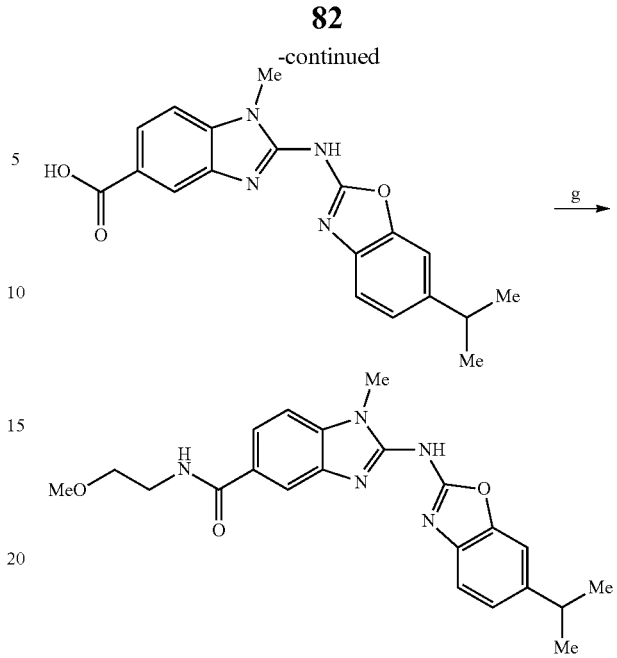

Conditions: a) NaNO$_3$, NaNO$_2$, 3M H$_2$SO$_4$, DCM, RT, 24 h; b) 10% Pd/C, MeOH, H$_2$, RT, 16 h; c) Potassium ethyl xanthate, ethanol, reflux, 16 h; d) SOCl$_2$, Cat•DMF, reflux, 2 h; e) NaH, ethyl 2-amino-1-methyl-1H-benzo[d]imidazole-5-carboxylate, 1,4-Dioxane, RT, 16 h; f) LiOH•H$_2$O, THF, ethanol, water, 60° C., 5 h; g) 2-methoxyethylamine, DPPA, DIPEA, DMF, 0° C. - RT, 16 h Step-a: Synthesis of 5-isopropyl-2-nitrophenol To a solution of 3-isopropylphenol (2.0 g, 14.7 mmol) in DCM (30 mL) and 3 M sulfuric acid (25 mL) was added sodium nitrate (1.37 g, 16.18 mmol) and sodium nitrite (10 mg, 0.14 mmol) at RT. Then the mixture was stirred for 24 h. The mixture was poured into ice water (100 mL) and extracted with DCM (2×50 mL). The combined organic layers were washed with brine solution (50 mL), dried over anhydrous sodium sulfate and concentrated in vacuum. The residue was purified by combiflash chromatography using 5% ethyl acetate in hexane as eluent to afford the titled compound (500 mg, 19%); $^1$H NMR (400 MHz, DMSO-d$_6$): δ 10.76 (s, 1H), 7.86 (d, J=8.8 Hz, 1H), 6.98 (d, J=1.5 Hz, 1H), 6.89 (dd, J=1.5 Hz, J=8.3 Hz, 1H), 2.92-2.89 (m, 1H), 1.19 (d, J=6.9 Hz, 6H); LC-MS: m/z 180.0 (M−1).

Step-b: Synthesis of 2-amino-5-isopropylphenol

The title compound was synthesized using the same procedure which was followed for compound 1e using 5-isopropyl-2-nitrophenol as starting material (Yield: 86%); $^1$H NMR (400 MHz, DMSO-d$_6$): δ 8.88 (bs, 1H), 6.50 (dd, J=1.9 Hz, J=10.7 Hz, 1H), 6.41 (d, J=2.0 Hz, 1H), 6.39 (d, J=2.0 Hz, 1H), 4.25 (s, 2H), 2.68-2.61 (m, 1H), 1.10 (d, J=6.8 Hz, 6H); LC-MS: m/z 152.15 (M+1)$^+$.

Step-c: Synthesis of 6-isopropylbenzo[d]oxazole-2-thiol

The title compound was synthesized using the same procedure which was followed for Example 32 Step-c using 2-amino-5-isopropylphenol as starting material (Yield: 68%); $^1$H NMR (400 MHz, DMSO-d$_6$): δ 13.74 (s, 1H), 7.41 (s, 1H), 7.20-7.13 (m, 2H), 3.0-2.93 (m, 1H), 1.21 (d, J=6.9 Hz, 6H); LC-MS: m/z 194.15 (M+1)$^+$.

Step-d: Synthesis of 2-chloro-6-isopropylbenzo[d]oxazole

The title compound was synthesized using the same procedure which was followed for Example 32 Step-d using 6-isopropylbenzo[d]oxazole-2-thiol as starting material and stirred for 2 h (Yield: 85%); $^1$H NMR (400 MHz, DMSO-$d_6$): δ 7.17 (s, 1H), 7.02-6.97 (m, 2H), 2.96-2.86 (m, 1H), 1.19 (d, J=6.8 Hz, 6H); LC-MS: m/z 196.0 (M+1)$^+$.

Step-e: Synthesis of ethyl 2-((6-isopropylbenzo[d]oxazol-2-yl)amino)-1-methyl-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 2-chloro-6-isopropylbenzo[d]oxazole as starting materials (Yield: 77%); $^1$H NMR (400 MHz, DMSO-$d_6$): δ 12.15 (bs, 1H), 8.22 (d, J=1.0 Hz, 1H), 7.86 (dd, J=1.0 Hz, J=8.3 Hz, 1H), 7.50 (d, J=8.3 Hz, 1H), 7.38 (d, J=8.3 Hz, 1H), 7.33 (s, 1H), 7.11 (d, J=7.8 Hz, 1H), 4.33 (q, J=7.0 Hz, 2H), 3.63 (s, 3H), 3.01-2.95 (m, 1H), 1.35 (t, J=7.0 Hz, 3H), 1.25 (d, J=6.8 Hz, 6H); LC-MS: m/z 379.1 (M+1)$^+$.

Step-f: Synthesis of 2-((6-isopropylbenzo[d]oxazol-2-yl)amino)-1-methyl-1H-benzo[d]imidazole-5-carboxylic acid The title compound was synthesized using the same procedure which was followed for compound 1h using ethyl 2-((6-isopropylbenzo[d]oxazol-2-yl)amino)-1-methyl-1H-benzo[d]imidazole-5-carboxylate as starting material and stirring at 60° C. for 5 h (Yield: 92%); $^1$H NMR (400 MHz, DMSO-$d_6$): δ 12.20 (bs, 2H), 8.18 (s, 1H), 7.86 (d, J=8.3 Hz, 1H), 7.49 (d, J=8.3 Hz, 1H), 7.39 (d, J=7.8 Hz, 1H), 7.33 (s, 1H), 7.10 (d, J=7.8 Hz, 1H), 3.63 (s, 3H), 2.98-2.97 (m, 1H), 1.25 (d, J=6.8 Hz, 6H); LC-MS: m/z 351.20 (M+1)$^+$.

Step-g: Synthesis of 2-((6-isopropylbenzo[d]oxazol-2-yl)amino)-N-(2-methoxyethyl)-1-methyl-1H-benzo[d]imidazole-5-carboxamide The title compound was synthesized using the same procedure which was followed for compound 1i using 2-((6-isopropylbenzo[d]oxazol-2-yl)amino)-1-methyl-1H-benzo[d]imidazole-5-carboxylic acid as starting material (Yield: 69%); $^1$H NMR (400 MHz, DMSO-$d_6$): δ 12.15 (bs, 1H), 8.44 (s, 1H), 8.07 (s, 1H), 7.75 (d, J=8.3 Hz, 1H), 7.46 (d, J=8.3 Hz, 1H), 7.37 (d, J=8.3 Hz, 1H), 7.32 (s, 1H), 7.09 (d, J=7.8 Hz, 1H), 3.63 (s, 3H), 3.48-3.44 (m, 4H), 3.28 (s, 3H), 2.98-2.97 (m, 1H), 1.25 (d, J=6.8 Hz, 6H); LC-MS: m/z 408.0 (M+1)$^+$.

Example 61. Synthesis of N-(2-hydroxyethyl)-2-((6-isopropylbenzo[d]oxazol-2-yl)amino)-1-methyl-1H-benzo[d]imidazole-5-carboxamide The title compound was synthesized using the same procedure which was followed for Example 6 Step-e using 2-((6-isopropylbenzo[d]oxazol-2-yl)amino)-1-methyl-1H-benzo[d]imidazole-5-carboxylic acid and 2-aminoethan-1-ol as starting materials. $^1$H NMR (400 MHz, DMSO-$d_6$): δ 12.50 (bs, 1H), 8.43 (bs, 1H), 8.08 (s, 1H), 7.82 (d, J=8.0 Hz, 1H), 7.55 (d, J=8.2 Hz, 1H), 7.38-7.36 (m, 2H), 7.16 (d, J=8.0 Hz, 1H), 3.67 (s, 3H), 3.54 (d, J=5.6 Hz, 2H), 3.36 (q, J=6.0 Hz, 2H), 3.02-2.99 (m, 1H), 1.25 (d, J=7.2 Hz, 6H); LC-MS: m/z 394.0 (M+1)$^+$.

Example 62. Synthesis of 2-((6-(difluoromethoxy)benzo[d]oxazol-2-yl)amino)-1-methyl-1H-benzo[d]imidazole-5-carboxylic acid

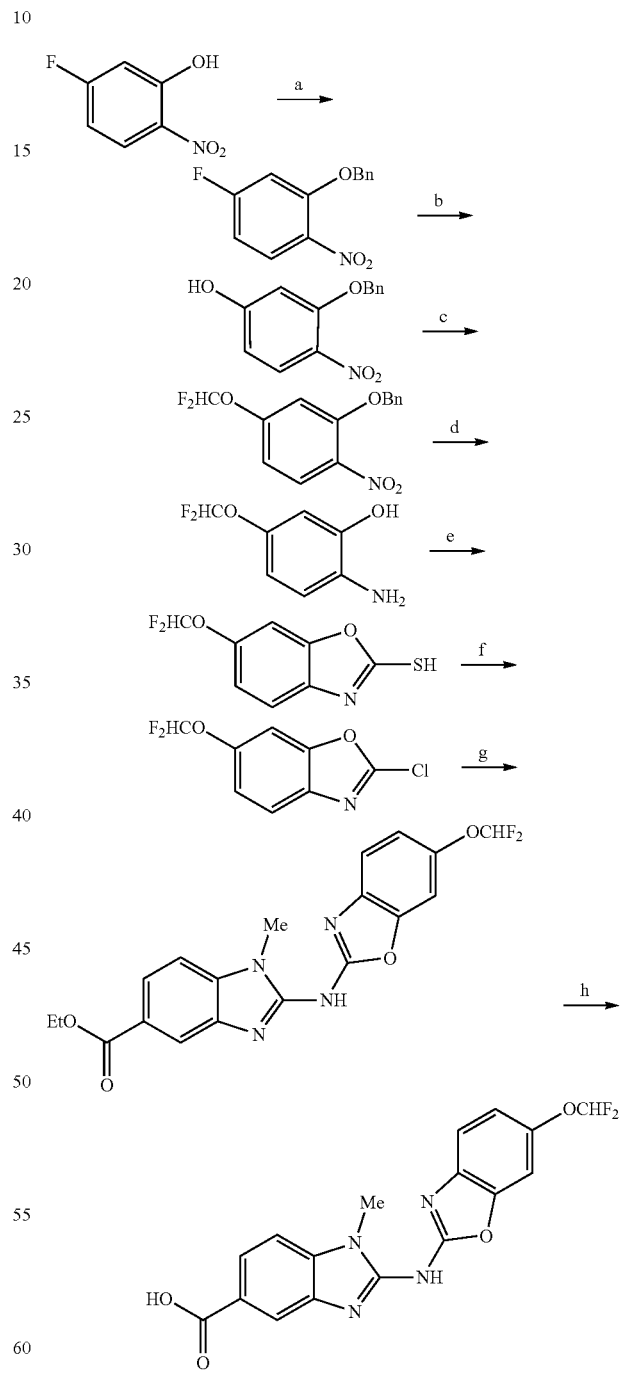

Conditions: a) K$_2$CO$_3$, Benzyl bromide, DMF, RT, 16 h; b) KOH, water, 100° C., 30 h; c) Diethyl (bromodifluoromethyl) phosphate, KOH, ACN and water (1:1), RT, 1 h; d) 10% Pd/C, MeOH, H$_2$, RT, 16 h, e) Potassium ethyl xanthate, ethanol, reflux, 16 h; f) SOCl$_2$, Cat•DMF, reflux, 2 h; g) NaH, ethyl 2-amino-1-methyl-1H-benzo[d]imidazole-5-carboxylate, 1,4-dioxane, RT, 16 h; f) LiOH•H$_2$O, THF, ethanol, water, 60° C., 16 h

Step-a: Synthesis of 2-(benzyloxy)-4-fluoro-1-nitrobenzene

To a stirred solution of 5-fluoro-2-nitrophenol (10 g, 63.7 mmol) in DMFA (100 mL) at RT was added potassium carbonate (10.54 g, 76.43 mmol) and benzyl bromide (7.56 mL, 63.7 mmol). The reaction mixture was then stirred at RT for 16 h. Once the reaction was completed (monitored by TLC), the reaction mixture was diluted with water (300 mL) and extracted with ethylacetate (2×100 mL). The combined organic layers were washed with cold water (2×200 mL), brine solution (100 mL), dried over anhydrous sodium sulfate and concentrated under vacuum. The residue was purified by combiflash column chromatography using 5% EtOAc in hexane as eluent to afford the titled compound (12.0 g, 76%); $^1$H NMR (400 MHz, DMSO-$d_6$): δ 8.04 (dd, J=5.8 Hz, J=9.3 Hz, 1H), 7.48-7.34 (m, 6H), 7.02-6.97 (m, 1H), 5.33 (s, 2H).

Step-b: Synthesis of 3-(benzyloxy)-4-nitrophenol

To a stirred solution of KOH (7.93 g, 141.7 mmol) in water (70 mL) at RT was added 2-(benzyloxy)-4-fluoro-1-nitrobenzene (7.0 g, 28.3 mmol) and the reaction mixture was stirred at 100° C. for 30 h. The reaction mixture was cooled to RT, diluted with water (100 mL), acidified with 3N HCl and extracted with ethyl acetate (3×50 mL). The combined organic layers were washed with brine solution (50 mL), dried over anhydrous sodium sulfate and concentrated under vacuum. The residue was purified by combiflash column chromatography using 20% EtOAc in hexane as eluent to afford the titled compound (2.0 g, 29%); $^1$H NMR (400 MHz, DMSO-$d_6$): δ 10.88 (s, 1H), 7.90 (d, J=8.8 Hz, 1H), 7.47 (t, J=7.4 Hz, 2H), 7.41-7.39 (m, 2H), 7.36-7.32 (m, 1H), 6.69 (d, J=2.0 Hz, 1H), 6.49 (dd, J=2.4 Hz, J=9.3 Hz, 1H), 5.25 (s, 2H); LC-MS: m/z 244.0 (M−1).

Step-c: Synthesis of 2-(benzyloxy)-4-(difluoromethoxy)-1-nitrobenzene

To a stirred solution of 3-(benzyloxy)-4-nitrophenol (1.1 g, 4.49 mmol) in acetonitrile (6 mL) at 0° C. was added potassium hydroxide (5.02 g, 89.79 mmol) in water (6 mL) and diethyl (bromodifluoromethyl) phosphonate (1.58 mL, 8.98 mmol). The reaction mixture was stirred at RT for 1 h and diluted with water (100 mL). The reaction mixture was extracted with ethyl acetate (3×60 mL). The combined organic layers were washed with brine solution (50 mL), dried over anhydrous sodium sulfate and concentrated under vacuum. The residue was purified by combiflash column chromatography using 10% EtOAc in hexane as eluent to afford the titled compound (1.2 g, 91%); $^1$H NMR (400 MHz, DMSO-$d_6$): δ 8.04 (d, J=9.3 Hz, 1H), 7.64-7.27 (m, 6H), 7.26 (d, J=2.5 Hz, 1H), 6.93 (dd, J=2.5 Hz, J=8.8 Hz, 1H), 5.34 (s, 2H).

Step-d: Synthesis of 2-amino-5-(difluoromethoxy)phenol

To a solution of 2-(benzyloxy)-4-(difluoromethoxy)-1-nitrobenzene (1.2 g, 4.07 mmol) in methanol (20 mL) was added 10% Pd/C (300 mg) under nitrogen atmosphere. The reaction mixture was stirred under hydrogen balloon for 16 h. The reaction mixture was filtered through a bed of celite and concentrated under vacuum to afford the title compound (600 mg, 84%); LC-MS: m/z 176.0 (M+1)$^+$.

Step-e: Synthesis of 6-(difluoromethoxy)benzo[d]oxazole-2-thiol

The title compound was synthesized using the same procedure which was followed for Example 32 Step-c using 2-amino-5-(difluoromethoxy)phenol as starting material (Yield: 81%); $^1$H NMR (400 MHz, DMSO-$d_6$): δ 13.96 (bs, 1H), 7.49 (d, J=2.0 Hz, 1H), 7.26 (d, J=8.3 Hz, 1H), 7.21 (t, J=73.2 Hz, 1H), 7.13 (dd, J=2.4 Hz, J=8.8 Hz, 1H); LC-MS: m/z 218.0 (M−1)$^+$.

Step-f: Synthesis of 2-chloro-6-(difluoromethoxy)benzo[d]oxazole

The title compound was synthesized using the same procedure which was followed for Example 32 Step-d using 6-(difluoromethoxy)benzo[d]oxazole-2-thiol as starting material and stirred for 2 h (Yield: 82%); $^1$H NMR (400 MHz, DMSO-$d_6$): δ 7.80 (d, J=8.8 Hz, 1H), 7.74 (d, J=2.5 Hz, 1H), 7.29-7.27 (m, 2H).

Step-g: Synthesis of ethyl 2-((6-(difluoromethoxy)benzo[d]oxazol-2-yl)amino)-1-methyl-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 2-chloro-6-(difluoromethoxy)benzo[d]oxazole as starting materials (Yield: 27%); $^1$H NMR (400 MHz, DMSO-$d_6$): δ 12.20 (bs, 1H), 8.23 (d, J=1.0 Hz, 1H), 7.88 (dd, J=1.5 Hz, J=8.4 Hz, 1H), 7.53 (d, J=8.3 Hz, 1H), 7.46 (d, J=8.3 Hz, 1H), 7.38-7.37 (m, 1H), 7.19 (s, 1H), 7.07-7.00 (m, 1H), 4.33 (q, J=7.0 Hz, 2H), 3.64 (s, 3H), 1.35 (t, J=7.1 Hz, 3H); LC-MS: m/z 403.0 (M+1)$^+$.

Step-h: Synthesis of 2-((6-(difluoromethoxy)benzo[d]oxazol-2-yl)amino)-1-methyl-1H-benzo[d]imidazole-5-carboxylic acid The title compound was synthesized using the same procedure which was followed for compound 1h using ethyl 2-((6-(difluoromethoxy)benzo[d]oxazol-2-yl)amino)-1-methyl-1H-benzo[d]imidazole-5-carboxylate as starting material (Yield: 93%); $^1$H NMR (400 MHz, DMSO-$d_6$): δ 12.80 (bs, 1H), 12.40 (bs, 1H), 8.19 (d, J=1.0 Hz, 1H), 7.87 (dd, J=1.4 Hz, J=8.3 Hz, 1H), 7.52-7.46 (m, 2H), 7.38-7.00 (m, 3H), 3.64 (s, 3H); LC-MS: m/z 375.0 (M+1)$^+$.

Example 63. Synthesis of 2-((6-(difluoromethoxy)benzo[d]oxazol-2-yl)amino)-N-(2-methoxyethyl)-1-methyl-1H-benzo[d]imidazole-5-carboxamide The title compound was synthesized using the same procedure which was followed for compound 1i using 2-((6-(difluoromethoxy)benzo[d]oxazol-2-yl)amino)-1-methyl-1H-benzo[d]imidazole-5-carboxylic acid and 2-methoxyethan-1-amine as starting materials; $^1$H NMR (400 MHz, DMSO-$d_6$): δ 12.25 (bs, 1H), 8.45 (t, J=5.2 Hz, 1H), 8.07 (s, 1H), 7.77 (d, J=8.4 Hz, 1H), 7.49-7.45 (m, 2H), 7.37 (s, 1H), 7.18 (s, 1H), 7.06-7.00 (m, 1H), 3.63 (s, 3H), 3.48-3.44 (m, 4H), 3.28 (s, 3H); LC-MS: m/z 432.0 (M+1)$^+$.

Example 64. Synthesis of 2-((6-(difluoromethoxy)benzo[d]oxazol-2-yl)amino)-N-(2-hydroxyethyl)-1-methyl-1H-benzo[d]imidazole-5-carboxamide The title compound was synthesized using the same procedure which was followed for Example 6 Step-e using 2-((6-(difluoromethoxy)benzo[d]oxazol-2-yl)amino)-1-methyl-1H-benzo[d]imidazole-5-carboxylic acid and 2-aminoethan-1-ol as starting materials; ¹H NMR (400 MHz, DMSO-d₆): δ 12.30 (bs, 1H), 8.38 (t, J=5.6 Hz, 1H), 8.08 (s, 1H), 7.78 (d, J=8.4 Hz, 1H), 7.50 (d, J=8.4 Hz, 1H), 7.46 (d, J=8.4 Hz, 1H), 7.38-7.00 (m, 3H), 3.64 (s, 3H), 3.53 (t, J=6.4 Hz, 2H), 3.35 (q, J=6.0 Hz, 2H); LC-MS: m/z 418.0 (M+1)⁺.

Example 65. Synthesis of N-(2-methoxyethyl)-1-methyl-2-((5-methylbenzo[d]oxazol-2-yl)amino)-1H-benzo[d]imidazole-5-carboxamide

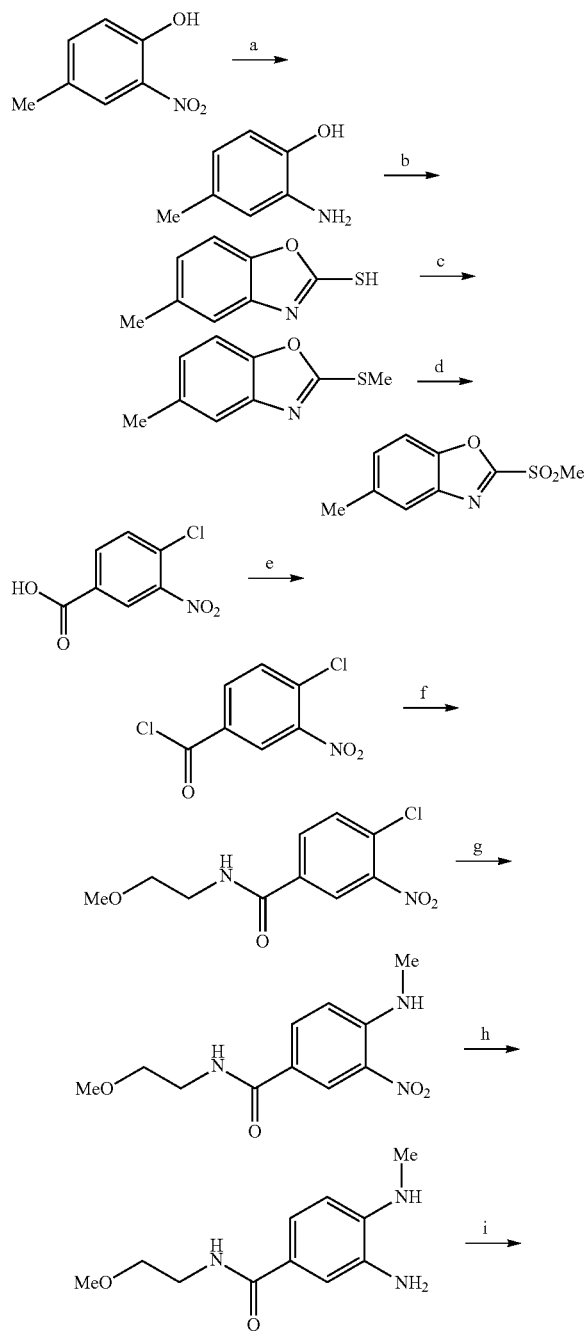

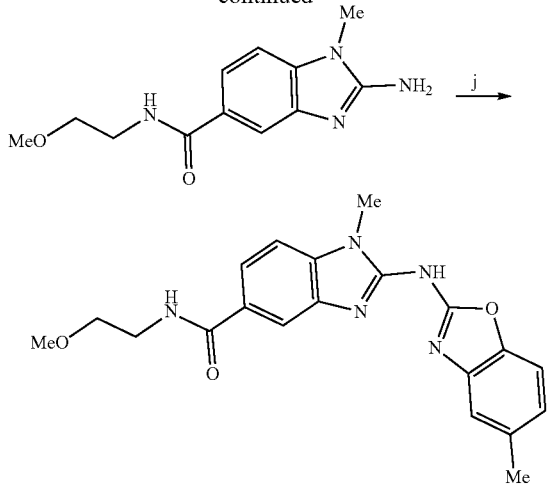

Conditions: a) 10% Pd/C, MeOH, H₂, RT, 16 h; b) Potassium ethyl xanthate, EtOH, Reflux, 16 h; c) K₂CO₃, MeI, ACN, 0° C. - RT, 3 h; d) m-CPBA, DCM, 0° C. - RT, 3 h; e) SOCl₂, Cat·DMF, DCM, Reflux, 4 h; f) 2-methoxyethan-1-amine, TEA, DCM, 0° C. - RT, 16 h; g) 2M methyl amine in THF, DIPEA, DMF, 70°C., 24 h; h) 10% Pd/C, MeOH, H₂, RT, 16 h; i) Cyanogen bromide, THF, H₂O, 50° C. to 60° C., 16 h; j) NaH, 5-methyl-2-(methylsulfonyl)benzo[d]oxazole, 1,4- Dioxane, RT, 16 h Step-a: Synthesis of 2-amino-4-methylphenol To a solution of 4-methyl-2-nitrophenol (1.75 g, 11.4 mmol) in methanol (15 mL) was added a slurry of 10% Pd/C (500 mg in 5 mL methanol) under nitrogen atmosphere. Then the reaction mixture was stirred under hydrogen gas balloon for 16 h. The reaction mixture was filtered through a bed of celite and concentrated under vacuum to afford the title compound (1.3 g, 93%); ¹H NMR (400 MHz, DMSO-d₆): δ 8.62 (bs, 1H), 6.49 (d, J=8.0 Hz, 1H), 6.38 (s, 1H), 6.17 (d, J=8.0 Hz, 1H), 4.36 (bs, 2H), 2.07 (s, 3H); LC-MS: m/z 124.2 (M+1)⁺.

Step-b: Synthesis of 5-methylbenzo[d]oxazole-2-thiol

To a solution of 2-amino-4-methylphenol (1.3 g, 10.5 mmol) in ethanol (15 mL) at RT was added potassium ethyl-xanthate (3.7 g, 22.2 mmol) and the reaction mixture was refluxed for 16 h. The reaction mixture was concentrated under vacuum and diluted with cold water (30 mL), acidified with 1 N HCl. The solid obtained was filtered and dried under vacuum to afford the title compound (1.3 g, 75%); ¹H NMR (400 MHz, DMSO-d₆): δ 13.78 (s, 1H), 7.37 (d, J=8.0 Hz, 1H), 7.07-7.05 (m, 2H), 2.36 (s, 3H); LC-MS: m/z 166.1 (M+1)⁺.

Step-c: Synthesis of 5-methyl-2-(methylthio)benzo[d]oxazole

To a solution of 5-methylbenzo[d]oxazole-2-thiol (1.3 g, 7.9 mmol) in acetonitrile (15 mL) at 0° C. was added potassium carbonate (1.3 g, 9.4 mmol) and methyl iodide (0.53 mL, 8.7 mmol) and the reaction mixture was stirred at RT for 3 h. The reaction mixture was concentrated under vacuum and diluted with water (30 mL), acidified with 1 N HCl. The solid obtained was filtered and dried under vacuum to afford the title compound (1.4 g, 99%); ¹H NMR (400

MHz, DMSO-d$_6$): δ 7.50 (d, J=8.0 Hz, 1H), 7.43 (s, 1H), 7.11 (d, J=8.4 Hz, 1H), 2.74 (s, 3H), 2.40 (s, 3H); LC-MS: m/z 180.1 (M+1)$^+$.

Step-d: Synthesis of 5-methyl-2-(methylsulfonyl) benzo[d]oxazole

To a solution of 5-methyl-2-(methylthio)benzo[d]oxazole (350 mg, 1.95 mmol) in DCM (10 mL) at 0° C. was added meta-chloroperbenzoic acid (2.14 g, 6.8 mmol) and the reaction mixture was stirred at RT for 3 h. The reaction mixture was diluted with DCM (100 mL), washed with saturated sodium bicarbonate solution (2×30 mL), aqueous 1N sodium hydroxide (30 mL), water (30 mL), brine (30 mL), dried over anhydrous sodium sulfate and concentrated under vacuum to afford the product which was immediately used in the next step without any further purification (340 mg); $^1$H NMR (400 MHz, DMSO-d$_6$): δ 7.84-7.79 (m, 2H), 7.49 (d, J=8.4 Hz, 1H), 3.65 (s, 3H), 2.48 (s, 3H).

Step-e: Synthesis of 4-chloro-3-nitrobenzoyl chloride

To a solution of 4-chloro-3-nitrobenzoic acid (15.0 g, 74.6 mmol) in DCM (150 mL) at 10° C. was added thionyl chloride (15.9 mL, 223.8 mmol) and DMFA (1 mL) and the reaction mixture was refluxed for 4 h. The reaction mixture was concentrated under vacuum to afford the product which was immediately used in the next step without any further purification (15.0 g).

Step-f: Synthesis of 4-chloro-N-(2-methoxyethyl)-3-nitrobenzamide

To a solution of 2-methoxyethan-1-amine (5.1 g, 68.2 mmol) in DCM (60 mL) at 0° C. was added triethylamine (20 mL, 138.6 mmol) and stirred for 10 min. Then a solution of 4-chloro-3-nitrobenzoyl chloride (15.0 g, 68.2 mmol) in DCM (50 mL) was added to the reaction mixture and stirred the contents at RT for 16 h. The reaction mixture was diluted with DCM (150 mL) and water (100 mL). Organic layer was separated and washed with water (150 mL), brine (100 mL), dried over anhydrous sodium sulfate and concentrated under vacuum to afford the title compound (18.5 g, 100%); $^1$H NMR (400 MHz, DMSO-d$_6$): δ 8.88 (bs, 1H), 8.51 (d, J=2.0 Hz, 1H), 8.14 (dd, J=2.0 Hz, J=8.4 Hz, 1H), 7.90 (d, J=8.4 Hz, 1H), 3.49-3.42 (m, 4H), 3.30 (s, 3H).

Step-g: Synthesis of N-(2-methoxyethyl)-4-(methylamino)-3-nitrobenzamide

To a solution of 4-chloro-N-(2-methoxyethyl)-3-nitrobenzamide (18.0 g, 69.8 mmol) in DMFA (180 mL) at 0° C. was added DIPEA (12.5 mL, 69.8 mmol) and 2 M methyl amine in THF (70 mL, 139.3 mmol). The reaction mixture was stirred at 70° C. for 24 h. The reaction mixture was cooled to RT, diluted with water (200 mL) and extracted with EtOAc (2×250 mL). The combined organic layers were washed with water (100 mL), brine (100 mL), dried over anhydrous sodium sulfate and concentrated under vacuum to give the product which was used in the next step without further purification (17.0 g, 96%); $^1$H NMR (400 MHz, DMSO-d$_6$): δ 8.65 (d, J=2.0 Hz, 1H), 8.54 (t, J=5.2 Hz, 1H), 8.42 (d, J=4.8 Hz, 1H), 8.02 (dd, J=1.6 Hz, J=9.2 Hz, 1H), 7.03 (d, J=9.2 Hz, 1H), 3.46-3.40 (m, 4H), 2.98 (d, J=3.2 Hz, 3H), 3.26 (s, 3H); LC-MS: m/z 254.1 (M+1)$^+$.

Step-h: Synthesis of 3-amino-N-(2-methoxyethyl)-4-(methylamino)benzamide

To a solution of N-(2-methoxyethyl)-4-(methylamino)-3-nitrobenzamide (6.0 g, 23.7 mmol) in methanol (100 mL) was added a slurry of 10% Pd/C (1.2 g in 20 mL methanol) under nitrogen atmosphere. The reaction mixture was stirred under hydrogen gas balloon for 16 h. The reaction mixture was filtered through a bed of celite and concentrated under vacuum to afford the title compound (4.0 g, 75%); $^1$H NMR (400 MHz, DMSO-d$_6$): δ 7.88 (t, J=5.2 Hz, 1H), 7.11-7.06 (m, 2H), 6.34 (d, J=8.0 Hz, 1H), 5.07 (bs, 1H), 4.54 (bs, 2H), 3.42-3.34 (m, 4H) 3.27 (s, 3H), 2.75 (d, J=2.8 Hz, 3H); LC-MS: m/z 224.2 (M+1)$^+$.

Step-i: Synthesis of 2-amino-N-(2-methoxyethyl)-1-methyl-1H-benzo[d]imidazole-5-carboxamide To a solution of 3-amino-N-(2-methoxyethyl)-4-(methylamino)benzamide (2.0 g, 8.92 mmol) in THF (10 mL) and water (20 mL) at RT was added cyanogen bromide (1.04 g, 9.82 mmol) and the reaction mixture was stirred at 50° C. to 60° C. for 16 h. The reaction mixture was cooled to RT and basified with saturated sodium bicarbonate solution, extracted with ethyl acetate (2×100 mL). The combined organic layers were washed with water (50 mL), brine (50 mL), dried over anhydrous sodium sulfate and concentrated under vacuum to afford the crude product which was purified by combiflash chromatography using 5% methanol in DCM as an eluent to afford the title compound (1.3 g, 59%); $^1$H NMR (400 MHz, DMSO-d$_6$): δ 8.26 (bs, 1H), 7.66 (s, 1H), 7.48 (d, J=7.6 Hz, 1H), 7.14 (d, J=8.0 Hz, 1H), 6.52 (bs, 2H), 3.51 (s, 3H), 3.45-3.41 (m, 4H), 3.26 (s, 3H); LC-MS: m/z 249.2 (M+1)$^+$.

Step-j: Synthesis of N-(2-methoxyethyl)-1-methyl-2-((5-methylbenzo[d]oxazol-2-yl)amino)-1H-benzo[d]imidazole-5-carboxamide To a solution of 2-amino-N-(2-methoxyethyl)-1-methyl-1H-benzo[d]imidazole-5-carboxamide (300 mg, 1.2 mmol) in 1,4-dioxane (5 mL) at 10° C. was added sodium hydride (60% dispersion in mineral oil) (96 mg, 2.4 mmol) and stirred for 10 min followed by the addition of 5-methyl-2-(methylsulfonyl)benzo[d]oxazole (306 mg, 1.45 mmol) and it was stirred at RT for 16 h. The reaction mixture was quenched with cold water (20 mL) and extracted with ethyl acetate (2×50 mL). The combined organic layers were washed with water (30 mL), brine (30 mL), dried over anhydrous sodium sulfate and concentrated under vacuum to obtain the crude product which was purified by combiflash chromatography using 2% methanol in DCM as an eluent to afford the title compound (6 mg, 1%); $^1$H NMR (400 MHz, DMSO-d$_6$): δ 12.2 (bs, 1H), 8.45 (t, J=5.2 Hz, 1H), 8.08 (d, J=1.6 Hz, 1H), 7.76 (dd, J=1.2 Hz, J=8.0 Hz, 1H), 7.47 (d, J=8.4 Hz, 1H), 7.30 (d, J=8.4 Hz, 1H), 7.26 (s, 1H), 6.93 (d, J=7.6 Hz, 1H), 3.62 (s, 3H), 3.50-3.42 (m, 4H), 3.29 (s, 3H), 2.49 (s, 3H); LC-MS: m/z 380.2 (M+1)$^+$.

Examples 66 and 67. Synthesis of 2-((5-fluorobenzo[d]oxazol-2-yl)amino)-1-methyl-1H-benzo[d]imidazole-5-carboxylic acid and Synthesis of 2-((5-fluorobenzo[d]oxazol-2-yl)amino)-N-(2-methoxyethyl)-1-methyl-1H-benzo[d]imidazole-5-carboxamide

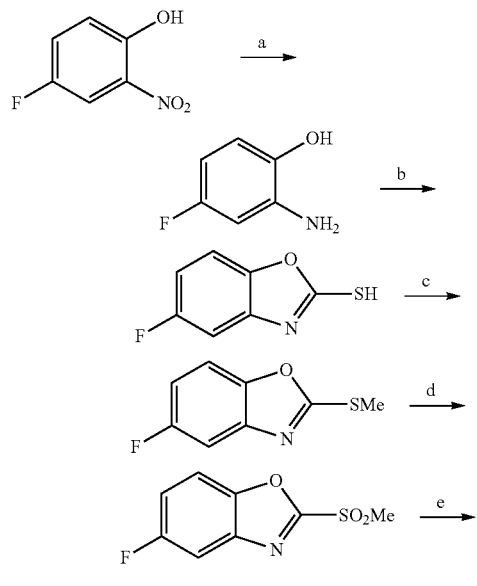

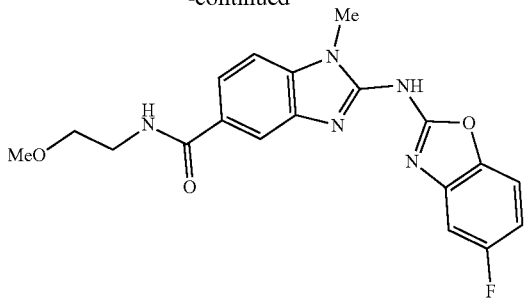

Conditions: a) 10% Pd/C, MeOH, $H_2$, RT, 16 h; b) Potassium ethyl xanthate, EtOH, Reflux, 16 h; c) $K_2CO_3$, MeI, ACN, RT, 16 h; d) m-CPBA, DCM, 0° C. - RT, 4 h; e) NaH, ethyl 2-amino-1-methyl-1H-benzo[d]imidazole-5-carboxylate, 1,4-Dioxane, RT, 16 h; f) LiOH·$H_2O$, THF, Ethanol, Water, 60° C., 16 h; g) 2-methyoxyethylamine, DPPA, DIPEA, DMF, 0° C. - RT, 16 h Step-a: Synthesis of 2-amino-4-fluorophenol The title compound was synthesized using the same procedure which was followed for Example 32 Step-b using 4-fluoro-2-nitrophenol as starting material (Yield: 91%); $^1$H NMR (400 MHz, DMSO-$d_6$): δ 8.88 (bs, 1H), 6.56-6.53 (m, 1H), 6.35 (dd, J=2.0 Hz, J=10.4 Hz, 1H), 6.13-6.08 (m, 1H), 4.78 (bs, 2H); LC-MS: m/z 128.1 (M+1)$^+$.

Step-b: Synthesis of 5-fluorobenzo[d]oxazole-2-thiol

The title compound was synthesized using the same procedure which was followed for Example 32 Step-c using 2-amino-4-fluorophenol as starting material (Yield: 86%); $^1$H NMR (400 MHz, DMSO-$d_6$): δ 14.01 (bs, 1H), 7.55-7.51 (m, 1H), 7.15-7.08 (m, 2H); LC-MS: m/z 170.0 (M+1)$^+$.

Step-c: Synthesis of 5-fluoro-2-(methylthio)benzo[d]oxazole

The title compound was synthesized using the same procedure which was followed for Compound 1b using 5-fluorobenzo[d]oxazole-2-thiol as starting material (stirring for 16 h) (Yield: 92%); $^1$H NMR (400 MHz, DMSO-$d_6$): δ 7.69-7.65 (m, 1H), 7.53 (dd, J=2.4 Hz, J=8.8 Hz, 1H), 7.19-7.11 (m, 1H), 2.76 (s, 3H); LC-MS: m/z 184.1 (M+1)$^+$.

Step-d: Synthesis of 5-fluoro-2-(methylsulfonyl)benzo[d]oxazole

The title compound was synthesized using the same procedure which was followed for compound 1c using 5-fluoro-2-(methylthio)benzo[d]oxazole as starting material (stirring for 4 h) (Yield: 99%); $^1$H NMR (400 MHz, DMSO-$d_6$): δ 8.05-8.01 (m, 1H), 7.94 (dd, J=2.4 Hz, J=8.0 Hz, 1H), 7.57-7.54 (m, 1H), 3.67 (s, 3H); LC-MS: m/z 216.0 (M+1)$^+$.

Step-e: Synthesis of ethyl 2-((5-fluorobenzo[d]oxazol-2-yl)amino)-1-methyl-1H-benzo[d]imidazole-5-carboxylate The title compound was synthesized using the same procedure which was followed for compound 1g using ethyl 2-amino-1-methyl-1H-benzo[d]imidazole-5-carboxylate and 5-fluoro-2-(methylsulfonyl)benzo[d]oxazole as starting materials (Yield: 26%); $^1$H NMR (400 MHz, DMSO-$d_6$): δ 12.34 (bs, 1H), 8.23 (s, 1H), 7.88 (dd, J=1.6 Hz, J=8.4 Hz, 1H), 7.49 (d, J=8.0 Hz, 1H), 7.46-7.42 (m, 1H), 7.23 (dd, J=2.4 Hz, J=9.2 Hz, 1H), 6.97-6.91 (m, 1H), 4.34 (q, J=6.4 Hz, 2H), 3.64 (s, 3H), 1.36 (t, J=4.4 Hz, 3H); LC-MS: m/z 355.2 (M+1)⁺.

Step-f: Synthesis of 2-((5-fluorobenzo[d]oxazol-2-yl)amino)-1-methyl-1H-benzo[d]imidazole-5-carboxylic acid The title compound was synthesized using the same procedure which was followed for compound 1h using ethyl 2-((5-fluorobenzo[d]oxazol-2-yl)amino)-1-methyl-1H-benzo[d]imidazole-5-carboxylate as starting material (Yield: 58%); ¹H NMR (400 MHz, DMSO-d₆): δ 12.8 (bs, 1H), 12.3 (bs, 1H), 8.19 (s, 1H), 7.87 (d, J=8.4 Hz, 1H), 7.51 (d, J=8.8 Hz, 1H), 7.45-7.42 (m, 1H), 7.24 (dd, J=2.4 Hz, J=8.8 Hz, 1H), 6.96-6.91 (m, 1H), 3.64 (s, 3H); LC-MS: m/z 327.2 (M+1)⁺.

Step-g: Synthesis of 2-((5-fluorobenzo[d]oxazol-2-yl)amino)-N-(2-methoxyethyl)-1-methyl-1H-benzo[d]imidazole-5-carboxamide The title compound was synthesized using the same procedure which was followed for compound 1i using 2-((5-fluorobenzo[d]oxazol-2-yl)amino)-1-methyl-1H-benzo[d]imidazole-5-carboxylic acid and 2-methoxyethylamine as starting materials (Yield: 62%); ¹H NMR (400 MHz, DMSO-d₆): δ 12.2 (bs, 1H), 8.20 (s, 1H), 8.06 (s, 1H), 7.76 (d, J=8.4 Hz, 1H), 7.44 (d, J=8.4 Hz, 1H), 7.40-7.37 (m, 1H), 7.20 (d, J=8.8 Hz, 1H), 6.89 (t, J=10.0 Hz, 1H), 3.63 (s, 3H), 3.50-3.45 (m, 4H), 3.09 (s, 3H); LC-MS: m/z 384.2 (M+1)⁺.

Examples 68 and 69. Synthesis of 2-((6-fluorobenzo[d]oxazol-2-yl)amino)-1-methyl-1H-benzo[d]imidazole-5-carboxylic acid and Synthesis of 2-((6-fluorobenzo[d]oxazol-2-yl)amino)-N-(2-methoxyethyl)-1-methyl-1H-benzo[d]imidazole-5-carboxamide

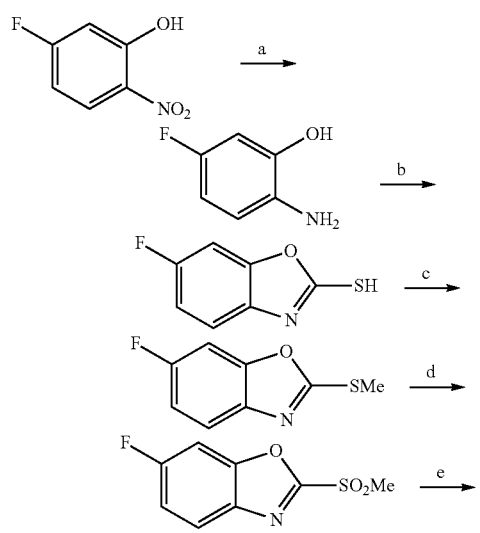

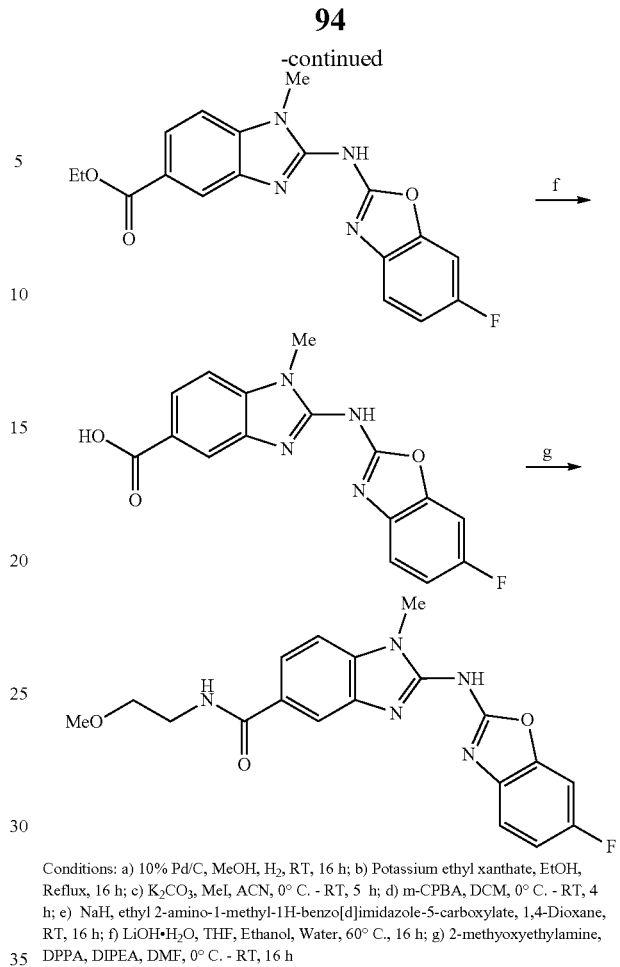

Conditions: a) 10% Pd/C, MeOH, H₂, RT, 16 h; b) Potassium ethyl xanthate, EtOH, Reflux, 16 h; c) K₂CO₃, MeI, ACN, 0° C. - RT, 5 h; d) m-CPBA, DCM, 0° C. - RT, 4 h; e) NaH, ethyl 2-amino-1-methyl-1H-benzo[d]imidazole-5-carboxylate, 1,4-Dioxane, RT, 16 h; f) LiOH·H₂O, THF, Ethanol, Water, 60° C., 16 h; g) 2-methyoxyethylamine, DPPA, DIPEA, DMF, 0° C. - RT, 16 h Step-a: Synthesis of 2-amino-5-fluorophenol The title compound was synthesized using the same procedure which was followed for Example 32 Step-b using 5-fluoro-2-nitrophenol as starting material (Yield: 92%); ¹H NMR (400 MHz, DMSO-d₆): δ 9.5 (bs, 1H), 6.54-6.51 (m, 1H), 6.46 (dd, J=2.8 Hz, J=10.0 Hz, 1H), 6.37-6.32 (m, 1H); LC-MS: m/z 128.2 (M+1)⁺.

Step-b: Synthesis of 6-fluorobenzo[d]oxazole-2-thiol

The title compound was synthesized using the same procedure which was followed for Example 32 Step-c using 2-amino-5-fluorophenol as starting material (Yield: 89%); ¹H NMR (400 MHz, DMSO-d₆): δ 13.94 (bs, 1H), 7.57 (dd, J=2.0 Hz, J=8.4 Hz, 1H), 7.25-7.22 (m, 1H), 7.19-7.14 (m, 1H); LC-MS: m/z 170.0 (M+1)⁺.

Step-c: Synthesis of 6-fluoro-2-(methylthio)benzo[d]oxazole

The title compound was synthesized using the same procedure which was followed for compound 1b using 6-fluorobenzo[d]oxazole-2-thiol as starting material (stirring for 5 h) (Yield: 99%); ¹H NMR (400 MHz, DMSO-d₆): δ 7.67-7.63 (m, 2H), 7.24-7.18 (m, 1H), 2.75 (s, 3H); LC-MS: m/z 184.0 (M+1)⁺.

Step-d: Synthesis of 6-fluoro-2-(methylsulfonyl) benzo[d]oxazole

The title compound was synthesized using the same procedure which was followed for compound 1c using 6-fluoro-2-(methylthio)benzo[d]oxazole as starting material (stirring for 4 h) (Yield: 95%); $^1$H NMR (400 MHz, DMSO-$d_6$): δ 8.08-8.02 (m, 1H), 8.01-7.99 (m, 1H), 7.56-7.46 (m, 1H), 3.67 (s, 3H).

Step-e: Synthesis of ethyl 2-((6-fluorobenzo[d]oxazol-2-yl)amino)-1-methyl-1H-benzo[d]imidazole-5-carboxylate The title compound was synthesized using the same procedure which was followed for compound 1g using ethyl 2-amino-1-methyl-1H-benzo[d]imidazole-5-carboxylate and 6-fluoro-2-(methylsulfonyl)benzo[d]oxazole as starting materials (Yield: 28%); $^1$H NMR (400 MHz, DMSO-$d_6$): δ 12.3 (bs, 1H), 8.23 (d, J=1.6 Hz, 1H), 7.88 (dd, J=2.0 Hz, J=8.4 Hz, 1H), 7.52 (d, J=8.4 Hz, 1H), 7.45-7.41 (m, 2H), 7.10-7.04 (m, 1H), 4.33 (q, J=6.8 Hz, 2H), 3.64 (s, 3H), 1.35 (t, J=7.2 Hz, 3H); LC-MS: m/z 355.1 (M+1)$^+$.

Step-f: Synthesis of 2-((6-fluorobenzo[d]oxazol-2-yl)amino)-1-methyl-1H-benzo[d]imidazole-5-carboxylic acid To a stirred solution of ethyl 2-((6-fluorobenzo[d]oxazol-2-yl)amino)-1-methyl-1H-benzo[d]imidazole-5-carboxylate (45 mg, 0.13 mmol) in a mixture of solvent of THF (1 mL), ethanol (1 mL) and water (0.5 mL) was added lithium hydroxide monohydrate (10 mg, 0.25 mmol). The reaction mixture was heated at 60° C. for 16 h with stirring. The reaction mixture was cooled to RT and concentrated under reduced pressure. The residue was dissolved in water (15 mL), acidified with 1 N HCl to obtain the solid which was filtered and dried under vacuum to afford the title compound (30 mg, 72%); $^1$H NMR (400 MHz, DMSO-$d_6$): δ 12.8 (bs, 1H), 12.3 (bs, 1H) 8.19 (d, J=1.6 Hz, 1H), 7.87 (dd, J=1.6 Hz, J=8.4 Hz, 1H), 7.50 (d, J=8.8 Hz, 1H), 7.46-7.41 (m, 2H), 7.09-7.03 (m, 1H), 3.63 (s, 3H); LC-MS: m/z 327.05 (M+1)$^+$.

Step-g: Synthesis of 2-((6-fluorobenzo[d]oxazol-2-yl)amino)-N-(2-methoxyethyl)-1-methyl-1H-benzo[d]imidazole-5-carboxamide To a stirred solution of 2-((6-fluorobenzo[d]oxazol-2-yl)amino)-1-methyl-1H-benzo[d]imidazole-5-carboxylic acid (30 mg, 0.09 mmol) in DMFA (2 mL) at 0° C. was added N-ethyldiisopropyl amine (0.03 mL, 0.18 mmol) and diphenylphosphoryl azide (0.02 mL, 0.09 mmol). The reaction mixture was stirred for 30 min, followed by the addition of 2-methoxyethylamine (6 mg, 0.09 mmol) and the reaction mixture was then stirred at RT for 16 h. Once the reaction was completed (monitored by TLC), the reaction mixture was diluted with cold water (6 mL) and stirred for 15 min. The solid obtained was filtered, washed with diethyl ether and dried under vacuum to afford the title compound (20 mg, 58%) as white solid; $^1$H NMR (400 MHz, DMSO-$d_6$): δ 12.2 (bs, 1H), 8.45 (t, J=5.2 Hz, 1H), 8.07 (d, J=1.2 Hz, 1H), 7.75 (dd, J=1.6 Hz, J=8.8 Hz, 1H), 7.49-7.40 (m, 3H), 7.08-7.03 (m, 1H), 3.63 (s, 3H), 3.50-3.43 (m, 4H), 3.39 (s, 3H); LC-MS: m/z 384.1 (M+1)$^+$.

Examples 70 and 71. Synthesis of 6-fluoro-1-methyl-2-((6-(trifluoromethoxy)benzo[d]oxazol-2-yl)amino)-1H-benzo[d]imidazole-5-carboxylic acid and Synthesis of 6-fluoro-N-(2-methoxyethyl)-1-methyl-2-((6-(trifluoromethoxy)benzo[d]oxazol-2-yl)amino)-1H-benzo[d]imidazole-5-carboxamide

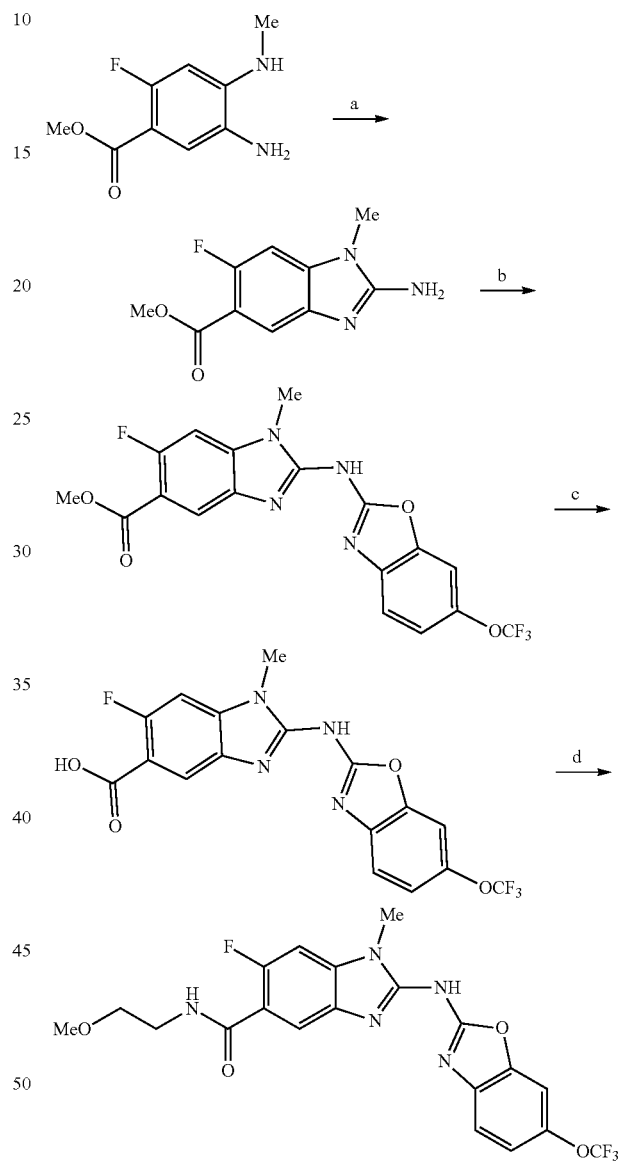

Conditions: a) Cyanogen bromide, THF, H$_2$O, 60° C., 16 h; b) NaH, 2-(methylsulfonyl)-6-(trifluoromethoxy)benzo[d]oxazole, 1,4-Dioxane, RT, 16 h; c) LiOH•H$_2$O, THF, MeOH, H$_2$O, 60° C., 16 h; d) 2-methoxyethylamine, DPPA, DIPEA, DMF, 0° C. - RT, 16 h

Step-a: Synthesis of methyl 2-amino-6-fluoro-1-methyl-1H-benzo[d]imidazole-5-carboxylate The title compound was synthesized using the same procedure which was followed for compound 1f using methyl 5-amino-2-fluoro-4-(methylamino)benzoate as starting material and heating to 60° C. for 16 h. (Yield: 89%); $^1$H NMR (400 MHz, DMSO-d₆): δ 7.54 (d, J=6.4 Hz, 1H), 7.16 (d, J=11.6 Hz, 1H), 6.69 (bs, 2H), 3.80 (s, 3H), 3.51 (s, 3H); LC-MS: m/z 224.1 (M+1)⁺.

Step-b: Synthesis of methyl 6-fluoro-1-methyl-2-((6-(trifluoromethoxy)benzo[d]oxazol-2-yl)amino)-1H-benzo[d]imidazole-5-carboxylate The title compound was synthesized using the same procedure which was followed for compound 1g using methyl 2-amino-6-fluoro-1-methyl-1H-benzo[d]imidazole-5-carboxylate and 2-(methylsulfonyl)-6-(trifluoromethoxy)benzo[d]oxazole as starting materials (Yield: 18%); ¹H NMR (400 MHz, DMSO-d₆): δ 12.3 (bs, 1H), 8.10 (d, J=6.0 Hz, 1H), 7.95-7.51 (m, 3H), 7.22 (d, J=8.4 Hz, 1H), 3.87 (s, 3H), 3.61 (s, 3H); LC-MS: m/z 425.1 (M+1)⁺.

Step-c: Synthesis of 6-fluoro-1-methyl-2-((6-(trifluoromethoxy)benzo[d]oxazol-2-yl)amino)-1H-benzo[d]imidazole-5-carboxylic acid The title compound was synthesized using the same procedure which was followed for compound 1h using methyl 6-fluoro-1-methyl-2-((6-(trifluoromethoxy)benzo[d]oxazol-2-yl)amino)-1H-benzo[d]imidazole-5-carboxylate as starting material and THF, methanol and water as solvents (2:2:1) (Yield: 66%); ¹H NMR (400 MHz, DMSO-d₆): δ 13.0 (bs, 1H), 12.3 (bs, 1H), 8.08 (d, J=6.0 Hz, 1H), 7.59 (s, 1H), 7.53-7.49 (m, 2H), 7.22 (d, J=7.2 Hz, 1H), 3.61 (s, 3H); LC-MS: m/z 411.1 (M−1)⁺.

Step-d: Synthesis of 6-fluoro-N-(2-methoxyethyl)-1-methyl-2-((6-(trifluoromethoxy)-benzo[d]oxazol-2-yl)amino)-1H-benzo[d]imidazole-5-carboxamide The title compound was synthesized using the same procedure which was followed for compound 1i using 6-fluoro-1-methyl-2-((6-(trifluoromethoxy)benzo[d]oxazol-2-yl)amino)-1H-benzo[d]imidazole-5-carboxylic acid and 2-methoxyethylamine as starting materials (Yield: 48%); ¹H NMR (400 MHz, DMSO-d₆): δ 12.3 (bs, 1H), 8.18 (d, J=4.0 Hz, 1H), 7.86 (d, J=6.4 Hz, 1H), 7.58 (s, 1H), 7.52-7.49 (m, 2H), 7.21 (d, J=9.2 Hz, 1H), 3.61 (s, 3H), 3.47-3.44 (m, 4H), 3.29 (s, 3H); LC-MS: m/z 468.1 (M+1)⁺.

Example 72. Synthesis of 2-(benzo[d]oxazol-2-ylamino)-6-fluoro-N-(2-(2-hydroxyethoxy)ethyl)-1-methyl-1H-benzo[d]imidazole-5-carboxamide

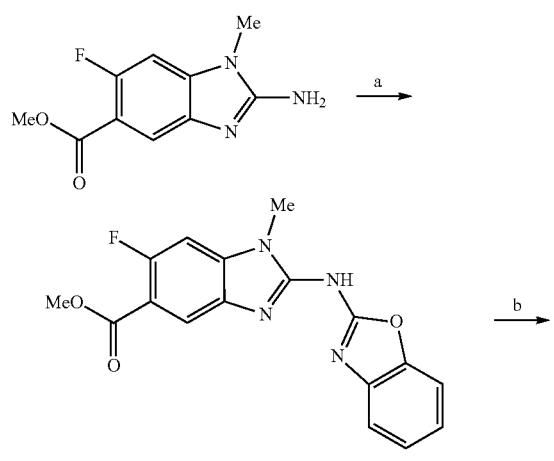

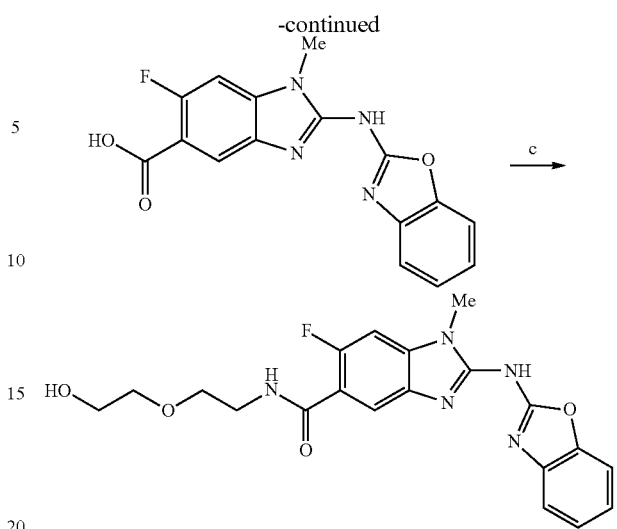

Conditions: a) NaH, 2-chlorobenzo[d]oxazole, 1,4-Dioxane, RT, 16 h; f) LiOH•H₂O, THF, MeOH, H₂O, 60° C., 16 h; g) 2-(2-aminoethoxy)ethan-1-ol, HBTU, DIPEA, DMF, 0° C. - RT, 16 h Step-a: Synthesis of methyl 2-(benzo[d]oxazol-2-ylamino)-6-fluoro-1-methyl-1H-benzo[d]imidazole-5-carboxylate The title compound was synthesized using the same procedure which was followed for Example 32 Step-e using methyl 2-amino-6-fluoro-1-methyl-1H-benzo[d]imidazole-5-carboxylate and 2-chlorobenzo[d]oxazole as starting materials (Yield: 66%); ¹H NMR (400 MHz, DMSO-d₆): δ 12.25 (bs, 1H), 8.09 (d, J=6.0 Hz, 1H), 7.55-7.44 (m, 3H), 7.24-7.22 (m, 1H), 7.17-7.12 (m, 1H), 3.86 (s, 3H), 3.60 (s, 3H); LC-MS: m/z 341.0 (M+1)⁺.

Step-b: Synthesis of 2-(benzo[d]oxazol-2-ylamino)-6-fluoro-1-methyl-1H-benzo[d]imidazole-5-carboxylic acid The title compound was synthesized using the same procedure which was followed for compound 1h using methyl 2-(benzo[d]oxazol-2-ylamino)-6-fluoro-1-methyl-1H-benzo[d]imidazole-5-carboxylate as starting material and methanol, THF and water (2:2:1) as solvent (Yield: 75%); ¹H NMR (400 MHz, DMSO-d₆): δ 12.80 (bs, 2H), 8.07 (d, J=6.8 Hz, 1H), 7.50-7.44 (m, 3H), 7.22 (t, J=6.8 Hz, 1H), 7.15-7.11 (m, 1H), 3.60 (s, 3H); LC-MS: m/z 327.0 (M+1)⁺.

Step-c: Synthesis of 2-(benzo[d]oxazol-2-ylamino)-6-fluoro-N-(2-(2-hydroxyethoxy)ethyl)-1-methyl-1H-benzo[d]imidazole-5-carboxamide The title compound was synthesized using the same procedure which was followed for Example 6 Step-e using 2-(benzo[d]oxazol-2-ylamino)-6-fluoro-1-methyl-1H-benzo[d]imidazole-5-carboxylic acid and 2-(2-aminoethoxy)ethan-1-ol as starting materials (Yield: 49%); ¹H NMR (400 MHz, DMSO-d₆): δ 12.20 (bs, 1H), 8.15 (bs, 1H), 7.86 (d, J=6.4 Hz, 1H), 7.50-7.47 (m, 2H), 7.43 (d, J=8.0 Hz, 1H), 7.23-7.19 (m, 1H), 7.14-7.10 (m, 1H), 4.60 (bs, 1H), 3.60 (s, 3H), 3.57-3.51 (m, 4H), 3.48-3.31 (m, 4H); LC-MS: m/z 414.05 (M+1)⁺.

Example 73. Synthesis of 2-((5-fluoro-1H-benzo[d]imidazol-2-yl)amino)-1-methyl-1H-benzo[d]imidazole-5-carboxylic acid

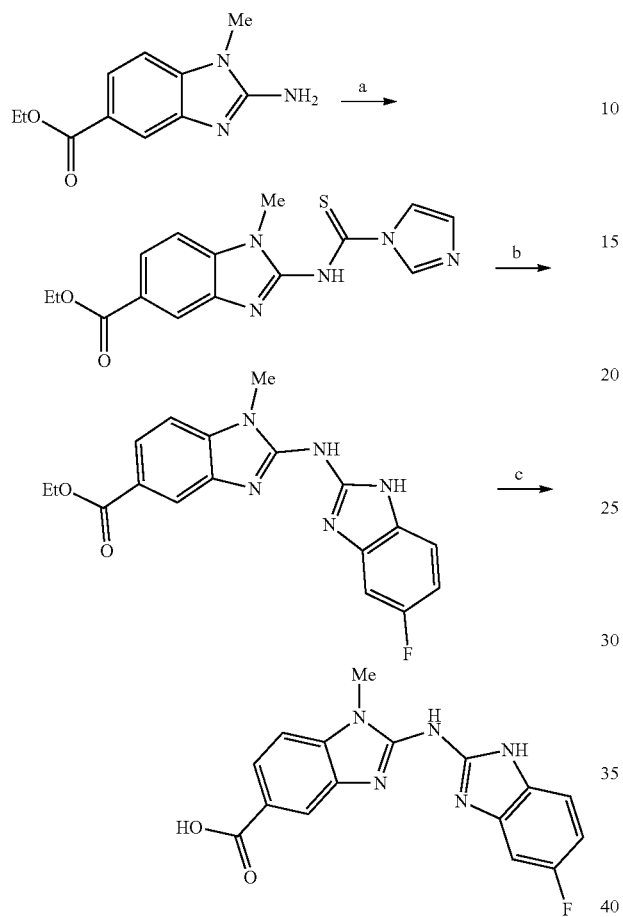

Conditions: a) 1,1′-thiocarbonyldiimidazole, ACN, 60° C., 16 h; b) 4-fluorobenzene-1,2-diamine, EDC•HCl, DMF, 100° C., 16 h; c) LiOH•H$_2$O, THF, MeOH, H$_2$O, 60° C., 16 h

Step-a: Synthesis of ethyl 2-(1H-imidazole-1-carbothioamido)-1-methyl-1H-benzo[d]imidazole-5-carboxylate To a solution of ethyl 2-amino-1-methyl-1H-benzo[d]imidazole-5-carboxylate (1.0 g, 4.5 mmol) in acetonitrile (20 mL) at RT was added 1,1′-thiocarbonyldiimidazole (1.06 g, 5.9 mmol) and stirred at 60° C. for 16 h. The reaction mixture was cooled to RT and stirred for 30 min. The solid obtained was filtered and dried under vacuum to afford the titled compound which was used in the next step without further purification (1.1 g, 73%); $^1$H NMR (400 MHz, DMSO-d$_6$): δ 13.4 (bs, 1H), 8.68 (s, 1H), 8.41 (d, J=1.6 Hz, 1H), 8.03 (s, 1H), 7.99 (dd, J=1.2 Hz, J=8.8 Hz, 1H), 7.75 (d, J=8.4 Hz, 1H), 7.01 (d, J=1.2 Hz, 1H), 4.35 (q, J=7.2 Hz, 2H), 3.79 (s, 3H), 1.36 (t, J=6.8 Hz, 3H).

Step-b: Synthesis of ethyl 2-((5-fluoro-1H-benzo[d]imidazol-2-yl)amino)-1-methyl-1H-benzo[d]imidazole-5-carboxylate To a stirred solution of ethyl 2-(1H-imidazole-1-carbothioamido)-1-methyl-1H-benzo[d]imidazole-5-carboxylate (900 mg, 2.74 mmol) in DMFA (15 mL) was added EDC HCl (1.05 g, 5.47 mmol) and heated to 60° C. for 10 min. The reaction mixture was cooled to RT, followed by the addition of 4-fluorobenzene-1,2-diamine (345 mg, 2.74 mmol) and it was heated at 100° C. for 16 h. The reaction mixture was cooled to RT, diluted with water (30 mL) and extracted with EtOAc (2×50 mL). The combined organic layer was washed with water (30 mL), brine (30 mL), dried over anhydrous sodium sulfate and concentrated under vacuum to afford a residue which was purified by combiflash chromatography using 0.5% methanol in DCM as an eluent to afford the title compound (200 mg, 21%); LC-MS: m/z 354.2 (M+1)$^+$.

Step-c: Synthesis of 2-((5-fluoro-1H-benzo[d]imidazol-2-yl)amino)-1-methyl-1H-benzo[d]imidazole-5-carboxylic acid To a stirred solution of ethyl 2-((5-fluoro-1H-benzo[d]imidazol-2-yl)amino)-1-methyl-1H-benzo[d]imidazole-5-carboxylate (200 mg, 0.57 mmol) in a mixture of solvent of THF (5 mL), methanol (5 mL) and water (5 mL) was added lithium hydroxide monohydrate (119 mg, 2.83 mmol). The reaction mixture was heated at 60° C. for 16 h with stirring. The reaction mixture was cooled to RT and concentrated under reduced pressure. The residue was dissolved in water (15 mL), acidified with 1 N HCl to obtain the solid which was filtered and dried under vacuum to afford the title compound (150 mg, 81%); $^1$H NMR (400 MHz, DMSO-d$_6$): δ 12.2 (bs, 2H), 8.04 (s, 1H), 7.75 (d, J=8.0 Hz, 1H), 7.32-7.26 (m, 2H), 7.13 (d, J=8.4 Hz, 1H), 6.88 (t, J=8.0 Hz, 1H), 3.62 (s, 3H); LC-MS: m/z 326.05 (M+1)$^+$.

Example 74. Synthesis of 1-(2-(dimethylamino)ethyl)-2-((6-(trifluoromethoxy)benzo[d]oxazol-2-yl)amino)-1H-benzo[d]imidazole-5-carboxylic acid

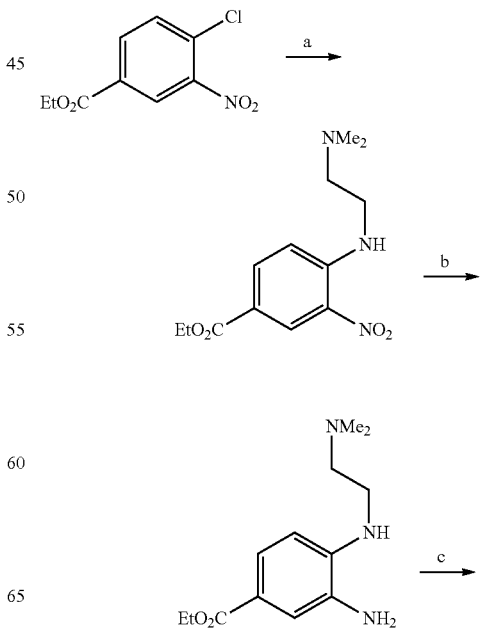

-continued

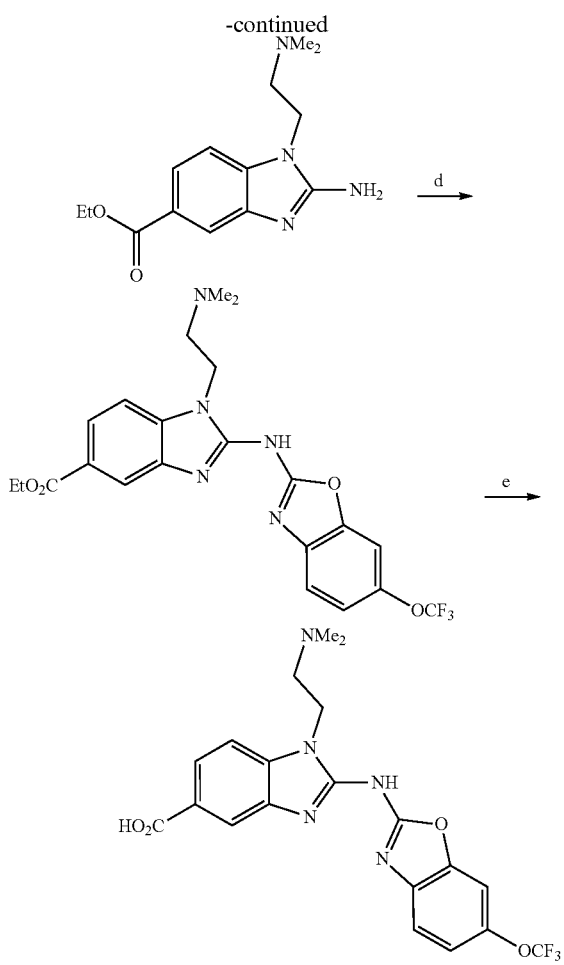

Conditions: a) N¹,N¹-dimethylethane-1,2-diamine, DIPEA, DMF, 60° C, 16 h; b) 10% Pd/C, MeOH, H₂, RT, 16 h; c) Cyanogen bromide, THF, H₂O, 60° C., 16 h; d) NaH, 2-(methylsulfonyl)-6-(trifluoromethoxy)benzo[d]oxazole, 1,4-Dioxane, RT, 16 h; e) LiOH·H₂O, THF, EtOH, H₂O, 60°C., 16 h Step-a: Synthesis of ethyl 4-((2-(dimethylamino)ethyl)amino)-3-nitrobenzoate To a solution of ethyl 4-chloro-3-nitrobenzoate (5.0 g, 21.8 mmol) in DMFA (40 mL) at RT was added DIPEA (9.5 mL, 54.4 mmol) and N¹,N¹-dimethylethane-1,2-diamine (2.87 g, 32.7 mmol) and the reaction mixture was stirred at 60° C. for 16 h. The reaction mixture was cooled to RT, diluted with cold water (250 mL) and stirred for 10 min. The precipitated solid was filtered and dried under vacuum to afford the title compound (4.8 g, 92%); $^1$H NMR (400 MHz, DMSO-$d_6$): δ 8.65 (t, J=4.4 Hz, 1H), 8.62 (d, J=2.0 Hz, 1H), 7.79 (dd, J=2.0 Hz, J=8.8 Hz, 1H), 7.13 (d, J=9.2 Hz, 1H), 4.32-4.26 (m, 2H), 3.47-3.43 (m, 2H), 2.57-2.52 (m, 2H), 2.22 (s, 6H), 1.33-1.28 (m, 3H); LC-MS: m/z 282.2 (M+1)⁺.

Step-b: Synthesis of ethyl 3-amino-4-((2-(dimethylamino)ethyl)amino)benzoate

The title compound was synthesized using the same procedure which was followed for compound 1e using ethyl 4-((2-(dimethylamino)ethyl)amino)-3-nitrobenzoate as starting material and stirring for 16 h. (Yield: 67%); $^1$H NMR (400 MHz, DMSO-$d_6$): δ 7.23 (dd, J=2.0 Hz, J=8.0 Hz, 1H), 7.18 (d, J=2.0 Hz, 1H), 6.45 (d, J=8.4 Hz, 1H), 5.09 (bs, 1H), 4.68 (s, 2H), 4.18 (q, J=6.8 Hz, 2H), 3.19-3.15 (m, 2H), 2.49-2.46 (m, 2H), 2.18 (s, 6H), 1.26 (t, J=6.8 Hz, 3H); LC-MS: m/z 252.2 (M+1)⁺.

Step-c: Synthesis of ethyl 2-amino-1-(2-(dimethylamino)ethyl)-1H-benzo[d]imidazole-5-carboxylate The title compound was synthesized using the same procedure which was followed for compound 1f using ethyl 3-amino-4-((2-(dimethylamino)ethyl)amino)benzoate as starting material and heating to 60° C. for 16 h. (Yield: 26%); LC-MS: m/z 277.2 (M+1)⁺.

Step-d: Synthesis of ethyl 1-(2-(dimethylamino)ethyl)-2-((6-(trifluoromethoxy)benzo[d]oxazol-2-yl)amino)-1H-benzo[d]imidazole-5-carboxylate The title compound was synthesized using the same procedure which was followed for compound 1g using ethyl 2-amino-1-(2-(dimethylamino)ethyl)-1H-benzo[d]imidazole-5-carboxylate and 2-(methylsulfonyl)-6-(trifluoromethoxy)benzo[d]oxazole as starting materials (Yield: 26%); $^1$H NMR (400 MHz, DMSO-$d_6$): δ 12.4 (bs, 1H), 8.25 (d, J=1.2 Hz, 1H), 7.87 (dd, J=1.2 Hz, J=8.4 Hz, 1H), 7.59-7.57 (m, 2H), 7.51 (d, J=8.4 Hz, 1H), 7.22 (d, J=8.8 Hz, 1H), 4.36-4.26 (m, 4H), 2.68 (q, J=6.8 Hz, 2H), 2.22 (s, 6H), 1.35 (t, J=6.8 Hz, 3H); LC-MS: m/z 478.1 (M+1)⁺.

Step-e: Synthesis of 1-(2-(dimethylamino)ethyl)-2-((6-(trifluoromethoxy)benzo[d]oxazol-2-yl)amino)-1H-benzo[d]imidazole-5-carboxylic acid The title compound was synthesized using the same procedure which was followed for compound 1h using ethyl 1-(2-(dimethylamino)ethyl)-2-((6-(trifluoromethoxy)benzo[d]oxazol-2-yl)amino)-1H-benzo[d]imidazole-5-carboxylate as starting material (Yield: 18%); $^1$H NMR (400 MHz, DMSO-$d_6$): δ 12.8 (bs, 1H), 12.3 (bs, 1H), 8.20 (d, J=1.6 Hz, 1H), 7.86 (dd, J=1.6 Hz, J=8.4 Hz, 1H), 7.59-7.51 (m, 3H), 7.21 (d, J=8.4 Hz, 1H), 4.27 (t, J=6.4 Hz, 2H), 2.79-2.66 (m, 2H), 2.21 (s, 6H); LC-MS: m/z 450.1 (M+1)⁺.

Examples 75 and 76. Synthesis of 1-(2-methoxyethyl)-2-((5-(trifluoromethoxy)-1H-benzo[d]imidazol-2-yl)amino)-1H-benzo[d]imidazole-5-carboxylic acid and Synthesis of N,1-bis(2-methoxyethyl)-2-((5-(trifluoromethoxy)-1H-benzo[d]imidazol-2-yl)amino)-1H-benzo[d]imidazole-5-carboxamide

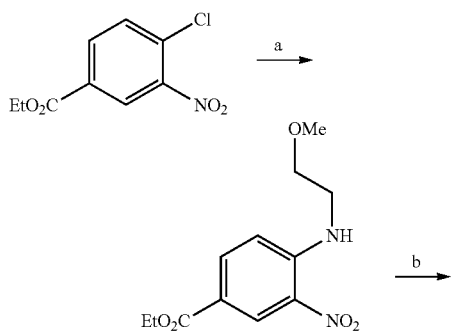

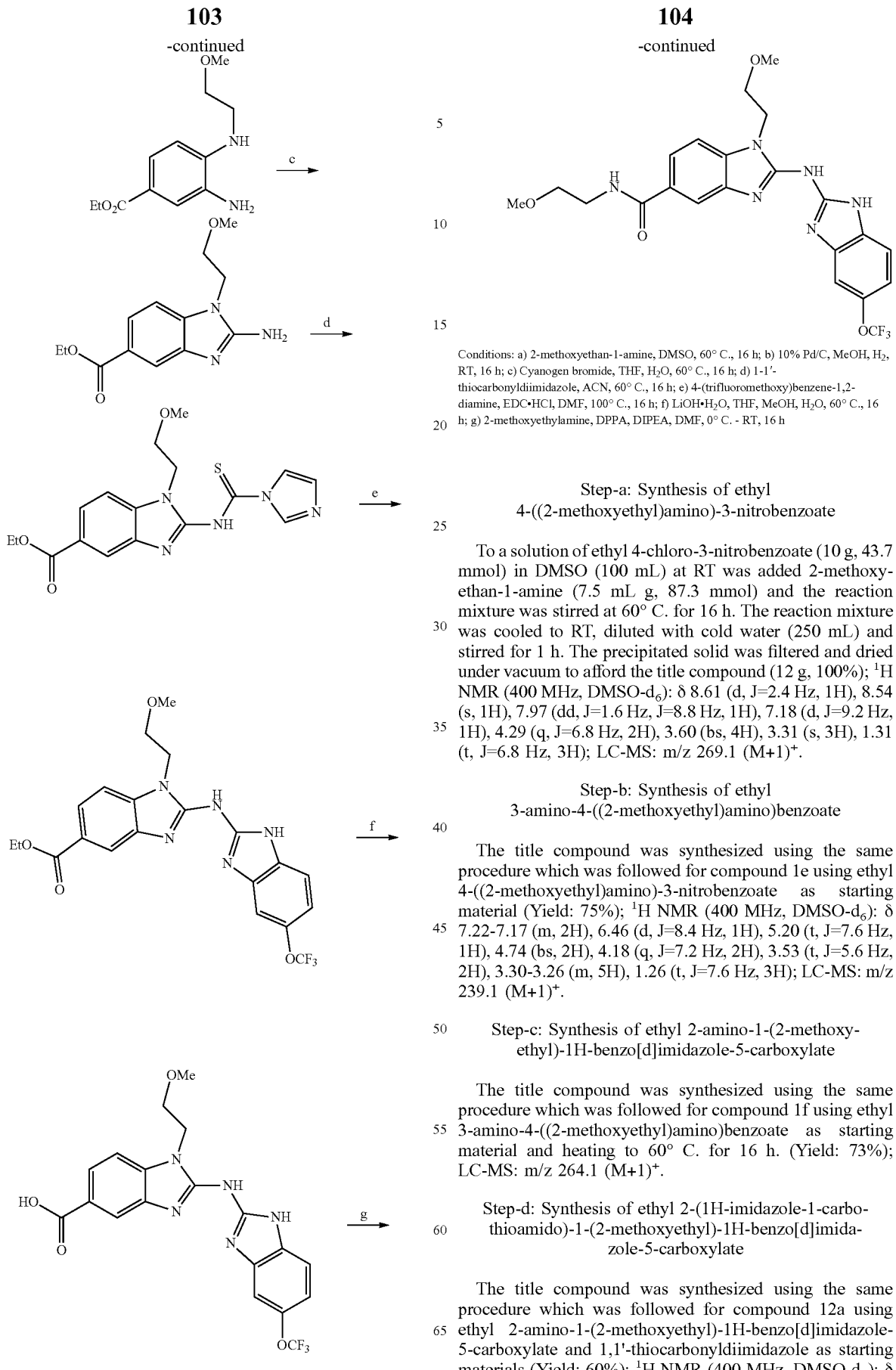

Conditions: a) 2-methoxyethan-1-amine, DMSO, 60° C., 16 h; b) 10% Pd/C, MeOH, H₂, RT, 16 h; c) Cyanogen bromide, THF, H₂O, 60° C., 16 h; d) 1-1′-thiocarbonyldiimidazole, ACN, 60° C., 16 h; e) 4-(trifluoromethoxy)benzene-1,2-diamine, EDC•HCl, DMF, 100° C., 16 h; f) LiOH•H₂O, THF, MeOH, H₂O, 60° C., 16 h; g) 2-methoxyethylamine, DPPA, DIPEA, DMF, 0° C. - RT, 16 h Step-a: Synthesis of ethyl 4-((2-methoxyethyl)amino)-3-nitrobenzoate To a solution of ethyl 4-chloro-3-nitrobenzoate (10 g, 43.7 mmol) in DMSO (100 mL) at RT was added 2-methoxy-ethan-1-amine (7.5 mL g, 87.3 mmol) and the reaction mixture was stirred at 60° C. for 16 h. The reaction mixture was cooled to RT, diluted with cold water (250 mL) and stirred for 1 h. The precipitated solid was filtered and dried under vacuum to afford the title compound (12 g, 100%); $^1$H NMR (400 MHz, DMSO-$d_6$): δ 8.61 (d, J=2.4 Hz, 1H), 8.54 (s, 1H), 7.97 (dd, J=1.6 Hz, J=8.8 Hz, 1H), 7.18 (d, J=9.2 Hz, 1H), 4.29 (q, J=6.8 Hz, 2H), 3.60 (bs, 4H), 3.31 (s, 3H), 1.31 (t, J=6.8 Hz, 3H); LC-MS: m/z 269.1 (M+1)$^+$.

Step-b: Synthesis of ethyl 3-amino-4-((2-methoxyethyl)amino)benzoate

The title compound was synthesized using the same procedure which was followed for compound 1e using ethyl 4-((2-methoxyethyl)amino)-3-nitrobenzoate as starting material (Yield: 75%); $^1$H NMR (400 MHz, DMSO-$d_6$): δ 7.22-7.17 (m, 2H), 6.46 (d, J=8.4 Hz, 1H), 5.20 (t, J=7.6 Hz, 1H), 4.74 (bs, 2H), 4.18 (q, J=7.2 Hz, 2H), 3.53 (t, J=5.6 Hz, 2H), 3.30-3.26 (m, 5H), 1.26 (t, J=7.6 Hz, 3H); LC-MS: m/z 239.1 (M+1)$^+$.

Step-c: Synthesis of ethyl 2-amino-1-(2-methoxyethyl)-1H-benzo[d]imidazole-5-carboxylate The title compound was synthesized using the same procedure which was followed for compound 1f using ethyl 3-amino-4-((2-methoxyethyl)amino)benzoate as starting material and heating to 60° C. for 16 h. (Yield: 73%); LC-MS: m/z 264.1 (M+1)$^+$.

Step-d: Synthesis of ethyl 2-(1H-imidazole-1-carbothioamido)-1-(2-methoxyethyl)-1H-benzo[d]imidazole-5-carboxylate The title compound was synthesized using the same procedure which was followed for compound 12a using ethyl 2-amino-1-(2-methoxyethyl)-1H-benzo[d]imidazole-5-carboxylate and 1,1′-thiocarbonyldiimidazole as starting materials (Yield: 60%); $^1$H NMR (400 MHz, DMSO-$d_6$): δ

13.5 (bs, 1H), 8.66 (s, 1H), 8.42 (s, 1H), 8.01-7.97 (m, 2H), 7.78 (d, J=8.8 Hz, 1H), 7.01 (s, 1H), 4.54 (t, J=4.8 Hz, 2H), 4.35 (q, J=7.2 Hz, 2H), 3.74 (t, J=4.8 Hz, 2H), 3.20 (s, 3H), 1.35 (t, J=7.2 Hz, 3H).

Step-e: Synthesis of ethyl 1-(2-methoxyethyl)-2-((5-(trifluoromethoxy)-1H-benzo[d]imidazol-2-yl)amino)-1H-benzo[d]imidazole-5-carboxylate The title compound was synthesized using the same procedure which was followed for compound 12b using ethyl 2-(1H-imidazole-1-carbothioamido)-1-(2-methoxyethyl)-1H-benzo[d]imidazole-5-carboxylate and 4-(trifluoromethoxy)benzene-1,2-diamine as starting materials (Yield: 38%); LC-MS: m/z 464.0 (M+1)⁺.

Step-f: Synthesis of 1-(2-methoxyethyl)-2-((5-(trifluoromethoxy)-1H-benzo[d]imidazol-2-yl)amino)-1H-benzo[d]imidazole-5-carboxylic acid The title compound was synthesized using the same procedure which was followed for compound 1h using ethyl 1-(2-methoxyethyl)-2-((5-(trifluoromethoxy)-1H-benzo[d]imidazol-2-yl)amino)-1H-benzo[d]imidazole-5-carboxylate as starting material and THF, methanol and water as solvents. (Yield: 65%); ¹H NMR (400 MHz, DMSO-d₆): δ 12.3 (bs, 3H), 8.08 (d, J=1.2 Hz, 1H), 7.74 (dd, J=1.6 Hz, J=8.4 Hz, 1H), 7.41 (d, J=8.4 Hz, 1H), 7.36-7.31 (m, 2H), 7.02 (d, J=8.0 Hz, 1H), 4.32 (t, J=5.2 Hz, 2H), 3.71 (t, J=6.0 Hz, 2H), 3.25 (s, 3H); LC-MS: m/z 436.0 (M+1)⁺.

Step-g: Synthesis of N,1-bis(2-methoxyethyl)-2-((5-(trifluoromethoxy)-1H-benzo[d]imidazol-2-yl)amino)-1H-benzo[d]imidazole-5-carboxamide The title compound was synthesized using the same procedure which was followed for compound 1i using 1-(2-methoxyethyl)-2-((5-(trifluoromethoxy)-1H-benzo[d]imidazol-2-yl)amino)-1H-benzo[d]imidazole-5-carboxylic acid and 2-methoxyethylamine as starting materials (Yield: 2%); ¹H NMR (400 MHz, DMSO-d₆): δ 12.23 (bs, 1H), 8.26-8.23 (m, 1H), 7.58-7.53 (m, 1H), 7.43-7.38 (m, 1H), 7.30-6.37 (m, 5H), 4.50-4.48 (m, 2H), 3.86-3.80 (m, 2H), 3.32 (s, 3H), 3.27-3.25 (m, 4H), 3.16 (s, 3H); LC-MS: m/z 493.1 (M+1)⁺.

Examples 77 and 78. Synthesis of 1-(2-methoxyethyl)-2-((6-(trifluoromethoxy)benzo[d]oxazol-2-yl)amino)-1H-benzo[d]imidazole-5-carboxylic acid and Synthesis of N,1-bis(2-methoxyethyl)-2-((6-(trifluoromethoxy)benzo[d]oxazol-2-yl)amino)-1H-benzo[d]imidazole-5-carboxamide

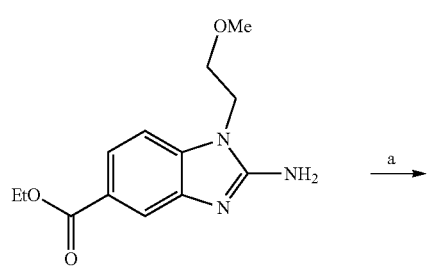

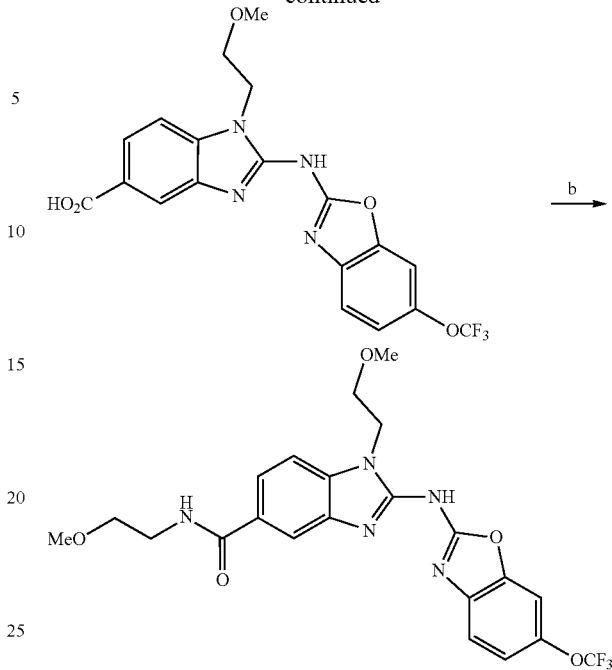

Conditions: a) NaH, 2-chloro-6-(trifluoromethoxy)benzo[d]oxazole, 1,4-Dioxane, 0° C.-90° C., 16 h; b) 2-methoxyethylamine, DPPA, DIPEA, DMF, 0° C. - RT, 16 h Step-a: Synthesis of 1-(2-methoxyethyl)-2-((6-(trifluoromethoxy)benzo[d]oxazol-2-yl)amino)-1H-benzo[d]imidazole-5-carboxylic acid To a solution of ethyl 2-amino-1-(2-methoxyethyl)-1H-benzo[d]imidazole-5-carboxylate (200 mg, 0.76 mmol) in 1,4-dioxane (10 mL) at 0° C. was added sodium hydride (60% dispersion in mineral oil) (107 mg, 2.66 mmol) and stirred for 10 min. 2-chloro-6-(trifluoromethoxy)benzo[d]oxazole (270 mg, 1.14 mmol) was added to the reaction mixture and stirred at 90° C. for 16 h. The reaction mixture was cooled to RT. Solvent was evaporated and the residue was diluted with cold water (20 mL), acidified with 1N HCl. The reaction mixture was extracted with ethyl acetate (2×50 mL). Combined organic layer was washed with water (30 mL), brine (30 mL), dried over anhydrous sodium sulfate and concentrated under vacuum. The residue was purified by combiflash chromatography using 2% methanol in DCM as an eluent to afford the title compound (70 mg, 21%); ¹H NMR (400 MHz, DMSO-d₆): δ 12.8 (bs, 1H), 12.3 (bs, 1H), 8.20 (d, J=1.6 Hz, 1H), 7.86 (dd, J=1.2 Hz, J=8.0 Hz, 1H), 7.58-7.52 (m, 3H), 7.22 (d, J=7.2 Hz, 1H), 4.36 (t, J=4.8 Hz, 2H), 3.74 (t, J=5.6 Hz, 2H), 3.24 (s, 3H); LC-MS: m/z 437.05 (M+1)⁺.

Step-b: Synthesis of N,1-bis(2-methoxyethyl)-2-((6-(trifluoromethoxy)benzo[d]oxazol-2-yl)amino)-1H-benzo[d]imidazole-5-carboxamide The title compound was synthesized using the same procedure which was followed for compound 1i using 1-(2-methoxyethyl)-2-((6-(trifluoromethoxy)benzo[d]oxazol-2-yl)amino)-1H-benzo[d]imidazole-5-carboxylic acid and 2-methoxyethylamine as starting materials (Yield: 2%); ¹H NMR (400 MHz, DMSO-d₆): δ 12.30 (bs, 1H), 8.45 (bs, 1H), 8.08 (s, 1H), 7.75 (d, J=8.4 Hz, 1H), 7.56 (s, 1H), 7.53-7.50 (m, 2H), 7.21 (d, J=8.4 Hz, 1H), 4.35 (t, J=4.8 Hz, 2H), 3.73 (t, J=5.2 Hz, 2H), 3.48-3.43 (m, 4H), 3.28 (s, 3H), 3.24 (s, 3H); LC-MS: m/z 494.15 (M+1)⁺.

Example 79 and 80. Synthesis of 1-(tetrahydro-2H-pyran-4-yl)-2-((6-(trifluoromethoxy)benzo[d]oxazol-2-yl)amino)-1H-benzo[d]imidazole-5-carboxylic acid and Synthesis of N-(2-methoxyethyl)-1-(tetrahydro-2H-pyran-4-yl)-2-((6-(trifluoromethoxy)benzo[d]oxazol-2-yl)amino)-1H-benzo[d]imidazole-5-carboxamide

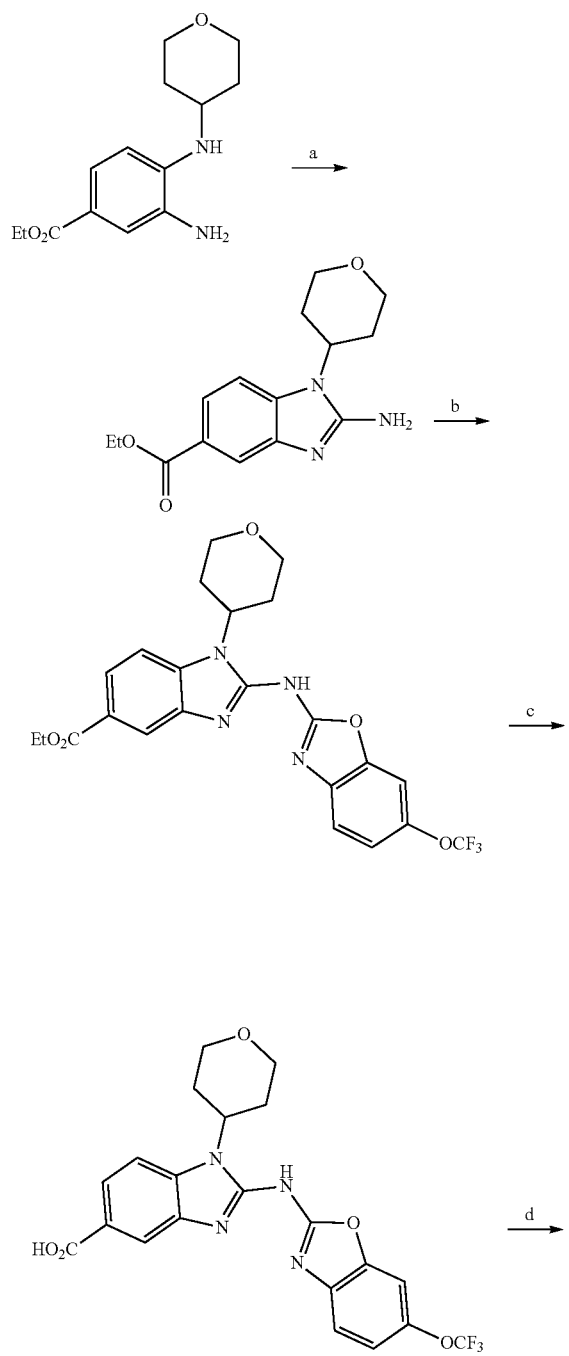

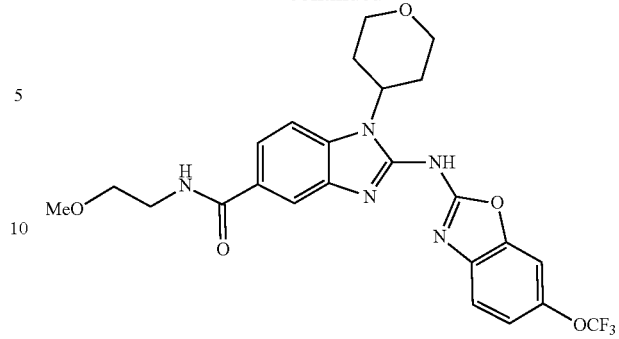

Conditions: a) Cyanogen bromide, THF, H₂O, 60° C., 16 h; b) NaH, 2-chloro-6-(trifluoromethoxy)benzo[d]oxazole, 1,4-Dioxane, RT, 16 h; c) LiOH·H₂O, THF, EtOH, H₂O, 60° C., 16 h; d) 2-methoxyethylamine, DPPA, DIPEA, DMF, 0° C. - RT, 16 h Step-a: Synthesis of ethyl 2-amino-1-(tetrahydro-2H-pyran-4-yl)-1H-benzo[d]imidazole-5-carboxylate The title compound was synthesized using the same procedure which was followed for compound 1f using ethyl 3-amino-4-((tetrahydro-2H-pyran-4-yl)amino)benzoate as starting material and heating to 60° C. (Yield: 92%); ¹H NMR (400 MHz, DMSO-d₆): δ 7.71 (s, 1H), 7.55 (dd, J=1.6 Hz, J=8.4 Hz, 1H), 7.41 (d, J=8.0 Hz, 1H), 6.65 (bs, 2H), 4.50-4.48 (m, 1H), 4.28 (q, J=7.2 Hz, 2H), 4.05-4.01 (m, 2H), 3.47 (t, J=11.2 Hz, 2H), 2.36-2.32 (m, 2H), 1.72 (d, J=10.4 Hz, 2H), 1.31 (t, J=6.8 Hz, 3H); LC-MS: m/z 290.1 (M+1)⁺.

Step-b: Synthesis of ethyl 1-(tetrahydro-2H-pyran-4-yl)-2-((6-(trifluoromethoxy)-benzo[d]oxazol-2-yl)amino)-1H-benzo[d]imidazole-5-carboxylate To a solution of ethyl 2-amino-1-(tetrahydro-2H-pyran-4-yl)-1H-benzo[d]imidazole-5-carboxylate (100 mg, 0.35 mmol) in 1,4-dioxane (2 mL) at RT was added sodium hydride (60% dispersion in mineral oil) (34 mg, 0.86 mmol) and stirred for 10 min. 2-chloro-6-(trifluoromethoxy)benzo[d]oxazole (99 g, 0.41 mmol) was added to the reaction mixture and stirred at RT for 16 h. The reaction mixture was concentrated and diluted with cold water (30 mL) and stirred at RT for 5 to 10 min. The solid obtained was filtered, dried under vacuum and purified by combiflash chromatography using 100% DCM as an eluent to afford the title compound (60 mg, 35%); ¹H NMR (400 MHz, DMSO-d₆): δ 12.40 (bs, 1H), 8.29 (d, J=1.6 Hz, 1H), 7.86 (dd, J=1.2 Hz, J=8.0 Hz, 1H), 7.74 (d, J=8.4 Hz, 1H), 7.58 (d, J=1.6 Hz, 1H), 7.52 (d, J=8.4 Hz, 1H), 7.21 (dd, J=1.6 Hz, J=8.8 Hz, 1H), 4.97-4.93 (m, 1H), 4.33 (q, J=7.6 Hz, 2H), 4.07-4.03 (m, 2H), 3.56 (t, J=9.2 Hz, 2H), 2.63-2.55 (m, 2H), 1.79 (d, J=9.2 Hz, 2H), 1.35 (t, J=6.8 Hz, 3H); LC-MS: m/z 491.1 (M+1)⁺.

Step-e: Synthesis of 1-(tetrahydro-2H-pyran-4-yl)-2-((6-(trifluoromethoxy)benzo[d]oxazol-2-yl)amino)-1H-benzo[d]imidazole-5-carboxylic acid The title compound was synthesized using the same procedure which was followed for compound 1h using ethyl 1-(tetrahydro-2H-pyran-4-yl)-2-((6-(trifluoromethoxy)benzo[d]oxazol-2-yl)amino)-1H-benzo[d]imidazole-5-carboxylate as starting material (Yield: 71%); ¹H NMR (400 MHz, DMSO-d₆): δ 12.8 (bs, 1H), 12.50 (bs, 1H), 8.24 (d, J=1.6 Hz, 1H), 7.86 (dd, J=1.2 Hz, J=8.8 Hz, 1H), 7.71 (d, J=8.0 Hz, 1H), 7.58 (d, J=1.2 Hz, 1H), 7.53 (d, J=8.8 Hz, 1H), 7.22 (d, J=10.4 Hz, 1H), 5.01-4.92 (m, 1H), 4.05 (dd, J=4.0 Hz, J=11.2 Hz, 2H), 3.58-3.53 (m, 2H), 2.67-2.57 (m, 2H), 1.78 (d, J=10.0 Hz, 2H); LC-MS: m/z 463.1 (M+1)+.

Step-f: Synthesis of N-(2-methoxyethyl)-1-(tetrahydro-2H-pyran-4-yl)-2-((6-(trifluoromethoxy)benzo[d]oxazol-2-yl)amino)-1H-benzo[d]imidazole-5-carboxamide The title compound was synthesized using the same procedure which was followed for compound 1i using 1-(tetrahydro-2H-pyran-4-yl)-2-((6-(trifluoromethoxy)benzo[d]oxazol-2-yl)amino)-1H-benzo[d]imidazole-5-carboxylic acid and 2-methoxyethylamine as starting materials (Yield: 76%); $^1$H NMR (400 MHz, DMSO-$d_6$): δ 12.3 (bs, 1H), 8.48 (t, J=5.2 Hz, 1H), 8.13 (d, J=1.2 Hz, 1H), 7.76 (dd, J=1.6 Hz, J=8.8 Hz, 1H), 7.68 (d, J=8.0 Hz, 1H), 7.57 (s, 1H), 7.52 (d, J=8.4 Hz, 1H), 7.21 (d, J=8.8 Hz, 1H), 4.98-4.92 (m, 1H), 4.07-4.04 (m, 2H), 3.56 (t, J=1.2 Hz, 2H), 3.49-3.44 (m, 4H), 3.28 (s, 3H), 2.67-2.58 (m, 2H), 1.78 (d, J=9.6 Hz, 2H); LC-MS: m/z 520.2 (M+1)+.

Example 81. Synthesis of N-(2-methoxyethyl)-1-(tetrahydro-2H-pyran-4-yl)-2-((5-(trifluoromethoxy)-1H-benzo[d]imidazol-2-yl)amino)-1H-benzo[d]imidazole-5-carboxamide

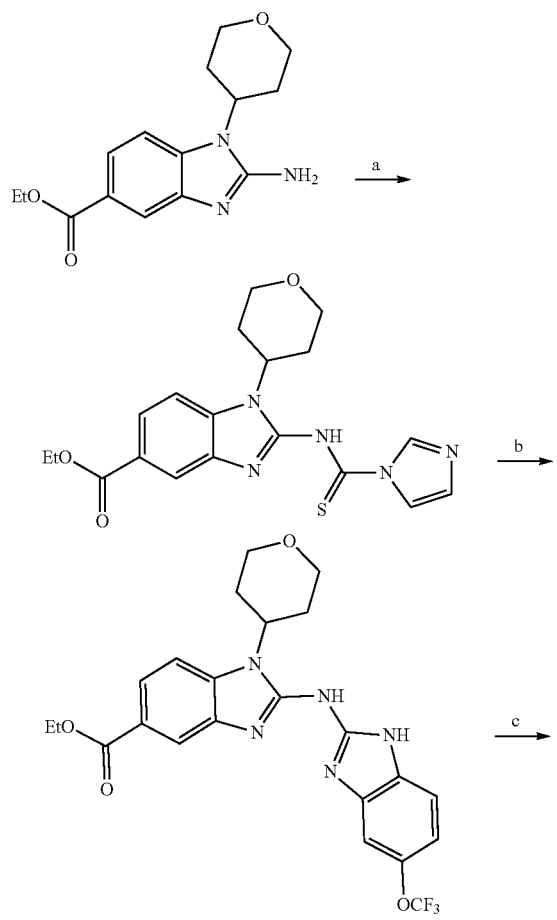

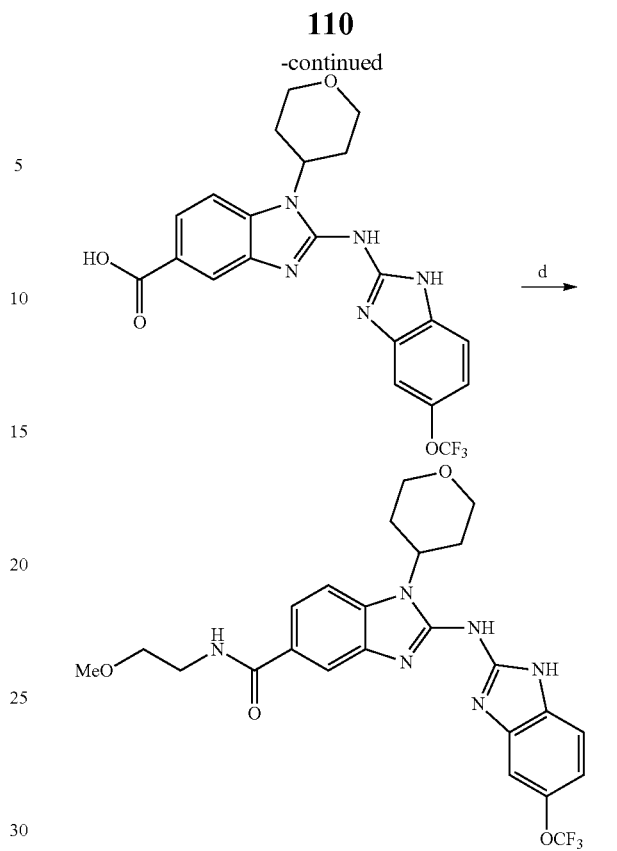

Conditions: a) 1,1'-thiocarbonyldiimidazole, ACN, 60° C., 16 h; b) 4-(trifluoromethoxy)benzene-1,2-diamine, EDC•HCl, DMF, 100° C., 16 h; c) LiOH•H$_2$O, THF, EtOH, H$_2$O, 60° C., 16 h; d) 2-methoxyethylamine, DPPA, DIPEA, DMF, 0° - RT, 16 h Step-a: Synthesis of ethyl 2-(1H-imidazole-1-carbothioamido)-1-(tetrahydro-2H-pyran-4-yl)-1H-benzo[d]imidazole-5-carboxylate The title compound was synthesized using the same procedure which was followed for compound 12a using ethyl 2-amino-1-(tetrahydro-2H-pyran-4-yl)-1H-benzo[d]imidazole-5-carboxylate and 1,1'-thiocarbonyldiimidazole as starting materials (Yield: 72%); $^1$H NMR (400 MHz, DMSO-$d_6$): δ 13.50 (bs, 1H), 8.64 (s, 1H), 8.43 (s, 1H), 7.98 (d, J=4.4 Hz, 1H), 7.96-7.94 (m, 1H), 7.09 (s, 1H), 6.72 (bs, 1H), 5.05-5.00 (m, 1H), 4.36-4.26 (m, 2H), 4.06-4.02 (m, 2H), 3.60 (t, J=11.6 Hz, 2H), 2.54-2.50 (m, 2H), 1.86 (d, J=9.6 Hz, 2H), 1.37-1.33 (m, 3H).

Step-b: Synthesis of ethyl 1-(tetrahydro-2H-pyran-4-yl)-2-((5-(trifluoromethoxy)-1H-benzo[d]imidazol-2-yl)amino)-1H-benzo[d]imidazole-5-carboxylate The title compound was synthesized using the same procedure which was followed for compound 12b using ethyl 2-(1H-imidazole-1-carbothioamido)-1-(tetrahydro-2H-pyran-4-yl)-1H-benzo[d]imidazole-5-carboxylate and 4-(trifluoromethoxy)benzene-1,2-diamine as starting materials (Yield: 46%); $^1$H NMR (400 MHz, DMSO-$d_6$): δ 12.3 (bs, 1H), 8.12 (d, J=6.4 Hz, 1H), 7.95 (s, 1H), 7.74 (dd, J=2.0 Hz, J=8.4 Hz, 1H), 7.57 (d, J=8.4 Hz, 1H), 7.37-7.32 (m, 2H), 7.06 (dd, J=1.6 Hz, J=8.4 Hz, 1H), 4.97-4.90 (m, 1H), 4.32 (q, J=6.8 Hz, 2H), 4.08-4.05 (m, 2H), 3.51 (t, J=11.6

Hz, 2H), 2.67-2.55 (m, 2H), 1.75 (d, J=9.6 Hz, 2H), 1.07 (t, J=8.4 Hz, 3H); LC-MS: m/z 490.0 (M+1)+.

Step-c: Synthesis of 1-(tetrahydro-2H-pyran-4-yl)-2-((5-(trifluoromethoxy)-1H-benzo[d]imidazol-2-yl)amino)-1H-benzo[d]imidazole-5-carboxylic acid The title compound was synthesized using the same procedure which was followed for compound 1h using ethyl 1-(tetrahydro-2H-pyran-4-yl)-2-((5-(trifluoromethoxy)-1H-benzo[d]imidazol-2-yl)amino)-1H-benzo[d]imidazole-5-carboxylate as starting material (Yield: 55%); $^1$H NMR (400 MHz, DMSO-$d_6$): δ 12.7 (bs, 3H), 8.04 (s, 1H), 7.80 (d, J=8.4 Hz, 1H), 7.65 (d, J=8.8 Hz, 1H), 7.42-7.35 (m, 2H), 7.12 (d, J=8.0 Hz, 1H), 4.93 (bs, 1H), 4.08-4.05 (m, 2H), 3.54-3.48 (m, 2H), 2.61-2.58 (m, 2H), 1.77 (d, J=10.0 Hz, 2H); LC-MS: m/z 462.15 (M+1)+.

Step-d: Synthesis of N-(2-methoxyethyl)-1-(tetrahydro-2H-pyran-4-yl)-2-((5-(trifluoromethoxy)-1H-benzo[d]imidazol-2-yl)amino)-1H-benzo[d]imidazole-5-carboxamide The title compound was synthesized using the same procedure which was followed for compound 1i using 1-(tetrahydro-2H-pyran-4-yl)-2-((5-(trifluoromethoxy)-1H-benzo[d]imidazol-2-yl)amino)-1H-benzo[d]imidazole-5-carboxylic acid and 2-methoxyethylamine as starting materials (Yield: 42%); $^1$H NMR (400 MHz, DMSO-$d_6$): δ 12.2 (bs, 2H), 8.37 (t, J=5.6 Hz, 1H), 8.02 (d, J=1.6 Hz, 1H), 7.64 (dd, J=1.2 Hz, J=8.0 Hz, 1H), 7.52 (d, J=8.8 Hz, 1H), 7.53-7.30 (m, 2H), 7.03 (d, J=8.0 Hz, 1H), 4.98-4.89 (m, 1H), 4.08-4.05 (m, 2H), 3.51-3.43 (m, 6H), 3.28 (s, 3H), 2.67-2.58 (m, 2H), 1.75-1.73 (m, 2H); LC-MS: m/z 519.1 (M+1)+.

Examples 82 and 83. Synthesis of 2-((5-chloro-1H-benzo[d]imidazol-2-yl)amino)-1-methyl-1H-benzo[d]imidazole-5-carboxylic acid and Synthesis of 2-((5-chloro-1H-benzo[d]imidazol-2-yl)amino)-N-(2-methoxyethyl)-1-methyl-1H-benzo[d]imidazole-5-carboxamide

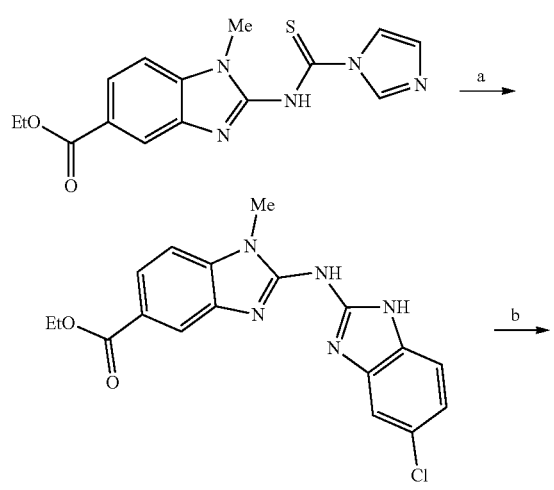

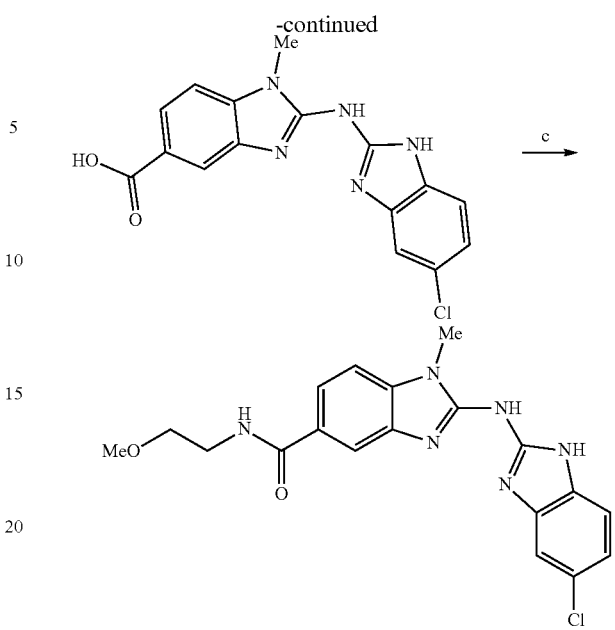

Conditions: a) 4-chlorobenzene-1,2-diamine, EDC•HCl, DMF, 100° C., 16 h b) LiOH•H$_2$O, THF, EtOH, H$_2$O, 60° C., 16 h; c) 2-methoxyethylamine, DPPA, DIPEA, DMF, 0° C., - RT, 16 h Step-a: Synthesis of ethyl 2-((5-chloro-1H-benzo[d]imidazol-2-yl)amino)-1-methyl-1H-benzo[d]imidazole-5-carboxylate The title compound was synthesized using the same procedure which was followed for compound 12b using ethyl 2-(1H-imidazole-1-carbothioamido)-1-methyl-1H-benzo[d]imidazole-5-carboxylate and 4-chlorobenzene-1,2-diamine as starting materials (Yield: 24%); $^1$H NMR (400 MHz, DMSO-$d_6$): δ 12.2 (bs, 2H), 8.10 (s, 1H), 7.76 (d, J=8.4 Hz, 1H), 7.40-7.29 (m, 3H), 7.09 (dd, J=1.2 Hz, J=8.4 Hz, 1H), 4.31 (q, J=6.8 Hz, 2H), 3.64 (s, 3H), 1.35 (t, J=6.8 Hz, 3H); LC-MS: m/z 370.05 (M+1)+.

Step-b: Synthesis of 2-((5-chloro-1H-benzo[d]imidazol-2-yl)amino)-1-methyl-1H-benzo[d]imidazole-5-carboxylic acid The title compound was synthesized using the same procedure which was followed for compound 1h using ethyl 2-((5-chloro-1H-benzo[d]imidazol-2-yl)amino)-1-methyl-1H-benzo[d]imidazole-5-carboxylate as starting material (Yield: 84%); $^1$H NMR (400 MHz, DMSO-$d_6$): δ 12.3 (bs, 3H), 8.07 (s, 1H), 7.76 (d, J=8.0 Hz, 1H), 7.37-7.29 (m, 3H), 7.07 (d, J=7.6 Hz, 1H), 3.63 (s, 3H); LC-MS: m/z 342.0 (M+1)+.

Step-c: Synthesis of 2-((5-chloro-1H-benzo[d]imidazol-2-yl)amino)-N-(2-methoxyethyl)-1-methyl-1H-benzo[d]imidazole-5-carboxamide The title compound was synthesized using the same procedure which was followed for compound 1i using 2-((5-chloro-1H-benzo[d]imidazol-2-yl)amino)-1-methyl-1H-benzo[d]imidazole-5-carboxylic acid and 2-methoxyethylamine as starting materials (Yield: 49%); $^1$H NMR (400 MHz, DMSO-$d_6$): δ 12.2 (bs, 2H), 8.36 (s, 1H), 7.99 (s, 1H), 7.66 (d, J=7.2 Hz, 1H), 7.35 (d, J=8.4 Hz, 1H), 7.30-7.28 (m, 2H), 7.06 (d, J=8.4 Hz, 1H), 3.62 (s, 3H), 3.48-3.43 (m, 4H), 3.17 (s, 3H); LC-MS: m/z 399.1 (M+1)⁺.

Examples 84 and 85. Synthesis of 1-ethyl-2-((6-(trifluoromethoxy)benzo[d]oxazol-2-yl)amino)-1H-benzo[d]imidazole-5-carboxylic acid and Synthesis of 1-ethyl-N-(2-methoxyethyl)-2-((6-(trifluoromethoxy)benzo[d]oxazol-2-yl)amino)-1H-benzo[d]imidazole-5-carboxamide

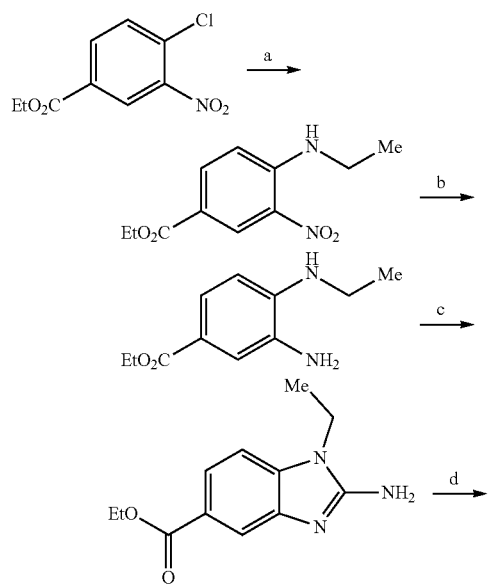

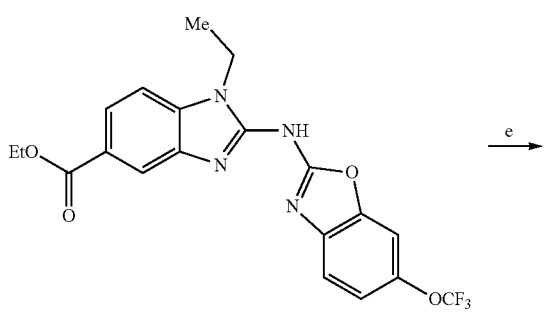

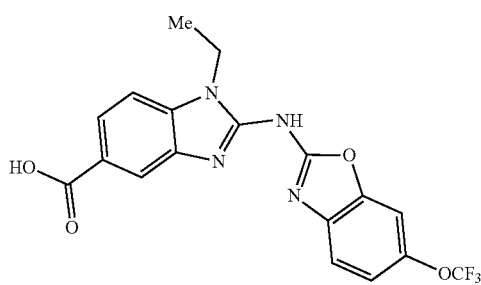

Conditions: a) Aq. Ethyl amine, DMF, 60° C., 16 h; b) 10% Pd/C, MeOH, H₂, RT, 16 h; c) Cyanogen bromide, THF, H₂O, 60° C., 16 h; d) NaH, 2-chloro-6-(trifluoromethoxy)benzo[d]oxazole, 1,4-Dioxane, RT, 16 h; e) LiOH•H₂O, THF, EtOH, H₂O, 60° C., 16 h; f) 2-methoxyethylamine, DPPA, DIPEA, DMF, 0° C.-RT, 16 h Step-a: Synthesis of ethyl 4-(ethylamino)-3-nitrobenzoate To a solution of ethyl 4-chloro-3-nitrobenzoate (4.0 g, 17.5 mmol) in DMFA (100 mL) at RT was added ethylamine (2.24 mL (70% aqueous solution), 34.9 mmol) and the reaction mixture was stirred at 60° C. for 16 h. The reaction mixture was cooled to RT, diluted with cold water (200 mL) and stirred for 15 min. The precipitated solid was filtered and dried under vacuum to afford the title product (3.0 g, 63%); $^1$H NMR (400 MHz, DMSO-$d_6$): δ 8.62 (d, J=2.0 Hz, 1H), 8.51 (t, J=5.2 Hz, 1H), 7.97 (dd, J=2.0 Hz, J=9.2 Hz, 1H), 7.14 (d, J=9.2 Hz, 1H), 4.29 (q, J=6.8 Hz, 2H), 3.49-3.42 (m, 2H), 1.33 (t, J=5.2 Hz, 3H), 1.23 (t, J=7.2 Hz, 3H); LC-MS: m/z 239.0 (M+1)⁺.

Step-b: Synthesis of ethyl 3-amino-4-(ethylamino)benzoate

The title compound was synthesized using the same procedure which was followed for compound 1e using ethyl 4-(ethylamino)-3-nitrobenzoate as starting material (Yield: 79%) and the crude compound was used in the next step without any purification.

Step-c: Synthesis of ethyl 2-amino-1-ethyl-1H-benzo[d]imidazole-5-carboxylate

The title compound was synthesized using the same procedure which was followed for compound 1f using ethyl 3-amino-4-(ethylamino)benzoate as starting material (Yield: 74%); $^1$H NMR (400 MHz, DMSO-$d_6$): δ 7.70 (s, 1H), 7.58 (dd, J=1.6 Hz, J=8.4 Hz, 1H), 7.23 (d, J=8.4 Hz, 1H), 6.66 (bs, 2H), 4.27 (q, J=7.2 Hz, 2H), 4.05 (q, J=6.8 Hz, 2H), 1.31 (t, J=6.8 Hz, 3H), 1.20 (t, J=7.6 Hz, 3H); LC-MS: m/z 234.1 (M+1)⁺.

Step-d: Synthesis of ethyl 1-ethyl-2-((6-(trifluoromethoxy)benzo[d]oxazol-2-yl)amino)-1H-benzo[d]imidazole-5-carboxylate The title compound was synthesized using the same procedure which was followed for compound 1g using ethyl 2-amino-1-ethyl-1H-benzo[d]imidazole-5-carboxylate and 2-chloro-6-(trifluoromethoxy)benzo[d]oxazole as starting materials (Yield: 54%); $^1$H NMR (400 MHz, DMSO-$d_6$): δ 12.3 (bs, 1H), 8.25 (d, J=1.6 Hz, 1H), 7.88 (dd, J=2.0 Hz, J=8.8 Hz, 1H), 7.60-7.57 (m, 2H), 7.51 (d, J=8.8 Hz, 1H), 7.22 (dd, J=1.6 Hz, J=8.8 Hz, 1H), 4.33 (q, J=7.2 Hz, 2H), 4.22 (q, J=7.6 Hz, 2H), 1.37-1.31 (m, 6H); LC-MS: m/z 435.05 (M+1)$^+$.

Step-e: Synthesis of 1-ethyl-2-((6-(trifluoromethoxy)benzo[d]oxazol-2-yl)amino)-1H-benzo[d]imidazole-5-carboxylic acid The title compound was synthesized using the same procedure which was followed for compound 1h using ethyl 1-ethyl-2-((6-(trifluoromethoxy)benzo[d]oxazol-2-yl)amino)-1H-benzo[d]imidazole-5-carboxylate as starting material (Yield: 75%); $^1$H NMR (400 MHz, DMSO-d$_6$): δ 12.8 (bs, 1H), 12.3 (bs, 1H), 8.21 (s, 1H), 7.88 (d, J=8.0 Hz, 1H), 7.58-7.57 (m, 2H), 7.52 (d, J=8.4 Hz, 1H), 7.20 (d, J=9.6 Hz, 1H), 4.22 (q, J=7.6 Hz, 2H), 1.33 (t, J=6.8 Hz, 3H); LC-MS: m/z 407.0 (M+1)$^+$.

Step-f: Synthesis of 1-ethyl-N-(2-methoxyethyl)-2-((6-(trifluoromethoxy)benzo[d]oxazol-2-yl)amino)-1H-benzo[d]imidazole-5-carboxamide The title compound was synthesized using the same procedure which was followed for compound 1i using 1-ethyl-2-((6-(trifluoromethoxy)benzo[d]oxazol-2-yl)amino)-1H-benzo[d]imidazole-5-carboxylic acid and 2-methoxyethylamine as starting materials (Yield: 58%); $^1$H NMR (400 MHz, DMSO-d$_6$): δ 12.3 (bs, 1H), 8.46 (s, 1H), 8.09 (s, 1H), 7.77 (d, J=8.4 Hz, 1H), 7.56-7.50 (m, 3H), 7.21 (d, J=8.0 Hz, 1H), 4.22 (q, J=7.6 Hz, 2H), 3.48-3.44 (m, 4H), 3.28 (s, 3H), 1.32 (t, J=7.6 Hz, 3H); LC-MS: m/z 464.1 (M+1)$^+$.

Example 86. Synthesis of 1-ethyl-N-(2-hydroxyethyl)-2-((6-(trifluoromethoxy)benzo[d]oxazol-2-yl)amino)-1H-benzo[d]imidazole-5-carboxamide

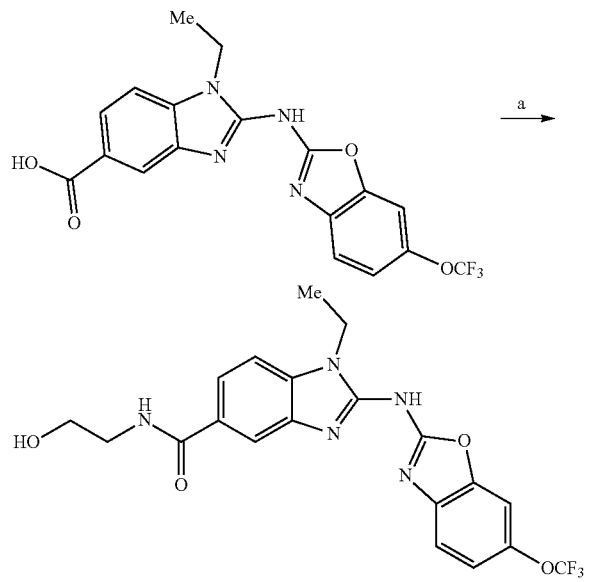

Conditions: a) 2-aminoethan-1-ol, HBTU, DIPEA, DMF, 0° C.-RT, 16 h

To a stirred solution of 1-ethyl-2-((6-(trifluoromethoxy)benzo[d]oxazol-2-yl)amino)-1H-benzo[d]imidazole-5-carboxylic acid (60 mg, 0.14 mmol) in DMFA (1 mL) at 0° C. was added N-ethyldiisopropyl amine (0.02 mL, 0.14 mmol) and HBTU (52 mg, 0.14 mmol). The reaction mixture was stirred for 30 min, followed by the addition of 2-aminoethan-1-ol (8 mg, 0.14 mmol) and stirring was continued at RT for 16 h. Once the reaction was completed (monitored by TLC), the reaction mixture was diluted with cold water (15 mL) and stirred for 15 min. The solid obtained was filtered, washed with diethyl ether and dried under vacuum to afford the title compound (20 mg, 30%) as white solid; $^1$H NMR (400 MHz, DMSO-d$_6$): δ 12.3 (bs, 1H), 8.37 (t, J=4.8 Hz, 1H), 8.09 (s, 1H), 7.78 (d, J=8.4 Hz, 1H), 7.56-7.49 (m, 3H), 7.21 (d, J=8.0 Hz, 1H), 4.72 (t, J=5.6 Hz, 1H), 4.22 (q, J=7.2 Hz, 2H), 3.53 (q, J=5.2 Hz, 2H), 3.39-3.37 (m, 2H), 1.32 (t, J=8.0 Hz, 3H); LC-MS: m/z 450.1 (M+1)$^+$.

Examples 87 and 88. Synthesis of 1-((tetrahydrofuran-3-yl)methyl)-2-((6-(trifluoromethoxy)-benzo[d]oxazol-2-yl)amino)-1H-benzo[d]imidazole-5-carboxylic acid Synthesis of N-(2-methoxyethyl)-1-((tetrahydrofuran-3-yl)methyl)-2-((6-(trifluoromethoxy)benzo[d]oxazol-2-yl)amino)-1H-benzo[d]imidazole-5-carboxamide

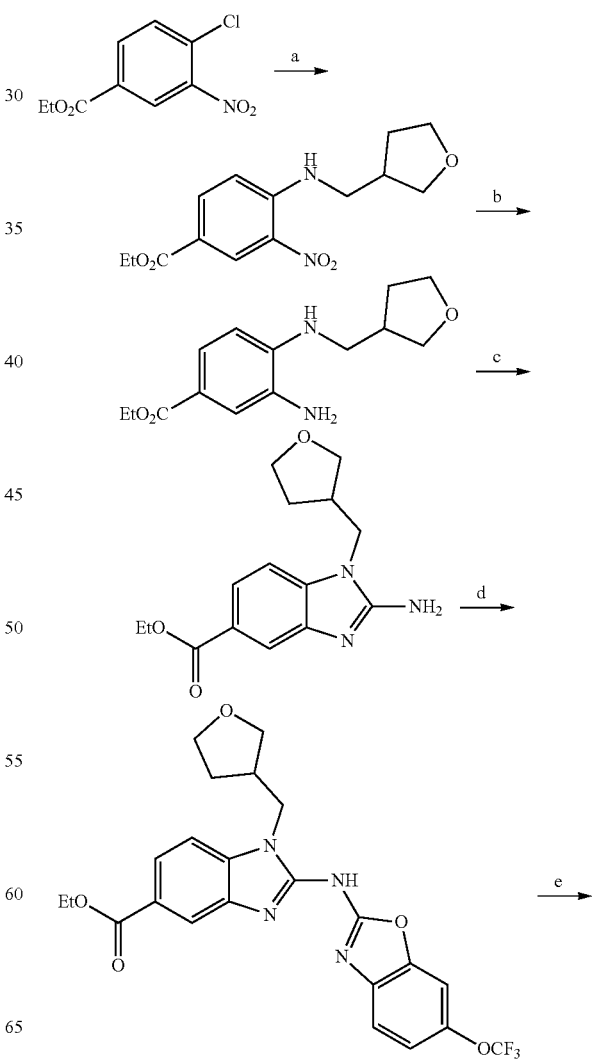

-continued

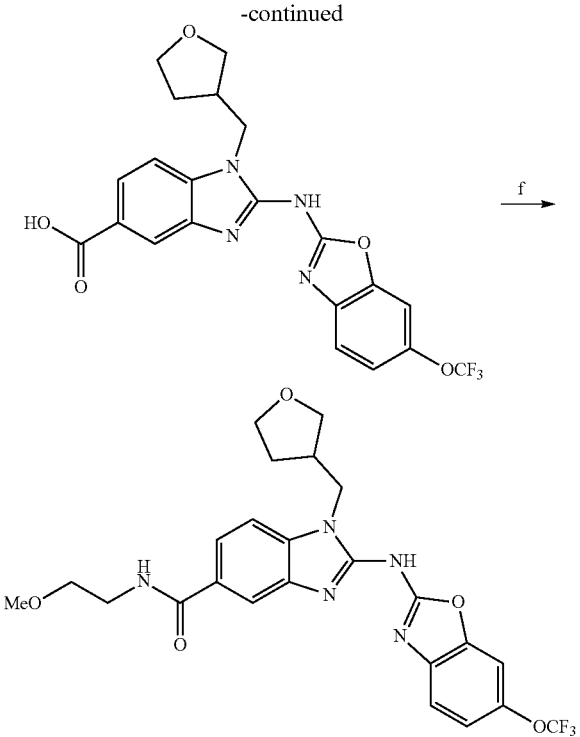

Conditions: a) (tetrahydrofuran-3-yl)methanamine, DIPEA, THF, 60° C., 16 h; b) 10% Pd/C, MeOH, H₂, RT, 16 h; c) Cyanogen bromide, THF, H₂O, 50° C., 16 h; d) NaH, 2-chloro-6-(trifluoromethoxy)benzo[d]oxazole, 1,4-Dioxane, RT, 16 h; e) LiOH·H₂O, THF, EtOH, H₂O, 60° C., 16 h; f) 2-methoxyethylamine, DPPA, DIPEA, DMF, 0° C.-RT, 16 h

Step-a: Synthesis of ethyl 3-nitro-4-(((tetrahydrofuran-3-yl)methyl)amino)benzoate To a solution of ethyl 4-chloro-3-nitrobenzoate (2.0 g, 8.7 mmol) in THF (40 mL) at RT was added DIPEA (4.6 mL, 26.1 mmol) and (tetrahydrofuran-3-yl)methanamine (1.06 g, 10.5 mmol) then the reaction mixture was stirred at 60° C. for 16 h. The reaction mixture was cooled to RT, diluted with cold water (200 mL) and stirred for 1 h. The solid precipitated was filtered and dried under vacuum to afford the title compound (2.4 g, 94%); ¹H NMR (400 MHz, DMSO-d₆): δ 8.62-8.59 (m, 2H), 7.97 (dd, J=2.0 Hz, J=9.2 Hz, 1H), 7.20 (d, J=8.8 Hz, 1H), 4.29 (q, J=7.6 Hz, 2H), 3.82-3.77 (m, 1H), 3.73-3.69 (m, 1H), 3.66-3.60 (m, 1H), 3.53-3.50 (m, 1H), 3.45-3.40 (m, 2H), 2.67-2.58 (m, 1H), 2.03-1.95 (m, 1H), 1.69-1.63 (m, 1H), 1.31 (t, J=7.2 Hz, 3H); LC-MS: m/z 295.0 (M+1)⁺.

Step-b: Synthesis of ethyl 3-amino-4-(((tetrahydrofuran-3-yl)methyl)amino)benzoate The title compound was synthesized using the same procedure which was followed for compound 1e using ethyl 3-nitro-4-(((tetrahydrofuran-3-yl)methyl)amino)benzoate as starting material (Yield: 86%); ¹H NMR (400 MHz, DMSO-d₆): δ 7.20 (dd, J=2.0 Hz, J=8.0 Hz, 1H), 7.16 (d, J=2.0 Hz, 1H), 6.46 (d, J=8.0 Hz, 1H), 5.26 (bs, 1H), 4.75 (s, 2H), 4.18 (q, J=7.2 Hz, 2H), 3.77-3.73 (m, 2H), 3.64-3.62 (m, 1H), 3.49-3.47 (m, 1H), 3.07 (t, J=6.4 Hz, 2H), 2.50-2.49 (m, 1H), 2.11-1.98 (m, 1H), 1.63-1.48 (m, 1H), 1.26 (t, J=7.2 Hz, 3H); LC-MS: m/z 265.1 (M+1)⁺.

Step-c: Synthesis of ethyl 2-amino-1-((tetrahydrofuran-3-yl)methyl)-1H-benzo[d]imidazole-5-carboxylate The title compound was synthesized using the same procedure which was followed for compound 1f using ethyl 3-amino-4-(((tetrahydrofuran-3-yl)methyl)amino)benzoate as starting material (Yield: 79%); ¹H NMR (400 MHz, DMSO-d₆): δ 7.70 (s, 1H), 7.58 (dd, J=1.6 Hz, J=8.4 Hz, 1H), 7.27 (d, J=8.4 Hz, 1H), 6.71 (s, 2H), 4.27 (q, J=6.8 Hz, 2H), 4.03 (d, J=8.0 Hz, 2H), 3.78-3.71 (m, 1H), 3.63-3.59 (m, 2H), 3.48-3.41 (m, 1H), 2.72-2.68 (m, 1H), 1.85-1.79 (m, 1H), 1.65-1.58 (m, 1H), 1.31 (t, J=7.2 Hz, 3H); LC-MS: m/z 290.1 (M+1)⁺.

Step-d: Synthesis of ethyl 1-((tetrahydrofuran-3-yl)methyl)-2-((6-(trifluoromethoxy)benzo[d]oxazol-2-yl)amino)-1H-benzo[d]imidazole-5-carboxylate The title compound was synthesized using the same procedure which was followed for Example 32 Step-e using ethyl 2-amino-1-ethyl-1H-benzo[d]imidazole-5-carboxylate and 2-chloro-6-(trifluoromethoxy)benzo[d]oxazole as starting materials (Yield: 44%); ¹H NMR (400 MHz, DMSO-d₆): δ 12.4 (bs, 1H), 8.26 (d, J=1.6 Hz, 1H), 7.88 (dd, J=1.6 Hz, J=8.4 Hz, 1H), 7.63 (d, J=8.4 Hz, 1H), 7.59 (s, 1H), 7.52 (d, J=8.4 Hz, 1H), 7.22 (d, J=7.6 Hz, 1H), 4.33 (q, J=7.2 Hz, 2H), 4.20-4.18 (m, 2H), 3.88-3.86 (m, 1H), 3.70-3.56 (m, 3H), 3.80-3.78 (m, 1H), 1.94-1.91 (m, 1H), 1.73-1.71 (m, 1H), 1.35 (t, J=7.2 Hz, 3H); LC-MS: m/z 491.15 (M+1)⁺.

Step-e: Synthesis of 1-((tetrahydrofuran-3-yl)methyl)-2-((6-(trifluoromethoxy)-benzo[d]oxazol-2-yl)amino)-1H-benzo[d]imidazole-5-carboxylic acid The title compound was synthesized using the same procedure which was followed for compound 1h using ethyl 1-((tetrahydrofuran-3-yl)methyl)-2-((6-(trifluoromethoxy)benzo[d]oxazol-2-yl)amino)-1H-benzo[d]imidazole-5-carboxylate as starting material (Yield: 76%); ¹H NMR (400 MHz, DMSO-d₆): δ 12.8 (bs, 1H), 12.3 (bs, 1H), 8.21 (s, 1H), 7.87 (d, J=8.0 Hz, 1H), 7.62-7.58 (m, 2H), 7.53 (d, J=8.8 Hz, 1H), 7.21 (d, J=8.4 Hz, 1H), 4.19 (d, J=7.6 Hz, 2H), 3.89-3.84 (m, 1H), 3.70-3.58 (m, 3H), 2.89-2.85 (m, 1H), 1.98-1.90 (m, 1H), 1.76-1.68 (m, 1H); LC-MS: m/z 463.1 (M+1)⁺.

Step-f: Synthesis of N-(2-methoxyethyl)-1-((tetrahydrofuran-3-yl)methyl)-2-((6-(trifluoromethoxy)benzo[d]oxazol-2-yl)amino)-1H-benzo[d]imidazole-5-carboxamide The title compound was synthesized using the same procedure which was followed for compound 1i using 1-((tetrahydrofuran-3-yl)methyl)-2-((6-(trifluoromethoxy)benzo[d]oxazol-2-yl)amino)-1H-benzo[d]imidazole-5-carboxylic acid and 2-methoxyethylamine as starting materials (Yield: 18%); ¹H NMR (400 MHz, DMSO-d₆): δ 12.3 (bs, 1H), 8.47 (s, 1H), 8.09 (s, 1H), 7.77 (d, J=7.6 Hz, 1H), 7.60-7.50 (m, 3H), 7.21 (d, J=8.0 Hz, 1H), 4.18 (bs, 2H), 3.87 (bs, 1H), 3.67-3.57 (m, 3H), 3.47 (bs, 4H), 3.28 (s, 3H), 2.88 (bs, 1H), 1.92 (bs, 1H), 1.73 (bs, 1H); LC-MS: m/z 520.15 (M+1)⁺.

Examples 89 and 90. Synthesis of 1-(2-(methylsulfonyl)ethyl)-2-((6-(trifluoromethoxy)benzo[d]oxazol-2-yl)amino)-1H-benzo[d]imidazole-5-carboxylic acid and Synthesis of N-(2-methoxyethyl)-1-(2-(methylsulfonyl)ethyl)-2-((6-(trifluoromethoxy)benzo[d]oxazol-2-yl)amino)-1H-benzo[d]imidazole-5-carboxamide

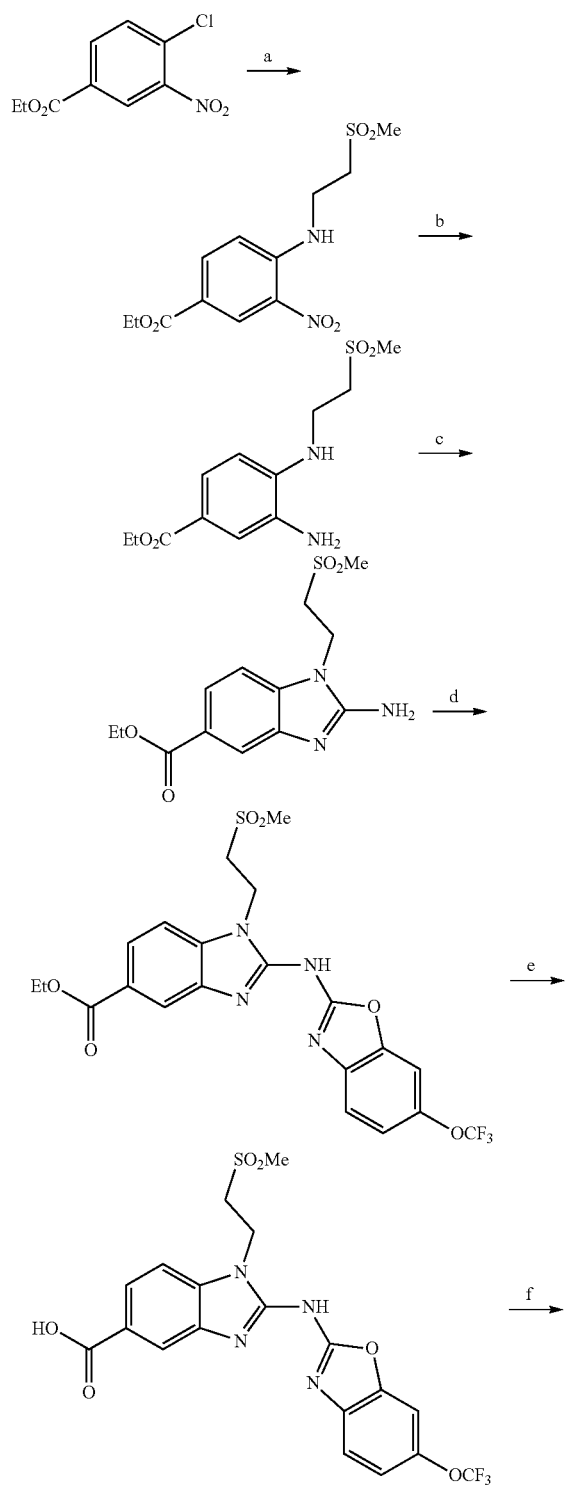

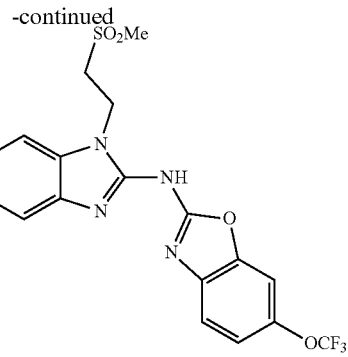

Conditions: a) 2-(methylsulfonyl)ethan-1-amine hydrochloride, DIPEA, DMF, 60° C., 16 h; b) 10% Pd/C, MeOH, H₂, RT, 16 h; c) Cyanogen bromide, THF, H₂O, 50° C., 16 h; d) NaH, 2-chloro-6-(trifluoromethoxy)benzo[d]oxazole, 1,4-Dioxane, RT, 16 h; e) LiOH•H₂O, THF, EtOH, H₂O, 60° C., 16 h; f) 2-methoxyethylamine, DPPA, DIPEA, DMF, 0° C.-RT, 16 h Step-a: Synthesis of ethyl 4-((2-(methylsulfonyl)ethyl)amino)-3-nitrobenzoate The title compound was synthesized using the same procedure which was followed for compound 3a using ethyl 4-chloro-3-nitrobenzoate and 2-(methylsulfonyl)ethan-1-amine hydrochloride as starting materials and heating to 60° C. (Yield: 89%); $^1$H NMR (400 MHz, DMSO-d$_6$): δ 8.69 (t, J=6.0 Hz, 1H), 8.63 (d, J=2.0 Hz, 1H), 8.02 (dd, J=2.0 Hz, J=8.8 Hz, 1H), 7.20 (d, J=9.2 Hz, 1H), 4.30 (q, J=6.8 Hz, 2H), 3.89 (q, J=5.6 Hz, 2H), 3.52 (t, J=6.8 Hz, 2H), 3.08 (s, 3H), 1.30 (t, J=6.8 Hz, 3H); LC-MS: m/z 317.0 (M+1)$^+$.

Step-b: Synthesis of ethyl 3-amino-4-((2-(methylsulfonyl)ethyl)amino)benzoate

The title compound was synthesized using the same procedure which was followed for compound 1e using ethyl 4-((2-(methylsulfonyl)ethyl)amino)-3-nitrobenzoate as starting material (Yield: 86%); $^1$H NMR (400 MHz, DMSO-d$_6$): δ 7.24-7.20 (m, 2H), 6.52 (d, J=8.4 Hz, 1H), 5.45 (t, J=5.2 Hz, 1H), 4.72 (s, 2H), 4.19 (q, J=7.2 Hz, 2H), 3.58 (q, J=6.4 Hz, 2H), 3.38 (t, J=6.8 Hz, 2H), 3.03 (s, 3H), 1.26 (t, J=6.8 Hz, 3H); LC-MS: m/z 287.0 (M+1)$^+$.

Step-c: Synthesis of ethyl 2-amino-1-(2-(methylsulfonyl)ethyl)-1H-benzo[d]imidazole-5-carboxylate The title compound was synthesized using the same procedure which was followed for compound 1f using ethyl 3-amino-4-((2-(methylsulfonyl)ethyl)amino)benzoate as starting material (Yield: 86%); $^1$H NMR (400 MHz, DMSO-d$_6$): δ 7.71 (d, J=1.2 Hz, 1H), 7.61 (dd, J=1.6 Hz, J=8.4 Hz, 1H), 7.28 (d, J=8.4 Hz, 1H), 6.75 (s, 2H), 4.47-4.40 (m, 2H), 4.30 (q, J=7.6 Hz, 2H), 3.55 (t, J=6.8 Hz, 2H), 3.03 (s, 3H), 1.31 (t, J=6.8 Hz, 3H).

Step-d: Synthesis of ethyl 1-(2-(methylsulfonyl)ethyl)-2-((6-(trifluoromethoxy)benzo[d]oxazol-2-yl)amino)-1H-benzo[d]imidazole-5-carboxylate The title compound was synthesized using the same procedure which was followed for compound 1g using ethyl 2-amino-1-(2-(methylsulfonyl)ethyl)-1H-benzo[d]imidazole-5-carboxylate and 2-chloro-6-(trifluoromethoxy)benzo[d]oxazole as starting materials (Yield: 24%); $^1$H NMR (400

MHz, DMSO-d$_6$): δ 13.4 (bs, 1H), 8.25 (d, J=1.6 Hz, 1H), 7.89 (dd, J=1.2 Hz, J=8.0 Hz, 1H), 7.63-7.61 (m, 2H), 7.54 (d, J=8.8 Hz, 1H), 7.56-7.51 (m, 1H), 4.61 (t, J=6.8 Hz, 2H), 4.34 (q, J=7.2 Hz, 2H), 3.73 (d), J=6.8 Hz, 2H), 3.14 (s, 3H), 1.35 (t, J=7.6 Hz, 3H); LC-MS: m/z 513.05 (M+1)$^+$.

Step-e: Synthesis of 1-(2-(methylsulfonyl)ethyl)-2-((6-(trifluoromethoxy)benzo[d]oxazol-2-yl)amino)-1H-benzo[d]imidazole-5-carboxylic acid The title compound was synthesized using the same procedure which was followed for compound 1h using ethyl 1-(2-(methylsulfonyl)ethyl)-2-((6-(trifluoromethoxy)benzo[d]oxazol-2-yl)amino)-1H-benzo[d]imidazole-5-carboxylate as starting material (Yield: 17%); $^1$H NMR (400 MHz, DMSO-d$_6$): δ 12.8 (bs, 1H), 12.4 (bs, 1H), 8.20 (d, J=1.2 Hz, 1H), 7.88 (dd, J=1.2 Hz, J=8.0 Hz, 1H), 7.61-7.59 (m, 2H), 7.54 (d, J=8.4 Hz, 1H), 7.22 (d, J=8.8 Hz, 1H), 4.61 (t, J=6.8 Hz, 2H), 3.72 (t, J=6.8 Hz, 2H), 3.14 (s, 3H); LC-MS: m/z 484.9 (M+1)$^+$.

Step-f: Synthesis of N-(2-methoxyethyl)-1-(2-(methylsulfonyl)ethyl)-2-((6-(trifluoromethoxy)benzo[d]oxazol-2-yl)amino)-1H-benzo[d]imidazole-5-carboxamide The title compound was synthesized using the same procedure which was followed for compound 1i using 1-(2-(methylsulfonyl)ethyl)-2-((6-(trifluoromethoxy)benzo[d]oxazol-2-yl)amino)-1H-benzo[d]imidazole-5-carboxylic acid and 2-methoxyethylamine as starting materials (Yield: 32%); $^1$H NMR (400 MHz, DMSO-d$_6$): δ 12.30 (bs, 1H), 8.48 (t, J=5.2 Hz, 1H), 8.08 (s, 1H), 7.77 (d, J=8.4 Hz, 1H), 7.67-7.54 (m, 3H), 7.21 (d, J=9.6 Hz, 1H), 4.60 (t, J=6.8 Hz, 2H), 3.74 (t, J=10.8 confirm coupling constant Hz, 2H), 3.48-3.44 (m, 4H), 3.28 (s, 3H), 3.14 (s, 3H); LC-MS: m/z 542.0 (M+1)$^+$.

Example 91. Synthesis of 2-((6-bromobenzo[d]oxazol-2-yl)amino)-1-methyl-1H-benzo[d]imidazole-5-carboxylic acid

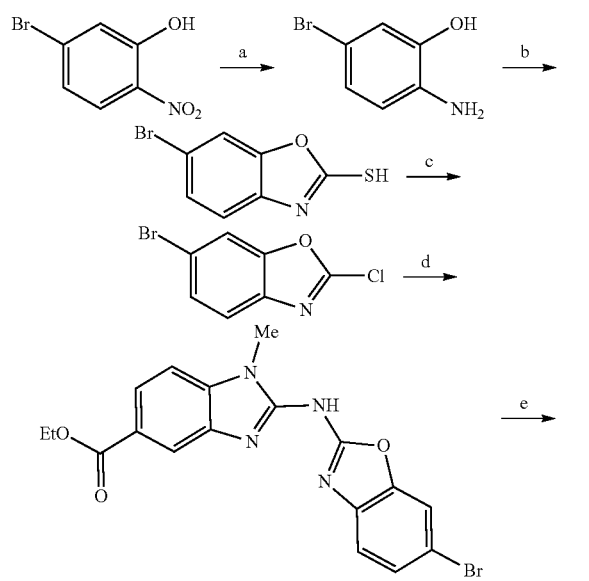

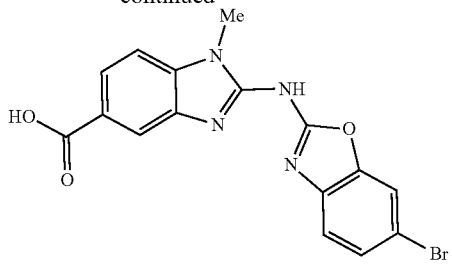

Conditions: a) SnCl$_2$, 2H$_2$O, EtOH, Reflux, 4 h; b) Potassium ethyl xanthate, EtOH, Reflux, 16 h; c) SOCl$_2$, Cat. DMF, Reflux, 3 h; d) NaH, ethyl 2-amino-1-methyl-1H-benzo[d]imidazole-5-carboxylate, 1,4-Dioxane, RT, 16 h; e) LiOH•H$_2$O, THF, EtOH, H$_2$O, 60° C., 16 h Step-a: Synthesis of 2-amino-5-bromophenol To a solution of 5-bromo-2-nitrophenol (4.0 g, 18.35 mmol) in ethanol (60 mL) at RT was added SnCl$_2$.2H$_2$O (20.6 g, 91.74 mmol) and the reaction mixture was refluxed for 4 h. The reaction mixture was cooled to RT, concentrated under reduced pressure. The residue was diluted with water (20 mL) and basified with saturated aqueous sodium bicarbonate solution, extracted with ethyl acetate (2×100 mL). The combined organic layer was washed with water (50 mL), brine (30 mL), dried over anhydrous sodium sulfate and concentrated under vacuum to afford the title compound (2.4 g, 70%); $^1$H NMR (400 MHz, DMSO-d$_6$): δ 9.44 (bs, 1H), 6.75 (d, J=2.4 Hz, 1H), 6.67 (dd, J=2.0 Hz, J=8.4 Hz, 1H), 6.51 (d, J=8.4 Hz, 1H), 4.65 (bs, 2H); LC-MS: m/z 190.0 (M+1)$^+$.

Step-b: Synthesis of 6-bromobenzo[d]oxazole-2-thiol

The title compound was synthesized using the same procedure which was followed for Example 32 Step-c using 2-amino-5-bromophenol as starting material (Yield: 98%); $^1$H NMR (400 MHz, DMSO-d$_6$): δ 14.0 (bs, 1H), 7.84 (d, J=1.6 Hz, 1H), 7.47 (dd, J=1.6 Hz, J=8.4 Hz, 1H), 7.18 (d, J=8.4 Hz, 1H); LC-MS: m/z 227.9 (M−1)$^-$.

Step-c: Synthesis of 6-bromo-2-chlorobenzo[d]oxazole

To a solution of 6-bromobenzo[d]oxazole-2-thiol (2.89 g, 12.56 mmol) in thionyl chloride (20 mL) at RT was added N,N-dimethylformamide (0.2 mL) and the reaction mixture was refluxed for 3 h. The reaction mixture was concentrated, diluted with cold water (50 mL) and extracted with EtOAc (2×50 mL). The combined organic layers were washed with saturated aqueous sodium bicarbonate solution (50 mL), brine solution (40 mL), dried over anhydrous sodium sulfate and concentrated under vacuum to afford the title compound (2.8 g, 96%); $^1$H NMR (400 MHz, DMSO-d$_6$): δ 8.14 (s, 1H), 7.72 (d, J=8.8 Hz, 1H), 7.62 (dd, J=2.0 Hz, J=8.8 Hz, 1H).

Step-d: Synthesis of ethyl 2-((6-bromobenzo[d]oxazol-2-yl)amino)-1-methyl-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 6-bromo-2-chlorobenzo[d]oxazole as starting materials (Yield: 20%); $^1$H NMR (400 MHz, DMSO-d$_6$): δ 11.56 (bs, 1H), 8.23 (d, J=1.6 Hz, 1H), 7.88 (dd, J=1.6 Hz, J=8.4 Hz, 1H), 7.72 (d, J=1.6 Hz, 1H), 7.54 (d, J=8.8 Hz, 1H), 7.38-7.36 (m, 2H), 4.33 (q, J=7.2 Hz, 2H), 3.64 (s, 3H), 1.35 (t, J=7.2 Hz, 3H); LC-MS: m/z 416.9 (M+1)$^+$.

Step-e: Synthesis of 2-((6-bromobenzo[d]oxazol-2-yl)amino)-1-methyl-1H-benzo[d]imidazole-5-carboxylic acid The title compound was synthesized using the same procedure which was followed for compound 1h using ethyl 2-((6-bromobenzo[d]oxazol-2-yl)amino)-1-methyl-1H-benzo[d]imidazole-5-carboxylate as starting material (Yield: 75%); $^1$H NMR (400 MHz, DMSO-d$_6$): δ 12.8 (bs, 1H), 12.3 (bs, 1H), 8.19 (s, 1H), 7.87 (d, J=8.4 Hz, 1H), 7.71 (d, J=1.6 Hz, 1H), 7.51 (d, J=8.8 Hz, 1H), 7.42-7.35 (m, 2H), 3.64 (s, 3H); LC-MS: m/z 388.9 (M+1)$^+$.

Example 92. Synthesis of N-(2-hydroxyethyl)-2-((6-methoxybenzo[d]oxazol-2-yl)amino)-1-methyl-1H-benzo[d]imidazole-5-carboxamide

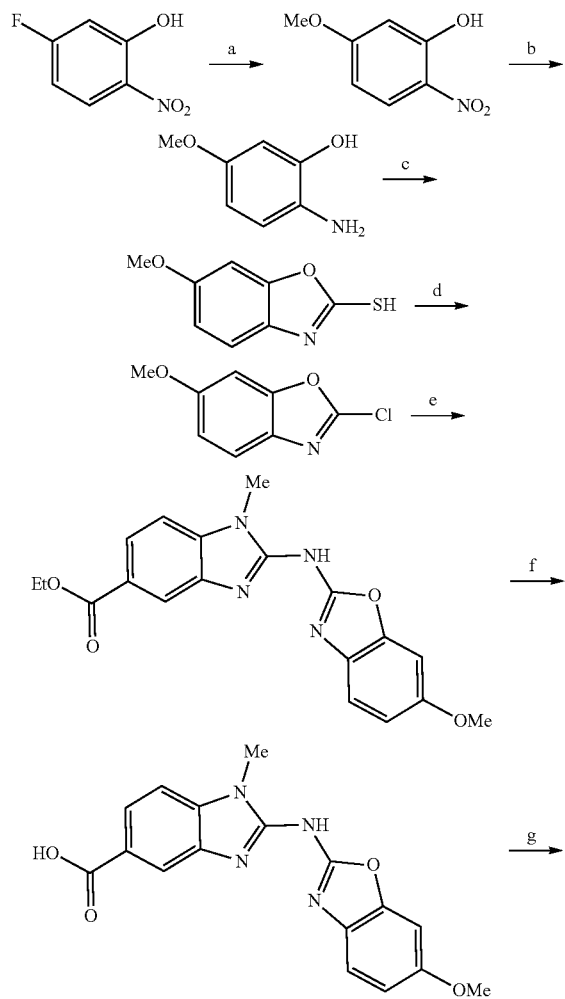

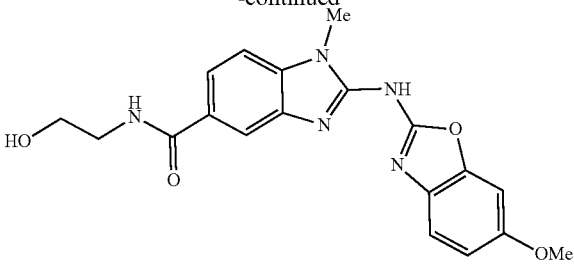

Conditions: a) NaOMe, MeOH, 60° C., 40 h; b) 10% Pd/C, MeOH, H$_2$, RT, 16 h; c) Potassium ethyl xanthate, EtOH, Reflux, 16 h; d) SOCl$_2$, Cat. DMF, Reflux, 2 h; e) NaH, ethyl 2-amino-1-methyl-1H-benzo[d]imidazole-5-carboxylate, 1,4-Dioxane, RT, 16 h; f) LiOH•H$_2$O, THF, EtOH, H$_2$O, 60° C., 16 h; g) 2-aminoethan-1-ol, HBTU, DIPEA, DMF, 0° C.-RT, 16 h Step-a: Synthesis of 5-methoxy-2-nitrophenol To a stirred suspension of sodium methoxide (0.86 g, 18.35 mmol) in methanol (50 mL) at RT was added a solution of 5-fluoro-2-nitrophenol (3.0 g, 19.1 mmol) in methanol (40 mL) through a syringe and the reaction mixture was heated at 60° C. for 40 h. The reaction mixture was cooled to RT, quenched with cold water (50 mL), acidified with 1 N HCl and extracted with ethyl acetate (2×100 mL). The combined organic layer was washed with water (50 mL), brine (50 mL), dried over anhydrous sodium sulfate and concentrated under vacuum. The residue was purified by combiflash chromatography using 3% ethyl acetate in hexane as an eluent to afford the title compound (2.0 g, 62%); $^1$H NMR (400 MHz, DMSO-d$_6$): δ 10.94 (s, 1H), 7.97 (d, J=9.6 Hz, 1H), 6.63 (d, J=2.4 Hz, 1H), 6.59 (dd, J=3.0 Hz, J=9.2 Hz, 1H), 3.83 (s, 3H); LC-MS: m/z 167.95 (M−1)$^-$.

Step-b: Synthesis of 2-amino-5-methoxyphenol

The title compound was synthesized using the same procedure which was followed for compound 1e using 5-methoxy-2-nitrophenol as starting material (Yield: 96%); $^1$H NMR (400 MHz, DMSO-d$_6$): δ 8.8 (bs, 1H), 6.49 (d, J=8.4 Hz, 1H), 6.30 (d, J=2.1 Hz, 1H), 6.18-6.14 (m, 1H), 3.58 (s, 3H); LC-MS: m/z 140.15 (M+1)$^+$.

Step-c: Synthesis of 6-methoxybenzo[d]oxazole-2-thiol

The title compound was synthesized using the same procedure which was followed for Example 32 Step-c using 2-amino-5-methoxyphenol as starting material (Yield: 72%); $^1$H NMR (400 MHz, DMSO-d$_6$): δ 13.7 (s, 1H), 7.21 (d, J=2.4 Hz, 1H), 7.13 (d, J=8.4 Hz, 1H), 6.88 (dd, J=2.0 Hz, J=8.4 Hz, 1H), 3.77 (s, 3H); LC-MS: m/z 182.0 (M+1)$^+$.

Step-d: Synthesis of 2-chloro-6-methoxybenzo[d]oxazole

The title compound was synthesized using the same procedure which was followed for Example 32 Step-d using 6-methoxybenzo[d]oxazole-2-thiol as starting material and stirred for 2 h (Yield: 91%); LC-MS: m/z 184.0 (M+1)$^+$.

Step-e: Synthesis of ethyl 2-((6-methoxybenzo[d]oxazol-2-yl)amino)-1-methyl-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 2-chloro-6-methoxybenzo[d]oxazole as starting materials (Yield: 18%); $^1$H NMR (400 MHz, DMSO-$d_6$): δ 12.3 (bs, 1H), 8.21 (d, J=1.4 Hz, 1H), 7.87 (dd, J=1.2 Hz, J=8.4 Hz, 1H), 7.50 (d, J=8.0 Hz, 1H), 7.36 (d, J=8.4 Hz, 1H), 7.13 (d, J=2.0 Hz, 1H), 6.83 (dd, J=2.4 Hz, J=8.4 Hz, 1H), 4.33 (q, J=6.8 Hz, 2H), 3.82 (s, 3H), 3.62 (s, 3H), 1.35 (t, J=7.2 Hz, 3H); LC-MS: m/z 367.0 (M+1)$^+$.

Step-f: Synthesis of 2-((6-methoxybenzo[d]oxazol-2-yl)amino)-1-methyl-1H-benzo[d]imidazole-5-carboxylic acid The title compound was synthesized using the same procedure which was followed for compound 1h using ethyl 2-((6-methoxybenzo[d]oxazol-2-yl)amino)-1-methyl-1H-benzo[d]imidazole-5-carboxylate as starting material (Yield: 79%); $^1$H NMR (400 MHz, DMSO-$d_6$): δ 12.5 (bs, 2H), 8.17 (s, 1H), 7.85 (dd, J=1.6 Hz, J=8.4 Hz, 1H), 7.47 (d, J=8.4 Hz, 1H), 7.37 (d, J=8.8 Hz, 1H), 7.12 (d, J=2.0 Hz, 1H), 6.82 (dd, J=2.4 Hz, J=8.8 Hz, 1H), 3.79 (s, 3H), 3.62 (s, 3H); LC-MS: m/z 339.0 (M+1)$^+$.

Step-g: Synthesis of N-(2-hydroxyethyl)-2-((6-methoxybenzo[d]oxazol-2-yl)amino)-1-methyl-1H-benzo[d]imidazole-5-carboxamide The title compound was synthesized using the same procedure which was followed for Example 6 Step-e using 2-((6-methoxybenzo[d]oxazol-2-yl)amino)-1-methyl-1H-benzo[d]imidazole-5-carboxylic acid and 2-aminoethan-1-ol as starting materials (Yield: 59%); $^1$H NMR (400 MHz, DMSO-$d_6$): δ 12.18 (bs, 1H), 8.35 (t, J=5.2 Hz, 1H), 8.05 (d, J=1.2 Hz, 1H), 7.75 (dd, J=1.6 Hz, J=8.4 Hz, 1H), 7.45 (d, J=8.4 Hz, 1H), 7.35 (d, J=8.4 Hz, 1H), 7.11 (d, J=2.4 Hz, 1H), 6.81 (dd, J=2.4 Hz, J=8.8 Hz, 1H), 4.72 (bs, 1H), 3.78 (s, 3H), 3.61 (s, 3H), 3.53 (t, J=6.0 Hz, 2H), 3.35-3.30 (m, 2H); LC-MS: m/z 382.0 (M+1)$^+$.

Examples 93 and 94. Synthesis of 1-((3-hydroxyoxetan-3-yl)methyl)-2-((6-(trifluoromethoxy)benzo[d]oxazol-2-yl)amino)-1H-benzo[d]imidazole-5-carboxylic acid and Synthesis of 1-((3-hydroxyoxetan-3-yl)methyl)-N-(2-methoxyethyl)-2-((6-(trifluoromethoxy)benzo[d]oxazol-2-yl)amino)-1H-benzo[d]imidazole-5-carboxamide

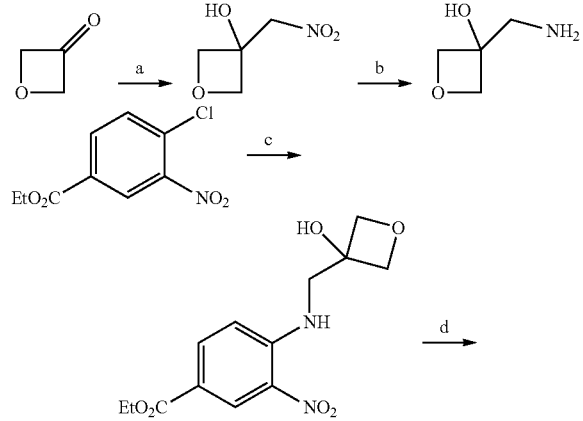

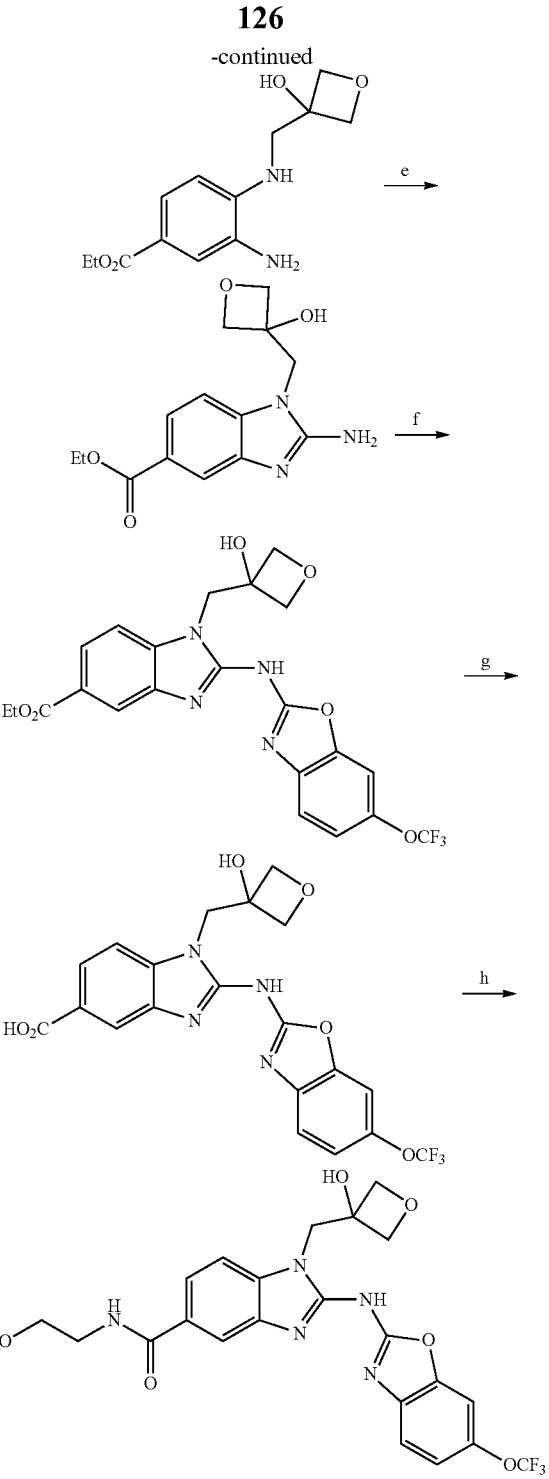

Conditions: a) Nitromethane, TEA, RT, 16 h; b) 10% Pd/C, MeOH, H$_2$, RT, 3 h; c) 3-(aminomethyl)oxetan-3-ol, DIPEA, DMF, 60° C., 16 h; d) 10% Pd/C, MeOH, H$_2$, RT, 16 h; e) Cyanogen bromide, THF, H$_2$O, 50° C., 16 h; f) NaH, 2-chloro-6-(trifluoromethoxy)benzo[d]oxazole, 1,4-Dioxane, RT, 16 h; g) LiOH•H$_2$O, THF, EtOH, H$_2$O, 60° C., 16 h; h) 2-methoxyethylamine, DPPA, DIPEA, DMF, 0° C.-RT, 16 h Step-a: Synthesis of 3-(nitromethyl)oxetan-3-ol To a solution of oxetan-3-one (10.0 g, 138.9 mmol) in nitromethane (25 mL) at 0° C. was added triethylamine (5 mL, 347.2 mmol) and the reaction mixture was stirred at RT for 16 h. The reaction mixture was concentrated under reduced pressure. The residue was purified by combi flash column chromatography using 40% ethyl acetate in hexane as an eluent to afford the title compound (14.0 g, 77%) as pale yellow liquid; $^1$H NMR (400 MHz, CDCl$_3$): δ 4.82 (s, 2H), 4.71 (d, J=8.0 Hz, 2H), 4.61 (d, J=8.0 Hz, 2H), 3.53 (s, 1H).

Step-b: Synthesis of 3-(aminomethyl)oxetan-3-ol

To a solution of 3-(nitromethyl)oxetan-3-ol (5.0 g, 37.6 mmol) in methanol (80 mL) was added a slurry of 10% Pd/C (2.0 g in 20 mL methanol) under nitrogen atmosphere. Then the reaction mixture was stirred under hydrogen gas balloon for 3 h. The reaction mixture was filtered through a bed of celite and concentrated under vacuum to afford the title compound (3.8 g, 98%); LC-MS: m/z 104.2 (M+1)$^+$.

Step-c: Synthesis of ethyl 4-(((3-hydroxyoxetan-3-yl)methyl)amino)-3-nitrobenzoate The title compound was synthesized using the same procedure which was followed for compound 3a using ethyl 4-chloro-3-nitrobenzoate and 3-(aminomethyl)oxetan-3-ol as starting materials heating to 60° C. (Yield: 54%); $^1$H NMR (400 MHz, DMSO-d$_6$): δ 8.62 (d, J=1.6 Hz, 1H), 8.53 (bs, 1H), 7.99 (dd, J=2.0 Hz, J=9.2 Hz, 1H), 7.29 (d, J=9.2 Hz, 1H), 6.35 (s, 1H), 4.51 (d, J=6.8 Hz, 2H), 4.44 (d, J=6.8 Hz, 2H), 4.29 (q, J=7.2 Hz, 2H), 3.75 (d, J=5.2 Hz, 2H), 1.31 (t, J=6.8 Hz, 3H); LC-MS: m/z 297.1 (M+1)$^+$.

Step-d: Synthesis of ethyl 3-amino-4-(((3-hydroxyoxetan-3-yl)methyl)amino)benzoate The title compound was synthesized using the same procedure which was followed for compound 1e using ethyl 4-(((3-hydroxyoxetan-3-yl)methyl)amino)-3-nitrobenzoate as starting material (Yield: 95%); $^1$H NMR (400 MHz, DMSO-d$_6$): δ 7.23-7.20 (m, 2H), 6.57 (d, J=8.4 Hz, 1H), 5.96 (bs, 1H), 5.04 (bs, 1H), 4.75 (s, 2H), 4.46-4.43 (m, 4H), 4.19 (q, J=7.2 Hz, 2H), 3.40 (d, J=5.6 Hz, 2H), 1.26 (t, J=6.8 Hz, 3H); LC-MS: m/z 267.1 (M+1)$^+$.

Step-e: Synthesis of ethyl 2-amino-1-((3-hydroxyoxetan-3-yl)methyl)-1H-benzo[d]imidazole-5-carboxylate The title compound was synthesized using the same procedure which was followed for compound 1f using ethyl 3-amino-4-(((3-hydroxyoxetan-3-yl)methyl)amino)benzoate as starting material (Yield: 70%); $^1$H NMR (400 MHz, DMSO-d$_6$): δ 7.72 (s, 1H), 7.59 (dd, J=1.6 Hz, J=8.0 Hz, 1H), 7.35 (d, J=8.0 Hz, 1H), 6.56 (s, 2H), 6.45 (s, 1H), 4.55 (d, J=6.4 Hz, 2H), 4.43 (d, J=6.0 Hz, 2H), 4.34 (s, 2H), 4.28 (q, J=6.8 Hz, 2H), 1.32 (t, J=5.2 Hz, 3H); LC-MS: m/z 292.1 (M+1)$^+$.

Step-f: Synthesis of ethyl 1-((3-hydroxyoxetan-3-yl)methyl)-2-((6-(trifluoromethoxy)benzo[d]oxazol-2-yl)amino)-1H-benzo[d]imidazole-5-carboxylate The title compound was synthesized using the same procedure which was followed for Example 32 Step-e using ethyl 2-amino-1-((3-hydroxyoxetan-3-yl)methyl)-1H-benzo[d]imidazole-5-carboxylate and 2-chloro-6-(trifluoromethoxy)benzo[d]oxazole as starting materials (Yield: 18%); $^1$H NMR (400 MHz, DMSO-d$_6$): δ 12.4 (bs, 1H), 8.24 (d, J=1.6 Hz, 1H), 7.85 (dd, J=1.6 Hz, J=8.4 Hz, 1H), 7.60-7.58 (m, 2H), 7.53 (d, J=8.4 Hz, 1H), 7.23 (dd, J=1.2 Hz, J=8.8 Hz, 1H), 6.18 (s, 1H), 4.79 (d, J=6.8 Hz, 2H), 4.50 (bs, 2H), 4.46 (d, J=6.8 Hz, 2H), 4.33 (q, J=6.8 Hz, 2H), 1.35 (t, J=7.6 Hz, 3H); LC-MS: m/z 493.0 (M+1)$^+$.

Step-g: Synthesis of 1-((3-hydroxyoxetan-3-yl)methyl)-2-((6-(trifluoromethoxy)benzo[d]oxazol-2-yl)amino)-1H-benzo[d]imidazole-5-carboxylic acid The title compound was synthesized using the same procedure which was followed for compound 1h using ethyl 1-((3-hydroxyoxetan-3-yl)methyl)-2-((6-(trifluoromethoxy)benzo[d]oxazol-2-yl)amino)-1H-benzo[d]imidazole-5-carboxylate as starting material (Yield: 49%); $^1$H NMR (400 MHz, DMSO-d$_6$): δ 12.8 (bs, 1H), 12.3 (bs, 1H), 8.19 (d, J=1.2 Hz, 1H), 7.84 (dd, J=1.2 Hz, J=8.0 Hz, 1H), 7.60-7.52 (m, 3H), 7.22 (dd, J=1.6 Hz, J=8.4 Hz, 1H), 6.18 (s, 1H), 4.79 (d, J=6.4 Hz, 2H), 4.51 (s, 2H), 4.46 (d, J=6.4 Hz, 2H); LC-MS: m/z 465.1 (M+1)$^+$.

Step-h: Synthesis of 1-((3-hydroxyoxetan-3-yl)methyl)-N-(2-methoxyethyl)-2-((6-(trifluoromethoxy)benzo[d]oxazol-2-yl)amino)-1H-benzo[d]imidazole-5-carboxamide The title compound was synthesized using the same procedure which was followed for compound 1i using 1-((3-hydroxyoxetan-3-yl)methyl)-2-((6-(trifluoromethoxy)benzo[d]oxazol-2-yl)amino)-1H-benzo[d]imidazole-5-carboxylic acid and 2-methoxyethylamine as starting materials. Crude product was purified by combiflash chromatography using 2% methanol in DCM as an eluent to afford the title compound (Yield: 28%); $^1$H NMR (400 MHz, DMSO-d$_6$): δ 12.3 (bs, 1H), 8.43 (t, J=5.2 Hz, 1H), 8.07 (s, 1H), 7.73 (d, J=8.8 Hz, 1H), 7.58 (s, 1H), 7.55-7.51 (m, 2H), 7.21 (d, J=8.4 Hz, 1H), 6.17 (s, 1H), 4.79 (d, J=6.8 Hz, 2H), 4.50 (s, 2H), 4.46 (d, J=6.4 Hz, 2H), 3.49-3.43 (m, 4H), 3.28 (s, 3H); LC-MS: m/z 522.0 (M+1)$^+$.

Example 95. Synthesis of N-(2-hydroxyethyl)-1-((3-hydroxyoxetan-3-yl)methyl)-2-((6-(trifluoromethoxy)benzo[d]oxazol-2-yl)amino)-1H-benzo[d]imidazole-5-carboxamide

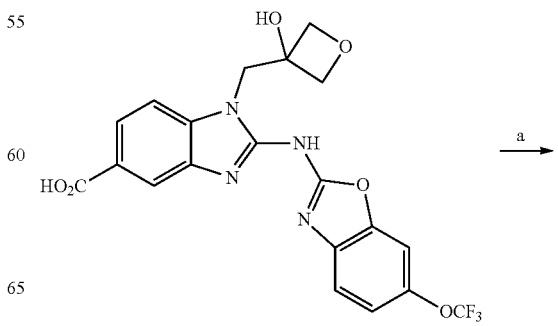

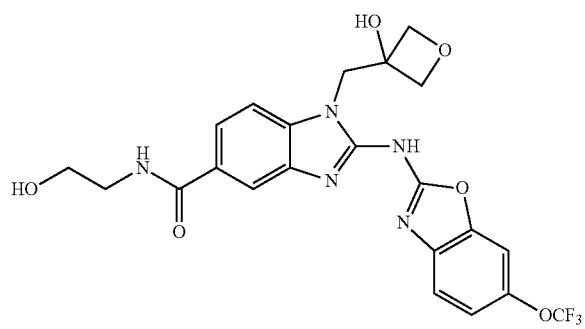

Conditions: a) 2-aminoethan-1-ol, HBTU, DIPEA, DMF, 0° C.-RT, 16 h

The title compound was synthesized using the same procedure which was followed for Example 6 Step-e using 1-((3-hydroxyoxetan-3-yl)methyl)-2-((6-(trifluoromethoxy)benzo[d]oxazol-2-yl)amino)-1H-benzo[d]imidazole-5-carboxylic acid and 2-aminoethan-1-ol as starting materials. Crude product was purified by combiflash chromatography using 3% methanol in DCM as an eluent to afford the title compound (Yield: 15%); $^1$H NMR (400 MHz, DMSO-$d_6$): δ 12.3 (bs, 1H), 8.35 (t, J=5.6 Hz, 1H), 8.07 (d, J=1.2 Hz, 1H), 7.73 (dd, J=1.6 Hz, J=8.4 Hz, 1H), 7.58 (s, 1H), 7.58-7.51 (m, 2H), 7.22 (dd, J=1.2 Hz, J=10.0 Hz, 1H), 6.17 (s, 1H), 4.80 (d, J=6.8 Hz, 2H), 4.71 (t, J=5.2 Hz, 1H), 4.51 (s, 2H), 4.46 (d, J=6.4 Hz, 2H), 3.55-3.51 (m, 2H), 3.37-27 (m, 2H); LC-MS: m/z 508.45 (M+1)$^+$.

Examples 96 and 97. Synthesis of 2-((6-chlorobenzo[d]oxazol-2-yl)amino)-1-methyl-1H-benzo[d]imidazole-5-carboxylic acid and Synthesis of 2-((6-chlorobenzo[d]oxazol-2-yl)amino)-N-(2-hydroxyethyl)-1-methyl-1H-benzo[d]imidazole-5-carboxamide

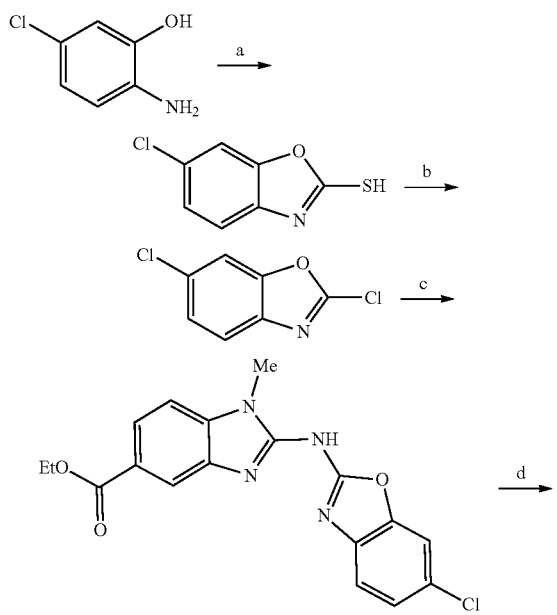

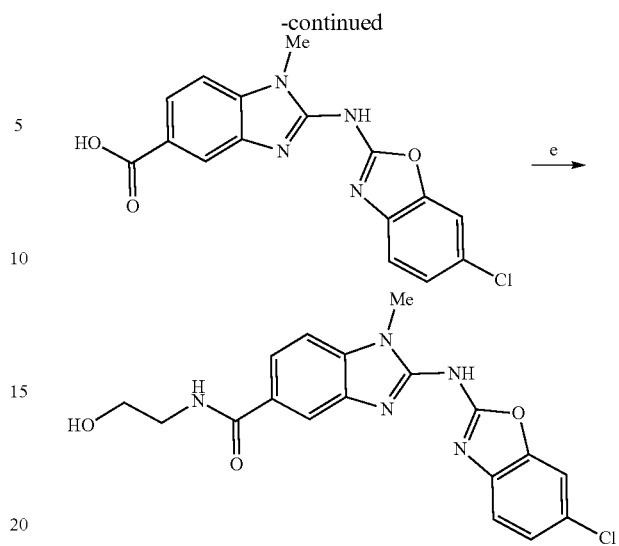

Conditions: a) Potassium ethyl xanthate, EtOH, Reflux, 16 h; b) SOCl$_2$, Cat. DMF, Reflux, 3 h; c) NaH, ethyl 2-amino-1-methyl-1H-benzo[d]imidazole-5-carboxylate, 1,4-Dioxane, RT, 16 h; d) LiOH·H$_2$O, THF, EtOH, H$_2$O, 60° C., 16 h; e) 2-aminoethan-1-ol, HBTU, DIPEA, DMF, 0° C.-RT, 16 h Step-a: Synthesis of 6-chlorobenzo[d]oxazole-2-thiol The title compound was synthesized using the same procedure which was followed for Example 32 Step-c using 2-amino-5-chlorophenol as starting material (Yield: 69%); $^1$H NMR (400 MHz, DMSO-$d_6$): δ 14.0 (bs, 1H), 7.73 (d, J=2.0 Hz, 1H), 7.35 (dd, J=1.6 Hz, J=8.0 Hz, 1H), 7.23 (d, J=8.8 Hz, 1H); LC-MS: m/z 184.0 (M−1)$^-$.

Step-b: Synthesis of 2,6-dichlorobenzo[d]oxazole

The title compound was synthesized using the same procedure which was followed for Example 32 Step-d using 6-chlorobenzo[d]oxazole-2-thiol as starting material (Yield: 69%); $^1$H NMR (400 MHz, DMSO-$d_6$): δ 8.01 (d, J=1.6 Hz, 1H), 7.77 (d, J=8.4 Hz, 1H), 7.51 (dd, J=2.0 Hz, J=8.4 Hz, 1H).

Step-c: Synthesis of ethyl 2-((6-chlorobenzo[d]oxazol-2-yl)amino)-1-methyl-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 2,6-dichlorobenzo[d]oxazole as starting materials (Yield: 24%); $^1$H NMR (400 MHz, DMSO-$d_6$): δ 12.3 (bs, 1H), 8.23 (d, J=1.6 Hz, 1H), 7.88 (d, J=8.0 Hz, 1H), 7.60 (d, J=2.0 Hz, 1H), 7.53 (d, J=8.4 Hz, 1H), 7.44 (d, J=8.0 Hz, 1H), 7.25 (dd, J=2.0 Hz, J=8.0 Hz, 1H), 4.33 (q, J=7.2 Hz, 2H), 3.64 (s, 3H), 1.35 (t, J=7.2 Hz, 3H); LC-MS: m/z 369.0 (M−1)$^-$.

Step-d: Synthesis of 2-((6-chlorobenzo[d]oxazol-2-yl)amino)-1-methyl-1H-benzo[d]imidazole-5-carboxylic acid The title compound was synthesized using the same procedure which was followed for compound 1h using ethyl 2-((6-chlorobenzo[d]oxazol-2-yl)amino)-1-methyl-1H-benzo[d]imidazole-5-carboxylate as starting material (Yield: 81%); ¹H NMR (400 MHz, DMSO-d₆): δ 12.8 (bs, 1H), 12.3 (bs, 1H), 8.19 (d, J=1.2 Hz, 1H), 7.87 (dd, J=1.6 Hz, J=8.4 Hz, 1H), 7.59 (d, J=2.0 Hz, 1H), 7.51 (d, J=8.4 Hz, 1H), 7.45 (d, J=8.4 Hz, 1H), 7.24 (dd, J=2.0 Hz, J=8.4 Hz, 1H), 3.64 (s, 3H); LC-MS: m/z 342.9 (M+1)⁺.

Step-e: Synthesis of 2-((6-chlorobenzo[d]oxazol-2-yl)amino)-N-(2-hydroxyethyl)-1-methyl-1H-benzo[d]imidazole-5-carboxamide The title compound was synthesized using the same procedure which was followed for Example 6 Step-e using 2-((6-chlorobenzo[d]oxazol-2-yl)amino)-1-methyl-1H-benzo[d]imidazole-5-carboxylic acid and 2-aminoethan-1-ol as starting materials (Yield: 53%); ¹H NMR (400 MHz, DMSO-d₆): δ 12.3 (bs, 1H), 8.37 (t, J=5.6 Hz, 1H), 8.08 (s, 1H), 7.78 (d, J=8.4 Hz, 1H), 7.58 (d, J=2.0 Hz, 1H), 7.49 (d, J=8.8 Hz, 1H), 7.44 (d, J=8.4 Hz, 1H), 7.24 (dd, J=2.0 Hz, J=8.4 Hz, 1H), 4.72 (t, J=5.2 Hz, 1H), 3.64 (s, 3H), 3.55-3.51 (m, 2H), 3.37-3.33 (m, 2H); LC-MS: m/z 386.1 (M+1)⁺.

Examples 98 and 99. Synthesis of 1-methyl-2-((6-(2,2,2-trifluoroethoxy)benzo[d]oxazol-2-yl)amino)-1H-benzo[d]imidazole-5-carboxylic acid and Synthesis of N-(2-methoxyethyl)-1-methyl-2-((6-(2,2,2-trifluoroethoxy)benzo[d]oxazol-2-yl)amino)-1H-benzo[d]imidazole-5-carboxamide

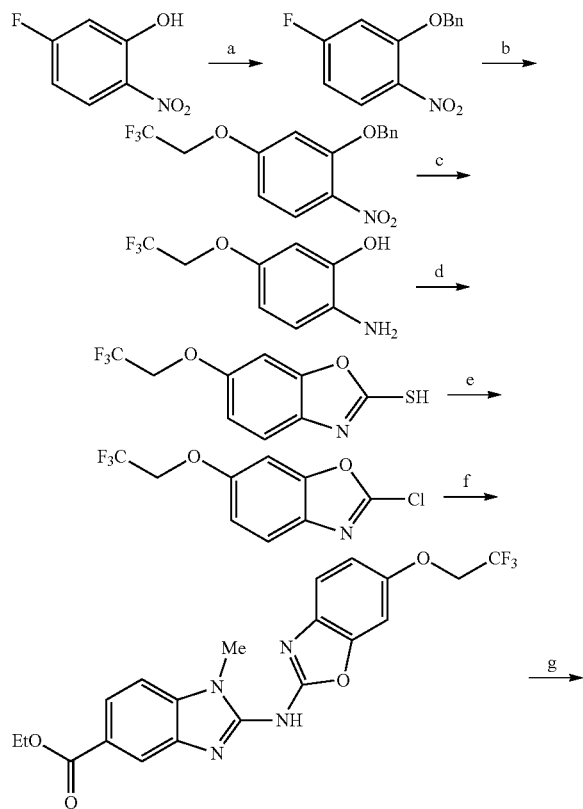

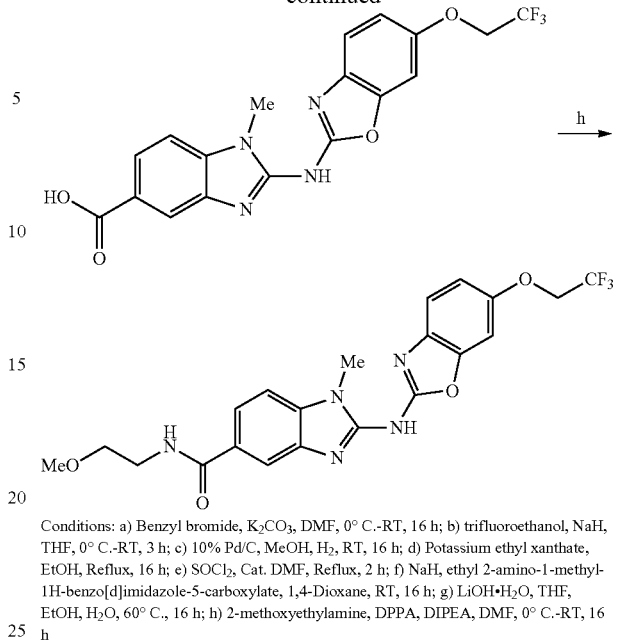

Conditions: a) Benzyl bromide, K₂CO₃, DMF, 0° C.-RT, 16 h; b) trifluoroethanol, NaH, THF, 0° C.-RT, 3 h; c) 10% Pd/C, MeOH, H₂, RT, 16 h; d) Potassium ethyl xanthate, EtOH, Reflux, 16 h; e) SOCl₂, Cat. DMF, Reflux, 2 h; f) NaH, ethyl 2-amino-1-methyl-1H-benzo[d]imidazole-5-carboxylate, 1,4-Dioxane, RT, 16 h; g) LiOH•H₂O, THF, EtOH, H₂O, 60° C., 16 h; h) 2-methoxyethylamine, DPPA, DIPEA, DMF, 0° C.-RT, 16 h Step-a: Synthesis of 2-(benzyloxy)-4-fluoro-1-nitrobenzene To a stirred solution of 5-fluoro-2-nitrophenol (8.0 g, 50.9 mmol) in DMFA (80 mL) at 0° C. was added potassium carbonate (14.0 g, 101.8 mmol) and benzyl bromide (5.4 mL, 45.8 mmol) and the reaction mixture was stirred at RT for 16 h. The reaction mixture was diluted with water (200 mL) and extracted with ethyl acetate (2×200 mL). The combined organic layer was washed with water (2×200 mL), brine (50 mL), dried over anhydrous sodium sulfate and concentrated under vacuum. The residue was purified by combiflash chromatography using 10% ethyl acetate in hexane as an eluent to afford the title compound (8.0 g, 64%); ¹H NMR (400 MHz, DMSO-d₆): δ 8.06-8.02 (m, 1H), 7.47-7.36 (m, 6H), 7.05-6.95 (m, 1H), 5.33 (s, 2H).

Step-b: Synthesis of 2-(benzyloxy)-1-nitro-4-(2,2,2-trifluoroethoxy)benzene

To a solution of trifluoroethanol (0.23 mL, 3.24 mmol) in THF (10 mL) at 0° C. was added sodium hydride (60% dispersion in mineral oil) (194 mg, 4.86 mmol) by portions and stirred for 1 h. Then a solution of 2-(benzyloxy)-4-fluoro-1-nitrobenzene (400 mg, 1.62 mmol) was added to the reaction mixture and stirred at RT for 2 h. The reaction mixture was concentrated and diluted with cold water (20 mL). Solid precipitated was filtered and dried under vacuum to afford the title compound (350 mg, 66%); ¹H NMR (400 MHz, DMSO-d₆): δ 8.01 (d, J=9.2 Hz, 1H), 7.48-7.33 (m, 5H), 7.11 (d, J=2.8 Hz, 1H), 6.82 (dd, J=2.4 Hz, J=8.8 Hz, 1H), 5.32 (s, 2H), 4.94 (q, J=8.8 Hz, 2H).

Step-c: Synthesis of 2-amino-5-(2,2,2-trifluoroethoxy)phenol

To a solution of 2-(benzyloxy)-1-nitro-4-(2,2,2-trifluoroethoxy)benzene (350 mg, 1.07 mmol) in methanol (10 mL) was added 10% Pd/C (50 mg) under nitrogen atmosphere. The reaction mixture was stirred under hydrogen gas balloon for 16 h. The reaction mixture was filtered through a bed of celite and concentrated under vacuum to afford the title compound (210 mg, 95%); $^1$H NMR (400 MHz, DMSO-d$_6$): δ 6.51 (d, J=8.8 Hz, 1H), 6.38 (d, J=2.4 Hz, 1H), 6.28 (dd, J=2.8 Hz, J=8.8 Hz, 1H), 4.48 (q, J=8.8 Hz, 2H); LC-MS: m/z 208.0 (M+1)$^+$.

Step-d: Synthesis of 6-(2,2,2-trifluoroethoxy)benzo[d]oxazole-2-thiol

The title compound was synthesized using the same procedure which was followed for Example 32 Step-c using 2-amino-5-(2,2,2-trifluoroethoxy)phenol as starting material (Yield: 79%); $^1$H NMR (400 MHz, DMSO-d$_6$): δ 13.8 (bs, 1H), 7.38 (d, J=2.4 Hz, 1H), 7.18 (d, J=8.8 Hz, 1H), 7.01 (dd, J=2.4 Hz, J=8.8 Hz, 1H), 4.79 (q, J=8.8 Hz, 2H); LC-MS: m/z 250.0 (M+1)$^+$.

Step-e: Synthesis of 2-chloro-6-(2,2,2-trifluoroethoxy)benzo[d]oxazole

The title compound was synthesized using the same procedure which was followed for Example 32 Step-d using 6-(2,2,2-trifluoroethoxy)benzo[d]oxazole-2-thiol as starting material and stirring for 2 h. (Yield: 87%); $^1$H NMR (400 MHz, DMSO-d$_6$): δ 7.69 (d, J=8.8 Hz, 1H), 7.60 (d, J=2.4 Hz, 1H), 6.15 (dd, J=2.4 Hz, J=8.8 Hz, 1H), 4.85 (q, J=8.8 Hz, 2H).

Step-f: Synthesis of ethyl 1-methyl-2-((6-(2,2,2-trifluoroethoxy)benzo[d]oxazol-2-yl)amino)-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 2-chloro-6-(2,2,2-trifluoroethoxy)benzo[d]oxazole starting materials (Yield: 21%); $^1$H NMR (400 MHz, DMSO-d$_6$): δ 12.3 (bs, 1H), 8.22 (d, J=1.6 Hz, 1H), 7.88 (dd, J=1.2 Hz, J=8.0 Hz, 1H), 7.51 (d, J=8.4 Hz, 1H), 7.39 (d, J=8.4 Hz, 1H), 7.29 (d, J=2.4 Hz, 1H), 6.94 (dd, J=2.4 Hz, J=8.4 Hz, 1H), 4.77 (q, J=8.8 Hz, 2H), 4.33 (q, J=7.2 Hz, 2H), 3.63 (s, 3H), 1.35 (t, J=7.2 Hz, 3H); LC-MS: m/z 435.35 (M+1)$^+$.

Step-g: Synthesis of 1-methyl-2-((6-(2,2,2-trifluoroethoxy)benzo[d]oxazol-2-yl)amino)-1H-benzo[d]imidazole-5-carboxylic acid The title compound was synthesized using the same procedure which was followed for compound 1h using ethyl 1-methyl-2-((6-(2,2,2-trifluoroethoxy)benzo[d]oxazol-2-yl)amino)-1H-benzo[d]imidazole-5-carboxylate as starting material (Yield: 62%); $^1$H NMR (400 MHz, DMSO-d$_6$): δ 12.5 (bs, 2H), 8.18 (d, J=1.2 Hz, 1H), 7.86 (dd, J=1.6 Hz, J=8.4 Hz, 1H), 7.48 (d, J=8.8 Hz, 1H), 7.40 (d, J=8.8 Hz, 1H), 7.29 (d, J=2.4 Hz, 1H), 6.93 (dd, J=2.4 Hz, J=8.8 Hz, 1H), 4.77 (q, J=9.2 Hz, 2H), 3.62 (s, 3H); LC-MS: m/z 407.0 (M+1)$^+$.

Step-h: Synthesis of N-(2-methoxyethyl)-1-methyl-2-((6-(2,2,2-trifluoroethoxy)benzo[d]oxazol-2-yl)amino)-1H-benzo[d]imidazole-5-carboxamide The title compound was synthesized using the same procedure which was followed for compound 1i using 1-methyl-2-((6-(2,2,2-trifluoroethoxy)benzo[d]oxazol-2-yl)amino)-1H-benzo[d]imidazole-5-carboxylic acid and 2-methoxyethylamine as starting materials (Yield: 70%); $^1$H NMR (400 MHz, DMSO-d$_6$): δ 12.2 (bs, 1H), 8.4 (t, J=5.6 Hz, 1H), 8.06 (s, 1H), 7.75 (d, J=8.0 Hz, 1H), 7.46 (d, J=8.0 Hz, 1H), 7.39 (d, J=8.0 Hz, 1H), 7.28 (d, J=1.6 Hz, 1H), 6.93 (dd, J=2.4 Hz, J=8.4 Hz, 1H), 4.77 (q, J=8.8 Hz, 2H), 3.62 (s, 3H), 3.48-3.43 (m, 4H), 3.28 (s, 3H); LC-MS: m/z 464.0 (M+1)$^+$.

Example 100. Synthesis of N-(2-hydroxyethyl)-1-methyl-2-((6-(2,2,2-trifluoroethoxy)benzo[d]oxazol-2-yl)amino)-1H-benzo[d]imidazole-5-carboxamide

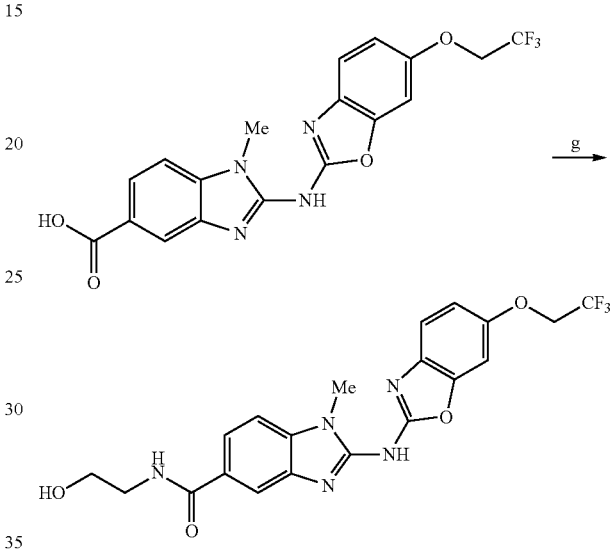

Conditions: a) 2-aminoethan-1-ol, HBTU, DIPEA, DMF, 0° C.-RT, 16 h

The title compound was synthesized using the same procedure which was followed for Example 6 Step-e using 1-methyl-2-((6-(2,2,2-trifluoroethoxy)benzo[d]oxazol-2-yl)amino)-1H-benzo[d]imidazole-5-carboxylic acid and 2-aminoethan-1-ol as starting materials (Yield: 63%); $^1$H NMR (400 MHz, DMSO-d$_6$): δ 12.5 (bs, 1H), 8.42 (t, J=5.2 Hz, 1H), 8.07 (s, 1H), 7.81 (d, J=8.4 Hz, 1H), 7.53 (d, J=8.4 Hz, 1H), 7.40 (d, J=8.8 Hz, 1H), 7.32 (d, J=2.4 Hz, 1H), 6.98 (dd, J=2.4 Hz, J=8.8 Hz, 1H), 4.80 (q, J=8.8 Hz, 2H), 3.66 (s, 3H), 3.54 (t, J=6.4 Hz, 2H), 3.36 (q, J=6.0 Hz, 2H); LC-MS: m/z 450.0 (M+1)$^+$.

Examples 101 and 102. Synthesis of 2-((6-(2-hydroxyethoxy)benzo[d]oxazol-2-yl)amino)-1-methyl-1H-benzo[d]imidazole-5-carboxylic acid and Synthesis of 2-((6-(2-hydroxyethoxy)benzo[d]oxazol-2-yl)amino)-N-(2-methoxyethyl)-1-methyl-1H-benzo[d]imidazole-5-carboxamide

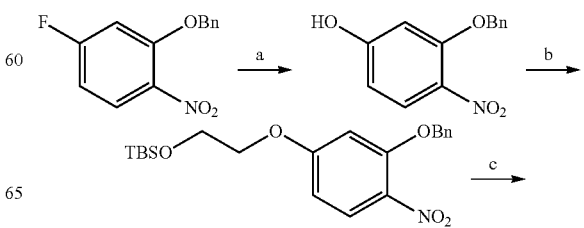

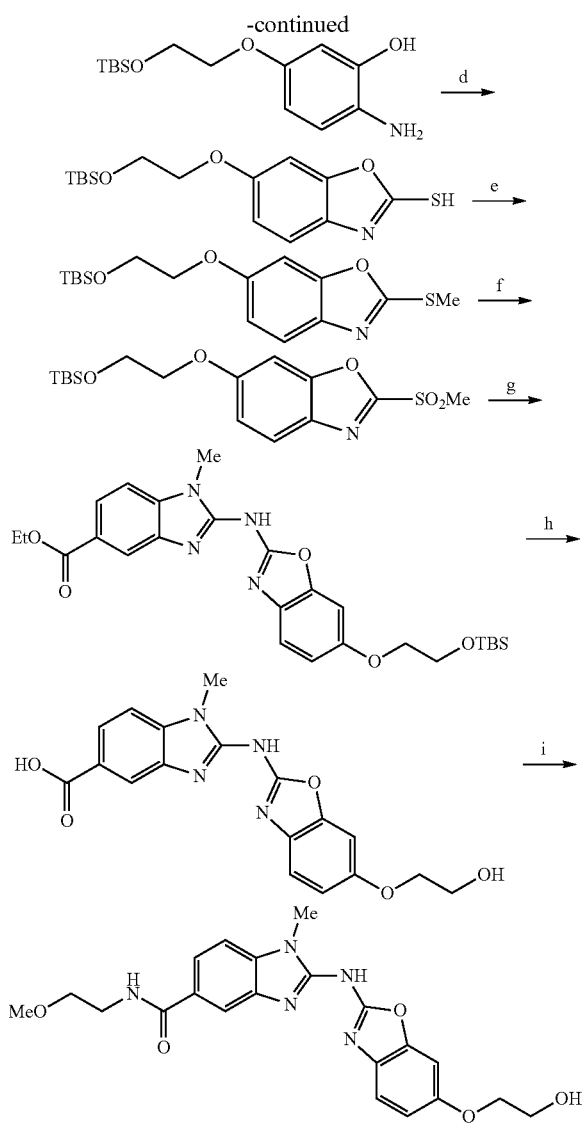

Conditions: a) KOH, water, 100° C., 30 h; b) (2-bromoethoxy)(tert-butyl)dimethylsilane, K₂CO₃, DMF, 130° C., 4 h; c) 10% Pd/C, MeOH, H₂, RT, 16 h; d) Potassium ethyl xanthate, EtOH, Reflux, 16 h; e) K₂CO₃, MeI, ACN, RT, 16 h; f) m-CPBA, DCM, 0° C.-RT, 4 h; g) NaH, ethyl 2-amino-1-methyl-1H-benzo[d]imidazole-5-carboxylate, 1,4-Dioxane, RT, 16 h; h) LiOH·H₂O, THF, EtOH, H₂O, 60° C., 16 h; h) 2-methoxyethylamine, DPPA, DIPEA, DMF, 0° C.-RT, 16 h

Step-a: Synthesis of 3-(benzyloxy)-4-nitrophenol

To a stirred suspension of 2-(benzyloxy)-4-fluoro-1-nitrobenzene (4.0 g, 16.2 mmol) in water (70 mL) at RT was added potassium hydroxide (4.53 g, 80.9 mmol) and the reaction mixture was stirred at 100° C. for 30 h. The reaction mixture was cooled to RT, diluted with water (50 mL) and acidified with 1 N HCl and extracted with ethyl acetate (3×100 mL). The combined organic layer was washed with water (50 mL), brine (50 mL), dried over anhydrous sodium sulfate and concentrated under vacuum to obtain the residue which was purified by combiflash chromatography using 20% ethyl acetate in hexane as an eluent to afford the title compound (1.5 g, 38%); $^1$H NMR (400 MHz, DMSO-$d_6$): δ 10.88 (s, 1H), 7.90 (d, J=8.8 Hz, 1H), 7.49-7.47 (m, 2H), 7.43-7.40 (m, 2H), 7.35 (d, J=6.8 Hz, 1H), 6.69 (d, J=2.4 Hz, 1H), 6.49 (dd, J=2.4 Hz, J=9.2 Hz, 1H), 5.25 (s, 2H).

Step-b: Synthesis of (2-(3-(benzyloxy)-4-nitrophenoxy)ethoxy)(tert-butyl)dimethylsilane To a stirred solution of 3-(benzyloxy)-4-nitrophenol (1.5 g, 6.1 mmol) in DMFA (15 mL) at RT was added potassium carbonate (2.1 g, 15.3 mmol) and (2-bromoethoxy)(tert-butyl)dimethylsilane (1.75 g, 7.3 mmol) in a seal tube and heated at 130° C. for 4 h. The reaction mixture was cooled to RT, diluted with water (50 mL) and extracted with ethyl acetate (2×50 mL). The combined organic layer was washed with water (2×500 mL), brine (30 mL), dried over anhydrous sodium sulfate and concentrated under vacuum to obtain the residue which was purified by combiflash chromatography using 5% ethyl acetate in hexane as an eluent to afford the title compound (8.0 g, 64%); $^1$H NMR (400 MHz, DMSO-$d_6$): δ 7.96 (d, J=8.8 Hz, 1H), 7.49-7.47 (m, 2H), 7.43-7.39 (m, 2H), 7.36-7.34 (m, 1H), 6.89 (d, J=2.4 Hz, 1H), 6.67 (dd, J=2.4 Hz, J=9.2 Hz, 1H), 5.32 (s, 2H), 4.17 (t, J=4.4 Hz, 2H), 3.92 (t, J=4.8 Hz, 2H), 0.86 (s, 9H), 0.02 (s, 6H).

Step-c: Synthesis of 2-amino-5-(2-((tert-butyldimethylsilyl)oxy)ethoxy)phenol The title compound was synthesized using the same procedure which was followed for compound 1e using (2-(3-(benzyloxy)-4-nitrophenoxy)ethoxy)(tert-butyl)dimethylsilane as starting material (Yield: 87%); $^1$H NMR (400 MHz, DMSO-$d_6$): δ 6.47 (d, J=8.0 Hz, 1H), 6.30 (d, J=2.8 Hz, 1H), 6.15 (dd, J=2.4 Hz, J=8.4 Hz, 1H), 3.84-3.80 (m, 4H), 0.87 (s, 9H), 0.02 (s, 6H); LC-MS: m/z 284.1 (M+1)⁺.

Step-d: Synthesis of 6-(2-((tert-butyldimethylsilyl)oxy)ethoxy)benzo[d]oxazole-2-thiol The title compound was synthesized using the same procedure which was followed for Example 32 Step-c using 2-amino-5-(2-((tert-butyldimethylsilyl)oxy)ethoxy)phenol as starting material (Yield: 77%). The crude compound was used in the next step without any analytical data.

Step-e: Synthesis of 6-(2-((tert-butyldimethylsilyl)oxy)ethoxy)-2-(methylthio)benzo[d]oxazole The title compound was synthesized using the same procedure which was followed for compound 1b using 6-(2-((tert-butyldimethylsilyl)oxy)ethoxy)benzo[d]oxazole-2-thiol as starting material and stirring for 16 h. (Yield: 80%); $^1$H NMR (400 MHz, DMSO-$d_6$): δ 7.50 (d, J=8.8 Hz, 1H), 7.28 (d, J=2.4 Hz, 1H), 6.91 (dd, J=2.8 Hz, J=8.8 Hz, 1H), 4.06 (t, J=4.4 Hz, 2H), 3.92 (t, J=5.2 Hz, 2H), 2.27 (s, 3H), 0.86 (s, 9H), 0.2 (s, 6H); LC-MS: m/z 340.0 (M+1)⁺.

Step-f: Synthesis of 6-(2-((tert-butyldimethylsilyl)oxy)ethoxy)-2-(methylsulfonyl)-benzo[d]oxazole The title compound was synthesized using the same procedure which was followed for compound 1c using 6-(2-((tert-butyldimethylsilyl)oxy)ethoxy)-2-(methylthio)benzo[d]oxazole as starting material and stirring for 4 h (Yield: 100%); $^1$H NMR (400 MHz, DMSO-$d_6$): δ 7.90-7.89 (m, 1H), 7.55 (d, J=8.0 Hz, 1H), 6.99-6.97 (m, 1H), 4.10 (t, J=4.8 Hz, 2H), 3.95 (t, J=5.2 Hz, 2H), 3.62 (s, 3H), 0.85 (s, 9H), 0.2 (s, 6H).

Step-g: Synthesis of ethyl 2-((6-(2-((tert-butyldimethylsilyl)oxy)ethoxy)benzo[d]oxazol-2-yl)amino)-1-methyl-1H-benzo[d]imidazole-5-carboxylate The title compound was synthesized using the same procedure which was followed for compound 1g using ethyl 2-amino-1-methyl-1H-benzo[d]imidazole-5-carboxylate and 6-(2-((tert-butyldimethylsilyl)oxy)ethoxy)-2-(methylsulfonyl)benzo[d]oxazole as starting materials (Yield: 17%); $^1$H NMR (400 MHz, DMSO-$d_6$): δ 12.2 (bs, 1H), 8.21 (d, J=1.6 Hz, 1H), 7.86 (dd, J=1.6 Hz, J=8.4 Hz, 1H), 7.49 (d, J=8.0 Hz, 1H), 7.35 (d, J=8.4 Hz, 1H), 7.12 (d, J=2.4 Hz, 1H), 6.81 (dd, J=1.6 Hz, J=8.0 Hz, 1H), 4.32 (q, J=7.6 Hz, 2H), 4.06-4.04 (m, 2H), 3.94-3.92 (m, 2H), 3.62 (s, 3H), 1.35 (t, J=6.8 Hz, 3H), 0.88 (s, 9H), 0.2 (s, 6H); LC-MS: m/z 511.1 (M+1)$^+$.

Step-h: Synthesis of 2-((6-(2-hydroxyethoxy)benzo[d]oxazol-2-yl)amino)-1-methyl-1H-benzo[d]imidazole-5-carboxylic acid To a stirred solution of ethyl 2-((6-(2-((tert-butyldimethylsilyl)oxy)ethoxy)benzo[d]oxazol-2-yl)amino)-1-methyl-1H-benzo[d]imidazole-5-carboxylate (80 mg, 0.15 mmol) in a mixture of solvent of THF (2 mL), ethanol (2 mL) and water (1 mL) was added lithium hydroxide monohydrate (32 mg, 0.78 mmol). The reaction mixture was heated at 60° C. for 16 h with stirring. The reaction mixture was cooled to RT and concentrated under reduced pressure. The residue was dissolved in water (20 mL) and acidified with 1 N HCl. The solid obtained was filtered and dried under vacuum to afford the title compound (50 mg, 87%); $^1$H NMR (400 MHz, DMSO-$d_6$): δ 12.8 (bs, 1H), 12.3 (bs, 1H), 8.16 (d, J=1.6 Hz, 1H), 7.85 (dd, J=1.6 Hz, J=8.4 Hz, 1H), 7.46 (d, J=8.4 Hz, 1H), 7.36 (d, J=8.4 Hz, 1H), 7.12 (d, J=2.4 Hz, 1H), 6.82 (dd, J=2.4 Hz, J=8.4 Hz, 1H), 4.85 (bs, 1H), 4.01 (t, J=4.8 Hz, 2H), 3.75-3.73 (m, 2H), 3.66 (s, 3H); LC-MS: m/z 369.0 (M+1)$^+$.

Step-i: Synthesis of 2-((6-(2-hydroxyethoxy)benzo[d]oxazol-2-yl)amino)-N-(2-methoxyethyl)-1-methyl-1H-benzo[d]imidazole-5-carboxamide The title compound was synthesized using the same procedure which was followed for compound 1i using 2-((6-(2-hydroxyethoxy)benzo[d]oxazol-2-yl)amino)-1-methyl-1H-benzo[d]imidazole-5-carboxylic acid and 2-methoxyethylamine as starting materials. The crude product was purified by combiflash chromatography using 4% methanol in DCM as an eluent (Yield: 17%); $^1$H NMR (400 MHz, DMSO-$d_6$): δ 12.2 (bs, 1H), 8.43 (t, J=5.2 Hz, 1H), 8.05 (d, J=1.2 Hz, 1H), 7.75 (dd, J=1.6 Hz, J=8.4 Hz, 1H), 7.45 (d, J=8.8 Hz, 1H), 7.35 (d, J=8.4 Hz, 1H), 7.12 (d, J=2.4 Hz, 1H), 6.82 (dd, J=2.8 Hz, J=8.8 Hz, 1H), 4.11 (t, J=4.4 Hz, 2H), 3.66 (t, J=4.4 Hz, 2H), 3.61 (s, 3H), 3.49-3.41 (m, 4H), 3.28 (bs, 1H), 3.24 (s, 3H); LC-MS: m/z 426.4 (M+1)$^+$.

Example 103. Synthesis of 2-((6-(2-hydroxyethoxy)benzo[d]oxazol-2-yl)amino)-N-(2-hydroxyethyl)-1-methyl-1H-benzo[d]imidazole-5-carboxamide

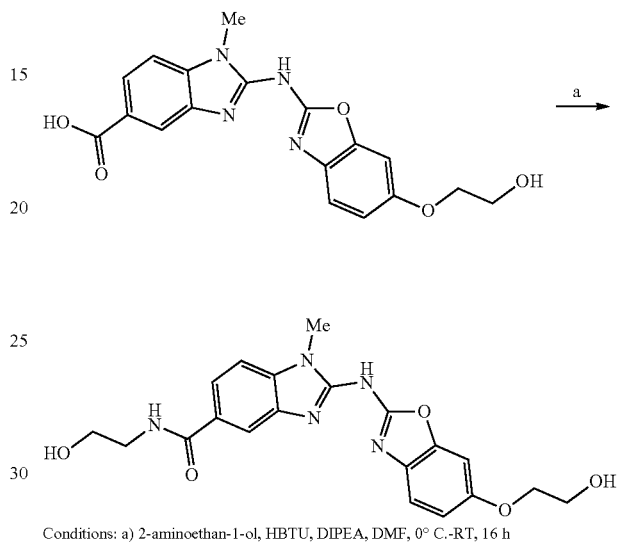

Conditions: a) 2-aminoethan-1-ol, HBTU, DIPEA, DMF, 0° C.-RT, 16 h

The title compound was synthesized using the same procedure which was followed for Example 6 Step-e using 2-((6-(2-hydroxyethoxy)benzo[d]oxazol-2-yl)amino)-1-methyl-1H-benzo[d]imidazole-5-carboxylic acid and 2-aminoethan-1-ol as starting materials. The crude product was purified by combiflash chromatography using 6% methanol in DCM as an eluent to afford the title compound (Yield: 18%); $^1$H NMR (400 MHz, DMSO-$d_6$): δ 12.05 (bs, 1H), 8.35 (t, J=5.2 Hz, 1H), 8.05 (s, 1H), 7.75 (d, J=8.0 Hz, 1H), 7.45 (d, J=8.4 Hz, 1H), 7.35 (d, J=8.4 Hz, 1H), 7.11 (d, J=2.4 Hz, 1H), 6.82 (dd, J=2.8 Hz, J=8.8 Hz, 1H), 4.85 (bs, 1H), 4.72 (t, J=4.8 Hz, 1H), 4.01 (t, J=4.8 Hz, 2H), 3.72 (q, J=4.4 Hz, 2H), 3.61 (s, 3H), 3.53 (q, J=5.6 Hz, 2H), 3.37-3.33 (m, 2H); LC-MS: m/z 412.0 (M+1)$^+$.

Example 104. Synthesis of 2-((6-(2-hydroxyethoxy)benzo[d]oxazol-2-yl)amino)-N-(2-(2-hydroxyethoxy)ethyl)-1-methyl-1H-benzo[d]imidazole-5-carboxamide

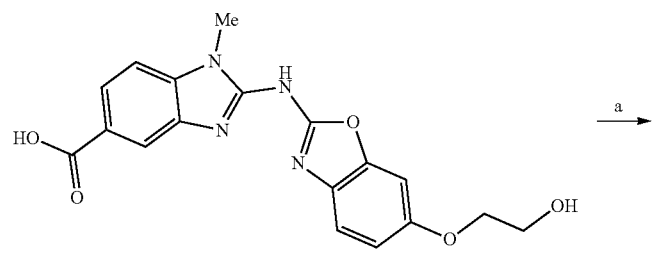

-continued

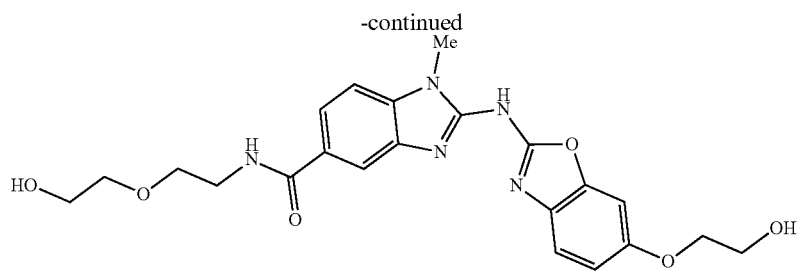

Conditions: a) 2-(2-aminoethoxy)ethan-1-ol, HBTU, DIPEA, DMF, 0° C.-RT, 16 h

The title compound was synthesized using the same procedure which was followed for Example 6 Step-e using 2-((6-(2-hydroxyethoxy)benzo[d]oxazol-2-yl)amino)-1-methyl-1H-benzo[d]imidazole-5-carboxylic acid and 2-(2-aminoethoxy)ethan-1-ol as starting materials. The crude product was purified by combiflash chromatography using 10% methanol in DCM as an eluent to afford the title compound (Yield: 18%); $^1$H NMR (400 MHz, DMSO-$d_6$): δ 12.05 (bs, 1H), 8.41 (bs, 1H), 8.04 (s, 1H), 7.74 (d, J=8.4 Hz, 1H), 7.45 (d, J=8.4 Hz, 1H), 7.35 (d, J=8.8 Hz, 1H), 7.11 (s, 1H), 6.82 (d, J=6.8 Hz, 1H), 4.61 (bs, 2H), 4.01 (t, J=4.4 Hz, 2H), 3.72 (t, J=4.8 Hz, 2H), 3.66 (s, 3H), 3.57-3.43 (m, 8H); LC-MS: m/z 456.3 (M+1)$^+$.

Example 105. Synthesis of N-(2-aminoethyl)-2-((6-(2-hydroxyethoxy)benzo[d]oxazol-2-yl)amino)-1-methyl-1H-benzo[d]imidazole-5-carboxamide hydrochloride

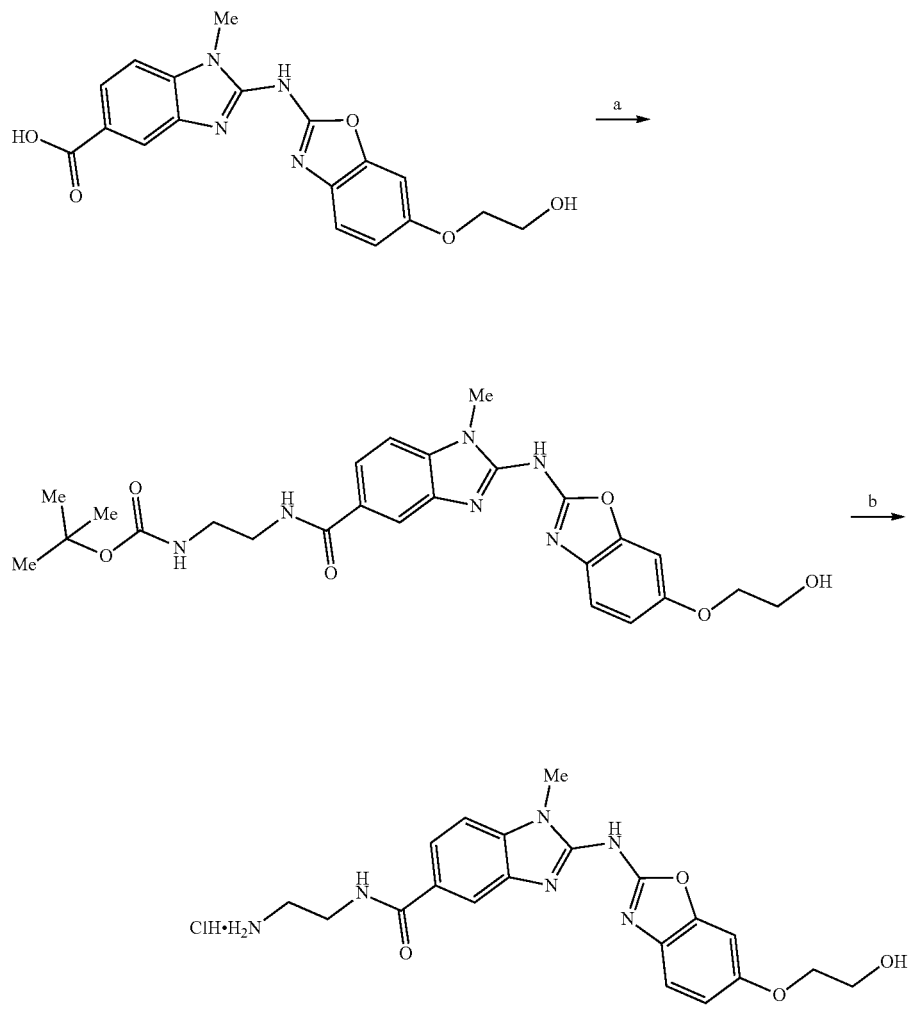

Conditions: a) tert-butyl (2-aminoethyl)carbamate, HBTU, DIPEA, DMF, 0° C.-RT, 16 h; b) HCl, 1,4-Dioxane, 0° C.-RT, 3 h

Step-a: Synthesis of tert-butyl (2-(2-((6-(2-hydroxy-ethoxy)benzo[d]oxazol-2-yl)amino)-1-methyl-1H-benzo[d]imidazole-5-carboxamido)ethyl)carbamate To a stirred solution of 2-((6-(2-hydroxyethoxy)benzo[d]oxazol-2-yl)amino)-1-methyl-1H-benzo[d]imidazole-5-carboxylic acid (100 mg, 0.27 mmol) in DMFA (2 mL) at 0° C. was added N-ethyldiisopropyl amine (0.09 mL, 0.54 mmol) and HBTU (102 mg, 0.27 mmol). The reaction mixture was stirred for 30 min, followed by the addition of tert-butyl (2-aminoethyl)carbamate (48 mg, 0.30 mmol) and stirring was continued at RT for 16 h. Once the reaction was complete, the reaction mixture was diluted with water (15 mL) and stirred for 15 min. The obtained solid was filtered, dried under vacuum to get the crude product which was purified by combiflash chromatography using 3% methanol in DCM as an eluent to afford the title compound (70 mg, 50%); $^1$H NMR (400 MHz, DMSO-$d_6$): δ 12.20 (bs, 1H), 8.39 (bs, 1H), 8.05 (s, 1H), 7.73 (d, J=8.4 Hz, 1H), 7.45 (d, J=8.4 Hz, 1H), 7.35 (d, J=8.0 Hz, 1H), 7.11 (d, J=2.0 Hz, 1H), 6.91 (bs, 1H), 6.82 (dd, J=2.0 Hz, J=8.4 Hz, 1H), 4.85 (bs, 1H), 4.01 (t, J=4.8 Hz, 2H), 3.72 (bs, 2H), 3.61 (s, 3H), 3.30 (2H merged with DMSO moisture peak), 3.12 (d, J=6.0 Hz, 2H), 1.38 (s, 9H); LC-MS: m/z 511.3 (M+1)$^+$.

Step-b: Synthesis of N-(2-aminoethyl)-2-((6-(2-hydroxyethoxy)benzo[d]oxazol-2-yl)amino)-1-methyl-1H-benzo[d]imidazole-5-carboxamide hydrochloride To a stirred solution of tert-butyl (2-(2-((6-(2-hydroxy-ethoxy)benzo[d]oxazol-2-yl)amino)-1-methyl-1H-benzo[d]imidazole-5-carboxamido)ethyl)carbamate (70 mg, 0.14 mmol) in 1,4-dioxane (3 mL) at 0° C. was added 4 M HCl in 1,4-dioxane (1 mL) and stirred at RT 3 h. The reaction mixture was concentrated under reduced pressure and the residue was triturated with diethyl ether and solvent was decanted. The obtained solid was dried under vacuum to afford the title compound (35 mg, 57%); $^1$H NMR (400 MHz, DMSO-$d_6$): δ 12.5 (bs, 1H), 8.78 (s, 1H), 8.12-8.07 (m, 4H), 7.90 (d, J=8.0 Hz, 1H), 7.56 (d, J=8.4 Hz, 1H), 7.36 (d, J=8.4 Hz, 1H), 7.18 (s, 1H), 6.88 (d, J=8.0 Hz, 1H), 4.02 (bs, 2H), 3.73 (bs, 2H), 3.66 (s, 3H), 3.56 (q, J=5.2 Hz, 2H), 3.02 (q, J=5.6 Hz, 2H); LC-MS: m/z 411.2 (M+1)$^+$.

Example 106. Synthesis of N-(2-((4,5-dihydro-1H-imidazol-2-yl)amino)ethyl)-2-((6-(2-hydroxyethoxy)benzo[d]oxazol-2-yl)amino)-1-methyl-1H-benzo[d]imidazole-5-carboxamide

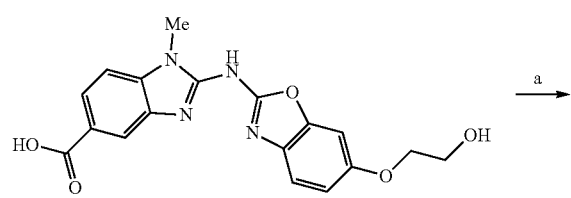

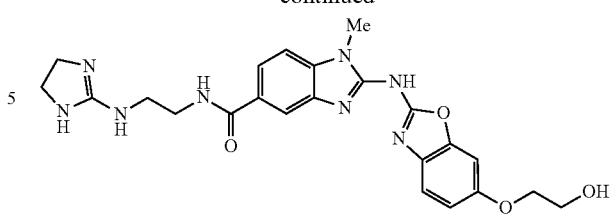

Conditions: a) N$^1$-4,5-dihydro-1H-imidazol-2-yl)ethane-1,2-diamine, HBTU, DIPEA, DMF, 0° C.-RT, 16 h The title compound was synthesized using the same procedure which was followed for Example 6 Step-e using 2-((6-(2-hydroxyethoxy)benzo[d]oxazol-2-yl)amino)-1-methyl-1H-benzo[d]imidazole-5-carboxylic acid and N1-(4,5-dihydro-1H-imidazol-2-yl)ethane-1,2-diamine as starting materials (Yield: 58%); $^1$H NMR (400 MHz, DMSO-$d_6$): δ 8.73 (bs, 1H), 8.49 (s, 1H), 8.05 (s, 1H), 7.75 (d, J=8.4 Hz, 1H), 7.41 (d, J=8.0 Hz, 1H), 7.31 (d, J=8.4 Hz, 1H), 7.08 (d, J=2.0 Hz, 1H), 6.79 (dd, J=1.6 Hz, J=8.0 Hz, 1H), 4.86 (bs, 1H), 4.00 (t, J=4.8 Hz, 2H), 3.72 (bs, 2H), 3.60-3.55 (m, 7H), 3.43 (bs, 2H), 3.30 (2H merged with DMSO moisture peak); LC-MS: m/z 479.2 (M+1)$^+$.

Examples 107 and 108. Synthesis of 2-((5-fluoro-6-(trifluoromethyl)benzo[d]oxazol-2-yl)amino)-1-methyl-1H-benzo[d]imidazole-5-carboxylic acid and Synthesis of 2-((5-fluoro-6-(trifluoromethyl)benzo[d]oxazol-2-yl)amino)-N-(2-hydroxyethyl)-1-methyl-1H-benzo[d]imidazole-5-carboxamide

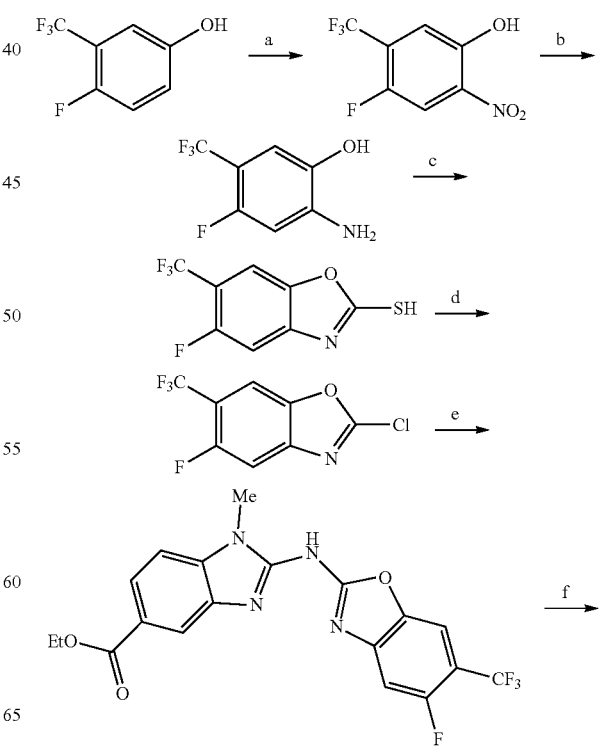

-continued

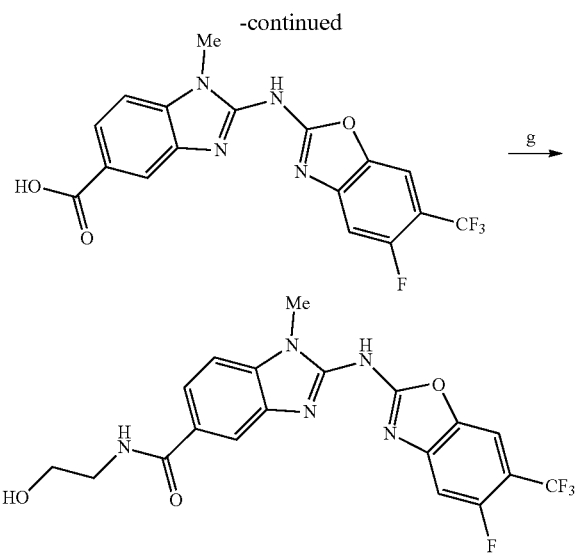

Conditions: a) HNO₃ (65-70%), AcOH, 0° C.-RT, 2 h; b) 10% Pd/C, MeOH, H₂, RT, 16 h; c) Potassium ethyl xanthate, EtOH, Reflux, 16 h; d) SOCl₂, Cat. DMF, Reflux, 2 h; e) NaH, ethyl 2-amino-1-methyl-1H-benzo[d]imidazole-5-carboxylate, 1,4-Dioxane, RT, 16 h; f) LiOH·H₂O, THF, EtOH, H₂O, 60° C., 16 h; g) 2-aminoethan-1-ol, HBTU, DIPEA, DMF, 0° C.-RT, 16 h

Step-a: Synthesis of 4-fluoro-2-nitro-5-(trifluoromethyl)phenol

To a solution of 4-fluoro-3-(trifluoromethyl)phenol (1 g, 5.6 mmol) in acetic acid (20 mL) was added 60% aqueous nitric acid (3 mL) in acetic acid (5 mL) dropwise at 10-15° C. The reaction mixture was stirred at room temperature for 2 h. Then the mixture was poured into ice water (50 mL) and extracted with EtOAc (3×50 mL). The combined organic layers were washed with water (2×50 mL), brine solution (30 mL), dried over anhydrous sodium sulfate and concentrated under vacuum to obtain the crude product which was purified by combiflash chromatography using 5% EtOAc in hexanes as eluent to afford the title compound (700 mg, 22%); ¹H NMR (400 MHz, DMSO-d₆): δ 11.71 (bs, 1H), 8.14 (d, J=10.4 Hz, 1H), 7.44 (d, J=5.6 Hz, 1H); LC-MS: m/z 224.0 (M−1)⁻.

Step-b: Synthesis of 2-amino-4-fluoro-5-(trifluoromethyl)phenol

The title compound was synthesized using the same procedure which was followed for compound 1e using 4-fluoro-2-nitro-5-(trifluoromethyl)phenol as starting material (Yield: 82%); ¹H NMR (400 MHz, DMSO-d₆): δ 9.54 (s, 1H), 6.78 (d, J=7.2 Hz, 1H), 6.48 (d, J=13.2 Hz, 1H), 5.5 (bs, 2H).

Step-c: Synthesis of 5-fluoro-6-(trifluoromethyl)benzo[d]oxazole-2-thiol

The title compound was synthesized using the same procedure which was followed for Example 32 Step-c using 2-amino-4-fluoro-5-(trifluoromethyl)phenol as starting material (Yield: 82%); ¹H NMR (400 MHz, DMSO-d₆): δ 14.4 (bs, 1H), 8.10 (d, J=5.6 Hz, 1H), 7.43 (d, J=9.6 Hz, 1H); LC-MS: m/z 236.0 (M−1)⁻.

Step-d: Synthesis of 2-chloro-5-fluoro-6-(trifluoromethyl)benzo[d]oxazole

The title compound was synthesized using the same procedure which was followed for Example 32 Step-d using 5-fluoro-6-(trifluoromethyl)benzo[d]oxazole-2-thiol as starting material and stirring for 2 h (Yield: 99%); ¹H NMR (400 MHz, DMSO-d₆): δ 7.74 (d, J=6.0 Hz, 1H), 7.30 (d, J=10.0 Hz, 1H).

Step-e: Synthesis of ethyl 2-((5-fluoro-6-(trifluoromethyl)benzo[d]oxazol-2-yl)amino)-1-methyl-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 2-chloro-5-fluoro-6-(trifluoromethyl)benzo[d]oxazole as starting materials (Yield: 52%); ¹H NMR (400 MHz, DMSO-d₆): δ 12.43 (bs, 1H), 8.22 (d, J=1.6 Hz, 1H), 7.88 (dd, J=1.6 Hz, J=8.4 Hz, 1H), 7.83 (d, J=6.0 Hz, 1H), 7.75 (d, J=8.4 Hz, 1H), 7.41 (d, J=11.2 Hz, 1H), 4.33 (q, J=7.2 Hz, 2H), 3.66 (s, 3H), 1.35 (t, J=7.2 Hz, 3H); LC-MS: m/z 423.0 (M+1)⁺.

Step-f: Synthesis of 2-((5-fluoro-6-(trifluoromethyl)benzo[d]oxazol-2-yl)amino)-1-methyl-1H-benzo[d]imidazole-5-carboxylic acid The title compound was synthesized using the same procedure which was followed for compound 1h using ethyl 2-((5-fluoro-6-(trifluoromethyl)benzo[d]oxazol-2-yl)amino)-1-methyl-1H-benzo[d]imidazole-5-carboxylate as starting material (Yield: 86%); ¹H NMR (400 MHz, DMSO-d₆): δ 12.4 (bs, 2H), 8.20 (s, 1H), 7.89 (d, J=8.4 Hz, 1H), 7.84 (d, J=6.4 Hz, 1H), 7.55 (d, J=8.8 Hz, 1H), 7.44 (d, J=11.2 Hz, 1H), 3.67 (s, 3H); LC-MS: m/z 395.1 (M+1)⁺.

Step-g: Synthesis of 2-((5-fluoro-6-(trifluoromethyl)benzo[d]oxazol-2-yl)amino)-N-(2-hydroxyethyl)-1-methyl-1H-benzo[d]imidazole-5-carboxamide The title compound was synthesized using the same procedure which was followed for Example 6 Step-e using 2-((5-fluoro-6-(trifluoromethyl)benzo[d]oxazol-2-yl)amino)-1-methyl-1H-benzo[d]imidazole-5-carboxylic acid and 2-aminoethan-1-ol as starting materials (Yield: 72%); ¹H NMR (400 MHz, DMSO-d₆): δ 12.35 (bs, 1H), 8.40 (bs, 1H), 8.09 (s, 1H), 7.84-7.79 (m, 2H), 7.54 (d, J=8.4 Hz, 1H), 7.44 (d, J=11.6 Hz, 1H), 4.50 (bs, 1H), 3.67 (s, 3H), 3.54 (t, J=6.4 Hz, 2H), 3.38-3.33 (m, 2H); LC-MS: m/z 438.0 (M+1)⁺.

Example 109. Synthesis of N-(2-methoxyethyl)-1-methyl-2-(oxazolo[5,4-b]pyridin-2-ylamino)-1H-benzo[d]imidazole-5-carboxamide

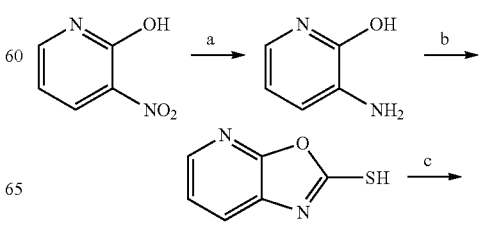

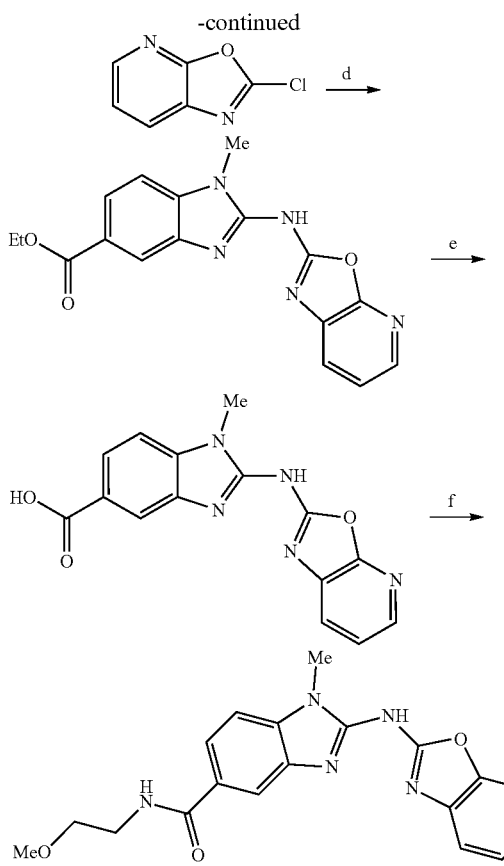

Conditions: a) 10% Pd/C, MeOH, H₂, RT, 16 h; b) Thiophosgene, THF, RT, 16 h; c) SOCl₂, Cat. DMF, Reflux, 2 h; d) NaH, ethyl 2-amino-1-methyl-1H-benzo[d]imidazole-5-carboxylate, 1,4-Dioxane, RT, 16 h; e) LiOH·H₂O, THF, EtOH H₂O, 60° C., 16 h; f) 2-methoxyethan-1-amine, DPPA, DIPEA, DMF, 0° C.-RT, 16 h Step-a: Synthesis of 3-aminopyridin-2-ol The title compound was synthesized using the same procedure which was followed for compound 1e using 3-nitropyridin-2-ol as starting material (Yield: 85%); $^1$H NMR (400 MHz, DMSO-d$_6$): δ 11.3 (bs, 1H), 6.59 (dd, J=2.0 Hz, J=6.8 Hz, 1H), 6.43 (dd, J=2.4 Hz, J=6.8 Hz, 1H), 5.98 (t, J=6.0 Hz, 1H), 4.97 (bs, 2H); LC-MS: m/z 111.25 (M+1)$^+$.

Step-b: Synthesis of oxazolo[5,4-b]pyridine-2-thiol

To a solution of 3-aminopyridin-2-ol (500 mg, 4.5 mmol) in THF (15 mL) at RT was added thiophosgene (0.41 mL, 5.4 mmol) slowly over a period of 15 min and stirred at RT for 16 h. The reaction mixture was quenched with saturated aqueous ammonium chloride solution (9 mL) and concentrated. Aqueous layer was basified with 10 N sodium hydroxide solution (5 mL) and extracted with ethyl acetate (2×30 mL), aqueous layer was acidified with 1 N HCl and extracted with ethyl acetate (2×100 mL). The organic layer was dried over anhydrous sodium sulfate and concentrated under vacuum to get the residue which was purified by combiflash chromatography using 2% methanol in DCM as an eluent to afford the title compound (200 mg, 29%); LC-MS: m/z 153.15 (M+1)$^+$.

Step-c: Synthesis of 2-chlorooxazolo[5,4-b]pyridine

To a solution of oxazolo[5,4-b]pyridine-2-thiol (200 mg, 1.31 mmol) in thionyl chloride (5 mL) at RT was added N,N-dimethylformamide (1 drop) and the reaction mixture was refluxed for 2 h. The reaction mixture was concentrated under reduced pressure and the crude compound was used in the next step without any further purification (220 mg); $^1$H NMR (400 MHz, DMSO-d$_6$): δ 8.40 (dd, J=1.6 Hz, J=4.8 Hz, 1H), 8.26 (dd, J=1.2 Hz, J=7.6 Hz, 1H), 7.56-7.53 (m, 1H); LC-MS: m/z 155.1 (M+1)$^+$.

Step-d: Synthesis of ethyl 1-methyl-2-(oxazolo[5,4-b]pyridin-2-ylamino)-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 2-chlorooxazolo[5,4-b]pyridine as starting materials (Yield: 20%); $^1$H NMR (400 MHz, DMSO-d$_6$): δ 8.24 (s, 1H), 8.02 (d, J=5.2 Hz, 1H), 7.89 (dd, J=1.6 Hz, J=8.8 Hz, 1H), 7.79 (d, J=7.2 Hz, 1H), 7.56 (d, J=8.4 Hz, 1H), 7.29-7.26 (m, 1H), 4.33 (q, J=7.2 Hz, 2H), 3.67 (s, 3H), 1.35 (t, J=6.8 Hz, 3H); LC-MS: m/z 338.15 (M+1)$^+$.

Step-e: Synthesis of 1-methyl-2-(oxazolo[5,4-b]pyridin-2-ylamino)-1H-benzo[d]imidazole-5-carboxylic acid The title compound was synthesized using the same procedure which was followed for compound 1h using ethyl 1-methyl-2-(oxazolo[5,4-b]pyridin-2-ylamino)-1H-benzo[d]imidazole-5-carboxylate as starting material (Yield: 54%); $^1$H NMR (400 MHz, DMSO-d$_6$): δ 12.8 (bs, 1H), 12.4 (bs, 1H), 8.20 (s, 1H), 8.01 (d, J=5.2 Hz, 1H), 7.89 (d, J=8.0 Hz, 1H), 7.79 (d, J=7.2 Hz, 1H), 7.54 (d, J=8.0 Hz, 1H), 7.28-7.25 (m, 1H), 3.67 (s, 3H); LC-MS: m/z 310.1 (M+1)$^+$.

Step-f: Synthesis of N-(2-methoxyethyl)-1-methyl-2-(oxazolo[5,4-b]pyridin-2-ylamino)-1H-benzo[d]imidazole-5-carboxamide The title compound was synthesized using the same procedure which was followed for compound 1i using 1-methyl-2-(oxazolo[5,4-b]pyridin-2-ylamino)-1H-benzo[d]imidazole-5-carboxylic acid and 2-methoxyethylamine as starting materials (Yield: 38%); $^1$H NMR (400 MHz, DMSO-d$_6$): δ 12.38 (bs, 1H), 8.47 (s, 1H), 8.09 (s, 1H), 8.0 (d, J=3.6 Hz, 1H), 7.79-7.77 (m, 2H), 7.52 (d, J=8.4 Hz, 1H), 7.27-7.24 (m, 1H), 3.66 (s, 3H), 3.48-3.44 (m, 4H), 3.28 (s, 3H); LC-MS: m/z 367.2 (M+1)$^+$.

Example 110. Synthesis of N-(2-hydroxyethyl)-1-methyl-2-(oxazolo[5,4-b]pyridin-2-ylamino)-1H-benzo[d]imidazole-5-carboxamide

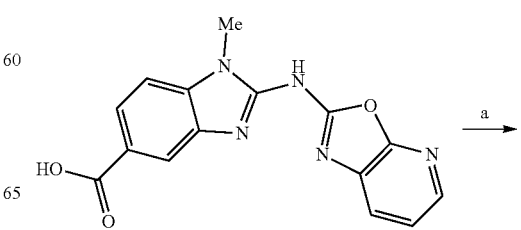

147

-continued

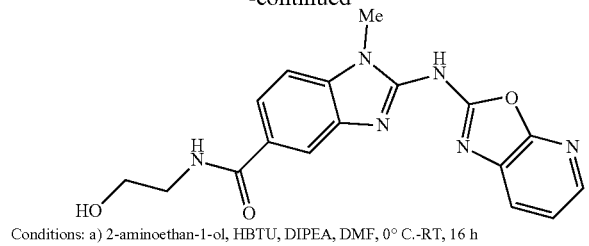

Conditions: a) 2-aminoethan-1-ol, HBTU, DIPEA, DMF, 0° C.-RT, 16 h

The title compound was synthesized using the same procedure which was followed for Example 6 Step-e using 1-methyl-2-(oxazolo[5,4-b]pyridin-2-ylamino)-1H-benzo[d]imidazole-5-carboxylic acid and 2-aminoethan-1-ol as starting materials (Yield: 51%); $^1$H NMR (400 MHz, DMSO-$d_6$): δ 12.3 (bs, 1H), 8.38 (bs, 1H), 8.09 (s, 1H), 8.01 (d, J=4.4 Hz, 1H), 7.80-7.76 (m, 2H), 7.52 (d, J=8.4 Hz, 1H), 7.25 (t, J=6.8 Hz, 1H), 4.72 (bs, 1H), 3.66 (s, 3H), 3.53 (bs, 2H), 3.35 (q, J=6.0 Hz, 2H); LC-MS: m/z 353.0 (M+1)$^+$.

Examples 111 and 112. Synthesis of 1-methyl-2-(oxazolo[4,5-b]pyridin-2-ylamino)-1H-benzo[d]imidazole-5-carboxylic acid and Synthesis of N-(2-methoxyethyl)-1-methyl-2-(oxazolo[4,5-b]pyridin-2-ylamino)-1H-benzo[d]imidazole-5-carboxamide

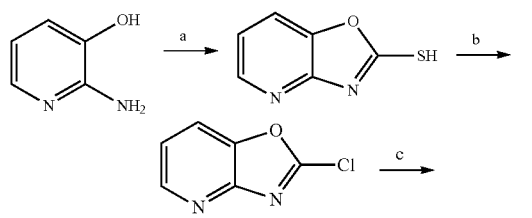

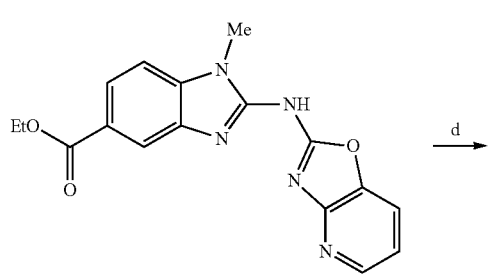

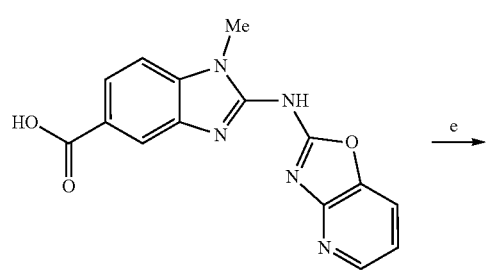

148

-continued

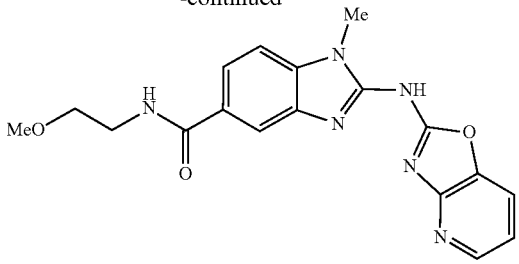

Conditions: a) CS$_2$, EtOH, Reflux, 12 h; b) SOCl$_2$, Cat. DMF, Reflux, 2 h; c) NaH, ethyl 2-amino-1-methyl-1H-benzo[d]imidazole-5-carboxylate, 1,4-Dioxane, RT, 16 h: d) LiOH·H$_2$O, THF, EtOH, H$_2$O, 60° C., 16 h; e) 2-methoxyethan-1-amine, DPPA, DIPEA, DMF, 0° C.-RT, 16 h Step-a: Synthesis of oxazolo[4,5-b]pyridine-2-thiol To a solution of 2-aminopyridin-3-ol (2.2 g, 20 mmol) in ethanol (40 mL) at RT was added potassium hydroxide (1.68 g, 30 mmol) and carbondisulfide (15 mL). The reaction mixture was refluxed for 12 h, then cooled to RT, diluted with water (75 mL) and neutralized with glacial acetic acid. A solid precipitated and was filtered and dried under vacuum to afford the title compound (1.8 g, 59%); $^1$H NMR (400 MHz, DMSO-$d_6$): δ 14.5 (s, 1H), 8.23 (dd, J=1.2 Hz, J=5.2 Hz, 1H), 7.88 (dd, J=1.6 Hz, J=8.4 Hz, 1H), 7.29-7.26 (m, 1H); LC-MS: m/z 153.1 (M+1)$^+$.

Step-b: Synthesis of 2-chlorooxazolo[4,5-b]pyridine

The title compound was synthesized using the same procedure which was followed for Example 32 Step-d using oxazolo[4,5-b]pyridine-2-thiol as starting material and heating for 2 h. (Yield: 100%); $^1$H NMR (400 MHz, DMSO-$d_6$): δ 8.01 (dd, J=1.6 Hz, J=5.6 Hz, 1H), 7.61 (dd, J=1.2 Hz, J=8.0 Hz, 1H), 7.10-7.06 (m, 1H); LC-MS: m/z 155.01 (M+1)$^+$.

Step-c: Synthesis of ethyl 1-methyl-2-(oxazolo[4,5-b]pyridin-2-ylamino)-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 2-chlorooxazolo[4,5-b]pyridine as starting materials (Yield: 32%); $^1$H NMR (400 MHz, DMSO-$d_6$): δ 7.98 (s, 1H), 7.94 (d, J=4.4 Hz, 1H), 7.62 (d, J=9.2 Hz, 1H), 7.36 (d, J=7.2 Hz, 1H), 7.21-7.18 (m, 1H), 6.77-6.74 (m, 1H), 4.32-4.26 (m, 2H), 3.57 (s, 3H), 1.38 (t, J=6.8 Hz, 3H); LC-MS: m/z 338.15 (M+1)$^+$.

Step-d: Synthesis of 1-methyl-2-(oxazolo[4,5-b]pyridin-2-ylamino)-1H-benzo[d]imidazole-5-carboxylic acid The title compound was synthesized using the same procedure which was followed for compound 1h using ethyl 1-methyl-2-(oxazolo[4,5-b]pyridin-2-ylamino)-1H-benzo[d]imidazole-5-carboxylate as starting material (Yield: 73%); $^1$H NMR (400 MHz, DMSO-$d_6$): δ 12.83 (bs, 1H), 12.44 (bs, 1H), 8.26-8.23 (m, 2H), 7.89 (d, J=8.4 Hz, 1H), 7.78 (d, J=7.6 Hz, 1H), 7.75 (d, J=8.4 Hz, 1H), 7.12-7.09 (m, 1H), 3.72 (s, 3H); LC-MS: m/z 310.15 (M+1)$^+$.

Step-e: Synthesis of N-(2-methoxyethyl)-1-methyl-2-(oxazolo[4,5-b]pyridin-2-ylamino)-1H-benzo[d]imidazole-5-carboxamide The title compound was synthesized using the same procedure which was followed for compound 1i using 1-methyl-2-(oxazolo[4,5-b]pyridin-2-ylamino)-1H-benzo[d]imidazole-5-carboxylic acid and 2-methoxyethylamine as starting materials (Yield: 53%); $^1$H NMR (400 MHz, DMSO-$d_6$): δ 12.4 (bs, 1H), 8.48 (bs, 1H), 8.23 (d, J=4.4 Hz, 1H), 8.13 (s, 1H), 7.79-7.75 (s, 2H), 7.53 (d, J=8.4 Hz, 1H), 7.11-7.08 (m, 1H), 3.67 (s, 3H), 3.48-3.44 (m, 4H), 3.29 (s, 3H); LC-MS: m/z 367.2 (M+1)$^+$.

Example 113. Synthesis of N-(2-hydroxyethyl)-1-methyl-2-((5-(trifluoromethyl)oxazolo[5,4-b]pyridin-2-yl)amino)-1H-benzo[d]imidazole-5-carboxamide

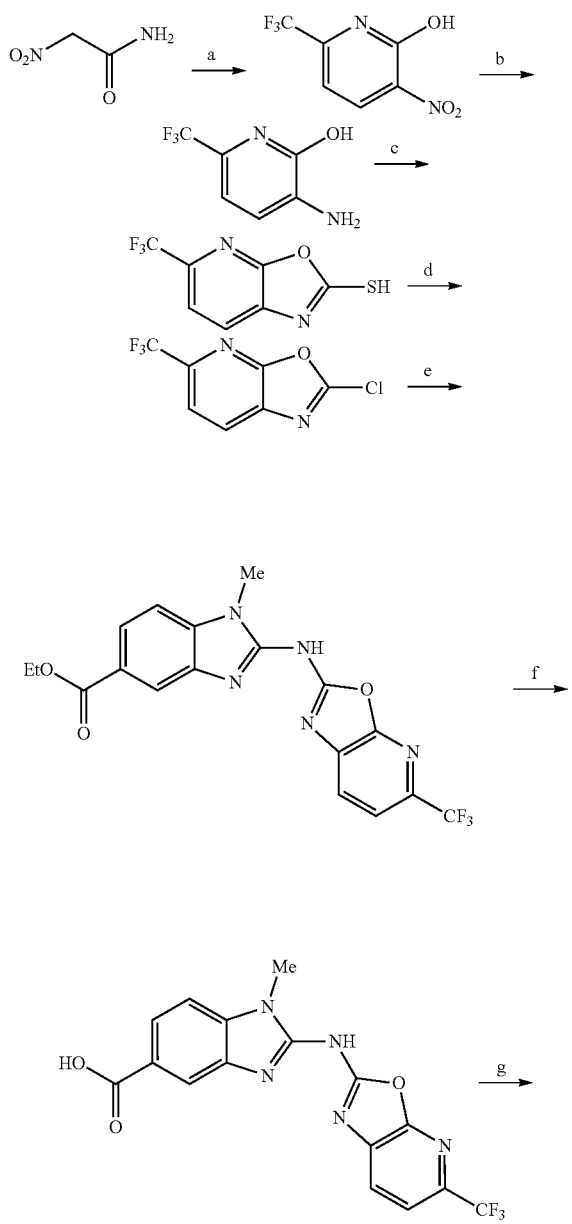

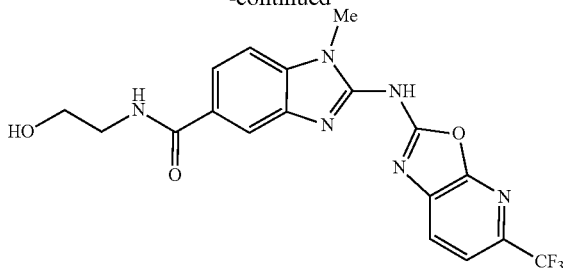

Conditions: a) ethyl (E)-5,5,5-trifluoro-4-oxopent-2-enoate, NaOET, EtOH, 90° C., 2 h; b) 10% Pd/C, MeOH, H2, RT, 16 h; c) Thiophosgene, THF, RT, 16 h; d) SOCl₂, Cat. DMF, reflux, 3 h; e) NaH, ethyl 2-amino-1-methyl-1H-benzo[d]imidazole-5-carboxylate, 1,4-Dioxane, RT, 16 h; f) LiOH·H2O, THF, EtOH, H2O, 60° C, 16 h; g) 2-aminoethan-1-ol, HBTU, DIPEA, DMF, 0° C.-RT, 16 h

Step-a: Synthesis of 3-nitro-6-(trifluoromethyl)pyridin-2-ol

To a solution of 2-nitroacetamide (5.0 g, 47.8 mmol) in ethanol (25 mL) at RT was added ethyl (E)-5,5,5-trifluoro-4-oxopent-2-enoate (11.24 g, 57.3 mmol) and 25% sodium ethoxide in ethanol (25.9 mL, 95.3 mmol). The reaction mixture was stirred at 90° C. for 2 h. Reaction mixture was cooled to RT, diluted with water (50 mL), acidified with 1N HCl and extracted with EtOAc (2×150 mL). The combined organic layers were washed brine solution (50 mL), dried over anhydrous sodium sulfate and concentrated under vacuum to get the residue which was purified by combiflash chromatography using 50% EtOAc in hexanes as eluent to afford the title compound (1.5 g); $^1$H NMR (400 MHz, DMSO-$d_6$): δ 8.58 (d, J=8.4 Hz, 1H), 7.84 (bs, 1H), 7.51 (d, J=7.6 Hz, 1H).

Step-b: Synthesis of 3-amino-6-(trifluoromethyl)pyridin-2-ol

The title compound was synthesized using the same procedure which was followed for compound 1e using 3-nitro-6-(trifluoromethyl)pyridin-2-ol as starting material (Yield: 82%); $^1$H NMR (400 MHz, DMSO-$d_6$): δ 11.7 (bs, 1H), 6.88 (bs, 1H), 6.69 (bs, 1H), 5.60 (s, 2H); LC-MS: m/z 179.1 (M+1)$^+$.

Step-c: Synthesis of 5-(trifluoromethyl)oxazolo[5,4-b]pyridine-2-thiol

The title compound was synthesized using the same procedure which was followed for Example 109 Step-b using 3-amino-6-(trifluoromethyl)pyridin-2-ol as starting material (Yield: 65%); $^1$H NMR (400 MHz, DMSO-$d_6$): δ 7.81-7.75 (m, 2H); LC-MS: m/z 219.0 (M−1).

Step-d: Synthesis of 2-chloro-5-(trifluoromethyl)oxazolo[5,4-b]pyridine

The title compound was synthesized using the same procedure which was followed for Example 32 Step-d using 5-(trifluoromethyl)oxazolo[5,4-b]pyridine-2-thiol as starting material (Yield: 74%). The crude compound was used in the next step without further purification.

Step-e: Synthesis of ethyl 1-methyl-2-((5-(trifluoromethyl)oxazolo[5,4-b]pyridin-2-yl)amino)-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 2-chloro-5-(trifluoromethyl)oxazolo[5,4-b]pyridine as starting materials (Yield: 43%); $^1$H NMR (400 MHz, DMSO-$d_6$): δ 12.5 (bs, 1H), 8.27 (s, 1H), 7.93-7.89 (m, 2H), 7.75 (d, J=12.4 Hz, 1H), 7.62 (d, J=8.4 Hz, 1H), 4.34 (q, J=6.8 Hz, 2H), 3.71 (s, 3H), 1.35 (t, J=7.2 Hz, 3H); LC-MS: m/z 406.1 (M+1)$^+$.

Step-f: Synthesis of 1-methyl-2-((5-(trifluoromethyl)oxazolo[5,4-b]pyridin-2-yl)amino)-1H-benzo[d]imidazole-5-carboxylic acid The title compound was synthesized using the same procedure which was followed for compound 1h using ethyl 1-methyl-2-((5-(trifluoromethyl)oxazolo[5,4-b]pyridin-2-yl)amino)-1H-benzo[d]imidazole-5-carboxylate as starting material (Yield: 75%); $^1$H NMR (400 MHz, DMSO-$d_6$): δ 8.20 (bs, 1H), 7.74-7.70 (m, 2H), 7.55 (d, J=6.8 Hz, 1H), 7.09 (d, J=8.4 Hz, 1H), 3.62 (s, 3H); LC-MS: m/z 378.1 (M+1)$^+$.

Step-g: Synthesis of N-(2-hydroxyethyl)-1-methyl-2-((5-(trifluoromethyl)oxazolo[5,4-b]pyridin-2-yl)amino)-1H-benzo[d]imidazole-5-carboxamide The title compound was synthesized using the same procedure which was followed for Example 6 Step-e using 1-methyl-2-((5-(trifluoromethyl)oxazolo[5,4-b]pyridin-2-yl)amino)-1H-benzo[d]imidazole-5-carboxylic acid and 2-aminoethan-1-ol as starting materials (Yield: 28%); $^1$H NMR (400 MHz, DMSO-$d_6$): δ 8.22 (bs, 1H), 7.78 (bs, 1H), 7.60 (d, J=8.0 Hz, 1H), 7.51 (bs, 1H), 7.31 (d, J=8.4 Hz, 2H), 4.70 (t, J=5.2 Hz, 1H), 3.67 (s, 3H), 3.50 (q, J=5.2 Hz, 2H), 3.36 (q, J=6.0 Hz, 2H); LC-MS: m/z 421.1 (M+1)$^+$.

Example 114. Synthesis of N-(2-(2-hydroxyethoxy)ethyl)-1-methyl-2-(thiazolo[4,5-b]pyrazin-2-ylamino)-1H-benzo[d]imidazole-5-carboxamide

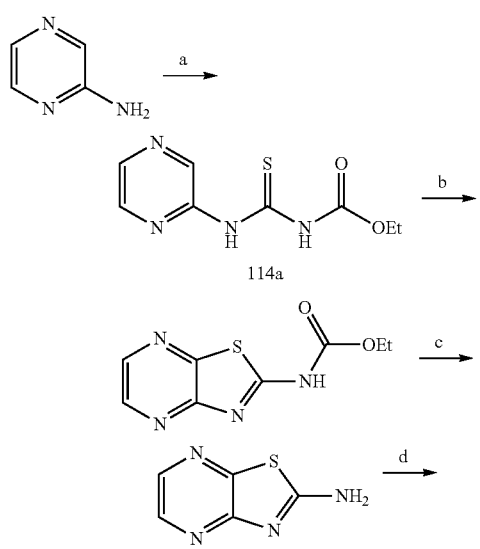

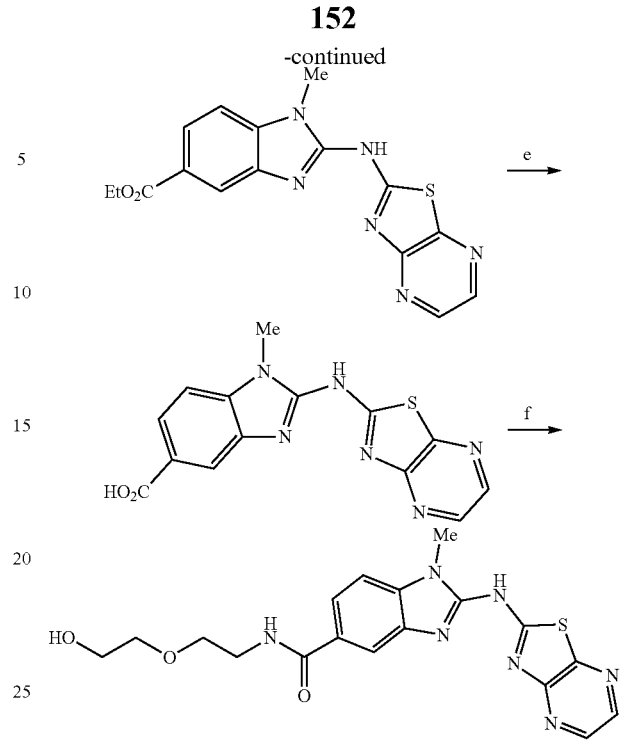

Conditions: a) O-ethyl carbonisothiocyanatidate, 1,4-Dioxane, RT 16 h; b) 6M HCl, 1,4-Dioxane, 50° C., 4 h; c) NaOH, H$_2$O, 120° C., 16 h; d) ethyl 3-amino-4-(methylamino)benzoate, 1,1′-thiocarbonyldiimidazole, EDC, DMF, 100° C., 18 h; e) LiOH·H$_2$O, THF, EtOH, H$_2$O, 60° C., 16 h; f) 2-(2-aminoethoxy)ethan-1-ol, HBTU, DIPEA, DMF, 0° C.-RT, 16 h Step-a: Synthesis of 114a To a stirred solution of pyrazin-2-amine (2.0 mg, 21.0 mmol) in 1,4-dioxane (20 mL) at RT was added O-ethyl carbonisothiocyanatidate (3.03 g, 23.1 mmol) and stirred at RT for 16 h. The reaction mixture was concentrated under vacuum. To the residue ethyl acetate was added and the precipitated solid was filtered and dried under vacuum to afford the title compound (2.0 g, 42%); $^1$H NMR (400 MHz, DMSO-$d_6$): δ 12.07 (s, 1H), 11.76 (s, 1H), 9.67 (s, 1H), 8.50 (s, 2H), 4.24 (q, J=7.2 Hz, 2H), 1.27 (t, J=7.2 Hz, 3H); LC-MS: m/z 227.0 (M+1)$^+$.

Step-b: Synthesis of ethyl thiazolo[4,5-b]pyrazin-2-ylcarbamate

To a stirred solution of 114a (1.8 g, 7.96 mmol) in 1,4-dioxane (9 mL) was added 6 M HCl (18 mL) and stirred at 50° C. for 4 h. The reaction mixture was cooled to RT and solid obtained was filtered and dried under vacuum to afford the title compound (1.5 g, 84%); $^1$H NMR (400 MHz, DMSO-$d_6$): δ 12.60 (bs, 1H), 8.58 (d, J=3.2 Hz, 1H), 8.44 (d, J=2.4 Hz, 1H), 4.29 (q, J=6.8 Hz, 2H), 1.30 (t, J=7.6 Hz, 3H); LC-MS: m/z 225.0 (M+1)$^+$.

Step-c: Synthesis of thiazolo[4,5-b]pyrazin-2-amine

To a solution of ethyl thiazolo[4,5-b]pyrazin-2-ylcarbamate (500 mg, 2.23 mmol) in water (5 mL) was added sodium hydroxide (267 mg, 6.69 mmol) and heated at 120° C. for 16 h. The reaction mixture was cooled to RT, acidified with 1 N HCl. The obtained solid was filtered and dried under vacuum to afford the title compound (300 mg, 88%); $^1$H NMR (400 MHz, DMSO-d₆): δ 8.42 (s, 2H), 8.23 (d, J=2.8 Hz, 1H), 8.03 (d, J=2.8 Hz, 1H); LC-MS: m/z 153.1 (M−1)⁺.

Step-d: Synthesis of ethyl 1-methyl-2-(thiazolo[4,5-b]pyrazin-2-ylamino)-1H-benzo[d]imidazole-5-carboxylate The title compound was synthesized using the same procedure which was followed for compound 2c using ethyl 3-amino-4-(methylamino)benzoate and thiazolo[4,5-b]pyrazin-2-amine as starting materials (Yield: 9%); ¹H NMR (400 MHz, DMSO-d₆): δ 12.63 (bs, 1H), 8.44 (d, J=2.4 Hz, 1H), 8.33 (s, 1H), 8.23 (d, J=2.8 Hz, 1H), 7.91 (dd, J=1.2 Hz, J=8.4 Hz, 1H), 7.60 (d, J=8.4 Hz, 1H), 4.33 (q, J=7.2 Hz, 2H), 3.67 (s, 3H), 1.35 (d, J=7.2 Hz, 3H); LC-MS: m/z 355.0 (M+1)⁺.

Step-e: Synthesis of 1-methyl-2-(thiazolo[4,5-b]pyrazin-2-ylamino)-1H-benzo[d]imidazole-5-carboxylic acid To a stirred solution of ethyl 1-methyl-2-(thiazolo[4,5-b]pyrazin-2-ylamino)-1H-benzo[d]imidazole-5-carboxylate (60 mg, 0.17 mmol) in a mixture of solvent of THF (1 mL), ethanol (1 mL) and water (0.5 mL) was added lithium hydroxide monohydrate (35 mg, 0.85 mmol). The reaction mixture was heated at 60° C. for 16 h with stirring. The reaction mixture was cooled to RT and concentrated under reduced pressure. The crude material was directly used in the next step (40 mg); LC-MS: m/z 326.95 (M+1)⁺.

Step-f: Synthesis of N-(2-(2-hydroxyethoxy)ethyl)-1-methyl-2-(thiazolo[4,5-b]pyrazin-2-ylamino)-1H-benzo[d]imidazole-5-carboxamide The title compound was synthesized using the same procedure which was followed for Example 6 Step-e using 1-methyl-2-(thiazolo[4,5-b]pyrazin-2-ylamino)-1H-benzo[d]imidazole-5-carboxylic acid and 2-(2-aminoethoxy)ethan-1-ol as starting materials (Yield: 59%); ¹H NMR (400 MHz, DMSO-d₆): δ 12.60 (bs, 1H), 8.46-8.41 (m, 2H), 8.20-8.14 (m, 2H), 7.78 (s, 1H), 7.56 (s, 1H), 4.60 (t, J=4.8 Hz, 1H), 3.70 (s, 3H), 3.59-3.43 (m, 8H); LC-MS: m/z 414.05 (M+1)⁺.

Examples 115 and 116. Synthesis of 2-((6-cyclopropylbenzo[d]oxazol-2-yl)amino)-1-methyl-1H-benzo[d]imidazole-5-carboxylic acid and Synthesis of 2-((6-cyclopropylbenzo[d]oxazol-2-yl)amino)-N-(2-methoxyethyl)-1-methyl-1H-benzo[d]imidazole-5-carboxamide

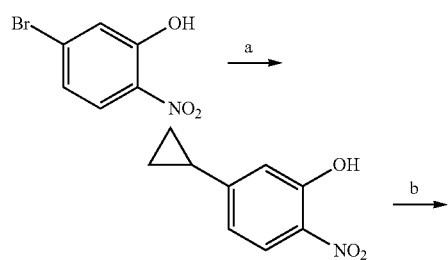

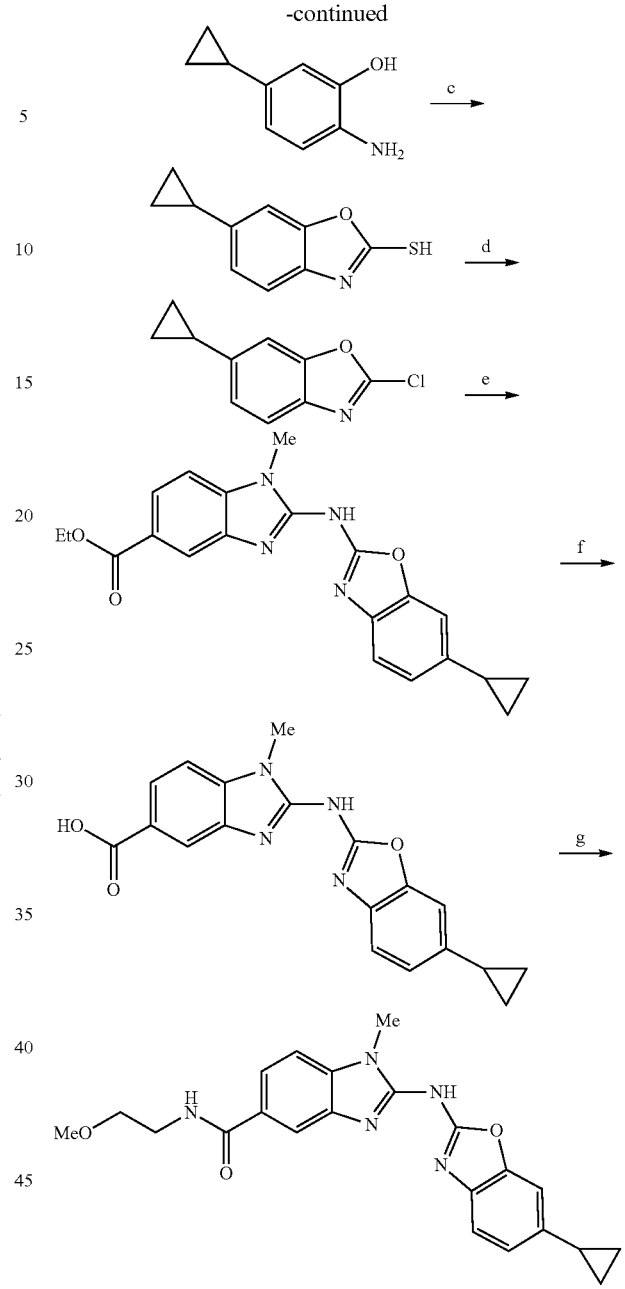

Conditions: a) Cyclopropyl boronic acid, Pd(OAc)₂, Tricyclohexyl phosphine, K₃PO₄, Toluene, H₂O, 100° C., 16 h; b) PtO₂, EtOH, THF, H₂, RT, 4 h; c) Potassium ethyl xanthate, EtOH, Reflux, 16 h; d) SOCl₂, Cat. DMF, Reflux, 3 h; e) NaH, ethyl 2-amino-1-methyl-1H-benzo[d]imidazole-5-carboxylate, 1,4-Dioxane, RT, 16 h; f) LiOH·H₂O, THF, EtOH, H₂O 60° C., 16 h; g) 2-methoxyethan-1-amine, DPPA, DIPEA, DMF, 0° C.-RT, 16 h Step-a: Synthesis of 5-cyclopropyl-2-nitrophenol To a stirred solution of 5-bromo-2-nitrophenol (2.0 g, 9.17 mmol) and cyclopropyl boronic acid (1.02 g, 11.92 mmol) in toluene (40 mL) was added potassium phosphate (6.81 g, 32.1 mmol), tricyclohexyl phosphine (0.25 g, 0.91 mmol) and water (2 mL). The reaction mixture was purged with nitrogen gas for 10 min and then palladium diacetate (0.1 g, 0.45 mmol) was added to the reaction mixture and it was heated at 100° C. for 16 h. The reaction mixture was cooled to RT, filtered through a celite bed and washed with ethyl acetate (150 mL). The organic layer was washed brine solution (50 mL), dried over anhydrous sodium sulfate and concentrated under vacuum to get the residue which was purified by combiflash chromatography using 100% hexane as an eluent to afford the title compound (0.9 g, 55%); $^1$H NMR (400 MHz, DMSO-d$_6$): δ 10.72 (bs, 1H), 7.82 (d, J=8.8 Hz, 1H), 6.82 (d, J=2.0 Hz, 1H), 6.68 (dd, J=2.0 Hz, J=8.8 Hz, 1H), 1.99-1.94 (m, 1H), 1.08-1.03 (m, 2H), 0.78-0.74 (m, 2H).

Step-b: Synthesis of 2-amino-5-cyclopropylphenol

To a solution of 5-cyclopropyl-2-nitrophenol (1.75 g, 11.4 mmol) in ethanol (4 mL) and THF (4 mL) was added a PtO$_2$ (12 mg). The reaction mixture was stirred under hydrogen gas balloon for 4 h. It was filtered through a celite bed and concentrated under vacuum to afford the title compound (250 mg, 100%); $^1$H NMR (400 MHz, DMSO-d$_6$): δ 8.99 (bs, 1H), 6.61-6.59 (m, 1H), 6.45 (d, J=2.0 Hz, 1H), 6.43-6.34 (m, 1H), 5.35 (bs, 2H), 1.74-1.65 (m, 1H), 0.80-0.75 (m, 2H), 0.48-0.44 (m, 2H).

Step-c: Synthesis of 6-cyclopropylbenzo[d]oxazole-2-thiol

The title compound was synthesized using the same procedure which was followed for Example 32 Step-c using 2-amino-5-cyclopropylphenol as starting material (Yield: 90%); $^1$H NMR (400 MHz, DMSO-d$_6$): δ 13.72 (bs, 1H), 7.22 (s, 1H), 7.11-7.04 (m, 2H), 2.02-1.98 (m, 1H), 0.98-0.94 (m, 2H), 0.71-0.67 (m, 2H); LC-MS: m/z 190.05 (M−1).

Step-d: Synthesis of 2-chloro-6-cyclopropylbenzo[d]oxazole

The title compound was synthesized using the same procedure which was followed for Example 32 Step-d using 6-cyclopropylbenzo[d]oxazole-2-thiol as starting material (Yield: 98%); $^1$H NMR (400 MHz, DMSO-d$_6$): δ 7.59 (d, J=8.0 Hz, 1H), 7.46 (s, 1H), 7.18 (d, J=8.4 Hz, 1H), 2.09-2.01 (m, 1H), 1.02-0.99 (m, 2H), 0.75-0.74 (m, 2H); LC-MS: m/z 194.0 (M+1)$^+$.

Step-e: Synthesis of ethyl 2-((6-cyclopropylbenzo[d]oxazol-2-yl)amino)-1-methyl-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 2-chloro-6-cyclopropylbenzo[d]oxazole as starting materials (Yield: 27%); $^1$H NMR (400 MHz, DMSO-d$_6$): δ 12.3 (bs, 1H), 8.22 (s, 1H), 7.87 (d, J=8.4 Hz, 1H), 7.50 (d, J=8.4 Hz, 1H), 7.33 (d, J=8.4 Hz, 1H), 7.15 (s, 1H), 6.97 (d, J=6.8 Hz, 1H), 4.35-4.27 (m, 2H), 3.62 (s, 3H), 2.02-1.98 (m, 1H), 1.36-1.30 (m, 3H), 0.97-0.92 (m, 2H), 0.71-0.67 (m, 2H); LC-MS: m/z 377.2 (M+1)$^+$.

Step-f: Synthesis of 2-((6-cyclopropylbenzo[d]oxazol-2-yl)amino)-1-methyl-1H-benzo[d]imidazole-5-carboxylic acid The title compound was synthesized using the same procedure which was followed for compound 1h using ethyl 2-((6-cyclopropylbenzo[d]oxazol-2-yl)amino)-1-methyl-1H-benzo[d]imidazole-5-carboxylate as starting material (Yield: 81%); $^1$H NMR (400 MHz, DMSO-d$_6$): δ 13.5-11.2 (bs, 2H), 8.18 (s, 1H), 7.91 (d, J=8.4 Hz, 1H), 7.58 (d, J=8.4 Hz, 1H), 7.34 (d, J=8.4 Hz, 1H), 7.22 (s, 1H), 7.04 (d, J=8.4 Hz, 1H), 3.67 (s, 3H), 2.06-2.02 (m, 1H), 1.00-0.95 (m, 2H), 0.72-0.68 (m, 2H); LC-MS: m/z 349.0 (M+1)$^+$.

Step-g: Synthesis of 2-((6-cyclopropylbenzo[d]oxazol-2-yl)amino)-N-(2-methoxyethyl)-1-methyl-1H-benzo[d]imidazole-5-carboxamide The title compound was synthesized using the same procedure which was followed for compound 1i using 2-((6-cyclopropylbenzo[d]oxazol-2-yl)amino)-1-methyl-1H-benzo[d]imidazole-5-carboxylic acid and 2-methoxyethylamine as starting materials (Yield: 46%); $^1$H NMR (400 MHz, DMSO-d$_6$): δ 12.2 (bs, 1H), 8.44 (t, J=5.2 Hz, 1H), 8.06 (d, J=1.6 Hz, 1H), 7.75 (d, J=8.4 Hz, 1H), 7.46 (d, J=8.4 Hz, 1H), 7.33 (d, J=8.0 Hz, 1H), 7.14 (s, 1H), 6.96 (dd, J=1.6 Hz, J=8.4 Hz, 1H), 3.62 (s, 3H), 3.48-3.43 (m, 4H), 3.28 (s, 3H), 2.02-1.98 (m, 1H), 0.96-0.92 (m, 2H), 0.70-0.66 (m, 2H); LC-MS: m/z 406.2 (M+1)$^+$.

Example 117. Synthesis of N-(2-(2-hydroxyethoxy)ethyl)-1-methyl-2-((7-(trifluoromethyl)benzo[d]oxazol-2-yl)amino)-1H-benzo[d]imidazole-5-carboxamide

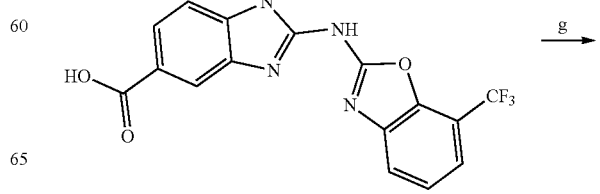

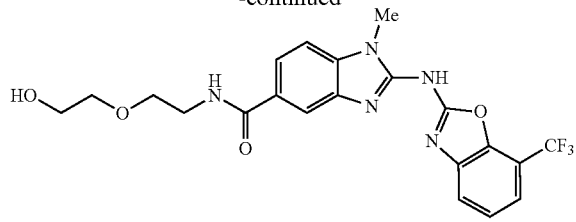

Conditions: a) NaNO₃, NaNO₂, H₂SO₄, DCM, RT, 16 h; b) 10% Pd/C, MeOH, H₂, RT, 4 h; c) Potassium ethyl xanthate, EtOH, reflux, 16 h; d) SOCl₂, Cat. DMF, reflux, 2 H; e) NaH, ethyl 2-amino-1-methyl-1H-benzo[d]imidazole-5-carboxylate, 1,4-Dioxane, RT, 16 h; f) LiOH·H₂O, THF, EtOH, H₂O, 60° C., 16 h; g) 2-(2-aminoethoxy)ethan-1-ol, HBTU, DIPEA, DMF, 0° C.-RT, 16 h

Step-a: Synthesis of 2-nitro-6-(trifluoromethyl)phenol

To 3 M sulfuric acid (25 mL) stirring at RT was added sodium nitrate (1.73 g, 20.37 mmol) and sodium nitrite (100 mg) followed by the addition of a solution of 2-(trifluoromethyl)phenol (3.0 g, 18.52 mmol) in DCM (40 mL) and stirred for 16 h. The mixture was poured into ice water (50 mL) and extracted with DCM (2×100 mL). The combined organic layers were washed with water (50 mL), brine solution (50 mL), dried over anhydrous sodium sulfate and concentrated under vacuum. The residue was purified by combiflash chromatography using 5% ethyl acetate in hexane as eluent to afford the titled compound (1.3 g, 40%); ¹H NMR (400 MHz, DMSO-d₆): δ 11.34 (bs, 1H), 8.27 (dd, J=1.6 Hz, J=8.4 Hz, 1H), 8.00 (dd, J=1.2 Hz, J=7.6 Hz, 1H), 7.21-7.17 (m, 1H).

Step-b: Synthesis of 2-amino-6-(trifluoromethyl)phenol

The title compound was synthesized using the same procedure which was followed for compound 1e using 2-nitro-6-(trifluoromethyl)phenol as starting material and stirring for 4 h (Yield: 90%); ¹H NMR (400 MHz, DMSO-d₆): δ 6.88-6.84 (m, 1H), 6.75-6.70 (m, 2H), 6.50 (bs, 2H); LC-MS: m/z 178.05 (M+1)⁺.

Step-c: Synthesis of 7-(trifluoromethyl)benzo[d]oxazole-2(3H)-thione

The title compound was synthesized using the same procedure which was followed for Example 32 Step-c using 2-amino-6-(trifluoromethyl)phenol as starting material (Yield: 65%); ¹H NMR (400 MHz, DMSO-d₆): δ 14.28 (bs, 1H), 7.59-7.53 (m, 2H), 7.49-7.45 (m, 1H); LC-MS: m/z 218.1 (M−1)⁻.

Step-d: Synthesis of 2-chloro-7-(trifluoromethyl)benzo[d]oxazole

The title compound was synthesized using the same procedure which was followed for Example 32 Step-d using 7-(trifluoromethyl)benzo[d]oxazole-2(3H)-thione as starting material and stirring for 2 h (Yield: 84%); ¹H NMR (400 MHz, DMSO-d₆): δ 8.11 (d, J=8.0 Hz, 1H), 7.84 (d, J=7.6 Hz, 1H), 7.64 (t, J=7.2 Hz, 1H).

Step-e: Synthesis of ethyl 1-methyl-2-((7-(trifluoromethyl)benzo[d]oxazol-2-yl)amino)-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 2-chloro-7-(trifluoromethyl)benzo[d]oxazole as starting materials (Yield: 36%); ¹H NMR (400 MHz, DMSO-d₆): δ 12.41 (s, 1H), 8.26 (d, J=1.6 Hz, 1H), 7.90 (dd, J=1.6 Hz, J=8.4 Hz, 1H), 7.75 (d, J=6.4 Hz, 1H), 7.57 (d, J=8.4 Hz, 1H), 7.44-7.38 (m, 2H), 4.33 (q, J=6.8 Hz, 2H), 3.67 (s, 3H), 1.35 (d, J=6.8 Hz, 3H); LC-MS: m/z 405.0 (M+1)⁺.

Step-f: Synthesis of 1-methyl-2-((7-(trifluoromethyl)benzo[d]oxazol-2-yl)amino)-1H-benzo[d]imidazole-5-carboxylic acid The title compound was synthesized using the same procedure which was followed for compound 1h using ethyl 1-methyl-2-((7-(trifluoromethyl)benzo[d]oxazol-2-yl)amino)-1H-benzo[d]imidazole-5-carboxylate as starting material (Yield: 75%); ¹H NMR (400 MHz, DMSO-d₆): δ 12.83 (bs, 1H), 12.40 (bs, 1H), 8.22 (d, J=1.6 Hz, 1H), 7.89 (dd, J=1.2 Hz, J=8.4 Hz, 1H), 7.75 (d, J=8.4 Hz, 1H), 7.55 (d, J=8.0 Hz, 1H), 7.43-7.37 (m, 2H), 3.67 (s, 3H); LC-MS: m/z 377.0 (M+1)⁺.

Step-g: Synthesis of N-(2-(2-hydroxyethoxy)ethyl)-1-methyl-2-((7-(trifluoromethyl)benzo[d]oxazol-2-yl)amino)-1H-benzo[d]imidazole-5-carboxamide The title compound was synthesized using the same procedure which was followed for Example 6 Step-e using 1-methyl-2-((7-(trifluoromethyl)benzo[d]oxazol-2-yl)amino)-1H-benzo[d]imidazole-5-carboxylic acid and 2-(2-aminoethoxy)ethan-1-ol as starting materials (Yield: 61%); ¹H NMR (400 MHz, DMSO-d₆): δ 12.30 (bs, 1H), 8.46 (t, J=5.2 Hz, 1H), 8.10 (d, J=1.2 Hz, 1H), 7.80-7.73 (m, 2H), 7.53 (d, J=8.4 Hz, 1H), 7.42-7.38 (m, 2H), 4.60 (bs, 1H), 3.67 (s, 3H), 3.58-3.43 (m, 8H); LC-MS: m/z 464.1 (M+1)⁺.

Example 118. Synthesis of N-(2-(2-hydroxyethoxy)ethyl)-2-((1-methyl-1H-benzo[d]imidazol-2-yl)amino)benzo[d]oxazole-5-carboxamide

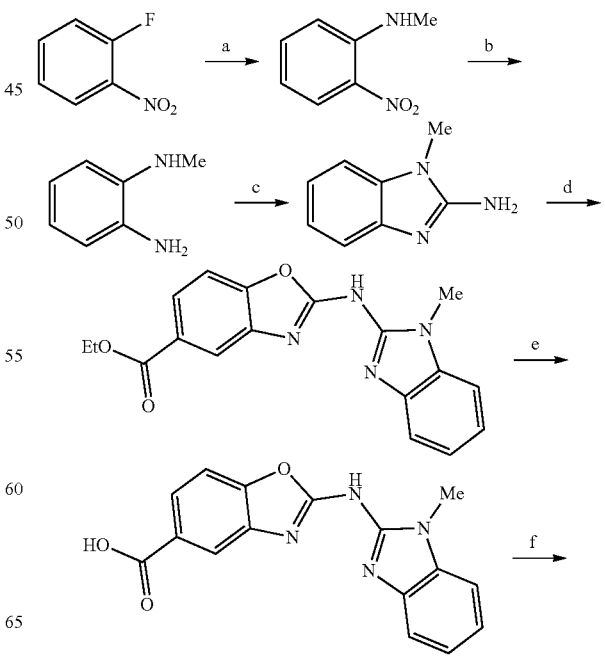

159

-continued

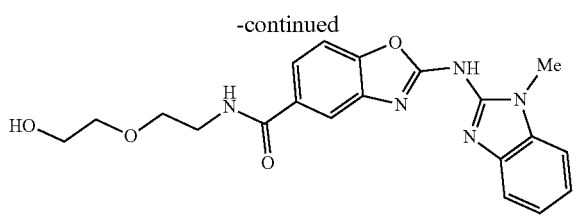

Conditions: a) Aq. Methyl amine, DMF, 60° C., 16 h; b) 10% Pd/C, MeOH, H₂, RT, 16 h; c) Cyanogen bromide, THF, H₂O, 50° C., 16 h; d) NaH, ethyl 2-chlorobenzo[d]oxazole-5-carboxylate, 1,4-Dioxane, RT, 16 h; e) LiOH•H₂O, THF, EtOH, H₂O, 60° C., 16 h; f) 2-(2-aminoethoxy)ethan-1-ol, HBTU, DIPEA, DMF, 0° C.-RT, 16 h Step-a: Synthesis of N-methyl-2-nitroaniline To a solution of 1-fluoro-2-nitrobenzene (1.0 g, 7.08 mmol) in DMFA (3 mL) at RT was added methyl amine (1 mL, 40% aqueous solution, 35.4 mmol) and the reaction mixture was stirred at 60° C. for 16 h. The reaction mixture was cooled to RT, diluted with cold water (50 mL) and stirred for 2 h. The solid obtained was filtered and dried under vacuum to afford the product as a yellow solid (700 mg, 75%); ¹H NMR (400 MHz, DMSO-d₆): δ 8.14 (bs, 1H), 8.06 (dd, J=1.2 Hz, J=8.8 Hz, 1H), 7.57-7.53 (m, 1H), 6.98 (d, J=8.8 Hz, 1H), 6.69-6.66 (m, 1H), 2.96 (d, J=4.8 Hz, 3H); LC-MS: m/z 153.0 (M+1)⁺.

Step-b: Synthesis of N¹-methylbenzene-1,2-diamine

The title compound was synthesized using the same procedure which was followed for compound 1e using N-methyl-2-nitroaniline as starting material (Yield: 98%); ¹H NMR (400 MHz, DMSO-d₆): δ 6.52-6.48 (m, 2H), 6.41-6.34 (m, 2H), 4.45 (bs, 2H), 2.68 (s, 3H); LC-MS: m/z 123.2 (M+1)⁺.

Step-c: Synthesis of 1-methyl-1H-benzo[d]imidazol-2-amine

The title compound was synthesized using the same procedure which was followed for compound 1f using N¹-methylbenzene-1,2-diamine as starting material (Yield: 83%); ¹H NMR (400 MHz, DMSO-d₆): δ 7.11-7.09 (m, 2H), 6.94-6.87 (m, 2H), 6.37 (s, 2H), 3.78 (s, 3H).

Step-d: Synthesis of ethyl 2-((1-methyl-1H-benzo[d]imidazol-2-yl)amino)benzo[d]oxazole-5-carboxylate The title compound was synthesized using the same procedure which was followed for Example 32 Step-e using 1-methyl-1H-benzo[d]imidazol-2-amine and ethyl 2-chlorobenzo[d]oxazole-5-carboxylate as starting materials (Yield: 31%); ¹H NMR (400 MHz, DMSO-d₆): δ 12.20 (bs, 1H), 7.99 (d, J=1.6 Hz, 1H), 7.76-7.74 (m, 1H), 7.64-7.62 (m, 1H), 7.52 (d, J=8.0 Hz, 1H), 7.45-7.43 (m, 1H), 7.26-7.23 (m, 2H), 4.32 (q, J=7.6 Hz, 2H), 3.63 (s, 3H), 1.35 (t, J=6.8 Hz, 3H); LC-MS: m/z 336.95 (M+1)⁺.

Step-e: Synthesis of 2-((1-methyl-1H-benzo[d]imidazol-2-yl)amino)benzo[d]oxazole-5-carboxylic acid The title compound was synthesized using the same procedure which was followed for compound 1h using ethyl 2-((1-methyl-1H-benzo[d]imidazol-2-yl)amino)benzo[d]

160 oxazole-5-carboxylate as starting material (Yield: 78%); ¹H NMR (400 MHz, DMSO-d₆): δ 12.80 (bs, 1H), 12.22 (bs, 1H), 7.98 (d, J=1.6 Hz, 1H), 7.76 (dd, J=2.0 Hz, J=8.4 Hz, 1H), 7.67-7.63 (m, 1H), 7.52 (d, J=8.4 Hz, 1H), 7.47-7.45 (m, 1H), 7.28-7.21 (m, 2H), 3.68 (s, 3H); LC-MS: m/z 309.1 (M+1)⁺.

Step-f: Synthesis of N-(2-(2-hydroxyethoxy)ethyl)-2-((1-methyl-1H-benzo[d]imidazol-2-yl)amino)benzo[d]oxazole-5-carboxamide The title compound was synthesized using the same procedure which was followed for Example 6 Step-e using 2-((1-methyl-1H-benzo[d]imidazol-2-yl)amino)benzo[d]oxazole-5-carboxylic acid and 2-(2-aminoethoxy)ethan-1-ol as starting materials. The crude product was purified by combiflash chromatography using 9% methanol in DCM as an eluent (Yield: 64%); ¹H NMR (400 MHz, DMSO-d₆): δ 12.30 (bs, 1H), 8.48 (t, J=5.2 Hz, 1H), 7.92 (s, 1H), 7.65-7.62 (m, 2H), 7.48-7.45 (m, 2H), 7.28-7.22 (m, 2H), 3.63 (s, 3H), 3.57-3.35 (m, 8H); LC-MS: m/z 396.2 (M+1)⁺.

Example 119. Synthesis of 2-(benzo[d]oxazol-2-ylamino)-N-(2-methoxyethoxy)-1-methyl-1H-benzo[d]imidazole-5-carboxamide

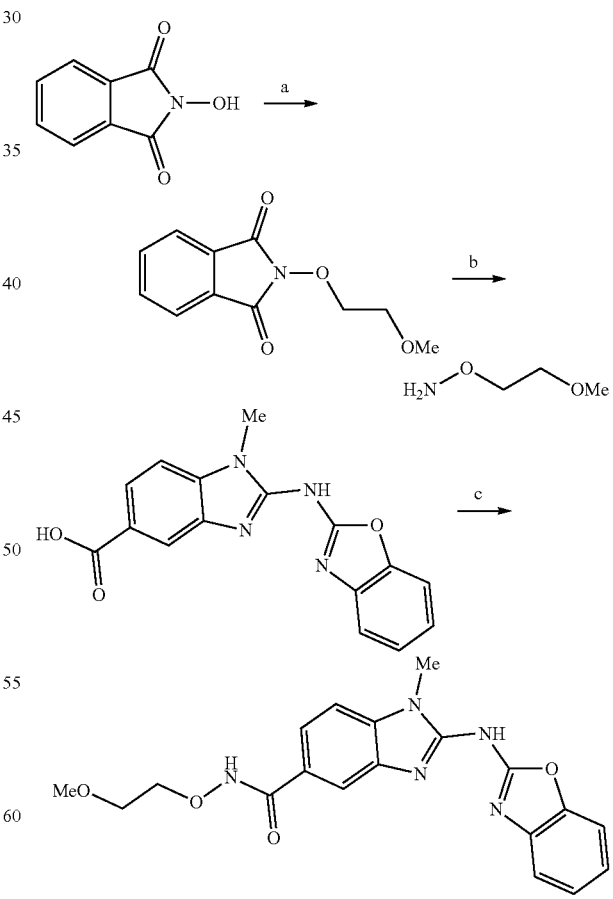

Conditions: a) 1-bromo-2-methoxyethane, TEA, DMF, 60° C., 16 h; b) Hydrazine hydrate, MeOH, reflux, 4 h; c) O-(2-methoxyethyl)hydroxylamine, DPPA, DIPEA, DMF, 0° C.-RT, 16 h

Step-a: Synthesis of 2-(2-methoxyethoxy)isoindoline-1,3-dione

To a stirred solution of N-hydroxyphthalimide (4.6 g, 28.2 mmol) in DMFA (15 mL) at RT was added triethyl amine (8.0 mL, 56.4 mmol) and 1-bromo-2-methoxyethane (4.0 mL, 42.3 mmol). The reaction mixture was then stirred at 60° C. for 16 h. Once the reaction was completed (monitored by TLC), the reaction mixture was cooled to RT, diluted with cold water (100 mL) and extracted with ethyl acetate (2×100 mL). The combined organic layers were washed with cold water (2×200 mL), brine solution (50 mL), dried over anhydrous sodium sulfate and concentrated under vacuum to afford the titled compound (2.8 g, 45%); $^1$H NMR (400 MHz, DMSO-d$_6$): δ 7.86 (s, 4H), 4.26 (t, J=4.4 Hz, 2H), 3.65-3.63 (m, 2H), 3.25 (s, 3H); LC-MS: m/z 222.20 (M+1)$^+$.

Step-b: Synthesis of O-(2-methoxyethyl)hydroxylamine

To a stirred solution of 2-(2-methoxyethoxy)isoindoline-1,3-dione (2.8 g, 12.6 mmol) in methanol (75 mL) at RT was added hydrazine hydrate (0.95 g, 19.0 mmol) and refluxed for 4 h. Then the reaction mixture was cooled to RT, filtered and the filtrate was concentrated. The residue obtained was stirred in diethyl ether (30 mL) and filtered. The filtrate was concentrated under vacuum to afford the titled compound (550 mg, 48%); $^1$H NMR (400 MHz, DMSO-d$_6$): δ 5.50 (s, 2H), 3.84-3.82 (m, 2H), 3.58-3.56 (m, 2H), 3.39 (s, 3H).

Step-c: Synthesis of 2-(benzo[d]oxazol-2-ylamino)-N-(2-methoxyethoxy)-1-methyl-1H-benzo[d]imidazole-5-carboxamide The title compound was synthesized using the same procedure which was followed for compound 1i using 2-(benzo[d]oxazol-2-ylamino)-1-methyl-1H-benzo[d]imidazole-5-carboxylic acid and O-(2-methoxyethyl)hydroxylamine as starting materials (Yield: 20%); $^1$H NMR (400 MHz, DMSO-d$_6$): δ 12.28 (s, 1H), 11.73 (s, 1H), 8.01 (s, 1H), 7.64 (d, J=8.3 Hz, 1H), 7.48 (d, J=7.8 Hz, 2H), 7.44 (d, J=7.8 Hz, 1H), 7.22 (t, J=7.8 Hz, 1H), 7.12 (t, J=7.9 Hz, 1H), 4.04 (t, J=4.2 Hz, 2H), 3.63 (s, 3H), 3.59 (t, J=4.2 Hz, 2H), 3.31 (s, 3H); LC-MS: m/z 382.0 (M+1)$^+$.

Example 120. Synthesis of 2-(benzo[d]oxazol-2-ylamino)-N-(2-hydroxypropoxy)-1-methyl-1H-benzo[d]imidazole-5-carboxamide

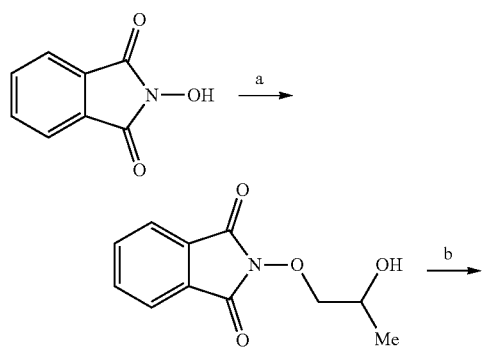

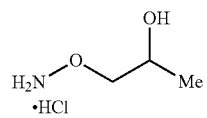

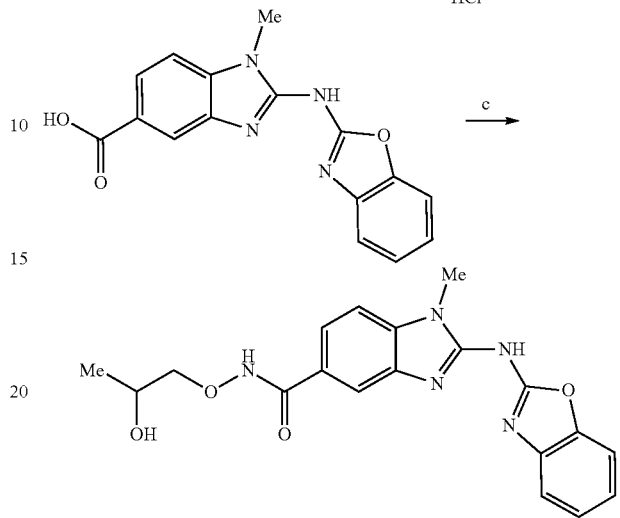

Conditions: a) 2-methyloxirane, DIPEA, Tetrabutylammonium bromide, Toluene, Reflux, 5 h; b) 6N Aq. HCl, RT, 16 h; c) 1-(aminooxy)propan-2-ol hydrochloride salt, HBTU, DIPEA, DMF, 0° C.-RT, 16 h

Step-a: Synthesis of 2-(2-hydroxypropoxy)isoindoline-1,3-dione

To a stirred solution of 2-hydroxyisoindoline-1,3-dione (5.0 g, 30.65 mmol) and 2-methyloxirane (4.1 mL, 61.3 mmol) in toluene (50 mL) at RT was added DIPEA (0.6 mL, 3.1 mmol) and tetrabutylammonium bromide (0.99 g, 3.1 mmol). The reaction mixture was then refluxed for 5 h. The mixture was cooled to RT, concentrated under reduced pressure and extracted with EtOAc (2×100 mL) and water (50 mL). The combined organic layers were washed with water (30 mL), brine solution (30 mL), dried over anhydrous sodium sulfate and concentrated under vacuum. The residue was purified by combiflash column chromatography using 100% dichloromethane as an eluent to afford the titled compound (4.0 g, 59%); $^1$H NMR (400 MHz, DMSO-d$_6$): δ 7.85 (s, 4H), 4.80 (d, J=4.8 Hz, 1H), 4.03-4.00 (m, 1H), 3.96-3.93 (m, 2H), 1.14 (d, J=6.0 Hz, 3H); LC-MS: m/z 222.1 (M+1)$^+$.

Step-b: Synthesis of 1-(aminooxy)propan-2-ol hydrochloride

A solution of 2-(2-hydroxypropoxy)isoindoline-1,3-dione (2.0 g, 9.0 mmol) in 6 N aqueous hydrochloric acid (15 mL) was stirred at RT for 16 h. The solid precipitated in the reaction mixture was removed by filtration and filtrate was concentrated under reduced pressure to afford the titled compound as hydrochloride salt (1.0 g), crude compound was used in the next step without further purification.

Step-c: Synthesis of 2-(benzo[d]oxazol-2-ylamino)-N-(2-hydroxypropoxy)-1-methyl-1H-benzo[d]imidazole-5-carboxamide To a stirred solution of 2-(benzo[d]oxazol-2-ylamino)-1-methyl-1H-benzo[d]imidazole-5-carboxylic acid (100 mg, 0.32 mmol) in DMFA (5 mL) at 0° C. was added N-ethyldiisopropyl amine (0.06 mL, 0.32 mmol) and HBTU (122 mg, 0.32 mmol). The reaction mixture was stirred for 30 min, followed by the addition of 1-(aminooxy)propan-2-ol hydrochloride (41 mg, 0.32 mmol) and stirring was continued at RT for 16 h. Once the reaction was completed (monitored by TLC), the reaction mixture was diluted with cold water (20 mL) and extracted with ethyl acetate (2×50 mL). The combined organic layers were washed with water (30 mL), brine solution (30 mL), dried over anhydrous sodium sulfate and concentrated under vacuum. The residue was purified by preparative HPLC method to afford the titled compound (35 mg, 28%).

| Preparative HPLC purification method details: | |
|---|---|
| DILUTION: | THF:ACN:WATER |
| MOBILE PHASE A: | 100% Water |
| MOBILE PHASE B: | 100% ACETONITRILE |
| GRADIENT: | 0/10, 6/20, 10/80 |
| FLOW: | 15 ml/min |
| COLUMN: | Luna (250 × 21.1 × 5 μm) |

$^1$H NMR (400 MHz, DMSO-$d_6$): δ 12.30 (bs, 1H), 11.7 (bs, 1H), 8.01 (d, J=1.2 Hz, 1H), 7.63 (dd, J=1.2 Hz, J=8.0 Hz, 1H), 7.48 (d, J=8.8 Hz, 2H), 7.43 (d, J=7.6 Hz, 1H), 7.21 (t, J=7.6 Hz, 1H), 7.12 (t, J=7.6 Hz, 1H), 4.90 (bs, 1H), 3.92-3.89 (m, 1H), 3.78-3.74 (m, 2H), 3.63 (s, 3H), 1.10 (d, J=6.4 Hz, 3H); LC-MS: m/z 382.05 (M+1)$^+$.

Example 121. Synthesis of 2-(benzo[d]oxazol-2-ylamino)-N-(2-(2-(dimethylamino)acetamido)ethoxy)-1-methyl-1H-benzo[d]imidazole-5-carboxamide

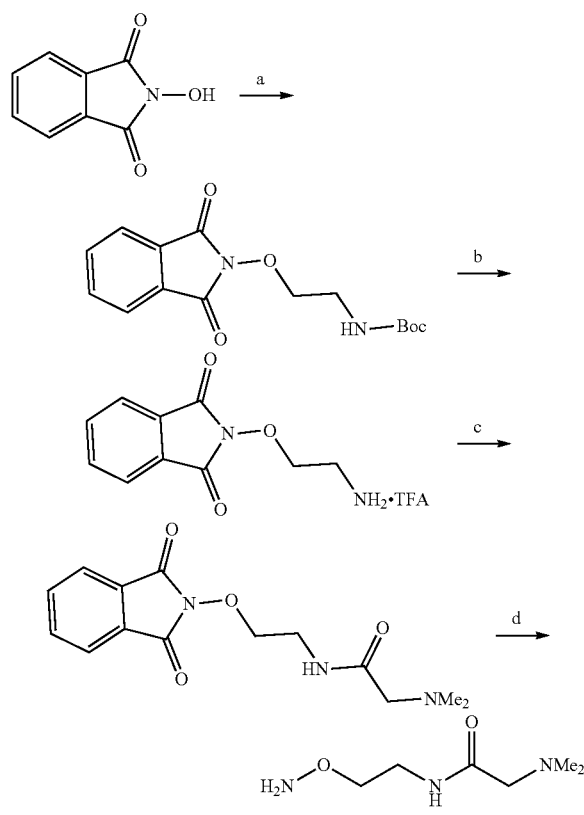

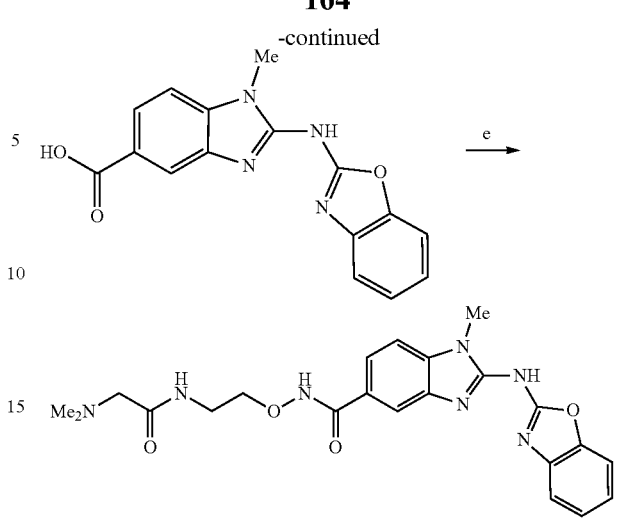

Conditions: a) tert-butyl (2-hydroxyethyl)carbamate, DIAD, Triphenyl phosphine, THF, 0° C.-RT, 16 h; b) TFA, DCM 0° C.-RT, 3 h; c) dimethylglycine, HATU, DIPEA, DMF, 0° C.-RT, 16 h; d) Hydrazine hydrate, Methanol, reflux, 4 h; e) N-(2-aminooxy)ethyl)-2-(dimethylamino)acetamide, HBTU, DIPEA, DMF, 0° C.-RT, 16 h Step-a: Synthesis of tert-butyl (2-((1,3-dioxoisoindolin-2-yl)oxy)ethyl)carbamate To a stirred solution of 2-hydroxyisoindoline-1,3-dione (5.0 g, 30.67 mmol) in THF (150 mL) at 0° C. was added tert-butyl (2-hydroxyethyl)carbamate (4.93 g, 30.67 mmol) and triphenylphosphine (8.03 g, 30.67 mmol). The reaction mixture was stirred for 10 min followed by the addition of diisopropyl azodicarboxylate (6.19 g, 30.67 mmol) and continued stirring at RT for 16 h. The reaction mixture was diluted with water (50 mL) and extracted with ethyl acetate (2×100 mL). The combined organic layers were washed with water (50 mL), brine solution (50 mL), dried over anhydrous sodium sulfate and concentrated under vacuum. The residue was purified by combiflash column chromatography using 10% ethyl acetate in hexane as an eluent to afford the titled compound (12.0 g, semi pure) which was used in the next step without any further purification; $^1$H NMR (400 MHz, DMSO-$d_6$): δ 7.86 (s, 4H), 6.82 (bs, 1H), 4.13 (t, J=5.6 Hz, 2H), 3.28-3.27 (m, 2H), 1.37 (s, 9H); LC-MS: m/z 207.0 (M-Boc)$^+$.

Step-b: Synthesis of 2-(2-aminoethoxy)isoindoline-1,3-dione trifluoroacetic acid salt To a stirred solution of tert-butyl (2-((1,3-dioxoisoindolin-2-yl)oxy)ethyl)carbamate (12.0 g, 39.08 mmol) in DCM (150 mL) at 0° C. was added trifluoroacetic acid (20 mL) and stirred at RT for 3 h. The reaction mixture was concentrated under vacuum, the residue was stirred in diethyl ether (50 mL) and the solid precipitated was filtered and dried under vacuum to afford the titled compound (3.8 g, 32%); $^1$H NMR (400 MHz, DMSO-$d_6$): δ 8.05 (bs, 3H), 7.90 (s, 4H), 4.34 (t, J=5.2 Hz, 2H), 3.38 (q, J=7.2 Hz, 2H).

Step-c: Synthesis of 2-(dimethylamino)-N-(2-((1,3-dioxoisoindolin-2-yl)oxy)ethyl)acetamide To a stirred solution of 2-(2-aminoethoxy)isoindoline-1,3-dione trifluoroacetate (1.0 g, 4.85 mmol) in DMFA (15 mL) at 0° C. was added dimethylglycine (499 mg, 4.85 mmol), N-ethyldiisopropyl amine (1.69 mL, 9.7 mmol) and HATU (2.02 g, 5.34 mmol) and the reaction mixture was stirred at RT for 16 h. Once the reaction was completed (monitored by TLC), the reaction mixture was diluted with water (50 mL) and extracted with ethyl acetate (2×50 mL). The combined organic layers were washed with water (30 mL), brine solution (30 mL), dried over anhydrous sodium sulfate and concentrated under vacuum. The residue was purified by combiflash column chromatography using 2% methanol in dichloromethane as an eluent to afford the titled compound (280 mg, 29%); LC-MS: m/z 292.1 (M+1)$^+$.

Step-d: Synthesis of N-(2-(aminooxy)ethyl)-2-(dimethylamino)acetamide

To a stirred solution of 2-(dimethylamino)-N-(2-((1,3-dioxoisoindolin-2-yl)oxy)ethyl)acetamide (280 mg, 0.96 mmol) in methanol (5 mL) at RT was added hydrazine hydrate (0.3 mL) and refluxed for 4 h. The reaction mixture was cooled to RT and concentrated on rotary evaporator. The residue obtained was stirred in diethyl ether (30 mL) and filtered. The filtrate was concentrated under vacuum to afford the titled compound (120 mg, 77%); $^1$H NMR (400 MHz, CDCl$_3$): δ 7.39 (bs, 1H), 5.50 (bs, 2H), 3.73 (t, J=5.2 Hz, 2H), 3.57-3.47 (m, 2H), 2.96 (s, 2H), 2.29 (s, 6H).

Step-e: Synthesis of 2-(benzo[d]oxazol-2-ylamino)-N-(2-(2-(dimethylamino)acetamido)ethoxy)-1-methyl-1H-benzo[d]imidazole-5-carboxamide To a stirred solution of 2-(benzo[d]oxazol-2-ylamino)-1-methyl-1H-benzo[d]imidazole-5-carboxylic acid (80 mg, 0.26 mmol) in DMFA (2 mL) at 0° C. was added N-ethyldiisopropyl amine (0.04 mL, 0.26 mmol) and HBTU (98 mg, 0.26 mmol). The reaction mixture was stirred for 30 min, followed by the addition of N-(2-(aminooxy)ethyl)-2-(dimethylamino)acetamide (41 mg, 0.26 mmol). The reaction mixture was then stirred at RT for 16 h. Once the reaction was completed (monitored by TLC), the reaction mixture was diluted with cold water (15 mL) and extracted with ethyl acetate (2×20 mL). The aqueous layer was concentrated under vacuum. The residue obtained was purified by preparative HPLC method to afford the titled compound (10 mg, 9%).

Preparative HPLC purification method details:

DILUTION: THF:ACN:WATER

MOBILE PHASE A: 10 mM aqueous ammonium acetatae

MOBILE PHASE B: 100% ACETONITRILE

GRADIENT: T/% B: 0/10, 10/50, 17/65, 19/90

FLOW: 15 ml/min

COLUMN: Phenomenex Luna (250×21.2×5 μm)

$^1$H NMR (400 MHz, DMSO-d$_6$): δ 12.30 (bs, 1H), 11.60 (bs, 1H), 8.01 (bs, 2H), 7.64 (d, J=8.8 Hz, 1H), 7.49-7.42 (m, 3H), 7.20 (t, J=8.0 Hz, 1H), 7.12 (t, J=8.0 Hz, 1H), 3.90 (s, 2H), 3.63 (s, 3H), 3.41 (q, J=6.0 Hz, 2H), 2.89 (s, 2H), 2.32 (s, 6H); LC-MS: m/z 452.2 (M+1)$^+$.

Example 122. Synthesis of N-(2-(dimethylamino)ethoxy)-1-methyl-2-((6-(trifluoromethyl)benzo[d]oxazol-2-yl)amino)-1H-benzo[d]imidazole-5-carboxamide

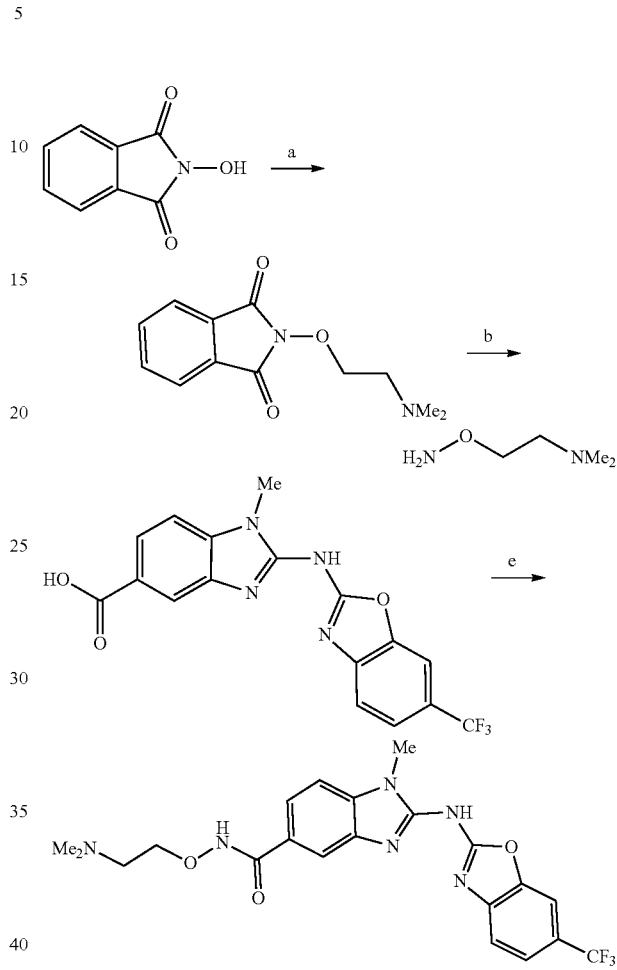

Conditions: a) 1-Chloro-2-dimethylaminoethane hydrochloride, TEA, DMF, 60° C., 16 h; b) Hydrazine hydrate, MeOH, reflux, 4 h; c) 2-(aminooxy)-N,N-dimethylethan-1-amine, HBTU, DIPEA, DMF, 0° C.-RT, 16 h Step-a: Synthesis of 2-(2-(dimethylamino)ethoxy)isoindoline-1,3-dione The title compound was synthesized using the same procedure which was followed for Example 119 Step-a using N-hydroxyphthalimide and 1-chloro-2-dimethylaminoethane hydrochloride as starting materials and 4 equivalents of triethyl amine (Yield: 17%); $^1$H NMR (400 MHz, DMSO-d$_6$): δ 7.86 (s, 4H), 4.21 (t, J=5.4 Hz, 2H), 2.61 (t, J=5.4 Hz, 2H), 2.18 (s, 6H); LC-MS: m/z 235.1 (M+1)$^+$.

Step-b: Synthesis of 2-(aminooxy)-N,N-dimethylethan-1-amine

The title compound was synthesized using the same procedure which was followed for Example 119 Step-b using 2-(2-(dimethylamino)ethoxy)isoindoline-1,3-dione as starting material (Yield: 34%); $^1$H NMR (400 MHz, DMSO-d$_6$): δ 5.88 (bs, 2H), 3.58 (t, J=5.9 Hz, 2H), 2.38 (t, J=5.9 Hz, 2H), 2.13 (s, 6H); LC-MS: m/z 105.20 (M+1)$^+$.

Step-c: Synthesis of N-(2-(dimethylamino)ethoxy)-1-methyl-2-((6-(trifluoromethyl)benzo[d]oxazol-2-yl)amino)-1H-benzo[d]imidazole-5-carboxamide The title compound was synthesized using the same procedure which was followed for Example 6 Step-e using 1-methyl-2-((6-(trifluoromethyl)benzo[d]oxazol-2-yl)amino)-1H-benzo[d]imidazole-5-carboxylic acid and 2-(aminooxy)-N,N-dimethylethan-1-amine as starting materials (Yield: 15%); $^1$H NMR (400 MHz, DMSO-$d_6$): δ 12.40 (bs, 2H), 8.01 (s, 1H), 7.82 (s, 1H), 7.66 (d, J=1.5 Hz, 1H), 7.64 (d, J=1.5 Hz, 1H), 7.61-7.51 (m, 2H), 3.99 (t, J=5.4 Hz, 2H), 3.66 (s, 3H), 2.55 (t, J=5.3 Hz, 2H), 2.22 (s, 6H); LC-MS: m/z 463.50 (M+1)$^+$.

Example 123. Synthesis of 2-(benzo[d]oxazol-2-ylamino)-N-(2-(dimethylamino)ethoxy)-1-methyl-1H-benzo[d]imidazole-5-carboxamide The title compound was synthesized using the same procedure which was followed for Example 6 Step-e using 2-(aminooxy)-N,N-dimethylethan-1-amine and 2-(benzo[d]oxazol-2-ylamino)-1-methyl-1H-benzo[d]imidazole-5-carboxylic acid as starting materials.

$^1$H NMR (400 MHz, DMSO-$d_6$): δ 12.30 (bs, 1H), 8.00 (s, 1H), 7.63 (d, J=8.4 Hz, 1H), 7.48 (d, J=8.4 Hz, 2H), 7.43 (d, J=8.0 Hz, 1H), 7.21 (t, J=7.2 Hz, 1H), 7.12 (t, J=7.6 Hz, 1H), 3.99 (t, J=6.0 Hz, 2H), 3.82 (s, 3H), 2.56 (t, J=5.2 Hz, 2H), 2.32 (s, 6H); LC-MS: m/z 395.1 (M−1)$^+$.

Example 124. Synthesis of N-(2-methoxyethoxy)-1-methyl-2-((6-(trifluoromethyl)benzo[d]oxazol-2-yl)amino)-1H-benzo[d]imidazole-5-carboxamide

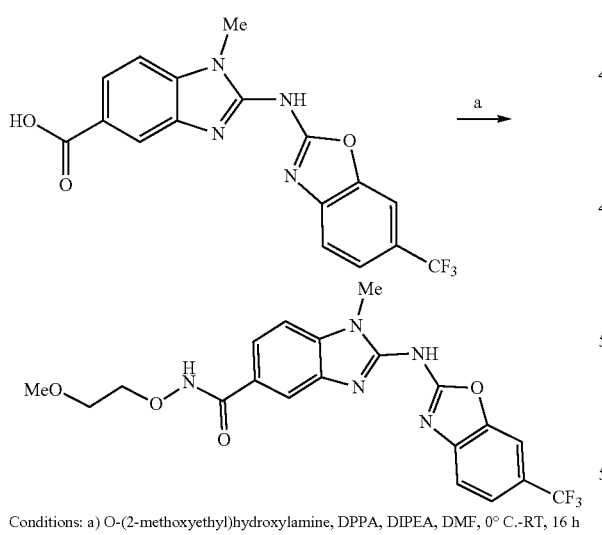

Conditions: a) O-(2-methoxyethyl)hydroxylamine, DPPA, DIPEA, DMF, 0° C.-RT, 16 h The title compound was synthesized using the same procedure which was followed for compound 1i using 1-methyl-2-((6-(trifluoromethyl)benzo[d]oxazol-2-yl)amino)-1H-benzo[d]imidazole-5-carboxylic acid and O-(2-methoxyethyl)hydroxylamine as starting materials (Yield: 28%); $^1$H NMR (400 MHz, DMSO-$d_6$): δ 12.39 (bs, 1H), 11.72 (s, 1H), 8.03 (s, 1H), 7.83 (s, 1H), 7.67 (d, J=8.3 Hz, 1H), 7.61 (d, J=8.3 Hz, 1H), 7.57-7.52 (m, 2H), 4.04 (t, J=4.4 Hz, 2H), 3.66 (s, 3H), 3.59 (t, J=4.4 Hz, 2H), 3.30 (s, 3H merged in DMSO); LC-MS: m/z 450.15 (M+1)$^+$.

Example 125. Synthesis of N-(2-hydroxyethoxy)-1-methyl-2-((6-(trifluoromethyl)benzo[d]oxazol-2-yl)amino)-1H-benzo[d]imidazole-5-carboxamide

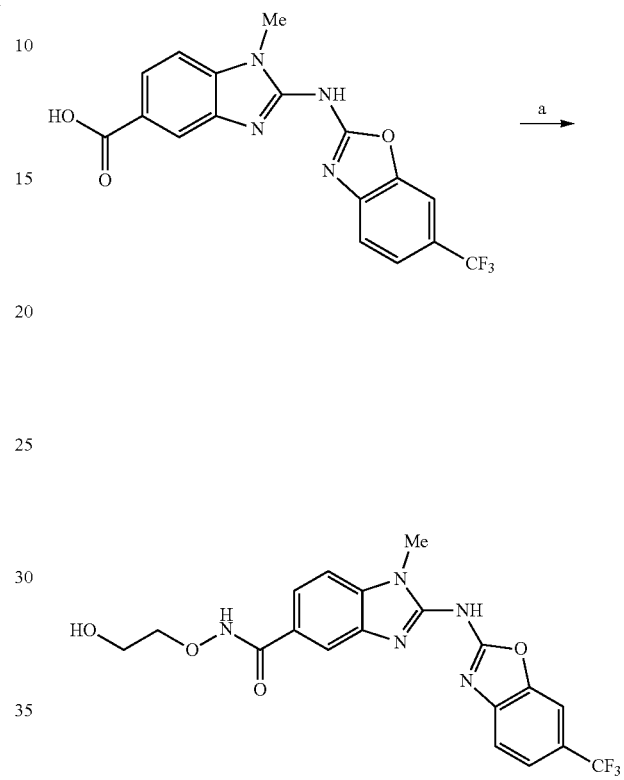

Conditions: a) 2-(aminooxy)ethan-1-ol, HBTU, DIPEA, DMF, 0° C.-RT, 16 h

The title compound was synthesized using the same procedure which was followed for Example 6 Step-e using 1-methyl-2-((6-(trifluoromethyl)benzo[d]oxazol-2-yl)amino)-1H-benzo[d]imidazole-5-carboxylic acid and 2-(aminooxy)ethan-1-ol as starting materials (Yield: 51%); $^1$H NMR (400 MHz, DMSO-$d_6$): δ 12.39 (bs, 1H), 11.73 (s, 1H), 8.04 (s, 1H), 7.84 (s, 1H), 7.68 (d, J=8.3 Hz, 1H), 7.61 (d, J=8.3 Hz, 1H), 7.57-7.53 (m, 2H), 4.78 (s, 1H), 3.94 (t, J=4.9 Hz, 2H), 3.67 (s, 3H), 3.66-3.63 (m, 2H); LC-MS: m/z 436.15 (M+1)$^+$.

Example 126. Synthesis of N-(2-hydroxyethoxy)-1-methyl-2-((6-(trifluoromethoxy)benzo[d]oxazol-2-yl)amino)-1H-benzo[d]imidazole-5-carboxamide

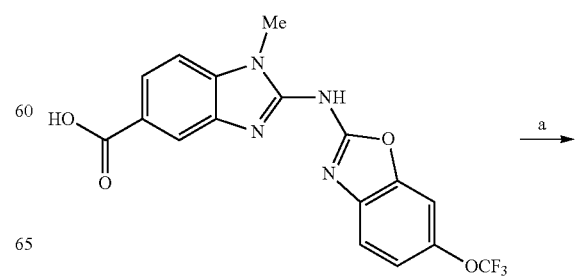

-continued

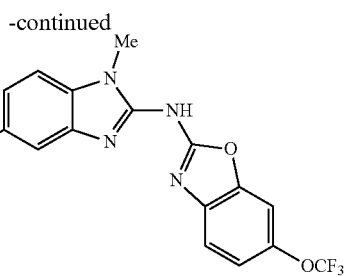

Conditions: a) 2-(aminooxy)ethan-1-ol, HBTU, DIPEA, DMF, 0° C.-RT, 16 h

The title compound was synthesized using the same procedure which was followed for Example 6 Step-e using 1-methyl-2-((6-(trifluoromethoxy)benzo[d]oxazol-2-yl)amino)-1H-benzo[d]imidazole-5-carboxylic acid and 2-(aminooxy)ethan-1-ol as starting materials (Yield: 58%); ¹H NMR (400 MHz, DMSO-d₆): δ 12.30 (bs, 1H), 11.72 (s, 1H), 8.02 (d, J=1.0 Hz, 1H), 7.66 (d, J=6.9 Hz, 1H), 7.58 (s, 1H), 7.53-7.51 (m, 2H), 7.22 (d, J=8.3 Hz, 1H), 4.78 (t, J=5.6 Hz, 1H), 3.94 (t, J=4.7 Hz, 2H), 3.64-3.62 (m, 5H); LC-MS: m/z 451.9 (M+1)⁺.

Example 127. Synthesis of N-(2-methoxyethoxy)-1-methyl-2-((6-(trifluoromethoxy)benzo[d]oxazol-2-yl)amino)-1H-benzo[d]imidazole-5-carboxamide

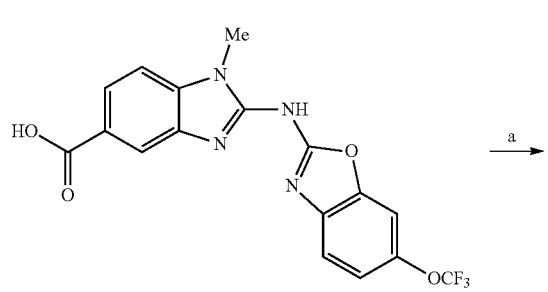

Conditions: a) O-(2-methoxyethyl)hydroxylamine, DPPA, DIPEA, DMF, 0° C.-RT, 16 h The title compound was synthesized using the same procedure which was followed for compound 1i using 1-methyl-2-((6-(trifluoromethoxy)benzo[d]oxazol-2-yl)amino)-1H-benzo[d]imidazole-5-carboxylic acid and O-(2-methoxyethyl)hydroxylamine as starting materials (Yield: 28%); ¹H NMR (400 MHz, DMSO-d₆): δ 12.30 (bs, 1H), 11.70 (s, 1H), 8.01 (d, J=1.4 Hz, 1H), 7.65 (dd, J=1.5 Hz, J=8.3 Hz, 1H), 7.58 (d, J=1.5 Hz, 1H), 7.53-7.49 (m, 2H), 7.22 (dd, J=1.5 Hz, J=8.3 Hz, 1H), 4.05-4.02 (m, 2H), 3.64 (s, 3H), 3.61-3.58 (m, 2H), 3.31 (s, 3H); LC-MS: m/z 466.0 (M+1)⁺.

Example 128. Synthesis of N-(2-hydroxyethoxy)-2-((6-(2-methoxyethoxy)benzo[d]oxazol-2-yl)amino)-1-methyl-1H-benzo[d]imidazole-5-carboxamide The title compound was synthesized using the same procedure which was followed for Example 6 Step-e using 2-(aminooxy)ethan-1-ol and 2-((6-(2-methoxyethoxy)benzo[d]oxazol-2-yl)amino)-1-methyl-1H-benzo[d]imidazole-5-carboxylic acid as starting materials. ¹H NMR (400 MHz, DMSO-d₆): δ 12.20 (bs, 1H), 11.68 (s, 1H), 7.98 (s, 1H), 7.63 (d, J=8.0 Hz, 1H), 7.46 (d, J=8.4 Hz, 1H), 7.35 (d, J=8.8 Hz, 1H), 7.12 (s, 1H), 6.82 (d, J=8.8 Hz, 1H), 4.78 (s, 1H), 4.11 (bs, 2H), 3.93 (bs, 2H), 3.67-3.61 (m, 7H), 3.32 (s, 3H merged with DMSO moisture peak); LC-MS: m/z 442.2 (M+1)⁺.

Example 129. Synthesis of N-(2-hydroxyethoxy)-2-((6-(2-hydroxyethoxy)benzo[d]oxazol-2-yl)amino)-1-methyl-1H-benzo[d]imidazole-5-carboxamide

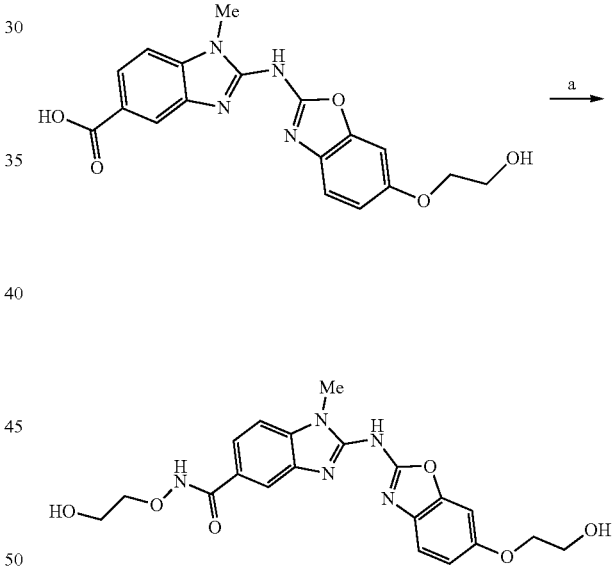

Conditions: a) 2-(aminooxy)ethan-1-ol, HBTU, DIPEA, DMF, 0° C.-RT, 16 h

The title compound was synthesized using the same procedure which was followed for Example 6 Step-e using 2-((6-(2-hydroxyethoxy)benzo[d]oxazol-2-yl)amino)-1-methyl-1H-benzo[d]imidazole-5-carboxylic acid and 2-(aminooxy)ethan-1-ol as starting materials. The crude product was purified by combiflash chromatography using 10% methanol in DCM as an eluent to afford the title compound (Yield: 14%); ¹H NMR (400 MHz, DMSO-d₆): δ 12.15 (bs, 1H), 11.67 (s, 1H), 7.98 (s, 1H), 7.63 (d, J=7.6 Hz, 1H), 7.45 (d, J=8.8 Hz, 1H), 7.35 (d, J=8.4 Hz, 1H), 7.11 (s, 1H), 6.82 (d, J=8.8 Hz, 1H), 4.83 (bs, 1H), 4.77 (bs, 1H), 4.01 (t, J=4.4 Hz, 2H), 3.93 (t, J=4.4 Hz, 2H), 3.72 (bs, 2H), 3.61 (bs, 5H); LC-MS: m/z 428.2 (M+1)⁺.

Example 130. Synthesis of 2-((5-fluoro-6-(trifluoromethyl)benzo[d]oxazol-2-yl)amino)-N-(2-hydroxyethoxy)-1-methyl-1H-benzo[d]imidazole-5-carboxamide

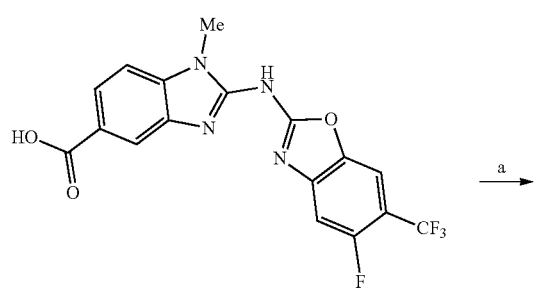

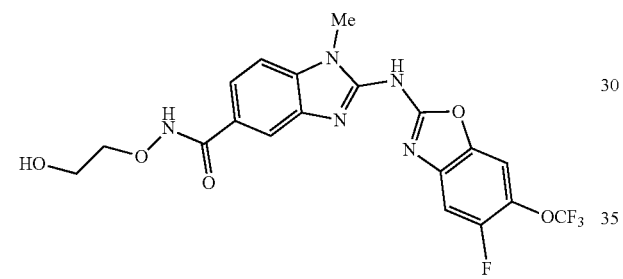

Conditions: a) 2-(aminooxy)ethan-1-ol, HBTU, DIPEA, DMF, 0° C.-RT, 16 h

The title compound was synthesized using the same procedure which was followed for Example 6 Step-e using 2-((5-fluoro-6-(trifluoromethyl)benzo[d]oxazol-2-yl)amino)-1-methyl-1H-benzo[d]imidazole-5-carboxylic acid and 2-(aminooxy)ethan-1-ol as starting materials (Yield: 61%); $^1$H NMR (400 MHz, DMSO-$d_6$): δ 12.45 (bs, 1H), 11.74 (s, 1H), 8.03 (s, 1H), 7.85 (d, J=5.6 Hz, 1H), 7.68 (d, J=8.4 Hz, 1H), 7.55 (d, J=8.0 Hz, 1H), 7.45 (d, J=11.2 Hz, 1H), 4.50 (bs, 1H), 3.94 (t, J=4.4 Hz, 2H), 3.66 (s, 3H), 3.64-3.63 (m, 2H); LC-MS: m/z 454.1 (M+1)$^+$.

Example 131 Synthesis of N-(2-hydroxyethoxy)-1-methyl-2-((6-methyl-4,5,6,7-tetrahydrobenzo[d]thiazol-2-yl)amino)-1H-benzo[d]imidazol-5-carboxamide

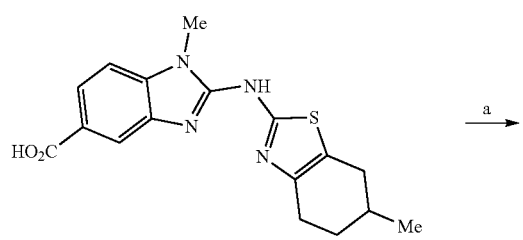

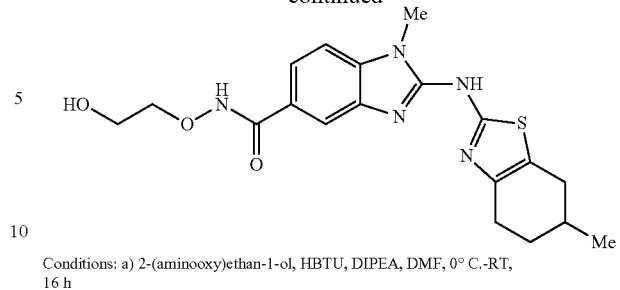

Conditions: a) 2-(aminooxy)ethan-1-ol, HBTU, DIPEA, DMF, 0° C.-RT, 16 h

The title compound was synthesized using the same procedure which was followed for Example 6 Step-e using 1-methyl-2-((6-methyl-4,5,6,7-tetrahydrobenzo[d]thiazol-2-yl)amino)-1H-benzo[d]imidazole-5-carboxylic acid and 2-(aminooxy)ethan-1-ol as starting materials (Yield: 43%); $^1$H NMR (400 MHz, DMSO-$d_6$): δ 12.05 (bs, 1H), 11.56 (s, 1H), 7.83 (s, 1H), 7.55 (dd, J=1.0 Hz, J=8.3 Hz, 1H), 7.35 (d, J=8.3 Hz, 1H), 4.78 (bs, 1H), 3.92 (t, J=4.9 Hz, 2H), 3.63-3.61 (m, 5H), 2.67-2.59 (m, 1H), 2.50 (2H merged with DMSO peak), 2.18-2.11 (m, 1H), 1.87-1.84 (m, 2H), 1.46-1.43 (m, 1H), 1.05 (d, J=6.3 Hz, 3H); LC-MS: m/z 402.2 (M+1)$^+$.

Example 132. Synthesis of 2-((6-acetylbenzo[d]oxazol-2-yl)amino)-N-(2-methoxyethoxy)-1-methyl-1H-benzo[d]imidazole-5-carboxamide

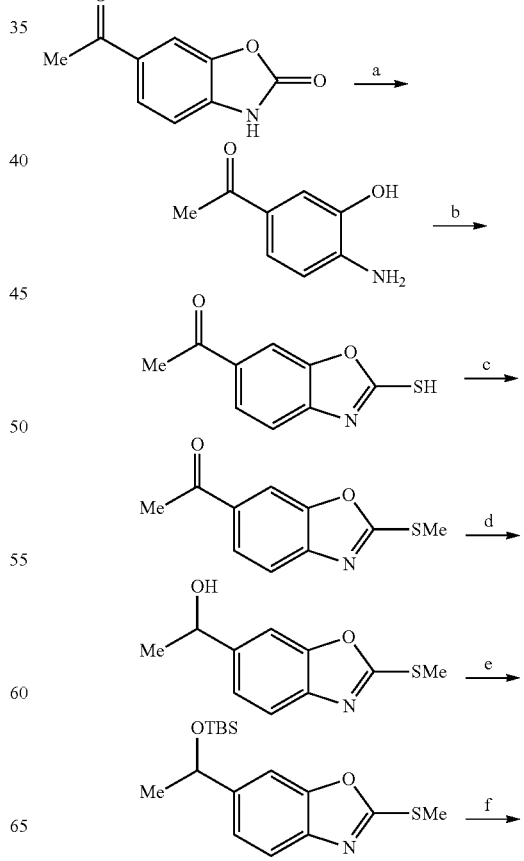

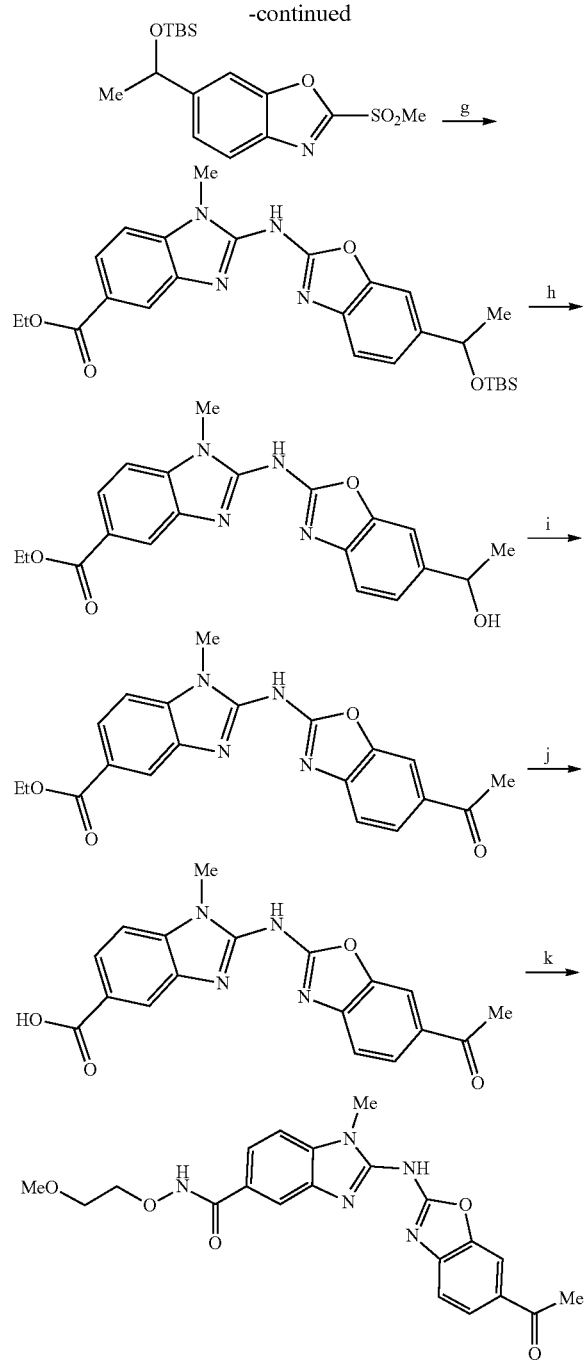

Conditions: a) 10% Aq. NaOH Solution, Reflux, 4 h; b) Potassium ethyl xanthate, EtOH, Reflux, 16 h; c) K₂CO₃, MeI, ACN, RT, 3 h; d) NaBH₄, MeOH, 0° C.-RT, 1 h; e) TBDMSCl, Imidazole, DCM, 0° C.-RT, 2 h; f) m-CPBA, DCM, 0° C.- RT, 4 h; g) NaH, ethyl 2-amino-1-methyl-1H-benzo[d]imidazole-5-carboxylate, 1,4-Dioxane, RT, 16 h; h) TBAF in THF, THF, 0° C.-RT, 16 h; i) Dess-martin periodinane, DCM, 0° C.-RT, 1 h; j) LiOH•H₂O, THF, EtOH, H₂O, 60° C., 16 h; k) O-(2-methoxyethyl)hydroxylamine, HBTU, DIPEA, DMF, 0° C.-RT, 16 h Step-a: Synthesis of 1-(4-amino-3-hydroxyphenyl)ethan-1-one A mixture of 6-acetylbenzo[d]oxazol-2(3H)-one (5.0 g, 28.2 mmol) in 10% aqueous sodium hydroxide (50 mL) was refluxed for 4 h. The reaction mixture was cooled to RT, acidified with 3 N HCl followed by basification to pH~8 with saturated sodium carbonate solution. The precipitated solid was filtered and dried under vacuum afford the title compound (4.1 g, 98%); ¹H NMR (400 MHz, DMSO-d₆): δ 9.34 (s, 1H), 7.28 (dd, J=2.0 Hz, J=8.4 Hz, 1H), 7.22 (d, J=2.0 Hz, 1H), 6.58 (d, J=8.4 Hz, 1H), 5.44 (s, 2H), 2.36 (s, 3H).

Step-b: Synthesis of 1-(2-mercaptobenzo[d]oxazol-6-yl)ethan-1-one

The title compound was synthesized using the same procedure which was followed for Example 32 Step-c using 1-(4-amino-3-hydroxyphenyl)ethan-1-one (Yield: 100%); ¹H NMR (400 MHz, DMSO-d₆): δ 14.2 (bs, 1H), 8.04 (s, 1H), 7.94 (d, J=8.0 Hz, 1H), 7.33 (d, J=8.0 Hz, 1H), 2.60 (s, 3H); LC-MS: m/z 192.02 (M−1)⁻.

Step-c: Synthesis of 1-(2-(methylthio)benzo[d]oxazol-6-yl)ethan-1-one

The title compound was synthesized using the same procedure which was followed for compound 1b using 1-(2-mercaptobenzo[d]oxazol-6-yl)ethan-1-one as starting material (Yield: 78%); ¹H NMR (400 MHz, DMSO-d₆): δ 8.22 (s, 1H), 7.98 (d, J=8.4 Hz, 1H), 7.73 (d, J=8.0 Hz, 1H), 2.80 (s, 3H), 2.67 (s, 3H).

Step-d: Synthesis of 1-(2-(methylthio)benzo[d]oxazol-6-yl)ethan-1-ol

To a stirred solution of 1-(2-(methylthio)benzo[d]oxazol-6-yl)ethan-1-one (4.1 g, 19.8 mmol) in methanol (80 mL) at 0° C. was added sodium borohydride (1.12 g, 29.7 mmol) and the reaction mixture was stirred for 1 h. The reaction mixture was quenched with cold water (100 mL) and extracted with EtOAc (2×150 mL). The combined organic layers were washed with water (50 mL), brine (50 mL), dried over anhydrous sodium sulfate and concentrated under vacuum to afford the titled compound (4.1 g, 100%); ¹H NMR (400 MHz, DMSO-d₆): δ 7.57-7.53 (m, 2H), 7.31 (dd, J=1.2 Hz, J=8.0 Hz, 1H), 5.28 (d, J=3.6 Hz, 1H), 4.85-4.80 (m, 1H), 2.74 (s, 3H), 1.35 (d, J=6.4 Hz, 3H).

Step-e: Synthesis of 6-(1-((tert-butyldimethylsilyl)oxy)ethyl)-2-(methylthio)benzo[d]oxazole To a stirred solution of 1-(2-(methylthio)benzo[d]oxazol-6-yl)ethan-1-ol (4.1 g, 19.6 mmol) in DCM (80 mL) at 0° C. was added imidazole (2.0 g, 29.4 mmol) and stirred for 5 min followed by the addition of TBDMSCl (3.5 g, 23.5 mmol) and it was stirred at RT for 2 h. The reaction mixture was diluted with water (100 mL) and extracted with DCM (2×150 mL). The combined organic layers were washed with water (50 mL), brine (50 mL), dried over anhydrous sodium sulfate and concentrated under vacuum to afford the titled compound (6.6 g, 100%); ¹H NMR (400 MHz, DMSO-d₆): δ 7.63-7.61 (m, 2H), 7.36 (d, J=8.0 Hz, 1H), 5.08 (q, J=6.4 Hz, 1H), 2.80 (s, 3H), 1.42 (d, J=6.0 Hz, 3H), 0.91 (s, 9H), 0.2 (s, 6H); LC-MS: m/z 324.1 (M+1)⁺.

Step-f: Synthesis of 6-(1-((tert-butyldimethylsilyl)oxy)ethyl)-2-(methylsulfonyl)-benzo[d]oxazole The title compound was synthesized using the same procedure which was followed for compound 1c using 6-(1-((tert-butyldimethylsilyl)oxy)ethyl)-2-(methylthio)benzo[d]oxazole as starting material and stirred for 4 h (Yield: 100%); $^1$H NMR (400 MHz, DMSO-d$_6$): δ 7.96-7.49 (m, 3H), 5.14-5.11 (m, 1H), 3.66 (s, 3H), 1.40 (d, J=6.0 Hz, 3H), 0.88 (s, 9H), 0.2 (s, 3H), −0.2 (s, 3H).

Step-g: Synthesis of ethyl 2-((6-(1-((tert-butyldimethylsilyl)oxy)ethyl)benzo[d]oxazol-2-yl)amino)-1-methyl-1H-benzo[d]imidazole-5-carboxylate The title compound was synthesized using the same procedure which was followed for compound 1g using ethyl 2-amino-1-methyl-1H-benzo[d]imidazole-5-carboxylate and 6-(1-((tert-butyldimethylsilyl)oxy)ethyl)-2-(methylsulfonyl)benzo[d]oxazole as starting materials (Yield: 31%); $^1$H NMR (400 MHz, DMSO-d$_6$): δ 12.3 (bs, 1H), 8.23 (d, J=1.6 Hz, 1H), 7.87 (dd, J=1.6 Hz, J=8.4 Hz, 1H), 7.51 (d, J=8.8 Hz, 1H), 7.42-7.39 (m, 2H), 7.20 (d, J=8.0 Hz, 1H), 5.0 (d, J=6.4 Hz, 1H), 4.32 (q, J=7.6 Hz, 2H), 3.63 (s, 3H), 1.40-1.33 (m, 6H), 0.87 (s, 9H), 0.001 (s, 3H), −0.036 (s, 3H).

Step-h: Synthesis of ethyl 2-((6-(1-hydroxyethyl)benzo[d]oxazol-2-yl)amino)-1-methyl-1H-benzo[d]imidazole-5-carboxylate To a stirred solution of ethyl 2-((6-(1-((tert-butyldimethylsilyl)oxy)ethyl)benzo[d]oxazol-2-yl)amino)-1-methyl-1H-benzo[d]imidazole-5-carboxylate (1.4 g, 2.8 mmol) in THF (30 mL) at 0° C. was added 1 M TBAF in THF (5.7 mL, 5.7 mmol) and the reaction mixture was stirred at RT for 16 h. The reaction mixture was quenched with saturated ammonium chloride solution (50 mL) and extracted with EtOAc (2×100 mL). The combined organic layers were washed with water (30 mL), brine (30 mL), dried over anhydrous sodium sulfate and concentrated under vacuum. The residue was stirred in pentane for 15 min and solid obtained was filtered and dried under vacuum to afford the titled compound (1.1 g, 100%); $^1$H NMR (400 MHz, DMSO-d$_6$): δ 12.3 (bs, 1H), 8.23 (s, 1H), 7.87 (d, J=8.4 Hz, 1H), 7.51 (d, J=8.4 Hz, 1H), 7.41-7.39 (m, 2H), 7.19 (d, J=7.6 Hz, 1H), 5.16 (bs, 1H), 4.80 (bs, 1H), 4.33 (q, J=7.2 Hz, 2H), 3.63 (s, 3H), 1.40-1.35 (m, 6H); LC-MS: m/z 381.15 (M+1)$^+$.

Step-i: Synthesis of ethyl 2-((6-acetylbenzo[d]oxazol-2-yl)amino)-1-methyl-1H-benzo[d]imidazole-5-carboxylate To a stirred solution of ethyl 2-((6-(1-hydroxyethyl)benzo[d]oxazol-2-yl)amino)-1-methyl-1H-benzo[d]imidazole-5-carboxylate (1.1 g, 2.9 mmol) in DCM (30 mL) at 0° C. was added Dess-martin periodinane (1.47 g, 3.5 mmol) and the reaction mixture was stirred for 1 h. The reaction mixture was diluted with DCM (100 mL), water (50 mL). The organic layer was washed with saturated sodium bicarbonate solution (2×50 mL), water (50), brine (30 mL), dried over anhydrous sodium sulfate and concentrated under vacuum to afford the titled compound (540 mg, 49%); $^1$H NMR (400 MHz, DMSO-d$_6$): δ 12.4 (bs, 1H), 8.26 (s, 1H), 8.00 (s, 1H), 7.91-7.89 (m, 2H), 7.58-7.51 (m, 2H), 4.34 (q, J=6.8 Hz, 2H), 3.87 (s, 3H), 2.66 (s, 3H), 1.35 (t, J=6.8 Hz, 3H); LC-MS: m/z 379.15 (M+1)$^+$.

Step-j: Synthesis of 2-((6-acetylbenzo[d]oxazol-2-yl)amino)-1-methyl-1H-benzo[d]-imidazole-5-carboxylic acid The title compound was synthesized using the same procedure which was followed for compound 1h using ethyl 2-((6-acetylbenzo[d]oxazol-2-yl)amino)-1-methyl-1H-benzo[d]imidazole-5-carboxylate as starting material (Yield: 68%); $^1$H NMR (400 MHz, DMSO-d$_6$): δ 12.8 (bs, 1H), 12.4 (s, 1H), 8.21 (s, 1H), 7.99 (s, 1H), 7.82-7.79 (m, 2H), 7.59-7.52 (m, 2H), 3.67 (s, 3H), 2.66 (s, 3H); LC-MS: m/z 351.1 (M+1)$^+$.

Step-k: Synthesis of 2-((6-acetylbenzo[d]oxazol-2-yl)amino)-N-(2-methoxyethoxy)-1-methyl-1H-benzo[d]imidazole-5-carboxamide The title compound was synthesized using the same procedure which was followed for Example 6 Step-e using 2-((6-acetylbenzo[d]oxazol-2-yl)amino)-1-methyl-1H-benzo[d]imidazole-5-carboxylic acid and O-(2-methoxyethyl)hydroxylamine as starting materials (Yield: 42%); $^1$H NMR (400 MHz, DMSO-d$_6$): δ 12.4 (bs, 1H), 11.7 (s, 1H), 8.02-7.99 (s, 2H), 7.99 (dd, J=1.6 Hz, J=8.4 Hz, 1H), 7.68-7.63 (m, 1H), 7.54-7.51 (m, 2H), 4.04 (t, J=4.4 Hz, 2H), 3.66 (s, 3H), 3.60 (t, J=4.4 Hz, 2H), 3.22 (s, 3H), 2.60 (s, 3H); LC-MS: m/z 424.15 (M+1)$^+$.

Example 133. Synthesis of N-(2-hydroxyethyl)-2-((6-(2-hydroxypropan-2-yl)benzo[d]oxazol-2-yl)amino)-1-methyl-1H-benzo[d]imidazole-5-carboxamide

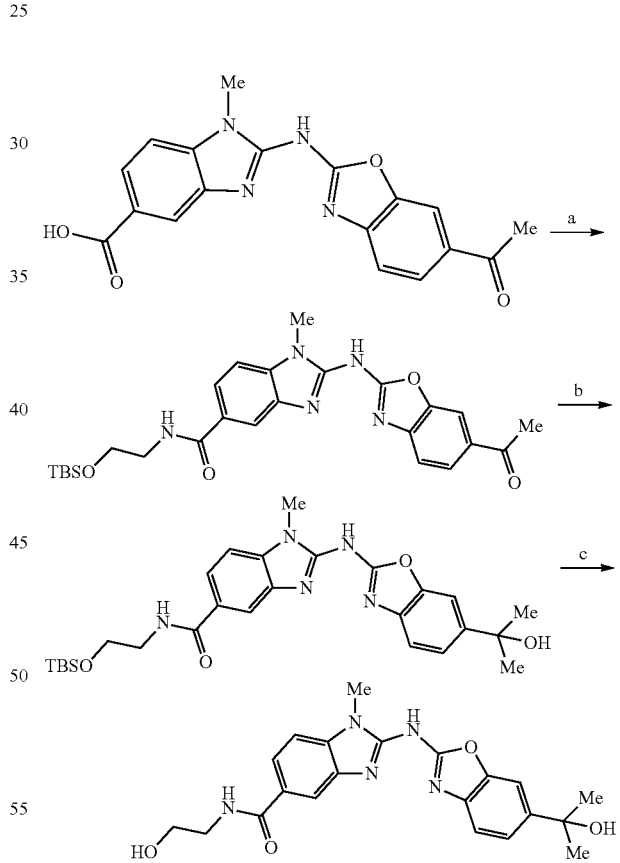

Conditions: a) 2-((tert-butyldimethylsilyl)oxy)ethan-1-amine, HBTU, DIPEA, DMF, 0° C.-RT, 16 h; b) CH$_3$MgBr in diethyl ether, THF, 0° C., 30 min; c) TBAF in THF, THF, 0° C.-RT, 4 h Step-a: Synthesis of 2-((6-acetylbenzo[d]oxazol-2-yl)amino)-N-(2-((tert-butyldimethylsilyl)oxy)ethyl)-1-methyl-1H-benzo[d]imidazole-5-carboxamide The title compound was synthesized using the same procedure which was followed for Example 6 Step-e using 2-((6-acetylbenzo[d]oxazol-2-yl)amino)-1-methyl-1H-benzo[d]imidazole-5-carboxylic acid and 2-((tert-butyldimethylsilyl)oxy)ethan-1-amine as starting materials (Yield: 48%); LC-MS: m/z 508.25 (M+1)⁺.

Step-b: Synthesis of N-(2-((tert-butyldimethylsilyl)oxy)ethyl)-2-((6-(2-hydroxypropan-2-yl)benzo[d]oxazol-2-yl)amino)-1-methyl-1H-benzo[d]imidazole-5-carboxamide To a stirred solution of 2-((6-acetylbenzo[d]oxazol-2-yl)amino)-N-(2-((tert-butyldimethylsilyl)oxy)ethyl)-1-methyl-1H-benzo[d]imidazole-5-carboxamide (200 mg, 0.39 mmol) in THF (5 mL) at 0° C. was added 3 M methyl magnesium bromide in diethyl ether (0.13 mL, 0.39 mmol) and the reaction mixture was stirred for 30 min. The reaction mixture was quenched with saturated aqueous ammonium chloride solution (20 mL) and extracted with ethyl acetate (2×50 mL). The combined organic layers were washed with brine (30 mL), dried over anhydrous sodium sulfate and concentrated under vacuum to afford the titled compound (100 mg, crude); LC-MS: m/z 524.3 (M+1)⁺.

Step-c: Synthesis of N-(2-hydroxyethyl)-2-((6-(2-hydroxypropan-2-yl)benzo[d]oxazol-2-yl)amino)-1-methyl-1H-benzo[d]imidazole-5-carboxamide The title compound was synthesized using the same procedure which was followed for Example 132 Step-h using N-(2-((tert-butyldimethylsilyl)oxy)ethyl)-2-((6-(2-hydroxypropan-2-yl)benzo[d]oxazol-2-yl)amino)-1-methyl-1H-benzo[d]imidazole-5-carboxamide as starting material and stirring for 4 h. Crude product was purified by preparative HPLC method (Yield: 6%).

| Preparative HPLC purification method details: | |
|---|---|
| DILUTION: | ACN:WATER |
| MOBILE PHASE A: | 0.1% formic acid in Water |
| MOBILE PHASE B: | 100% ACETONITRILE |
| GRADIENT: | 0/10, 2/10, 6/100, 10/100, 11/10, 12/10 |
| FLOW: | 1.0 ml/min |
| COLUMN: | Kinetex C-18 (250 × 21.1 × 5 μm) |

¹H NMR (400 MHz, DMSO-d₆): δ 12.23 (bs, 1H), 8.35 (bs, 1H), 8.06 (s, 1H), 7.76 (d, J=6.8 Hz, 1H), 7.51 (s, 1H), 7.46 (d, J=8.4 Hz, 1H), 7.37 (d, J=8.4 Hz, 1H), 7.30 (d, J=8.4 Hz, 1H), 5.03 (bs, 1H), 4.73 (bs, 1H), 3.62 (s, 3H), 3.53 (bs, 2H), 3.35-3.34 (m, 2H), 1.47 (s, 6H); LC-MS: m/z 410.2 (M+1)⁺.

Example 134. Synthesis of N-(2-(2-hydroxyethoxy)ethyl)-1-methyl-2-((6-(thiazol-4-yl)benzo[d]oxazol-2-yl)amino)-1H-benzo[d]imidazole-5-carboxamide

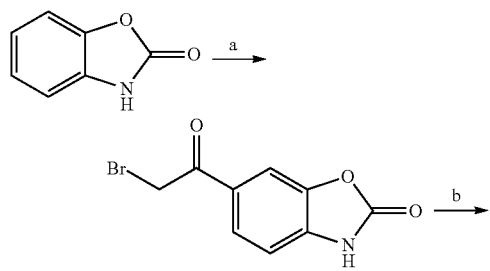

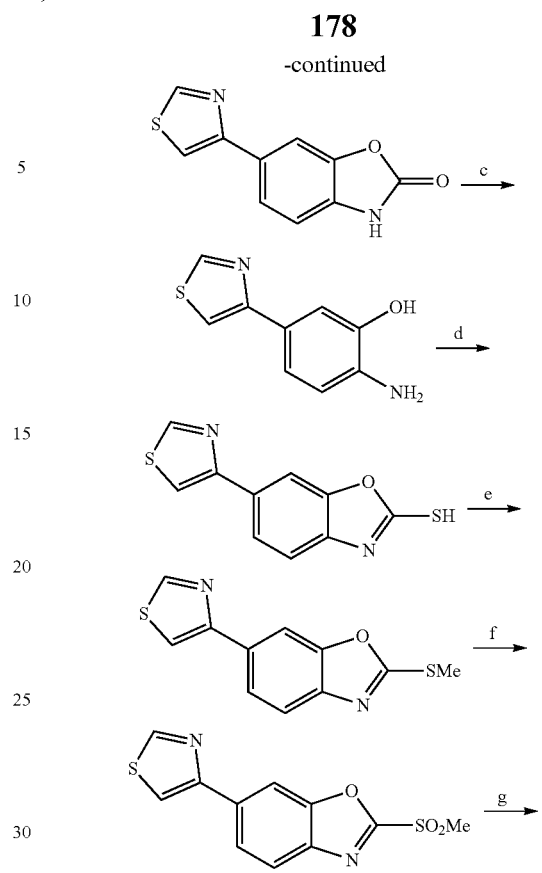

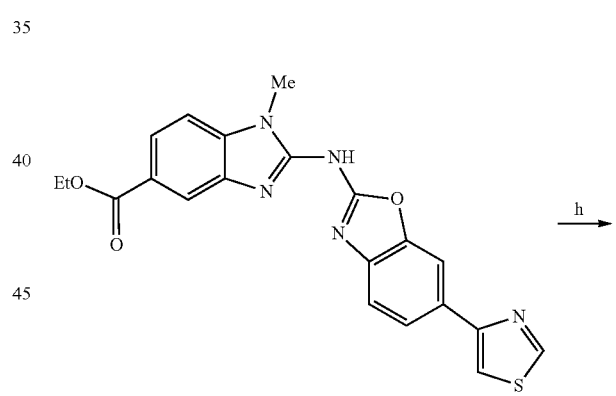

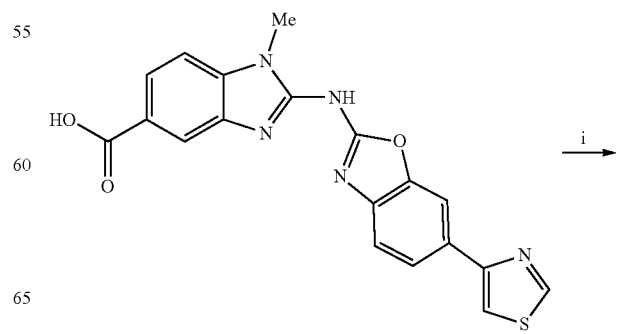

-continued

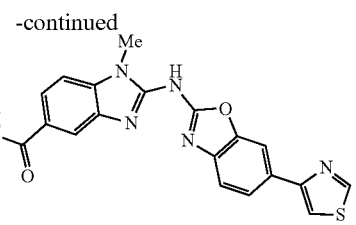

Conditions: a) AlCl₃, DMF, 2-bromoacetyl chloride, 0° C.,-75° C., 2.5 h; b) Formamide, P₂S₅, 1-4-Dioxane, Reflux, 18 h; c) NaOH, H₂O, Reflux, 16 h; d) Potassium ethyl xanthate, EtOH, Reflux, 16 h; e) K₂CO₃, MeI, ACN, RT, 4 h; f) m-CPBA, DCM, 0° C.-RT, 4 h; g) NaH, ethyl 2-amino-1-methyl-1H-benzo[d]imidazole-5-carboxylate, 1-4-Dioxane, RT, 16 h; h) LiOH•H₂O, THF, EtOH, H₂O, 60° C., 16 h; k) 2-(2-aminoethoxy)ethan-1-ol, HBTU, DIPEA, DMF, 0° C.-RT, 16 h

Step-a: Synthesis of 6-(2-bromoacetyl)benzo[d]oxazol-2(3H)-one

DMFA (5.75 mL, 74 mmol) was added to dropwise to AlCl₃ (34.5 g, 259.3 mmol) and the mixture was stirred at 45° C. for 30 min. Then benzo[d]oxazol-2(3H)-one (5.0 g, 37 mmol) and 2-bromoacetyl chloride (4.6 mL, 55.5 mmol) was added to the reaction mixture and stirred at 75° C. for 2 h. The reaction mixture was cooled to RT and poured over ice and stirred for 10 min. The precipitated solid was filtered and dried under vacuum to afford the titled compound (4.0 g, 42%); ¹H NMR (400 MHz, DMSO-d₆): δ 12.13 (bs, 1H), 7.90-7.87 (m, 2H), 7.23 (d, J=7.6 Hz, 1H), 4.89 (s, 2H); LC-MS: m/z 253.9 (M−1)⁻.

Step-b: Synthesis of 6-(thiazol-4-yl)benzo[d]oxazol-2(3H)-one

To a stirred solution of formamide (5.49 mL, 137.7 mmol) in 1,4-dioxane (100 mL) at RT was added phosphorus pentasulfide (6.1 g, 27.5 mmol) and heated at 100° C. for 2 h. The solid precipitated was removed by filtration and the filtrate was added to 6-(2-bromoacetyl)benzo[d]oxazol-2(3H)-one (13.5, 13.7 mmol). The reaction mixture was stirred at 100° C. for 16 h and concentrated on rotary evaporator to remove 1,4-dioxane. The residue was diluted with ethyl acetate (150 mL), water (100 mL) and extracted. Organic layer was washed with water (50 mL), brine (50 mL), dried over anhydrous sodium sulfate and concentrated under vacuum. The residue was purified by combiflash chromatography using 30% ethyl acetate in hexane as an eluent to afford the title compound (1.2 g, 40%); ¹H NMR (400 MHz, DMSO-d₆): δ 11.72 (s, 1H), 9.18 (d, J=1.6 Hz, 1H), 8.12 (d, J=1.2 Hz, 1H), 7.88 (s, 1H), 7.83 (d, J=8.0 Hz, 1H), 7.15 (d, J=8.0 Hz, 1H); LC-MS: m/z 219.0 (M+1)⁺.

Step-c: Synthesis of 2-amino-5-(thiazol-4-yl)phenol

To a stirred solution of 6-(thiazol-4-yl)benzo[d]oxazol-2(3H)-one (600 mg, 2.75 mmol) in water (6 mL) at RT was added sodium hydroxide (1.09 g, 27.5 mmol) and heated at 100° C. for 16 h. The reaction mixture was cooled to RT, quenched with saturated ammonium chloride solution and extracted with ethyl acetate (100 mL). Organic layer was washed with water brine (50 mL), dried over anhydrous sodium sulfate and concentrated under vacuum to afford the title compound (400 mg, 76%); ¹H NMR (400 MHz, DMSO-d₆): δ 9.13 (bs, 1H), 9.06 (d, J=1.2 Hz, 1H), 7.65 (d, J=1.6 Hz, 1H), 7.31 (d, J=1.2 Hz, 1H), 7.19 (d, J=7.6 Hz, 1H), 6.61 (d, J=8.4 Hz, 1H), 4.71 (bs, 2H); LC-MS: m/z 193.0 (M+1)⁺.

Step-d: Synthesis of 6-(thiazol-4-yl)benzo[d]oxazole-2(3H)-thione

The title compound was synthesized using the same procedure which was followed for Example 32 Step-c using 2-amino-5-(thiazol-4-yl)phenol (Yield: 92%); ¹H NMR (400 MHz, DMSO-d₆): δ 13.99 (s, 1H), 9.22 (d, J=1.6 Hz, 1H), 8.23 (d, J=1.6 Hz, 1H), 8.10 (d, J=1.2 Hz, 1H), 7.99 (dd, J=1.6 Hz, J=8.4 Hz, 1H), 7.31 (d, J=8.4 Hz, 1H); LC-MS: m/z 234.95 (M+1)⁺.

Step-e: Synthesis of 2-(methylthio)-6-(thiazol-4-yl)benzo[d]oxazole

The title compound was synthesized using the same procedure which was followed for compound 1b using 6-(thiazol-4-yl)benzo[d]oxazole-2(3H)-thione as starting material stirring for 4 hours (Yield: 84%); ¹H NMR (400 MHz, DMSO-d₆): δ 9.21 (bs, 1H), 8.24-8.23 (m, 2H), 8.01 (d, J=8.4 Hz, 1H), 8.69 (d, J=8.4 Hz, 1H), 2.78 (s, 3H); LC-MS: m/z 249.0 (M+1)⁺.

Step-f: Synthesis of 2-(methylsulfonyl)-6-(thiazol-4-yl)benzo[d]oxazole

The title compound was synthesized using the same procedure which was followed for compound 1c using 2-(methylthio)-6-(thiazol-4-yl)benzo[d]oxazole as starting material and stirring for 4 h. Crude compound was used in the next step without any analytical data.

Step-g: Synthesis of ethyl 1-methyl-2-((6-(thiazol-4-yl)benzo[d]oxazol-2-yl)amino)-1H-benzo[d]imidazole-5-carboxylate The title compound was synthesized using the same procedure which was followed for compound 1g using ethyl 2-amino-1-methyl-1H-benzo[d]imidazole-5-carboxylate and 2-(methylsulfonyl)-6-(thiazol-4-yl)benzo[d]oxazole as starting materials (Yield: 26%); ¹H NMR (400 MHz, DMSO-d₆): δ 12.4 (bs, 1H), 9.20 (d, J=4.4 Hz, 1H), 8.25 (s, 1H), 8.22 (s, 1H), 8.08 (s, 1H), 7.92-7.87 (m, 2H), 7.54-7.50 (m, 2H), 4.33 (q, J=7.6 Hz, 2H), 3.66 (s, 3H), 1.35 (t, J=6.8 Hz, 3H); LC-MS: m/z 420.05 (M+1)⁺.

Step-h: Synthesis of 1-methyl-2-((6-(thiazol-4-yl)benzo[d]oxazol-2-yl)amino)-1H-benzo[d]imidazole-5-carboxylic acid The title compound was synthesized using the same procedure which was followed for compound 1h using ethyl 1-methyl-2-((6-(thiazol-4-yl)benzo[d]oxazol-2-yl)amino)-1H-benzo[d]imidazole-5-carboxylate as starting material and stirring for 5 h (Yield: 71%); ¹H NMR (400 MHz, DMSO-d₆): δ 9.16 (s, 1H), 8.00 (s, 1H), 7.95 (s, 1H), 7.81 (s, 1H), 7.77 (d, J=8.0 Hz, 1H), 7.66 (d, J=8.4 Hz, 1H), 7.20 (d, J=7.6 Hz, 1H), 7.06 (d, J=8.4 Hz, 1H), 3.59 (s, 3H); LC-MS: m/z 392.1 (M+1)⁺.

Step-i: Synthesis of N-(2-(2-hydroxyethoxy)ethyl)-1-methyl-2-((6-(thiazol-4-yl)benzo[d]oxazol-2-yl)amino)-1H-benzo[d]imidazole-5-carboxamide The title compound was synthesized using the same procedure which was followed for Example 6 Step-e using

181

1-methyl-2-((6-(thiazol-4-yl)benzo[d]oxazol-2-yl)amino)-1H-benzo[d]imidazole-5-carboxylic acid and 2-(2-aminoethoxy)ethan-1-ol as starting materials. Crude product was purified by combiflash chromatography using 20% Methanol in DCM as an eluent (Yield: 28%); $^1$H NMR (400 MHz, DMSO-d$_6$): δ 12.3 (bs, 1H), 9.19 (s, 1H), 8.45 (bs, 1H), 8.13-8.04 (m, 3H), 7.91 (d, J=7.6 Hz, 1H), 7.77 (d, J=8.4 Hz,

182

1H), 7.51 (d, J=8.0 Hz, 2H), 3.66 (s, 3H), 3.56-3.44 (m, 8H); LC-MS: m/z 479.05 (M+1)$^+$.

Example 135. Synthesis of N-(2-(2-hydroxyethoxy)ethyl)-1-methyl-2-((6-(3-methyl-2-oxooxazolidin-5-yl)benzo[d]oxazol-2-yl)amino)-1H-benzo[d]imidazole-5-carboxamide

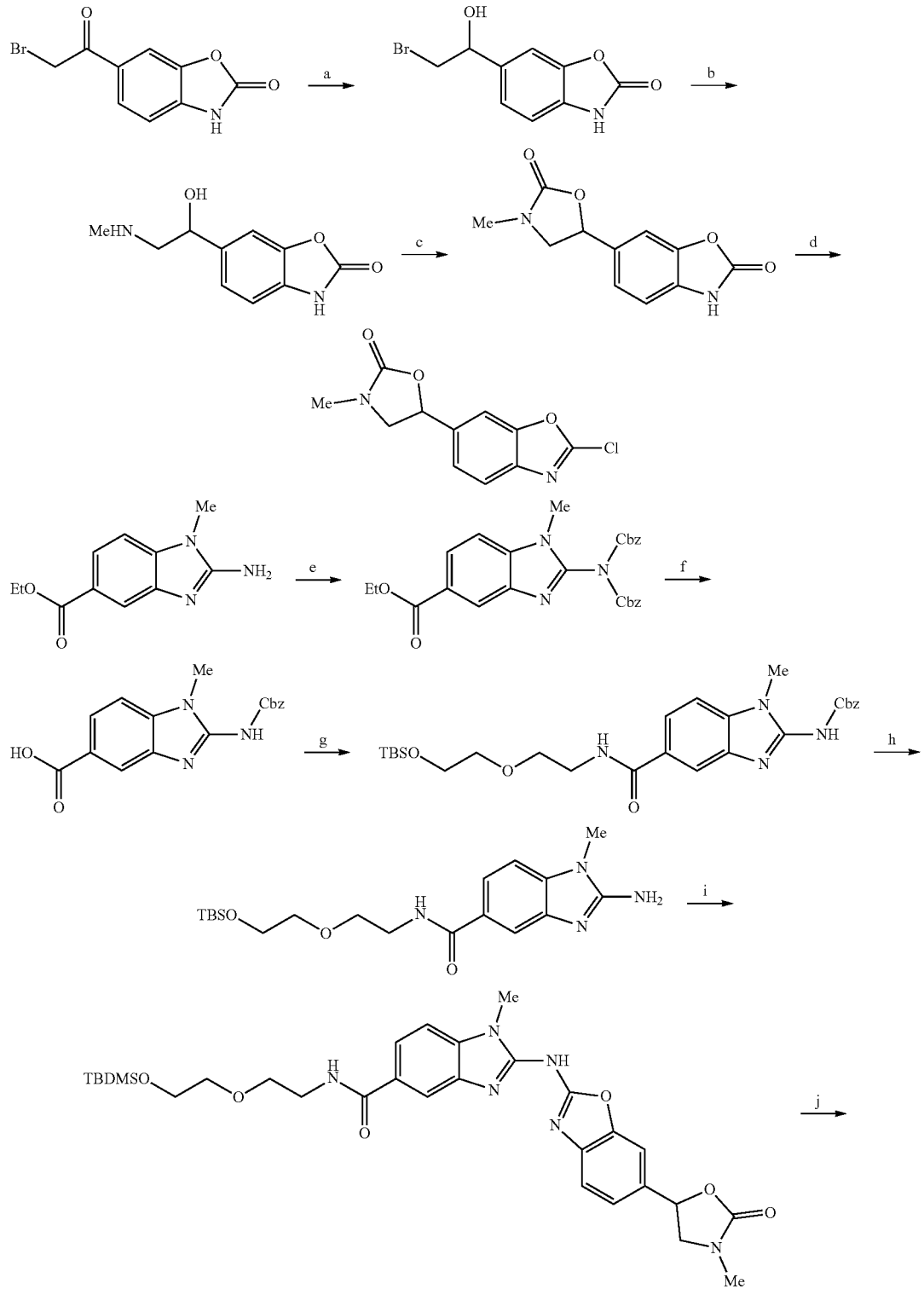

-continued

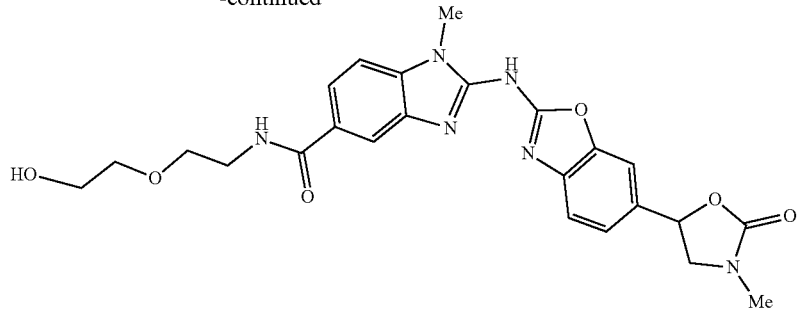

Conditions: a) NaBH₄, MeOH, 0° C.-RT, 1 h; b) 40% Aq. methylamine, RT, 30 min; c) CDI, DMF, 100° C., 16 h; d) POCl₃, TEA, reflux, 5 h; e) NaHCO₃, Benzyl chloformate in toluene, acetone, H₂O, 0° C.-RT, 16 h; f) LiOH•H₂O, THF, EtOH, H₂O, 80°C., 16 h; g) 2-(2-((tert-butyldimethylsilyl)oxy)ethoxy)ethan-1-amine, HBTU, DIPEA, DMF, 0° C.-RT, 16 h; h) Pd/C, H₂, MeOH, RT, 6 h; i) 5-(2-chlorobenzo[d]oxazol-6-yl)-3-methyloxazolidin-2-one, NaH, 1,4-Dioxane, RT, 3 h; j)TBAF, THF, RT 16 h Step-a: Synthesis of 6-(2-bromo-1-hydroxyethyl) benzo[d]oxazol-2(3H)-one To a stirred solution of 6-(2-bromoacetyl)benzo[d]oxazol-2(3H)-one (4.0 g, 15.62 mmol) in methanol (50 mL) at 0° C. was added sodium borohydride (587 mg, 15.62 mmol) portion wise and the reaction mixture was stirred for 1 h. The reaction mixture was quenched with water (100 mL) and concentrated under reduced pressure to remove methanol. The aqueous layer was extracted with EtOAc (3×100 mL). Combined organic layers were washed with brine (30 mL), dried over anhydrous sodium sulfate and concentrated under vacuum to afford the titled compound (4.0 g, 99%); LC-MS: m/z 257.9 (M+1)⁺.

Step-b: Synthesis of 6-(1-hydroxy-2-(methylamino) ethyl)benzo[d]oxazol-2(3H)-one A mixture of 6-(2-bromo-1-hydroxyethyl)benzo[d]oxazol-2(3H)-one (4.0 g, 15.5 mmol) in 40% aqueous methylamine (20 mL) was stirred at RT for 30 min. The reaction mixture was concentrated under vacuum and the residue was purified by combiflash chromatography using 5% methanol in DCM as an eluent to afford the title compound (1.8 g, 56%); ¹H NMR (400 MHz, DMSO-d₆): δ 11.8 (bs, 1H), 8.9 (bs, 1H), 7.47 (d, J=1.2 Hz, 1H), 7.28 (dd, J=1.2 Hz, J=8.0 Hz, 1H), 7.17 (d, J=8.0 Hz, 1H), 5.68 (t, J=4.8 Hz, 1H), 4.29 (t, J=6.4 Hz, 1H), 3.81-3.74 (m, 2H), 1.24 (s, 3H); LC-MS: m/z 209.05 (M+1)⁺.

Step-c: Synthesis of 6-(3-methyl-2-oxooxazolidin-5-yl)benzo[d]oxazol-2(3H)-one

To a stirred solution of 6-(1-hydroxy-2-(methylamino)ethyl)benzo[d]oxazol-2(3H)-one (1.8 g, 8.65 mmol) in DMFA (20 mL) at RT was added 1,1'-carbonyldiimidazole (1.54 g, 9.52 mmol). The reaction mixture was heated to 100° C. with stirring for 16 h. The reaction mixture was cooled to RT, diluted with water (100 mL) and extracted with ethyl acetate (3×100 mL). The combined organic layer was washed brine solution (50 mL), dried over anhydrous sodium sulfate and concentrated under vacuum. The residue was purified by combiflash chromatography using 1% methanol in DCM as an eluent to afford the title compound (500 mg, 25%); ¹H NMR (400 MHz, DMSO-d6): δ 7.22 (s, 1H), 7.09 (d, J=8.0 Hz, 1H), 7.01 (d, J=8.0 Hz, 1H), 3.57-3.54 (m, 1H), 3.45-3.41 (m, 1H), 3.34-3.30 (m, 1H), 2.16 (s, 3H).

Step-d: Synthesis of 5-(2-chlorobenzo[d]oxazol-6-yl)-3-methyloxazolidin-2-one

A 50 mL round bottom flask was charged with 6-(3-methyl-2-oxooxazolidin-5-yl)benzo[d]oxazol-2(3H)-one (500 mg, 2.14 mmol) and POCl₃ (0.98 mL, 10.68 mmol) followed by slow addition of triethyl amine (1.51 mL, 10.68 mmol) at 0° C. The reaction mixture was heated to reflux for 5 h. The reaction mixture was cooled to RT, poured over ice and extracted with ethyl acetate (2×50 mL). The combined organic layer was washed with saturated sodium bicarbonate solution (2×50 mL), water (50 mL), brine solution (30 mL), dried over anhydrous sodium sulfate and concentrated under vacuum. The residue was purified by combiflash chromatography using 50% EtOAc in hexane as an eluent to afford the title compound (120 mg, 22%); ¹H NMR (400 MHz, DMSO-d6): δ 7.58 (s, 1H), 7.35 (dd, J=1.6 Hz, J=8.0 Hz, 1H), 7.19 (d, J=7.6 Hz, 1H), 4.64 (bs, 1H), 4.23-4.19 (m, 1H), 4.16-4.11 (m, 1H), 2.46 (s, 3H).

Step-e: Synthesis of ethyl 2-(bis((benzyloxy)carbonyl)amino)-1-methyl-1H-benzo[d]imidazole-5-carboxylate To a stirred solution of ethyl 2-amino-1-methyl-1H-benzo[d]imidazole-5-carboxylate (1.0 g, 3.24 mmol) in acetone (10 mL) and water (10 mL) at 0° C. was added sodium bicarbonate (722 mg, 6.88 mmol) and benzyl chloroformate (1.2 mL, 4.22 mmol, 50% in toluene). The reaction mixture was stirred at RT for 16 h. The reaction mixture was diluted with water (100 mL) and extracted with ethyl acetate (2×100 mL). The combined organic layer was washed brine solution (50 mL), dried over anhydrous sodium sulfate and concentrated under vacuum.

The crude compound was used in the next step without any further purification (2.2 g, 99%); LC-MS: m/z 488.2 (M+1)⁺.

Step-f: Synthesis of 2-(((benzyloxy)carbonyl)amino)-1-methyl-1H-benzo[d]imidazole-5-carboxylic acid To a stirred solution of ethyl 2-(bis((benzyloxy)carbonyl)amino)-1-methyl-1H-benzo[d]imidazole-5-carboxylate (2.2 g, 4.52 mmol) in a mixture of solvent of THF (15 mL), ethanol (15 mL) and water (10 mL) was added lithium hydroxide monohydrate (948 mg, 22.6 mmol). The reaction mixture was heated at 80° C. for 16 h with stirring. The reaction mixture was cooled to RT and concentrated under reduced pressure. The residue was dissolved in water (30 mL), acidified with 1 N HCl and extracted with ethyl acetate (2×150 mL). The combined organic layer was washed brine solution (50 mL), dried over anhydrous sodium sulfate and concentrated under vacuum to give the crude compound which was used in the next step without any further purification (1.4 g, 95%); LC-MS: m/z 326.1 (M+1)$^+$.

Step-g: Synthesis of benzyl (5-((2-(2-((tert-butyldimethylsilyl)oxy)ethoxy)ethyl)carbamoyl)-1-methyl-1H-benzo[d]imidazol-2-yl)carbamate The title compound was synthesized using the same procedure which was followed for Example 6 Step-e using 2-(((benzyloxy)carbonyl)amino)-1-methyl-1H-benzo[d]imidazole-5-carboxylic acid and 2-(2-((tert-butyldimethylsilyl)oxy)ethoxy)ethan-1-amine as starting materials (Yield: 66%); $^1$H NMR (400 MHz, DMSO-d$_6$): δ 12.20 (bs, 1H), 8.42 (t, J=5.2 Hz, 1H), 7.85 (s, 1H), 7.68 (d, J=8.4 Hz, 1H), 7.41-7.33 (m, 6H), 5.08 (s, 2H), 3.66 (t, J=5.2 Hz, 2H), 3.54-3.38 (m, 9H), 0.81 (s, 9H), 0.03 (s, 6H); LC-MS: m/z 527.25 (M+1)$^+$.

Step-h: Synthesis of 2-amino-N-(2-(2-((tert-butyldimethylsilyl)oxy)ethoxy)ethyl)-1-methyl-1H-benzo[d]imidazole-5-carboxamide To a solution of benzyl (5-((2-(2-((tert-butyldimethylsilyl)oxy)ethoxy)ethyl)carbamoyl)-1-methyl-1H-benzo[d]imidazol-2-yl)carbamate (320 mg, 0.61 mmol) in methanol (8 mL) was added 10% Pd/C (40 mg) under nitrogen atmosphere. Then the reaction mixture was stirred under hydrogen gas balloon for 6 h. The reaction mixture was filtered through a bed of celite and concentrated under vacuum to afford the title compound (170 mg, 71%); $^1$H NMR (400 MHz, DMSO-d$_6$): δ 8.22 (t, J=4.8 Hz, 1H), 7.65 (s, 1H)), 7.45 (d, J=8.0 Hz, 1H), 7.14 (d, J=8.0 Hz, 1H), 6.52 (s, 2H), 3.69 (t, J=4.8 Hz, 2H), 3.55-3.46 (m, 7H), 3.41-3.37 (m, 2H), 0.84 (s, 9H), 0.01 (s, 6H); LC-MS: m/z 393.65 (M+1)$^+$.

Step-i: Synthesis of N-(2-(2-((tert-butyldimethylsilyl)oxy)ethoxy)ethyl)-1-methyl-2-((6-(3-methyl-2-oxooxazolidin-5-yl)benzo[d]oxazol-2-yl)amino)-1H-benzo[d]imidazole-5-carboxamide The title compound was synthesized using the same procedure which was followed for Example 32 Step-e using 2-amino-N-(2-(2-((tert-butyldimethylsilyl)oxy)ethoxy)ethyl)-1-methyl-1H-benzo[d]imidazole-5-carboxamide and 5-(2-chlorobenzo[d]oxazol-6-yl)-3-methyloxazolidin-2-one as starting materials stirring for 3 h (Yield: 74%); $^1$H NMR (400 MHz, DMSO-d$_6$): δ 11.74 (bs, 1H), 8.43 (t, J=5.2 Hz, 1H), 8.05 (d, J=1.2 Hz, 1H), 7.77 (dd, J=1.6 Hz, J=8.4 Hz, 1H), 7.56 (d, J=8.4 Hz, 1H), 7.42 (d, J=1.2 Hz, 1H), 7.25 (dd, J=1.6 Hz, J=8.4 Hz, 1H), 7.15 (d, J=8.0 Hz, 1H), 4.87 (t, J=7.2 Hz, 1H), 4.35 (t, J=9.2 Hz, 1H), 3.82-3.76 (m, 5H), 3.68 (t, J=5.2 Hz, 2H), 3.54-3.52 (m, 2H), 3.48-3.31 (m, 2H), 2.62 (s, 3H), 0.84 (s, 9H), −0.01 (s, 3H), −0.02 (s, 3H); LC-MS: m/z 609.3 (M+1)$^+$.

Step-j: Synthesis of N-(2-(2-hydroxyethoxy)ethyl)-1-methyl-2-((6-(3-methyl-2-oxooxazolidin-5-yl)benzo[d]oxazol-2-yl)amino)-1H-benzo[d]imidazole-5-carboxamide To a stirred solution of N-(2-(2-((tert-butyldimethylsilyl)oxy)ethoxy)ethyl)-1-methyl-2-((6-(3-methyl-2-oxooxazolidin-5-yl)benzo[d]oxazol-2-yl)amino)-1H-benzo[d]imidazole-5-carboxamide (30 mg, 0.05 mmol) in THF (2 mL) at 0° C. was added 1 M TBAF in THF (0.1 mL) and the reaction mixture was stirred at RT for 16 h. The reaction mixture was quenched with saturated ammonium chloride solution (10 mL) and extracted with EtOAc (2×30 mL). The combined organic layers were washed with water (20 mL), brine (20 mL), dried over anhydrous sodium sulfate and concentrated under vacuum to obtain a residue which was purified by combiflash chromatography using 5% methanol in DCM as an eluent to afford the title compound (14 mg, 58%); $^1$H NMR (400 MHz, DMSO-d$_6$): δ 11.8 (bs, 1H), 8.43 (t, J=5.2 Hz, 1H), 8.06 (s, 1H), 7.78 (d, J=8.8 Hz, 1H), 7.57 (d, J=8.0 Hz, 1H), 7.38 (s, 1H), 7.21 (d, J=8.0 Hz, 1H), 7.13 (d, J=7.6 Hz, 1H), 4.87 (t, J=8.0 Hz, 1H), 4.59 (s, 1H), 4.35 (t, J=9.2 Hz, 1H), 3.82 (t, J=9.2 Hz, 1H), 3.78 (s, 3H), 3.56-3.41 (m, 8H), 2.63 (s, 3H); LC-MS: m/z 495.2 (M+1)$^+$.

Example 136. Synthesis of N-(2-(2-hydroxyethoxy)ethyl)-1-methyl-2-((6-morpholinobenzo[d]oxazol-2-yl)amino)-1H-benzo[d]imidazole-5-carboxamide

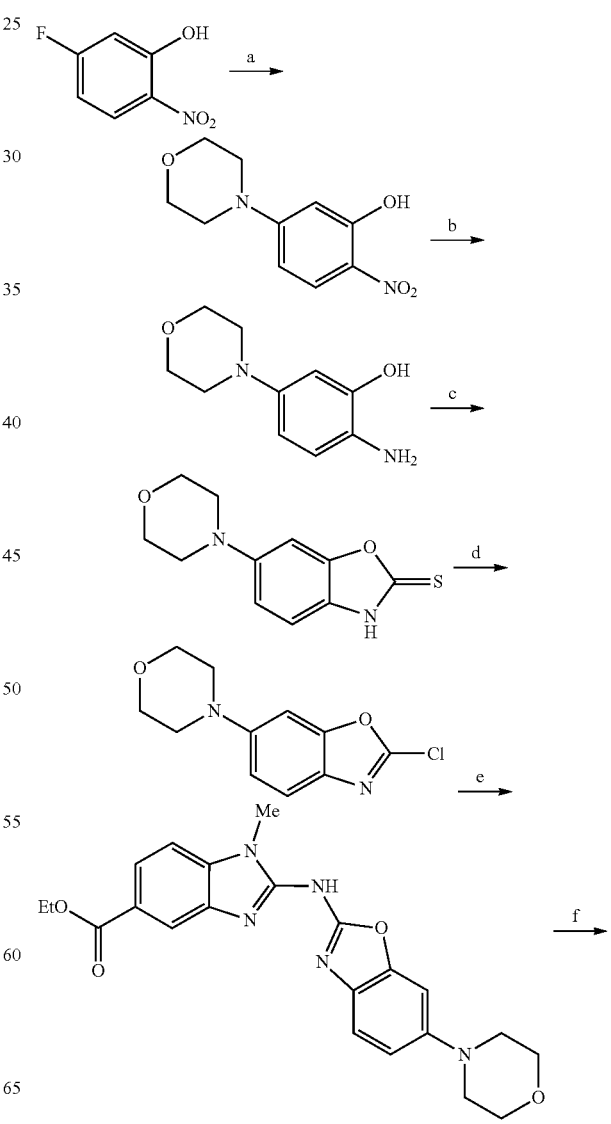

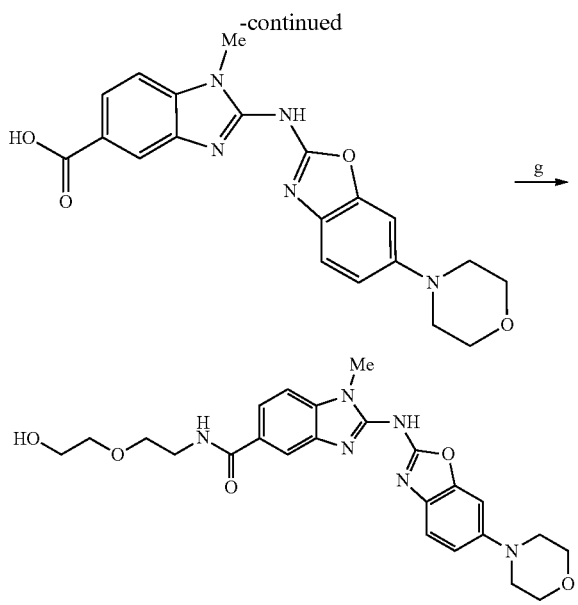

Conditions: a) Morpholine, ACN, 60° C., 2 h; b) 10% Pd/C. MeOH, H₂, RT, 3 h; c) Potassium ethyl xanthate, EtOH, Reflux, 16 h; d) SOCl₂, Cat.DMF, DCM, RT, 1 h; e) NaH, ethyl 2-amino-1-methyl-1H-benzo[d]imidazole-5-carboxylate, 1,4-Dioxane, RT, 16 h; f) LiOH·H₂O, THF, EtOH, H₂O, 60° C., 16 h; g) 2-(2-aminoethoxy)ethan-1-ol, HBTU, DIPEA, DMF, 0° C.-RT, 16 h Step-a: Synthesis of 5-morpholino-2-nitrophenol To a stirred solution of 5-fluoro-2-nitrophenol (5.0 g, 31.84 mmol) in acetonitrile (50 mL) at RT was added morpholine (8.31 g, 95.54 mmol) and the reaction mixture was heated at 60° C. for 2 h. The reaction mixture was cooled to RT, diluted with cold water (300 mL) and the precipitated solid was filtered and dried under vacuum to afford the title compound (5.0 g, 70%); $^1$H NMR (400 MHz, DMSO-d$_6$): δ 10.9 (bs, 1H), 7.88 (d, J=9.2 Hz, 1H), 6.65 (dd, J=2.4 Hz, J=9.6 Hz, 1H), 6.44 (d, J=2.8 Hz, 1H), 3.70 (t, J=5.2 Hz, 4H), 3.41 (t, J=4.8 Hz, 4H); LC-MS: m/z 225.1 (M+1)⁺.

Step-b: Synthesis of 2-amino-5-morpholinophenol

The title compound was synthesized using the same procedure which was followed for compound 1e using 5-morpholino-2-nitrophenol as starting material and stirred for 3 h (Yield: 81%); $^1$H NMR (400 MHz, DMSO-d$_6$): δ 8.8 (bs, 1H), 6.48 (d, J=8.0 Hz, 1H), 6.33 (d, J=2.4 Hz, 1H), 6.19 (dd, J=2.8 Hz, J=8.8 Hz, 1H), 3.68 (t, J=5.2 Hz, 4H), 2.84 (t, J=4.8 Hz, 4H); LC-MS: m/z 195.1 (M+1)⁺.

Step-c: Synthesis of 6-morpholinobenzo[d]oxazole-2(3H)-thione

The title compound was synthesized using the same procedure which was followed for Example 32 Step-c using 2-amino-5-morpholinophenol as starting material (Yield: 75%); $^1$H NMR (400 MHz, DMSO-d$_6$): δ 13.6 (s, 1H), 7.14 (d, J=2.4 Hz, 1H), 7.09 (d, J=8.8 Hz, 1H), 6.91 (dd, J=2.4 Hz, J=8.8 Hz, 1H), 3.73 (t, J=4.4 Hz, 4H), 3.10 (t, J=4.8 Hz, 4H); LC-MS: m/z 237.1 (M+1)⁺.

Step-d: Synthesis of 2-chloro-6-morpholinobenzo[d]oxazole

To a solution of 6-morpholinobenzo[d]oxazole-2(3H)-thione (500 mg, 1.12 mmol) in DCM (10 mL) at RT was added thionyl chloride (0.79 mL, 10.6 mmol) and dimethylformamide (0.2 mL) and the reaction mixture was stirred at RT for 1 h. The reaction mixture was poured on cold water (50 mL), basified with saturated sodium bicarbonate solution and extracted with DCM (2×50 mL). The combined organic layers were washed with brine solution (30 mL), dried over anhydrous sodium sulfate and concentrated under vacuum. The residue was purified by combiflash chromatography using 30% EtOAc in hexane as eluent to afford the title compound (300 mg, 60%); $^1$H NMR (400 MHz, DMSO-d$_6$): δ 7.56 (d, J=8.8 Hz, 1H), 7.29 (d, J=2.4 Hz, 1H), 7.09 (dd, J=2.4 Hz, J=8.8 Hz, 1H), 3.75 (t, J=4.8 Hz, 4H), 3.16 (t, J=4.8 Hz, 4H); LC-MS: m/z 239.0 (M+1)⁺.

Step-e: Synthesis of ethyl 1-methyl-2-((6-morpholinobenzo[d]oxazol-2-yl)amino)-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 2-chloro-6-morpholinobenzo[d]oxazole as starting materials (Yield: 37%); $^1$H NMR (400 MHz, DMSO-d$_6$): δ 12.2 (bs, 1H), 8.20 (d, J=1.2 Hz, 1H), 7.86 (dd, J=1.6 Hz, J=8.4 Hz, 1H), 7.49 (d, J=8.4 Hz, 1H), 7.33 (d, J=8.4 Hz, 1H), 7.09 (d, J=2.4 Hz, 1H), 6.87 (dd, J=2.4 Hz, J=8.8 Hz, 1H), 4.32 (q, J=8.4 Hz, 2H), 3.76 (t, J=4.4 Hz, 4H), 3.61 (s, 3H), 3.09 (t, J=4.8 Hz, 4H), 1.35 (t, J=7.2 Hz, 3H); LC-MS: m/z 422.1 (M+1)⁺.

Step-f: Synthesis of 1-methyl-2-((6-morpholinobenzo[d]oxazol-2-yl)amino)-1H-benzo[d]imidazole-5-carboxylic acid The title compound was synthesized using the same procedure which was followed for compound 1h using ethyl 1-methyl-2-((6-morpholinobenzo[d]oxazol-2-yl)amino)-1H-benzo[d]imidazole-5-carboxylate as starting material (Yield: 71%); $^1$H NMR (400 MHz, DMSO-d$_6$): δ 12.5 (bs, 1H), 8.16 (d, J=1.2 Hz, 1H), 7.85 (d, J=8.4 Hz, 1H), 7.46 (d, J=8.4 Hz, 1H), 7.34 (d, J=8.8 Hz, 1H), 7.08 (d, J=2.0 Hz, 1H), 6.86 (dd, J=2.0 Hz, J=8.8 Hz, 1H), 3.76 (t, J=4.4 Hz, 4H), 3.61 (s, 3H), 3.09 (t, J=4.4 Hz, 4H); LC-MS: m/z 394.0 (M+1)⁺.

Step-g: Synthesis of N-(2-(2-hydroxyethoxy)ethyl)-1-methyl-2-((6-morpholinobenzo[d]-oxazol-2-yl)amino)-1H-benzo[d]imidazole-5-carboxamide The title compound was synthesized using the same procedure which was followed for Example 6 Step-e using 1-methyl-2-((6-morpholinobenzo[d]oxazol-2-yl)amino)-1H-benzo[d]imidazole-5-carboxylic acid and 2-(2-aminoethoxy)ethan-1-ol as starting materials (Yield: 98%); $^1$H NMR (400 MHz, DMSO-d$_6$): δ 12.4 (bs, 1H), 8.49 (t, J=4.8 Hz, 1H), 8.05 (d, J=1.2 Hz, 1H), 7.78 (d, J=7.2 Hz, 1H), 7.52 (d, J=7.2 Hz, 1H), 7.34 (d, J=8.4 Hz, 1H), 7.15 (s, 1H), 6.94 (d, J=7.2 Hz, 1H), 3.86 (bs, 4H), 3.64 (s, 3H), 3.56-3.54 (m, 4H), 3.47-3.45 (m, 4H), 3.14 (bs, 4H); LC-MS: m/z 481.2 (M+1)⁺.

Example 137. Synthesis of N-(2-(2-hydroxyethoxy)ethyl)-1-methyl-2-((6-(pyrrolidin-1-yl)benzo[d]oxazol-2-yl)amino)-1H-benzo[d]imidazole-5-carboxamide

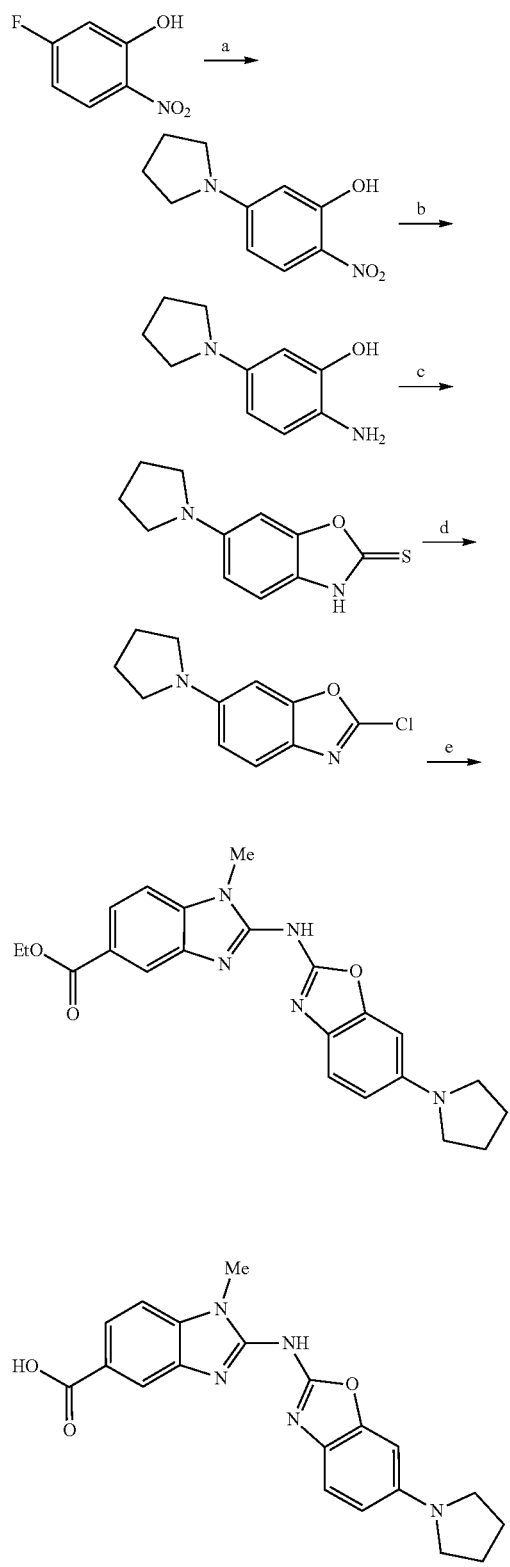

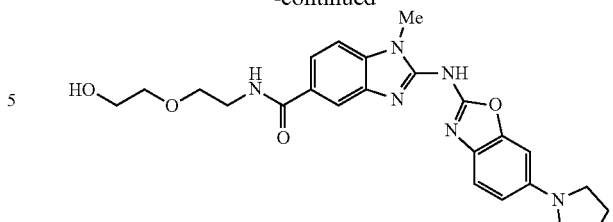

Conditions: a) Pyrrolidine, Acetonitrile, 100° C., 12 h; b) 10% Pd/C, MeOH, H₂, RT, 4 h; c) Potassium ethyl xanthate, Ethanol, Reflux, 16 h; d) SOCl₂, DCM, 0° C., 1 h; e) NaH, ethyl 2-amino-1-methyl-1H-benzo[d]imidazole-5-carboxylate, 1,4-Dioxane, 0° C.-RT, 4 H; f) LiOH·H₂O, THF, Ethanol, Water, 60° C., 16 h; g) 2-(2-Aminoethoxy)ethan-1-ol, HBTU, DIPEA, DMF, 0° C.,-RT, 16 h

Step-a: Synthesis of 2-nitro-5-(pyrrolidin-1-yl)phenol

To a solution of 5-fluoro-2-nitrophenol (2.0 g, 12.73 mmol) in acetonitrile 20 mL) at RT was added pyrrolidine (3.15 mL, 38.21 mmol) and stirred at 100° C. for 12 h. The reaction mixture was concentrated under vacuum and the residue was purified by combi-flash column chromatography using 30% ethyl acetate in hexane as an eluent to afford the titled compound (1.5 g, 57%); $^1$H NMR (400 MHz, DMSO-$d_6$): δ 7.85 (d, J=9.2 Hz, 1H), 6.28 (dd, J=2.4 Hz, J=9.2 Hz, 1H), 6.02 (d, J=2.4 Hz, 1H), 3.39-3.36 (m, 4H), 1.98-1.94 (m, 4H).

Step-b: Synthesis of 2-amino-5-(pyrrolidin-1-yl)phenol

To a solution of 2-nitro-5-(pyrrolidin-1-yl)phenol (1.5 g, 7.20 mmol) in methanol (300 mL) was added 10% Pd/C (300 mg) under nitrogen atmosphere. The reaction mixture was stirred under hydrogen balloon for 4 h. The reaction mixture was filtered through a celite bed and the filtrate was concentrated under vacuum to afford the crude compound (1.3 g) which was used in the next step without any further purification and structural confirmation by analytical technique.

Step-c: Synthesis of 6-(pyrrolidin-1-yl)benzo[d]oxazole-2(3H)-thione

To a solution of 2-amino-5-(pyrrolidin-1-yl)phenol (1.3 g, 7.30 mmol) in ethanol (13 mL) at RT was added potassium ethyl-xanthate (2.3 g, 14.6 mmol) and the reaction mixture was refluxed for 16 h. The reaction mixture was concentrated under vacuum and diluted with cold water (50 mL), acidified with 1 N HCl. The solid obtained was filtered and dried under vacuum to afford the titled compound (0.8 g, 50%) which was used in the next step without further purification; $^1$H NMR (400 MHz, DMSO-$d_6$): δ 13.50 (bs, 1H), 7.03 (d, J=8.4 Hz, 1H), 6.65 (d, J=2.0 Hz, 1H), 6.46 (dd, J=2.0 Hz, J=8.4 Hz, 1H), 3.22-3.19 (m, 4H), 1.97-1.94 (m, 4H); LC-MS: m/z 220.9 (M+1)⁺.

Step-d: Synthesis of 2-chloro-6-(pyrrolidin-1-yl)benzo[d]oxazole

To a solution of 6-(pyrrolidin-1-yl)benzo[d]oxazole-2 (3H)-thione (400 mg, 1.82 mmol) in DCM (10 mL) at 0° C. was added thionyl chloride (0.66 mL, 9.09 mmol) and the reaction mixture was stirred at 0° C. for 1 h. The reaction mixture was quenched with water (20 mL), extracted with EtOAc (2×50 mL). The combined organic layers were washed with saturated sodium bicarbonate solution (30 mL), brine solution (30 mL), dried over anhydrous sodium sulfate and concentrated under vacuum to afford the titled compound (300 mg, 74%) which was used in the next step without further purification; $^1$H NMR (400 MHz, CD$_3$OD): δ 6.91 (d, J=8.4 Hz, 1H), 6.48 (d, J=2.0 Hz, 1H), 6.42 (dd, J=2.4 Hz, J=8.8 Hz, 1H), 3.21-3.16 (m, 4H), 1.96-1.91 (m, 4H).

Step-e: Synthesis of ethyl 1-methyl-2-((6-(pyrrolidin-1-yl)benzo[d]oxazol-2-yl)amino)-1H-benzo[d]imidazole-5-carboxylate To a stirred solution of ethyl 2-amino-1-methyl-1H-benzo[d]imidazole-5-carboxylate (200 mg, 0.91 mmol) in 1,4-dioxane (5 mL) at 0° C. was added sodium hydride (60% dispersion in mineral oil) (73 mg, 1.82 mmol) and stirred for 30 min followed by the addition of 2-chloro-6-(pyrrolidin-1-yl)benzo[d]oxazole (243 mg, 1.09 mmol). The reaction mixture was stirred at RT for 4 h and then quenched with cold water (20 mL) and extracted with EtOAc (2×50 mL). Combined organic layers were washed with water (30 mL), brine (30 mL), dried over anhydrous sodium sulfate and concentrated under vacuum. The residue was purified by combi-flash column chromatography using 3% methanol in DCM as an eluent to afford the titled compound (150 mg, 40%); $^1$H NMR (400 MHz, DMSO-d$_6$): δ 12.10 (bs, 1H), 8.18 (d, J=1.6 Hz, 1H), 7.85 (dd, J=1.2 Hz, J=8.4 Hz, 1H), 7.46 (d, J=8.4 Hz, 1H), 7.29 (d, J=8.8 Hz, 1H), 6.64 (d, J=2.0 Hz, 1H), 6.46 (dd, J=2.0 Hz, J=8.4 Hz, 1H), 4.32 (q, J=6.8 Hz, 2H), 3.60 (s, 3H), 3.26-3.23 (m, 4H), 1.99-1.95 (m, 4H), 1.35 (t, J=6.8 Hz, 3H); LC-MS: m/z 406.2 (M+1)$^+$.

Step-f: Synthesis of 1-methyl-2-((6-(pyrrolidin-1-yl)benzo[d]oxazol-2-yl)amino)-1H-benzo[d]imidazole-5-carboxylic acid To a stirred solution of ethyl 1-methyl-2-((6-(pyrrolidin-1-yl)benzo[d]oxazol-2-yl)amino)-1H-benzo[d]imidazole-5-carboxylate (150 mg, 0.37 mmol) in a mixture of solvent of [THF (2 mL), ethanol (2 mL) and water (1 mL)] was added lithium hydroxide monohydrate (77 mg, 1.85 mmol). The reaction mixture was heated at 60° C. for 16 h. The reaction mixture was cooled to RT and concentrated under reduced pressure. The residue was dissolved in water, acidified with 1 N HCl to obtain the solid which was filtered and dried under vacuum to afford the titled compound (120 mg, 86%); $^1$H NMR (400 MHz, DMSO-d$_6$): δ 7.87 (s, 1H), 7.61 (d, J=7.6 Hz, 1H), 7.00 (d, J=8.4 Hz, 1H), 6.95 (d, J=7.6 Hz, 1H), 6.50 (s, 1H), 6.31 (d, J=7.2 Hz, 1H), 3.52 (s, 3H), 3.25-3.21 (m, 4H), 1.97-1.93 (m, 4H); LC-MS: m/z 376.0 (M−1).

Step-g: Synthesis of N-(2-(2-hydroxyethoxy)ethyl)-1-methyl-2-((6-(pyrrolidin-1-yl)benzo[d]oxazol-2-yl)amino)-1H-benzo[d]imidazole-5-carboxamide To a stirred solution of 1-methyl-2-((6-(pyrrolidin-1-yl)benzo[d]oxazol-2-yl)amino)-1H-benzo[d]imidazole-5-carboxylic acid (120 mg, 0.32 mmol) in DMFA (5 mL) at 0° C. was added N-ethyldiisopropyl amine (0.08 mL, 0.48 mmol) and HBTU (180 mg, 0.48 mmol). The reaction mixture was stirred for 30 min, followed by the addition of 2-(2-aminoethoxy)ethan-1-ol (80 mg, 0.48 mmol) and stirring was continued at RT for 16 h. Once the reaction was completed (monitored by TLC), the reaction mixture was diluted with cold water (20 mL) and extracted with EtOAc (2×50 mL). Combined organic layers were washed with water (25 mL), brine (25 mL), dried over anhydrous sodium sulfate and concentrated under vacuum. The residue was purified by preparative HPLC purification method to afford the titled compound (15 mg, 10%);

| Preparative HPLC purification method details: | |
|---|---|
| DILUTION: | THF + Acetonitrile:Water (50:50) |
| MOBILE PHASE A: | 0.1% Formic acid in water |
| MOBILE PHASE B: | Acetonitrile (100%) |
| GRADIENT: | T/% B: 0/15, 10/35 |
| FLOW RATE: | 15 mL/min |
| COLUMN: | Agilent ZORBAX XDB C18 (150 × 21.2 × 5 μm) |

$^1$H NMR (400 MHz, DMSO-d$_6$): δ 12.0 (bs, 1H), 8.40 (t, J=5.2 Hz, 1H), 8.03 (s, 1H), 7.73 (d, J=8.4 Hz, 1H), 7.43 (d, J=8.4 Hz, 1H), 7.28 (d, J=8.4 Hz, 1H), 6.63 (bs, 1H), 6.46 (bs, 1H), 4.63 (s, 1H), 3.59 (s, 3H), 3.57-3.39 (m, 8H), 3.24 (bs, 4H), 1.97 (bs, 4H); LC-MS: m/z 465.20 (M+1)$^+$.

Example 138. Synthesis of N-(2-(2-hydroxyethoxy)ethyl)-1-methyl-2-((6-((tetrahydro-2H-pyran-4-yl)oxy)benzo[d]oxazol-2-yl)amino)-1H-benzo[d]imidazole-5-carboxamide

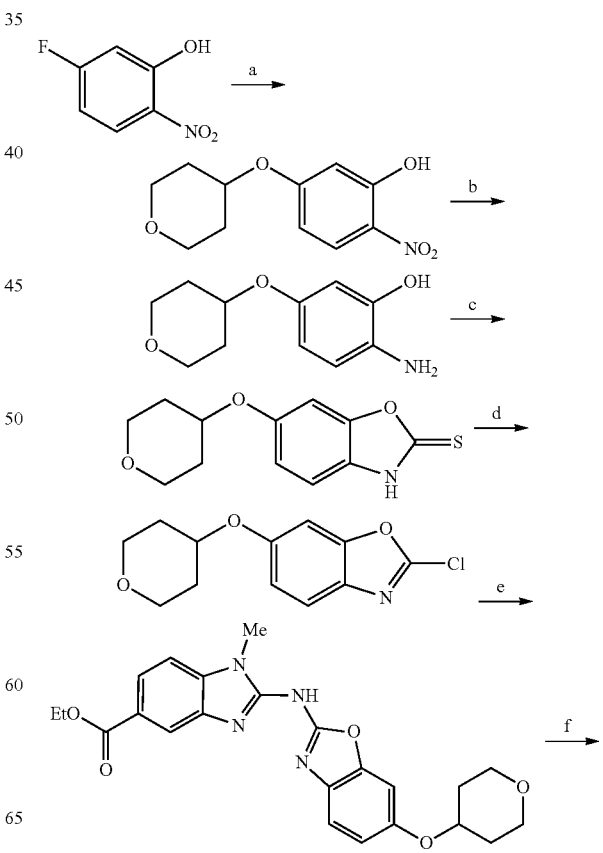

-continued

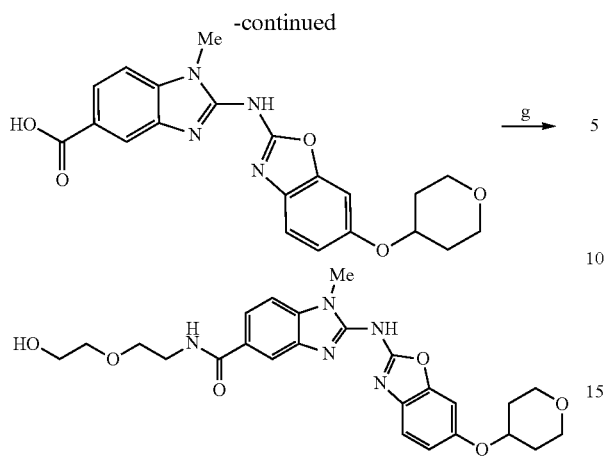

Conditions: a) Tetrahydro-2H-pyran-4-ol, NaH, DMF, 60° C., 16 h; b) 10% Pd/C, MeOH, H₂, RT, 6 h; c) Potassium ethyl xanthate, EtOH, Reflux, 16 h; d) SOCl₂, Cat.DMF, Reflux, 3 h; e) NaH, ethyl 2-amino-1-methyl-1H-benzo[d]imidazole-5-carboxylate, 1,4-Dioxane, RT, 16 h; f) LiOH•H₂O, THF, EtOH, H₂O, 60° C., 16 h; g) 2-(2-aminoethoxy)ethan-1-ol, HBTU, DIPEA, DMF, 0° C.-RT, 16 h

Step-a: Synthesis of 2-nitro-5-((tetrahydro-2H-pyran-4-yl)oxy)phenol

To a solution of tetrahydro-2H-pyran-4-ol (2.27 mL, 22.29 mmol) in DMFA (15 mL) at 10° C. was added sodium hydride (60% dispersion in mineral oil) (1.27 g, 31.84 mmol) and stirred for 5 min, followed by the addition of 5-fluoro-2-nitrophenol (1.0 g, 6.37 mmol) to the reaction mixture and it was stirred at 60° C. for 16 h. The reaction mixture was cooled to RT, quenched with cold water (100 mL) and neutralized with 1 N HCl. The precipitated solid was filtered and dried under vacuum to afford the title compound (1.0 g, 33%); $^1$H NMR (400 MHz, DMSO-$d_6$): δ 10.90 (bs, 1H), 7.95 (d, J=9.2 Hz, 1H), 6.68 (d, J=2.0 Hz, 1H), 6.63 (dd, J=2.4 Hz, J=9.2 Hz, 1H), 4.71-4.68 (m, 1H), 3.86-3.82 (m, 2H), 3.52-3.49 (m, 2H), 1.99-1.97 (m, 2H), 1.64-1.56 (m, 2H).

Step-b: Synthesis of 2-amino-5-((tetrahydro-2H-pyran-4-yl)oxy)phenol

The title compound was synthesized using the same procedure which was followed for compound 1e using 2-nitro-5-((tetrahydro-2H-pyran-4-yl)oxy)phenol as starting material and stirring for 6 h (Yield: 87%); $^1$H NMR (400 MHz, DMSO-$d_6$): δ 9.0 (bs, 1H), 6.47 (d, J=8.4 Hz, 1H), 6.32 (d, J=2.8 Hz, 1H), 6.21 (dd, J=2.4 Hz, J=8.4 Hz, 1H), 4.22-4.17 (m, 1H), 3.83-3.78 (m, 2H), 3.44-3.40 (m, 2H), 1.89-1.85 (m, 2H), 1.54-1.45 (m, 2H); LC-MS: m/z 209.95 (M+1)⁺.

Step-c: Synthesis of 6-((tetrahydro-2H-pyran-4-yl)oxy)benzo[d]oxazole-2(3H)-thione The title compound was synthesized using the same procedure which was followed for Example 32 Step-c using 2-amino-5-((tetrahydro-2H-pyran-4-yl)oxy)phenol as starting material (Yield: 75%); $^1$H NMR (400 MHz, DMSO-$d_6$): δ 13.74 (bs, 1H), 7.30 (d, J=2.4 Hz, 1H), 7.12 (d, J=8.8 Hz, 1H), 6.92 (dd, J=2.4 Hz, J=8.4 Hz, 1H), 4.59-4.53 (m, 1H), 3.87-3.82 (m, 2H), 3.47-3.40 (m, 2H), 1.98-1.93 (m, 2H), 1.61-1.52 (m, 2H); LC-MS: m/z 252.1 (M+1)⁺.

Step-d: Synthesis of 2-chloro-6-((tetrahydro-2H-pyran-4-yl)oxy)benzo[d]oxazole The title compound was synthesized using the same procedure which was followed for Example 32 Step-d using 6-((tetrahydro-2H-pyran-4-yl)oxy)benzo[d]oxazole-2(3H)-thione as starting material (Yield: 25%); $^1$H NMR (400 MHz, DMSO-$d_6$): δ 7.59 (d, J=8.8 Hz, 1H), 7.47 (d, J=2.0 Hz, 1H), 7.02 (dd, J=2.0 Hz, J=8.8 Hz, 1H), 4.62-4.59 (m, 1H), 3.85-3.77 (m, 2H), 3.49-3.43 (m, 2H), 1.97-1.94 (m, 2H), 1.61-1.52 (m, 2H); LC-MS: m/z 254.1 (M+1)⁺.

Step-e: Synthesis of ethyl 1-methyl-2-((6-((tetrahydro-2H-pyran-4-yl)oxy)benzo[d]oxazol-2-yl)amino)-1H-benzo[d]imidazole-5-carboxylate The title compound was synthesized using the same procedure which was followed for Example 32 Step-e using ethyl 2-amino-1-methyl-1H-benzo[d]imidazole-5-carboxylate and 2-chloro-6-((tetrahydro-2H-pyran-4-yl)oxy)benzo[d]oxazole as starting materials (Yield: 23%); $^1$H NMR (400 MHz, DMSO-$d_6$): δ 12.20 (bs, 1H), 8.21 (d, J=1.2 Hz, 1H), 7.85 (dd, J=1.6 Hz, J=8.4 Hz, 1H), 7.49 (d, J=8.4 Hz, 1H), 7.35 (d, J=8.8 Hz, 1H), 7.19 (d, J=2.4 Hz, 1H), 6.85 (dd, J=2.0 Hz, J=8.8 Hz, 1H), 4.56-4.54 (m, 1H), 4.32 (q, J=7.2 Hz, 2H), 3.88-3.85 (m, 2H), 3.62 (s, 3H), 3.51-3.44 (m, 2H), 2.00-1.98 (m, 2H), 1.61-1.58 (m, 2H), 1.35 (q, J=6.8 Hz, 3H); LC-MS: m/z 437.2 (M+1)⁺.

Step-f: Synthesis of 1-methyl-2-((6-((tetrahydro-2H-pyran-4-yl)oxy)benzo[d]oxazol-2-yl)amino)-1H-benzo[d]imidazole-5-carboxylic acid The title compound was synthesized using the same procedure which was followed for compound 1h using ethyl 1-methyl-2-((6-((tetrahydro-2H-pyran-4-yl)oxy)benzo[d]oxazol-2-yl)amino)-1H-benzo[d]imidazole-5-carboxylate as starting material (Yield: 67%); $^1$H NMR (400 MHz, DMSO-$d_6$): δ 12.40 (bs, 1H), 8.17 (d, J=1.2 Hz, 1H), 7.86 (dd, J=1.2 Hz, J=8.4 Hz, 1H), 7.49 (d, J=8.4 Hz, 1H), 7.36 (d, J=5.6 Hz, 1H), 7.20 (d, J=2.4 Hz, 1H), 6.86 (dd, J=2.4 Hz, J=8.8 Hz, 1H), 4.57-4.53 (m, 1H), 3.88-3.84 (m, 2H), 3.62 (s, 3H), 3.51-3.44 (m, 2H), 2.00-1.95 (m, 2H), 1.61-1.58 (m, 2H); LC-MS: m/z 409.1 (M+1)⁺.

Step-g: Synthesis of N-(2-(2-hydroxyethoxy)ethyl)-1-methyl-2-((6-((tetrahydro-2H-pyran-4-yl)oxy)benzo[d]oxazol-2-yl)amino)-1H-benzo[d]imidazole-5-carboxamide The title compound was synthesized using the same procedure which was followed for Example 6 Step-e using 1-methyl-2-((6-((tetrahydro-2H-pyran-4-yl)oxy)benzo[d]oxazol-2-yl)amino)-1H-benzo[d]imidazole-5-carboxylic acid and 2-(2-aminoethoxy)ethan-1-ol as starting materials. The crude product was purified by combiflash chromatography using 4% methanol in DCM as an eluent (Yield: 40%); $^1$H NMR (400 MHz, DMSO-$d_6$): δ 12.17 (bs, 1H), 8.44 (d, J=5.6 Hz, 1H), 8.05 (d, J=1.2 Hz, 1H), 7.74 (dd, J=1.6 Hz, J=8.4 Hz, 1H), 7.46 (d, J=8.4 Hz, 1H), 7.34 (d, J=8.4 Hz, 1H), 7.18 (d, J=2.0 Hz, 1H), 6.84 (dd, J=2.4 Hz, J=8.8 Hz, 1H), 4.62 (bs, 1H), 4.57-4.51 (m, 1H), 3.89-3.84 (m, 2H), 3.61 (s, 3H), 3.55-3.33 (m, 10H), 1.98-1.95 (m, 2H), 1.61-1.57 (m, 2H); LC-MS: m/z 496.2 (M+1)+

Examples 139, 140 and 141. Synthesis of 1-(2-(benzo[d]oxazol-2-ylamino)-1-methyl-1H-benzo[d]imidazol-5-yl)-2,2,2-trifluoroethan-1-one, Synthesis of (Z)-1-(2-(benzo[d]oxazol-2-ylamino)-1-methyl-1H-benzo[d]imidazol-5-yl)-2,2,2-trifluoroethan-1-one oxime and Synthesis of N-(5-(1-amino-2,2,2-trifluoroethyl)-1-methyl-1H-benzo[d]imidazol-2-yl)benzo[d]oxazol-2-amine

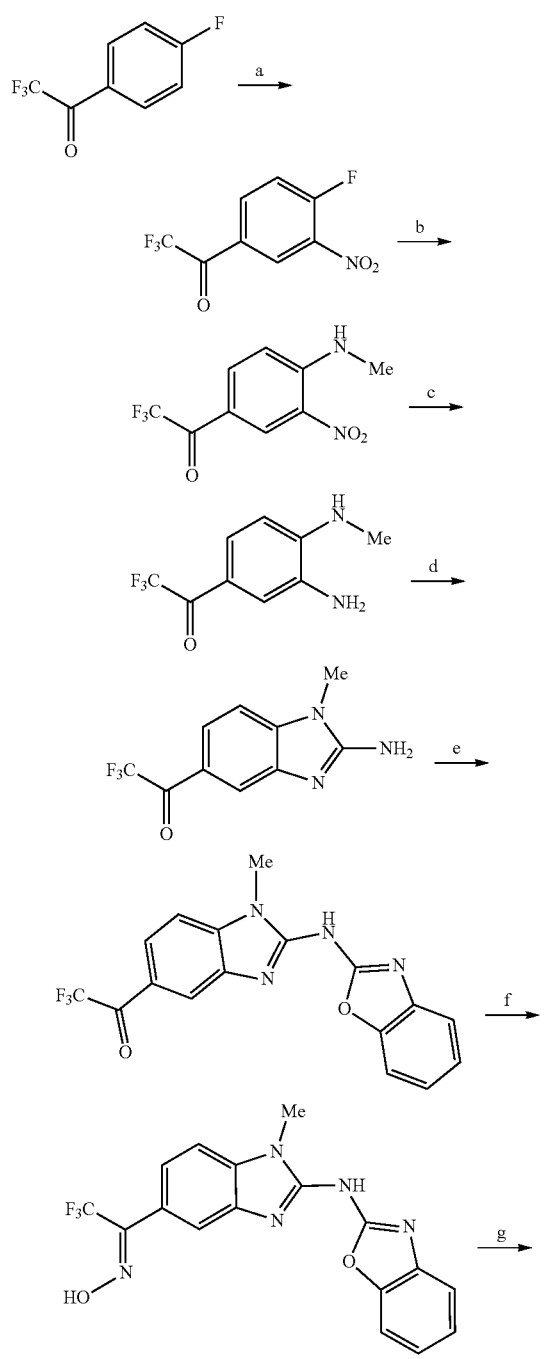

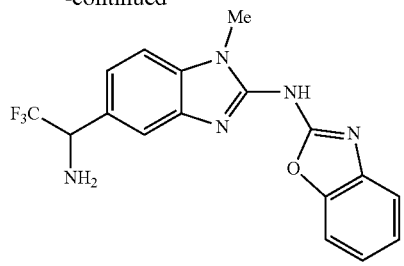

Conditions: a) Conc.H2SO4, Fuming nitric acid, 0° C.-RT, 2 h; b) Aq.Methyl amine, DMF, 0° C.-RT, 2 h; c) Iron, Conc.HCl, MeOH, 0° C.-RT, 1 h, 60° C., 1 h; d) Cyanogen bromide, THF, Water, 60° C., 16 h; e) 2-Chlorobenzoxazole, Sodiumhydride, 1,4-Dioxane, 0° C.-RT, 16 h; f) hydroxylamine hydrochloride, Potassium acetate, Ethanol, reflux, 16 h; g) LiAlH4, (1M solution in THF), THF, 10° C., 4 h Step-a: Synthesis of 2,2,2-trifluoro-1-(4-fluoro-3-nitrophenyl)ethan-1-one To a solution of 2,2,2-trifluoro-1-(4-fluorophenyl)ethan-1-one (3.0 g, 15.62 mmol) in conc. sulfuric acid (12 mL) at 0° C. was added fuming nitric acid (0.9 mL) and stirred at RT for 2 h. The reaction mixture was quenched with cold water (100 mL) and extracted with ethyl acetate (200 mL). Organic layer was washed with cold water (2×50 mL), brine solution (50 mL), dried over anhydrous sodium sulfate and concentrated under vacuum to afford the titled compound (3.5 g, 94%) which was used in the next step without further purification; $^1$H NMR (400 MHz, DMSO-$d_6$): δ 8.80 (d, J=6.8 Hz, 1H), 8.37 (d, J=8.8 Hz, 1H), 7.54 (t, J=9.4 Hz, 1H).

Step-b: Synthesis of 2,2,2-trifluoro-1-(4-(methylamino)-3-nitrophenyl)ethan-1-one To a stirred solution of 2,2,2-trifluoro-1-(4-fluoro-3-nitrophenyl)ethan-1-one (3.5 g, 14.7 mmol) in DMFA (17.5 mL) at 0° C. was added 40% aqueous methyl amine (3.5 mL) and the reaction mixture was stirred at RT for 2 h. The reaction mixture was diluted with cold water (100 mL) and extracted with ethyl acetate (2×100 mL). Combined organic layers were washed with water (2×50 mL), brine solution (50 mL), dried over anhydrous sodium sulfate and concentrated under vacuum to afford the titled compound (3.3 g, 89%) which was used in the next step without further purification; $^1$H NMR (400 MHz, DMSO-$d_6$): δ 8.99 (bs, 1H), 8.69 (s, 1H), 8.05 (d, J=9.2 Hz, 1H), 7.19 (d, J=9.2 Hz, 1H), 3.06 (d, J=4.8 Hz, 3H); LC-MS: m/z 247.1 (M−1).

Step-c: Synthesis of 1-(3-amino-4-(methylamino)phenyl)-2,2,2-trifluoroethan-1-one To a stirred solution of 2,2,2-trifluoro-1-(4-(methylamino)-3-nitrophenyl)ethan-1-one (2.0 g, 8.1 mmol) in methanol (20 mL) at 0° C. was added iron (2.25 g, 40.3 mmol) and conc. hydrochloric acid (5.0 mL, 40.3 mmol). The reaction mixture was stirred at RT for 1 h and then heated at 60° C. with stirring for another 1 h. The reaction mixture was cooled to RT, diluted with methanol (30 mL) and filtered through a celite pad. The filtrate was concentrated and diluted with water (50 mL), basified with saturated sodium bicarbonate solution and extracted with EtOAc (2×50 mL). The combined organic layers were washed with water (30 mL), brine (30 mL), dried over anhydrous sodium sulfate and concentrated under vacuum to afford the titled compound (1.5 g, 84%) which was used in the next step without further purification; ¹H NMR (400 MHz, DMSO-d₆): δ 7.35 (d, J=8.4 Hz, 1H), 7.21 (s, 1H), 6.50 (d, J=8.8 Hz, 1H), 6.30 (bs, 1H), 4.96 (s, 2H), 2.85 (d, J=4.8 Hz, 3H); LC-MS: m/z 218.90 (M+1)⁺.

Step-d: Synthesis of 1-(2-amino-1-methyl-1H-benzo[d]imidazol-5-yl)-2,2,2-trifluoroethan-1-one To a stirred solution of 1-(3-amino-4-(methylamino)phenyl)-2,2,2-trifluoroethan-1-one (1.0 g, 4.6 mmol) in THF (10 mL) and water (10 mL) at RT was added cyanogen bromide (0.58 g, 5.5 mmol) and the reaction mixture was stirred at 60° C. for 16 h. The reaction mixture was concentrated under reduced pressure and the residue was diluted with water (50 mL), basified with saturated sodium bicarbonate solution and extracted with EtOAc (2×100 mL). Combined organic layers were washed with water (50 mL), brine (500 mL), dried over anhydrous sodium sulfate and concentrated under vacuum to afford the titled compound which was used in the next step without further purification (900 mg, 81%); ¹H NMR (400 MHz, DMSO-d₆): δ 7.75 (s, 1H), 7.70 (d, J=8.4 Hz, 1H), 7.38 (d, J=8.4 Hz, 1H), 6.96 (s, 2H), 3.58 (s, 3H); LC-MS: m/z 244.1 (M+1)⁺.

Step-e: Synthesis of 1-(2-(benzo[d]oxazol-2-ylamino)-1-methyl-1H-benzo[d]imidazol-5-yl)-2,2,2-trifluoroethan-1-one To a stirred solution of 1-(2-amino-1-methyl-1H-benzo[d]imidazol-5-yl)-2,2,2-trifluoroethan-1-one (900 mg, 3.70 mmol) in 1,4-dioxane (20 mL) at 0° C. was added sodium hydride (60% dispersion in mineral oil) (518 mg, 12.96 mmol) and stirred for 15 min followed by the addition of 2-chlorobenzoxazole (567 mg, 3.70 mmol). The reaction mixture was stirred at RT for 16 h. The reaction mixture was then quenched with cold water (30 mL) and extracted with EtOAc (2×50 mL). Combined organic layers were washed with water (30 mL), brine (30 mL), dried over anhydrous sodium sulfate and concentrated under vacuum. The residue was purified by combi flash column chromatography using 100% DCM as an eluent to afford the titled compound (700 mg, 52%); ¹H NMR (400 MHz, DMSO-d₆): δ 12.50 (bs, 1H), 8.35 (s, 1H), 7.97 (d, J=8.8 Hz, 1H), 7.67 (d, J=8.8 Hz, 1H), 7.52-7.46 (m, 2H), 7.25 (t, J=7.8 Hz, 1H), 7.16 (t, J=7.8 Hz, 1H), 3.67 (s, 3H); LC-MS: m/z 361.1 (M+1)⁺.

Step-f: Synthesis of (Z)-1-(2-(benzo[d]oxazol-2-ylamino)-1-methyl-1H-benzo[d]imidazol-5-yl)-2,2,2-trifluoroethan-1-one oxime To a stirred solution of 1-(2-(benzo[d]oxazol-2-ylamino)-1-methyl-1H-benzo[d]imidazol-5-yl)-2,2,2-trifluoroethan-1-one (700 mg, 1.94 mmol) in ethanol (20 mL) at RT was added hydroxylamine hydochloride (405 mg, 5.83 mmol) and potassium acetate (572 mg, 5.83 mmol). The reaction mixture was stirred at 80° C. for 16 h. Once the reaction was completed (monitored by TLC), the reaction mixture was concentrated under reduced pressure and diluted with water (50 mL) and extracted with EtOAc (2×100 mL). Combined organic layers were washed with water (50 mL), brine (30 mL), dried over anhydrous sodium sulfate and concentrated under vacuum. The residue was purified by combi flash column chromatography using 2% methanol in DCM as an eluent to afford the titled compound (500 mg, 68%); ¹H NMR (400 MHz, DMSO-d₆): δ 13.05 (bs, 1H), 12.40 (bs, 1H), 7.81-7.76 (m, 1H), 7.59-7.53 (m, 1H), 7.48-7.46 (m, 2H), 7.41-7.37 (m, 1H), 7.24 (t, J=7.4 Hz, 1H), 7.15 (t, J=7.6 Hz, 1H), 3.65 (s, 3H); LC-MS: m/z 376.1 (M+1)⁺.

Step-g: Synthesis of N-(5-(1-amino-2,2,2-trifluoroethyl)-1-methyl-1H-benzo[d]imidazol-2-yl)benzo[d]oxazol-2-amine To a stirred solution of (Z)-1-(2-(benzo[d]oxazol-2-ylamino)-1-methyl-1H-benzo[d]imidazol-5-yl)-2,2,2-trifluoroethan-1-one oxime (300 mg, 0.80 mmol) in THF (5 mL) at 10° C. was added 1 M solution of lithium aluminium hydride (1.6 mL, 1.60 mmol). The reaction mixture was stirred at 10° C. for 4 h. Once the reaction was completed (monitored by TLC), the reaction mixture was quenched with 1N sodium hydroxide solution (5 mL), diluted with water (10 mL) and extracted with EtOAc (2×30 mL). Combined organic layers were washed with water (20 mL), brine (20 mL), dried over anhydrous sodium sulfate and concentrated under vacuum. The residue was purified by preparative HPLC method to afford the titled compound (100 mg, 35%).

| Preparative HPLC purification method details: | |
|---|---|
| DILUTION: | THF + ACN:WATER (50:50) |
| MOBILE PHASE A: | 0.1% formic acid in Water |
| MOBILE PHASE B: | 100% ACETONITRILE |
| GRADIENT: | T/% B: 0/15, 10/40 |
| FLOW RATE: | 15 mL/min |
| COLUMN: | Kinetex C-18 (250 × 21.1 × 5 μm) |

¹H NMR (400 MHz, DMSO-d₆): δ 12.20 (bs, 1H), 7.73 (s, 1H), 7.46-7.36 (m, 4H), 7.20 (t, J=7.2 Hz, 1H), 7.10 (t, J=7.2 Hz, 1H), 4.59-4.57 (m, 1H), 3.61 (s, 3H); LC-MS: m/z 362.3 (M+1)⁺.

Two isomers of this compound were separated by chiral HPLC purification.

| Chiral HPLC purification method details: | |
|---|---|
| DILUTION: | IPA:DCM (90:10) |
| MOBILE PHASE A: | 0.1% DEA in Hexane |
| MOBILE PHASE B: | IPA:DCM (90:10) % |
| ISOCRATIC: | A:B (40:60) |
| FLOW RATE: | 15 mL/min |

Peak-1 Analytical Data:
¹H NMR (400 MHz, DMSO-d₆): δ 12.20 (bs, 1H), 7.73 (s, 1H), 7.46-7.36 (m, 4H), 7.20 (t, J=7.2 Hz, 1H), 7.10 (t, J=7.2 Hz, 1H), 4.59-4.57 (m, 1H), 3.61 (s, 3H); LC-MS: m/z 362.05 (M+1)⁺.

Peak-2 Analytical Data:
¹H NMR (400 MHz, DMSO-d₆): δ 12.20 (bs, 1H), 7.73 (s, 1H), 7.46-7.36 (m, 4H), 7.20 (t, J=7.2 Hz, 1H), 7.10 (t, J=7.2 Hz, 1H), 4.60-4.58 (m, 1H), 3.61 (s, 3H); LC-MS: m/z 362.05 (M+1)⁺.

Example 142. Synthesis of 1-(2-(benzo[d]oxazol-2-ylamino)-1-methyl-1H-benzo[d]imidazol-5-yl)-2,2,2-trifluoroethan-1-ol

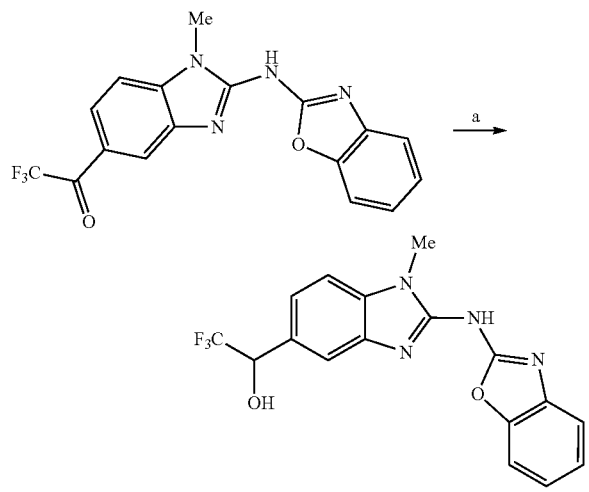

Conditions: a) Sodium borohydride, MeOH, 0° C.-RT, 1 h

To a stirred solution of 1-(2-(benzo[d]oxazol-2-ylamino)-1-methyl-1H-benzo[d]imidazol-5-yl)-2,2,2-trifluoroethan-1-one (50 mg, 0.14 mmol) in methanol (3 mL) at 0° C. was added sodium borohydride (6 mg, 0.15 mmol) and the reaction mixture was stirred at RT for 1 h. The reaction mixture was quenched with cold water (10 mL) and extracted with EtOAc (2×20 mL). The combined organic layers were washed with water (15 mL), brine (15 mL), dried over anhydrous sodium sulfate and concentrated under vacuum. The residue was purified by combi flash column chromatography using 2% methanol in DCM as an eluent to afford the titled compound (40 mg, 80%); $^1$H NMR (400 MHz, DMSO-d$_6$): δ 12.30 (bs, 1H), 7.77 (s, 1H), 7.46-7.34 (m, 4H), 7.20 (t, J=7.6 Hz, 1H), 7.10 (t, J=7.6 Hz, 1H), 6.90 (bs, 1H), 5.24-5.22 (m, 1H), 3.62 (s, 3H); LC-MS: m/z 363.30 (M+1)$^+$.

Example 143. ELISA Assay to Measure Human Heme Oxygenase-1 (HMOX-1) in HepG2 lysate Reagents and Technical Notes:

ELISA capture antibody, standard HO-1, detection antibody and streptavidin HRP were supplied in the DuoSet IC Human total HO-1 ELISA from R&D systems (DYC3776-2). The substrate cocktail was KPL LumiGLO reserve Chemiluminescent Substrate (54-71-00). PBS was Corning Cellgro Cell Culture (21-040-CV). 10×PBS+0.05% tween20 (PBST) was from KPL.

All incubations of the plate were at room temperature (20° C.) in a closed drawer.

The ELISA plate was processed manually. All loadings were with a multichannel pipet. Plates were emptied by shaking into the sink and tapping onto paper towels to remove any remaining reagent. Plate washing was accomplished by loading all wells with PBS+0.05% tween20 (PBST) using a squirt bottle, shaking the PBST out and tapping the plate onto paper towels.

Preparation of the ELISA Plate:

1. anti-HO-1 capture antibody was 1440 µg/ml after reconstitution in PBS. This antibody was diluted to 8 µg/ml in PBS and 50 µl per well was added to a 384 well greiner "lumitrac 200" plate. Incubated overnight.
2. The plate was emptied and 100 µl PBS+1% BSA added to all wells. Incubated 90 minutes at room temperature.

Preparation of HepG2 Lysate:
1. Cells were cultured in a 96-well tissue culture plate washed with PBS and then the plate frozen at –70° C. overnight. Plates were allowed to warm to ice temperature in an ice bucket. 20 µl of PBS, 0.5% Triton X100, 1 mM EDTA with 1×HALT™ protease inhibitors was added to each well and the plates incubated on ice for 1 hour.
2. The lysates were frozen at –20° C. overnight.

Measurement of HMOX1 ("HO-1")
1. In a polypropylene 384 well plate, human HO-1 (after reconstitution in PBS+0.5% Triton+1 mM EDTA) was serially diluted from 20 ng/ml 2-fold in PBS+0.5% triton-X100, 1 mM EDTA to make a 12-point standard curve including a zero point.
2. In a polypropylene 96 well plate, HepG2 lysate was diluted 1 to 20 in Diluent #4 from DUOSET kit in which the assay standard is also diluted.
3. The PBS+1% BSA was emptied from the ELISA plate and 30 µl of all samples and standards were added (duplicates recommended). The plate was incubated 90 minutes.
4. Emptied plate and washed 4 times with PBST.
5. Diluted HO-1 detection antibody to 200 ng/ml in PBS+1% BSA and added 30 µl to all wells. Incubated 90 minutes.
6. Emptied plate and washed 4 times with PBST.
7. Added 30 µl streptavidin HRP at 1/200 in PBS+1% BSA (stock streptavidin concentration not specified) to all wells. Incubated 30 minutes.
8. Emptied plate and washed 4 times with PBST.
9. Diluted Lumiglo reserve reagent two parts buffer to one part lumiglo substrate. Added 30 µl to all wells. Incubated 5 minutes.
10. Measured chemiluminescence on spectramax M5 using 150 ms integration.

Table 1 below lists EC$_{50}$ and fold changes of human HMOX1 protein levels relative to DMSO control upon treatment with representative compounds.

Example 144. Kinetic Solubility

10 µL of 10 mM DMSO stock solution were aliquotted to 490 µL of DMSO solution and separately 490 µL of Dulbecco's phosphate buffer saline, DPBS, pH 7.4 solution in 1.2 mL 96-well plates in duplicate. Final concentration was 200 µM of the test compound. Samples were incubated at 25° C. with shaking at 200 rpm for 16 h. Samples were centrifuged at 3500 rpm for 20 min at 25° C., and supernatant was submitted for HPLC analysis.

Kinetic solubility was measured using the following equation:

$$\text{Kinetic Solubility in } \mu m = \frac{\text{Test } Conc. \ \mu m \times \text{Peak area of compound in } DPBS \text{ sample (2\% } DMSO \text{ solution)}}{\text{Peak area of compound in 100\% } DMSO}$$

The kinetic solubility data of representative compounds of the present invention are provided in Table 1 below.

TABLE 1

| Example No. | Structure | IUPAC name | EC$_{50}$ (μM) | Maximum Fold induction | Solubility (μM) |
|---|---|---|---|---|---|
| Comparator 1 | 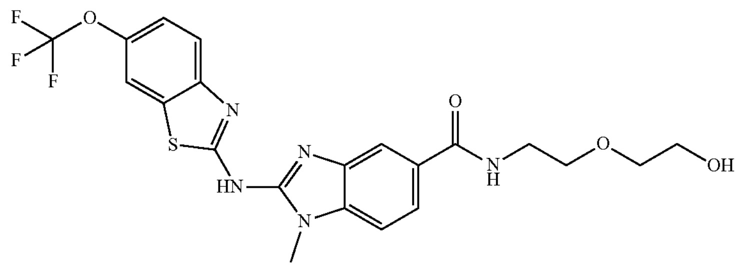 [SMILES: Cn1c(Nc2nc3ccc(OC(F)(F)F)cc3s2)nc2cc(C(=O)NCCOCCO)ccc21] | 1-methyl-2-(6-trifluoromethoxy-benzothiazol-2-ylamino)-1H-benzoimidazole-5-carboxylic acid [2-(2-hydroxy-ethoxy)-ethyl]-amide | 0.9* | | ND |
| 1h | 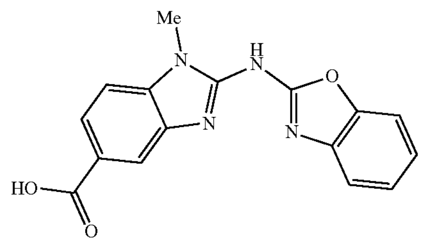 [SMILES: Cn1c(Nc2nc3ccccc3o2)nc2cc(C(=O)O)ccc21] | 2-(benzo[d]oxazol-2-ylamino)-1-methyl-1H-benzo[d]imidazole-5-carboxylic acid | 4.4* | 7-38 | ND |
| 1i | 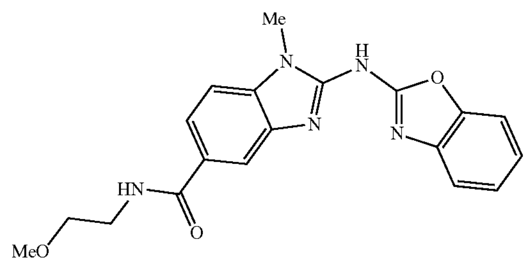 [SMILES: COCCNC(=O)c1ccc2c(c1)nc(Nc1nc3ccccc3o1)n2C] | 2-(benzo[d]oxazol-2-ylamino)-N-(2-methoxyethyl)-1-methyl-1H-benzo[d]imidazole-5-carboxamide | 0.8* | 6-15 | ND |

TABLE 1-continued

| Example No. | Structure | IUPAC name | EC$_{50}$ (μM) | Maximum Fold induction | Solubility (μM) |
|---|---|---|---|---|---|
| 2d | 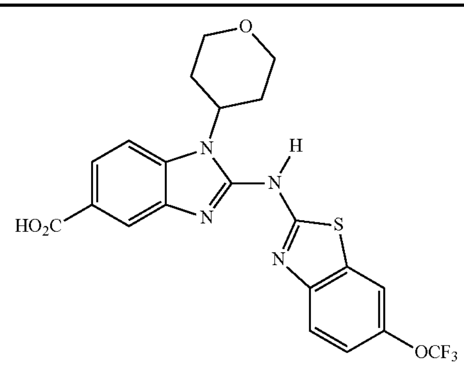 | 1-(tetrahydro-2H-pyran-4-yl)-2-((6-(trifluoromethoxy)benzo[d]thiazol-2-yl)amino)-1H-benzo[d]imidazole-5-carboxylic acid | N/A | 10 (n = 2) | ND |
| 2e | 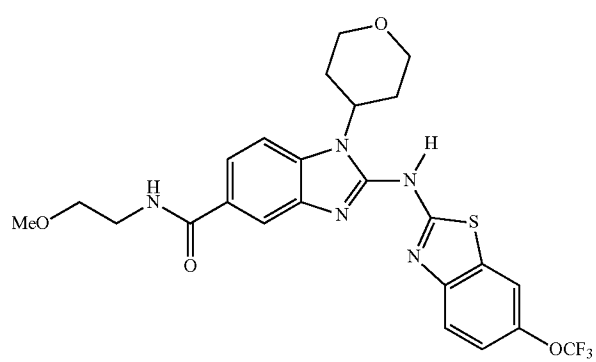 [SMILES: COCCNC(=O)c1ccc2c(c1)nc(Nc1nc3ccc(OC(F)(F)F)cc3s1)n2C1CCOCC1] | N-(2-methoxyethyl)-1-(tetrahydro-2H-pyran-4-yl)-2-((6-(trifluoromethoxy)benzo[d]thiazol-2-yl)amino)-1H-benzo[d]imidazole-5-carboxamide | 3.8* | 20-33 | ND |

TABLE 1-continued

| Example No. | Structure | IUPAC name | EC$_{50}$ (µM) | Maximum Fold induction | Solubility (µM) |
|---|---|---|---|---|---|
| 3d | 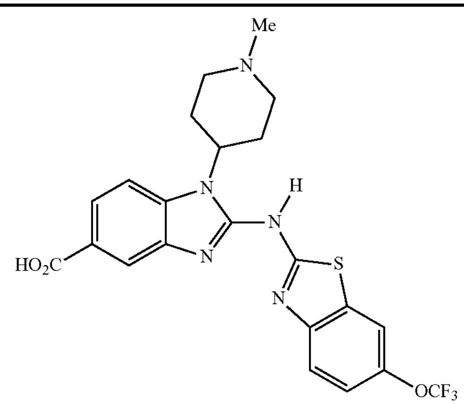 | 1-(1-methylpiperidin-4-yl)-2-((6-(trifluoromethoxy)benzo[d]thiazol-2-yl)amino)-1H-benzo[d]imidazole-5-carboxylic acid | 9.2* | 13 | ND |
| 3e | 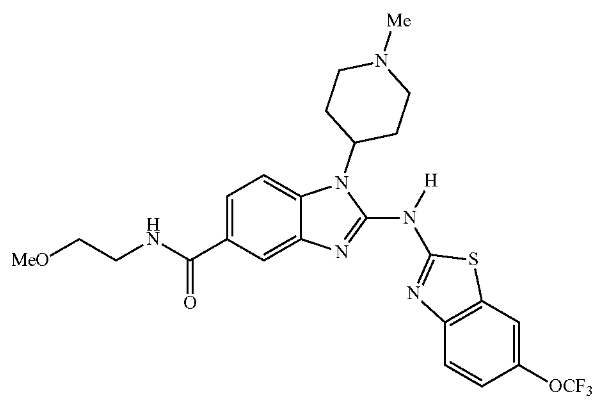 [SMILES: COCCNC(=O)c1ccc2c(c1)nc(Nc1nc3ccc(OC(F)(F)F)cc3s1)n2C1CCN(C)CC1] | N-(2-methoxyethyl)-1-(1-methylpiperidin-4-yl)-2-((6-(trifluoromethoxy)benzo[d]thiazol-2-yl)amino)-1H-benzo[d]imidazole-5-carboxamide | 1.1* | 6-46 | ND |

TABLE 1-continued

| Example No. | Structure | IUPAC name | EC$_{50}$ (μM) | Maximum Fold induction | Solubility (μM) |
|---|---|---|---|---|---|
| 4d | 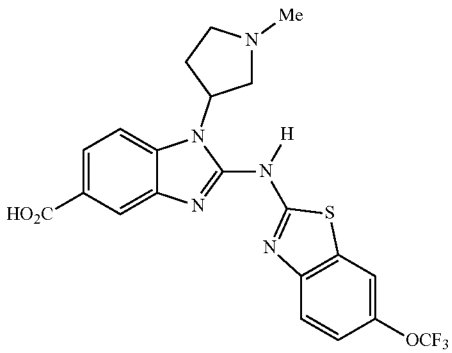 [SMILES: CN1CCC(n2c(Nc3nc4ccc(OC(F)(F)F)cc4s3)nc3cc(C(=O)O)ccc32)C1] | 1-(1-methylpyrrolidin-3-yl)-2-((6-(trifluoromethoxy)benzo[d]thiazol-2-yl)amino)-1H-benzo[d]imidazole-5-carboxylic acid | 4.7* | 29-33 | ND |
| 4e | 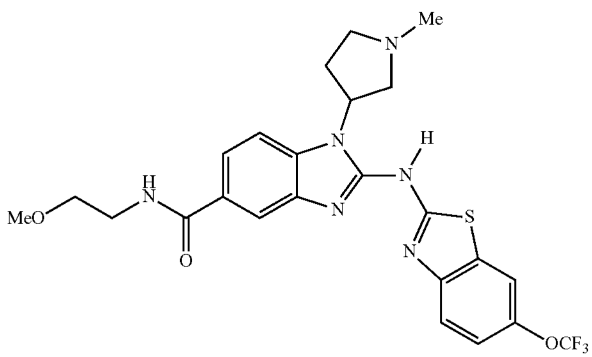 [SMILES: COCCNC(=O)c1ccc2c(c1)nc(Nc1nc3ccc(OC(F)(F)F)cc3s1)n2C1CCN(C)C1] | N-(2-methoxyethyl)-1-(1-methylpyrrolidin-3-yl)-2-((6-(trifluoromethoxy)benzo[d]thiazol-2-yl)amino)-1H-benzo[d]imidazole-5-carboxamide | N/A | 19 | ND |
| 5 | 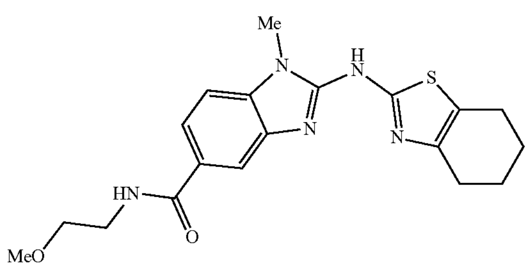 [SMILES: COCCNC(=O)c1ccc2c(c1)nc(Nc1nc3c(s1)CCCC3)n2C] | N-(2-methoxyethyl)-1-methyl-2-((4,5,6,7-tetrahydrobenzo[d]thiazol-2-yl)amino)-1H-benzo[d]imidazole-5-carboxamide | | | |

TABLE 1-continued

| Example No. | Structure | IUPAC name | EC$_{50}$ (µM) | Maximum Fold induction | Solubility (µM) |
|---|---|---|---|---|---|
| 6 | 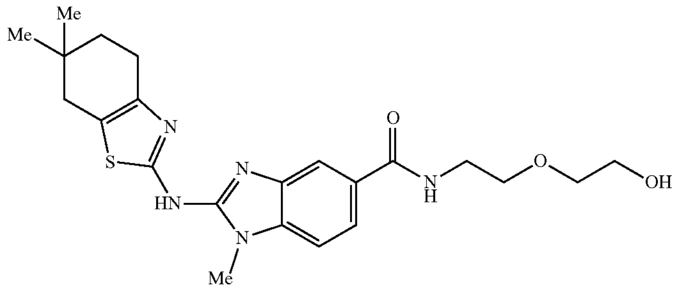 [SMILES: Cn1c(Nc2nc3c(s2)CC(C)(C)CC3)nc2cc(C(=O)NCCOCCO)ccc21] | 2-((6,6-dimethyl-4,5,6,7-tetrahydrobenzo[d]thiazol-2-yl)amino)-N-(2-(2-hydroxyethoxy)ethyl)-1-methyl-1H-benzo[d]imidazole-5-carboxamide | | | |
| 7 | 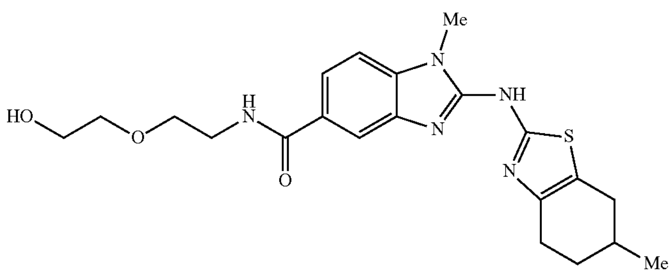 [SMILES: CC1CCc2nc(Nc3nc4cc(C(=O)NCCOCCO)ccc4n3C)sc2C1] | N-(2-(2-hydroxyethoxy)ethyl)-1-methyl-2-((6-methyl-4,5,6,7-tetrahydrobenzo[d]thiazol-2-yl)amino)-1H-benzo[d]imidazole-5-carboxamide | | | |
| 8 | 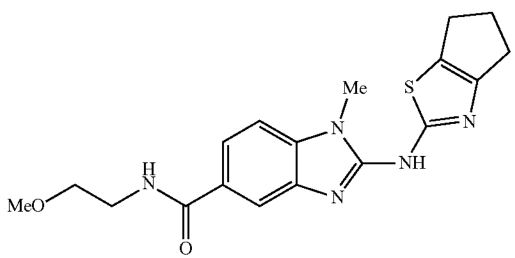 [SMILES: COCCNC(=O)c1ccc2c(c1)nc(Nc1nc3c(s1)CCC3)n2C] | 2-((5,6-dihydro-4H-cyclopenta[d]thiazol-2-yl)amino)-N-(2-methoxyethyl)-1-methyl-1H-benzo[d]imidazole-5-carboxamide | | | |

TABLE 1-continued

| Example No. | Structure | IUPAC name | EC$_{50}$ (µM) | Maximum Fold induction | Solubility (µM) |
|---|---|---|---|---|---|
| 9 | 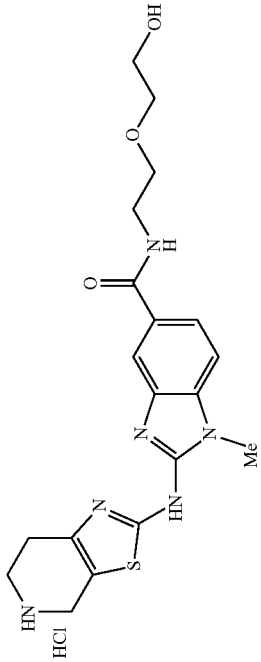 | N-(2-(2-hydroxyethoxy)ethyl)-1-methyl-2-((4,5,6,7-tetrahydrothiazolo[5,4-c]pyridin-2-yl)amino)-1H-benzo[d]imidazole-5-carboxamide hydrochloride | | | |
| 10 | 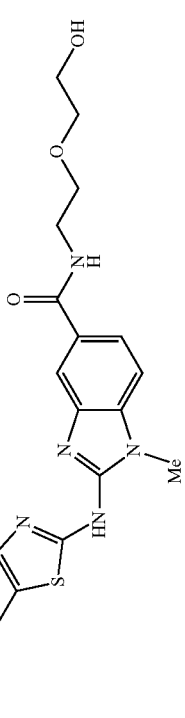 | 2-((5-acetyl-4,5,6,7-tetrahydrothiazolo[5,4-c]pyridin-2-yl)amino)-N-(2-(2-hydroxyethoxy)ethyl)-1-methyl-1H-benzo[d]imidazole-5-carboxamide | ND | 2 | 8.6 |
| 11 | 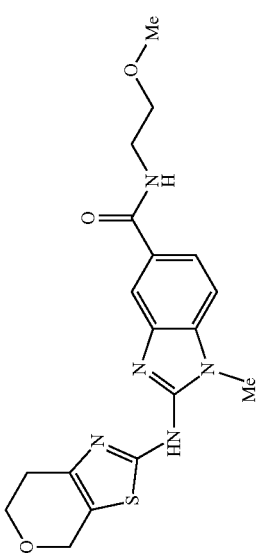 | 2-((6,7-dihydro-4H-pyrano[4,3-d]thiazol-2-yl)amino)-N-(2-methoxyethyl)-1-methyl-1H-benzo[d]imidazole-5-carboxamide | 6.6 | 5 | ND |

TABLE 1-continued

| Example No. | Structure | IUPAC name | EC$_{50}$ (µM) | Maximum Fold induction | Solubility (µM) |
|---|---|---|---|---|---|
| 12 | 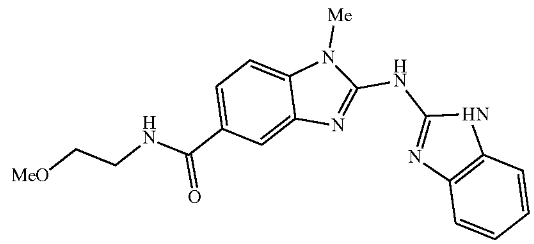 [SMILES: COCCNC(=O)c1ccc2c(c1)nc(Nc1nc3ccccc3[nH]1)n2C] | 2-((1H-benzo[d]imidazol-2-yl)amino)-N-(2-methoxyethyl)-1-methyl-1H-benzo[d]imidazole-5-carboxamide | 4.5 | 5.5 | ND |
| 13 | 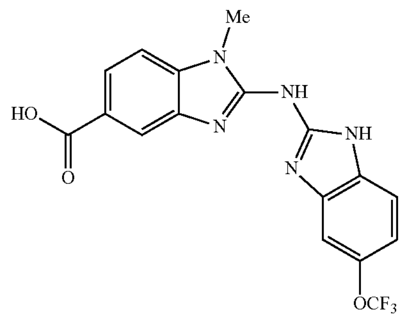 [SMILES: Cn1c(Nc2nc3cc(OC(F)(F)F)ccc3[nH]2)nc2cc(C(=O)O)ccc21] | 1-methyl-2-((5-(trifluoromethoxy)-1H-benzo[d]imidazol-2-yl)amino)-1H-benzo[d]imidazole-5-carboxylic acid | 1.9* | 6-27 | ND |
| 14 | 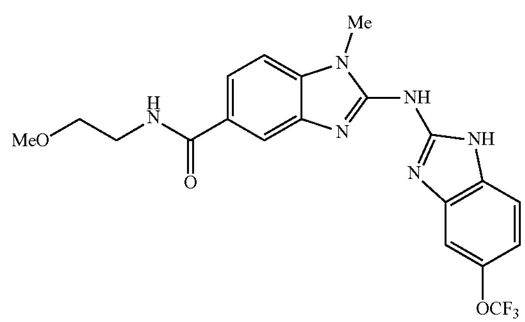 [SMILES: COCCNC(=O)c1ccc2c(c1)nc(Nc1nc3cc(OC(F)(F)F)ccc3[nH]1)n2C] | N-(2-methoxyethyl)-1-methyl-2-((5-(trifluoromethoxy)-1H-benzo[d]imidazol-2-yl)amino)-1H-benzo[d]imidazole-5-carboxamide | 2.3* | 6.25 | 4.2 |

TABLE 1-continued

| Example No. | Structure | IUPAC name | EC$_{50}$ (μM) | Maximum Fold induction | Solubility (μM) |
|---|---|---|---|---|---|
| 15 | 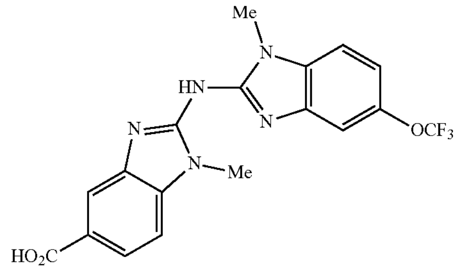 [SMILES: Cn1c(Nc2nc3cc(C(=O)O)ccc3n2C)nc2cc(OC(F)(F)F)ccc21] | 1-methyl-2-((1-methyl-5-(trifluoromethoxy)-1H-benzo[d]imidazol-2-yl)amino)-1H-benzo[d]imidazole-5-carboxylic acid | 5.3* | 11-13 | ND |
| 16 | 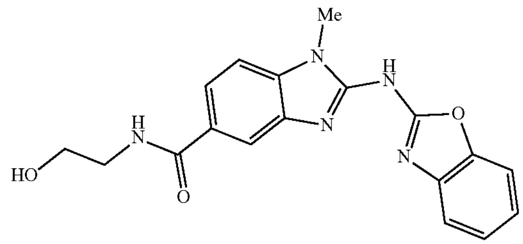 [SMILES: Cn1c(Nc2nc3ccccc3o2)nc2cc(C(=O)NCCO)ccc21] | 2-(benzo[d]oxazol-2-ylamino)-N-(2-hydroxyethyl)-1-methyl-1H-benzo[d]imidazole-5-carboxamide | 0.7* | 8-27 | 11.7 |
| 17 | 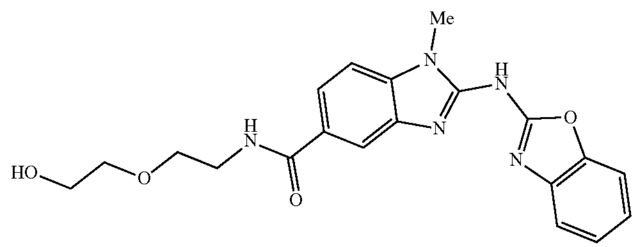 [SMILES: Cn1c(Nc2nc3ccccc3o2)nc2cc(C(=O)NCCOCCO)ccc21] | 2-(benzo[d]oxazol-2-ylamino)-N-(2-(2-hydroxyethyl)ethyl)-1-methyl-1H-benzo[d]imidazole-5-carboxamide | 1.4* | 11-40 | 11.6 |

TABLE 1-continued

| Example No. | Structure | IUPAC name | EC$_{50}$ (µM) | Maximum Fold induction | Solubility (µM) |
|---|---|---|---|---|---|
| 18 | 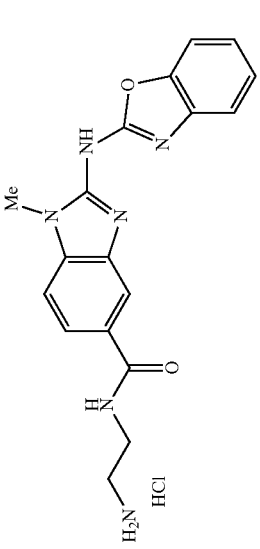 | N-(2-aminoethyl)-2-(benzo[d]oxazol-2-ylamino)-1-methyl-1H-benzo[d]imidazole-5-carboxamide hydrochloride | 0.7* | 41-52 | 12.4 |
| 19 | 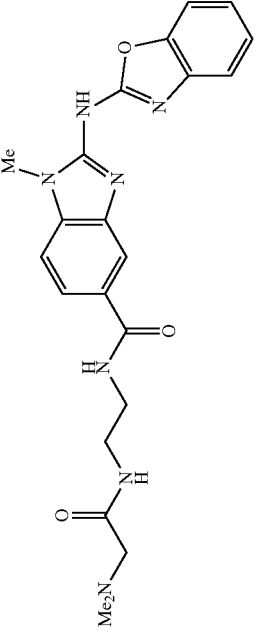 | 2-(benzo[d]oxazol-2-ylamino)-N-(2-(2-dimethylamino)acetamido)ethyl)-1-methyl-1H-benzo[d]imidazole-5-carboxamide | 1.8* | 14-26 | ND |
| 20 | 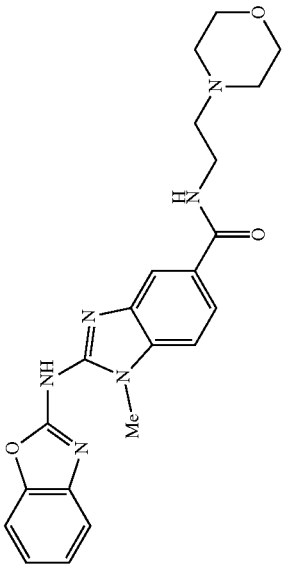 | 2-(benzo[d]oxazol-2-ylamino)-1-methyl-N-(2-morpholinoethyl)-1H-benzo[d]imidazole-5-carboxamide | 1.0 | 8 | 7.3 |

TABLE 1-continued

| Example No. | Structure | IUPAC name | EC$_{50}$ (μM) | Maximum Fold induction | Solubility (μM) |
|---|---|---|---|---|---|
| 21 | 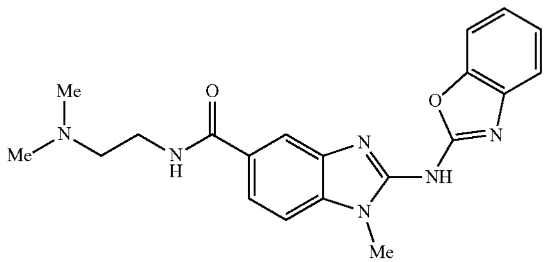 [SMILES: CN(C)CCNC(=O)c1ccc2c(c1)nc(Nc1nc3ccccc3o1)n2C] | 2-(benzo[d]oxazol-2-ylamino)-N-(2-(dimethylamino)ethyl)-1-methyl-1H-benzo[d]imidazole-5-carboxamide | 1.1 | 14 | N/A |
| 22 | 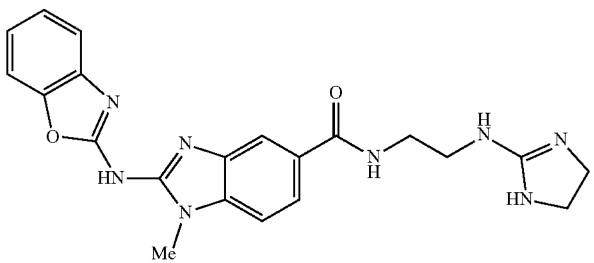 [SMILES: Cn1c(Nc2nc3ccccc3o2)nc2cc(C(=O)NCCNC3=NCCN3)ccc21] | 2-(benzo[d]oxazol-2-ylamino)-N-(2-((4,5-dihydro-1H-imidazol-2-yl)amino)ethyl)-1-methyl-1H-benzo[d]imidazole-5-carboxamide | | | |
| 23 | 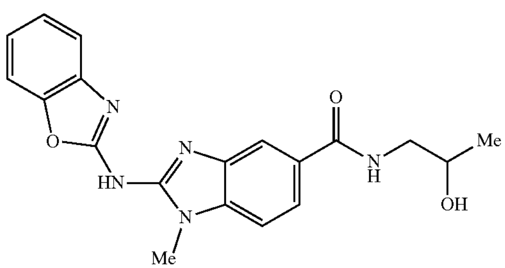 [SMILES: CC(O)CNC(=O)c1ccc2c(c1)nc(Nc1nc3ccccc3o1)n2C] | 2-(benzo[d]oxazol-2-ylamino)-N-(2-hydroxypropyl)-1-methyl-1H-benzo[d]imidazole-5-carboxamide | 2.1* | 25-61 | >20 |

TABLE 1-continued

| Example No. | Structure | IUPAC name | EC$_{50}$ (μM) | Maximum Fold induction | Solubility (μM) |
|---|---|---|---|---|---|
| 24 | 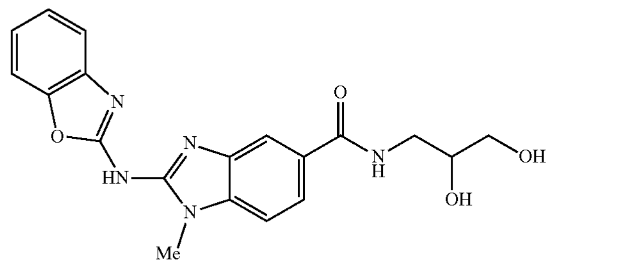 [SMILES: Cn1c(Nc2nc3ccccc3o2)nc2cc(C(=O)NCC(O)CO)ccc21] | 2-(benzo[d]oxazol-2-ylamino)-N-(2,3-dihydroxypropyl)-1-methyl-1H-benzo[d]imidazole-5-carboxamide | ND | 49 | 12.4 |
| 25 | 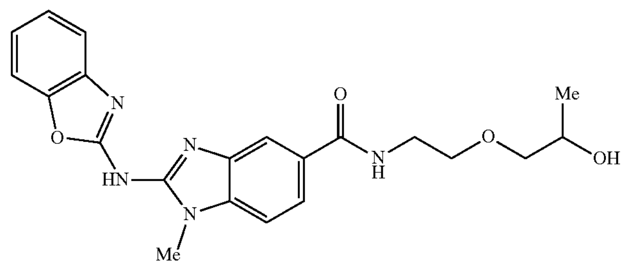 [SMILES: CC(O)COCCNC(=O)c1ccc2c(c1)nc(Nc1nc3ccccc3o1)n2C] | 2-(benzo[d]oxazol-2-ylamino)-N-(2-(2-hydroxypropoxy)ethyl)-1,6-dimethyl-1H-benzo[d]imidazole-5-carboxamide | 2.2 | 26 | 6.1 |
| 26 | 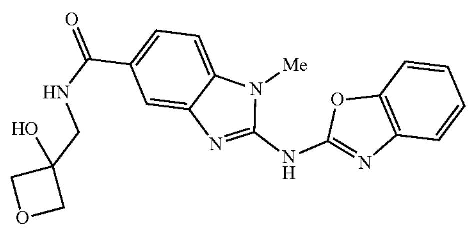 [SMILES: Cn1c(Nc2nc3ccccc3o2)nc2cc(C(=O)NCC3(O)COC3)ccc21] | 2-(benzo[d]oxazol-2-ylamino)-N-((3-hydroxyoxetan-3-yl)methyl)-1-methyl-1H-benzo[d]imidazole-5-carboxamide | 2.0 | 26 | 8.6 |

TABLE 1-continued

| Example No. | Structure | IUPAC name | EC$_{50}$ (μM) | Maximum Fold induction | Solubility (μM) |
|---|---|---|---|---|---|
| 27 | 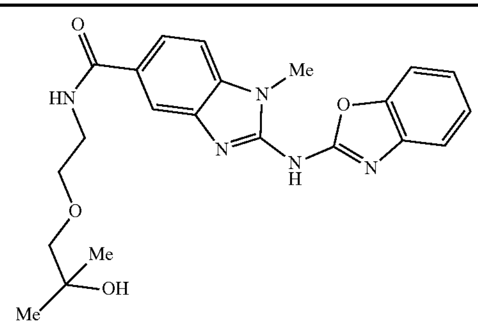 | 2-(benzo[d]oxazol-2-ylamino)-N-(2-(2-hydroxy-2-methylpropoxy)ethyl)-1-methyl-1H-benzo[d]imidazole-5-carboxamide | ND | 17 | 10.6 |
| 28 | 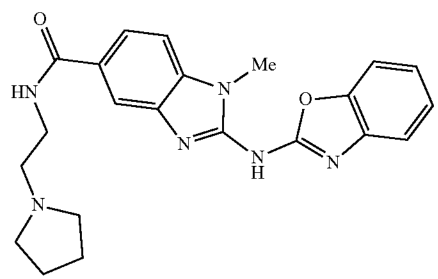 [SMILES: Cn1c(Nc2nc3ccccc3o2)nc2cc(C(=O)NCCN3CCCC3)ccc21] | 2-(benzo[d]oxazol-2-ylamino)-1-methyl-N-(2-(pyrrolidin-1-yl)ethyl)-1H-benzo[d]imidazole-5-carboxamide | 1.6* | 41 | 11.3 |
| 29 | 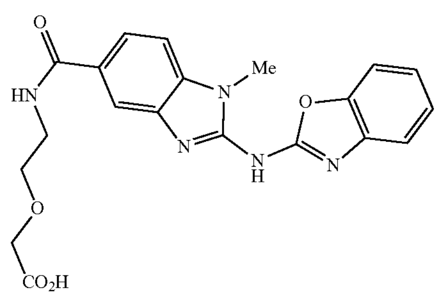 [SMILES: Cn1c(Nc2nc3ccccc3o2)nc2cc(C(=O)NCCOCC(=O)O)ccc21] | 2-(2-(2-(benzo[d]oxazol-2-ylamino)-1-methyl-1H-benzo[d]imidazole-5-carboxamido)ethoxy)acetic acid | ND | 12 | 19.3 |

TABLE 1-continued

| Example No. | Structure | IUPAC name | EC$_{50}$ (μM) | Maximum Fold induction | Solubility (μM) |
|---|---|---|---|---|---|
| 30 | 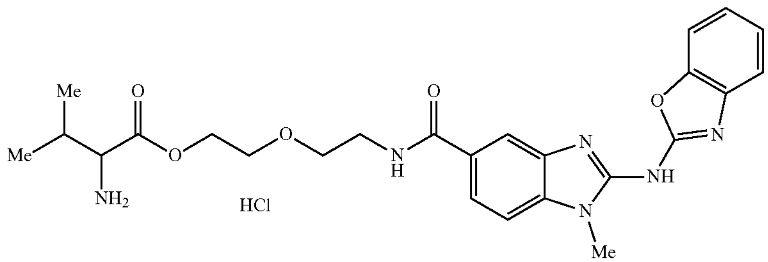 [SMILES: CC(C)C(N)C(=O)OCCOCCNC(=O)c1ccc2c(c1)nc(Nc1nc3ccccc3o1)n2C ; Cl] | 2-(2-(benzo[d]oxazol-2-ylamino)-1-methyl-1H-benzo[d]imidazole-5-carboxamido)ethoxy)ethyl DL-valinate hydrochloride | 3.5* | 25-53 | 3.2 |
| 31 | 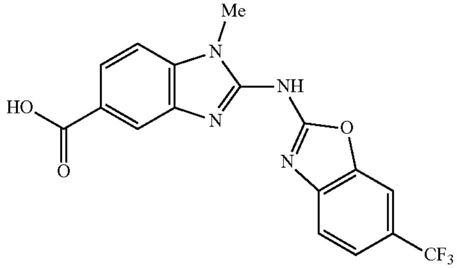 [SMILES: Cn1c(Nc2nc3ccc(C(F)(F)F)cc3o2)nc2cc(C(=O)O)ccc21] | 1-methyl-2-((6-(trifluoromethyl)benzo[d]oxazol-2-yl)amino)-1H-benzo[d]imidazole-5-carboxylic acid | 1.1* | 25-29 | 14.9 |
| 32 | 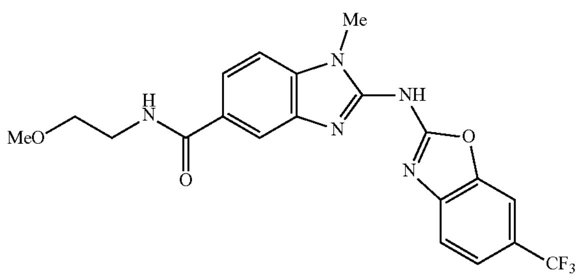 [SMILES: COCCNC(=O)c1ccc2c(c1)nc(Nc1nc3ccc(C(F)(F)F)cc3o1)n2C] | N-(2-methoxyethyl)-1-methyl-2-((6-(trifluoromethyl)benzo[d]oxazol-2-yl)amino)-1H-benzo[d]imidazole-5-carboxamide | 0.5* | 14-50 | 1.4 |

TABLE 1-continued

| Example No. | Structure | IUPAC name | EC$_{50}$ (μM) | Maximum Fold induction | Solubility (μM) |
|---|---|---|---|---|---|
| 33 | 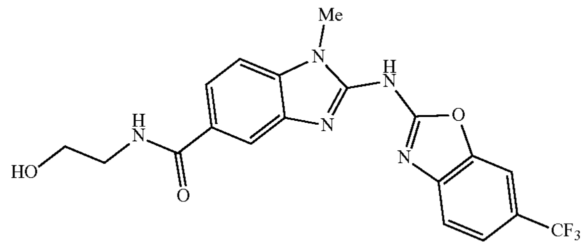 [SMILES: Cn1c(Nc2nc3ccc(C(F)(F)F)cc3o2)nc2cc(C(=O)NCCO)ccc21] | N-(2-hydroxyethyl)-1-methyl-2-(((6-(trifluoromethyl)benzo[d]oxazol-2-yl)amino)-1H-benzo[d]imidazole-5-carboxamide | 0.3* | 32-45 | 0.9 |
| 34 | 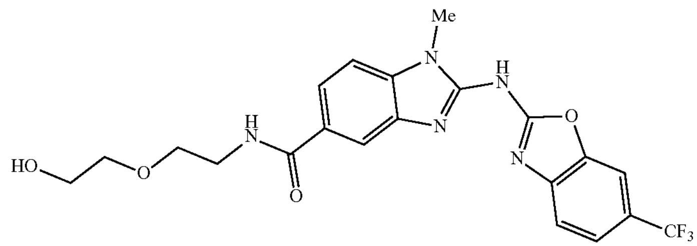 [SMILES: Cn1c(Nc2nc3ccc(C(F)(F)F)cc3o2)nc2cc(C(=O)NCCOCCO)ccc21] | N-(2-(2-hydroxyethoxy)ethyl)-1-methyl-2-((6-(trifluoromethyl)benzo[d]oxazol-2-yl)amino)-1H-benzo[d]imidazole-5-carboxamide | 0.8* | 31-36 | 8.0 |
| 35 | 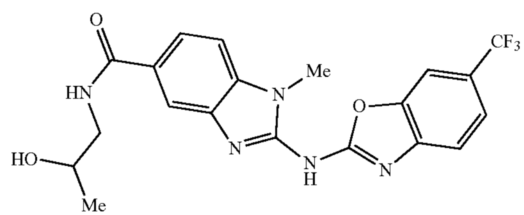 [SMILES: CC(O)CNC(=O)c1ccc2c(c1)nc(Nc1nc3ccc(C(F)(F)F)cc3o1)n2C] | N-(2-hydroxypropyl)-1-methyl-2-(((6-(trifluoromethyl)benzo[d]oxazol-2-yl)amino)-1H-benzo[d]imidazole-5-carboxamide | 1.2* | 37 | <2 |
| 36 | 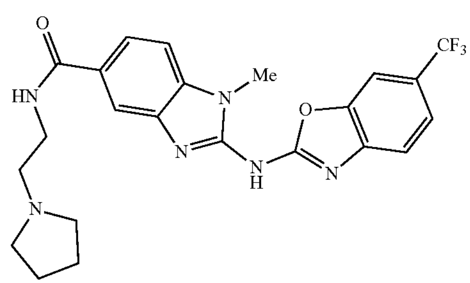 [SMILES: Cn1c(Nc2nc3ccc(C(F)(F)F)cc3o2)nc2cc(C(=O)NCCN3CCCC3)ccc21] | 1-methyl-N-(2-(pyrrolidin-1-yl)ethyl)-2-((6-(trifluoromethyl)benzo[d]oxazol-2-yl)amino)-1H-benzo[d]imidazole-5-carboxamide | 1.3* | 42 | 2.8 |

TABLE 1-continued

| Example No. | Structure | IUPAC name | EC$_{50}$ (μM) | Maximum Fold induction | Solubility (μM) |
|---|---|---|---|---|---|
| 37 | 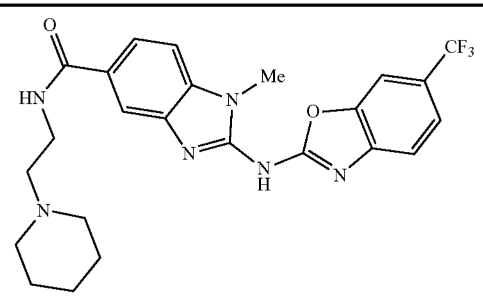 | 1-methyl-N-(2-(piperidin-1-yl)ethyl)-2-((6-(trifluoromethyl)benzo[d]oxazol-2-yl)amino)-1H-benzo[d]imidazole-5-carboxamide | ND | 28 | <2 |
| 38 | 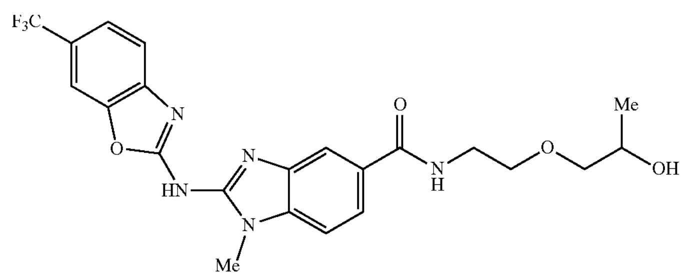 [SMILES: CC(O)COCCNC(=O)c1ccc2c(c1)nc(Nc1nc3ccc(C(F)(F)F)cc3o1)n2C] | N-(2-(2-hydroxypropoxy)ethyl)-1-methyl-2-((6-(trifluoromethyl)benzo[d]oxazol-2-yl)amino)-1H-benzo[d]imidazole-5-carboxamide | 1.3* | 30 | <2 |
| 39 | 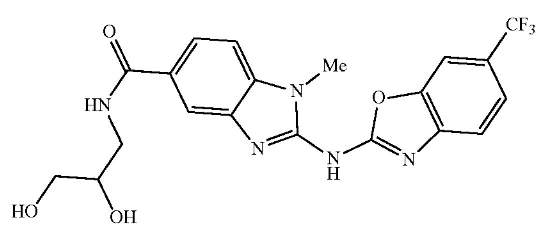 [SMILES: Cn1c(Nc2nc3ccc(C(F)(F)F)cc3o2)nc2cc(C(=O)NCC(O)CO)ccc21] | N-(2,3-dihydroxypropyl)-1-methyl-2-((6-(trifluoromethyl)benzo[d]oxazol-2-yl)amino)-1H-benzo[d]imidazole-5-carboxamide | 0.95* | 56-82 | 2.1 |

TABLE 1-continued

| Example No. | Structure | IUPAC name | EC$_{50}$ (μM) | Maximum Fold induction | Solubility (μM) |
|---|---|---|---|---|---|
| 40 | 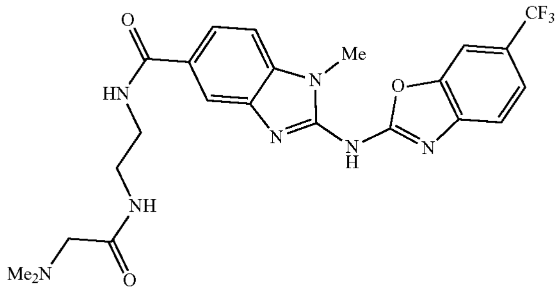 [SMILES: CN(C)CC(=O)NCCNC(=O)c1ccc2c(c1)nc(Nc1nc3ccc(C(F)(F)F)cc3o1)n2C] | N-(2-(2-(dimethylamino)acetamido)ethyl)-1-methyl-2-((6-(trifluoromethyl)benzo[d]oxazol-2-yl)amino)-1H-benzo[d]imidazole-5-carboxamide | 0.69* | 56-93 | 0.5 |
| 41 | 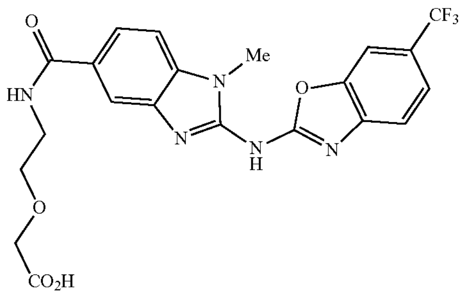 [SMILES: Cn1c(Nc2nc3ccc(C(F)(F)F)cc3o2)nc2cc(C(=O)NCCOCC(=O)O)ccc21] | 2-(2-(1-methyl-2-((6-(trifluoromethyl)benzo[d]oxazol-2-yl)amino)-1H-benzo[d]imidazole-5-carboxamido)ethoxy)acetic acid | 4.8* | 35-39 | 13.8 |
| 42 | 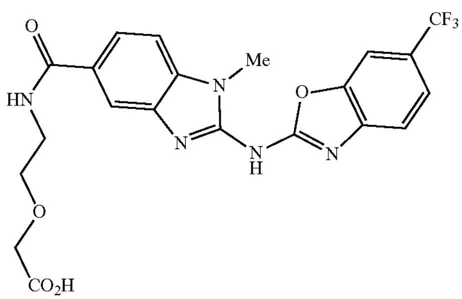 [SMILES: Cn1c(Nc2nc3ccc(C(F)(F)F)cc3o2)nc2cc(C(=O)NCCOCC(=O)O)ccc21] | N-(2-(2-hydroxy-2-methylpropoxy)ethyl)-1-methyl-2-((6-(trifluoromethyl)benzo[d]oxazol-2-yl)amino)-1H-benzo[d]imidazole-5-carboxamide | 2.3* | 29 | 3.6 |

TABLE 1-continued

| Example No. | Structure | IUPAC name | EC$_{50}$ (μM) | Maximum Fold induction | Solubility (μM) |
|---|---|---|---|---|---|
| 43 | 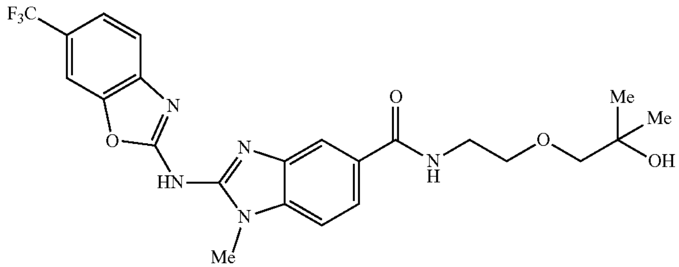 [SMILES: Cn1c(Nc2nc3ccc(C(F)(F)F)cc3o2)nc2cc(C(=O)NCCOCC(C)(C)O)ccc21] | N-(2-(2-hydroxyethoxy)ethyl)-1-methyl-2-((5-(trifluoromethyl)benzo[d]oxazol-2-yl)amino)-1H-benzo[d]imidazole-5-carboxamide | 1.3* | 56 | 8.0 |
| 44 | 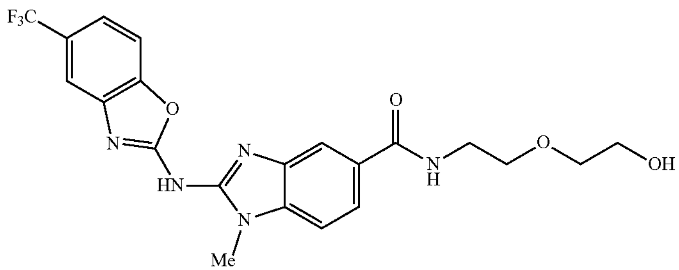 [SMILES: Cn1c(Nc2nc3cc(C(F)(F)F)ccc3o2)nc2cc(C(=O)NCCOCCO)ccc21] | 1-methyl-2-(6-(trifluoromethoxy)benzo[d]oxazol-2-yl)amino)-1H-benzo[d]imidazole-5-carboxylic acid | 1.3* | 9-14 | ND |
| 45 | 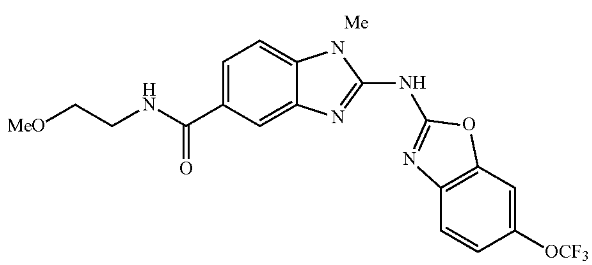 [SMILES: COCCNC(=O)c1ccc2[nH]c(Nc3nc4ccc(OC(F)(F)F)cc4o3)nc2c1] | N-(2-methoxyethyl)-1-methyl-2-((6-(trifluoromethoxy)benzo[d]oxazol-2-yl)amino)-1H-benzo[d]imidazole-5-carboxamide | 0.64* | 10-28 | 0.2 |
| 46 | 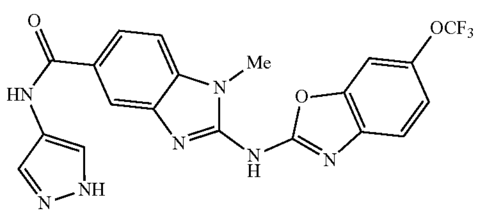 [SMILES: Cn1c(Nc2nc3ccc(OC(F)(F)F)cc3o2)nc2cc(C(=O)Nc3cn[nH]c3)ccc21] | 1-methyl-N-(1H-pyrazol-4-yl)-2-((6-(trifluoromethoxy)benzo[d]oxazol-2-yl)amino)-1H-benzo[d]imidazole-5-carboxamide | 2.2* | 14-20 | <5 |

TABLE 1-continued

| Example No. | Structure | IUPAC name | EC$_{50}$ (µM) | Maximum Fold induction | Solubility (µM) |
|---|---|---|---|---|---|
| 47 | 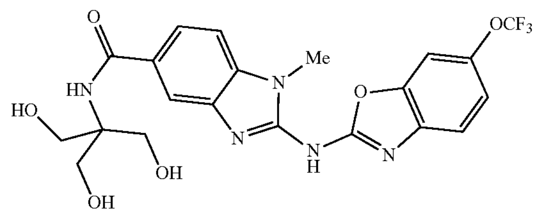 [SMILES: Cn1c(Nc2nc3ccc(OC(F)(F)F)cc3o2)nc2cc(C(=O)NC(CO)(CO)CO)ccc21] | N-(1,3-dihydroxy-2-(hydroxymethyl)propan-2-yl)-1-methyl-2-((6-(trifluoromethoxy)benzo[d]oxazol-2-yl)amino)-1H-benzo[d]imidazole-5-carboxamide | 1.6* | 13-16 | <2 |
| 48 | 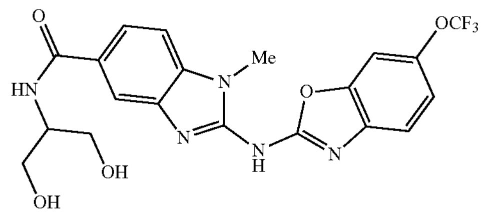 [SMILES: Cn1c(Nc2nc3ccc(OC(F)(F)F)cc3o2)nc2cc(C(=O)NC(CO)CO)ccc21] | N-(1,3-dihydroxypropan-2-yl)-1-methyl-2-((6-(trifluoromethoxy)benzo[d]oxazol-2-yl)amino)-1H-benzo[d]imidazole-5-carboxamide | 2.0* | 13-20 | 3.9 |
| 49 | 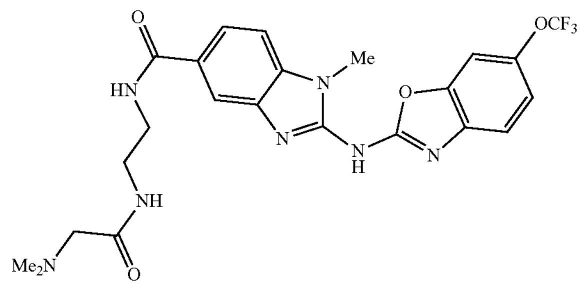 [SMILES: CN(C)CC(=O)NCCNC(=O)c1ccc2c(c1)nc(Nc1nc3ccc(OC(F)(F)F)cc3o1)n2C] | N-(2-(2-(dimethylamino)acetamido)ethyl)-1-methyl-2-((6-(trifluoromethoxy)benzo[d]oxazol-2-yl)amino)-1H-benzo[d]imidazole-5-carboxamide | 0.8* | 14-23 | <2 |
| 50 | 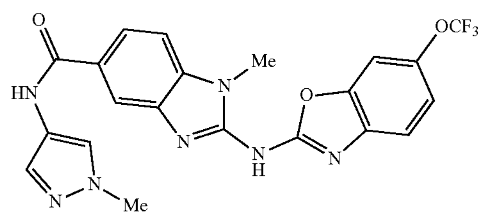 [SMILES: Cn1cc(NC(=O)c2ccc3c(c2)nc(Nc2nc4ccc(OC(F)(F)F)cc4o2)n3C)cn1] | 1-methyl-N-(1-methyl-1H-pyrazol-4-yl)-2-((6-(trifluoromethoxy)benzo[d]oxazol-2-yl)amino)-1H-benzo[d]imidazole-5-carboxamide | ND | 12-18 | 4.0 |

TABLE 1-continued

| Example No. | Structure | IUPAC name | EC$_{50}$ (μM) | Maximum Fold induction | Solubility (μM) |
|---|---|---|---|---|---|
| 51 | 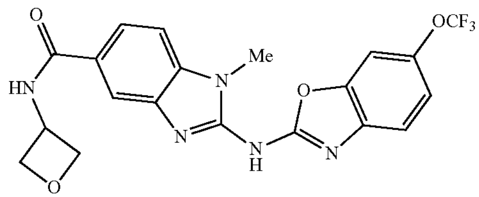 [SMILES: Cn1c(Nc2nc3ccc(OC(F)(F)F)cc3o2)nc2cc(C(=O)NC3COC3)ccc21] | 1-methyl-N-(oxetan-3-yl)-2-((6-(trifluoromethoxy)benzo[d]oxazol-2-yl)amino)-1H-benzo[d]imidazole-5-carboxamide | 1.4* | 30-57 | <2 |
| 52 | 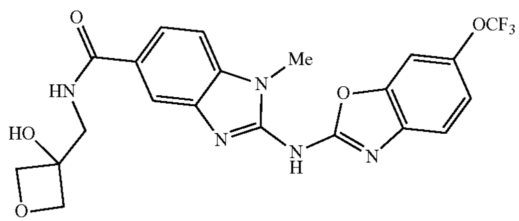 [SMILES: Cn1c(Nc2nc3ccc(OC(F)(F)F)cc3o2)nc2cc(C(=O)NCC3(O)COC3)ccc21] | N-((3-hydroxyoxetan-3-yl)methyl)-1-methyl-2-((6-(trifluoromethoxy)benzo[d]oxazol-2-yl)amino)-1H-benzo[d]imidazole-5-carboxamide | 1.0 | 27 | <2 |
| 53 | 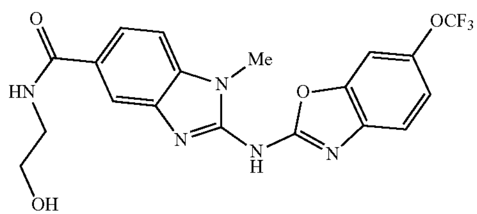 [SMILES: Cn1c(Nc2nc3ccc(OC(F)(F)F)cc3o2)nc2cc(C(=O)NCCO)ccc21] | N-(2-hydroxyethyl)-1-methyl-2-((6-(trifluoromethoxy)benzo[d]oxazol-2-yl)amino)-1H-benzo[d]imidazole-5-carboxamide | 1.1* | 29-38 | 7.3 |
| 54 | 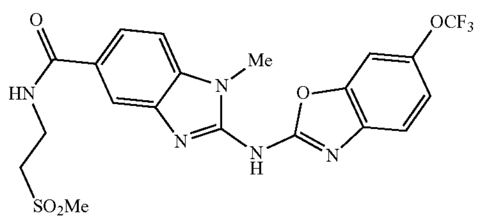 | 1-methyl-N-(2-(methylsulfonyl)ethyl)-2-((6-(trifluoromethoxy)benzo[d]oxazol-2-yl)amino)-1H-benzo[d]imidazole-5-carboxamide | 3.2* | 31-37 | ND |

TABLE 1-continued

| Example No. | Structure | IUPAC name | EC$_{50}$ (µM) | Maximum Fold induction | Solubility (µM) |
|---|---|---|---|---|---|
| 55 | 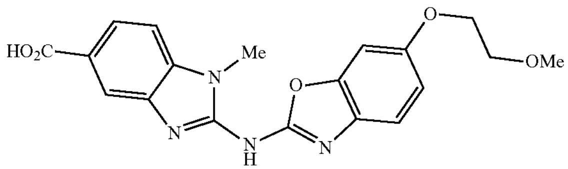 [SMILES: COCCOc1ccc2nc(Nc3nc4cc(C(=O)O)ccc4n3C)oc2c1] | 2-((6-(2-methoxyethoxy)benzo[d]oxazol-2-yl)amino)-1-methyl-1H-benzo[d]imidazole-5-carboxylic acid | 4.5 | 15 | ND |
| 56 | 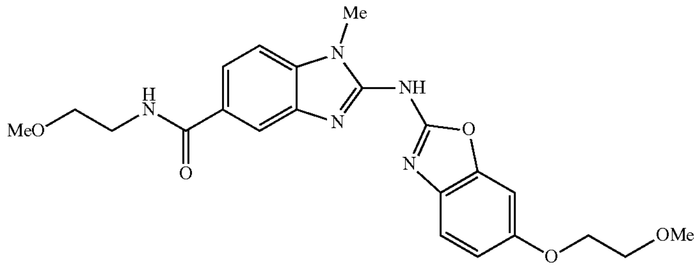 [SMILES: COCCNC(=O)c1ccc2c(c1)nc(Nc1nc3ccc(OCCOC)cc3o1)n2C] | 2-((6-(2-methoxyethoxy)benzo[d]oxazol-2-yl)amino)-N-(2-methoxyethyl)-1-methyl-1H-benzo[d]imidazole-5-carboxamide | 1.4* | 21-38 | 9.7 |
| 57 | 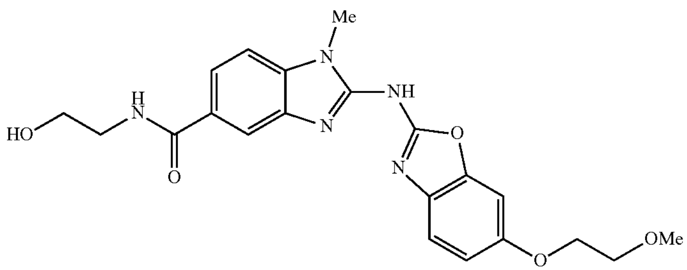 [SMILES: COCCOc1ccc2nc(Nc3nc4cc(C(=O)NCCO)ccc4n3C)oc2c1] | N-(2-hydroxyethyl)-2-((6-(2-methoxyethoxy)benzo[d]oxazol-2-yl)amino)-1-methyl-1H-benzo[d]imidazole-5-carboxamide | 1.2* | 34-40 | 11.2 |
| 58 | 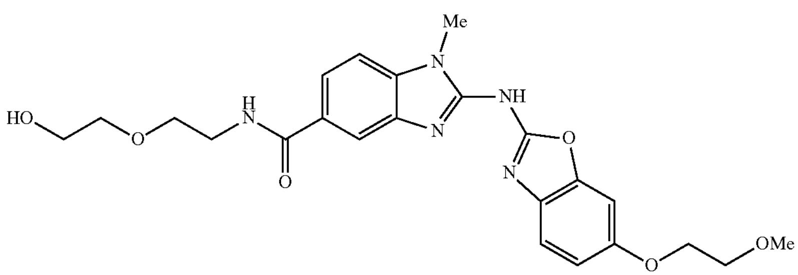 [SMILES: COCCOc1ccc2nc(Nc3nc4cc(C(=O)NCCOCCO)ccc4n3C)oc2c1] | N-(2-(2-hydroxyethoxy)ethyl)-2-((6-(2-methoxyethoxy)benzo[d]oxazol-2-yl)amino)-1-methyl-1H-benzo[d]imidazole-5-carboxamide | 1.7* | 41-60 | 7.7 |

TABLE 1-continued

| Example No. | Structure | IUPAC name | EC$_{50}$ (μM) | Maximum Fold induction | Solubility (μM) |
|---|---|---|---|---|---|
| 59 | 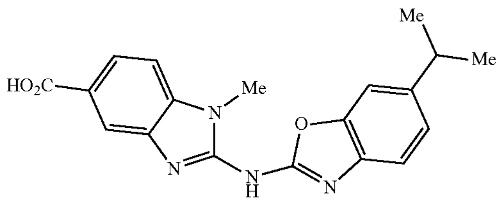 [SMILES: CC(C)c1ccc2nc(Nc3nc4cc(C(=O)O)ccc4n3C)oc2c1] | 2-((6-isopropylbenzo[d]oxazol-2-yl)amino)-1-methyl-1H-benzo[d]imidazole-5-carboxylic acid | 3.3 | 30 | ND |
| 60 | 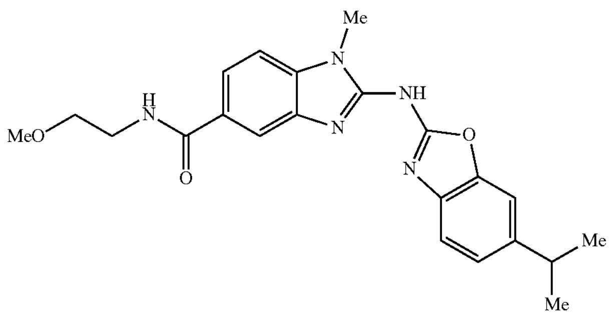 [SMILES: COCCNC(=O)c1ccc2c(c1)nc(Nc1nc3ccc(C(C)C)cc3o1)n2C] | 2-((6-isopropylbenzo[d]oxazol-2-yl)amino)-N-(2-methoxyethyl)-1-methyl-1H-benzo[d]imidazole-5-carboxamide | 0.7* | 42-56 | 0.9 |
| 61 | 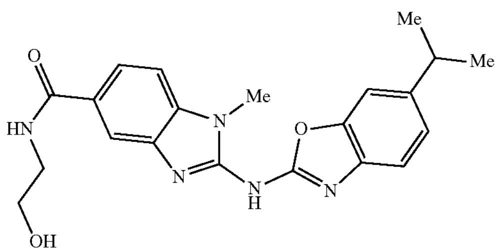 [SMILES: CC(C)c1ccc2nc(Nc3nc4cc(C(=O)NCCO)ccc4n3C)oc2c1] | N-(2-hydroxyethyl)-2-((6-isopropylbenzo[d]oxazol-2-yl)amino)-1-methyl-1H-benzo[d]imidazole-5-carboxamide | 1.5 | 60 | 1.2 |

TABLE 1-continued

| Example No. | Structure | IUPAC name | EC$_{50}$ (µM) | Maximum Fold induction | Solubility (µM) |
|---|---|---|---|---|---|
| 62 | 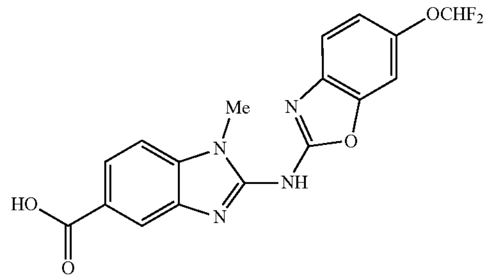 [SMILES: Cn1c(Nc2nc3ccc(OC(F)F)cc3o2)nc2cc(C(=O)O)ccc21] | 2-((6-(difluoromethoxy)benzo[d]oxazol-2-yl)amino)-1-methyl-1H-benzo[d]imidazole-5-carboxylic acid | 5.1* | 15-24 | 16.2 |
| 63 | 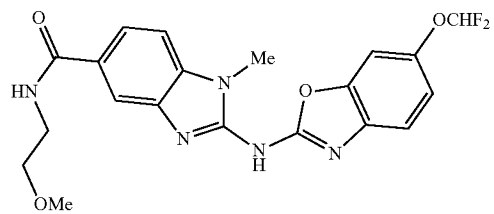 [SMILES: COCCNC(=O)c1ccc2c(c1)nc(Nc1nc3ccc(OC(F)F)cc3o1)n2C] | 2-((6-(difluoromethoxy)benzo[d]oxazol-2-yl)amino)-N-(2-methoxyethyl)-1-methyl-1H-benzo[d]imidazole-5-carboxamide | 1.3* | 11-15 | 0.8 |
| 64 | 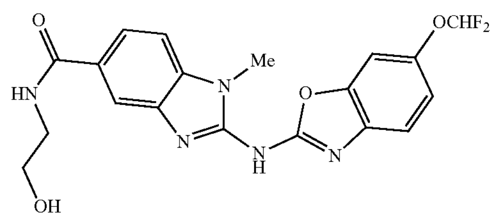 [SMILES: Cn1c(Nc2nc3ccc(OC(F)F)cc3o2)nc2cc(C(=O)NCCO)ccc21] | 2-((6-(difluoromethoxy)benzo[d]oxazol-2-yl)amino)-N-(2-hydroxyethyl)-1-methyl-1H-benzo[d]imidazole-5-carboxamide | 1.8* | 11-18 | 2.0 |
| 65 | 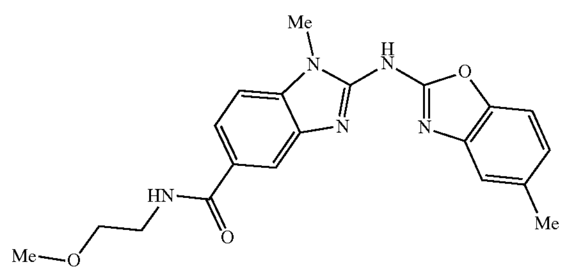 [SMILES: COCCNC(=O)c1ccc2c(c1)nc(Nc1nc3cc(C)ccc3o1)n2C] | N-(2-methoxyethyl)-1-methyl-2-((5-methylbenzo[d]oxazol-2-yl)amino)-1H-benzo[d]imidazole-5-carboxamide | 1.2* | 15.42 | ND |

TABLE 1-continued

| Example No. | Structure | IUPAC name | EC$_{50}$ (μM) | Maximum Fold induction | Solubility (μM) |
|---|---|---|---|---|---|
| 66 | 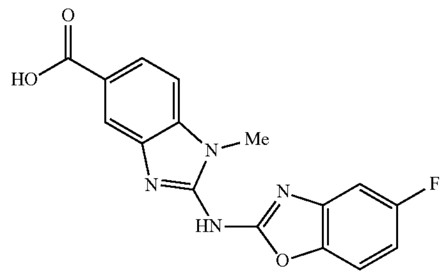 [SMILES: Cn1c(Nc2nc3cc(F)ccc3o2)nc2cc(C(=O)O)ccc21] | 2-((5-fluorobenzo[d]oxazol-2-yl)amino)-1-methyl-1H-benzo[d]imidazole-5-carboxylic acid | 5.4* | 19-22 | ND |
| 67 | 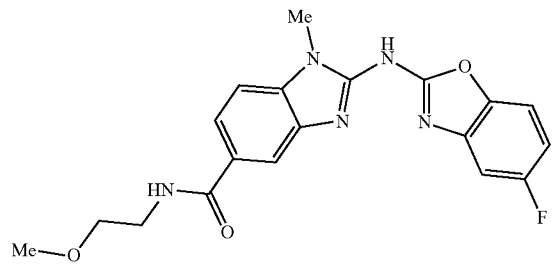 [SMILES: COCCNC(=O)c1ccc2c(c1)nc(Nc1nc3cc(F)ccc3o1)n2C] | 2-((5-fluorobenzo[d]oxazol-2-yl)amino)-N-(2-methoxyethyl)-1-methyl-1H-benzo[d]imidazole-5-carboxamide | 0.91* | 18-56 | <5 |
| 68 | 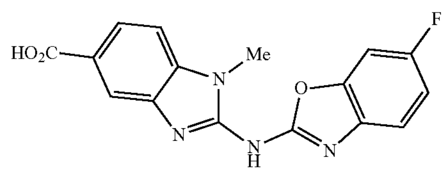 [SMILES: Cn1c(Nc2nc3ccc(F)cc3o2)nc2cc(C(=O)O)ccc21] | 2-((6-fluorobenzo[d]oxazol-2-yl)amino)-1-methyl-1H-benzo[d]imidazole-5-carboxylic acid | 2.0* | 16-21 | ND |
| 69 | 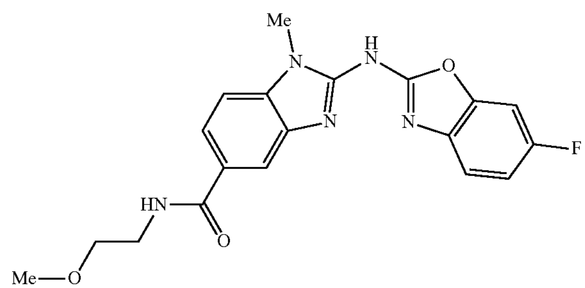 [SMILES: COCCNC(=O)c1ccc2c(c1)nc(Nc1nc3ccc(F)cc3o1)n2C] | 2-((6-fluorobenzo[d]oxazol-2-yl)amino)-N-(2-methoxyethyl)-1-methyl-1H-benzo[d]imidazole-5-carboxamide | 0.66* | 13-36 | <5 |

TABLE 1-continued

| Example No. | Structure | IUPAC name | EC$_{50}$ (µM) | Maximum Fold induction | Solubility (µM) |
|---|---|---|---|---|---|
| 70 | 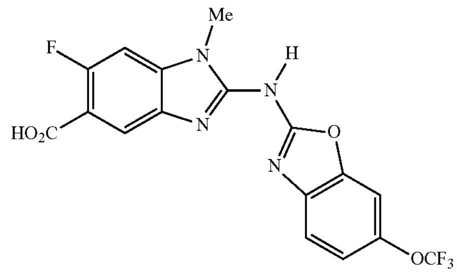 [SMILES: Cn1c(Nc2nc3ccc(OC(F)(F)F)cc3o2)nc2cc(C(=O)O)c(F)cc21] | 6-fluoro-1-methyl-2-((6-(trifluoromethoxy)benzo[d]oxazol-2-yl)amino)-1H-benzo[d]imidazole-5-carboxylic acid | 3.2* | 8-11 | ND |
| 71 | 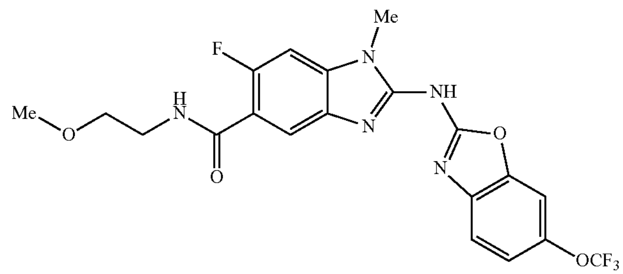 [SMILES: COCCNC(=O)c1cc2nc(Nc3nc4ccc(OC(F)(F)F)cc4o3)n(C)c2cc1F] | 6-fluoro-N-(2-methoxyethyl)-1-methyl-2-((6-(trifluoromethoxy)benzo[d]oxazol-2-yl)amino)-1H-benzo[d]imidazole-5-carboxamide | 0.73* | 8-12 | 0.3 |
| 72 | 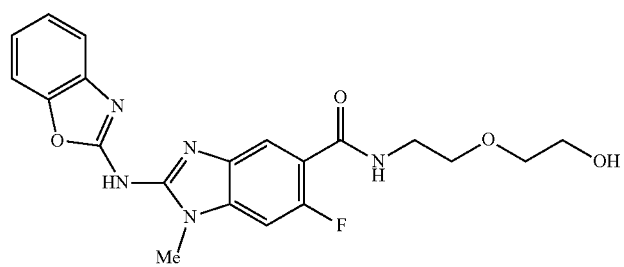 [SMILES: Cn1c(Nc2nc3ccccc3o2)nc2cc(C(=O)NCCOCCO)c(F)cc21] | 2-(benzo[d]oxazol-2-ylamino)-6-fluoro-N-(2-(2-hydroxyethoxy)ethyl)-1-methyl-1H-benzo[d]imidazole-5-carboxamide | 1.1* | 31-72 | 2.7 |

TABLE 1-continued

| Example No. | Structure | IUPAC name | EC$_{50}$ (μM) | Maximum Fold induction | Solubility (μM) |
|---|---|---|---|---|---|
| 73 | 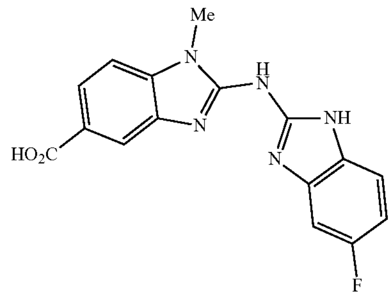 [SMILES: Cn1c(Nc2nc3cc(F)ccc3[nH]2)nc2cc(C(=O)O)ccc21] | 2-((5-fluoro-1H-benzo[d]imidazol-2-yl)amino)-1-methyl-1H-benzo[d]imidazole-5-carboxylic acid | 2.9* | 8-12 | ND |
| 74 | 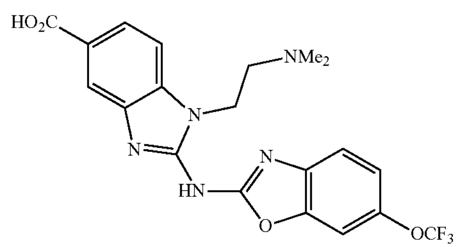 | 1-(2-(dimethylamino)ethyl)-2-((6-(trifluoromethoxy)benzo[d]oxazol-2-yl)amino)-1H-benzo[d]imidazole-5-carboxylic acid | 3.6* | 17-28 | ND |
| 75 | 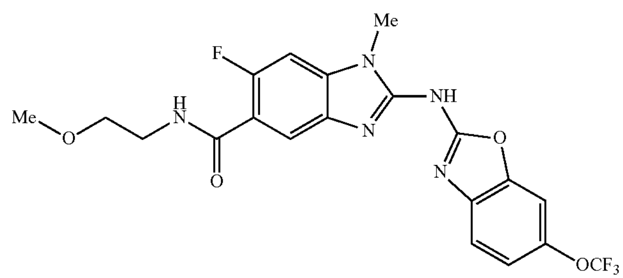 [SMILES: COCCNC(=O)c1cc2nc(Nc3nc4ccc(OC(F)(F)F)cc4o3)n(C)c2cc1F] | 1-(2-methoxyethyl)-2-((5-(trifluoromethoxy)benzo[d]imidazol-2-yl)amino)-1H-benzo[d]imidazole-5-carboxylic acid | 0.37* | 15-25 | 11.6 |

TABLE 1-continued

| Example No. | Structure | IUPAC name | EC$_{50}$ (μM) | Maximum Fold induction | Solubility (μM) |
|---|---|---|---|---|---|
| 76 | 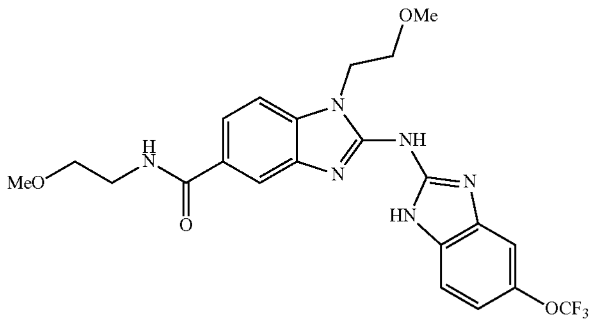 [SMILES: COCCNC(=O)c1ccc2c(c1)nc(Nc1nc3cc(OC(F)(F)F)ccc3[nH]1)n2CCOC] | N,1-bis(2-methoxyethyl)-2-((5-(trifluoromethoxy)-1H-benzo[d]imidazol-2-yl)amino)-1H-benzo[d]imidazole-5-carboxamide | 2.7* | 18-20 | ND |
| 77 | 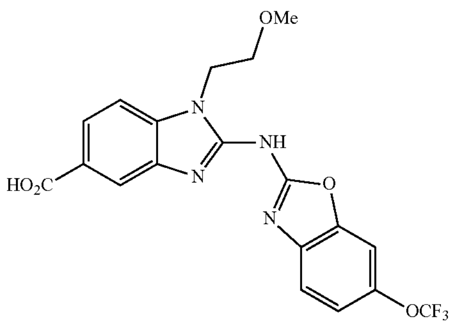 | 1-(2-methoxyethyl)-2-((6-(trifluoromethoxy)benzo[d]oxazol-2-yl)amino)-1H-benzo[d]imidazole-5-carboxylic acid | 4.1* | 27-28 | ND |
| 78 | 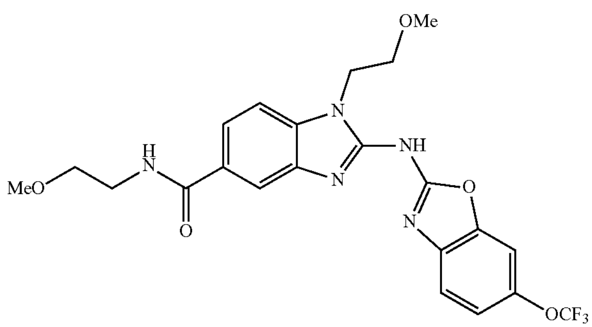 | N,1-bis(2-methoxyethyl)-2-((6-(trifluoromethoxy)benzo[d]oxazol-2-yl)amino)-1H-benzo[d]imidazole-5-carboxamide | 2.2* | 21-23 | ND |

TABLE 1-continued

| Example No. | Structure | IUPAC name | EC$_{50}$ (µM) | Maximum Fold induction | Solubility (µM) |
|---|---|---|---|---|---|
| 79 | 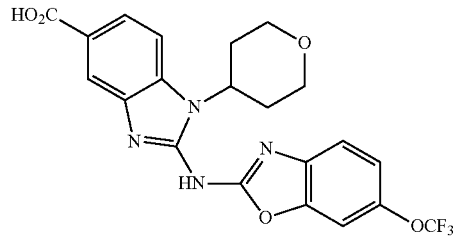 | 1-(tetrahydro-2H-pyran-4-yl)-2-((6-(trifluoromethoxy)benzo[d]oxazol-2-yl)amino)-1H-benzo[d]imidazole-5-carboxylic acid | 4.0* | 27-51 | 12.4 |
| 80 | 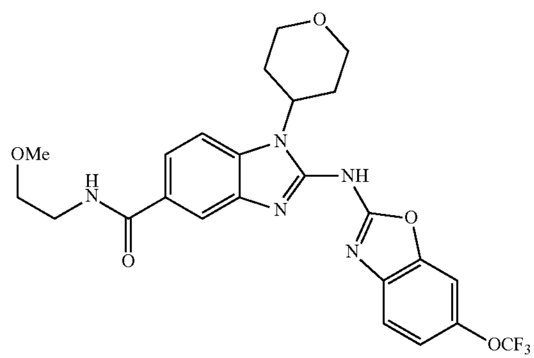 [SMILES: COCCNC(=O)c1ccc2c(c1)nc(Nc1nc3ccc(OC(F)(F)F)cc3o1)n2C1CCOCC1] | N-(2-methoxyethyl)-1-(tetrahydro-2H-pyran-4-yl)-2-((6-(trifluoromethoxy)benzo[d]oxazol-2-yl)amino)-1H-benzo[d]imidazole-5-carboxamide | 1.9* | 22-23 | ND |
| 81 | 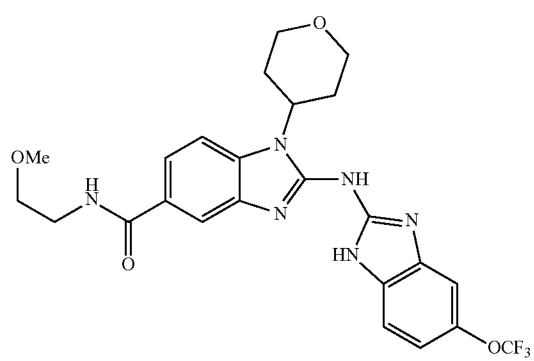 [SMILES: COCCNC(=O)c1ccc2c(c1)nc(Nc1nc3cc(OC(F)(F)F)ccc3[nH]1)n2C1CCOCC1] | N-(2-methoxyethyl)-1-(tetrahydro-2H-pyran-4-yl)-2-((5-(trifluoromethoxy)-1H-benzo[d]imidazol-2-yl)amino)-1H-benzo[d]imidazole-5-carboxamide | 2.3* | 19-30 | ND |

TABLE 1-continued

| Example No. | Structure | IUPAC name | EC$_{50}$ (µM) | Maximum Fold induction | Solubility (µM) |
|---|---|---|---|---|---|
| 82 | 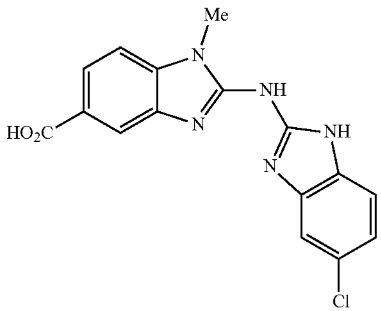 [SMILES: Cn1c(Nc2nc3cc(Cl)ccc3[nH]2)nc2cc(C(=O)O)ccc21] | 2-((5-chloro-1H-benzo[d]imidazol-2-yl)amino)-1-methyl-1H-benzo[d]imidazole-5-carboxylic acid | 2.4* | 29-33 | ND |
| 83 | 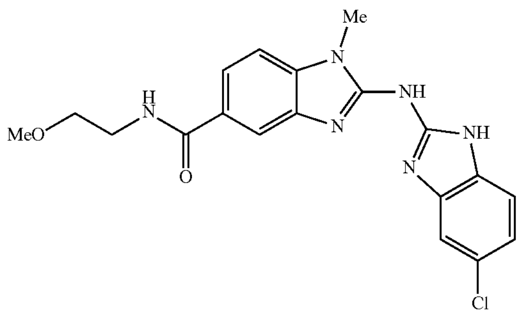 [SMILES: COCCNC(=O)c1ccc2c(c1)nc(Nc1nc3cc(Cl)ccc3[nH]1)n2C] | 2-((5-chloro-1H-benzo[d]imidazol-2-yl)amino)-N-(2-methoxyethyl)-1-methyl-1H-benzo[d]imidazole-5-carboxamide | 1.8* | 16-21 | ND |
| 84 | 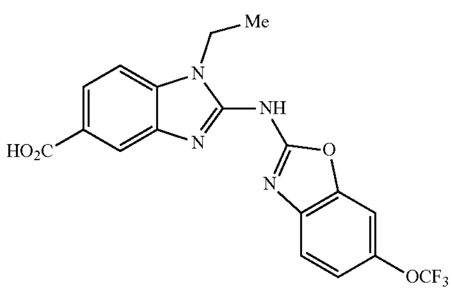 [SMILES: CCn1c(Nc2nc3ccc(OC(F)(F)F)cc3o2)nc2cc(C(=O)O)ccc21] | 1-ethyl-2-((6-(trifluoromethoxy)benzo[d]oxazol-2-yl)amino)-1H-benzo[d]imidazole-5-carboxylic acid | 5.4 | 17 | ND |

TABLE 1-continued

| Example No. | Structure | IUPAC name | EC$_{50}$ (μM) | Maximum Fold induction | Solubility (μM) |
|---|---|---|---|---|---|
| 85 | 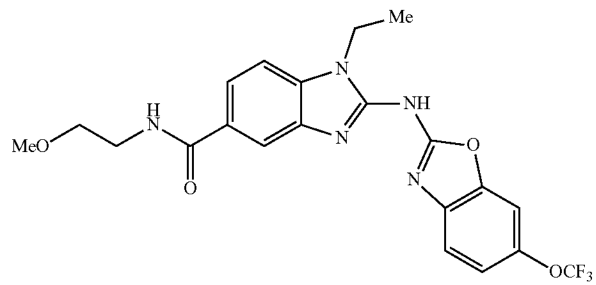 [SMILES: CCn1c(Nc2nc3ccc(OC(F)(F)F)cc3o2)nc2cc(C(=O)NCCOC)ccc21] | 1-ethyl-N-(2-methoxyethyl)-2-((6-(trifluoromethoxy)benzo[d]oxazol-2-yl)amino)-1H-benzo[d]imidazole-5-carboxamide | 1.3* | 13-36 | 3.3 |
| 86 | 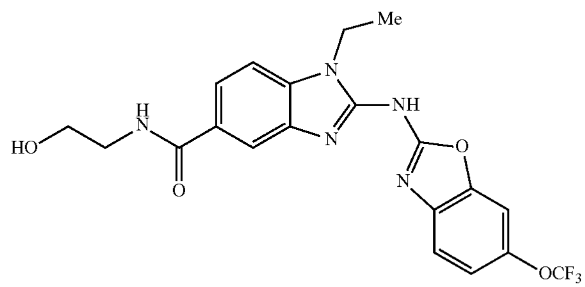 [SMILES: CCn1c(Nc2nc3ccc(OC(F)(F)F)cc3o2)nc2cc(C(=O)NCCO)ccc21] | 1-ethyl-N-(2-hydroxyethyl)-2-((6-(trifluoromethoxy)benzo[d]oxazol-2-yl)amino)-1H-benzo[d]imidazole-5-carboxamide | 1.3* | 15-32 | 7.1 |
| 87 | 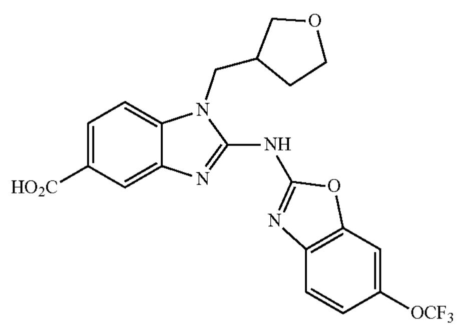 [SMILES: O=C(O)c1ccc2c(c1)nc(Nc1nc3ccc(OC(F)(F)F)cc3o1)n2CC1CCOC1] | 1-((tetrahydrofuran-3-yl)methyl)-2-((6-(trifluoromethoxy)benzo[d]oxazol-2-yl)amino)-1H-benzo[d]imidazole-5-carboxylic acid | 6.8 | 21 | ND |

TABLE 1-continued

| Example No. | Structure | IUPAC name | EC$_{50}$ (μM) | Maximum Fold induction | Solubility (μM) |
|---|---|---|---|---|---|
| 88 | 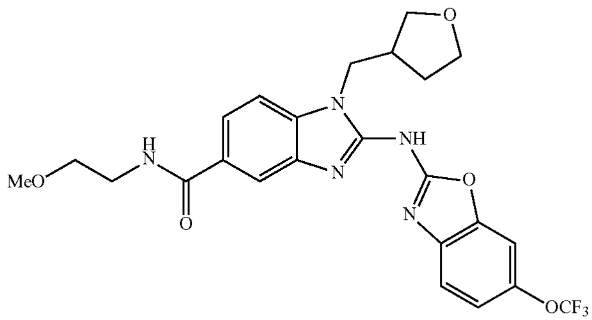 [SMILES: COCCNC(=O)c1ccc2c(c1)nc(Nc1nc3ccc(OC(F)(F)F)cc3o1)n2CC1CCOC1] | N-(2-methoxyethyl)-1-(((tetrahydrofuran-3-yl)methyl)-2-((6-(trifluoromethoxy)benzo[d]oxazol-2-yl)amino)-1H-benzo[d]imidazole-5-carboxamide | 1.5* | 13-37 | 3.9 |
| 89 | 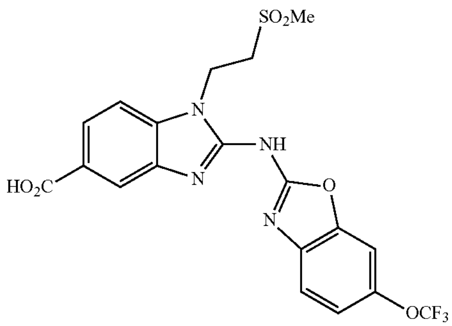 [SMILES: CS(=O)(=O)CCn1c(Nc2nc3ccc(OC(F)(F)F)cc3o2)nc2cc(C(=O)O)ccc21] | 1-(2-(methylsulfonyl)ethyl)-2-((6-(trifluoromethoxy)benzo[d]oxazol-2-yl)amino)-1H-benzo[d]imidazole-5-carboxylic acid | ND | 10 | ND |
| 90 | 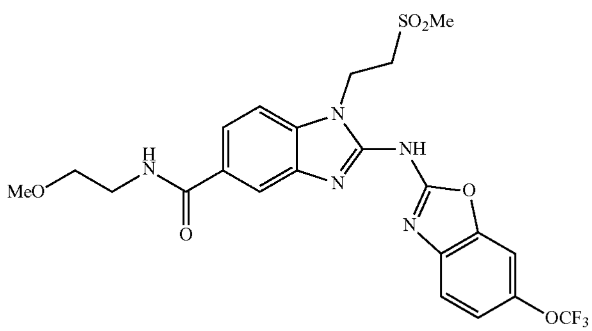 [SMILES: COCCNC(=O)c1ccc2c(c1)nc(Nc1nc3ccc(OC(F)(F)F)cc3o1)n2CCS(C)(=O)=O] | N-(2-methoxyethyl)-1-(2-(methylsulfonyl)ethyl)-2-((6-(trifluoromethoxy)benzo[d]oxazol-2-yl)amino)-1H-benzo[d]imidazole-5-carboxamide | 4.8 | 22 | ND |

TABLE 1-continued

| Example No. | Structure | IUPAC name | EC$_{50}$ (μM) | Maximum Fold induction | Solubility (μM) |
|---|---|---|---|---|---|
| 91 | 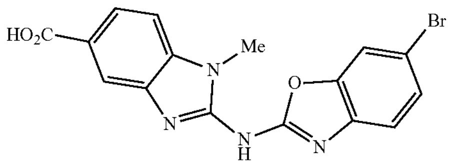 [SMILES: Cn1c(Nc2nc3ccc(Br)cc3o2)nc2cc(C(=O)O)ccc21] | 2-((6-bromobenzo[d]oxazol-2-yl)amino)-1-methyl-1H-benzo[d]imidazole-5-carboxylic acid | 2.5* | 17-26 | 2.6 |
| 92 | 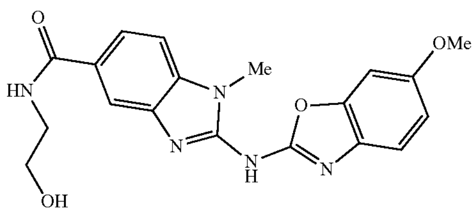 [SMILES: COc1ccc2nc(Nc3nc4cc(C(=O)NCCO)ccc4n3C)oc2c1] | N-(2-hydroxyethyl)-2-((6-methoxybenzo[d]oxazol-2-yl)amino)-1-methyl-1H-benzo[d]imidazole-5-carboxamide | 1.4* | 12-20 | 3.5 |
| 93 | 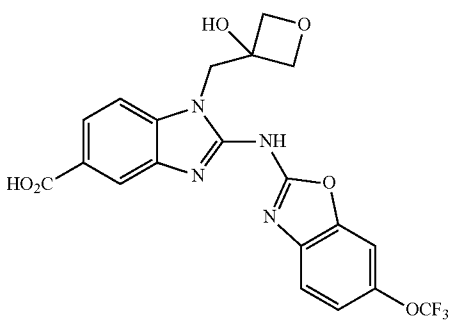 [SMILES: O=C(O)c1ccc2c(c1)nc(Nc1nc3ccc(OC(F)(F)F)cc3o1)n2CC1(O)COC1] | 1-((3-hydroxyoxetan-3-yl)methyl)-2-((6-(trifluoromethoxy)benzo[d]oxazol-2-yl)amino)-1H-benzo[d]imidazole-5-carboxylic acid | ND | 22 | ND |
| 94 | 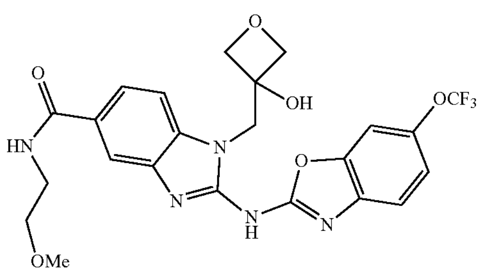 [SMILES: COCCNC(=O)c1ccc2c(c1)nc(Nc1nc3ccc(OC(F)(F)F)cc3o1)n2CC1(O)COC1] | 1-((3-hydroxyoxetan-3-yl)methyl)-N-(2-methoxyethyl)-2-((6-(trifluoromethoxy)benzo[d]oxazol-2-yl)amino)-1H-benzo[d]imidazole-5-carboxamide | 1.3 | 28 | 0.3 |

TABLE 1-continued

| Example No. | Structure | IUPAC name | EC$_{50}$ (µM) | Maximum Fold induction | Solubility (µM) |
|---|---|---|---|---|---|
| 95 | 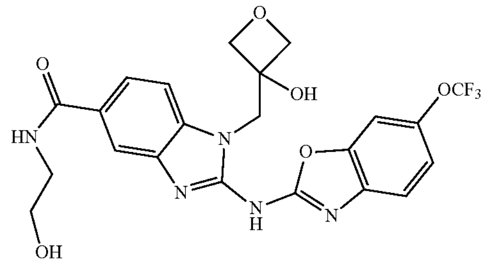 [SMILES: O=C(NCCO)c1ccc2c(c1)nc(Nc1nc3ccc(OC(F)(F)F)cc3o1)n2CC1(O)COC1] | N-(2-hydroxyethyl)-1-((3-hydroxyoxetan-3-yl)methyl)-2-((6-(trifluoromethoxy)benzo[d]oxazol-2-yl)amino)-1H-benzo[d]imidazole-5-carboxamide | 1.6 | 21 | ND |
| 96 | 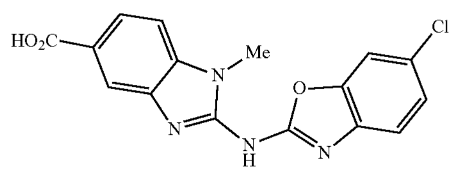 [SMILES: Cn1c(Nc2nc3ccc(Cl)cc3o2)nc2cc(C(=O)O)ccc21] | 2-((6-chlorobenzo[d]oxazol-2-yl)amino)-1-methyl-1H-benzo[d]imidazole-5-carboxylic acid | 2.8* | 39-56 | ND |
| 97 | 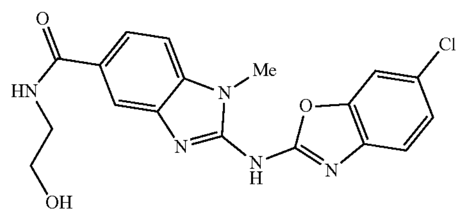 [SMILES: Cn1c(Nc2nc3ccc(Cl)cc3o2)nc2cc(C(=O)NCCO)ccc21] | 2-((6-chlorobenzo[d]oxazol-2-yl)amino)-N-(2-hydroxyethyl)-1-methyl-1H-benzo[d]imidazole-5-carboxamide | 1.4* | 33-51 | <5 |
| 98 | 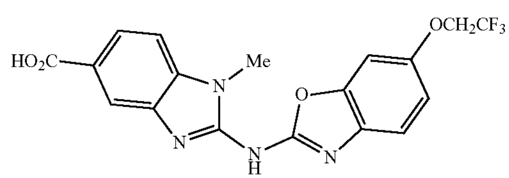 | 1-methyl-2-((6-(2,2,2-trifluoroethoxy)benzo[d]oxazol-2-yl)amino)-1H-benzo[d]imidazole-5-carboxylic acid | 4.1* | 36-56 | ND |

TABLE 1-continued

| Example No. | Structure | IUPAC name | EC$_{50}$ (µM) | Maximum Fold induction | Solubility (µM) |
|---|---|---|---|---|---|
| 99 | 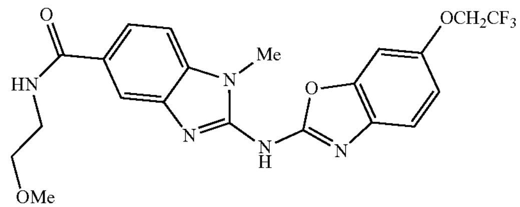 | N-(2-methoxyethyl)-1-methyl-2-((6-(2,2,2-trifluoroethoxy)benzo[d]oxazol-2-yl)amino)-1H-benzo[d]imidazole-5-carboxamide | 0.92* | 25-31 | 0.4 |
| 100 | 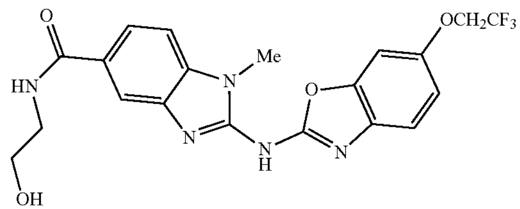 | N-(2-hydroxyethyl)-1-methyl-2-((6-(2,2,2-trifluoroethoxy)benzo[d]oxazol-2-yl)amino)-1H-benzo[d]imidazole-5-carboxamide | 1.2* | 24-35 | 5.3 |
| 101 | 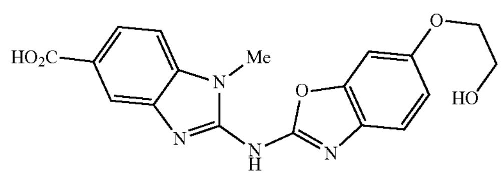 [SMILES: Cn1c(Nc2nc3ccc(OCCO)cc3o2)nc2cc(C(=O)O)ccc21] | 2-((6-(2-hydroxyethoxy)benzo[d]oxazol-2-yl)amino)-1-methyl-1H-benzo[d]imidazole-5-carboxylic acid | ND | 21 | ND |
| 102 | 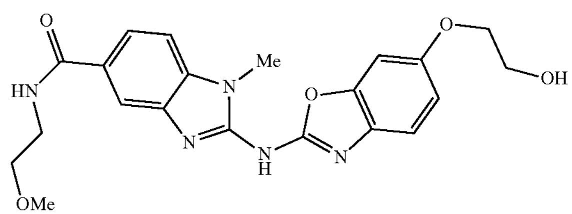 [SMILES: COCCNC(=O)c1ccc2c(c1)nc(Nc1nc3ccc(OCCO)cc3o1)n2C] | 2-((6-(2-hydroxyethoxy)benzo[d]oxazol-2-yl)amino)-N-(2-methoxyethyl)-1-methyl-1H-benzo[d]imidazole-5-carboxamide | 1.3* | 26-40 | 5.3 |

TABLE 1-continued

| Example No. | Structure | IUPAC name | EC$_{50}$ (μM) | Maximum Fold induction | Solubility (μM) |
|---|---|---|---|---|---|
| 103 | 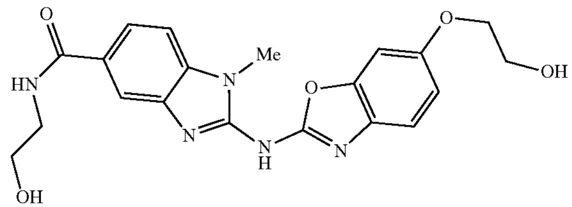 [SMILES: Cn1c(Nc2nc3ccc(OCCO)cc3o2)nc2cc(C(=O)NCCO)ccc21] | 2-((6-(2-hydroxyethoxy)benzo[d]oxazol-2-yl)amino)-N-(2-hydroxyethyl)-1-methyl-1H-benzo[d]imidazole-5-carboxamide | 3.1* | 37-39 | >20 |
| 104 | 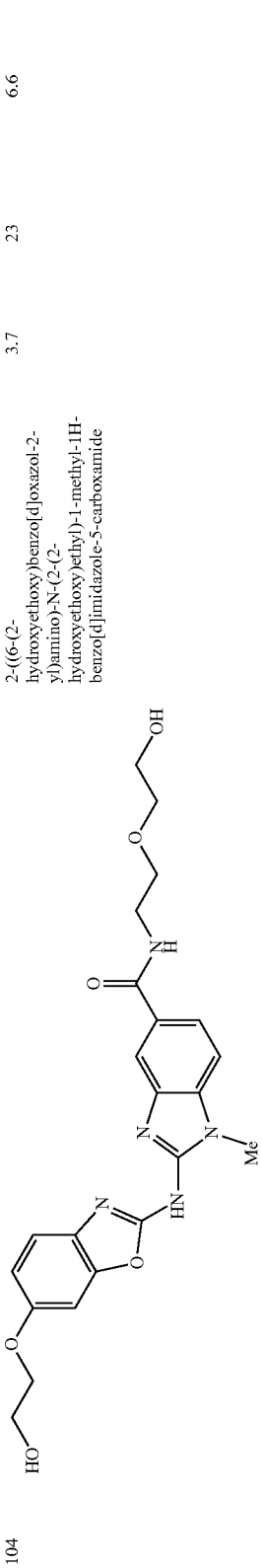 | 2-((6-(2-hydroxyethoxy)benzo[d]oxazol-2-yl)amino)-N-(2-(2-hydroxyethoxy)ethyl)-1-methyl-1H-benzo[d]imidazole-5-carboxamide | 3.7 | 23 | 6.6 |
| 105 | 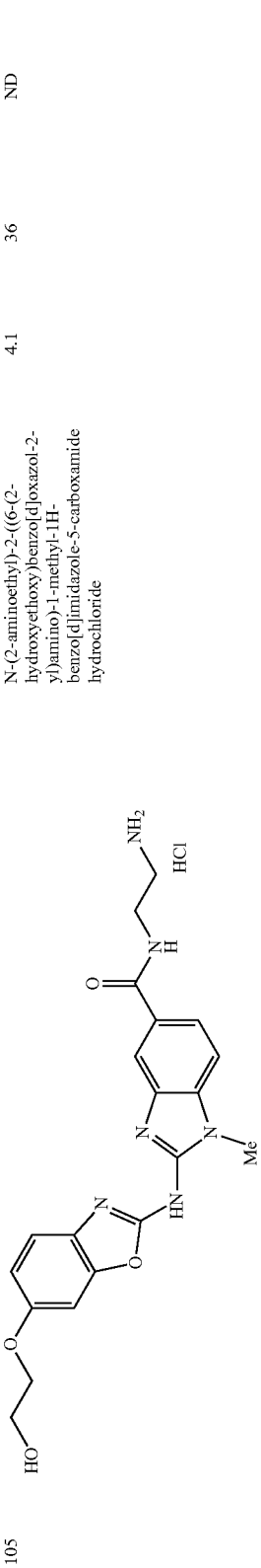 | N-(2-aminoethyl)-2-((6-(2-hydroxyethoxy)benzo[d]oxazol-2-yl)amino)-1-methyl-1H-benzo[d]imidazole-5-carboxamide hydrochloride | 4.1 | 36 | ND |

TABLE 1-continued

| Example No. | Structure | IUPAC name | EC$_{50}$ (μM) | Maximum Fold induction | Solubility (μM) |
|---|---|---|---|---|---|
| 106 | 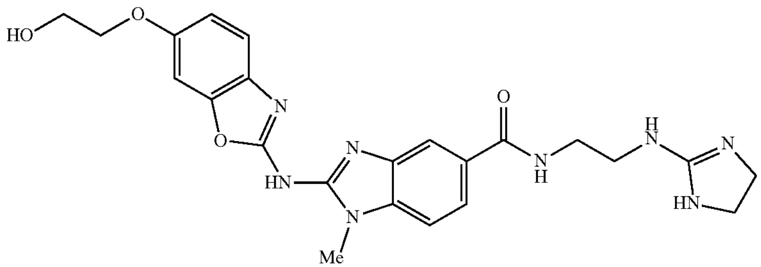 [SMILES: Cn1c(Nc2nc3ccc(OCCO)cc3o2)nc2cc(C(=O)NCCNC3=NCCN3)ccc21] | N-(2-((4,5-dihydro-1H-imidazol-2-yl)amino)ethyl)-2-((6-(2-hydroxyethoxy)benzo[d]oxazol-2-yl)amino)-1-methyl-1H-benzo[d]imidazole-5-carboxamide | ND | 6 | ND |
| 107 | 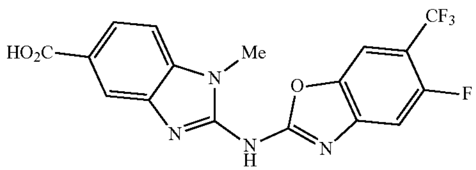 [SMILES: Cn1c(Nc2nc3cc(F)c(C(F)(F)F)cc3o2)nc2cc(C(=O)O)ccc21] | 2-((5-fluoro-6-(trifluoromethyl)benzo[d]oxazol-2-yl)amino)-1-methyl-1H-benzo[d]imidazole-5-carboxylic acid | 4.5 | 45 | ND |
| 108 | 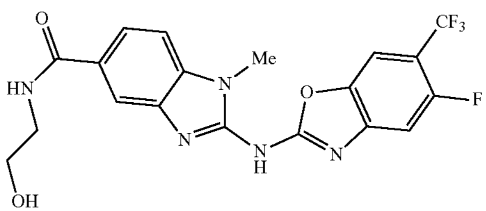 [SMILES: Cn1c(Nc2nc3cc(F)c(C(F)(F)F)cc3o2)nc2cc(C(=O)NCCO)ccc21] | 2-((5-fluoro-6-(trifluoromethyl)benzo[d]oxazol-2-yl)amino)-N-(2-hydroxyethyl)-1-methyl-1H-benzo[d]imidazole-5-carboxamide | 1.5 | 29 | 0.3 |
| 109 | 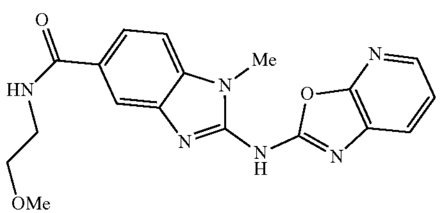 [SMILES: COCCNC(=O)c1ccc2c(c1)nc(Nc1nc3cccnc3o1)n2C] | N-(2-methoxyethyl)-1-methyl-2-(oxazolo[5,4-b]pyridin-2-ylamino)-1H-benzo[d]imidazole-5-carboxamide | 6.1 | 26 | 7.4 |

TABLE 1-continued

| Example No. | Structure | IUPAC name | EC$_{50}$ (μM) | Maximum Fold induction | Solubility (μM) |
|---|---|---|---|---|---|
| 110 | 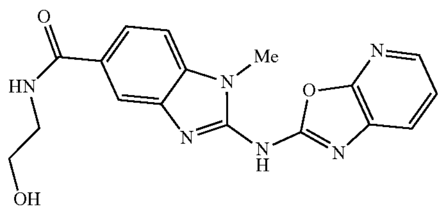 [SMILES: Cn1c(Nc2nc3cccnc3o2)nc2cc(C(=O)NCCO)ccc21] | N-(2-hydroxyethyl)-1-methyl-2-(oxazolo[5,4-b]pyridin-2-ylamino)-1H-benzo[d]imidazole-5-carboxamide | 7.6 | 60 | 18.9 |
| 111 | 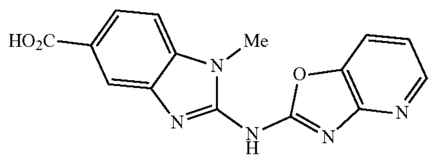 [SMILES: Cn1c(Nc2nc3ncccc3o2)nc2cc(C(=O)O)ccc21] | 1-methyl-2-(oxazolo[4,5-b]pyridin-2-ylamino)-1H-benzo[d]imidazole-5-carboxylic acid | ND | 3 | ND |
| 112 | 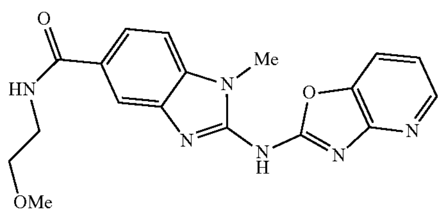 [SMILES: COCCNC(=O)c1ccc2c(c1)nc(Nc1nc3ncccc3o1)n2C] | N-(2-methoxyethyl)-1-methyl-2-(oxazolo[4,5-b]pyridin-2-ylamino)-1H-benzo[d]imidazole-5-carboxamide | ND | 15 | ND |
| 113 | 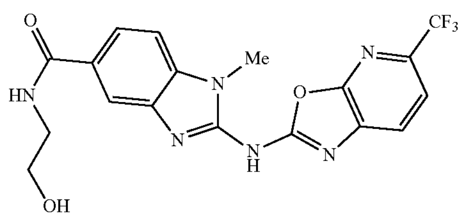 [SMILES: Cn1c(Nc2nc3ccc(C(F)(F)F)nc3o2)nc2cc(C(=O)NCCO)ccc21] | N-(2-hydroxyethyl)-1-methyl-2-((5-(trifluoromethyl)oxazolo[5,4-b]pyridin-2-yl)amino)-1H-benzo[d]imidazole-5-carboxamide | ND | 20 | 9.1 |

TABLE 1-continued

| Example No. | Structure | IUPAC name | EC$_{50}$ (μM) | Maximum Fold induction | Solubility (μM) |
|---|---|---|---|---|---|
| 114 | 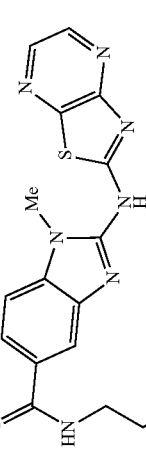 | N-(2-(2-hydroxyethoxy)ethyl)-1-methyl-2-(thiazolo[4,5-b]pyrazin-2-ylamino)-1H-benzo[d]imidazole-5-carboxamide | ND | 33 | 12.2 |
| 115 | 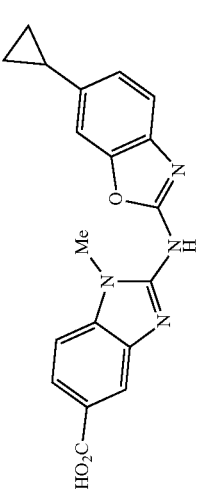 | 2-((6-cyclopropylbenzo[d]oxazol-2-yl)amino)-1-methyl-1H-benzo[d]imidazole-5-carboxylic acid | 6.2 | 71 | ND |
| 116 | 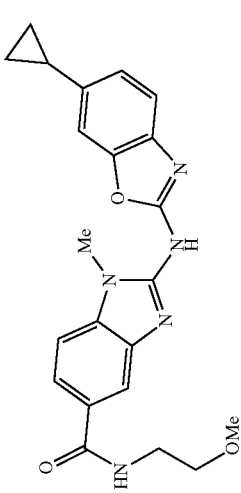 | 2-((6-cyclopropylbenzo[d]oxazol-2-yl)amino)-N-(2-methoxyethyl)-1-methyl-1H-benzo[d]imidazole-5-carboxamide | 3.0* | 32-38 | ND |

TABLE 1-continued

| Example No. | Structure | IUPAC name | EC$_{50}$ (μM) | Maximum Fold induction | Solubility (μM) |
|---|---|---|---|---|---|
| 117 | 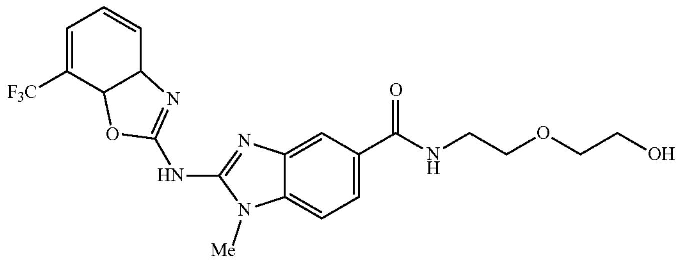 [SMILES: Cn1c(NC2=NC3C=CC=C(C(F)(F)F)C3O2)nc2cc(C(=O)NCCOCCO)ccc21] | N-(2-(2-hydroxyethoxy)ethyl)-1-methyl-2-((7-(trifluoromethyl)benzo[d]oxazol-2-yl)amino)-1H-benzo[d]imidazole-5-carboxamide | 1.8* | 38 | 1.2 |
| 118 | 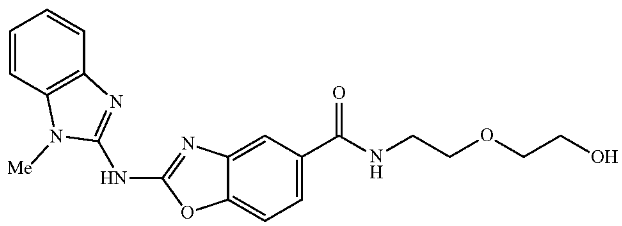 [SMILES: Cn1c(Nc2nc3cc(C(=O)NCCOCCO)ccc3o2)nc2ccccc21] | N-(2-(2-hydroxyethoxy)ethyl)-2-((1-methyl-1H-benzo[d]imidazol-2-yl)amino)benzo[d]oxazole-5-carboxamide | 8.0 | 24 | ND |
| 119 | 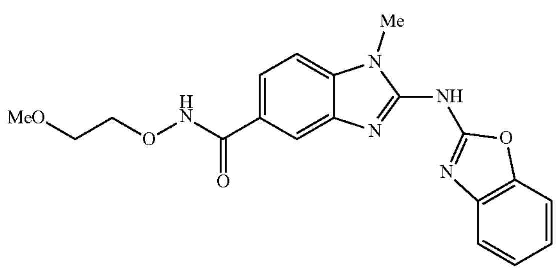 [SMILES: COCCONC(=O)c1ccc2c(c1)nc(Nc1nc3ccccc3o1)n2C] | 2-(benzo[d]oxazol-2-ylamino)-N-(2-methoxyethoxy)-1-methyl-1H-benzo[d]imidazole-5-carboxamide | 0.6* | 47-65 | 0.5 |
| 120 | 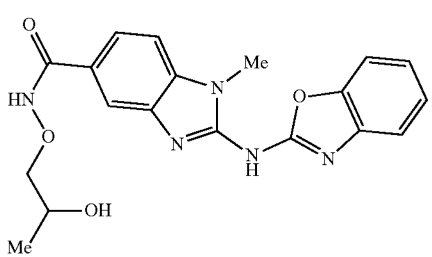 [SMILES: CC(O)CONC(=O)c1ccc2c(c1)nc(Nc1nc3ccccc3o1)n2C] | 2-(benzo[d]oxazol-2-ylamino)-N-(2-hydroxypropoxy)-1-methyl-1H-benzo[d]imidazole-5-carboxamide | 2.0 | 26 | 6.5 |

TABLE 1-continued

| Example No. | Structure | IUPAC name | EC$_{50}$ (μM) | Maximum Fold induction | Solubility (μM) |
|---|---|---|---|---|---|
| 121 | 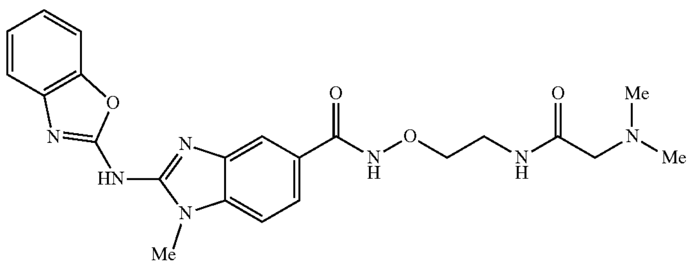 [SMILES: CN(C)CC(=O)NCCONC(=O)c1ccc2c(c1)nc(Nc1nc3ccccc3o1)n2C] | 2-(benzo[d]oxazol-2-ylamino)-N-(2-(2-(dimethylamino)acetamido)ethoxy)-1-methyl-1H-benzo[d]imidazole-5-carboxamide | 1.4* | 22-23 | 9.0 |
| 122 | 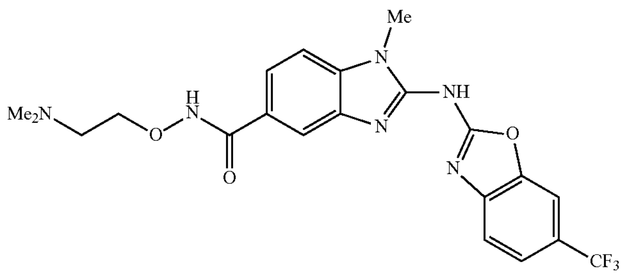 [SMILES: CN(C)CCONC(=O)c1ccc2c(c1)nc(Nc1nc3ccc(C(F)(F)F)cc3o1)n2C] | N-(2-(dimethylamino)ethoxy)-1-methyl-2-((6-(trifluoromethyl)benzo[d]oxazol-2-yl)amino)-1H-benzo[d]imidazole-5-carboxamide | 0.4* | 51-67 | 5.1 |
| 123 | 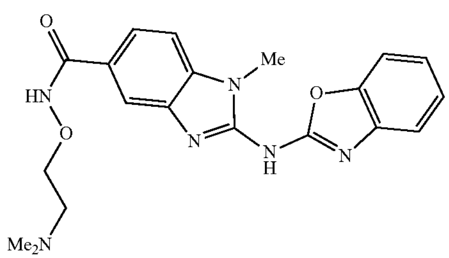 [SMILES: CN(C)CCONC(=O)c1ccc2c(c1)nc(Nc1nc3ccccc3o1)n2C] | 2-(benzo[d]oxazol-2-ylamino)-N-(2-(dimethylamino)ethoxy)-1-methyl-1H-benzo[d]imidazole-5-carboxamide | ND | 22 | 10.5 |

TABLE 1-continued

| Example No. | Structure | IUPAC name | EC$_{50}$ (µM) | Maximum Fold induction | Solubility (µM) |
|---|---|---|---|---|---|
| 124 | 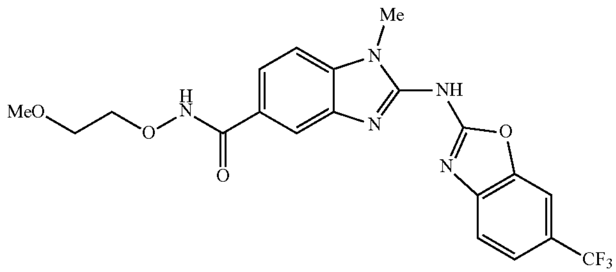 [SMILES: COCCONC(=O)c1ccc2c(c1)nc(Nc1nc3ccc(C(F)(F)F)cc3o1)n2C] | N-(2-methoxyethoxy)-1-methyl-2-((6-(trifluoromethyl)benzo[d]oxazol-2-yl)amino)-1H-benzo[d]imidazole-5-carboxamide | 0.2* | 31-52 | <2 |
| 125 | 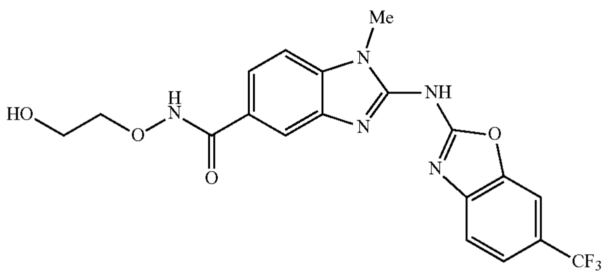 [SMILES: Cn1c(Nc2nc3ccc(C(F)(F)F)cc3o2)nc2cc(C(=O)NOCCO)ccc21] | N-(2-hydroxyethoxy)-1-methyl-2-((6-(trifluoromethyl)benzo[d]oxazol-2-yl)amino)-1H-benzo[d]imidazole-5-carboxamide | 0.3* | 32-59 | 3.5 |
| 126 | 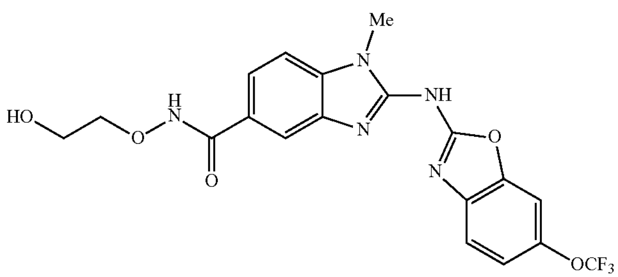 [SMILES: Cn1c(Nc2nc3ccc(OC(F)(F)F)cc3o2)nc2cc(C(=O)NOCCO)ccc21] | N-(2-hydroxyethoxy)-1-methyl-2-((6-(trifluoromethoxy)benzo[d]oxazol-2-yl)amino)-1H-benzo[d]imidazole-5-carboxamide | 0.5* | 33-37 | 2.1 |

TABLE 1-continued

| Example No. | Structure | IUPAC name | EC$_{50}$ (μM) | Maximum Fold induction | Solubility (μM) |
|---|---|---|---|---|---|
| 127 | 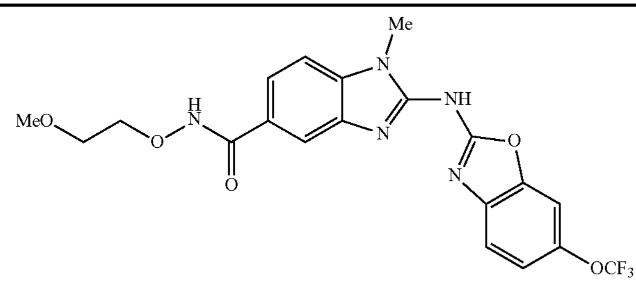 | N-(2-methoxyethoxy)-1-methyl-2-((6-(trifluoromethoxy)benzo[d]oxazol-2-yl)amino)-1H-benzo[d]imidazole-5-carboxamide | 0.5* | 27-36 | <2 |
| 128 | 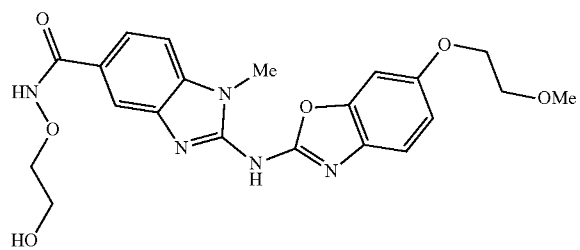 [SMILES: COCCOc1ccc2nc(Nc3nc4cc(C(=O)NOCCO)ccc4n3C)oc2c1] | N-(2-hydroxyethoxy)-2-((6-(2-methoxyethoxy)benzo[d]oxazol-2-yl)amino)-1-methyl-1H-benzo[d]imidazole-5-carboxamide | 1.2* | 48-75 | 4.7 |
| 129 | 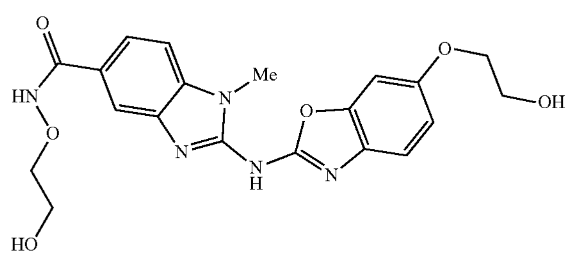 [SMILES: Cn1c(Nc2nc3ccc(OCCO)cc3o2)nc2cc(C(=O)NOCCO)ccc21] | N-(2-hydroxyethoxy)-2-((6-(2-hydroxyethoxy)benzo[d]oxazol-2-yl)amino)-1-methyl-1H-benzo[d]imidazole-5-carboxamide | 3.4* | 54-58 | 14.1 |
| 130 | 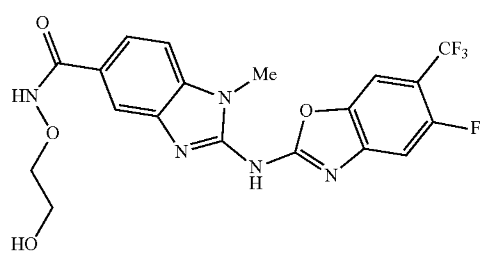 [SMILES: Cn1c(Nc2nc3cc(F)c(C(F)(F)F)cc3o2)nc2cc(C(=O)NOCCO)ccc21] | 2-((5-fluoro-6-(trifluoromethyl)benzo[d]oxazol-2-yl)amino)-N-(2-hydroxyethoxy)-1-methyl-1H-benzo[d]imidazole-5-carboxamide | 0.74* | 42 | <2 |

TABLE 1-continued

| Example No. | Structure | IUPAC name | EC$_{50}$ (µM) | Maximum Fold induction | Solubility (µM) |
|---|---|---|---|---|---|
| 131 | 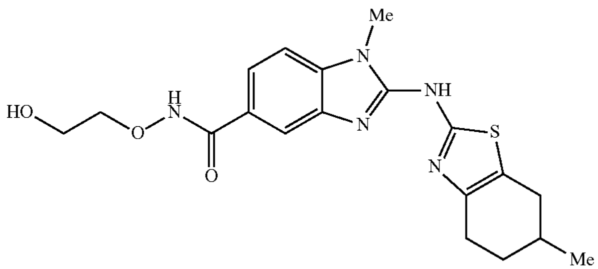 [SMILES: CC1CCc2nc(Nc3nc4cc(C(=O)NOCCO)ccc4n3C)sc2C1] | N-(2-hydroxyethoxy)-1-methyl-2-(((6-methyl-4,5,6,7-tetrahydrobenzo[d]thiazol-2-yl)amino)-1H-benzo[d]imidazole-5-carboxamide | 1.4* | 35-62 | 6.7 |
| 132 | 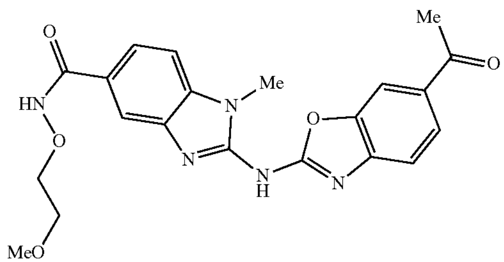 [SMILES: COCCONC(=O)c1ccc2c(c1)nc(Nc1nc3ccc(C(C)=O)cc3o1)n2C] | 2-((6-acetylbenzo[d]oxazol-2-yl)amino)-N-(2-methoxyethoxy)-1-methyl-1H-benzo[d]imidazole-5-carboxamide | 1.5 | 39 | 3.1 |
| 133 | 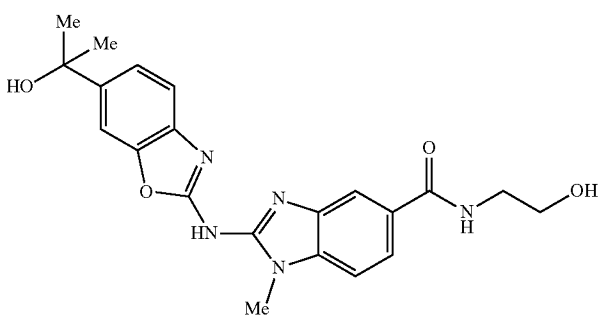 [SMILES: Cn1c(Nc2nc3ccc(C(C)(C)O)cc3o2)nc2cc(C(=O)NCCO)ccc21] | N-(2-hydroxyethyl)-2-((6-(2-hydroxypropan-2-yl)benzo[d]oxazol-2-yl)amino)-1-methyl-1H-benzo[d]imidazole-5-carboxamide | 5.3 | 17 | 9.2 |

TABLE 1-continued

| Example No. | Structure | IUPAC name | EC$_{50}$ (μM) | Maximum Fold induction | Solubility (μM) |
|---|---|---|---|---|---|
| 134 | 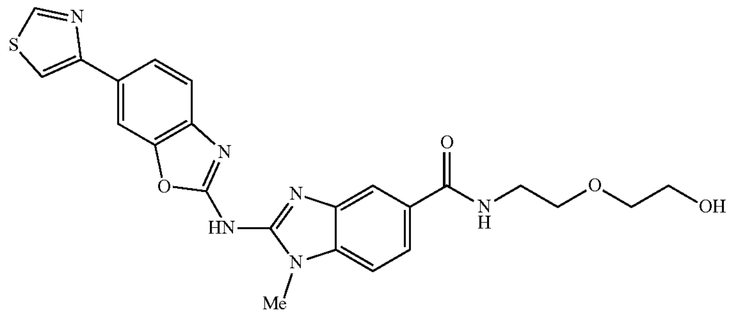 [SMILES: Cn1c(Nc2nc3ccc(-c4cscn4)cc3o2)nc2cc(C(=O)NCCOCCO)ccc21] | N-(2-(2-hydroxyethoxy)ethyl)-1-methyl-2-((6-(thiazol-4-yl)benzo[d]oxazol-2-yl)amino)-1H-benzo[d]imidazole-5-carboxamide | 1.4* | 42-70 | <2 |
| 135 | 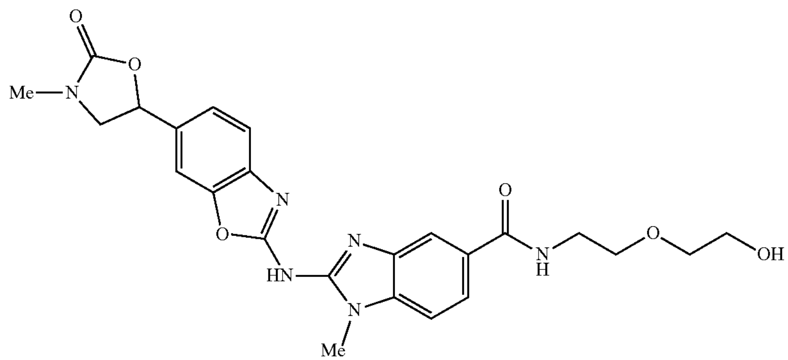 [SMILES: CN1CC(c2ccc3nc(Nc4nc5cc(C(=O)NCCOCCO)ccc5n4C)oc3c2)OC1=O] | N-(2-(2-hydroxyethoxy)ethyl)-1-methyl-2-((6-(3-methyl-2-oxooxazolidin-5-yl)benzo[d]oxazol-2-yl)amino)-1H-benzo[d]imidazole-5-carboxamide | NA | 1 | ND |

TABLE 1-continued

| Example No. | Structure | IUPAC name | EC$_{50}$ (μM) | Maximum Fold induction | Solubility (μM) |
|---|---|---|---|---|---|
| 136 | 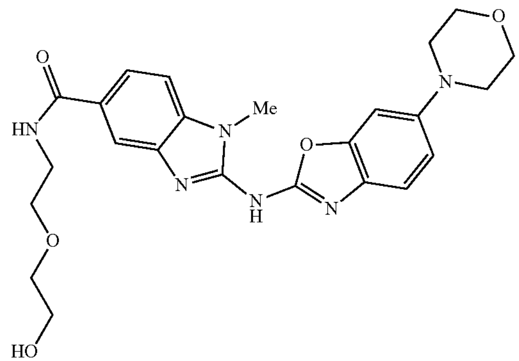 [SMILES: Cn1c(Nc2nc3ccc(N4CCOCC4)cc3o2)nc2cc(C(=O)NCCOCCO)ccc21] | N-(2-(2-hydroxyethoxy)ethyl)-1-methyl-2-((6-morpholinobenzo[d]oxazol-2-yl)amino)-1H-benzo[d]imidazole-5-carboxamide | 2.9* | 36 | 10.6 |
| 137 | 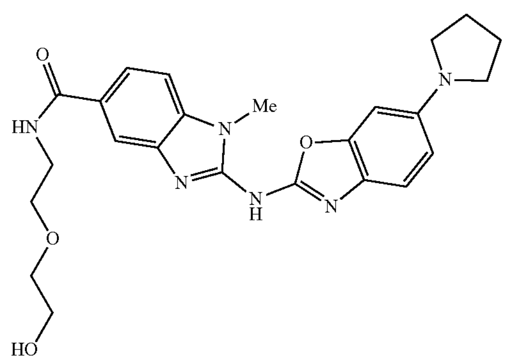 [SMILES: Cn1c(Nc2nc3ccc(N4CCCC4)cc3o2)nc2cc(C(=O)NCCOCCO)ccc21] | N-(2-(2-hydroxyethoxy)ethyl)-1-methyl-2-((6-(pyrrolidin-1-yl)benzo[d]oxazol-2-yl)amino)-1H-benzo[d]imidazole-5-carboxamide | 1.3* | 24-70 | 6.9 |

TABLE 1-continued

| Example No. | Structure | IUPAC name | EC$_{50}$ (μM) | Maximum Fold induction | Solubility (μM) |
|---|---|---|---|---|---|
| 138 | 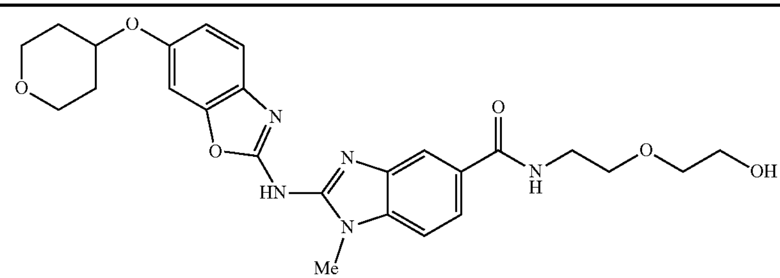 | N-(2-(2-hydroxyethoxy)ethyl)-1-methyl-2-((6-((tetrahydro-2H-pyran-4-yl)oxy)benzo[d]oxazol-2-yl)amino)benzo[d]oxazole-5-carboxamide | 2.0* | 20 | ND |
| 139 | 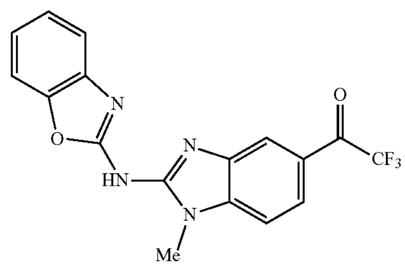 [SMILES: Cn1c(Nc2nc3ccccc3o2)nc2cc(C(=O)C(F)(F)F)ccc21] | 1-(2-(benzo[d]oxazol-2-ylamino)-1-methyl-1H-benzo[d]imidazol-5-yl)-2,2,2-trifluoroethan-1-one | 2.6 | 21 | <2 |
| 140 | 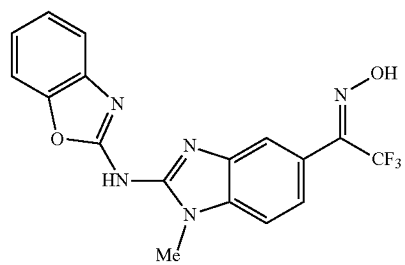 [SMILES: Cn1c(Nc2nc3ccccc3o2)nc2cc(/C(=N/O)C(F)(F)F)ccc21] | (Z)-1-(2-(benzo[d]oxazol-2-ylamino)-1-methyl-1H-benzo[d]imidazol-5-yl)-2,2,2-trifluoroethan-1-one oxime | ND | 19 | ND |

TABLE 1-continued

| Example No. | Structure | IUPAC name | EC$_{50}$ (μM) | Maximum Fold induction | Solubility (μM) |
|---|---|---|---|---|---|
| 141 | (structure with NH$_2$, CF$_3$, benzimidazole-Me, benzoxazole) | N-(5-(1-amino-2,2,2-trifluoroethyl)-1-methyl-1H-benzo[d]imidazol-2-yl)benzo[d]oxazol-2-amine | 3.6* | 22 | 9.0 |
| 142 | (structure with OH, CF$_3$, benzimidazole-Me, benzoxazole) | 1-(2-(benzo[d]oxazol-2-ylamino)-1-methyl-1H-benzo[d]imidazol-5-yl)-2,2,2-trifluoroethan-1-ol | 3.3* | 27 | ND |

*Average of 2 or more EC$_{50}$ determinations
ND = Not Determined
NA = Not Active

Example 145. hERG Assay

Cell Lines and Cell Culture

HEK 293 cell line stably expressing hERG channel (Cat # K1236) was purchased from Invitrogen. The cells were cultured in 85% DMEM, 10% dialyzed FBS, 0.1 mM NEAA, 25 mM HEPES, 100 U/mL Penicillin-Streptomycin and 5 μg/mL Blasticidin and 400 μg/mL Geneticin. Cells were split using TrypLE™ Express about three times a week, and maintained between ~40% to ~80% confluence. Before the assay, the cells were transferred onto the coverslips at $5 \times 10^5$ cells/per 6 cm cell culture dish and induced with doxycycline at 1 μg/mL for 48 hours.

Solution Preparations

1) External solution (in mM): 132 NaCl, 4 KCl, 3 $CaCl_2$, 0.5 $MgCl_2$, 11.1 glucose, and 10 HEPES (pH adjusted to 7.35 with NaOH)
2) Internal solution (in mM): 140 KCl, 2 $MgCl_2$, 10 EGTA, 10 HEPES and 5 MgATP (pH adjusted to 7.35 with KOH)
3) hERG currents were tested in presence of 10 μM compound concentration with final concentration of DMSO of 0.1%.

Experimental Procedure

1) Removed the coverslip from the cell culture dish and placed it on the microscope stage in bath chamber.
2) Located a desirable cell using the 10× objective. Located the tip of the electrode under the microscope using the 10× objective by focusing above the plane of the cells. Once the tip was in focus, advanced the electrode downwards towards the cell using the coarse controls of the manipulator, while simultaneously moving the objective to keep the tip in focus.
3) When directly over the cell, switched to the 40× objective and used the fine controls of the manipulator to approach the surface of the cell in small steps.
4) Applied gentle suction through the side-port of the electrode holder to form a gigaohm seal.
5) Used the Cfast to remove the capacity current that was in coincidence with the voltage step. Obtained the whole cell configuration by applying repetitive, brief, strong suction until the membrane patch ruptured.
6) Set membrane potential to −60 mV at this point to ensure that hERG channels were not open. The spikes of capacity current should then be cancelled using the Cslow on the amplifier. 7) Set holding potential to −90 mV for 500 ms; recorded current at 50 kHz and filtered at 10 kHz. Leaking current was tested at −80 mV for 500 ms.
8) The hERG current was elicited by depolarizing at +30 mV for 4.8 seconds and then the voltage was taken back to −50 mV for 5.2 seconds to remove the inactivation and observe the deactivating tail current. The maximum amount of tail current size was used to determine hERG current amplitude.
9) Recorded current for 120 seconds to assess the current stability. Only stable cells with recording parameters above threshold were applied for the compound administrations.
10) Firstly vehicle control was applied to the cells to establish the baseline. Once the hERG current was found to be stabilized for 5 minutes, test compound was applied. hERG current in the presence of test compound was recorded for approximately 5 minutes to reach steady state and then 5 sweeps were captured. In order to ensure the good performance of cultured cells and operations, the positive control, Dofetilide, with 5 dose concentration was also used to test the same batch of cells.

Data Analysis

The following criteria were used to determine data acceptability.

1) Initial seal resistance >1 GΩ;
2) Leak currents <50% of the control peak tail currents at any time;
3) The peak tail amplitude >250 pA;
4) Membrane resistance Rm>500 MΩ;
5) Access resistance (Ra)<10 MΩ;
6) Apparent run-down of peak current <2.5% per min.

Data that met the above criteria for hERG current quality were further analyzed as the following steps.

1) Percent hERG current inhibition was calculated using the following equation.
   Note: PatchMaster or Clampfit software was used to extract the peak current from the original data.

$$\text{Peak current inhibition} = \frac{(1 - \text{Peak tail current}_{compound})}{\text{Peak tail current}_{vehicle}} \times 100$$

2) The dose response curve of test compounds was plotted with percentage of hERG current inhibition against the concentration of test compounds using Graphpad Prism 6.0, and fit to a sigmoid dose-response curve with a variable slope.

hERG data for selected compounds in manual patch clamp assay are provided in Table 2 below. Notably, hERG values were measured only for compounds that showed >5 μM solubility. Accurate measurement of hERG activity was not possible for compounds with solubility below

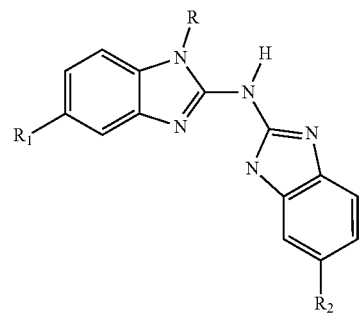

R: Methyl

TABLE 2

| ID # | X | $R_1$ | $R_2$ | hERG inhibition @ 10 uM |
|---|---|---|---|---|
| Comparator 1 | S | —$CONHCH_2CH_2OCH_2CH_2OH$ | —$OCF_3$ | 66% |
| Comparator 2 | S | —$CONHCH_2CH_2NHCOCH_2N(Me)_2$ | —$OCF_3$ | 93% |

TABLE 2-continued

| ID # | X | $R_1$ | $R_2$ | hERG inhibition @ 10 uM |
|---|---|---|---|---|
| Compound A | S | —CONHCH$_2$CH$_2$OCH$_2$CH$_2$OH | —H | 20% |
| Ex 7[1] | S | —CONHCH$_2$CH$_2$OCH$_2$CH$_2$OH | —CH$_3$ | 6% |
| Ex 34 | O | —CONHCH$_2$CH$_2$OCH$_2$CH$_2$OH | —CF$_3$ | 61% |
| Ex 122 | O | —CONHOCH$_2$CH$_2$N(Me)$_2$ | —CF$_3$ | 87% |
| Ex 31 | O | —COOH | —CF$_3$ | 0% |
| Ex 137 | O | —CONHCH$_2$CH$_2$OCH$_2$CH$_2$OH | —N-pyrrolidine | 18% |
| Ex 16 | O | —CONHCH$_2$CH$_2$OH | H | 35% |
| Ex 17 | O | —CONHCH$_2$CH$_2$OCH$_2$CH$_2$OH | H | 16% |
| Ex 18 | O | —CONHCH$_2$CH$_2$NH$_2$ | H | 12% |
| Ex 19 | O | —CONHCH$_2$CH$_2$NHCOCH$_2$N(Me)$_2$ | H | 29% |
| Ex 23 | O | —CONHCH$_2$CH(OH)CH$_3$ | H | 24% |
| Ex 25 | O | —CONHCH$_2$CH$_2$OCH$_2$CH(OH)CH$_3$ | H | 8% |
| Ex 26 | O | —CONHCH$_2$C(OH)(—CH$_2$OCH$_2$—) | H | 18% |
| Ex 20 | O | —CONHCH$_2$CH$_2$—N-morpholine | H | 59% |
| Ex 123 | O | —CONHOCH$_2$CH$_2$N(Me)$_2$ | H | 54% |
| Ex 28 | O | —CONHCH$_2$CH$_2$—N-pyrrolidine | H | 64% |
| Ex 121 | O | —CONHOCH$_2$CH$_2$NHCOCH$_2$N(Me)$_2$ | H | 66% |
| Ex 69 | O | —CONHCH$_2$CH$_2$OMe | F | 38% |
| Ex 56 | O | —CONHCH$_2$CH$_2$OMe | —OCH$_2$CH$_2$OMe | 35% |
| Ex 57 | O | —CONHCH$_2$CH$_2$OH | —OCH$_2$CH$_2$OMe | 15% |
| Ex 58 | O | —CONHCH$_2$CH$_2$OCH$_2$CH$_2$OH | —OCH$_2$CH$_2$OMe | 11% |
| Ex 128 | O | —CONHOCH$_2$CH$_2$OH | —OCH$_2$CH$_2$OMe | 18% |
| Ex 62 | O | —COOH | —OCHF$_2$ | 13% |
| Ex 44 | O | —COOH | —OCF$_3$ | 15% |
| Ex 86[2] | O | —CONHCH$_2$CH$_2$OH | —OCF$_3$ | 64% |
| Ex 53 | O | —CONHCH$_2$CH$_2$OH | —OCF$_3$ | 70% |
| Ex 13 | NH | —COOH | —OCF$_3$ | 34% |
| Ex 75[3] | NH | —COOH | —OCF$_3$ | 9% |
| Ex 73 | NH | —COOH | —F | 5% |
| Ex 14 | NH | —CONHCH$_2$CH$_2$OMe | —OCF$_3$ | 87% |

[1]Example 7 is a tetrahydrobenzo[d]thiazole compound instead of a benzothiazole compound.
[2]R is ethyl.
[3]R is CH$_2$CH$_2$OMe.

Example 146. Microscale Thermophoresis (MST) Assay/Bach 1 Binding Assay

Outline of Protein Expression/Production

Human BACH1 (construct-ID: 10×HIS-GP-BACH1 (aa179-736)-Thrombin-FLAG) was expressed in Sf9 insect cells. Protein purification was performed using affinity chromatography, followed by size-exclusion chromatography. Quality of resulting protein was judged using SDS-PAGE analysis.

Assay Principle

The MST technology is based on measurement of protein movement along a temperature gradient. Thereby, fluorescently labeled protein is loaded into capillaries, where an infrared laser heats a small volume. Before and during heating, fluorescent intensity is measured at the site of irradiation and the loss of fluorescence in the IR laser focus is quantified.

Two major factors contribute to change of fluorescence signal. First of all, the so-called TRIC (Temperature Related Intensity Change) effect is caused by the temperature-dependency of fluorophore's quantum yield. Herein, the extent of the temperature dependence depends on the chemical environment, which may be changed by the binding of a ligand (e.g. compound, peptide) to the target. Moreover, Kd value between ligand and target can depend on temperature. Second, thermophoresis, which is defined as movement of fluorescent molecules along temperature gradient, is a major contributor to change of fluorescence. Hereby, protein movement along the gradient depends on hydrodynamic radius, charge and hydration shell. These properties can change upon association of the labeled protein with another species, e.g. compound. Thereby, MST detects the differences in protein movement with increasing ligand concentration: from this, the fraction of ligand bound protein and a Kd value can be determined.

MST Assay Protocol

For Kd determination of compounds binding BACH1, the following protocol was applied: 10×HIS-GP-BACH1 (aa179-736)-Thrombin-FLAG (expressed and purified at Proteros) was fluorescently labeled via its lysine-residues (2nd gen NHS-NT.647 dye).

Experiments were performed using the experimental device Monolith NT.115 Pico, NanoTemper Technologies, with MST power set to medium and excitation power set to 2% at a reaction temperature of 25° C.

10 nM fluorescently labeled BACH1 was applied to reaction buffer containing 50 mM HEPES pH 8.0, 100 mM NaCl, 5% glycerol, 0.05% Tween20 and 1 mM DTT in a reaction volume of 8 µL using Monolith NT.115 Premium Capillaries. Compounds were applied at a maximal concentration of 103 µM with 15 subsequent factor 2 dilutions.

Kd data for selected compounds in MST assay are provided in Table 3 below.

TABLE 3

| Example Number | Kd (µM) | Kd error (µM) |
|---|---|---|
| 17 | 0.25 | 0.051 |
| 33 | 0.26 | 0.051 |
| 56 | 0.25 | 0.15 |
| 112 | 0.56 | 0.13 |
| 124 | 0.20 | 0.089 |

From the data provided in Table 3 above, it can be inferred the compounds of the present invention also bind to Bach1.

Example 147. HMOX1 Inducers of the Invention Strongly Increase In Vitro Expression of HMOX1

RNA Isolation and Quantification of Gene Expression

Inducing HMOX1 expression has been shown to reduce vaso-occlusive crises (VOCs), in particular, heme-induced vaso-occlusion in Sickle cell disease (SCD) mice (Belcher J D, et al. Antioxid Redox Signal 2017, 26:748-762; Krishnamoorthy S, et al. JCI Insight 2017, 2:e96409). HepG2 cells were seeded at 250 k/well in 12-well tissue culture plates coated with collagen (collagen I, rat tail (thin plate coating); ENZO Life Sciences) for approximately 24 hours. The seeded cells were then treated with dose titration of the compound of Example 17 or dimethyl fumarate (DMF) (a Nrf2 activator; Fisher Scientific) via media change, with biological triplicates performed for each treatment. After approximately 24 hours of treatment, cells were visually inspected to confirm that no toxicity occurred with compound treatment. The treated cells were washed with PBS, aspirated, parafilmed and frozen at −80° C. prior to RNA isolation. RNA was isolated using Machery-Nagel isolation kit (NucleoSpin® RNA: catalog 740955.250) and then quantitated using ThermoFisher Nanodrop.

RNA was diluted for Nanostring gene expression analysis. The diluted RNA at an input of 200 ng RNA was run on a Nanostring instrument, which was supported with nCounter® SPRINT Profiler System and nSolver4.0 Software, nCounter® SPRINT Cartridge, nCounter® SPRINT Reagent Pack, and nCounter® SPRINT Hybridization Buffer. Analysis was done manually using raw data obtained from nSolver4.0 Software. CLTC, POLR2A, RPL27 and TBP were used as reference genes for normalization. Data was graphed as fold change compared to DMSO treatment.

The relative mRNA levels of the HMOX1 gene in HepG2 cells treated with the compound of Example 17 or DMF were measured according to the methods described above. Note that for gene expression comparative analysis between the compound of Example 17 and DMF, HepG2 cells were treated with the test compound for 24 hours (results shown in FIG. 1).

It was found that the compound of Example 17 induced HMOX1 expression much more strongly than another Nrf2 activator DMF (FIG. 1A). For example, 30 µM of the compound of Example 17 induced HMOX1 expression 4 times higher than 250 µM DMF.

Figure 1B:
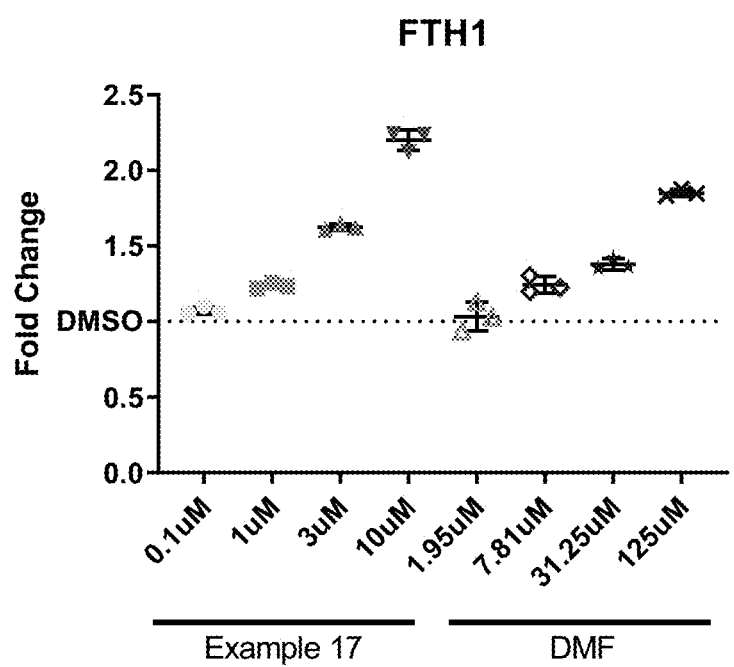

The relative mRNA levels were also compared for several other Bach1-responsive genes in HepG2 cells treated with the compound of Example 17 versus Nrf2 activator DMF. Additionally, the compound of Example 17 and DMF induced FTH1 expressions with comparable fold increases (FIG. 1B).

Examples 148. HMOX Inducers of the Invention Reduce Vaso-occlusion in SCD Mice Increase Fetal Hemoglobin (HbF) in SCD Mice Dosing Scheme of HMOX Inducers to HbSS Townes Sickle Mice HbSS Townes sickle mice were oral gavaged once daily with Vehicle or the compound of Example 17 listed below for 8 days. To minimize experimental inconsistency, fresh formulation was prepared every day and vortexed prior to drawing test article into syringe for each dosing, and dosing was performed by the same individual throughout the day. The last-day dose was administered by oral gavage 4 hours prior to hemin infusion described below.

1. Vehicle (0.5% w/v Tween 80 in 0.45% w/v methyl cellulose)
2. the compound of Example 17 (10 mg/kg PO dosing)
3. the compound of Example 17 (25 mg/kg PO dosing)
4. the compound of Example 17 (50 mg/kg PO dosing)

Measurement of Vaso-Occlusion (Stasis)

Male and female sickle mice, approximately 12 weeks of age, were weighed before surgery. Animals were anesthetized with a mixture of ketamine (106 mg/kg) and xylazine (7.2 mg/kg) and dorsal skin-fold chambers (DSFCs) were surgically implanted. On the same day anesthetized mice were placed on a special intravital microscopy stage, and 20-22 flowing subcutaneous venules in the DSFC window were selected and mapped. After venule selection and mapping, hemin chloride (2.677 mM; Frontier Scientific), dissolved in sterile saline containing sodium carbonate (11.36 mM; Sigma-Aldrich) and D-sorbitol (9.59 mM; Sigma-Aldrich), was filtered (0.22 µm), diluted 1:10 in sterile saline (267.7 µM hemin, final) and infused into the tail veins of mice (0.012 ml/g, 3.2 µmols heme/kg body weight). All of the selected venules were re-examined at 1 h after hemin infusion, and the number of static (no flow) venules was counted and expressed as percent stasis. Four hours after hemin infusion, mice were euthanized in a $CO_2$ atmosphere and the liver, spleen and kidneys were removed, flash frozen, and stored at −85° C.

Measurement of F-Cells

Heparinized whole blood was collected 4 hours after hemin infusion from the inferior vena cava of HbSS Townes mice administered Vehicle or the compound of Example 17. F-cells were stained on whole blood smears by the Kleihauer-Betke method using a fetal cell stain kit (Simmler) according to the manufacturer's instructions. F-cells and total erythrocytes were counted in 4 separate microscopic fields at 100× magnification for each mouse. The F-cells were expressed as a percentage of total erythrocytes (i.e., red blood cells). Human fetal cord blood was used as a positive control.

Figure 2:
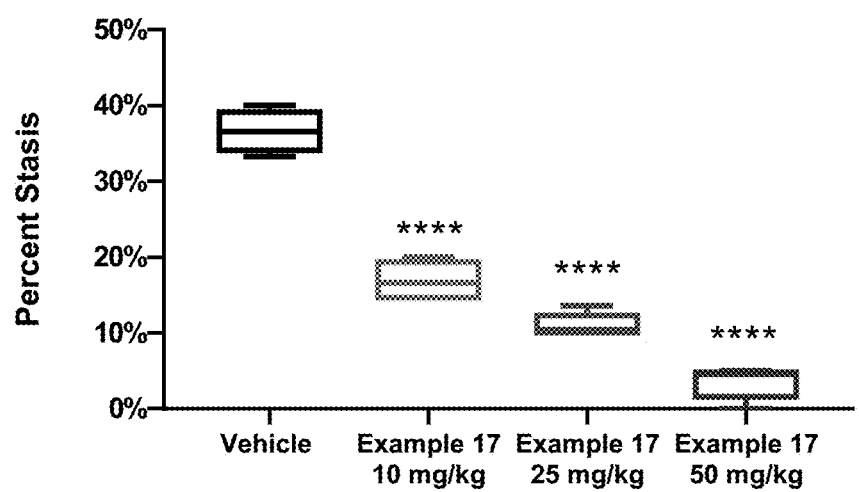
FIG. 2 depicts a graph showing that the compound of Example 17 dose responsively inhibit microvascular stasis in Townes-SS sickle mice. Townes-SS mice were gavaged once daily with Vehicle or the compound of Example 17 for 8 days. After the last gavage dorsal skin-fold chambers were implanted on the mice and 20-22 flowing venules were selected and mapped in the subcutaneous skin using intravital microscopy. Mice were then infused via the tail vein with Panhematin (3.2 μmots heme/kg body weight). One hour after infusion each venule was re-examined for microvascular stasis (no flow) and data are expressed as % stasis. Stasis values are means+SD. One-Way ANOVA with Dunnett's Multiple comparison to Vehicle ****P<0.0001

Vaso-occlusion is a hallmark of SCD. To evaluate whether the disclosed compounds can effectively reduce vaso-occlusion, heme-induced vaso-occlusion (stasis) was measured in the subcutaneous venules of HbSS-Townes sickle mice with implanted dorsal skinfold chambers (DSFCs) according to the methods described above. As shown in FIG. 2, microvascular stasis was significantly reduced in HbSS-Townes mice administered with the compound of Example 17 as compared with those administered with the Vehicle at one hour after heme infusion. Furthermore, the compound of Example 17 dose responsively inhibited microvascular stasis (FIG. 2). For the compound of Example 17, stasis was reduced to ~17% with 10 mg/kg dosage, to ~12% with 25 mg/kg dosage, and to ~5% with 50 mg/kg dosage.

Figure 3:
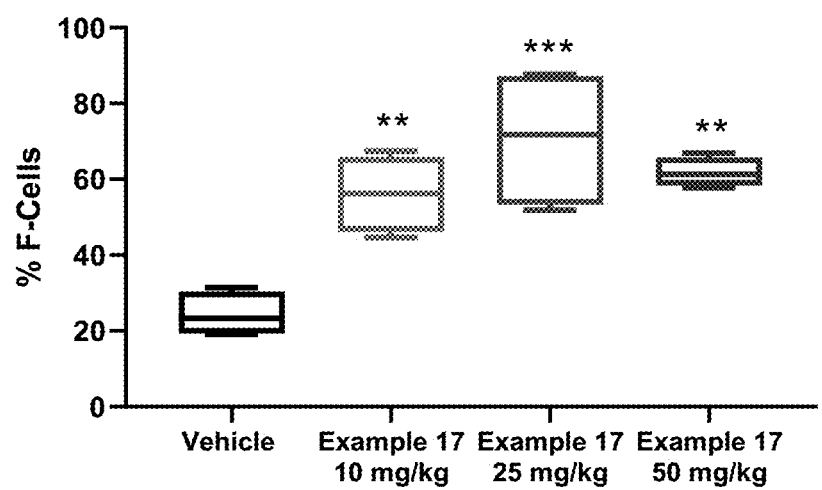
FIG. 3 depicts a graph showing the percentage of F-cells increase in Townes-SS mice treated with the compound of Example 17. Blood smears were made using heparinized whole blood for F-cells staining. Stained F-cells and total red blood cells were counted on the blood smears in four fields; mean=77 red blood cells/field. F-cells are expressed as a percentage of total red blood cells. Values are means+SD. One-Way ANOVA with Dunnett's Multiple comparison to Vehicle p≤0.01, *p≤0.001, ****p≤0.0001

At high enough concentrations, HbF can inhibit hemoglobin S (HbS) polymerization and subsequent hemolysis and vaso-occlusion (Krishnamoorthy S, et al. JCI Insight 2017, 2: e96409). To evaluate whether HMOX Inducers of the Invention can effectively increase HbF, F-cells (i.e., HbF-containing red blood cells) were measured as a percentage of total red blood cells according to the methods described above. As shown in FIG. 3, percent F-cells were significantly increased in HbSS-Townes mice administered the compound of Example 17 as compared with those administered with the vehicle. Specifically, percent F-cells were increased to ~55-70% at all doses tested for the compound of Example 17, more than doubled than the mice administered with the vehicle. The increase in percent F-cells did not appear to be dose responsive.

The results as shown above demonstrate that the compounds of the present invention are HMOX inducers and Bach 1 binders/inhibitors, and can be used to treat SCD at least through binding Bach 1, increasing HMOX1 activity, increasing HbF, and reducing vaso-occlusion.

Example 149. Glutathione (GSH) Levels in Primary Human Endothelial Cells

Primary human pulmonary artery endothelial cells (HPAEC) (Lonza # CC-2530) cultured in endothelial cell growth medium-2 (EGM2 media, Lonza # CC-3162) were seeded in white 96-well plate (Corning® #3610) at 12.5 k cells per well and placed at 37° C. in 5% $CO_2$. 18-24 hr post seeding, cells were treated with the compound of Example 17 via media change. 24 hr post treatment with the compound, cells were treated using a freshly prepared hemin stock (Sigma-Aldrich #51280 in 0.1N NaOH) alone or with the compound of Example 17. After 30 min of hemin stress, cells were visually inspected for toxicity, with no toxicity being noted. Media was aspirated off and GSH-Glo™ Glutathione Assay (Promega # V6911) was run following the manufacturer's protocol. White bottom plate seal (PerkinElmer #6005199) was used during read. Analysis was done using Softmax Pro.

Figure 4:
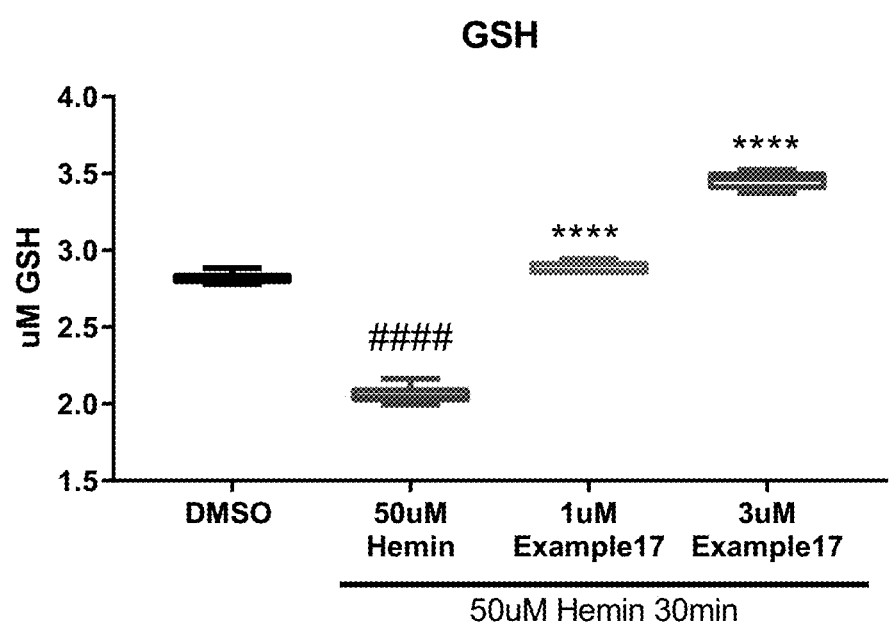
FIG. 4 depicts a graph showing the glutathione (GSH) levels in primary human endothelial cells. Two-Tailed Unpaired t test compared to DMSO #### p≤0.0001, One-Way ANOVA with Dunnett's Multiple comparison to Hemin (GSH Graph) ****p≤0.0001

The results are shown in FIG. 4. While hemin induces oxidative stress in primary human pulmonary arterial endothelial cells, thereby reducing GSH levels, pre-incubation with a HMOX inducer/Bach 1 inhibitor (e.g., the compound of Example 17) protects these cells from hemin mediated oxidative stress.

Example 150. Gene Expression in Primary Human Endothelial Cells

Inflammatory conditions in endothelial cells increase expression of adhesion molecules, such as VCAM-1, ICAM-1 and E-selectin through NF-kB signaling. HMOX1−/− endothelial cells show increased expression of VCAM-1 in response to TNF stimulation, as compared to HMOX+/+endothelial cells. See Seldon et al., J Immunol Dec. 1, 2007, 179 (11) 7840-7851.

Primary human pulmonary artery endothelial cells (HPAEC) (Lonza # CC-2530) were seeded in 12-well plates (TrueLine # TR5001) at 200 k cells per well and placed at 37° C. in 5% $CO_2$. 18-24 hr post seeding, cells were treated with the compound of Example 17 via media change. 24 hr post treatment with the compound, cells were treated with 10 ng/mL TNFa (Invitrogen # PHC3015 in $H_2O$) alone or with the compound of Example 17. After 4 hours of treatment, cells were visually inspected for toxicity, with no toxicity being noted. Media was aspirated off, cells were washed once with 1×PBS (Corning #21-040-CV), aspirated dry, parafilmed and placed at −80° C. until RNA isolation. RNA was isolated with the NucleoSpin® kits (MACHEREY-NAGEL #740955.250, USA) following kit protocol. RNA was used to generate cDNA using the High-Capacity cDNA Reverse Transcription Kit (ThermoFisher #4368814, USA) in 20 µL reactions. After reverse transcription was completed, cDNA was diluted 1:10 with water. 20 ng cDNA was mixed with water, iQ™ SYBR® Green Supermix (BioRad #170-8886), and 300 nM primer (IDT # NM_001078) for a total 10 ul reaction and loaded into 384-well white qPCR plates and subsequently analyzed using BioRad CFX384. Raw data was exported from software (Biorad CFX Manager, USA) and imported into a spreadsheet (Microsoft Excel, USA). To calculate fold change, the $\Delta$Ct on a per sample basis was calculated as Ct (Gene of interest)−Ct (Average of reference genes). The $\Delta\Delta$Ct was then calculated as $\Delta$Ct (experimental sample)−Average $\Delta$Ct (control group). Fold change was calculated as $2^{-\Delta\Delta C_T}$.

Figure 5:
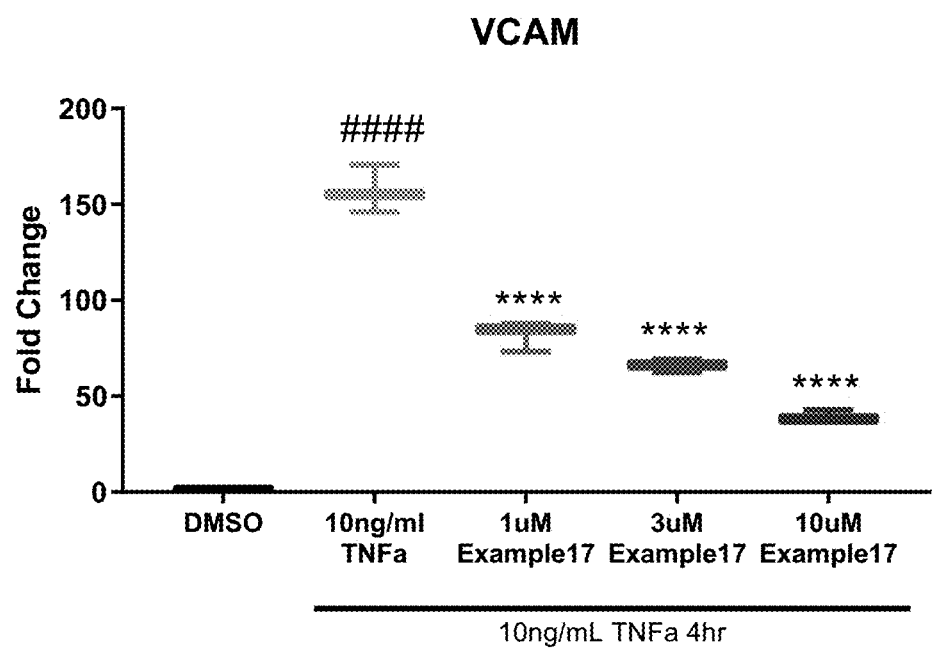
FIG. 5 depicts a graph showing fold change of gene expression in primary human endothelial cells. #### p≤0.0001, One-Way ANOVA with Dunnett's Multiple comparison to TNFa (VCAM graph) ****p≤0.0001

The results are shown in FIG. 5. Specifically, human primary endothelial cells were activated using TNF-α stimulation. For example, TNF-α induces expression of vascular cell adhesion molecule (VCAM) in primary human pulmonary arterial endothelial cells. Yet, pre-treatment with a HMOX inducer/Bach 1 inhibitor (e.g., the compound of Example 17) reduced this TNF-α mediated endothelial cell activation as evidenced by the reduction of the expression of the adhesion molecule VCAM-1.

Example 151. PK Study 9-10 week old male C57BL/6 mice were dosed orally with 50 mg/kg of the test compound formulated in 5% w/v tween 80 and 0.5% methyl cellulose. At 0.5 and 4 h post dosing, whole blood was collected, animals were sacrificed and brain tissues were collected. The blood samples were immediately placed on ice, and centrifuged within 60 min at 4° C. for 3 min at 14000 rpm to obtain plasma. Plasma was transferred by pipette to pre-labeled Eppendorf tubes, stored at −80° C. until analyzed.

Brain tissue samples were collected and rinsed with fresh ice cold 0.9% NaCl solution, dried quickly and thereafter frozen on dry ice/liquid nitrogen and stored at −70±10° C. until analyzed. Homogenization was done using phosphate buffer saline and used for analysis. Bioanalysis was performed using LC-MS/MS (API 4000).

The test results are provided in Table 4 below. The compound of Example 56 compound showed good brain penetration.

TABLE 4

| | Example 17 | | Example 56 | | Comparator 1** | |
|---|---|---|---|---|---|---|
| Matrix | 0.5 hr | 4 hr | 0.5 hr | 4 hr | 1 hr | 4 hr |
| Plasma (ng/ml) | 4235 ± 771 | 72 ± 38 | 4239 ± 428 | 281 ± 318 | 2073 ± 318 | 288 ± 124 |

TABLE 4-continued

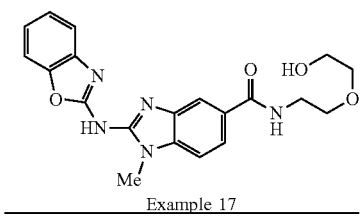 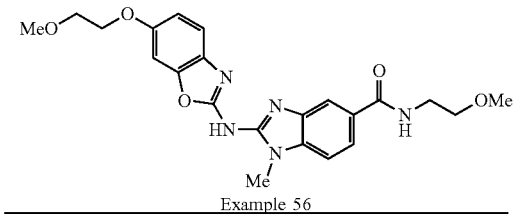

| | Example 17 | | Example 56 | | Comparator 1** | |
|---|---|---|---|---|---|---|
| Matrix | 0.5 hr | 4 hr | 0.5 hr | 4 hr | 1 hr | 4 hr |
| Brain (ng/g) | 188 ± 83 | N/A* | 4227 ± 600 | 122 ± 153 | N/A | N/A |

*Not available
**The compound of Example 17 and the compound of Example 56 were measured in the same study. Comparator 1 was measured in a previous study.

Example 152. PD Study 9-10 week old male C57BL/6 mice were dosed orally with 50 mg/kg of vehicle or compound formulated in 5% w/v tween 80 and 0.5% methyl cellulose. At indicated time points (3 and 6 hours or or 4 and 8 hours post-dosing as shown in the results below), whole blood was collected, animal was sacrificed and liver was collected. Blood samples were transferred to vials containing 4 µL of 10% w/v EDTA, centrifuged at 6000 rpm for 8 in below 10° C. to obtain plasma. Samples were frozen and later processed for HMOX1 protein levels as indicated below:
HMOX 1 Protein Levels: Mouse Liver
Preparation of Homogenization/Lysis Buffer
The homogenization buffer was prepared according Table A.

TABLE A

Preparation of homogenization Buffer

| | Stock | Final | Volume |
|---|---|---|---|
| Hepes (Ameresco #J848 - 100 ml) | 1M | 25 mM | 2.5 ml |
| NaCl (BostonBioProducts #A28Q12R) | 5M | 300 mM | 6 ml |
| MgCl$_2$ (Sigma #7786-30-3) | 1M | 1.5 mM | 150 ul |
| EDTA (Ameresco #E177 - 500 ml) | 0.5M | 20 uM | 4 ul |
| Triton X-100 (Sigma #T8787 - 250 ml) | 100% | 0.10% | 100 ul |
| MiliQ H2O | | | 91.246 ml |
| Final Volume | | | 100 mL |

Immediately prior to use, add DTT (ThermoScientific #R0861) to a final concentration of 5 mM and 100× Halt Protease & Phosphatase Inhibitor Cocktail (ThermoScientific #78440) to a final concentration of 1×.
Preparation of Mouse Liver Samples
Liver samples were crushed by mortar and pestle under freezing conditions. Pulverized tissue was transferred into pre-chilled bead ruptor OMNI tubes (OMNI International, Cat #19-628). 1 mL of homogenization buffer (+DTT and HALT) was added to pulverized tissue and tubes were placed on ice. Samples were loaded and run through bead ruptor at speed 5.64 m/s, for two 20 sec cycles with 10 sec dwell between cycles and samples were immediately returned to ice. All material was transferred to a new chilled 2 mL Eppendorf tube. Samples were centrifuged for 5 minutes at 2,000 rpm at 4° C. Supernatant was transferred to a fresh chilled 1.7 mL Eppendorf tube. Samples were centrifuged for 5 minutes at 2,000 rpm at 4° C. The supernatant, consisting of cytosol and microsomes, was transferred to a fresh chilled 1.7 mL Eppendorf tube. Samples were stored at −80° C. Microsome samples were quantitated using Pierce 660 Assay (ThermoFisher Cat #22660) with pre-diluted BSA standards (ThermoFisher Cat #23208) ranging from 125-2000 ug/mL. Each sample was diluted to 10 ng/ul for an ELISA input of 0.5 ug in 50 ul.
Preparation of Assay Reagents
All assay reagents were provided in the Heme Oxygenase 1 (HO1) Mouse SimpleStep ELISA Kit (Abcam # ab204524). Prior to use, all reagents were equilibrated to room temperature. 1× Wash Buffer PT was prepared by diluting 10× Wash Buffer PT 1:10 with deionized water. Antibody cocktail was prepared by diluting the 10× Capture Antibody and 10× Detector Antibody to 1× in Antibody Diluent 5BI. Mouse heme oxygenase 1 protein standard was reconstituted using 500 ul homogenization buffer (Table A), mixed and held at room temperature for 10 minutes prior to dilution. An eight point standard curve was generated by diluting the Stock Standard 1:2 for standard curve ranging from 10,000-156.3 pg/mL.
Heme Oxygenase 1 (HO1) Mouse SimpleStep ELISA
50 ul of all samples and standards were added to appropriate wells in duplicate. 50 ul of 1× Antibody Cocktail was added to each well. The plate was sealed with provided seal and incubated at room temperature on a plate shaker at 400 rpm. After one hour incubation, the Antibody Cocktail was aspirated and the wells were washed three times with 350 ul 1× Wash Buffer PT, aspirating completely between each step. After the last wash was aspirated dry, 100 ul TMB Substrate was added to each well and the plate was incubated in the dark at room temperature for 10 minutes on a plate shaker at 400 rpm. After the 10 minute incubation, 100 ul of Stop Solution was added to each well. Plate was shaken at 400 rpm for 1 minute to mix. Softmax Pro 7.0.3 was used to read OD at 450 nm as well as for analysis.
Heme Oxygenase 1 Protein Levels in Mouse Plasma
Preparation of Assay Reagents
All assay reagents were provided in the Heme Oxygenase 1 (HO1) Mouse SimpleStep ELISA Kit (Abcam # ab204524). 1× Wash Buffer PT was prepared by diluting 10× Wash Buffer PT 1:10 with deionized water. Antibody cocktail was prepared by diluting the 10× Capture Antibody and 10× Detector Antibody to 1× in Antibody Diluent 5BI. Mouse heme oxygenase 1 protein standard was reconstituted using 500 ul Sample Diluent NS, mixed and held at room temperature for 10 minutes prior to dilution. An eight point standard curve was generated by diluting the Stock Standard 1:2 for standard curve ranging from 5,000-78.1 pg/mL.

Preparation of Plasma Sample

Prior to ELISA, frozen plasma was thawed on ice. Plasma samples were diluted 1:10 in Sample Diluent NS for a final concentration of 10% plasma.

Heme Oxygenase 1 (HO1) Mouse SimpleStep ELISA 50 ul of samples and standards were added to appropriate wells in duplicate. 50 ul of 1× Antibody Cocktail was added to each well. The plate was sealed with provided seal and incubated at room temperature on a plate shaker at 400 rpm. After one hour incubation, the Antibody Cocktail was aspirated and the wells were washed three times with 350 ul 1× Wash Buffer PT, aspirating completely between each step. After the last wash was aspirated dry, 100 ul TMB Substrate was added to each well and the plate was incubated in the dark at room temperature for 10 minutes on a plate shaker at 400 rpm. After the 10 minute incubation, 100 ul of Stop Solution was added to each well. Plate was shaken at 400 rpm for 1 minute to mix. Softmax Pro 7.0.3 was used to read OD at 450 nm as well as for analysis.

Representative compounds of the present disclosure were tested and the results are provided in Table 5 blow. Plasma and liver protein levels assessed by mouse HMOX1 ELISA assay (kit) and were compared to time-matched vehicle control mice to give fold induction. Carboxylic acids showed modest increase in HMOX1 protein, although concentrations were well above $EC_{50}$ (30-100×).

TABLE 5

| | | HMOX1 $EC_{50}$ h (uM) | Plasma Protein (3 h, 6 h) | Liver Conc uM (3 h, 6 h) | Liver Protein (3 h, 6 h) |
|---|---|---|---|---|---|
| Comparator 1 | | 0.9 | 1.1× | 12.2 | 1.6× |
| 50 mpk Study 667 | | | 1.3× | 1.3 | 3.2× |
| Ex. 13 50 mpk Study 667 | Carboxylic Acid | 1.9 | 1.1× 0.8× | 63 5.4 | 1.8× 1.2× |
| Ex. 44 50 mpk Study 667 | Carboxylic Acid | 2.0 | 1.0 1.1× | 217 162 | 1.6× 2.1× |
| Ex. 17 50 mpk Study 702* | | 1.4 | 1.7×* 1.1×* | 11 4.9 | 3.3×* 3.1×* |

*Time points were 4 and 8 hours instead of 3 and 6 hours.

The invention claimed is:

1. A compound represented by structural formula (III-B):

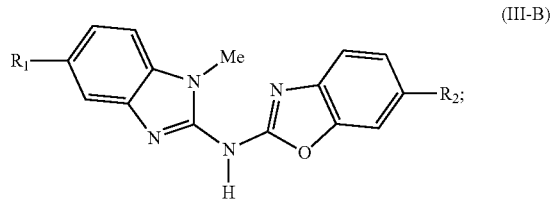

(III-B)

or a pharmaceutically acceptable salt thereof, wherein
$R_1$ is —C(=O)NH($C_1$-$C_4$)alkyl optionally substituted with —OH, —$NH_2$, —($C_1$-$C_4$)-alkoxy, or —($C_1$-$C_4$) hydroxyalkoxy, and
$R_2$ is H.

2. The compound of claim 1, or a pharmaceutically acceptable salt thereof, wherein
$R_1$ is —C(=O)NH($C_1$-$C_4$)alkyl substituted with —OH.

3. The compound of claim 2, wherein the compound is: 2-(benzo[d]oxazol-2-ylamino)-N-(2-hydroxyethyl)-1-methyl-1H-benzo[d]imidazole-5-carboxamide or a pharmaceutically acceptable salt thereof.

4. The compound of claim 1, or a pharmaceutically acceptable salt thereof, wherein
$R_1$ is —C(=O)NH($C_1$-$C_4$)alkyl substituted with —$NH_2$.

5. The compound of claim 4, wherein the compound is: N-(2-aminoethyl)-2-(benzo[d]oxazol-2-ylamino)-1-methyl-1H-benzo[d]imidazole-5-carboxamide or a pharmaceutically acceptable salt thereof.

6. The compound of claim 1, or a pharmaceutically acceptable salt thereof, wherein
$R_1$ is —C(=O)NH($C_1$-$C_4$)alkyl substituted with —($C_1$-$C_4$)hydroxyalkoxy.

7. The compound of claim 6, wherein the compound is: 2-(benzo[d]oxazol-2-ylamino)-N-(2-(2-hydroxyethoxy) ethyl)-1-methyl-1H-benzo[d]imidazole-5-carboxamide or a pharmaceutically acceptable salt thereof.

8. A pharmaceutical composition comprising a pharmaceutically acceptable carrier or diluent and the compound of claim 1, or a pharmaceutically acceptable salt thereof.

9. A method of increasing the activity of or the amount of HMOX-1 in a human subject comprising: administering to a human subject an effective amount of the compound of claim 1, or a pharmaceutically acceptable salt thereof.

10. A method of activating transcription factor Nrf2 in a human subject comprising: administering to a human subject an effective amount of a compound of claim 1, or a pharmaceutically acceptable salt thereof.

11. A method of reducing the amount of ROS in a human subject comprising: administering to a human subject an effective amount of the compound of claim 1, or a pharmaceutically acceptable salt thereof.

* * * * *